US012678446B2

(12) United States Patent
Barrett et al.

(10) Patent No.: US 12,678,446 B2
(45) **Date of Patent: *Jul. 14, 2026**

(54) BENZODIAZEPINE DERIVATIVES USEFUL IN TREATING A RESPIRATORY SYNCYTIAL VIRUS INFECTION

(71) Applicant: PFIZER INC., New York, NY (US)

(72) Inventors: Matthew Barrett, Stevenage (GB); George Stuart Cockerill, Stevenage (GB); James Good, Stevenage (GB); Craig Alex Avery, Nottingham (GB); Edward James Cochrane, Nottingham (GB); Stefan Paul Jones, Nottingham (GB); Stuart Thomas Onions, Nottingham (GB); Andrew Joseph Warner, Nottingham (GB)

(73) Assignee: Pfizer Inc., New York, NY (US)

( * ) Notice: Subject to any disclaimer, the term of this patent is extended or adjusted under 35 U.S.C. 154(b) by 511 days.

This patent is subject to a terminal disclaimer.

(21) Appl. No.: 18/004,504

(22) PCT Filed: Jul. 7, 2021

(86) PCT No.: PCT/GB2021/051731

§ 371 (c)(1),
(2) Date: Jan. 10, 2023

(87) PCT Pub. No.: WO2022/008911

PCT Pub. Date: Jan. 13, 2022

(65) Prior Publication Data

US 2023/0270751 A1 Aug. 31, 2023

(30) Foreign Application Priority Data

Jul. 7, 2020 (GB) ..................................... 2010409

(51) Int. Cl.
*A61K 31/5513* (2006.01)
*A61K 45/06* (2006.01)
*A61P 31/14* (2006.01)

(52) U.S. Cl.
CPC .......... *A61K 31/5513* (2013.01); *A61K 45/06* (2013.01); *A61P 31/14* (2018.01)

(58) Field of Classification Search
CPC ..... A61K 31/5513; A61K 45/06; A61P 31/14; C07D 513/04; C07D 519/00
See application file for complete search history.

(56) References Cited

U.S. PATENT DOCUMENTS

| | | | |
|---|---|---|---|
| 2006/0040923 A1 | 2/2006 | Carter et al. | |
| 2007/0142403 A1 | 6/2007 | Powell et al. | |

(Continued)

FOREIGN PATENT DOCUMENTS

| | | | |
|---|---|---|---|
| EP | 1727551 | B1 | 9/2009 |
| WO | 2004/026843 | A1 | 4/2004 |

(Continued)

OTHER PUBLICATIONS

Park et al Liquid chromatographic resolution of 3-amino-1,4-benzodiazepin-2-one derivatives on various Pirkle-type chiral stationary phases. Chirality, 23: E16-E21. (2011) (Year: 2011).*

(Continued)

*Primary Examiner* — Savitha M Rao
*Assistant Examiner* — Elena Vladimirovna Vishnyakova
(74) *Attorney, Agent, or Firm* — John A. Wichtowski

(57) ABSTRACT

Benzodiazepine derivatives of formula (Ie) wherein one $R^1$ and $R^2$ is a benzodiazepinyl-containing group of formula (II) in which $R^8$ is H or halo; the other of $R^1$ and $R^2$ is a group Z selected from H, $C_3$-$C_6$ cycloalkyl, halo, —$NHR^9$, benzyl, phenyl, 4- to 10-membered heterocyclyl and 4- to 10-membered heteroaryl, wherein phenyl, heterocyclyl and heteroaryl are unsubstituted or substituted by one or two substituents selected from 4- to 10-membered heterocyclyl which is unsubstituted or substituted by OR, and from $C_1$-$C_6$ alkyl, $C_1$-$C_6$ hydroxyalkyl, $C_1$-$C_6$ haloalkyl, $C_3$-$C_6$ cycloalkyl, halo, —OR, —$(CH_2)_mOR$, —$NR_2$, —$(CH_2)_mNR_2$, —NHR", —$SO_mNR_2$, —$SO_mR$, —SR, nitro, —$CO_2R$, —CN, —$CONR_2$, —NHCOR, —$CH_2NR^{10}R^{11}$ and —$NR^{10}R^{11}$, in which each R is independently H or $C_1$-$C_6$ alkyl, R" is $C_3$-$C_6$ cycloalkyl and m is 1 or 2; $R^9$ is selected from phenyl and 4- to 10-membered heteroaryl wherein phenyl and heteroaryl are unsubstituted or substituted by halo; $R^{10}$ and $R^{11}$ are each independently H or $C_1$-$C_6$ alkyl; or $R^{10}$ and $R^{11}$ form, together with the N atom to which they are attached, either (a) a morpholine ring which is optionally bridged by a —$CH_2$— group linking two ring carbon atoms that are positioned para to each other, or (b) a spiro group of the following formula (b): and ring A is a ring of one of the following structural formulae (I-1), (I-2) and (I-3): and ring A is a ring of one of the following structural formulae (I-1), (I-2) and (I-3): in which Y is selected from O, S, $SO_2$ and NR, wherein R is as defined above, and each of $R^2$ to $R^7$ is independently H, $C_1$-$C_6$ alkyl, $C_1$-$C_6$ hydroxyalkyl, $C_3$-$C_6$ cycloalkyl, halo, —OR, —$CH_2OR$, —$NR_2$, —$CH_2NR^{12}R^{13}$, —NRCOOR, —$CH_2OR$, —$SO_mNR_2$, —$SO_mR$, —$CH_2SO_mR$, nitro, —$CO_2R$, —CN, —$CONR_2$ or —NHCOR, in which R and m are as defined above and $R^{12}$ and $R^{13}$ are each independently H, $C_1$-$C_6$ alkyl, benzyl, 4- to 10-membered heterocyclyl or $R^2$ and $R^{13}$ form, together with the N atom to which they are attached, a 4- to 10-membered heteroaryl which is unsubstituted or a 4- to 10-membered heterocyclyl which is unsubstituted or substituted with $C_1$-$C_6$ alkyl or halo, or any two of $R^2$ to $R^7$ that bond to the same carbon atom form a spiro ring selected from a $C_3$-$C_6$ cycloalkyl spiro ring and a spiro oxetane ring of the following structure: (Formula A) and the pharmaceutically acceptable salts thereof are inhibitors of RSV and can therefore be used to treat or prevent an RSV infection.

(Continued)

(Ie)

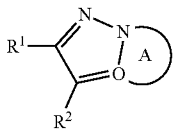

(II)

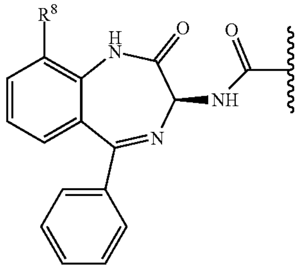

(b)

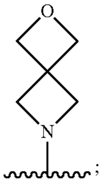

(I-1)

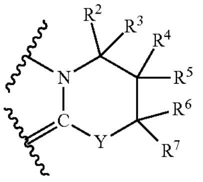

(I-2)

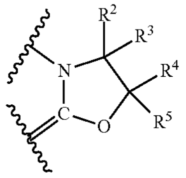

(I-3)

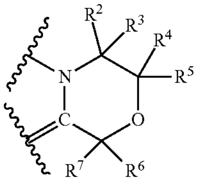

-continued (A)

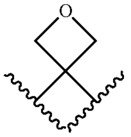

9 Claims, No Drawings

(56) References Cited

U.S. PATENT DOCUMENTS

| | | | |
|---|---|---|---|
| 2007/0185096 A1 | 8/2007 | Powell et al. | |
| 2008/0139536 A1 | 6/2008 | Dowdell et al. | |
| 2018/0354912 A1 | 12/2018 | Or et al. | |
| 2019/0152968 A1 * | 5/2019 | Blaisdell | C07D 413/14 |

FOREIGN PATENT DOCUMENTS

| | | |
|---|---|---|
| WO | 2004/098589 A1 | 11/2004 |
| WO | 2004/106310 A1 | 12/2004 |
| WO | 2005/089769 A1 | 9/2005 |
| WO | 2005/089770 A1 | 9/2005 |
| WO | 2005/089771 A1 | 9/2005 |
| WO | 2005/090319 A1 | 9/2005 |
| WO | 2006/113140 A2 | 10/2006 |
| WO | 2011/027156 A1 | 3/2011 |
| WO | 2011/151651 A1 | 12/2011 |
| WO | 2011/151652 A1 | 12/2011 |
| WO | 2016/166546 A1 | 10/2016 |
| WO | 2017/015449 A1 | 1/2017 |
| WO | 2018/033714 A1 | 2/2018 |
| WO | 2018/085378 A1 | 5/2018 |
| WO | 2018/129287 A1 | 7/2018 |
| WO | 2018/152413 A1 | 8/2018 |
| WO | 2018/226801 A1 | 12/2018 |
| WO | 2019/094920 A1 | 5/2019 |
| WO | 2020/190935 A1 | 9/2020 |
| WO | 2021/032992 A1 | 2/2021 |
| WO | 2021/079121 A1 | 4/2021 |
| WO | 2021/084280 A1 | 5/2021 |
| WO | 2022/008911 A1 | 1/2022 |
| WO | 2022/008912 A1 | 1/2022 |

OTHER PUBLICATIONS

Chapman et al., "RSV604, a novel inhibitor of respiratory syncytial virus replication." Antimicrobial agents and chemotherapy 51.9 (2007): 3346-3353.

International Preliminary Report on Patentability issued in PCT/GB2021/051731; mailed on Jan. 19, 2023; 7 pp.

International Search Report issued in PCT/GB2021/051731; mailed on Oct. 15, 2021; 3 pp.

Written Opinion issued in PCT/GB2021/051731; mailed on Oct. 15, 2021; 5 pp.

* cited by examiner

BENZODIAZEPINE DERIVATIVES USEFUL IN TREATING A RESPIRATORY SYNCYTIAL VIRUS INFECTION

CROSS-REFERENCE TO RELATED APPLICATIONS

This application is the U.S. National Stage of PCT/GB2021/051731 with international filing date of Jul. 7, 2021 and which claims priority to GB 2010409.7 with filing date of Jul. 7, 2020, the entire contents of both application are incorporated herein by reference for all purposes.

FIELD OF THE INVENTION

The present invention relates to benzodiazepine derivatives and to their use in treating or preventing a respiratory syncytial virus (RSV) infection.

BACKGROUND TO THE INVENTION

RSV is a negative-sense, single-stranded RNA virus of the Paramyxoviridae family. RSV is readily transmitted by secretions from an infected person via surfaces or hand-to-hand transfer. Unlike influenza, it is not transmitted by small-particle aerosols. Following successful inoculation, the incubation period is between four and six days during which time the virus spreads from the nasopharynx to the lower respiratory tract by fusion of infected with uninfected cells and by sloughing of the necrotic epithelium. In infants, coupled with increased mucus secretion and oedema, this can lead to mucus plugging causing hyper-inflation and collapse of distal lung tissue indicative of bronchiolitis. Hypoxia is common and the ability to feed is often impaired because of respiratory distress. In RSV pneumonia, inflammatory infiltration of the airways consists of mononuclear cells and is more generalised, with involvement of the bronchioles, bronchi and alveoli. The duration and degree of viral shedding has been found to correlate with the clinical signs and severity of disease.

RSV is the leading cause of serious respiratory tract infections in infants and young children throughout the world. The highest morbidity and mortality occur in those born prematurely and for those with chronic lung or heart disease, although many infants hospitalised for RSV infection are otherwise healthy. Severe RSV infection in infancy can lead to several years of recurrent wheezing and is linked to the later development of asthma.

RSV is also a major cause of morbidity and mortality in the elderly and in immunocompromised children and adults as well as those with chronic obstructive pulmonary disease (COPD) and congestive heart failure (CHF).

RSV has a seasonal incidence; it is highly predictable and occurs in the winters of both hemispheres, from September to May in Europe and North America, peaking in December and January, and can occur throughout the year in tropical countries. It affects >90% of infants and young children by the age of two years and as natural immunity is short-lived; many will be re-infected each year. As with influenza, in elderly people, RSV causes around 10% of winter hospitalisations with an associated mortality of 10%.

Current anti-RSV treatment involves the use of a monoclonal antibody to RSV, called palivizumab. Such use of palivizumab is a prophylactic, rather than therapeutic, treatment of RSV. Although this antibody is often effective, its use is restricted to preterm infants and infants at high risk. Indeed, its limited utility means that it is unavailable for many people in need of anti-RSV treatment. There is therefore an urgent need for effective alternatives to existing anti-RSV treatment.

Small molecules have also been proposed as inhibitors of RSV. These include benzimidazoles and benzodiazepines. For instance, the discovery and initial development of RSV604, a benzodiazepine compound having sub-micromolar anti-RSV activity, is described in Antimicrobial Agents and Chemotherapy, September 2007, 3346-3353 (Chapman et a). Benzodiazepine inhibitors of RSV are also disclosed in publications including WO2004/026843 and WO2005/089770 (Arrow Therapeutics Limited); WO2016/166546 and WO2018/033714 (Durham University); and WO2017/015449, WO2018/129287 and WO2018/226801 (Enanta Pharmaceuticals, Inc.).

There exists a need to identify further compounds that have anti-RSV activity, in particular compounds having a combination of potent anti-viral activity and favourable pharmacokinetic properties.

SUMMARY OF THE INVENTION

It has now been found that a novel series of benzodiazepine derivatives have potent anti-RSV activity with favourable pharmacokinetics and good physicochemical properties. Accordingly, the present invention provides a compound which is a benzodiazepine derivative of formula (Ie):

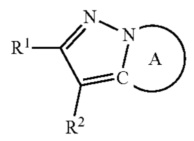

(Ie)

wherein:

one of $R^1$ and $R^2$ is a benzodiazepinyl-containing group of formula (II):

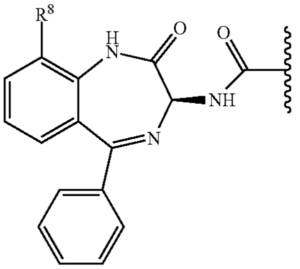

(II)

in which $R^8$ is H or halo;

the other of $R^1$ and $R^2$ is a group Z selected from H, $C_3$-$C_6$ cycloalkyl, halo, —$NHR^9$, benzyl, phenyl, 4- to 10-membered heterocyclyl and 4- to 10-membered heteroaryl, wherein phenyl, heterocyclyl and heteroaryl are unsubstituted or substituted by one or two substituents selected from 4- to 10-membered heterocyclyl which is unsubstituted or substituted by OR, and from $C_1$-$C_6$ alkyl, $C_1$-$C_6$ hydroxyalkyl, $C_1$-$C_6$ haloalkyl, $C_3$-$C_6$ cycloalkyl, halo, —OR, —$(CH_2)_m$OR, —$NR_2$, —$(CH_2)_m NR_2$, —NHR", —$SO_m NR_2$, —$SO_m$R, —SR, nitro, —$CO_2R$, —CN, —$CONR_2$, —NHCOR, —$CH_2NR^{10}R^{11}$ and —$NR^{10}R^{11}$, in which each R is independently H or $C_1$-$C_6$ alkyl, R" is $C_3$-$C_6$ cycloalkyl and m is 1 or 2;

$R^9$ is selected from phenyl and 4- to 10-membered heteroaryl, wherein phenyl and heteroaryl are unsubstituted or substituted by halo;

$R^{10}$ and $R^{11}$ are each independently H or $C_1$-$C_6$ alkyl; or $R^{10}$ and $R^{11}$ form, together with the N atom to which they are attached, either (a) a morpholine ring which is optionally bridged by a —$CH_2$— group linking two ring carbon atoms that are positioned para to each other, or (b) a spiro group of the following formula (b):

(b)

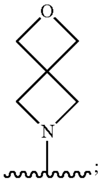

and ring A is a ring of one of the following structural formulae (I-1), (I-2) and (I-3):

(I-1)

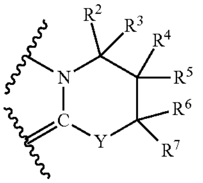

(I-2)

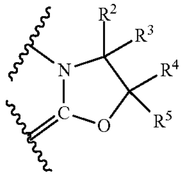

(I-3)

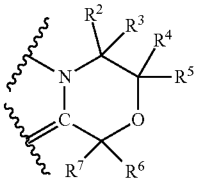

in which Y is selected from O, S, $SO_2$ and NR, wherein R is as defined above, and each of $R^2$ to $R^7$ is independently H, $C_1$-$C_6$ alkyl, $C_1$-$C_6$ hydroxyalkyl, $C_3$-$C_6$ cycloalkyl, halo, —OR, —$CH_2OR$, —$NR_2$, —$CH_2NR^{12}R^{13}$, —NRCOOR, —$CH_2OR$, —$SO_mNR_2$, —$SO_mR$, —$CH_2SO_mR$, nitro, —$CO_2R$, —CN, —$CONR_2$ or —NHCOR, in which R and m are as defined above and $R^{12}$ and $R^{13}$ are each independently H, $C_1$-$C_6$ alkyl, benzyl, 4- to 10-membered heterocyclyl or $R^{12}$ and $R^{13}$ form, together with the N atom to which they are attached, a 4- to 10-membered heteroaryl which is unsubstituted or a 4- to 10-membered heterocyclyl which is unsubstituted or substituted with $C_1$-$C_6$ alkyl or halo, or any two of $R^2$ to $R^7$ that bond to the same carbon atom form a spiro ring selected from a $C_3$-$C_6$ cycloalkyl spiro ring and a spiro oxetane ring of the following structure:

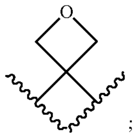

;

or a pharmaceutically acceptable salt thereof.

In one embodiment, the present invention provides a compound which is a benzodiazepine derivative of formula (I):

(I)

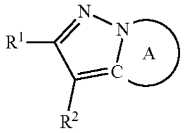

wherein:

one of $R^1$ and $R^2$ is a benzodiazepinyl-containing group of formula (II):

(II)

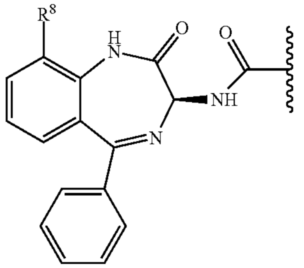

in which $R^1$ is H or halo;

the other of $R^1$ and $R^2$ is a group Z selected from H, $C_3$-$C_6$ cycloalkyl, —$NHR^9$, phenyl and 4- to 10-membered heteroaryl, wherein phenyl and heteroaryl are unsubstituted or substituted by one or two substituents selected from $C_1$-$C_6$ alkyl, $C_1$-$C_6$ hydroxyalkyl, $C_1$-$C_6$ haloalkyl, $C_3$-$C_6$ cycloalkyl, halo, —OR, —NHR", —$SO_mNR_2$, —$SO_mR$, nitro, —$CO_2R$, —CN, —$CONR_2$, —NHCOR and —$NR^{10}R^{11}$, in which each R is independently H or $C_1$-$C_6$ alkyl, R" is $C_3$-$C_6$ cycloalkyl and m is 1 or 2;

$R^9$ is selected from phenyl and 4- to 10-membered heteroaryl;

$R^{10}$ and $R^{11}$ are each independently H or $C_1$-$C_6$ alkyl; or $R^{10}$ and $R^{11}$ form, together with the N atom to which they are attached, either (a) a morpholine ring which is optionally bridged by a —$CH_2$— group linking two ring carbon atoms that are positioned para to each other, or (b) a spiro group of the following formula (b):

(b)

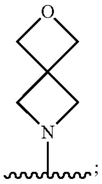

and ring A is a ring of one of the following structural formulae (I-1), (I-2) and (I-3):

(I-1)

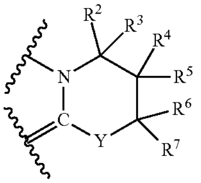

(I-2)

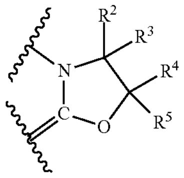

(I-3)

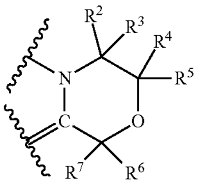

in which Y is selected from O, S, $SO_2$ and NR, wherein R is as defined above, and each of $R^2$ to $R^7$ is independently H, $C_1$-$C_6$ alkyl, $C_3$-$C_6$ cycloalkyl, halo, —OR, —$NR_2$, —$CH_2OR$, —$SO_mNR_2$, —$SO_mR$, nitro, —$CO_2R$, —CN, —$CONR_2$ or —NHCOR, in which R and m are as defined above, or any two of $R^2$ to $R^7$ that bond to the same carbon atom form a spiro ring selected from a $C_3$-$C_6$ cycloalkyl spiro ring and a spiro oxetane ring of the following structure:

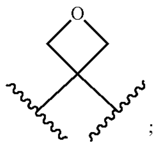 [SMILES: *C1(*)COC1]

or a pharmaceutically acceptable salt thereof.

In one aspect, the benzodiazepine derivative of the invention has the following structural formula (Ie'):

(Ie')

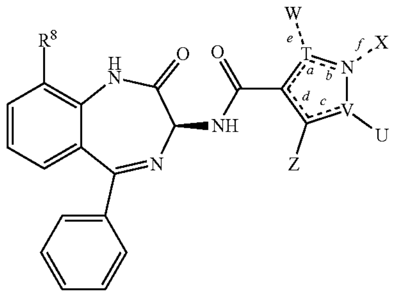

wherein:

$R^8$ is H or halo;

and either (i) T is N and V is C;

a, c and f are bonds, and b, d and e are absent;

Z is selected from H, $C_3$-$C_6$ cycloalkyl, halo, —$NHR^9$, benzyl, phenyl, 4- to 10-membered heterocyclyl and 4- to 10-membered heteroaryl, wherein phenyl, heterocyclyl and heteroaryl are unsubstituted or substituted by one or two substituents selected from 4- to 10-membered heterocyclyl which is unsubstituted or substituted by OR, and from $C_1$-$C_6$ alkyl, $C_1$-$C_6$ hydroxyalkyl, $C_1$-$C_6$ haloalkyl, $C_3$-$C_6$ cycloalkyl, halo, —OR, —$(CH_2)_mOR$, —$NR_2$, —$(CH_2)_mNR_2$, —NHR", —$SO_mNR_2$, —$SO_mR$, —SR, nitro, —$CO_2R$, —CN, —$CONR_2$, —NHCOR, —$CH_2NR^{10}R^{11}$ and —$NR^{10}R^{11}$, in which each R is independently H or $C_1$-$C_6$ alkyl, $R^{11}$ is $C_3$-$C_6$ cycloalkyl and m is 1 or 2;

$R^9$ is selected from phenyl and 4- to 10-membered heteroaryl, wherein phenyl and heteroaryl are unsubstituted or substituted by halo;

$R^{10}$ and $R^{11}$ are each independently H or $C_1$-$C_6$ alkyl; or $R^{10}$ and $R^{11}$ form, together with the N atom to which they are attached, either (a) a morpholine ring which is optionally bridged by a —$CH_2$— group linking two ring carbon atoms that are positioned para to each other, or (b) a spiro group of the following formula (b):

(b)

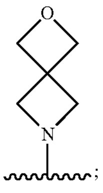

and

X and U form, with the N and C atoms to which they are attached, a ring of the following formula (I'-1) or (I'-2):

(I'-1)

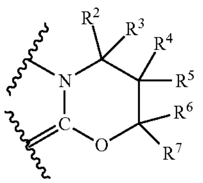

-continued (I-2)

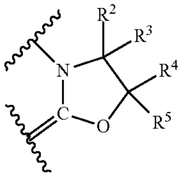

wherein each of $R^2$ to $R^7$ is independently H, $C_1$-$C_6$ alkyl, $C_1$-$C_6$ hydroxyalkyl, $C_3$-$C_6$ cycloalkyl, halo, —OR, —$CH_2$OR, —$NR_2$, —$CH_2NR^{12}R^{13}$, —NRCOOR, —$CH_2$OR, —$SO_mNR_2$, —$SO_mR$, —$CH_2SO_mR$, nitro, —$CO_2$R, —CN, —$CONR_2$ or —NHCOR, in which R and m are as defined above and $R^{12}$ and $R^{13}$ are each independently H, $C_1$-$C_6$ alkyl, benzyl, 4- to 10-membered heterocyclyl or $R^{12}$ and $R^{13}$ form, together with the N atom to which they are attached, a 4- to 10-membered heteroaryl which is unsubstituted or a 4- to 10-membered heterocyclyl which is unsubstituted or substituted with $C_1$-$C_6$ alkyl or halo, or any two of $R^2$ to $R^7$ that bond to the same carbon atom form a spiro ring selected from a $C_3$-$C_6$ cycloalkyl spiro ring and a spiro oxetane ring of the following structure:

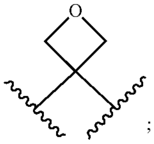 [SMILES: *C1(*)COC1]

;

or (ii) T is C, V is N, ---b---, ---d--- and ---e--- are bonds, and ---a---, ---c--- and ---f--- are absent;

W takes the definitions given for Z in clause (i) above; and

U and Z form, with the N and C atoms to which they are attached, a ring of the following formula (I-1) or (I-3):

(I-1)

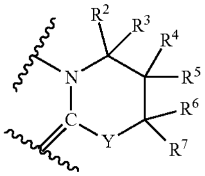

(I-3)

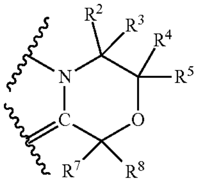

wherein Y is selected from O, S, $SO_2$ and NR, wherein R is as defined in clause (i) above; and $R^2$ to $R^7$ are as defined in clause (i) above;

or a pharmaceutically acceptable salt thereof.

In one embodiment of this aspect, the benzodiazepine derivative of the invention has the following structural formula (I'):

(I')

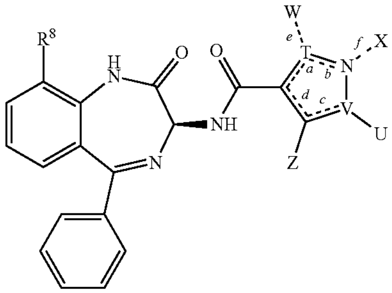

wherein:

$R^8$ is H or halo;

and either (i) T is N and V is C;

---a---, ---c--- and ---f--- are bonds, and ---b---, ---d--- and ---e--- are absent;

Z is selected from H, $C_3$-$C_6$ cycloalkyl, —$NHR^9$, phenyl and 4- to 10-membered heteroaryl, wherein phenyl and heteroaryl are each unsubstituted or substituted by one or two substituents selected from $C_1$-$C_6$ alkyl, $C_3$-$C_6$ cycloalkyl, halo, —OR, —NHR", —$SO_mNR_2$, —$SO_mR$, nitro, —$CO_2$R, —CN, —$CONR_2$, —NHCOR and —$NR^{10}R^{11}$, in which each R is independently H or $C_1$-$C_6$ alkyl, R" is $C_3$-$C_6$ cycloalkyl and m is 1 or 2;

$R^9$ is selected from phenyl and 4- to 10-membered heteroaryl;

$R^{10}$ and $R^{11}$ are each independently H or $C_1$-$C_6$ alkyl; or $R^{10}$ and $R^{11}$ form, together with the N atom to which they are attached, either (a) a morpholine ring which is optionally bridged by a —$CH_2$— group linking two ring carbon atoms that are positioned para to each other, or (b) a spiro group of the following formula (b):

(b)

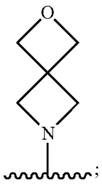

;

and

X and U form, with the N and C atoms to which they are attached, a ring of the following formula (I'-1) or (I'-2):

(I'-1)

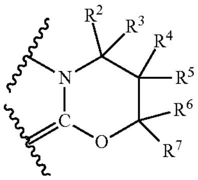

-continued (I-2)

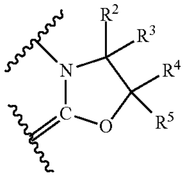

wherein each of $R^2$ to $R^7$ is independently H, $C_1$-$C_6$ alkyl, $C_3$-$C_6$ cycloalkyl, halo, —OR, —$NR_2$, —$CH_2OR$, —$SO_mNR_2$, —$SO_mR$, nitro, —$CO_2R$, —CN, —$CONR_2$ or —NHCOR in which R and m are as defined above, or any two of $R^2$ to $R^7$ that bond to the same carbon atom form a spiro ring selected from a $C_3$-$C_6$ cycloalkyl spiro ring and a spiro oxetane ring of the following structure:

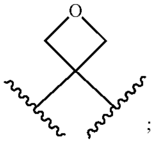 [SMILES: *C1(*)COC1]

;

or (ii) T is C, V is N, ---b---, ---d--- and ---e--- are bonds, and ---a---, ---c--- and ---f--- are absent;

W takes the definitions given for Z in clause (i) above; and U and Z form, with the N and C atoms to which they are attached, a ring of the following formula (I-1) or (I-3):

(I-1)

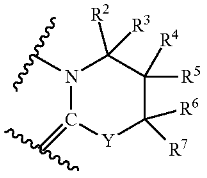

(I-3)

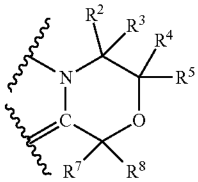

wherein Y is selected from O, S, $SO_2$ and NR, wherein R is as defined in clause (i) above; and $R^2$ to $R^7$ are as defined in clause (i) above;

or a pharmaceutically acceptable salt thereof.

DETAILED DESCRIPTION OF THE INVENTION

When any group, ring, substituent or moiety defined herein is substituted, it is typically substituted by Q as defined below.

A $C_{1-6}$ alkyl group or moiety is linear or branched. A $C_{1-6}$ alkyl group is typically a $C_{1-4}$ alkyl group, or a $C_{4-6}$ alkyl group. Examples of $C_{1-6}$ alkyl groups and moieties include methyl, ethyl, n-propyl, i-propyl, n-butyl, i-butyl, t-butyl, n-pentyl, i-pentyl (i.e. 3-methylbut-1-yl), t-pentyl (i.e. 2-methylbut-2-yl), neopentyl (i.e. 2,2-dimethylpropan-1-yl), n-hexyl, i-hexyl (i.e. 4-methylpentan-1-yl), t-hexyl (i.e. 3-methylpentan-3-yl) and neopentyl (i.e. 3,3-dimethylbutan-1-yl). For the avoidance of doubt, where two alkyl moieties are present in a group, the alkyl moieties may be the same or different. A $C_{1-6}$ alkyl group is unsubstituted or substituted, typically by one or more groups Q as defined below. For example, a $C_{1-6}$ alkyl group is unsubstituted or substituted by 1, 2 or 3 groups Q as defined below.

Q is halo, nitro, —CN, OH, $C_{1-6}$ alkoxy, $C_{1-6}$ hydroxyalkyl, $C_{1-6}$ alkylthio, $C_{1-6}$ alkyl, $C_{1-6}$ haloalkyl, $C_{1-4}$ haloalkoxy, —$CO_2R'$, —$NR'_2$, —SR', —S(═O)R', —$S(═O)_2R'$, $C_3$-$C_{10}$ cycloalkyl, 5 to 10-membered heterocyclyl, 5- to 12-membered aryl or 5- to 10-membered heteroaryl, wherein each R' is independently selected from H, $C_{1-6}$ alkyl, $C_{3-10}$ cycloalkyl, 5 to 10-membered heterocyclyl, $C_6$-$C_{10}$ aryl and 5- to 10-membered heteroaryl. For the avoidance of doubt, the alkyl, alkoxy, alkylthio, cycloalkyl, heterocyclyl, aryl and heteroaryl moieties in these definitions are themselves typically unsubstituted.

A $C_{1-6}$ alkoxy group is linear or branched. It is typically a $C_{1-4}$ alkoxy group, for example a methoxy, ethoxy, propoxy, i-propoxy, n-propoxy, n-butoxy, sec-butoxy or tert-butoxy group. A $C_{1-6}$ alkoxy group is unsubstituted or substituted, typically by one or more groups Q as defined above.

A $C_{1-6}$ alkylthio group is linear or branched. It is typically a $C_{1-4}$ alkylthio group, for example a methylthio, ethylthio, propylthio, i-propylthio, n-propylthio, n-butylthio, sec-butylthio or tert-butylthio group. A $C_{1-6}$ alkylthio group is unsubstituted or substituted, typically by one or more groups Q as defined above.

A halogen or halo group is F, Cl, Br or I. Typically it is F or Cl. A $C_{1-6}$ alkyl group substituted by halogen may be denoted "$C_{1-6}$ haloalkyl", which means a $C_{1-6}$ alkyl group as defined above in which one or more hydrogens is replaced by halo. Likewise a $C_{1-6}$ alkoxy group substituted by halogen may be denoted "$C_{1-6}$ haloalkoxy", which means a $C_{1-6}$ alkoxy group as defined above in which one or more hydrogens is replaced by halo. Typically, $C_{1-6}$ haloalkyl or $C_{1-6}$ haloalkoxy is substituted by 1, 2 or 3 said halogen atoms. Haloalkyl and haloalkoxy groups include perhaloalkyl and perhaloalkoxy groups such as —$CX_3$ and —$OCX_3$ wherein X is a halogen, for example —$CF_3$—$CCl_3$—$OCF_3$ and —$OCCl_3$.

A $C_{1-6}$ hydroxyalkyl group is a $C_{1-6}$ alkyl group as defined above, substituted by one or more OH groups. Typically, it is substituted by one, two or three OH groups. Preferably, it is substituted by a single OH group.

A $C_6$-$C_{10}$ aryl group is an aromatic carbocyclic group containing from 6 to 10 carbon atoms. It is monocyclic or a fused bicyclic ring system in which an aromatic ring is fused to another aromatic carbocyclic ring. Examples of a $C_6$-$C_{10}$ aryl group include phenyl and naphthyl. When substituted, an aryl group is typically substituted by a group Q as defined above, for instance by 1, 2 or 3, groups selected from a group Q as defined above. More particularly, a substituted aryl group such as a substituted phenyl group is substituted by 1 or 2 groups selected from $C_1$-$C_6$ alkyl, halo, —$OR^8$ and —$N(R^8)_2$ wherein $R^8$ is H or $C_1$-$C_6$ alkyl, each $R^8$ being the same or different when two are present.

A $C_{3-10}$ cycloalkyl group is a saturated hydrocarbon ring having from 3 to 10 carbon atoms. A $C_{3-10}$ cycloalkyl group may be, for instance, $C_3$-$C_7$ cycloalkyl such as cyclopropyl, cyclobutyl, cyclopentyl, cyclohexyl, or cycloheptyl. Typically it is $C_3$-$C_6$ cycloalkyl, for example cyclopropyl, cyclobutyl, cyclopentyl or cyclohexyl. In one embodiment it is cyclopropyl. A $C_{3-10}$ cycloalkyl group is unsubstituted or substituted, typically by one or more groups Q as defined above.

A 4- to 10-membered heteroaryl group or moiety is a 4- to 10-membered aromatic heterocyclic group which contains 1, 2, 3, or 4 heteroatoms selected from O, N and S. It is monocyclic or bicyclic. Typically it contains one N atom and 0, 1, 2 or 3 additional heteroatoms selected from O, S and N. It may be, for example, a monocyclic 5- to 7-membered heteroaryl group, for instance a 5- or 6-membered N-containing heteroaryl group. Examples include pyridyl, pyrazinyl, pyrimidinyl, pyridazinyl, furanyl, thienyl, pyrazolidinyl, pyrrolyl, oxadiazolyl, oxazolyl, isoxazolyl, thiazolyl, thiadiazolyl, imidazolyl and pyrazolyl groups. Furanyl, thienyl, imidazolyl, pyridyl and pyrimidyl groups are preferred. It may alternatively be a bicyclic heteroaryl group, for instance an 8- to 10-membered bicyclic heteroaryl group. Examples include quinolyl, isoquinolyl, quinazolyl, quinoxalinyl, indolyl, isoindolyl, indazolyl, imidazopyridazinyl, pyrrolopyridinyl, pyrazolopyrimidinyl and pyrrolopyrimidinyl. When substituted, a heteroaryl group (monocyclic or bicyclic) is typically substituted by one or more, e.g. 1, 2 or 3, groups selected from $C_{1-4}$ alkyl and a group Q as defined above.

A 4- to 10-membered heterocyclyl group is a monocyclic or bicyclic non-aromatic, saturated or unsaturated ring system containing 5 to 10 carbon atoms and at least one atom or group selected from N, O, S, SO, $SO_2$ and CO, more typically N or O. When the ring system is bicyclic, one ring may be saturated and one ring unsaturated. Typically, it is a $C_{4-10}$ ring system in which 1, 2 or 3 of the carbon atoms in the ring are replaced with an atom or group selected from O, S, $SO_2$, CO and NH. More typically it is a monocyclic ring, preferably a monocyclic $C_4$-$C_6$ ring. Examples include piperidyl, piperidin-2,6-dionyl, piperidin-2-onyl, piperazinyl, morpholinyl, thiomorpholinyl, S,S-dioxothiomorpholinyl, 1,3-dioxolanyl, pyrrolidinyl, azetidinyl, diazinanyl, imidazol-2-onyl, pyrrolidin-2-onyl, oxetanyl, tetrahydrofuranyl and tetrahydropyranyl moieties.

For the avoidance of doubt, although the above definitions of heteroaryl and heterocyclyl groups refer to an "N" atom which can be present in the ring, it will be evident to a skilled chemist that any such N atom will be protonated (or will carry a substituent as defined above) if it is attached to each of its adjacent ring atoms via a single bond. Such protonated forms are embraced within the present definitions of heteroaryl and heterocyclyl groups.

In formula (Ie) or formula (I) as defined above, ring A is typically a ring of formula (I-1) in which Y is O, S or $SO_2$. More typically, ring A is a ring of formula (I-1) in which Y is O.

In formula (Ie) or formula (I), when $R^1$ is the group of formula (II) and $R^2$ is Z, A is typically a ring of formula (I-1) in which Y is O, or is a ring of formula (I-2).

In formula (Ie) or formula (I), when $R^1$ is Z and $R^2$ is the group of formula (II), A is typically a ring of formula (I-1) in which Y is O, S or $SO_2$, or is a ring of formula (I-3). Most typically Y in this embodiment is O.

When in formula (Ie) or (Ie') or formula (I) or (I') the group Z is 4- to 10-membered heteroaryl, the group may be selected from those listed in the general definition above. Typically it is selected from pyridyl, pyrazolyl, indazolyl, pyrimidinyl, thienyl and furanyl. More typically it is pyridyl.

When in formula (Ie) or (Ie') or formula (I) or (I') the group Z is 4- to 10-membered heterocyclyl, the group may be selected from those listed in the general definition above. Typically it is a monocyclic $C_4$-$C_6$ ring. More typically it is piperidyl.

In formula (Ie) or (Ie') or formula (I) or (I'), when the substituent on Z is a 4- to 10-membered heterocyclyl, the group may be selected from those listed in the general definition above. Typically it is a monocyclic $C_4$-$C_6$ ring in which 1 of the carbon atoms in the ring is replaced with an atom or group selected from 0 and NH. More typically it is selected from pyrrolidinyl, azetidinyl, oxetanyl, and tetrahydropyranyl.

In formula (Ie) or (Ie') or formula (I) or (I'), when the substituent on Z is a group $—NR^{10}R^{11}$ in which $R^{10}$ and $R^{11}$ form, together with the N atom to which they are attached, a morpholine ring which is bridged by a $—CH_2—$ group linking two ring carbon atoms that are positioned para to each other, the group $—NR^{10}R^{11}$ has the following structure (c) or (d):

(c)

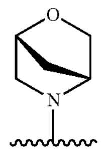

(d)

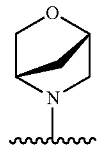

In one embodiment of formula (Ie) or formula (I) as defined above, the benzodiazepine derivative is of formula (Ia):

(Ia)

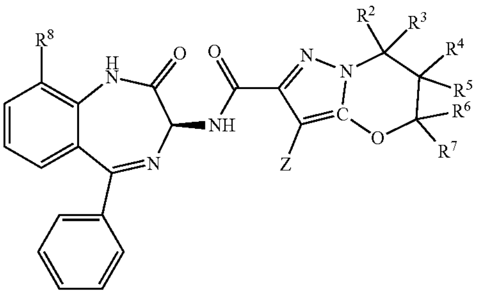

in which all the groups are as defined above for formula (Ie) or formula (I).

In another embodiment of formula (Ie) or formula (I) as defined above, the benzodiazepine derivative is of formula (Ib):

(Ib)

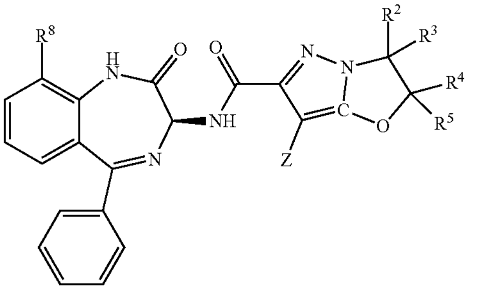

in which all the groups are as defined above for formula (Ie) or formula (I).

In a further embodiment of formula (Ie) or formula (I) as defined above, the benzodiazepine derivative is of formula (Ic):

(Ic)

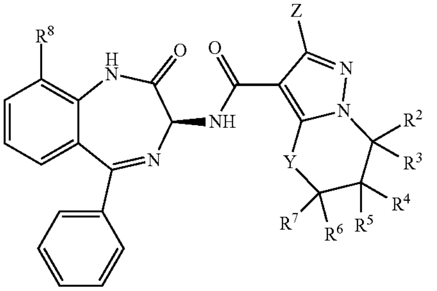

in which all the groups are as defined above for formula (Ie) or formula (I).

In a further embodiment of formula (Ie) or formula (I) as defined above, the benzodiazepine derivative is of formula (Id):

(Id)

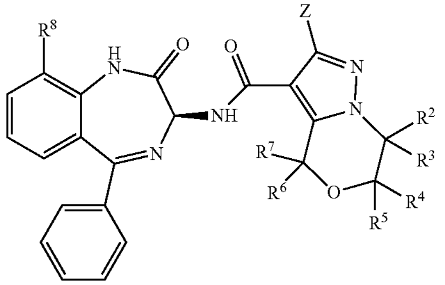

in which all the groups are as defined above for formula (Ie) or formula (I).

In the above formulae (Ie), (Ie'), (I), (I'), (Ia), (Ib), (Ic) and (Id), $R^8$ is typically H or F.

In the above formulae (Ie), (Ie'), (I), (I') and (Ic), Y is typically O, S or $SO_2$. More typically Y is O or $SO_2$. Most typically Y is O. When Y is NR, then R is typically a $C_{1-4}$ alkyl group.

In the above formulae (Ie), (Ie'), (Ia), (Ib), (Ic) and (Id), Z is typically selected from H, halo, cyclopropyl, cyclohexyl and the following structures:

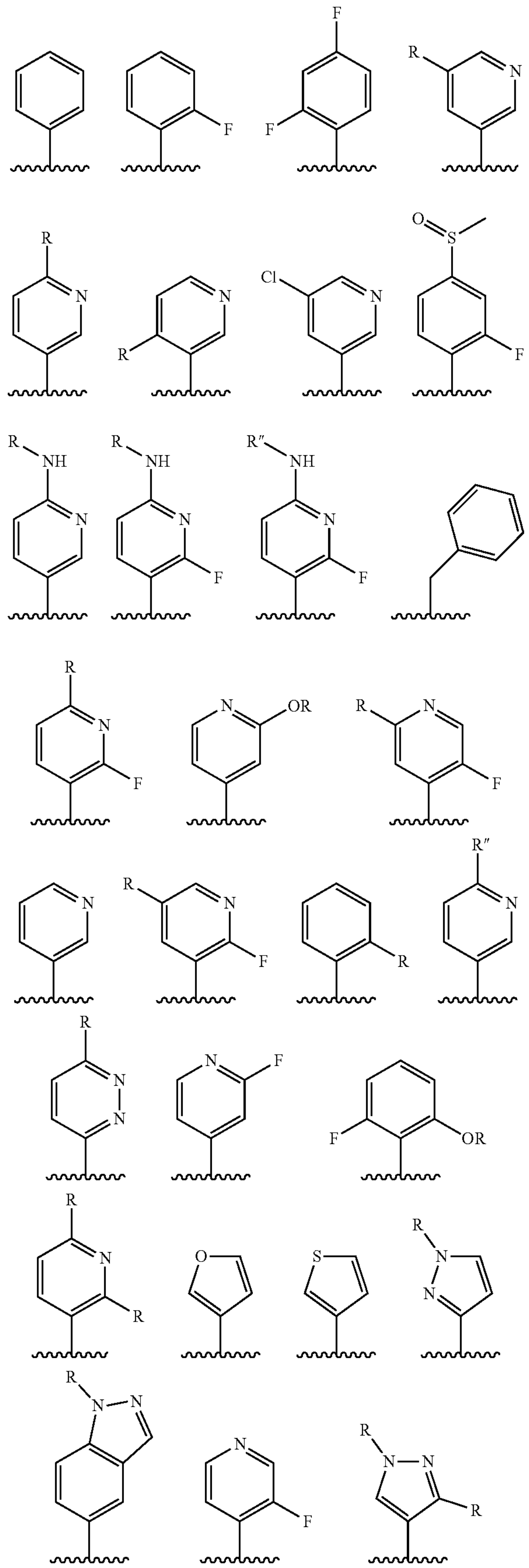

-continued
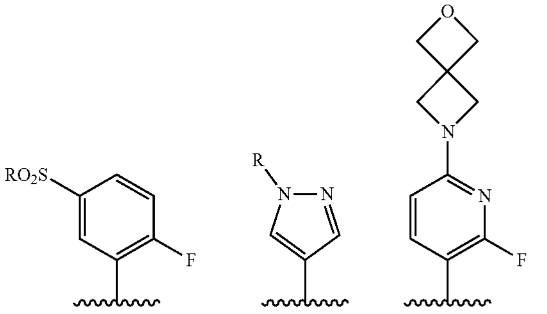
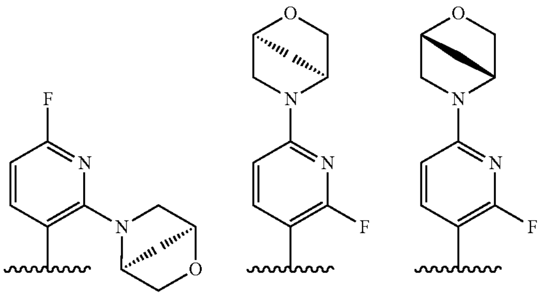
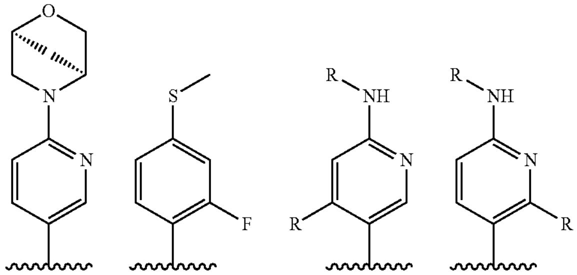
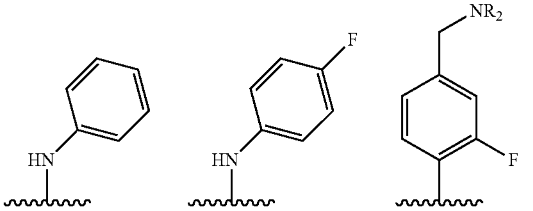
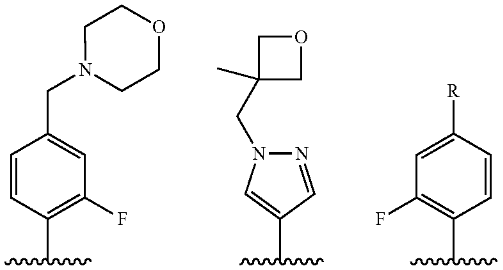
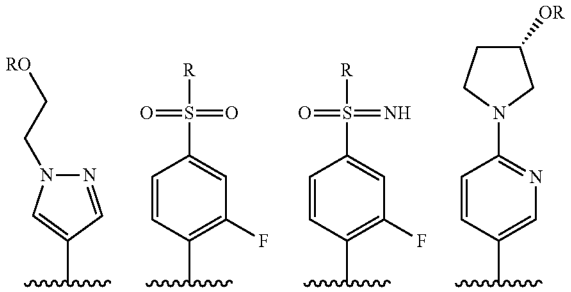
-continued
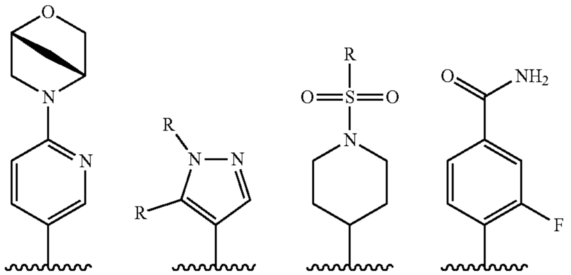
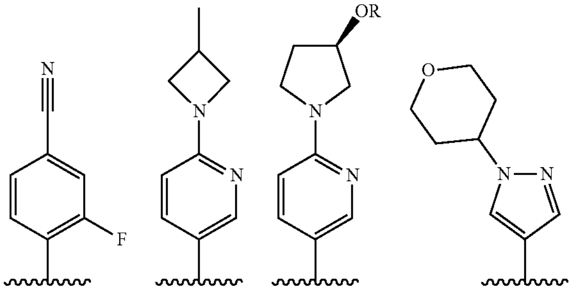
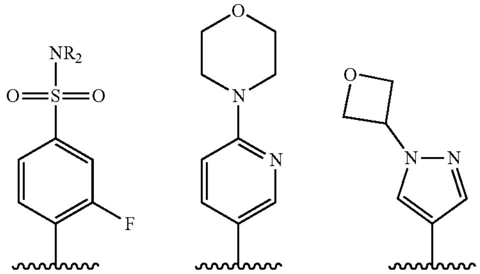
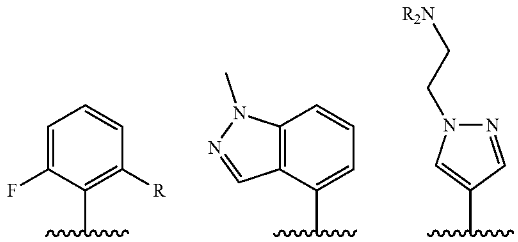
in which R and R" are as defined above for formula (Ie). Typically R is $C_1$-$C_3$ alkyl and R" is cyclopropyl.
The above definitions of Z are typically also taken by W in formula (Ie').
In one embodiment of the above formulae (I), (I'), (Ia), (Ib), (Ic) and (Id), Z is typically selected from H, cyclopropyl and the following structures:
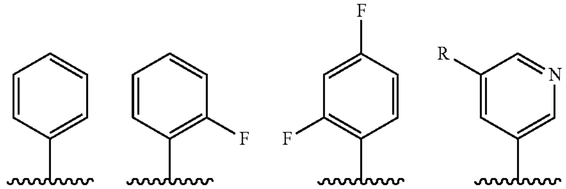

-continued

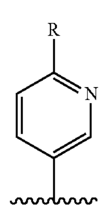

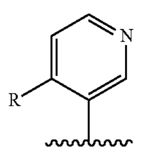

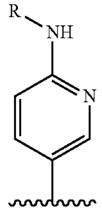

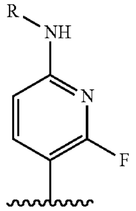

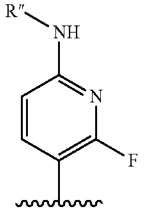

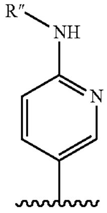

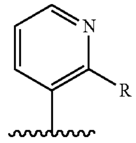

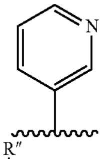

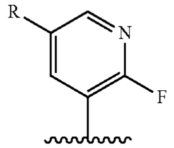

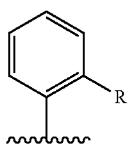

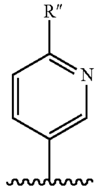

in which R and R" are as defined above for formula (I). Typically R is $C_1$-$C_3$ alkyl and R" is cyclopropyl.

The above definitions of Z are typically also taken by W in formula (I').

In formulae (Ie), (Ie'), (Ia), (Ib), (Ic) and (Id), each of $R^2$ to $R^7$ is typically H, $C_1$-$C_6$ alkyl, $C_1$-$C_6$ hydroxyalkyl, $C_3$-$C_6$ cycloalkyl, —$CH_2OR$, —$CH_2NR^{12}R^{13}$, —NRCOOR, —$CH_2SO_mR$, or halo, in which R and m are as defined above and $R^{12}$ and $R^{13}$ are each independently H, $C_1$-$C_6$ alkyl, benzyl, 4- to 10-membered heterocyclyl or $R^{12}$ and $R^{13}$ form, together with the N atom to which they are attached, a 4- to 10-membered heteroaryl which is unsubstituted or a 4- to 10-membered heterocyclyl which is unsubstituted or substituted with $C_1$-$C_6$ alkyl or halo, or any two of $R^2$ to $R^7$ that bond to the same carbon atom form a spiro ring selected from a $C_3$-$C_6$ cycloalkyl spiro ring and a spiro oxetane ring of the following structure:

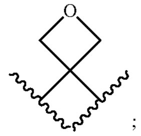

;

and the rest of $R^2$ to $R^7$ are H.

In one embodiment of formulae (I), (I'), (Ia), (Ib), (Ic) and (Id), each of $R^2$ to $R^7$ is typically H, $C_1$-$C_6$ alkyl, $C_3$-$C_6$ cycloalkyl or halo, or any two of $R^2$ to $R^7$ that bond to the same carbon atom form a spiro ring selected from a $C_3$-$C_6$ cycloalkyl spiro ring and a spiro oxetane ring of the following structure:

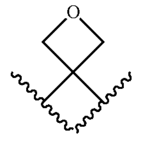

and the rest of $R^2$ to $R^7$ are H.

For instance, in formulae (Ie), (Ie'), (Ia), (Ib), (Ic) and (Id) $R^2$ to $R^7$ may take the following values:

each of $R^2$ to $R^7$ is H; or one or two of $R^2$ to $R^7$ are independently $C_1$-$C_3$ alkyl and the rest of $R^2$ to $R^7$ are H; or any two of $R^2$ to $R^7$ that bond to the same carbon atom form a spiro ring selected from a $C_3$-$C_6$ cycloalkyl spiro ring and a spiro oxetane ring of the structure:

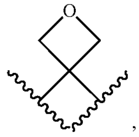

, and the rest of $R^2$ to $R^7$ are H.

For instance, in formulae (Ie), (Ie'), (Ia), (Ib), (Ic) and (Id), $R^2$ to $R^7$ may take the following values:

each of $R^2$ to $R^7$ is H; or one of $R^4$ and $R^7$ is $C_1$-$C_3$ alkyl and the rest of $R^2$ to $R^7$ are H; or $R^4$ and $R^5$ are both $C_1$-$C_3$ alkyl, or $R^4$ and $R^5$ together form a spiro ring which is a cyclopropyl spiro ring or a spiro oxetane ring of the structure defined above, and the rest of $R^2$ to $R^7$ are H; or $R^6$ and $R^7$ together form a spiro ring which is cyclopropyl spiro ring, and the rest of $R^2$ to $R^7$ are H.

For instance, in formulae (Ie), (Ie'), (Ia), (Ib), (Ic) and (Id), $R^2$ to $R^7$ may take the following values:

each of $R^2$ to $R^7$ is H; or one of $R^2$ to $R^7$ is $C_1$-$C_3$ alkyl, $C_1$-$C_3$ hydroxyalkyl, —NRCOOR such as tert-butyl(methyl)carbamate, or —$CH_2NR^{12}R^{13}$ wherein $R^{12}$ and $R^{13}$ are each independently H, $C_1$-$C_6$ alkyl, benzyl, 4- to 10-membered heterocyclyl or $R^{12}$ and $R^{13}$ form, together with the N atom to which they are attached, a 4- to 10-membered heteroaryl, for instance pyrazole, which is unsubstituted or a 4- to 10-membered heterocyclyl, for instance morpholine or diazinane, which is unsubstituted or substituted with $C_1$-$C_6$ alkyl or halo, and the rest of $R^2$ to $R^7$ are H; or any two of $R^2$ to $R^7$ that bond to the same carbon atom form a spiro ring selected from a $C_3$-$C_6$ cycloalkyl spiro ring and a spiro oxetane ring of the structure:

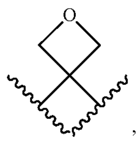

, and the rest of $R^2$ to $R^7$ are H.

In one embodiment, for instance, in formulae (I), (I'), (Ia), (Ib), (Ic) and (Id) $R^2$ to $R^7$ may take the following values:

each of $R^2$ to $R^7$ is H; or one or two of $R^2$ to $R^7$ are independently $C_1$-$C_3$ alkyl and the rest of $R^2$ to $R^7$ are H; or any two of $R^2$ to $R^7$ that bond to the same carbon atom form a spiro ring selected from a $C_3$-$C_6$ cycloalkyl spiro ring and a spiro oxetane ring of the structure:

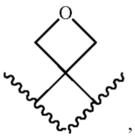

, and the rest of $R^2$ to $R^7$ are H.

For instance, in formulae (I), (I'), (Ia), (Ib), (Ic) and (Id), $R^2$ to $R^7$ may take the following values:

each of $R^2$ to $R^7$ is H; or one of $R^4$ and $R^7$ is $C_1$-$C_3$ alkyl and the rest of $R^2$ to $R^7$ are H; or $R^4$ and $R^5$ are both $C_1$-$C_3$ alkyl, or $R^4$ and $R^5$ together form a spiro ring which is a cyclopropyl spiro ring or a spiro oxetane ring of the structure defined above, and the rest of $R^2$ to $R^7$ are H; or $R^6$ and $R^7$ together form a spiro ring which is cyclopropyl spiro ring, and the rest of $R^2$ to $R^7$ are H.

The bond linking each of $R^2$ to $R^7$ to the adjacent C atom may be oriented above or below the plane of the five- or six-membered saturated ring, i.e. depicted as  or 

For instance, in any of formulae (Ie), (Ie'), (I), (I'), (Ia), (Ib), (Ic) and (Id) as defined above, with any of the values of $R^2$ to $R^7$ set out above, $R^4$ may be $R^4$ or $R^4$. Similarly and independently, $R^7$ may be  $R^7$ or $R^7$. In such embodiments, $R^4$ and $R^7$ are typically $C_1$-$C_3$ alkyl.

In formulae (Ie), (Ie'), (I), (I') and (Ic) having any of the foregoing values of $R^2$ to $R^7$, and any orientations of $R^2$ to $R^7$, Y is typically O, S or $SO_2$. More typically Y is O or $SO_2$. Most typically Y is O.

Specific compounds of the invention include the following:

2-(2,4-Difluorophenyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

2-(2,4-Difluorophenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-[6-(Ethylamino)-2-fluoropyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

N-[(3S)-9-Fluoro-2-oxo-5-phenyl-1,3-dihydro-1,4-benzodiazepin-3-yl]-2-[2-fluoro-6-(propan-2-ylamino)pyridin-3-yl]-6,7-dihydro-5H-pyrazolo[5,1-b][1,3]oxazine-3-carboxamide;

N-[(3S)-9-fluoro-2-oxo-5-phenyl-2,3-dihydro-1H-1,4-benzodiazepin-3-yl]-2-(2-fluorophenyl)-5,5-dimethyl-5H,6H,7H-pyrazolo[3,2-b][1,3]oxazine-3 carboxamide;

N-[(3S)-9-Fluoro-2-oxo-5-phenyl-1,3-dihydro-1,4-benzodiazepin-3-yl]-2-(2-methylphenyl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)spiro[6,7-dihydropyrazolo[5,1-b][1,3]oxazine-5,1'-cyclopropane]-3-carboxamide;

N-[(3S)-9-fluoro-2-oxo-5-phenyl-2,3-dihydro-1H-1,4-benzodiazepin-3-yl]-2-(2-fluorophenyl)-5-(propan-2-yl)-5H,6H,7H-pyrazolo[3,2-b][1,3]oxazine-3-carboxamide;

(6S)—N-[(3S)-9-fluoro-2-oxo-5-phenyl-1,3-dihydro-1,4-benzodiazepin-3-yl]-2-(2-fluorophenyl)-6-methyl-6,7-dihydro-5H-pyrazolo[5,1-b][1,3]oxazine-3-carboxamide;

(6R)—N-[(3S)-9-fluoro-2-oxo-5-phenyl-1,3-dihydro-1,4-benzodiazepin-3-yl]-2-(2-fluorophenyl)-6-methyl-6,7-dihydro-5H-pyrazolo[5,1-b][1,3]oxazine-3-carboxamide;

6-Ethyl-N-[(3S)-9-fluoro-2-oxo-5-phenyl-2,3-dihydro-1H-1,4-benzodiazepin-3-yl]-2-(2-fluorophenyl)-5H,6H,7H-pyrazolo[3,2-b][1,3]oxazine-3-carboxamide;

N-[(3S)-9-Fluoro-2-oxo-5-phenyl-2,3-dihydro-1H-1,4-benzodiazepin-3-yl]-2-(2-fluorophenyl)-6-(propan-2-yl)-5H,6H,7H-pyrazolo[3,2-b][1,3]oxazine-3-carboxamide;

6-Cyclopropyl-N-[(3S)-9-fluoro-2-oxo-5-phenyl-2,3-dihydro-1H-1,4-benzodiazepin-3-yl]-2-(2-fluorophenyl)-5H,6H,7H-pyrazolo[3,2-b][1,3]oxazine-3-carboxamide;

N-[(3S)-9-fluoro-2-oxo-5-phenyl-2,3-dihydro-1H-1,4-benzodiazepin-3-yl]-2-(2-fluorophenyl)-6-propyl-5H,6H,7H-pyrazolo[3,2-b][1,3]oxazine-3-carboxamide;

2-[6-(Cyclopropylamino)pyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

N-[(3S)-2-Oxo-5-phenyl-1,3-dihydro-1,4-benzodiazepin-3-yl]-2-pyridin-3-yl-6,7-dihydro-5H-pyrazolo[5,1-b][1,3]oxazine-3-carboxamide N-[(3S)-9-Fluoro-2-oxo-5-phenyl-1,3-dihydro-1,4-benzodiazepin-3-yl]-2-pyridin-3-yl-6,7-dihydro-5H-pyrazolo[5,1-b][1,3]oxazine-3-carboxamide;

2-(6-Cyclopropylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-[6-(propan-2-ylamino)pyridin-3-yl]-6,7-dihydro-5H-pyrazolo[5,1-b][1,3]oxazine-3-carboxamide;

2-[6-(Ethylamino)pyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

N-[(3S)-2-oxo-5-phenyl-1,3-dihydro-1,4-benzodiazepin-3-yl]-2-phenyl-6,7-dihydro-5H-pyrazolo[5,1-b][1,3]oxazine-3-carboxamide;

N-[(3 S)-9-fluoro-2-oxo-5-phenyl-1,3-dihydro-1,4-benzodiazepin-3-yl]-2-phenyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-(2-fluorophenyl)-5-methyl-6,7-dihydro-5H-pyrazolo[5,1-b][1,3]oxazine-3-carboxamide;

N-[(3S)-2-oxo-5-phenyl-1,3-dihydro-1,4-benzodiazepin-3-yl]-2-phenylspiro[5,7-dihydropyrazolo[5,1-b][1,3]oxazine-6,3'-oxetane]-3-carboxamide;

2-(2-Fluorophenyl)-N-[(3S)-2-oxo-5-phenyl-1,3-dihydro-1,4-benzodiazepin-3-yl]spiro[5,7-dihydropyrazolo[5,1-b][1,3]oxazine-6,3'-oxetane]-3-carboxamide;

(5R)—N-[(3S)-9-fluoro-2-oxo-5-phenyl-1,3-dihydro-1,4-benzodiazepin-3-yl]-2-[2-fluoro-6-(propan-2-ylamino)pyridin-3-yl]-5-methyl-6,7-dihydro-5H-pyrazolo[5,1-b][1,3]oxazine-3-carboxamide;

(5S)—N-[(3S)-9-fluoro-2-oxo-5-phenyl-1,3-dihydro-1,4-benzodiazepin-3-yl]-2-[2-fluoro-6-(propan-2-ylamino)pyridin-3-yl]-5-methyl-6,7-dihydro-5H-pyrazolo[5,1-b][1,3]oxazine-3-carboxamide;

2-(2,4-Difluorophenyl)-N-[(3S)-9-fluoro-2-oxo-5-phenyl-2,3-dihydro-1H-1,4-benzodiazepin-3-yl]-4,4-dioxo-5H,6H,7H-4λ6-pyrazolo[3,2-b][1,3]thiazine-3-carboxamide;

2-(2-Fluorophenyl)-N-[(3S)-9-fluoro-2-oxo-5-phenyl-2,3-dihydro-1H-1,4-benzodiazepin-3-yl]-4,4-dioxo-5H,6H,7H-4λ6-pyrazolo[3,2-b][1,3]thiazine-3-carboxamide;

2-(2,4-Difluorophenyl)-N-[(3S)-9-fluoro-2-oxo-5-phenyl-2,3-dihydro-1H-1,4-benzodiazepin-3-yl]-5H,6H,7H-pyrazolo[3,2-b][1,3]thiazine-3-carboxamide;

N-[(3S)-9-Fluoro-2-oxo-5-phenyl-2,3-dihydro-1H-1,4-benzodiazepin-3-yl]-2-(2-fluorophenyl)-5H,6H,7H-pyrazolo[3,2-b][1,3]thiazine-3-carboxamide;

3-(2-Fluorophenyl)-N-[(3S)-2-oxo-5-phenyl-1,3-dihydro-1,4-benzodiazepin-3-yl]-6,7-dihydro-5H-pyrazolo[5,1-b][1,3]oxazine-2-carboxamide;

7-(2-Fluorophenyl)-N-[(3S)-2-oxo-5-phenyl-1,3-dihydro-1,4-benzodiazepin-3-yl]-2,3-dihydropyrazolo[5,1-b][1,3]oxazole-6-carboxamide;

3-[6-(Cyclopropylamino)-2-fluoropyridin-3-yl]-N-[(3S)-2-oxo-5-phenyl-1,3-dihydro-1,4-benzodiazepin-3-yl]-6,7-dihydro-5H-pyrazolo[5,1-b][1,3]oxazine-2-carboxamide;

2-[6-(Cyclopropylamino)-2-fluoropyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(2-Fluorophenyl)-6,6-dimethyl-N-[(3S)-2-oxo-5-phenyl-1,3-dihydro-1,4-benzodiazepin-3-yl]-5,7-dihydropyrazolo[5,1-b][1,3]oxazine-3-carboxamide;

N-[(3 S)-9-fluoro-2-oxo-5-phenyl-1,3-dihydro-1,4-benzodiazepin-3-yl]-2-(2-fluorophenyl)-6,6-dimethyl-5,7-dihydropyrazolo[5,1-b][1,3]oxazine-3-carboxamide;

(5R)-2-(5-Chloropyridin-3-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(5-Chloropyridin-3-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2-Fluorophenyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5S)-2-(2-Fluorophenyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5S)—N-[(3S)-9-fluoro-2-oxo-5-phenyl-1,3-dihydro-1,4-benzodiazepin-3-yl]-2-(2-fluorophenyl)-5-methyl-6,7-dihydro-5H-pyrazolo[5,1-b][1,3]oxazine-3-carboxamide;

2-(2-Fluoro-5-methylpyridin-3-yl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

2-(2-Fluoro-5-methylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-[6-(Cyclopropylamino)-2-fluoropyridin-3-yl]-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

2-Cyclopropyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2-Methoxypyridin-4-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2-methoxypyridin-4-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-[6-(2-Hydroxypropyl)pyridin-3-yl]-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(3-fluoropyridin-4-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-[6-(ethylamino)-3-pyridyl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-(5-cyclopropyl-2-fluoro-3-pyridyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-(4-ethyl-2-fluoro-phenyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-5-methyl-2-(6-morpholino-3-pyridyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-(6-morpholino-3-pyridyl)-6,7-dihydro-5H-pyrazolo[5,1-b][1,3]oxazine-3-carboxamide;

(5R)-2-(2,6-dimethyl-3-pyridyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2,6-dimethyl-3-pyridyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-(2-ethylpyrimidin-5-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2-ethylpyrimidin-5-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-(3-furyl)-5-methyl-6,7-dihydro-5H-pyrazolo[5,1-b][1,3]oxazine-3-carboxamide;

(5R)-2-(3-furyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-(3-thienyl)-6,7-dihydro-5H-pyrazolo[5,1-b][1,3]oxazine-3-carboxamide;

(5R)-5-methyl-N-[(3S)-2-oxo-5-phenyl-1,3-dihydro-1,4-benzodiazepin-3-yl]-2-(3-thienyl)-6,7-dihydro-5H-pyrazolo[5,1-b][1,3]oxazine-3-carboxamide;

(5R)-2-(6-ethyl-2-methyl-3-pyridyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(6-ethyl-2-methyl-3-pyridyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[6-(isopropylamino)-3-pyridyl]-5-methyl-6,7-dihydro-5H-pyrazolo[5,1-b][1,3]oxazine-3-carboxamide;

(5R)-2-(1-Ethylpyrazol-3-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5S)-5-methyl-2-[6-(propan-2-ylamino)pyridin-3-yl]-N-(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-5-Methyl-2-(6-propan-2-ylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-5-Methyl-N-[(3S)-9-fluoro-2-oxo-5-phenyl-1,3-dihydro-1,4-benzodiazepin-3-yl]-2-[6-(trideuteriomethylamino)pyridin-3-yl]-6,7-dihydro-5H-pyrazolo[5,1-b][1,3]oxazine-3-carboxamide;

(5R)-2-(2-Fluoro-6-methylpyridin-3-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2-Fluoro-6-methylpyridin-3-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(6-Ethylpyridin-3-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(4-Ethyl-2-fluorophenyl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5S)—N-[(3S)-9-fluoro-2-oxo-5-phenyl-1,3-dihydro-1,4-benzodiazepin-3-yl]-2-(3-fluoropyridin-4-yl)-5-methyl-6,7-dihydro-5H-pyrazolo[5,1-b][1,3]oxazine-3-carboxamide;

(5R)-5-Methyl-2-(6-methylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-[6-(2-Hydroxypropyl)pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(5-Fluoro-2-methylpyridin-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(3-fluoropyridin-4-yl)-6,7-dihydro-5H-pyrazolo[5,1-b][1,3]oxazine-3-carboxamide;

(5R)-5-methyl-2-phenyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2,4-difluorophenyl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-5-methyl-2-(1-methylindazol-5-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(1-Ethylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-[6-(2-Hydroxy-2-methylpropyl)pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-5-Methyl-N-[(3S)-9-fluoro-2-oxo-5-phenyl-1,3-dihydro-1,4-benzodiazepin-3-yl]-2-[6-[(1R,4R)-2-oxa-5-azabicyclo[2.2.1]heptan-5-yl]pyridin-3-yl]-6,7-dihydro-5H-pyrazolo[5,1-b][1,3]oxazine-3-carboxamide;

(5S)-5-methyl-N-[(3R)-9-fluoro-2-oxo-5-phenyl-1,3-dihydro-1,4-benzodiazepin-3-yl]-2-[6-[(1S,4S)-2-oxa-5-azabicyclo[2.2.1]heptan-5-yl]pyridin-3-yl]-6,7-dihydro-5H-pyrazolo[5,1-b][1,3]oxazine-3-carboxamide;

(5R)-2-[2-Fluoro-6-[(1S,4S)-2-oxa-5-azabicyclo[2.2.1]heptan-5-yl]-3-pyridyl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-[6-Fluoro-2-[(1S,4S)-2-oxa-5-azabicyclo[2.2.1]heptan-5-yl]pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-[2-Fluoro-6-[(1R,4R)-2-oxa-5-azabicyclo[2.2.1]heptan-5-yl]pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-[2-Fluoro-6-(2-oxa-6-azaspiro[3.3]heptan-6-yl)pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-5-Methyl-2-[4-methyl-6-(propan-2-ylamino)pyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-5-Methyl-2-[2-methyl-6-(propan-2-ylamino)pyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5S)-5-Methyl-N-[(3S)-9-fluoro-2-oxo-5-phenyl-1,3-dihydro-1,4-benzodiazepin-3-yl]-2-[6-[(1R,4R)-2-oxa-5-azabicyclo[2.2.1]heptan-5-yl]pyridin-3-yl]-6,7-dihydro-5H-pyrazolo[5,1-b][1,3]oxazine-3-carboxamide;

(5R)-2-Anilino-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-Anilino-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(4-Fluoroanilino)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-(1-methylpyrazol-4-yl)-6,7-dihydro-5H-pyrazolo[5,1-b][1,3]oxazine-3-carboxamide;

2-(1-Ethylpyrazol-4-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-[4-[(Dimethylamino)methyl]-2-fluorophenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-[2-Fluoro-4-(morpholin-4-ylmethyl)phenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-[4-(Diethylaminomethyl)-2-fluorophenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

N-[(3S)-2-oxo-5-phenyl-1,3-dihydro-1,4-benzodiazepin-3-yl]-2-(1-propan-2-ylpyrazol-4-yl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-[1-[(3-methyloxetan-3-yl)methyl]pyrazol-4-yl]-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-7-methyl-6,7-dihydro-5H-pyrazolo[5,1-b][1,3]oxazine-3-carboxamide;

2-(6-Ethylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide-carboxamide;

tert-butyl N-[3-[[(3S)-9-fluoro-2-oxo-5-phenyl-1,3-dihydro-1,4-benzodiazepin-3-yl]carbamoyl]-2-(2-fluorophenyl)-6,7-dihydro-5H-pyrazolo[5,1-b][1,3]oxazin-6-yl]-N-methylcarbamate;

tert-butyl N-ethyl-N-[3-[[(3S)-9-fluoro-2-oxo-5-phenyl-1,3-dihydro-1,4-benzodiazepin-3-yl]carbamoyl]-2-(2-fluorophenyl)-6,7-dihydro-5H-pyrazolo[5,1-b][1,3]oxazin-6-yl]carbamate;

(5S)-2-benzyl-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6-(hydroxymethyl)-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-[1-(oxan-4-yl)pyrazol-4-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-(1-propan-2-ylpyrazol-4-yl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6-(methoxymethyl)-6,7-dihydro-5H-pyrazolo[5,1-b][1,3]oxazine-3-carboxamide;

(5R)-2-cyclohexyl-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-(1,3-dimethylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-[1-(oxetan-3-yl)pyrazol-4-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[1-(2-hydroxyethyl)pyrazol-4-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-[1-(2,2,2-trifluoroethyl)pyrazol-4-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[1-(2-methoxyethyl)pyrazol-4-yl]-5-methyl-6,7-dihydro-5H-pyrazolo[5,1-b][1,3]oxazine-3-carboxamide;

(5R)-2-[1-(Difluoromethyl)pyrazol-4-yl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-(1,5-Dimethylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[1-(2-hydroxy-2-methylpropyl)pyrazol-4-yl]-5-methyl-6,7-dihydro-5H-pyrazolo[5,1-b][1,3]oxazine-3-carboxamide;

N-[(3S)-9-Fluoro-2-oxo-5-phenyl-1,3-dihydro-1,4-benzodiazepin-3-yl]-2-(2-fluorophenyl)-5-(hydroxymethyl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6-(pyrazol-1-ylmethyl)-6,7-dihydro-5H-pyrazolo[5,1-b][1,3]oxazine-3-carboxamide;

(5R)-2-(1-cyclopropylpyrazol-4-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(1-cyclopropylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5S)-2-(6-ethylpyridin-3-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

2-(2,4-Difluorophenyl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide;

2-(2,6-Difluorophenyl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide;

2-(1-Ethylpyrazol-4-yl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide;

2-(2,4-Difluorophenyl)-6-(hydroxymethyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5S)-2-(6-ethylpyridin-3-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

2-(6-Ethylpyridin-3-yl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide;

2-[2-Fluoro-4-(hydroxymethyl)phenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(2-Fluoro-4-methylsulfonylphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(2-Fluoropyridin-3-yl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2-Fluoro-4-methylsulfonylphenyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

2-(4-Cyano-2-fluorophenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(2-Fluoro-6-methoxyphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(2-Fluoro-6-methylphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2-Fluoro-4-methylsulfonylphenyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

2-(4-Carbamoyl-2-fluorophenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-[2-Fluoro-4-(methylsulfonimidoyl)phenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[6-(3-methoxyazetidin-1-yl)pyridin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[6-[(3R)-3-methoxypyrrolidin-1-yl]pyridin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[6-[(3S)-3-methoxypyrrolidin-1-yl]pyridin-3-yl]-5-methyl-6,7-dihydro-5H-pyrazolo[5,1-b][1,3]oxazine-3-carboxamide;

N-[(3 S)-9-fluoro-2-oxo-5-phenyl-1,3-dihydro-1,4-benzodiazepin-3-yl]-2-(1-methylindazol-4-yl)-6,7-dihydro-5H-pyrazolo[5,1-b][1,3]oxazine-3-carboxamide;

N-[(3 S)-9-fluoro-2-oxo-5-phenyl-1,3-dihydro-1,4-benzodiazepin-3-yl]-2-(1-propan-2-ylpyrazol-4-yl)-6,7-dihydro-5H-pyrazolo[5,1-b][1,3]oxazine-3-carboxamide;

2-(1-Methylindazol-4-yl)-N-[(3S)-2-oxo-5-phenyl-1,3-dihydro-1,4-benzodiazepin-3-yl]-6,7-dihydro-5H-pyrazolo [5,1-b][1,3]oxazine-3-carboxamide;

N-[(3S)-9-fluoro-2-oxo-5-phenyl-1,3-dihydro-1,4-benzodiazepin-3-yl]-2-[1-(2,2,2-trifluoroethyl)pyrazol-4-yl]-6,7-dihydro-5H-pyrazolo[5,1-b][1,3]oxazine-3-carboxamide;

N-[(3S)-2-oxo-5-phenyl-1,3-dihydro-1,4-benzodiazepin-3-yl]-2-[1-(2,2,2-trifluoroethyl)pyrazol-4-yl]-6,7-dihydro-5H-pyrazolo[5,1-b][1,3]oxazine-3-carboxamide;

N-[(3S)-9-Fluoro-2-oxo-5-phenyl-1,3-dihydro-1,4-benzodiazepin-3-yl]-2-[1-(oxan-4-yl)pyrazol-4-yl]-6,7-dihydro-5H-pyrazolo[5,1-b][1,3]oxazine-3-carboxamide;

(5R)-2-[2-Fluoro-4-(hydroxymethyl)phenyl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-[2-Fluoro-4-(hydroxymethyl)phenyl]-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[6-(hydroxymethyl)pyridin-3-yl]-5-methyl-6,7-dihydro-5H-pyrazolo[5,1-b][1,3]oxazine-3-carboxamide;

(5S)—N-[(3S)-9-fluoro-2-oxo-5-phenyl-1,3-dihydro-1,4-benzodiazepin-3-yl]-5-methyl-2-[1-(oxan-4-yl)pyrazol-4-yl]-6,7-dihydro-5H-pyrazolo[5,1-b][1,3]oxazine-3-carboxamide;

(5S)—N-[(3S)-9-fluoro-2-oxo-5-phenyl-1,3-dihydro-1,4-benzodiazepin-3-yl]-5-methyl-2-[1-(2,2,2-trifluoroethyl) pyrazol-4-yl]-6,7-dihydro-5H-pyrazolo[5,1-b][1,3]oxazine-3-carboxamide;

(5S)-2-(1-Ethylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-(1H-pyrazol-4-yl)-6,7-dihydro-5H-pyrazolo[5,1-b][1,3]oxazine-3-carboxamide;

2-(2-Fluorophenyl)-6-hydroxy-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-(1-methylsulfonylpiperidin-4-yl)-6,7-dihydro-5H-pyrazolo[5,1-b][1,3]oxazine-3-carboxamide;

(5R)-5-Methyl-2-(1-methylsulfonylpiperidin-4-yl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(2S)—N-[(3S)-9-fluoro-2-oxo-5-phenyl-1,3-dihydro-1,4-benzodiazepin-3-yl]-6-(2-fluorophenyl)-2-methyl-2,3-dihydropyrazolo[5,1-b][1,3]oxazole-7-carboxamide;

6-(Diethylaminomethyl)-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

(5R)-2-[1-[2-(dimethylamino)ethyl]pyrazol-4-yl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

5-[(Dimethylamino)methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-5-(morpholin-4-ylmethyl)-6,7-dihydro-5H-pyrazolo[5,1-b][1,3]oxazine-3-carboxamide;

N-[(3 S)-9-fluoro-2-oxo-5-phenyl-1,3-dihydro-1,4-benzodiazepin-3-yl]-2-(2-fluorophenyl)-6-[[methyl(oxan-4-yl) amino]methyl]-6,7-dihydro-5H-pyrazolo[5,1-b][1,3]oxazine-3-carboxamide;

N-[(3 S)-9-fluoro-2-oxo-5-phenyl-1,3-dihydro-1,4-benzodiazepin-3-yl]-2-(2-fluorophenyl)-6-[[methyl(oxetan-3-yl) amino]methyl]-6,7-dihydro-5H-pyrazolo[5,1-b][1,3]oxazine-3-carboxamide;

(5R)-2-[4-[(dimethylamino)methyl]-2-fluorophenyl]-N-[(3S)-9-fluoro-2-oxo-5-phenyl-1,3-dihydro-1,4-benzodiazepin-3-yl]-5-methyl-6,7-dihydro-5H-pyrazolo[5,1-b] [1,3]oxazine-3-carboxamide;

6-[(Dimethylamino)methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6-[(4-methylpiperazin-1-yl)methyl]-6,7-dihydro-5H-pyrazolo[5,1-b][1,3]oxazine-3-carboxamide;

N-[(3 S)-9-fluoro-2-oxo-5-phenyl-1,3-dihydro-1,4-benzodiazepin-3-yl]-2-(2-fluorophenyl)-6-(morpholin-4-ylmethyl)-6,7-dihydro-5H-pyrazolo[5,1-b][1,3]oxazine-3-carboxamide;

6-[[Benzyl(ethyl)amino]methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

2-(2-Fluorophenyl)-6-methoxy-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(6-Ethylpyridin-3-yl)-N-[(3S)-2-oxo-5-phenyl-1,3-dihydro-1,4-benzodiazepin-3-yl]spiro[5,7-dihydropyrazolo [5,1-b][1,3]oxazine-6,1'-cyclobutane]-3-carboxamide;

2-(6-Ethylpyridin-3-yl)-N-[(3S)-9-fluoro-2-oxo-5-phenyl-1,3-dihydro-1,4-benzodiazepin-3-yl]spiro[5,7-dihydropyrazolo[5,1-b][1,3]oxazine-6,1'-cyclobutane]-3-carboxamide;

2-[6-(Propan-2-ylamino)pyridin-3-yl]-N-[(3S)-2-oxo-5-phenyl-1,3-dihydro-1,4-benzodiazepin-3-yl]spiro[5,7-dihydropyrazolo[5,1-b][1,3]oxazine-6,1'-cyclopropane]-3-carboxamide;

2-[6-(Propan-2-ylamino)pyridin-3-yl]-N-[(3S)-9-fluoro-2-oxo-5-phenyl-1,3-dihydro-1,4-benzodiazepin-3-yl]spiro[5,7-dihydropyrazolo[5,1-b][1,3]oxazine-6,1'-cyclopropane]-3-carboxamide;

2-(6-Ethylpyridin-3-yl)-N-[(3S)-2-oxo-5-phenyl-1,3-dihydro-1,4-benzodiazepin-3-yl]spiro[5,7-dihydropyrazolo[5,1-b][1,3]oxazine-6,1'-cyclopropane]-3-carboxamide;

2-(6-Ethylpyridin-3-yl)-N-[(3S)-9-fluoro-2-oxo-5-phenyl-1,3-dihydro-1,4-benzodiazepin-3-yl]spiro[5,7-dihydropyrazolo[5,1-b][1,3]oxazine-6,1'-cyclopropane]-3-carboxamide;

N-[(3S)-9-fluoro-2-oxo-5-phenyl-1,3-dihydro-1,4-benzodiazepin-3-yl]-2-(2-fluorophenyl)-6-(pyrrolidin-1-ylmethyl)-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[2-fluoro-4-[(propan-2-ylamino)methyl]phenyl]-5-methyl-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6-(methylsulfonylmethyl)-6,7-dihydro-5H-pyrazolo[5,1-b][1,3]oxazine-3-carboxamide;

2-(2-Fluorophenyl)-N-[(3S)-9-fluoro-2-oxo-5-phenyl-1,3-dihydro-1,4-benzodiazepin-3-yl]spiro[5,7-dihydropyrazolo[5,1-b][1,3]oxazine-6,1'-cyclobutane]-3-carboxamide;

6-[(3,3-Difluoropyrrolidin-1-yl)methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-5-(pyrrolidin-1-ylmethyl)-6,7-dihydro-5H-pyrazolo[5,1-b][1,3]oxazine-3-carboxamide;

(6R*)—N-[(3S)-9-fluoro-2-oxo-5-phenyl-1,3-dihydro-1,4-benzodiazepin-3-yl]-2-(2-fluorophenyl)-6-(hydroxymethyl)-6,7-dihydro-5H-pyrazolo[5,1-b][1,3]oxazine-3-carboxamide;

(6S*)—N-[(3S)-9-fluoro-2-oxo-5-phenyl-1,3-dihydro-1,4-benzodiazepin-3-yl]-2-(2-fluorophenyl)-6-(hydroxymethyl)-6,7-dihydro-5H-pyrazolo[5,1-b][1,3]oxazine-3-carboxamide;

(6R*)-2-(2,6-Difluorophenyl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide;

(6S*)-2-(2,6-Difluorophenyl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide;

(6R*)-6-[(Dimethylamino)methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

(6S*)-6-[(Dimethylamino)methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

(5R*)-2-(2,6-Difluorophenyl)-5-(hydroxymethyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5S*)-2-(2,6-Difluorophenyl)-5-(hydroxymethyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R*)-2-(2,6-Difluorophenyl)-N-[(3S)-9-fluoro-2-oxo-5-phenyl-1,3-dihydro-1,4-benzodiazepin-3-yl]-5-(hydroxymethyl)-6,7-dihydro-5H-pyrazolo[5,1-b][1,3]oxazine-3-carboxamide;

(5S*)-2-(2,6-Difluorophenyl)-N-[(3S)-9-fluoro-2-oxo-5-phenyl-1,3-dihydro-1,4-benzodiazepin-3-yl]-5-(hydroxymethyl)-6,7-dihydro-5H-pyrazolo[5,1-b][1,3]oxazine-3-carboxamide;

(5R*)—N-[(3S)-9-Fluoro-2-oxo-5-phenyl-1,3-dihydro-1,4-benzodiazepin-3-yl]-2-(2-fluorophenyl)-5-(hydroxymethyl)-6,7-dihydro-5H-pyrazolo[5,1-b][1,3]oxazine-3-carboxamide;

(5S*)-2-(2-Fluorophenyl)-5-(hydroxymethyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R*)—N-[(3S)-9-fluoro-2-oxo-5-phenyl-1,3-dihydro-1,4-benzodiazepin-3-yl]-2-(2-fluorophenyl)-5-(methoxymethyl)-6,7-dihydro-5H-pyrazolo[5,1-b][1,3]oxazine-3-carboxamide;

(5S*)—N-[(3S)-9-fluoro-2-oxo-5-phenyl-1,3-dihydro-1,4-benzodiazepin-3-yl]-2-(2-fluorophenyl)-5-(methoxymethyl)-6,7-dihydro-5H-pyrazolo[5,1-b][1,3]oxazine-3-carboxamide;

6-(Ethylaminomethyl)-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

2-(2-Fluoro-4-methylsulfanylphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(2-Fluoro-4-methylsulfinylphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-Bromo-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(2,6-Difluorophenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(4-Ethylsulfonyl-2-fluorophenyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-(2-Fluoro-5-methylsulfonylphenyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)—N-[(3S)-9-Fluoro-2-oxo-5-phenyl-1,3-dihydro-1,4-benzodiazepin-3-yl]-2-(2-fluoro-4-sulfamoylphenyl)-5-methyl-6,7-dihydro-5H-pyrazolo[5,1-b][1,3]oxazine-3-carboxamide;

(5R)-2-[4-(Dimethylsulfamoyl)-2-fluorophenyl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-(1-Ethylsulfonylpiperidin-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(2R)-6-(2-Fluorophenyl)-2-methyl-N-[(3S)-2-oxo-5-phenyl-1,3-dihydro-1,4-benzodiazepin-3-yl]-2,3-dihydropyrazolo[5,1-b][1,3]oxazole-7-carboxamide;

and the pharmaceutically acceptable salts thereof.

The compounds of the invention may contain asymmetric or chiral centres, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Compounds of formula (Ie) or formula (I) containing one or more chiral centre may be used in enantiomerically or diastereoisomerically pure form, or in the form of a mixture of isomers.

The present invention embraces all geometric and positional isomers of compounds of the invention as defined above. For example, if a compound of the invention incorporates a double bond or a fused ring, the cis- and trans-forms, as well as mixtures thereof, are embraced within the scope of the invention. Both the single positional isomers and mixture of positional isomers are also within the scope of the present invention.

The compounds of the present invention may exist in unsolvated as well as solvated forms with pharmaceutically acceptable solvents such as water, ethanol, and the like, and it is intended that the invention embrace both solvated and unsolvated forms. The compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol tautomerizations. Valence tautomers include interconversions by reorganization of some of the bonding electrons.

The present invention embraces all isotopologues of compounds of the invention as defined above. Thus, any atom present in a compound of the invention as defined above, or in any intermediate or starting compound, may be present in any available naturally-occurring isotopic form. For instance, a carbon atom may be $^{12}C$ or $^{13}C$. A hydrogen atom may be $^{1}H$ or $^{2}H$ (deuterium). A compound of the invention as defined above may thus be prepared in deuterated form, with one or more hydrogen atoms present as $^{2}H$. Any hydrogen atoms or combination thereof may be present as deuterium.

Compounds of the invention can be prepared by the synthetic methods described in the Examples that follow, or by analogy with such methods using appropriate starting materials and methodologies familiar to the skilled chemist. The preparation typically comprises, as a final step, an amide coupling reaction in which the central amide linkage in formula (Ie) or formula (I) as defined above is formed. Compounds of the invention may thus be prepared by the amide coupling reactions designated Procedure A, Procedure B, Procedure C, Procedure D, Procedure E, Procedure F and Procedure G in the Examples, or by analogy with any of Procedure A, Procedure B, Procedure C, Procedure D, Procedure E, Procedure F and Procedure G using appropriate synthetic intermediates. Such intermediates may be prepared by analogous methods to those described in the Preparatory Examples.

A benzodiazepine derivative of formula (Ie) or formula (I) can be converted into a pharmaceutically acceptable salt thereof, and a salt can be converted into the free compound, by conventional methods. For instance, a benzodiazepine derivative of formula (Ie) or formula (I) can be contacted with a pharmaceutically acceptable acid to form a pharmaceutically acceptable salt. A pharmaceutically acceptable salt is a salt with a pharmaceutically acceptable acid or base.

Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

Compounds of the present invention have been found in biological tests to be inhibitors of respiratory syncytial virus (RSV). They possess a combination of potent anti-RSV activity with good bioavailability and good physicochemical properties. This combination of properties makes the compounds therapeutically useful and superior as drug candidates to many compounds disclosed in the prior art references discussed earlier.

Accordingly, the present invention further provides a compound which is a benzodiazepine derivative of formula (Ie) or formula (I), as defined above, or a pharmaceutically acceptable salt thereof, for use in a method of treating the human or animal body by therapy.

The invention also provides a compound of the invention as defined above for use in a method treating or preventing an RSV infection. Still further, the present invention provides the use of a compound of the invention as defined above in the manufacture of a medicament for use in treating or preventing an RSV infection. A subject suffering from or susceptible to an RSV infection may thus be treated by a method comprising the administration thereto of a compound of the invention as defined above. The condition of the subject may thereby be improved or ameliorated.

The RSV infection is typically a respiratory tract infection. The RSV infection may be an infection in a child, for instance a child under ten years of age or an infant under two years of age. In one embodiment the invention provides a compound as defined above for use in treating or preventing an RSV infection in paediatric patients. Alternatively the infection may be an infection in a mature or elderly adult, for instance an adult over 60 years of age, an adult over 70 years of age, or an adult over 80 years of age. The invention further provides a compound for use in treating or preventing an RSV infection in geriatric patients.

The RSV infection may be an infection in an immunocompromised individual or an individual suffering from COPD or CIF. In another embodiment, the RSV infection is an infection in a non-compromised individual, for instance an individual who is otherwise healthy.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection, infusion, or by inhalation or nebulaisation. The compound is preferably given by oral administration.

The dosage depends on a variety of factors including the age, weight and condition of the patient and the route of administration. Daily dosages can vary within wide limits and will be adjusted to the individual requirements in each particular. Typically, however, the dosage adopted for each route of administration when a compound is administered alone to adult humans is 0.0001 to 650 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A unit dose form such as a tablet or a capsule will usually contain 1-250 mg of active ingredient. For example, a compound of formula (Ie) or formula (I) could be administered to a human patient at a dose of between 100-250 mg either once a day, twice or three times a day. For example, a compound of formula (Ie) or formula (I) could be administered to a human patient at a dose of between 100-250 mg either once a day, twice or three times a day.

The compounds of formula (Ie) or formula (I) and pharmaceutically acceptable salts thereof may be used on their own. Alternatively, they may be administered in the form of a pharmaceutical composition. The present invention therefore also provides a pharmaceutical composition comprising a compound of formula (Ie) or formula (I) or a pharmaceutically acceptable salt thereof as hereinbefore defined, in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The invention further provides a process for the preparation of a pharmaceutical composition of the invention which comprises mixing a compound of formula (Ie) or formula (I) or a pharmaceutically acceptable salt thereof as hereinbefore defined with a pharmaceutically acceptable adjuvant, diluent or carrier.

The compounds of the invention may be administered in a variety of dosage forms. Thus, they can be administered orally, for example as tablets, troches, lozenges, aqueous or oily suspensions, solutions, dispersible powders or granules. The compounds of the invention may also be administered parenterally, whether subcutaneously, intravenously, intramuscularly, intrasternally, transdermally, by infusion techniques or by inhalation or nebulisation. The compounds may also be administered as suppositories.

Solid oral forms of the pharmaceutical composition of the invention may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulfates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride. Further suitable carriers for suspensions include sterile water, hydroxypropylmethyl cellulose (HPMC), polysorbate 80, polyvinylpyrrolidone (PVP), aerosol AOT (i.e. sodium 1,2-bis(2-ethylhexoxycarbonyl)ethanesulphonate), pluronic F127 and/or captisol (i.e. sulfobutylether-beta-cyclodextrin). The compounds of the invention may, for example, be formulated as aqueous suspensions in a carrier selected from:

(i) 0.5% w/v hydroxypropylmethyl cellulose (HPMC)/0.1% w/v polysorbate 80;
(ii) 0.67% w/v polyvinylpyrrolidone (PVP)/0.33% w/v aerosol AOT (sodium 1,2-bis(2-ethylhexoxycarbonyl) ethanesulphonate);
(iii) 1% w/v pluronic F 127; and
(iv) 0.5% w/v polysorbate 80.

The carriers may be prepared by standard procedures known to those of skill in the art. For example, each of the carriers (i) to (iv) may be prepared by weighing the required amount of excipient into a suitable vessel, adding approximately 80% of the final volume of water and magnetically stirring until a solution is formed. The carrier is then made up to volume with water. The aqueous suspensions of compounds of formula (Ie) or formula I may be prepared by weighing the required amount of a compound of formula I into a suitable vessel, adding 100% of the required volume of carrier and magnetically stirring.

Solutions for injection or infusion may contain as carrier, for example, sterile water or preferably they may be in the form of sterile, aqueous, isotonic saline solutions.

The compounds of the invention may also be administered in conjunction with other compounds used for the treatment of viral infections. Thus, the invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment or prevention of a viral infection, particularly infection by RSV.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

Suitable therapeutic agents for use in the combination therapies include (i) RSV fusion inhibitors
(ii) other RSV nucleocapsid (N)-protein inhibitors;
(iii) other RSV protein inhibitors, such as those that inhibit the phosphoprotein (P) protein and large (L) protein;
(iv) nucleoside or polymerase inhibitors that inhibit the L protein;

(v) anti-RSV monoclonal antibodies, such as the F-protein antibodies;
(vi) immunomodulating toll-like receptor compounds;
(vii) other respiratory virus anti-virals, such as anti-influenza and anti-rhinovirus compounds; and/or
(viii) anti-inflammatory compounds.

The RSV nucleocapsid (N)-protein plays a pivotal role in viral transcription and replication, mediating the interaction between the genomic RNA and the virally encoded RNA-dependent RNA polymerase. The RSV P- and L-proteins are components of RSV's virally encoded RNA-dependent RNA polymerase.

According to a further aspect of the invention, there is provided a compound of the formula (Ie) or formula (I) or a pharmaceutically acceptable salt thereof as hereinbefore defined in combination with one or more of the therapeutic agents listed as (i) to (vi) above for use in the treatment of RSV.

The Examples that follow serve to illustrate the invention further. The Preparatory Examples relate to the preparation of starting materials and intermediates used to prepare the compounds of the Examples. Neither the Examples nor the Preparatory Examples limit the invention in any way.

EXAMPLES

Reagents were obtained from commercial sources and were used without further purification. Anhydrous solvents were purchased from commercial suppliers, used as supplied and stored under $N_2$. Reactions were performed with anhydrous solvents under an atmosphere of $N_2$ unless otherwise noted. All temperatures are in ° C. TLC was performed on aluminium backed silica gel plates with fluorescence indicator at 254 nM (median pore size 60 Å). Flash column chromatography was performed using a Biotage Isolera One system using KP-Sil or Ultra silica gel columns or an Isco CombiFlash Rf using FlashPure or RediSep Rf/RediSep Rf Gold silica gel columns. Reverse phase column chromatography was performed on an Isco CombiFlash Rf using Teledyne ISCO RediSep Rf C18 columns. Ion exchange chromatography was performed on Isolute SCX-2: silica-propylsulfonic acid solid phase extraction cartridge washing with appropriate solvents selected from water, MeCN and MeOH.

NMR spectra were recorded on a 400, 500, 600 or 700 MHz spectrometer at ambient probe temperature (nominal 298 K). Chemical shifts (δ) are given in ppm and calibrated by using the residual peak of the solvent as the internal standard ($CDCl_3$, δ=7.26 ppm; DMSO-$d_6$, δ=2.50 ppm). Coupling constants are given in Hertz (Hz). 0.5H corresponds to 1H of a diastereomeric peak in the $^1H$ NMR assignment. LRMS were recorded using an Advion Plate Express expression$^L$ compact mass spectrometer equipped with an APCI or ESI ion source, with switching between positive and negative ion mode.

LCMS analysis was performed using a Waters Acquity UPLC with either a CSH C18 or BEH C18 column (2.1×30 mm) at 40° C. at 0.77 mL/min with a linear 5-95% acetonitrile gradient appropriate for the lipophilicity of the compound over 1, 3, 4 or 10 minutes. The aqueous portion of the mobile phase was 0.1% formic acid (CSH C18 column) or 10 mM ammonium bicarbonate (BEH C18 column). LC-UV chromatograms were recorded using a Waters Acquity photodiode array detector between 210 and 400 nm. Mass spectra were recorded using a Waters Acquity QDa detector with ES switching between positive and negative ion mode.

Method A: 3 min Acidic
Method B: 3 min Basic
Method C: 10 min Acidic
Method D: 10 min Basic
Method E: 1 min Acidic
Method F: 4 min Acidic Preparative HPLC was performed at ambient column temperature by the following methods. HPLC Method 1: Gemini NX (30 mm×150 mm, 5 μm) at 42 mL/min and UV detection at 210 nm. HPLC Method 2: Luna Phenomenex C18 (150×30 mm, 5 μm) column at 42 mL/min and UV detection at 210 nm. HPLC Method 3: Waters X-Bridge BEH C18 (30 mm×100 mm, 5 μm) column at 40 mL/min and UV detection across all wavelengths with PDA. HPLC Method 4: XSelect CSH C18 column (30 mm×150 mm, 5 μm) at 42 mL/min and UV detection at 220 nm. Preparative chiral HPLC was performed by the following methods. Preparative chiral HPLC method 1: ChiralPAK IC (20×250 mm; 5 μm), ambient column temperature, flow rate 20 mL/min, UV detection at 220 nm. Preparative chiral HPLC method 2: Lux iC5 (21.2 mm×250 mm, 5 μm), ambient column temperature, flow rate 21 mL/min, UV detection at 210 nm. Analytical chiral HPLC was performed at ambient column temperature by the following method. Analytical Chiral HPLC Method 1A: ChiralPAK IC-3 column (2.1×150 mm, 3 μm) at 1.0 mL/min.

Preparative SFC was performed by the following methods. SFC Method 1: Torus Diol (19 mm×150 mm, 5 μm), column temperature 40° C., flow rate 68 mL/min 100 BarG pressure, detector wavelength 237 nm. SFC Method 2: Torus Diol (19 mm×150 mm, 5 μm), column temperature 40° C., flow rate 68 mL/min 150 BarG pressure, detector wavelength 210 nm. Preparative chiral SFC was performed by the following methods. Preparative chiral SFC method 1: Chiralpak IA (250×10 mm, 5 μm), column temperature 40° C., flow rate 15 mL/min, 120 BarG pressure, detector wavelength 210-400 nM. Preparative chiral SFC method 2: Lux C1 (21.2 mm×250 mm, 5 μm), column temperature 40° C., flow rate 50 mL/min, 100 BarG pressure, detector wavelength 210 nm. Preparative chiral SFC method 3: Lux C4 (21.2 mm×250 mm, 5 μm), column temperature 40° C., flow rate 50 mL/min, 125 BarG pressure, detector wavelength 210 nm. Analytical chiral SFC was performed by the following methods. Analytical chiral SFC method 1A: Chiralpak IG (4.6 mm×250 mm, 5 μm), column temperature 40° C., flow Rate 4 mL/min, detector wavelength 210-400 nm, 125 barG back pressure. Analytical chiral SFC method 2A: Lux C1 (4.6 mm×250 mm, 5 μm), column temperature 40° C., flow rate 4 mL/min, detector wavelength 210-400 nm, 125 barG back pressure. Analytical chiral SFC method 3A: Lux C4 (4.6 mm×250 mm, 5 μm), column temperature 40° C., flow rate 4 mL/min, detector wavelength 210-400 nm, 125 barG back pressure.

Preparatory intermediates 3-bromo-6-ethyl-2-methylpyridine, 5-bromo-6-methyl-N-propan-2-ylpyridin-2-amine, 1-(5-bromopyridin-2-yl)-2-methylpropan-2-ol and 5-bromo-4-methyl-N-propan-2-ylpyridin-2-amine were prepared according to the methods described in WO/2021/032992. Preparatory examples (3S)-3-amino-5-phenyl-1,3-dihydro-1,4-benzodiazepin-2-one and (3S)-3-amino-9-fluoro-5-phenyl-1,3-dihydro-1,4-benzodiazepin-2-one were prepared using methods described in WO/2004/026843, WO/2005/090319, and WO/2017/015449.

Examples with undefined stereocenters were prepared and tested as a mixture of diastereomers unless otherwise specified.

Abbreviations

| | |
|---|---|
| APCI | Atmospheric pressure chemical ionization |
| BSA | Benzene sulfonic acid |
| DIPEA | N,N-Diisopropylethylamine |
| DMF | N,N-Dimethylformamide |
| DMSO | Dimethyl sulfoxide |
| dppf | 1,1'-Bis(diphenylphosphino)ferrocene |
| ES | Electrospray ionisation |
| eq. | Equivalents |
| H | Hour(s) |
| LCMS | Liquid chromatography mass spectrometry |
| LRMS | Low resolution mass spectrometry |
| mCPBA | meta-Chloroperoxybenzoic acid |
| MSA | Methane sulfonic acid |
| MsCl | Methanesulfonyl chloride |
| MTBE | Methyl tert-butyl ether |
| MWI | Microwave irradiation |
| Pd-170 | XPhos Pd(crotyl)Cl |
| pTSA | p-Toluene sulfonic acid |
| Rt | room temperature |
| THF | Tetrahydrofuran |
| TsCl | p-toluenesulfonyl chloride |
| HATU | 1-[Bis(dimethylamino)methylene]-1H-1,2,3-triazolo[4,5-b]pyridinium 3-oxid hexafluorophosphate, N-[(dimethylamino)-1H-1,2,3-triazolo-[4,5-b]pyridin-1-ylmethylene]-N-methylmethanaminium hexafluorophosphate N-oxide |
| SFC | Supercritical fluid chromatography |
| XPhos | 2-Dicyclohexylphosphino-2',4',6' triisopropylbiphenyl |

PREPARATORY EXAMPLES

1A Ethyl 3,5-dibromo-1H-pyrazole-4-carboxylate

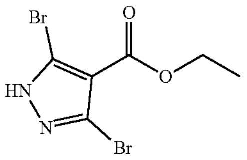

A solution of ethyl 1H-pyrazole-4-carboxylate (5.5 g, 39.3 mmol) in EtOH (60 mL) was cooled to 0° C., then sodium acetate (22.5 g, 271 mmol) in water (90 mL) was added, followed by bromine (8.25 mL, 161 mmol). The reaction mixture was stirred at rt over the weekend. Sat. aq. $Na_2S_2O_3$ (100 mL) and EtOAc (50 mL) were added the phases separated, and the aqueous phase extracted with EtOAc (2×50 mL). The combined organic phases were washed with brine (100 mL), dried ($Na_2SO_4$) and concentrated under reduced pressure. The crude product was purified by flash chromatography (0-40% MTBE in iso-hexanes) to afford a white solid (10.3 g, 84%). LCMS (method A) 297.3/299.4/301.4 $[M+H]^+$ at 1.10 min. $^1H$ NMR (500 MHz, DMSO-$d_6$) δ 14.53 (s, 1H), 4.25 (q, J=7.1 Hz, 2H), 1.29 (t, J=7.1 Hz, 3H).

2A [(3R)-3-Hydroxybutyl]methanesulfonate

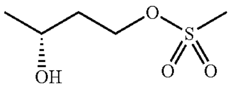

$NEt_3$ (1.1 mL, 7.89 mmol), followed by MsCl (0.3 mL, 3.88 mmol) were added to a solution of (3R)-butane-1,3-diol (1.00 g, 11.1 mmol) in $CH_2Cl_2$ (10 mL) at 0° C. and stirred for 10 min at 0° C. The reaction was allowed to attain rt and quenched with sat. aq. $NaHCO_3$ (10 mL) and $CH_2Cl_2$ (10 mL) and the phases separated. The aqueous phase was extracted with $CH_2Cl_2$ (2×10 mL), and the combined organic phases was washed with 50% brine (20 mL), dried ($MgSO_4$) and concentrated under reduced pressure. Purification by flash chromatography (0-50% EtOAc in iso-hexanes) afforded a colourless oil (310 mg, 16%). $^1H$ NMR (500 MHz, $CDCl_3$) δ 4.49-4.41 (m, 1H), 4.37-4.30 (m, 1H), 4.06-3.95 (m, 1H), 3.02 (s, 3H), 2.01-1.84 (m, 1H), 1.83-1.73 (m, 1H), 1.72 (d, J=4.8 Hz, 1H), 1.26 (d, J=6.3 Hz, 3H).

2B [(3S)-3-Hydroxybutyl]methanesulfonate

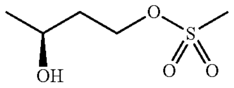

Prepared by an analogous procedure to that described for intermediate 2A. $^1H$ NMR (500 MHz, $CDCl_3$) δ 4.49-4.41 (m, 1H), 4.37-4.30 (m, 1H), 4.02-3.99 (m, 1H), 3.02 (s, 3H), 2.00-1.88 (m, 1H), 1.83-1.73 (m, 1H), 1.70 (d, J=4.9 Hz, 1H), 1.26 (d, J=6.2 Hz, 3H).

2C (3-Hydroxy-3-methylbutyl) methanesulfonate

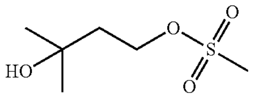

Prepared by an analogous procedure to that described for intermediate 2A. $^1H$ NMR (700 MHz, $CDCl_3$) δ 4.41 (t, J=6.9 Hz, 2H), 3.01 (s, 3H), 1.95 (t, J=6.9 Hz, 2H), 1.28 (d, J=0.5 Hz, 6H).

2D 2-(2,2-Dimethyl-1,3-dioxolan-4-yl)ethyl methanesulfonate

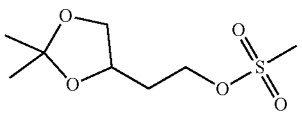

MsCl (1.53 mL, 19.750 mmol) was added dropwise to a cooled (0° C.) solution of 2-(2,2-dimethyl-1,3-dioxolan-4-yl)ethanol (2 mL, 14.11 mmol) and $NEt_3$ (5.11 mL, 36.68 mmol) in $CH_2Cl_2$ (40 mL), then allowed to warm to rt and stirred for 3 h. The reaction was quenched with 1 M aq. HCl, and the organic layer was washed with brine, passed through a phase separation cartridge and the solvent removed under reduced pressure to give a colourless oil (2.81 g, 80% yield). $^1H$ NMR (500 MHz, $CDCl_3$) δ 4.46-4.32 (m, 2H), 4.29-4.18 (m, 1H), 4.15-4.09 (m, 1H), 3.65-3.58 (m, 1H), 3.04 (s, 3H), 2.10-1.90 (m, 2H), 1.43 (s, 3H), 1.37 (s, 3H).

3A [3-(Hydroxymethyl)oxetan-3-yl]methyl 4-methylbenzenesulfonate

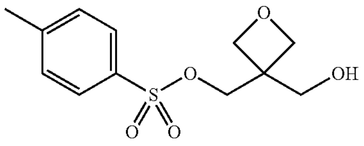 [SMILES: Cc1ccc(S(=O)(=O)OCC2(CO)COC2)cc1]

$NEt_3$ (3.1 mL, 22.2 mmol) and then TsCl (2.12 g, 11.1 mmol) were added to a cooled (0° C.) solution of [3-(hydroxymethyl)oxetan-3-yl]methanol (1.31 g, 11.1 mmol) in $CH_2Cl_2$ (10 mL) and stirred for 10 min at 0° C. The reaction was allowed to attain rt, quenched with sat. aq. $NaHCO_3$ (10 mL) and $CH_2Cl_2$ (10 mL) and the phases separated. The aqueous phase was extracted with $CH_2Cl_2$ (2×10 mL) and the combined organic phase was washed with 50% brine (20 mL), dried ($MgSO_4$) and concentrated under reduced pressure. Purification by flash chromatography (0-50% EtOAc in iso-hexanes) to afford a colourless oil (826 mg, 26%). $^1$H NMR (500 MHz, $CDCl_3$) δ 7.84-7.78 (m, 2H), 7.41-7.35 (m, 2H), 4.43 (d, J=6.7 Hz, 2H), 4.36 (d, J=6.6 Hz, 2H), 4.31 (s, 2H), 3.91 (d, J=5.5 Hz, 2H), 2.47 (s, 3H), 1.86 (t, J=5.4 Hz, 1H).

3B (3R)-3-Hydroxybutyl]4-methylbenzenesulfonate

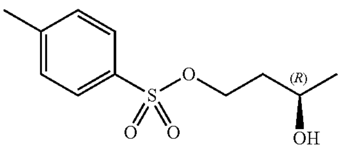

A solution of TsCl (11.02 g, 57.81 mmol) in $CH_2Cl_2$ (25 mL) was added over 30 minutes by dropwise addition to a cooled (0° C.) solution of (R)-(−)-1,3-butanediol (4.99 mL, 55.59 mmol) and $NEt_3$ (11.62 mL, 83.39 mmol) in $CH_2Cl_2$ (40 mL). The reaction was allowed to warm to rt and stirred for 16 h. Water (100 mL) was added, and the mixture was stirred for 5 minutes. The organic layer was separated, washed with water and brine (80 mL each), dried ($MgSO_4$) and the solvent removed under reduced pressure. Purification by flash chromatography (5-60% EtOAc:heptane) afforded a pale yellow oil (9.04 g, 67%). $^1$H NMR (400 MHz, DMSO-$d_6$) δ 7.83-7.71 (m, 2H), 7.48 (d, J=8.0 Hz, 2H), 4.56 (d, J=5.0 Hz, 1H), 4.16-3.99 (m, 2H), 3.68-3.53 (m, 1H), 2.42 (s, 3H), 1.70-1.49 (m, 2H), 1.00 (d, J=6.2 Hz, 3H). LRMS m/z (APCI+) 245.0 $[M+H]^+$.

The following intermediate compounds were prepared in an analogous manner to that described for intermediate 3B. 4-Dimethylaminopyridine (0.1 eq.) was employed in the preparation of intermediate 3D.

TABLE 1

Preparatory examples prepared by tosylation.

| Preparatory Example | Name | Structure | $^1$H NMR δ (DMSO-$d_6$) | LRMS APCI+ m/z; TLC $R_f$ |
|---|---|---|---|---|
| 3C | [(3S)-3-Hydroxybutyl] 4-methylbenzene-sulfonatex | 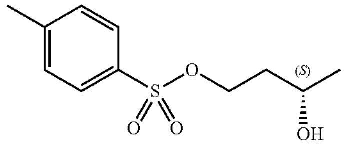 | (500 MHz) 7.82-7.76 (m, 2H), 7.52-7.46 (m, 2H), 4.56 (d, J = 5.0 Hz, 1H), 4.14-4.03 (m, 2H), 3.68-3.56 (m, 1H), 2.43 (s, 3H), 1.70-1.53 (m, 2H), 1.01 (d, J = 6.2 Hz, 3H). | Not available |
| 3D | (2,2-Dimethyl-1,3-dioxan-5-yl)methyl 4-methylbenzene-sulfonate | 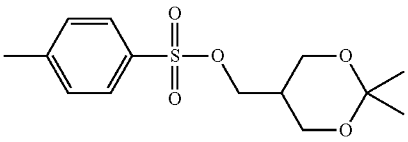 | (400 MHz) 7.80 (d, J = 8.3 Hz, 2H), 7.49 (d, J = 8.0 Hz, 2H), 4.10 (d, J = 7.3 Hz, 2H), 3.85 (dd, J = 12.0, 3.8 Hz, 2H), 3.54 (dd, J = 12.0, 5.3 Hz, 2H), 2.42 (s, 3H), 1.93-1.77 (m, 1H), 1.29 (s, 3H), 1.19 (s, 3H). | 301.6 $[M + H]^+$ |
| 3E | [(2R)-2-Hydroxypropyl] 4-methylbenzene-sulfonate | 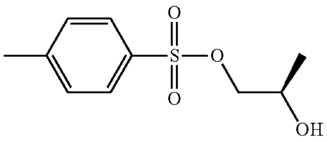 | (700 MHz) 7.84-7.74 (m, 2H), 7.53-7.42 (m, 2H), 4.98 (s, 1H), 3.84-3.80 (m, 1H), 3.80-3.73 (m, 2H), 2.42 (s, 3H), 0.98 (d, J = 6.1 Hz, 3H). | 231.0 $[M + H]^+$ |

4A 1-(2-Bromoethyl)cyclopropan-1-ol

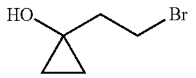

Titanium(IV) isopropoxide (0.35 mL, 1.20 mmol) was added to a solution of methyl 3-bromopropionate (1.31 mL, 11.98 mmol) in THE (80 mL). The solution was cooled to 0° C. and EtMgBr (3.0 M in $Et_2O$; 8.78 mL, 26.4 mmol) added slowly. The reaction was stirred at rt over the weekend. The reaction was quenched with sat. aq. $NH_4Cl$ (50 mL), stirred for 10 min, then 1 M aq. HCl added (50 mL) and stirred at rt for 2 h. The resulting solution was extracted with EtOAc (3×50 mL), and the combined organic extracts washed with brine (50 mL), dried ($MgSO_4$) and concentrated under reduced pressure to afford an orange oil (1.52 g, 77%). $^1$H NMR (700 MHz, $CDCl_3$) δ 3.61 (t, J=7.3 Hz, 2H), 2.12 (t, J=7.6, 2H), 0.84-0.75 (m, 2H), 0.65-0.53 (m, 2H).

5A S-(3-bromopropyl) ethanethioate

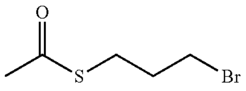

Potassium ethanethioate (563 mg, 4.93 mmol) was added portion-wise to a solution of 1,3-dibromopropane (0.5 mL, 4.93 mmol) in DMF (10 mL) and stirred at rt for 6 h. The reaction was diluted with water (20 mL) and extracted with MTBE (3×20 mL). The combined organic extracts were washed with brine, dried ($MgSO_4$), and concentrated under reduced pressure. Purification by flash chromatography (0-30% MTBE in iso-hexanes) gave a colourless oil (516 mg, 53%). $^1$H NMR (500 MHz, $CDCl_3$) δ 3.47 (t, J=6.5 Hz, 2H), 3.03 (t, J=7.0 Hz, 2H), 2.36 (s, 3H), 2.15 (p, J=6.7 Hz, 2H).

6A Ethyl 3,5-dibromo-1-(3-hydroxypropyl)pyrazole-4-carboxylate

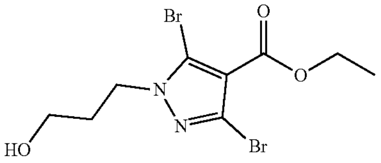 [SMILES: CCOC(=O)c1c(Br)nn(CCCO)c1Br]

A solution of intermediate 1A (500 mg, 1.68 mmol), $K_2CO_3$ (465 mg, 3.30 mmol) and 3-bromopropan-1-ol (0.16 mL, 1.77 mmol) in MeCN (6 mL) was heated at 80° C. for 3 h. The reaction was cooled to rt and filtered, washing with MeCN (3×20 mL). The filtrate was concentrated under reduced pressure and the crude product purified by flash chromatography (0-50% EtOAc in iso-hexanes) to afford a colourless oil (561 mg, 89%). LCMS (Method A) 355.1/357.1/359.1 [M+H] at 1.11 min. $^1$H NMR (500 MHz, $CDCl_3$) δ 4.40-4.32 (m, 4H), 3.67 (q, J=5.7 Hz, 2H), 2.12-2.04 (m, 2H), 1.75 (t, J=5.4 Hz, 1H), 1.39 (t, J=7.1 Hz, 3H).

The following intermediate compounds were prepared in an analogous manner to that described for intermediate 6A from intermediate 1A and the denoted reagent/intermediate.

TABLE 2

Preparatory examples prepared via general N-alkylation procedure described for 6A

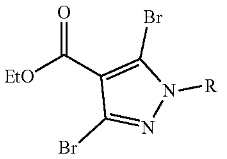

| Preparatory Example | Name | R | $^1$H NMR δ | LCMS (ES+); LRMS (APCI+) m/z | Reagent/ Intermediate |
|---|---|---|---|---|---|
| 6B | Ethyl 3,5-dibromo-1-[(3R)-3-hydroxybutyl] pyrazole-4-carboxylate | 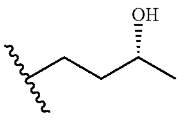 [SMILES: *CC[C@@H](C)O] | Not available | LCMS (method A) 369.5/371.5/373.5 [M + H]$^+$ at 1.21 min. | 2A or 3B |
| 6C | Ethyl 3,5-dibromo-1-[(3S)-3-hydroxybutyl] pyrazole-4-carboxylate | 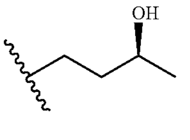 [SMILES: *CC[C@H](C)O] | (500 MHz, $CDCl_3$) 4.43-4.30 (m, 4H), 3.83-3.75 (m, 1H), 2.07-1.97 (m, 1H), 1.92-1.81 (m, 2H), 1.39 (t, J = 7.1 Hz, 3H), 1.24 (d, J = 6.3 Hz, 3H). | LCMS (method A) 369.5/371.5/373.5 [M + H]$^+$ at 1.20 min | 2B or 3C |
| 6D | 3,5-Dibromo-1-(3-hydroxy-3-methylbutyl) pyrazole-4-carboxylate | 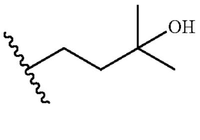 [SMILES: *CCC(C)(C)O] | (700 MHz, DMSO-$d_6$) 4.52 (s, 1H), 4.31-4.22 (m, 4H), 1.92-1.76 (m, 2H), 1.29 (t, J = 7.1 Hz, 3H), 1.14 (s, 6H). | LRMS 382.7/384.7/386.7 [M + H]$^+$ | 2C |

TABLE 2-continued

Preparatory examples prepared via general N-alkylation procedure described for 6A

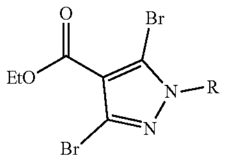

| Preparatory Example | Name | R | $^1$H NMR δ | LCMS (ES+); LRMS (APCI+) m/z | Reagent/ Intermediate |
|---|---|---|---|---|---|
| 6E | Ethyl 3,5-dibromo-1-[2-(1-hydroxycyclopropyl)ethyl] pyrazole-4-carboxylate | 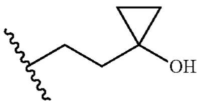 [SMILES: *CCC1(O)CC1] | (700 MHz, DMSO-$d_6$) 5.28 (s, 1H), 4.42-4.35 (m, 2H), 4.26 (q, J = 7.1 Hz, 2H), 1.97-1.86 (m, 2H), 1.30 (t, J = 7.1 Hz, 3H), 0.64-0.50 (m, 2H), 0.36-0.27 (m, 2H). | LRMS 380.6/382.6/ 384.6 $[M + H]^+$ | 4A |
| 6F | Ethyl 3,5-dibromo-1-(3-hydroxy-2-methylpropyl) pyrazole-4-carboxylate | 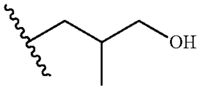 [SMILES: *CC(C)CO] | (700 MHz, DMSO-$d_6$) 4.71 (t, J = 5.1 Hz, 1H), 4.29-4.20 (m, 3H), 4.01 (dd, J = 13.8, 8.5 Hz, 1H), 3.36-3.27 (m, 2H), 2.26-2.02 (m, 1H), 1.30 (t, J = 7.1 Hz, 3H), 0.80 (d, J = 6.8 Hz, 3H). | LRMS 368.7/370.7/ 372.7 $[M + H]^+$ | 3-Bromo-2-methyl-1-propanol |
| 6E | Ethyl 3,5-dibromo-1-[(2S)-3-hydroxy-2-methylpropyl] pyrazole-4-carboxylate | 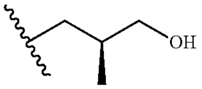 [SMILES: *C[C@H](C)CO] | (700 MHz, DMSO-$d_6$) 4.70 (t, J = 5.2 Hz, 1H), 4.28-4.22 (m, 3H), 4.00 (dd, J = 13.8, 8.5 Hz, 1H), 3.38-3.25 (m, 4H), 2.19-2.10 (m, 1H), 1.30 (t, J = 7.1 Hz, 3H), 0.79 (d, J = 6.9 Hz, 3H). | LRMS 368.6/370.5/ 372.5 $[M + H]^+$ | (R)-(−)-3-bromo-2-methyl-1-propanol |
| 6H | Ethyl 3,5-dibromo-1-(3-hydroxy-2,2-dimethylpropyl) pyrazole-4-carboxylate | 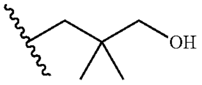 [SMILES: *CC(C)(C)CO] | (500 MHz, $CDCl_3$) 4.36 (q, J = 7.1 Hz, 2H), 4.13 (s, 2H), 3.31 (s, 2H), 2.90 (br s, 1H), 1.39 (t, J = 7.1 Hz, 3H), 0.96 (s, 6H). | LCMS (method A) 383.2/385.2/ 387.2 $[M + H]^+$ at 1.35 min | 3-Bromo-2,2-dimethyl-propan-1-ol |
| 6I | Ethyl 3,5-dibromo-1-[[3-(hydroxymethyl) oxetan-3-yl]methyl] pyrazole-4-carboxylate | 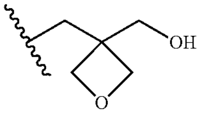 [SMILES: *CC1(CO)COC1] | (500 MHz, $CDCl_3$) 4.68 (d, J = 6.7 Hz, 2H), 4.60 (s, 2H), 4.45 (d, J = 6.7 Hz, 2H), 4.36 (q, J = 7.1 Hz, 2H), 3.83 (d, J = 5.9 Hz, 2H), 2.36 (t, J = 5.8 Hz, 1H), 1.39 (t, J = 7.1 Hz, 3H). | LCMS (method A) 397.2/399.2/ 401.2 $[M + H]^+$ at 1.08 min. | 3A |
| 6J | Ethyl 3,5-dibromo-1-[2-(2,2-dimethyl-1,3-dioxolan-4-yl)ethyl]pyrazole-4-carboxylate | 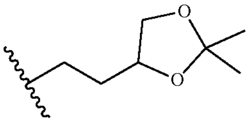 [SMILES: *CCC1COC(C)(C)O1] | (500 MHz, $CDCl_3$) 4.44-4.29 (m, 4H), 4.16-4.04 (m, 2H), 3.57 (dd, J = 7.9, 6.3 Hz, 1H), 2.21-2.00 (m, 2H), 1.46-1.34 (m, 9H). | LCMS (method A) 427.3 $[M + H]^+$ at 1.53 min. | 2D |
| 6K | Ethyl 3,5-dibromo-1-[(2,2-dimethyl-1,3-dioxan-5-yl)methyl] pyrazole-4-carboxylate | 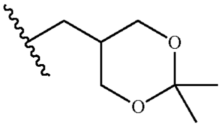 [SMILES: *CC1COC(C)(C)OC1] | (400 MHz, DMSO-$d_6$) 4.35 (d, J = 7.4 Hz, 2H), 4.26 (q, J = 7.1 Hz, 2H), 3.91 (dd, J = 12.1, 3.6 Hz, 2H), 3.52 (dd, J = 12.1, 4.7 Hz, 2H), 2.17-2.07 (m, 1H), 1.34 (d, J = 5.7 Hz, 6H), 1.29 (t, J = 7.1 Hz, 3H). | LRMS 425.7/427.7/ 429.7 $[M + H]^+$ | 3D |
| 6L | Ethyl 3,5-dibromo-1-[(2R)-2-hydroxypropyl] pyrazole-4-carboxylate | 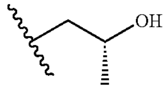 [SMILES: *C[C@@H](C)O] | (400 MHz, DMSO-$d_6$) δ 5.03 (d, J = 5.1 Hz, 1H), 4.26 (q, J = 7.1 Hz, 2H), 4.14-3.98 (m, 3H), 1.29 (t, J = 7.1 Hz, 3H), 1.09 (d, J = 6.1 Hz, 3H). | LRMS 355.0/357.0/ 359.0 $[M + H]^+$ | 3E |

7A Ethyl 1-(3-acetylsulfanylpropyl)-3,5-dibromopyrazole-4-carboxylate

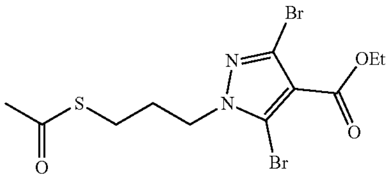 [SMILES: CCOC(=O)c1c(Br)nn(CCCSC(C)=O)c1Br]

A solution of intermediate 1A (650 mg, 2.18 mmol), $K_2CO_3$ (1.21 g, 8.73 mmol), and intermediate 5A (516 mg, 2.62 mmol) in MeCN (10 mL) was heated at 80° C. for 3 h. The reaction was cooled to rt and filtered, and the filtrate concentrated to give an orange oil (937 mg, 79%) which was used without further purification. LCMS (Method E): m/z 413.1/415.1/417.1 $[M+H]^+$ at 0.70 min.

8A Ethyl 3,5-dibromo-1-[2-(hydroxymethyl)butyl]pyrazole-4-carboxylate

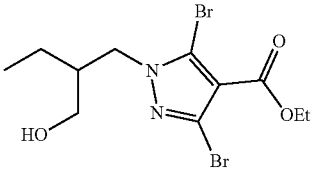 [SMILES: CCOC(=O)c1c(Br)nn(CC(CC)CO)c1Br]

Imidazole (654 mg, 9.6 mmol) and $PPh_3$ (2.52 g, 9.6 mmol) were added to a solution of 2-ethylpropane-1,3-diol (1.0 g, 9.6 mmol) in THE (30 mL), stirred for 1 min, then $I_2$ (3.17 g, 12.5 mmol) added. The reaction was stirred at rt for 1 h, then quenched with sat. aq. $Na_2S_2O_3$ (25 mL) and diluted with $CH_2Cl_2$ (25 mL). The separated aqueous layer was extracted with $CH_2Cl_2$ (2×25 ml), and the combined organic extracts washed with brine (25 mL), dried ($Na_2SO_4$), and the solvent removed under reduced pressure to afford a colourless oil (4.00 g) which was used directly in the next reaction without further purification. A solution of intermediate 1A (1.00 g, 3.36 mmol), crude 2-(iodomethyl)butan-1-ol (4.00 g, 9.60 mmol) and $Cs_2CO_3$ (1.43 g, 4.36 mmol) in MeCN (15 mL) was heated at 80° C. for 3 h, then stirred at rt for 16 h. The reaction was cooled to rt and filtered, washing with MeCN (2×15 ml). The filtrate was concentrated under reduced pressure, and purified by flash chromatography (10-40% EtOAc:heptane) to afford a colourless oil (740 mg, 57%). $^1H$ NMR (400 MHz, DMSO-$d_6$) δ 4.65 (t, J=5.0 Hz, 1H), 4.31-4.18 (m, 3H), 4.15-4.04 (m, 1H), 2.00-1.90 (m, 1H), 1.40-1.26 (m, 4H), 1.25-1.12 (m, 1H), 0.84 (t, J=7.5 Hz, 3H). LRMS (APCI+) m/z 383.0/385.0/387.0 $[M+H]^+$.

The following intermediates were prepared in an analogous manner to intermediate 8A.

TABLE 3

Preparatory examples prepared by general N-Alkylation procedure described for intermediate 8A.

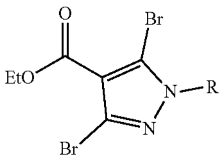

| Preparatory Example | Name | R | $^1H$ NMR δ (400 MHz, DMSO-$d_6$) | LRMS (APCI+) m/z |
|---|---|---|---|---|
| 8B | Ethyl 3,5-dibromo-1-[2-(hydroxymethyl)pentyl]pyrazole-4-carboxylate | 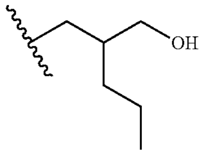 [SMILES: *CC(CO)CCC] | 4.64 (t, J = 5.0 Hz, 1H), 4.26 (q, J = 7.1 Hz, 2H), 4.22-4.02 (m, 2H), 2.09-1.95 (m, 1H), 1.39-1.06 (m, 7H), 0.82 (t, J = 7.1 Hz, 3H). | 396.9/398.9/400.9 $[M + H]^+$. |
| 8C | Ethyl 3,5-dibromo-1-[2-(hydroxymethyl)-3-methylbutyl]pyrazole-4-carboxylate | 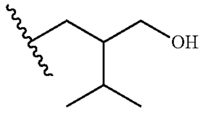 [SMILES: *CC(CO)C(C)C] | 4.56 (t, J = 4.8 Hz, 1H), 4.25 (q, J = 7.1 Hz, 2H), 4.18 (dd, J = 7.3, 4.9 Hz, 2H), 1.97-1.86 (m, 1H), 1.77-1.63 (m, 1H), 1.29 (t, J = 7.1 Hz, 3H), 0.90 (dd, J = 7.0, 1.7 Hz, 6H). | 397.0/399.0/401.0 $[M + H]^+$. |
| 8D | Ethyl 3,5-dibromo-1-[[1-(hydroxymethyl)cyclopropyl]methyl]pyrazole-4-carboxylate | 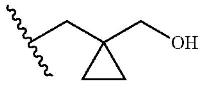 [SMILES: *CC1(CO)CC1] | 4.68-4.56 (m, 1H), 4.31-4.17 (m, 4H), 3.25-3.14 (m, 2H), 1.30 (t, J = 7.1 Hz, 3H), 0.61-0.41 (m, 4H). | 380.9/382.9/384.9 $[M + H]^+$ |

TABLE 3-continued

Preparatory examples prepared by general N-Alkylation procedure described for intermediate 8A.

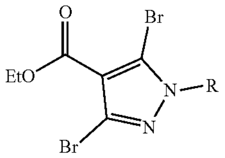

| Preparatory Example | Name | R | $^1$H NMR δ (400 MHz, DMSO-$d_6$) | LRMS (APCI+) m/z |
|---|---|---|---|---|
| 8E | Ethyl 3,5-dibromo-1-(3-hydroxy-4-methylpentyl) pyrazole-4-carboxylate | 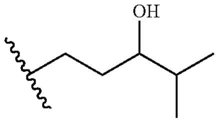 [SMILES: *CCC(O)C(C)C] | 4.63 (d, J = 5.6 Hz, 1H), 4.36-4.16 (m, 4H), 3.25-3.14 (m, 1H), 1.93-1.81 (m, 1H), 1.76-1.61 (m, 1H), 1.61-1.48 (m, 1H), 1.29 (t, J = 7.1 Hz, 3H), 0.82 (d, J = 6.8 Hz, 6H). | 396.9/398.9/400.9 [M + H]$^+$. |
| 8F | Ethyl 3,5-dibromo-1-(3-hydroxy-2-phenylmethoxypropyl)pyrazole-4-carboxylate | 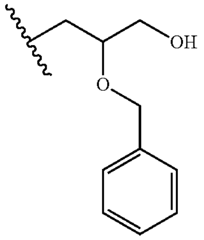 [SMILES: *CC(CO)OCc1ccccc1] | 7.25-7.17 (m, 3H), 7.10 7.02 (m, 2H), 4.96 (t, J = 5.6 Hz, 1H), 4.53 (d, J = 12.2 Hz, 1H), 4.36-4.18 (m, 4H), 3.88-3.72 (m, 1H), 3.60-3.46 (m, 2H), 1.31 (t, J = 7.1 Hz, 3H). | 460.9/462.9/464.9 [M + H]$^+$ |
| 8G | Ethyl 3,5-dibromo-1-[[1-(hydroxymethyl) cyclobutyl]methyl] pyrazole-4-carboxylate | 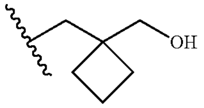 [SMILES: *CC1(CO)CCC1] | 4.82 (t, J = 5.1 Hz, 1H), 4.26 (q, J = 7.1 Hz, 2H), 4.22 (s, 2H), 3.38 (d, J = 5.2 Hz, 2H), 1.90-1.81 (m, 2H), 1.81-1.72 (m, 3H), 1.71-1.58 (m, 1H), 1.30 (t, J = 7.1 Hz, 3H). | 395.0/397.0/399.0 [M + H]$^+$ |
| 8H | Ethyl 3,5-dibromo-1-[3-hydroxy-2-[(2-methylpropan-2-yl)oxycarbonylamino] propyl]pyrazole-4-carboxylate | 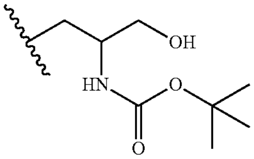 [SMILES: *CC(CO)NC(=O)OC(C)(C)C] | 6.72 (d, J = 9.2 Hz, 1H), 4.93 (t, J = 5.6 Hz, 1H), 4.40 (dd, J = 13.9, 4.0 Hz, 1H), 4.34-4.16 (m, 3H), 4.12-4.00 (m, 1H), 3.94-3.78 (m, 1H), 3.43-3.38 (m, 2H), 1.33-1.22 (m, 12H). | 414.3/416.3/418.3 [M + H]$^+$ |

9A Ethyl 2-bromo-6,7-dihydro-5H-pyrazolo[5,1-b][1,3]oxazine-3-carboxylate

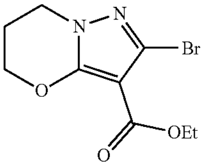 [SMILES: CCOC(=O)c1c(Br)nn2c1OCCC2]

NaH (60% dispersion in mineral oil, 225 mg, 5.63 mmol) was added to a cooled (0° C.) solution of intermediate 6A (1.00 g, 2.81 mmol) in THE (150 mL). The reaction was stirred at rt for ~48 h, quenched with water (20 mL) and diluted with EtOAc (20 mL). The separated aqueous phase was extracted with EtOAc (2×10 mL). The combined organic phases were washed with brine (50 mL), dried ($MgSO_4$), and concentrated under reduced pressure. Purification by flash chromatography (0-80% EtOAc in iso-hexanes) afforded a white solid (655 mg, 85%). LCMS (Method A) 275.2/277.2 [M+H]$^+$ at 0.97 min. $^1$H NMR (500 MHz, DMSO-$d_6$) δ 4.45-4.39 (m, 2H), 4.16 (q, J=7.1 Hz, 2H), 4.05 (t, J=6.1 Hz, 2H), 2.24-2.16 (m, 2H), 1.23 (t, J=7.1 Hz, 3H).

The following intermediate compounds were prepared in an analogous manner to intermediate 9A.

TABLE 4

| Preparatory Examples prepared via general cyclisation procedure | | | | |
|---|---|---|---|---|
| Prepar-atory Example | Name | Structure | $^1H$ NMR δ | LCMS (ES+); LRMS (APCI+) m/z |
| 9B | Ethyl (5R)-2-bromo-5-methyl-6,7-dihydro-5H-pyrazolo[5,1-b][1,3]oxazine-3-carboxylate | 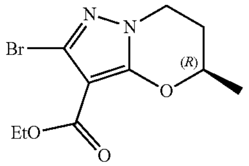 | (500 MHz, $CDCl_3$) δ 4.56-4.46 (m, 1H), 4.29 (q, J = 7.1 Hz, 2H), 4.21-4.13 (m, 1H), 4.13-4.03 (m, 1H), 2.26-2.18 (m, 1H), 2.15-2.03 (m, 1H), 1.55 (t, J = 3.2 Hz, 3H), 1.35 (t, J = 7.1 Hz, 3H). | LCMS (method E) 289.7/291.7 $[M + H]^+$ at 1.09 min |
| 9C | Ethyl (5S)-2-bromo-5-methyl-6,7-dihydro-5H-pyrazolo[5,1-b][1,3]oxazine-3-carboxylate | 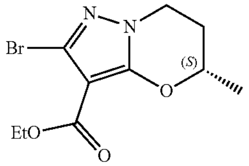 | (500 MHz, $CDCl_3$) δ 4.56-4.46 (m, 1H), 4.29 (q, J = 7.1 Hz, 2H), 4.21-4.13 (m, 1H), 4.13-4.03 (m, 1H), 2.29-2.18 (m, 1H), 2.15-2.03 (m, 1H), 1.58-1.53 (m, 3H), 1.35 (t, J = 7.1 Hz, 3H). | LCMS (method A) 289.2/291.2 $[M + H]^+$ at 1.09 min |
| 9D | Ethyl 2-bromo-5,5-dimethyl-6,7-dihydropyrazolo[5,1-b][1,3]oxazine-3-carboxylate | 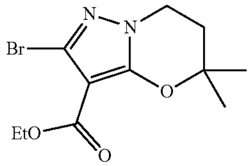 [SMILES: CCOC(=O)c1c(Br)nn2c1OC(C)(C)CC2] | (700 MHz, DMSO-$d_6$) δ 4.14 (q, J = 7.1 Hz, 2H), 4.07 (t, J = 6.4 Hz, 2H), 2.13 (t, J = 6.4 Hz, 2H), 1.41 (s, 6H), 1.23 (t, J = 7.1 Hz, 3H). | LRMS 303.1/305.1 $[M + H]^+$ |
| 9E | Ethyl 2-bromo-7-propan-2-yl-6,7-dihydro-5H-pyrazolo[5,1-b][1,3]oxazine-3-carboxylate | 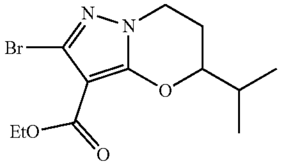 [SMILES: CCOC(=O)c1c(Br)nn2c1OC(C(C)C)CC2] | (400 MHz, DMSO-$d_6$) δ 4.23-3.98 (m, 5H), 2.30-2.17 (m, 1H), 2.08-1.86 (m, 2H), 1.23 (t, J = 7.1 Hz, 3H), 1.03 (d, J = 6.7 Hz, 3H), 0.98 (d, J = 6.8 Hz, 3H). | LRMS 317.0/319.0 $[M + H]^+$ |
| 9F | Ethyl 2-bromospiro[6,7-dihydropyrazolo[5,1-b][1,3]oxazine-5,1'-cyclopropane]-3-carboxylate | 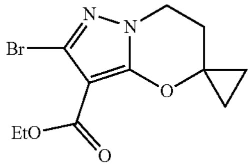 [SMILES: CCOC(=O)c1c(Br)nn2c1OC1(CC2)CC1] | (400 MHz, DMSO-$d_6$) δ 4.19 (t, J = 6.1 Hz, 2H), 4.13 (q, J = 7.1 Hz, 2H), 2.24 (t, J = 6.1 Hz, 2H), 1.21 (t, J = 7.1 Hz, 3H), 1.10-1.01 (m, 2H), 0.92-0.84 (m, 2H). | LRMS 300.8/302.8 $[M + H]^+$ |
| 9G | Ethyl (6S)-2-bromo-6-methyl-6,7-dihydro-5H-pyrazolo[5,1-b][1,3]oxazine-3-carboxylate | 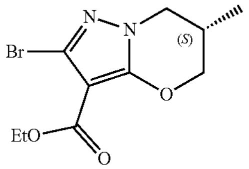 | (700 MHz, DMSO-$d_6$) δ 4.43 (ddd, J = 10.7, 3.6, 1.4 Hz, 1H), 4.20-4.10 (m, 3H), 4.06 (dd, J = 10.7, 9.3 Hz, 1H), 3.69 (dd, J = 12.1, 8.9 Hz, 1H), 2.46-2.37 (m, 1H), 1.23 (t, J = 7.1 Hz, 3H), 1.01 (d, J = 6.8 Hz, 3H). | LRMS 288.7/290.7 $[M + H]^+$ |
| 9H | Ethyl 2-bromo-6,6-dimethyl-5,7-dihydropyrazolo[5,1-b][1,3]oxazine-3-carboxylate | 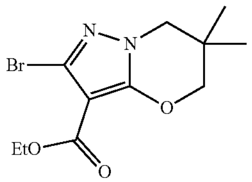 [SMILES: CCOC(=O)c1c(Br)nn2c1OCC(C)(C)C2] | (500 MHz, $CDCl_3$) δ 4.31 (q, J = 7.1 Hz, 2H), 4.03 (s, 2H), 3.80 (s, 2H), 1.35 (t, J = 7.1 Hz, 3H), 1.15 (s, 6H). | LCMS (method A) 302.6/305.6 $[M + H]^+$ at 1.20 min |

TABLE 4-continued

| Preparatory Examples prepared via general cyclisation procedure | | | | |
|---|---|---|---|---|
| Preparatory Example | Name | Structure | $^1H$ NMR δ | LCMS (ES+); LRMS (APCI+) m/z |
| 9I | Ethyl 2-bromospiro[5,7-dihydropyrazolo[5,1-b][1,3]oxazine-6,3'-oxetane]-3-carboxylate | 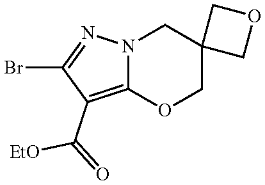 [SMILES: CCOC(=O)c1c(Br)nn2c1OCC1(COC1)C2] | (500 MHz, $CDCl_3$) δ 4.64-4.57 (m, 6H), 4.34 (s, 2H), 4.30 (q, J = 7.1 Hz, 2H), 1.35 (t, J = 7.1 Hz, 3H). | LCMS (method A) 317.7/319.7 $[M + H]^+$ at 0.94 min |
| 9J | Ethyl 2-bromo-6-ethyl-6,7-dihydro-5H-pyrazolo[5,1-b][1,3]oxazine-3-carboxylate | 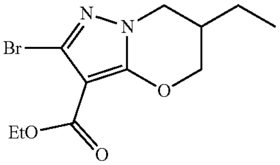 [SMILES: CCOC(=O)c1c(Br)nn2c1OCC(CC)C2] | (400 MHz, DMSO-$d_6$) δ 4.53-4.44 (m, 1H), 4.23-4.08 (m, 4H), 3.74 (dd, J = 12.1, 8.8 Hz, 1H), 2.29-2.15 (m, 1H), 1.49-1.28 (m, 2H), 1.22 (t, J = 7.1 Hz, 3H), 0.95 (t, J = 7.5 Hz, 3H). | LRMS 302.9/304.9 $[M + H]^+$ |
| 9K | Ethyl 2-bromo-6-propyl-6,7-dihydro-5H-pyrazolo[5,1-b][1,3]oxazine-3-carboxylate | 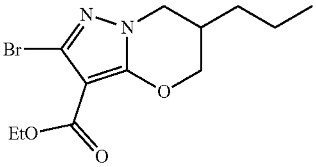 [SMILES: CCCC1COc2c(C(=O)OCC)c(Br)nn2C1] | (400 MHz, DMSO-$d_6$) δ 4.48 (ddd, J = 10.9, 3.5, 1.3 Hz, 1H), 4.21-4.06 (m, 4H), 3.73 (dd, J = 12.1, 8.9 Hz, 1H), 2.36-2.26 (m, 1H), 1.42-1.26 (m, 4H), 1.22 (t, J = 7.1 Hz, 3H), 0.89 (t, J = 6.9 Hz, 3H). | LRMS 317.0/319.0 $[M + H]^+$ |
| 9L | Ethyl 2-bromo-6-propan-2-yl-6,7-dihydro-5H-pyrazolo[5,1-b][1,3]oxazine-3-carboxylate | 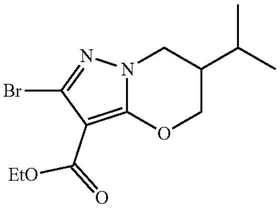 [SMILES: CCOC(=O)c1c(Br)nn2c1OCC(C(C)C)C2] | (400 MHz, DMSO-$d_6$) δ 4.62-4.49 (m, 1H), 4.25-4.03 (m, 4H), 3.83 (dd, J = 12.2, 9.9 Hz, 1H), 2.16-2.01 (m, 1H), 1.69-1.52 (m, 1H), 1.22 (t, J = 7.1 Hz, 3H), 0.95 (dd, J = 8.7, 6.8 Hz, 6H). | LRMS 317.0/319.0 $[M + H]^+$ |
| 9M | Ethyl 2-bromospiro[5,7-dihydropyrazolo[5,1-b][1,3]oxazine-6,1'-cyclopropane]-3-carboxylate | 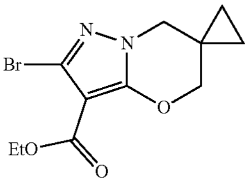 [SMILES: CCOC(=O)c1c(Br)nn2c1OCC1(CC1)C2] | (400 MHz, DMSO-$d_6$) δ 4.24 (s, 2H), 4.17 (q, J = 7.1 Hz, 2H), 3.97 (s, 2H), 1.23 (t, J = 7.1 Hz, 3H), 0.78 (s, 4H). | LRMS 301.0/303.0 $[M + H]^+$ |

9N Ethyl (6R)-2-bromo-6-methyl-6,7-dihydro-5H-pyrazolo[5,1-b][1,3]oxazine-3-carboxylate

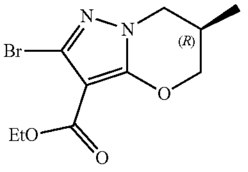

Prepared by the procedure described for intermediate 9A with intermediate 6F (2.33 g, 6.31 mmol) to afford ethyl 2-bromo-6-methyl-6,7-dihydro-5H-pyrazolo[5,1-b][1,3]oxazine-3-carboxylate (1.71 g, 94%). Separation by chiral SFC method 3 with an isocratic mixture of 30:70 EtOH:$CO_2$ (0.2% v/v $NH_3$); second eluting enantiomer] afforded the title compound as a white solid (670 mg, 40%). $^1H$ NMR (700 MHz, DMSO-$d_6$) δ 4.44 (ddd, J=10.7, 3.6, 1.3 Hz, 1H), 4.22-4.11 (m, 3H), 4.07 (dd, J=10.7, 9.3 Hz, 1H), 3.70 (dd, J=12.0, 8.9 Hz, 1H), 2.46-2.37 (m, 1H), 1.24 (t, J=7.1 Hz, 3H), 1.01 (d, J=6.9 Hz, 3H). LRMS (APCI+) m/z 289.0/291.0 $[M+H]^+$.

The following intermediate compounds were prepared in an analogous manner to intermediate 9A. Intermediates 9Q, 9R and 9T were prepared with 1 eq., 1.05 eq. and 1.1 eq. of NaH respectively.

TABLE 5

| Preparatory Example | Name | Structure | $^1H$ NMR δ (DMSO-$d_6$) | LRMS APCI+ m/z |
|---|---|---|---|---|
| Preparatory Examples prepared via general cyclisation procedure | | | | |
| 9O | Ethyl 2-bromo-6-[(2-methylpropan-2-yl)oxycarbonylamino]-6,7-dihydro-5H-pyrazolo[5,1-b][1,3]oxazine-3-carboxylate | 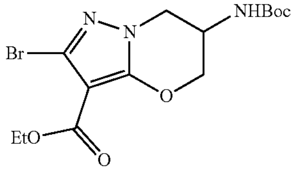 [SMILES: CCOC(=O)c1c(Br)nn2c1OCC(NC(=O)OC(C)(C)C)C2] | (400 MHz) δ 6.72 (d, J = 9.2 Hz, 1H), 4.93 (t, J = 5.6 Hz, 1H), 4.40 (dd, J = 13.9, 4.0 Hz, 1H), 4.34-4.16 (m, 2H), 4.12-4.00 (m, 1H), 3.94-3.78 (m, 1H), 3.43-3.38 (m, 2H), 1.33-1.22 (m, 12H). | 414.3/ 416.3/ 418.3 $[M + H]^+$ |
| 9P | Ethyl 2-bromo-6-phenylmethoxy-6,7-dihydro-5H-pyrazolo[5,1-b][1,3]oxazine-3-carboxylate | 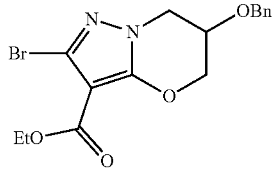 [SMILES: CCOC(=O)c1c(Br)nn2c1OCC(OCc1ccccc1)C2] | — | 381.0/ 383.0 $[M + H]^+$ |
| 9Q | Ethyl 2-bromospiro[5,7-dihydropyrazolo[5,1-b][1,3]oxazine-6,1'-cyclobutane]-3-carboxylate | 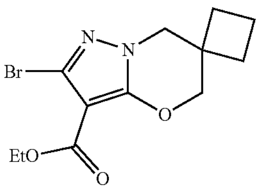 [SMILES: CCOC(=O)c1c(Br)nn2c1OCC1(CCC1)C2] | (300 MHz) δ 4.37 (s, 2H), 4.17 (q, J = 7.1 Hz, 2H), 4.07 (s, 2H), 2.09-1.83 (m, 6H), 1.23 (t, J = 7.1 Hz, 3H). | 315.0/ 317.0 $[M + H]^+$ |
| 9R | Ethyl 2-bromo-6-(hydroxymethyl)-6,7-dihydro-5H-pyrazolo[5,1-b][1,3]oxazine-3-carboxylate | 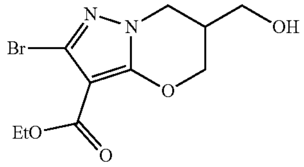 [SMILES: CCOC(=O)c1c(Br)nn2c1OCC(CO)C2] | (400 MHz) δ 5.01 (t, J = 5.3 Hz, 1H), 4.49 (dd, J = 10.9, 3.3 Hz, 1H), 4.27 (dd, J = 10.9, 7.8 Hz, 1H), 4.22-4.08 (m, 3H), 3.88 (dd, J = 12.3, 7.4 Hz, 1H), 3.47 (dd, J = 6.5, 5.3 Hz, 2H), 2.49-2.35 (m, 2H), 1.23 (t, J = 7.1 Hz, 3H). | 305.4/ 307.4 $[M + H]^+$ |
| 9S | Ethyl 2-bromo-5-(hydroxymethyl)-6,7-dihydro-5H-pyrazolo[5,1-b][1,3]oxazine-3-carboxylate | 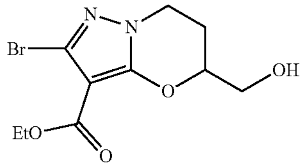 [SMILES: CCOC(=O)c1c(Br)nn2c1OC(CO)CC2] | (400 MHz) δ 5.20-5.06 (m, 1H), 4.49-4.35 (m, 1H), 4.24-3.97 (m, 4H), 3.67 (t, J = 5.0 Hz, 2H), 2.27-2.16 (m, 1H), 2.17-2.00 (m, 1H), 1.23 (t, J = 7.1 Hz, 3H). | 305.0/ 307.0 $[M + H]^+$ |
| 9T | Ethyl (2R)-6-bromo-2-methyl-2,3-dihydropyrazolo[5,1-b][1,3]oxazole-7-carboxylate | 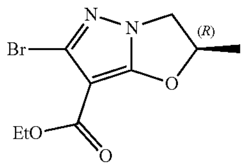 | (400 MHz) δ 5.68-5.54 (m, 1H), 4.45 (dd, J = 9.3, 8.3 Hz, 1H), 4.25-4.09 (m, 2H), 3.95 (dd, J = 9.3, 7.9 Hz, 1H), 1.56 (d, J = 6.4 Hz, 3H), 1.22 (t, J = 7.1 Hz, 3H). | 275.0/ 277.0 $[M + H]^+$ |

10A Ethyl 2-bromo-6,7-dihydro-5H-pyrazolo[5,1-b][1,3]thiazine-3-carboxylate

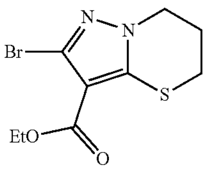 [SMILES: CCOC(=O)c1c(Br)nn2c1SCCC2]

Crude intermediate 7A (937 mg, 2.26 mmol) was added to a solution of $K_2CO_3$ (1.56 g, 11.3 mmol) in water/EtOH (1:1; 12 mL) and heated at 70° C. for 2 h. The volatiles were removed under reduced pressure, water (50 mL) and EtOAc (50 mL) added, and the separated aqueous layer extracted with EtOAc (2×50 mL). The combined organic extracts were washed with brine (100 mL), dried ($MgSO_4$), and concentrated under reduced pressure to give a colourless oil (644 mg, 980%) that was used without further purification. LCMS (Method E): m/z 291.7/293.6 $[M+H]^+$ at 0.59 min.

11A Ethyl 6,7-dihydro-5H-pyrazolo[5,1-b][1,3]oxazine-2-carboxylate

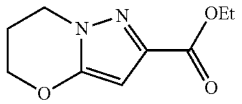 [SMILES: CCOC(=O)c1cc2n(n1)CCCO2]

$K_2CO_3$ (1.98 g, 14.3 mmol), followed by 1,2-dibromoethane (0.4 mL, 3.90 mmol) were added to a solution of ethyl 5-hydroxy-1H-pyrazole-3-carboxylate (550 mg, 3.52 mmol) in MeCN (25 mL) and the reaction heated at 80° C. overnight. The reaction was cooled to rt, filtered, washing with MeCN (2×20 mL) and the filtrate concentrated under reduced pressure. Purification by flash chromatography (40-100% EtOAc in iso-hexanes) afforded a white solid (690 mg, 99%). LCMS (Method A) 169.2 $(M-OEt)^+$ at 0.86 min. $^1H$ NMR (500 MHz, $CDCl_3$) δ 6.02 (s, 1H), 4.38 (q, J=7.1 Hz, 2H), 4.34-4.28 (m, 2H), 4.25 (t, J=6.3 Hz, 2H), 2.32-2.24 (m, 2H), 1.38 (t, J=7.1 Hz, 3H).

11B Ethyl 2,3-dihydropyrazolo[5,1-b][1,3]oxazole-6-carboxylate

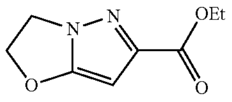 [SMILES: CCOC(=O)c1cc2n(n1)CCO2]

Prepared by an analogous procedure to that described for intermediate 11A with 1,3-dibromoethane. LCMS (Method A) 155.1 $(M-OEt)^+$ at 0.78 min. $^1H$ NMR (500 MHz, DMSO-$d_6$) δ 5.87 (s, 1H), 5.11 (dd, J=8.6, 7.6 Hz, 2H), 4.35 (dd, J=8.6, 7.6 Hz, 2H), 4.23 (q, J=7.1 Hz, 2H), 1.26 (t, J=7.1 Hz, 3H).

12A Ethyl 3-bromo-6,7-dihydro-5H-pyrazolo[5,1-b][1,3]oxazine-2-carboxylate

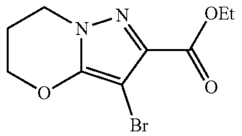 [SMILES: CCOC(=O)c1nn2c(c1Br)OCCC2]

N-bromosuccinimide (650 mg, 3.65 mmol) was added to a cooled (0° C.) solution of intermediate 11A in MeCN (6 mL), then the reaction mixture stirred at rt for 2 h. Sat. aq. $NaHCO_3$ (20 mL) and EtOAc (20 mL) were added, and the separated aqueous phase extracted with EtOAc (2×10 mL). The combined organic phases were washed with brine (20 mL), dried ($MgSO_4$), and the solvent removed under reduced pressure. Purification by flash chromatography (30-80%, EtOAc in iso-hexanes) afforded a colourless gum (888 mg, 96%). LCMS (Method A) 229.1/231.1 $(M-OEt)^+$ at 1.07 min. $^1H$ NMR (500 MHz, $CDCl_3$) δ 4.46-4.36 (m, 4H), 4.25 (t, J=6.2 Hz, 2H), 2.37-2.26 (m, 2H), 1.40 (t, J=7.1 Hz, 3H).

12B Ethyl 7-bromo-2,3-dihydropyrazolo[5,1-b][1,3]oxazole-6-carboxylate

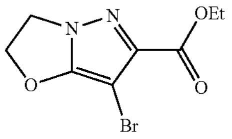 [SMILES: CCOC(=O)c1nn2c(c1Br)OCC2]

Prepared by an analogous procedure to that described for intermediate 12A. $^1H$ NMR (500 MHz, $CDCl_3$) δ 5.16-5.13 (m, 2H), 4.47-4.36 (m, 4H), 1.41 (t, J=7.1 Hz, 3H).

13A Ethyl 2-(2-fluorophenyl)-6,7-dihydro-5H-pyrazolo[5,1-b][1,3]oxazine-3-carboxylate

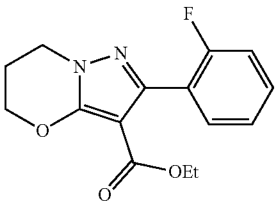 [SMILES: CCOC(=O)c1c(-c2ccccc2F)nn2c1OCCC2]

$Pd(PPh_3)_4$ (74 mg, 0.060 mmol) was added to a vial containing intermediate 9A (118 mg, 0.430 mmol), 2-fluorophenylboronic acid (120 mg, 0.86 mmol) and $K_2CO_3$ (178 mg, 1.29 mmol), and 1,4-dioxane:water (2:1; 3 mL) added. The mixture was sparged with $N_2$ and heated to 100° C. for 16 h. The reaction mixture was cooled to rt, $Pd(PPh_3)_4$ (74 mg, 0.060 mmol) and 2-fluorophenylboronic acid (240 mg, 1.72 mmol) added, sparged with $N_2$ and heated to 100° C. for 4 h. The reaction was partitioned between EtOAc (10 mL) and water (10 mL), separated and the aqueous phase extracted with EtOAc (3×10 mL). The combined organic extracts were washed with brine (20 mL), dried ($Na_2SO_4$) and concentrated under reduced pressure. Purification by flash chromatography (0-80% EtOAc in iso-hexanes) afforded a brown oil (208 mg, 63%). LCMS (method A) 290.9 $[M+H]^+$ at 1.14 min. $^1H$ NMR (500 MHz, DMSO-$d_6$) δ 7.48-7.40 (m, 1H), 7.39 (ddd, J=7.6, 1.9 Hz, 1H), 7.25-7.17 (m, 2H), 4.48-4.42 (m, 2H), 4.14 (t, J=6.1 Hz, 2H), 4.05-3.96 (m, 2H), 2.29-2.21 (m, 2H), 1.03 (t, J=7.1 Hz, 3H).

14A Ethyl 2-(2-fluoro-5-methylpyridin-3-yl)-6,7-dihydro-5H-pyrazolo[5,1-b][1,3]oxazine-3-carboxylate (Suzuki-Miyaura Procedure A)

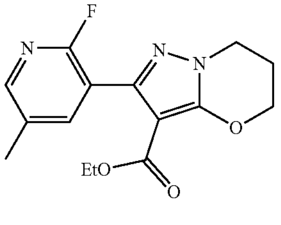 [SMILES: CCOC(=O)c1c(-c2cc(C)cnc2F)nn2c1OCCC2]

A reaction vessel was charged with intermediate 9A (140 mg, 0.510 mmol), (2-fluoro-5-methylpyridin-3-yl)boronic acid (158 mg, 1.02 mmol), $K_3PO_4$ (130 mg, 0.610 mmol), XPhos (12 mg, 0.030 mmol) and Pd-170 (XPhos Pd(crotyl) Cl; 18 mg, 0.030 mmol). The reaction vessel was evacuated, filled with $N_2$, then THE (4 mL) and water (1 mL) added. The reaction mixture was sparged with $N_2$ and heated at 65° C. overnight. The cooled reaction mixture was diluted with $CH_2Cl_2$ (25 mL), washed with brine (3x25 mL), the organic phase dried ($Na_2SO_4$) and concentrated under reduced pressure. Purification by flash chromatography (0-100% EtOAc in iso-hexanes) afforded a white solid (130 mg, 78%). LCMS (Method A) 306.6 $[M+H]^+$ at 1.03 min. $^1H$ NMR (500 MHz, DMSO-$d_6$) δ 8.11-8.04 (m, 1H), 7.76 (dd, J=9.1, 2.5 Hz, 1H), 4.50-4.39 (m, 2H), 4.15 (t, J=6.1 Hz, 2H), 4.02 (q, J=7.1 Hz, 2H), 2.32 (s, 3H), 2.30-2.17 (m, 2H), 1.04 (t, J=7.1 Hz, 3H).

The following intermediate compounds were prepared in an analogous manner to intermediate 14A. The procedure may be performed at temperatures varying from 60-70° C., and the stoichiometry of $K_3PO_4$ employed may be varied from 1.2 to 2.0 eq. Intermediates 16C, 16E and 16F were prepared from the corresponding pinacol ester. Intermediates 16D, 16E and 16F were prepared using Pd-170 (10 mol %), XPhos (20 mol %) and 4 eq. of $K_3PO_4$.

TABLE 6

Preparatory examples prepared via Suzuki-Miyaura procedure A.

| Preparatory Example | Name | Structure | $^1H$ NMR δ (500 MHz) | LCMS (ES+) m/z |
|---|---|---|---|---|
| 14B | Ethyl 2-phenyl-6,7-dihydro-5H-pyrazolo[5,1-b][1,3]oxazine-3-carboxylate | 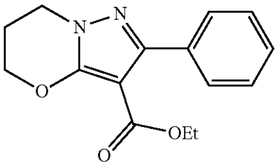 [SMILES: CCOC(=O)c1c(-c2ccccc2)nn2c1OCCC2] | (DMSO-$d_6$) 7.59-7.51 (m, 2H), 7.41-7.31 (m, 3H), 4.46-4.41 (m, 2H), 4.13 (t, J = 6.1 Hz, 2H), 4.08 (q, J = 7.1 Hz, 2H), 2.28-2.20 (m, 2H), 1.13 (t, J = 7.1 Hz, 3H) | (method A) 273.5 $[M + H]^+$ at 1.14 min |
| 14C | Ethyl 2-(2,6-difluoropyridin-3-yl)-6,7-dihydro-5H-pyrazolo[5,1-b][1,3]oxazine-3-carboxylate | 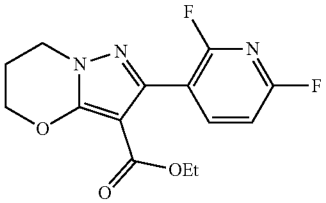 [SMILES: CCOC(=O)c1c(-c2ccc(F)nc2F)nn2c1OCCC2] | (DMSO-$d_6$) 8.20-8.11 (m, 1H), 7.24 (dd, J = 8.1, 2.5 Hz, 1H), 4.50-4.44 (m, 2H), 4.16 (t, J = 6.1 Hz, 2H), 4.04 (q, J = 7.1 Hz, 2H), 2.26 (p, J = 5.8 Hz, 2H), 1.06 (t, J = 7.1 Hz, 3H). | (method A) 310.4 $[M + H]^+$ at 1.10 min |
| 15A | Ethyl 2-cyclopropyl-6,7-dihydro-5H-pyrazolo[5,1-b][1,3]oxazine-3-carboxylate | 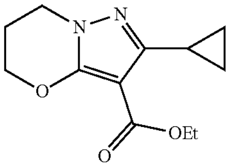 [SMILES: CCOC(=O)c1c(C2CC2)nn2c1OCCC2] | (DMSO-$d_6$) 4.37-4.31 (m, 2H), 4.15 (q, J = 7.1 Hz, 2H), 3.97-3.91 (m, 2H), 2.41 (tt, J = 8.4, 5.2 Hz, 1H), 2.19-2.09 (m, 2H), 1.22 (t, J = 7.1 Hz, 3H), 0.85-0.76 (m, 2H), 0.78-0.70 (m, 2H). | (method A) 237.7 $[M + H]^+$ at 1.00 min |
| 16A | Ethyl (5R)-2-(2-fluorophenyl)-5-methyl-6,7-dihydro-5H-pyrazolo[5,1-b][1,3]oxazine-3-carboxylate | 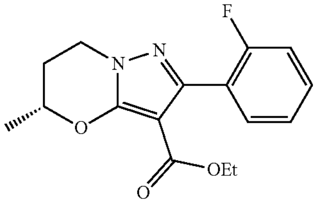 [SMILES: CCOC(=O)c1c(-c2ccccc2F)nn2c1O[C@H](C)CC2] | (DMSO-$d_6$) 7.48-7.36 (m, 2H), 7.25-7.17 (m, 2H), 4.65-4.57 (m, 1H), 4.19-4.11 (m, 2H), 4.02-3.95 (m, 2H), 2.32-2.23 (m, 1H), 2.10-1.99 (m, 1H), 1.44 (d, J = 6.3 Hz, 3H), 1.02 (t, J = 7.1 Hz, 3H). | (method A) 305.3 $[M + H]^+$ at 1.23 min |
| 16B | Ethyl (5R)-2-(2,6-difluoropyridin-3-yl)-5-methyl-6,7-dihydro-5H-pyrazolo[5,1-b][1,3]oxazine-3-carboxylate | 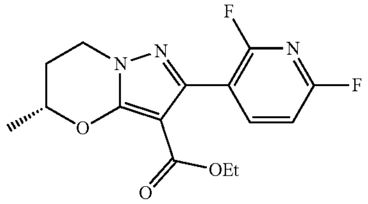 [SMILES: CCOC(=O)c1c(-c2ccc(F)nc2F)nn2c1O[C@H](C)CC2] | ($CDCl_3$) 8.01-7.93 (m, 1H), 6.87 (dd, J = 8.0, 2.8 Hz, 1H), 4.62-4.52 (m, 1H), 4.30-4.22 (m, 1H), 4.21-4.17 (m, 1H), 4.15 (q, J = 7.0 Hz, 2H), 2.33-2.25 (m, 1H), 2.22-2.10 (m, 1H), 1.60 (d, J = 6.4 Hz, 3H), 1.15 (t, J = 7.1 Hz, 3H). | (method A) 324.3 $[M + H]^+$ at 1.21 min |
| 16C | Ethyl (5R)-5-methyl-2-(6-methylpyridin-3-yl)-6,7-dihydro-5H-pyrazolo[5,1-b][1,3]oxazine-3-carboxylate | 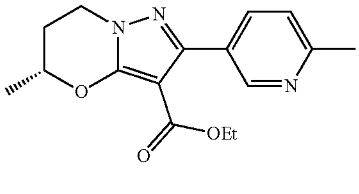 | (DMSO-$d_6$) δ 8.61-8.57 (m, 1H), 7.83 (dd, J = 8.0, 2.3 Hz, 1H), 7.26 (d, J = 8.0 Hz, 1H), 4.64-4.54 (m, 1H), 4.20-4.11 (m, 2H), 4.08 (q, J = 7.1 Hz, 2H), 2.49 (s, 3H), 2.32-2.23 (m, 1H), 2.09-1.97 (m, 1H), 1.44 (d, J = 6.4 Hz, 3H), 1.14 (t, J = 7.1 Hz, 3H). | (method A) 302.3 $[M + H]^+$ at 0.65 min |

TABLE 6-continued

| Preparatory examples prepared via Suzuki-Miyaura procedure A. | | | | |
|---|---|---|---|---|
| Preparatory Example | Name | Structure | $^1$H NMR δ (500 MHz) | LCMS (ES+) m/z |
| 16D | Ethyl (5R)-5-methyl-2-(3-methylpyridin-4-yl)-6,7-dihydro-5H-pyrazolo[5,1-b][1,3]oxazine-3-carboxylate | 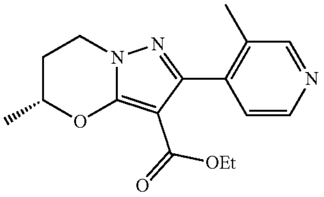 [SMILES: CCOC(=O)c1c(-c2ccncc2C)nn2c1O[C@H](C)CC2] | (DMSO-$d_6$) 8.45 (s, 1H), 8.39 (d, J = 4.8 Hz, 1H), 7.16 (d, J = 4.9 Hz, 1H), 4.68-4.53 (m, 1H), 4.20-4.11 (m, 2H), 3.96 (q, J = 7.1 Hz, 2H), 2.32-2.24 (m, 1H), 2.13 (s, 3H), 2.11-1.98 (m, 1H), 1.45 (d, J = 6.3 Hz, 3H), 0.99 (t, J = 7.1 Hz, 3H). | (method E) 302.3 $[M + H]^+$ at 0.60 min |
| 16E | Ethyl (5R)-2-(furan-3-yl)-5-methyl-6,7-dihydro-5H-pyrazolo[5,1-b][1,3]oxazine-3-carboxylate | 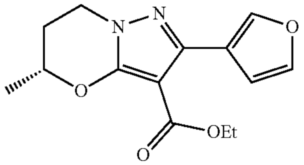 [SMILES: CCOC(=O)c1c(-c2ccoc2)nn2c1O[C@H](C)CC2] | ($CDCl_3$) 8.25 (dd, J = 1.6, 0.8 Hz, 1H), 7.42 (t, J = 1.7 Hz, 1H), 6.88 (dd, J = 1.9, 0.8 Hz, 1H), 4.55-4.45 (m, 1H), 4.28 (q, J = 7.1 Hz, 2H), 4.25-4.19 (m, 1H), 4.17-4.09 (m, 1H), 2.28-2.18 (m, 1H), 2.15-2.05 (m, 1H), 1.56 (d, J = 6.3 Hz, 3H), 1.34 (t, J = 7.1 Hz, 3H). | (method E) 277.3 $[M + H]^+$ at 0.58 min |
| 16F | Ethyl (5R)-5-methyl-2-thiophen-3-yl-6,7-dihydro-5H-pyrazolo[5,1-b][1,3]oxazine-3-carboxylate | 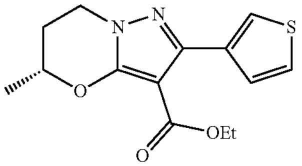 [SMILES: CCOC(=O)c1c(-c2ccsc2)nn2c1O[C@H](C)CC2] | (DMSO-$d_6$) 8.02 (dd, J = 3.0, 1.2 Hz, 1H), 7.50 (dd, J = 5.0, 3.0 Hz, 1H), 7.46 (dd, J = 5.0, 1.3 Hz, 1H), 4.65-4.47 (m, 1H), 4.21-4.05 (m, 4H), 2.31-2.21 (m, 1H), 2.10-1.93 (m, 1H), 1.43 (d, J = 6.3 Hz, 3H), 1.21 (t, J = 7.1 Hz, 3H). | (method E) 293.3 $[M + H]^+$ at 0.61 min |
| 17A | Ethyl (5S)-2-(2-fluorophenyl)-5-methyl-6,7-dihydro-5H-pyrazolo[5,1-b][1,3]oxazine-3-carboxylate | 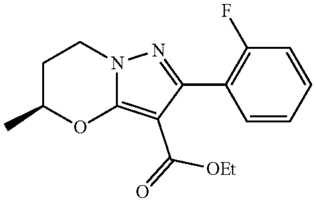 [SMILES: CCOC(=O)c1c(-c2ccccc2F)nn2c1O[C@@H](C)CC2] | (DMSO-$d_6$) 7.48-7.36 (m, 2H), 7.25-7.17 (m, 2H), 4.65-4.57 (m, 1H), 4.20-4.11 (m, 2H), 4.03-3.94 (m, 2H), 2.32-2.24 (m, 1H), 2.11-1.99 (m, 1H), 1.44 (d, J = 6.3 Hz, 3H), 1.02 (t, J = 7.1 Hz, 3H). | (method A) 305.6 $[M + H]^+$ at 1.23 min |
| 17B | Ethyl (5S)-2-(2,6-difluoropyridin-3-yl)-5-methyl-6,7-dihydro-5H-pyrazolo[5,1-b][1,3]oxazine-3-carboxylate | 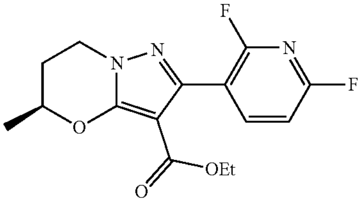 [SMILES: CCOC(=O)c1c(-c2ccc(F)nc2F)nn2c1O[C@@H](C)CC2] | ($CDCl_3$) 8.01-7.93 (m, 1H), 6.87 (dd, J = 8.0, 2.8 Hz, 1H), 4.62-4.52 (m, 1H), 4.30-4.22 (m, 1H), 4.21-4.16 (m, 1H), 4.15 (q, J = 7.0 Hz, 2H), 2.33-2.25 (m, 1H), 2.22-2.10 (m, 1H), 1.60 (d, J = 6.4 Hz, 3H), 1.15 (t, J = 7.1 Hz, 3H). | (method A) 323.7 $[M + H]^+$ at 1.20 min |
| 18A | Ethyl 2-(2-fluorophenyl)-6,6-dimethyl-5,7-dihydropyrazolo[5,1-b][1,3]oxazine-3-carboxylate | 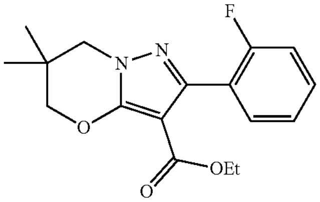 [SMILES: CCOC(=O)c1c(-c2ccccc2F)nn2c1OCC(C)(C)C2] | ($CDCl_3$) 4.31 (q, J = 7.1 Hz, 2H), 4.03 (s, 2H), 3.80 (s, 2H), 1.35 (t, J = 7.1 Hz, 3H), 1.15 (s, 6H). | (method E) 319.7 $[M + H]^+$ at 0.61 min |
| 19A | Ethyl 2-phenylspiro[5,7-dihydropyrazolo[5,1-b][1,3]oxazine-6,3'-oxetane]-3-carboxylate | 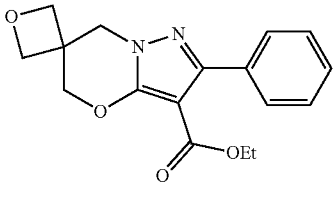 [SMILES: CCOC(=O)c1c(-c2ccccc2)nn2c1OCC1(COC1)C2] | ($CDCl_3$) 7.63-7.56 (m, 2H), 7.42-7.34 (m, 3H), 4.66 (q, J = 6.9 Hz, 4H), 4.62 (s, 2H), 4.41 (s, 2H), 4.19 (q, J = 7.1 Hz, 2H), 1.19 (t, J = 7.1 Hz, 3H). | (method A) 315.4 $[M + H]^+$ at 1.10 min |

TABLE 6-continued

Preparatory examples prepared via Suzuki-Miyaura procedure A.

| Preparatory Example | Name | Structure | $^{1}H$ NMR δ (500 MHz) | LCMS (ES+) m/z |
|---|---|---|---|---|
| 19B | Ethyl 2-(2-fluorophenyl) spiro[5,7-dihydropyrazolo[5,1-b][1,3]oxazine-6,3'-oxetane]-3-carboxylate | 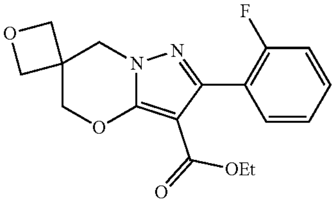 [SMILES: CCOC(=O)c1c(-c2ccccc2F)nn2c1OCC1(COC1)C2] | ($CDCl_3$) 7.43 (td, J = 7.4, 1.8 Hz, 1H), 7.41-7.33 (m, 1H), 7.18 (td, J = 7.5, 1.1 Hz, 1H), 7.13-7.05 (m, 1H), 4.70-4.61 (m, 6H), 4.42 (s, 2H), 4.14 (q, J = 7.1 Hz, 2H), 1.10 (t, J = 7.1 Hz, 3H). | (method A) 333.4 $[M + H]^+$ at 1.10 min |
| 20A | Ethyl 2-(2-fluorophenyl)-6,7-dihydro-5H-pyrazolo[5,1-b][1,3]thiazine-3-carboxylate | 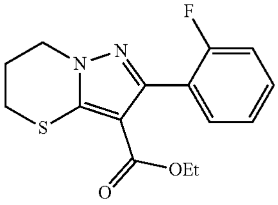 [SMILES: CCOC(=O)c1c(-c2ccccc2F)nn2c1SCCC2] | Not available | (method E) 307.3 $[M + H]^+$ at 0.62 min |
| 20B | Ethyl 2-(2,4-difluorophenyl)-6,7-dihydro-5H-pyrazolo[5,1-b][1,3]thiazine-3-carboxylate | 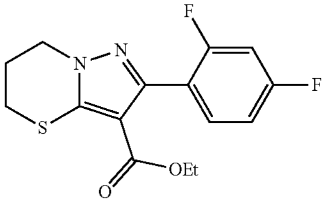 [SMILES: CCOC(=O)c1c(-c2ccc(F)cc2F)nn2c1SCCC2] | Not available | (method E) 325.2 $[M + H]^+$ at 0.64 min |

21A Ethyl 2-(6 fluoropyridin-3 yl)-6,7-dihydro-5H-pyrazolo[5,1-b][1,3]oxazine-3-carboxylate (Suzuki-Miyaura Procedure B)

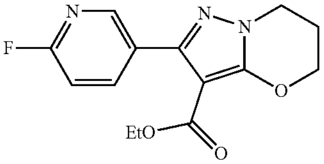 [SMILES: CCOC(=O)c1c(-c2ccc(F)nc2)nn2c1OCCC2]

Intermediate 9A (300 mg, 1.09 mmol), XPhos Pd G2 (43 mg, 0.055 mmol) and 2-fluoropyridine-5-boronic acid (231 mg, 1.64 mmol) were combined in a microwave vial, which was sealed, evacuated and sparged with $N_2$ (3×). $K_3PO_4$ (2 M aq; 1.09 mL, 2.18 mmol) and THE (3 mL), which had both been degassed with $N_2$, were added and the vial heated by MWI at 80° C. for 0.5 h. The cooled mixture was concentrated under reduced pressure and the resulting residue was purified by flash chromatography (50-100% EtOAc in heptane) to afford an off-white solid (270 mg, 85%). $^{1}H$ NMR (400 MHz, DMSO-$d_6$) δ 8.48-8.33 (m, 1H), 8.15 (td, J=8.3, 2.5 Hz, 1H), 7.22 (ddd, J=8.6, 2.9, 0.7 Hz, 1H), 4.55-4.37 (m, 2H), 4.22-3.99 (m, 4H), 2.31-2.19 (m, 2H), 1.14 (t, J=7.1 Hz, 3H). LRMS (APCI+) m/z 292.4 $[M+H]^+$.

The following intermediate compounds were prepared in an analogous manner to intermediate 21A. The reaction time varied between 30 min to 1 h 30 min, with heating by MWI or by conventional heating.

TABLE 7

Preparatory examples prepared via Suzuki-Miyaura procedure B.

| Preparatory Example | Name | Structure | $^{1}H$ NMR δ (DMSO-$d_6$) | LRMS APCI+ m/z; TLC $R_f$ |
|---|---|---|---|---|
| 21B | Ethyl 2-(2-methylphenyl)-6,7-dihydro-5H-pyrazolo[5,1-b][1,3]oxazine-3-carboxylate | 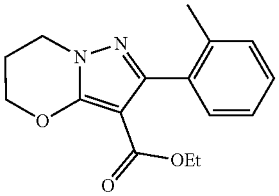 [SMILES: CCOC(=O)c1c(-c2ccccc2C)nn2c1OCCC2] | (400 MHz) 7.29-7.10 (m, 4H), 4.49-4.38 (m, 2H), 4.12 (t, J = 6.1 Hz, 2H), 3.95 (q, J = 7.0 Hz, 1H), 2.29-2.19 (m, 2H), 2.11 (s, 3H), 0.98 (t, J = 7.1 Hz, 3H). | 286.6 $[M + H]^+$ |

TABLE 7-continued

Preparatory examples prepared via Suzuki-Miyaura procedure B.

| Preparatory Example | Name | Structure | $^1H$ NMR δ (DMSO-$d_6$) | LRMS APCI+ m/z; TLC $R_f$ |
|---|---|---|---|---|
| 21C | Ethyl 2-(6-cyclopropylpyridin-3-yl)-6,7-dihydro-5H-pyrazolo[5,1-b][1,3]oxazine-3-carboxylate | 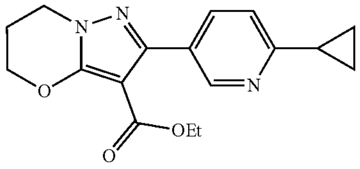 [SMILES: CCOC(=O)c1c(-c2ccc(C3CC3)nc2)nn2c1OCCC2] | Not available | 313.8 [M + H]$^+$; $R_f$ = 0.29 (EtOAc) |
| 21D | Ethyl 2-pyridin-3-yl-6,7-dihydro-5H-pyrazolo[5,1-b][1,3]oxazine-3-carboxylate | 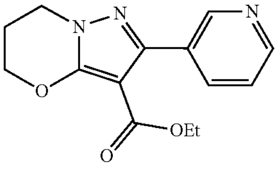 [SMILES: CCOC(=O)c1c(-c2cccnc2)nn2c1OCCC2] | (400 MHz) 8.72 (dd, J = 2.2, 0.9 Hz, 1H), 8.55 (dd, J = 4.8, 1.7 Hz, 1H), 7.94 (ddd, J = 7.9, 2.3, 1.7 Hz, 1H), 7.42 (ddd, J = 7.9, 4.8, 0.9 Hz, 1H), 4.49-4.42 (m, 2H), 4.15 (t, J = 6.1 Hz, 2H), 4.09 (q, J = 7.1 Hz, 2H), 2.30-2.15 (m, 2H), 1.13 (t, J = 7.1 Hz, 3H). | 273.9 [M + H]$^+$ |
| 21E | Ethyl 2-(2,4-difluorophenyl)-6,7-dihydro-5H-pyrazolo[5,1-b][1,3]oxazine-3-carboxylate, | 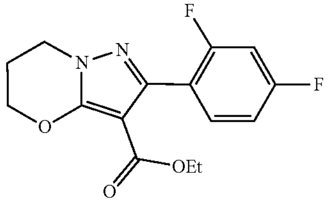 [SMILES: CCOC(=O)c1c(-c2ccc(F)cc2F)nn2c1OCCC2] | Not available | 308.7 [M + H]$^+$ $R_f$ = 0.25 (2:1 EtOAc: heptane) |
| 21F | Ethyl 2-[2-fluoro-4-(hydroxymethyl)phenyl]-6,7-dihydro-5H-pyrazolo[5,1-b][1,3]oxazine-3-carboxylate | 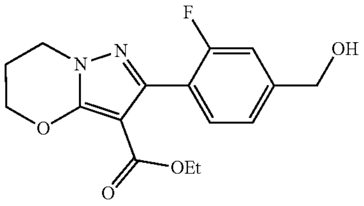 [SMILES: CCOC(=O)c1c(-c2ccc(CO)cc2F)nn2c1OCCC2] | (400 MHz) δ 7.33 (t, J = 7.7 Hz, 1H), 7.18-7.07 (m, 2H), 5.36 (t, J = 5.8 Hz, 1H), 4.54 (d, J = 5.8 Hz, 2H), 4.44 (dd, J = 5.8, 4.6 Hz, 2H), 4.14 (t, J = 6.1 Hz, 2H), 4.01 (q, J = 7.1 Hz, 2H), 2.30-2.20 (m, 2H), 1.05 (t, J = 7.1 Hz, 3H). | 320.5 [M + H]$^+$ |
| 21G | Ethyl 2-(2-fluoro-4-methylsulfonylphenyl)-6,7-dihydro-5H-pyrazolo[5,1-b][1,3]oxazine-3-carboxylate | 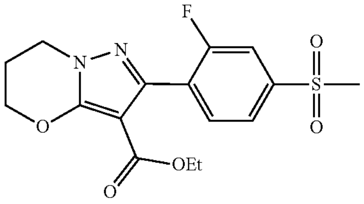 [SMILES: CCOC(=O)c1c(-c2ccc(S(C)(=O)=O)cc2F)nn2c1OCCC2] | (400 MHz) δ 7.85-7.77 (m, 2H), 7.73-7.65 (m, 1H), 4.54-4.42 (m, 2H), 4.17 (t, J = 6.1 Hz, 2H), 4.03 (q, J = 7.1 Hz, 2H), 3.32 (s, 3H), 2.32-2.21 (m, 2H), 1.06 (t, J = 7.1 Hz, 3H). | 368.6 [M + H]$^+$ |
| 21H | Ethyl 2-(1-methylindazol-4-yl)-6,7-dihydro-5H-pyrazolo[5,1-b][1,3]oxazine-3-carboxylate | 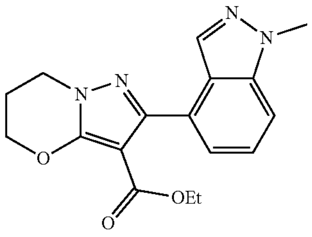 [SMILES: CCOC(=O)c1c(-c2cccc3c2cnn3C)nn2c1OCCC2] | (400 MHz) δ 7.91 (d, J = 1.0 Hz, 1H), 7.65-7.61 (m, 1H), 7.40 (dd, J = 8.4, 7.1 Hz, 1H), 7.30 (dd, J = 7.1, 0.8 Hz, 1H), 4.47 (dd, J = 5.8, 4.6 Hz, 2H), 4.19 (t, J = 6.1 Hz, 2H), 4.06 (s, 3H), 4.00 (q, J = 7.1 Hz, 2H), 2.28 (q, J = 5.6 Hz, 2H), 1.00 (t, J = 7.1 Hz, 3H). | 327.5 [M + H]$^+$ |
| 21I | Ethyl 2-(2-fluoropyridin-3-yl)-6,7-dihydro-5H-pyrazolo[5,1-b][1,3]oxazine-3-carboxylate | 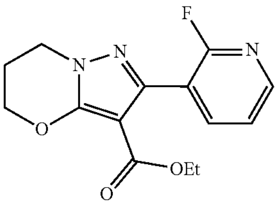 [SMILES: CCOC(=O)c1c(-c2cccnc2F)nn2c1OCCC2] | (400 MHz) δ 8.27 (ddd, J = 4.9, 2.0, 1.0 Hz, 1H), 7.95 (ddd, J = 9.4, 7.4, 2.0 Hz, 1H), 7.41 (ddd, J = 7.1, 4.9, 1.9 Hz, 1H), 4.52-4.40 (m, 2H), 4.16 (t, J = 6.1 Hz, 2H), 4.02 (q, J = 7.1 Hz, 2H), 2.32-2.19 (m, 2H), 1.03 (t, J = 7.1 Hz, 3H). | 291.2 [M + H]$^+$ |

TABLE 7-continued

| Preparatory examples prepared via Suzuki-Miyaura procedure B. | | | | |
|---|---|---|---|---|
| Preparatory Example | Name | Structure | $^1$H NMR δ (DMSO-$d_6$) | LRMS APCI+ m/z; TLC $R_f$ |
| 21J | Ethyl 2-(1-ethylpyrazol-4-yl)-6,7-dihydro-5H-pyrazolo[5,1-b][1,3]oxazine-3-carboxylate | 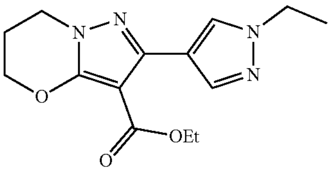 [SMILES: CCOC(=O)c1c(-c2cnn(CC)c2)nn2c1OCCC2] | Not availabe | 291.3 [M + H]$^+$ $R_f$ = 0.30 (EtOAc) |
| 21K | Ethyl 2-(1-propan-2-ylpyrazol-4-yl)-6,7-dihydro-5H-pyrazolo[5,1-b][1,3]oxazine-3-carboxylate | 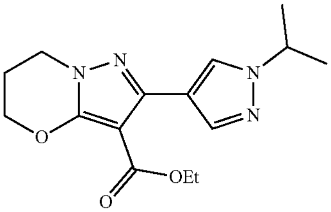 [SMILES: CCOC(=O)c1c(-c2cnn(C(C)C)c2)nn2c1OCCC2] | (400 MHz) δ 8.21 (d, J = 0.7 Hz, 1H), 7.83 (d, J = 0.7 Hz, 1H), 4.51 (hept, J = 6.6 Hz, 1H), 4.41 (dd, J = 5.8, 4.6 Hz, 2H), 4.17 (q, J = 7.1 Hz, 2H), 4.07 (t, J = 6.1 Hz, 2H), 2.25-2.16 (m, 2H), 1.42 (d, J = 6.6 Hz, 6H), 1.23 (t, J = 7.1 Hz, 3H). | 305.4 [M + H]$^+$ |
| 21L | Ethyl 2-[1-(2,2,2-trifluoroethyl)pyrazolo-4-yl]-6,7-dihydro-5H-pyrazolo[5,1-b][1,3]oxazine-3-carboxylate | 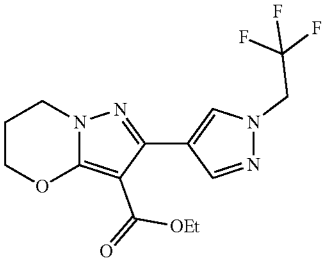 [SMILES: CCOC(=O)c1c(-c2cnn(CC(F)(F)F)c2)nn2c1OCCC2] | (400 MHz) δ 8.40 (s, 1H), 7.95 (d, J = 0.6 Hz, 1H), 5.19 (q, J = 9.2 Hz, 2H), 4.47-4.38 (m, 2H), 4.18 (q, J = 7.1 Hz, 2H), 4.09 (t, J = 6.1 Hz, 2H), 2.26-2.15 (m, 2H), 1.23 (t, J = 7.1 Hz, 3H). | 345.4 [M + H]$^+$ |
| 21M | Ethyl 2-[1-(oxan-4-yl)pyrazol-4-yl]-6,7-dihydro-5H-pyrazolo[5,1-b][1,3]oxazine-3-carboxylate | 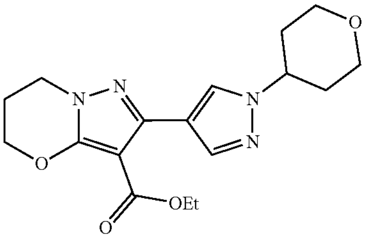 [SMILES: CCOC(=O)c1c(-c2cnn(C3CCOCC3)c2)nn2c1OCCC2] | (400 MHz) δ 8.25 (d, J = 0.6 Hz, 1H), 7.85 (d, J = 0.6 Hz, 1H), 4.48-4.36 (m, 3H), 4.17 (q, J = 7.1 Hz, 2H), 4.08 (t, J = 6.1 Hz, 2H), 4.01-3.90 (m, 2H), 3.46 (td, J = 11.5, 3.1 Hz, 2H), 2.26-2.15 (m, 2H), 2.02-1.86 (m, 4H), 1.23 (t, J = 7.1 Hz, 3H). | 347.5 [M + H]$^+$ |
| 22A | Ethyl 2-(2-fluorophenyl)-5,5-dimethyl-6,7-dihydropyrazolo[5,1-b][1,3]oxazine-3-carboxylate | 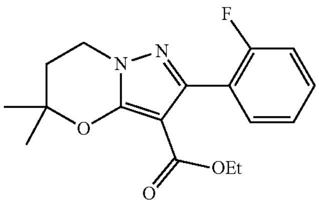 [SMILES: CCOC(=O)c1c(-c2ccccc2F)nn2c1OC(C)(C)CC2] | (700 MHz) 7.49-7.37 (m, 2H), 7.29-7.10 (m, 2H), 4.16 (t, J = 6.3 Hz, 2H), 3.98 (q, J = 7.1 Hz, 2H), 2.18 (t, J = 6.3 Hz, 2H), 1.45 (s, 6H), 1.01 (t, J = 7.1 Hz, 3H). | 318.9 [M + H]$^+$ |
| 23A | Ethyl 2-(2-fluorophenyl)spiro[6,7-dihydropyrazolo[5,1-b][1,3]oxazine-5,1'-cyclopropane]-3-carboxylate | 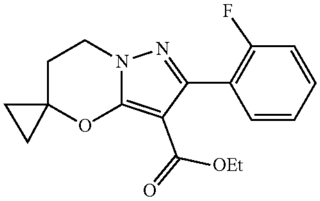 [SMILES: CCOC(=O)c1c(-c2ccccc2F)nn2c1OC1(CC2)CC1] | (700 MHz) 7.50-7.39 (m, 2H), 7.27-7.19 (m, 2H), 4.27 (t, J = 6.1 Hz, 2H), 3.97 (q, J = 7.1 Hz, 2H), 2.29 (t, J = 6.1 Hz, 2H), 1.13-1.06 (m, 2H), 1.01 (t, J = 7.1 Hz, 3H), 0.94-0.82 (m, 2H). | 316.9 [M + H]$^+$ |

TABLE 7-continued

| Preparatory examples prepared via Suzuki-Miyaura procedure B. | | | | |
|---|---|---|---|---|
| Preparatory Example | Name | Structure | $^1$H NMR δ (DMSO-$d_6$) | LRMS APCI+ m/z; TLC $R_f$ |
| 24A | Ethyl 2-(2-fluorophenyl)-7-propan-2-yl-6,7-dihydro-5H-pyrazolo[5,1-b][1,3]oxazine-3-carboxylate | 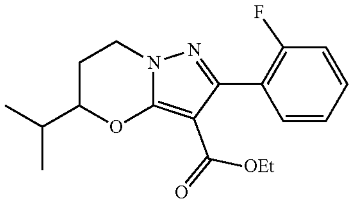 | (400 MHz) 7.50-7.32 (m, 2H), 7.31-7.11 (m, 2H), 4.29-4.06 (m, 3H), 4.06-3.91 (m, 2H), 2.16-1.85 (m, 3H), 1.16-0.89 (m, 9H). | 333.1 [M + H]$^+$ |
| 25A | Ethyl (6R)-2-(2-fluorophenyl)-6-methyl-6,7-dihydro-5H-pyrazolo[5,1-b][1,3]oxazine-3-carboxylate | 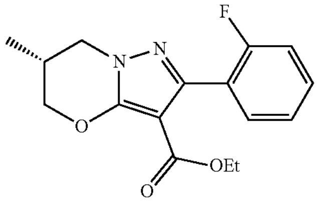 [SMILES: CCOC(=O)c1c(-c2ccccc2F)nn2c1OC[C@H](C)C2] | (700 MHz) 7.47-7.37 (m, 2H), 7.29-7.15 (m, 2H), 4.51-4.41 (m, 1H), 4.24 (dd, J = 12.2, 5.3 Hz, 1H), 4.13-4.06 (m, 1H), 4.05-3.94 (m, 2H), 3.78 (ddd, J = 11.7, 8.6, 1.3 Hz, 1H), 2.48 (s, 1H), 1.10-0.99 (m, 6H). | 304.8 [M + H]$^+$ |
| 25B | Ethyl (6S)-2-(2-fluorophenyl)-6-methyl-6,7-dihydro-5H-pyrazolo[5,1-b][1,3]oxazine-3-carboxylate | 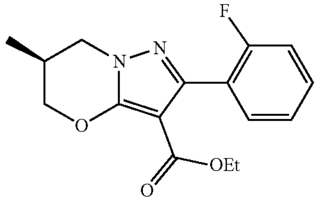 [SMILES: CCOC(=O)c1c(-c2ccccc2F)nn2c1OC[C@@H](C)C2] | (700 MHz) 7.47-7.37 (m, 2H), 7.26-7.20 (m, 2H), 4.46 (ddd, J = 10.7, 3.6, 1.4 Hz, 1H), 4.23 (ddd, J = 12.1, 5.4, 1.4 Hz, 1H), 4.09 (dd, J = 10.7, 9.5 Hz, 1H), 4.01 (qd, J = 7.1, 0.7 Hz, 2H), 3.78 (dd, J = 12.1, 9.0 Hz, 1H), 1.07-1.00 (m, 6H). | 304.9 [M + H]$^+$ |
| 25C | Ethyl 6-ethyl-2-(2-fluorophenyl)-6,7-dihydro-5H-pyrazolo[5,1-b][1,3]oxazine-3-carboxylate | 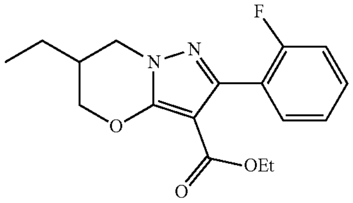 [SMILES: CCOC(=O)c1c(-c2ccccc2F)nn2c1OCC(CC)C2] | (400 MHz) δ 7.51-7.34 (m, 2H), 7.28-7.17 (m, 2H), 4.51 (ddd, J = 10.9, 3.5, 1.2 Hz, 1H), 4.31-4.21 (m, 1H), 4.14 (dd, J = 10.9, 9.3 Hz, 1H), 4.07-3.95 (m, 2H), 3.82 (dd, J = 12.2, 9.0 Hz, 1H), 2.30-2.19 (m, 1H), 1.49-1.30 (m, 2H), 1.04 (t, J = 7.1 Hz, 3H), 0.99 (t, J = 7.5 Hz, 3H). | 319.0 [M + H]$^+$ |
| 25D | Ethyl 2-(2-fluorophenyl)-6-propyl-6,7-dihydro-5H-pyrazolo[5,1-b][1,3]oxazine-3-carboxylate | 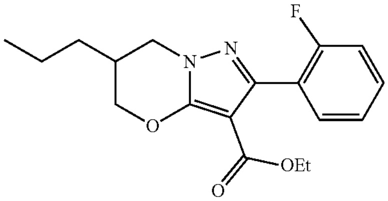 [SMILES: CCCC1COc2c(C(=O)OCC)c(-c3ccccc3F)nn2C1] | (400 MHz) 7.50-7.35 (m, 2H), 7.28-7.14 (m, 2H), 4.56-4.46 (m, 1H), 4.29-4.20 (m, 1H), 4.13 (dd, J = 10.9, 9.5 Hz, 1H), 4.07-3.94 (m, 2H), 3.82 (dd, J = 12.2, 9.1 Hz, 1H), 2.41-2.32 (m, 1H), 1.51-1.28 (m, 4H), 1.03 (t, J = 7.1 Hz, 3H), 0.92 (t, J = 6.9 Hz, 3H). | 333.1 [M + H]$^+$ |
| 25E | Ethyl 2-(2-fluorophenyl)-6-propan-2-yl-6,7-dihydro-5H-pyrazolo[5,1-b][1,3]oxazine-3-carboxylate | 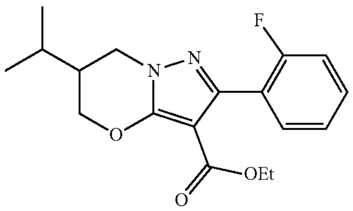 | (400 MHz) 7.48-7.37 (m, 2H), 7.26-7.19 (m, 2H), 4.59 (dd, J = 11.0, 3.3 Hz, 1H), 4.25-4.15 (m, 2H), 4.01 (q, J = 7.1 Hz, 2H), 3.93 (dd, J = 12.3, 10.0 Hz, 1H), 2.22-2.04 (m, 1H), 1.76-1.55 (m, 1H), 1.12-0.90 (m, 9H). | 333.1 [M + H]$^+$ |
| 25F | Ethyl 2-(2-fluorophenyl)spiro[5,7-dihydropyrazolo[5,1-b][1,3]oxazine-6,1'-cyclopropane]-3-carboxylate | 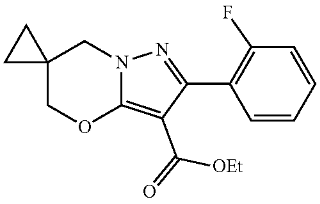 | (400 MHz) 7.50-7.34 (m, 2H), 7.26-7.12 (m, 2H), 4.26 (s, 2H), 4.05 (s, 2H), 4.01 (q, J = 7.1 Hz, 2H), 1.03 (t, J = 7.1 Hz, 3H), 0.82 (s, 4H). | 317.1 [M + H]$^+$ |

TABLE 7-continued

Preparatory examples prepared via Suzuki-Miyaura procedure B.

| Preparatory Example | Name | Structure | $^1H$ NMR δ (DMSO-$d_6$) | LRMS APCI+ m/z; TLC $R_f$ |
|---|---|---|---|---|
| 25G | Ethyl 2-(2-fluorophenyl)spiro [5,7-dihydropyrazolo[5,1-b][1,3] oxazine-6,1'-cyclobutane]-3-carboxylate | 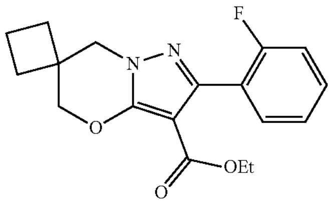 [SMILES: CCOC(=O)c1c(-c2ccccc2F)nn2c1OCC1(CCC1)C2] | (400 MHz) 7.49-7.37 (m, 2H), 7.32-7.16 (m, 2H), 4.39 (s, 2H), 4.15 (s, 2H), 4.00 (q, J = 7.1 Hz, 2H), 2.12-1.90 (m, 6H), 1.03 (t, J = 7.1 Hz, 3H). | 331.3 $[M + H]^+$ |

26A Ethyl 2-(2,4-difluorophenyl)-4,4-dioxo-6,7-dihydro-5H-pyrazolo[5,1-b][1,3]thiazine-3-carboxylate

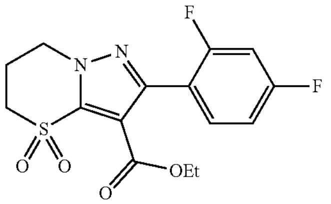 [SMILES: CCOC(=O)c1c(-c2ccc(F)cc2F)nn2c1S(=O)(=O)CCC2]

mCPBA (125 mg, 0.510 mmol) was added to a cooled (0° C.) solution of intermediate 20B (65.5 mg, 0.2 mmol) in $CH_2Cl_2$ (5 mL) and stirred at rt for 18 h. The reaction was diluted with $CH_2Cl_2$ (50 mL) and quenched with 10% w/v aq. $Na_2S_2O_3$ (100 mL). The separated organic phase was washed with sat. aq. $NaHCO_3$ (100 mL) and brine (100 mL), passed through a phase separation cartridge and concentrated in vacuo to give a white solid (60 mg, 83%) that was used without further purification. LCMS (Method E): m/z 357.2 $[M+H]^+$ at 0.59 min.

26B Ethyl 2-(2-fluorophenyl)-4,4-dioxo-6,7-dihydro-5H-pyrazolo[5,1-b][1,3]thiazine-3-carboxylate

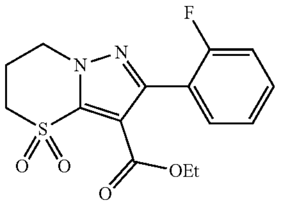 [SMILES: CCOC(=O)c1c(-c2ccccc2F)nn2c1S(=O)(=O)CCC2]

Prepared by an analogous procedure to that described for intermediate 26A. LCMS (Method E): m/z 339.2 $[M+H]^+$ at 0.57 min.

27A Ethyl 3-(2-fluorophenyl)-6,7-dihydro-5H-pyrazolo[5,1-b][1,3]oxazine-2-carboxylate

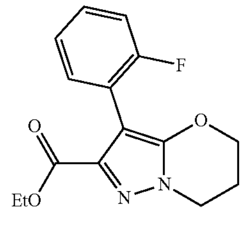 [SMILES: CCOC(=O)c1nn2c(c1-c1ccccc1F)OCCC2]

A vial was charged with Pd-170 (20 mg, 0.030 mmol), 2-fluorophenylboronic acid (155 mg, 1.10 mmol), intermediate 12A (150 mg, 0.55 mmol) and $K_3PO_4$ (130 mg, 0.610 mmol). The vial was evacuated, filled with $N_2$, THE (2 mL) added, sparged with $N_2$ and heated at 70° C. overnight. The reaction mixture was partitioned between EtOAc (20 mL) and 1:1 water-brine (20 mL). The aqueous phase was extracted with EtOAc (2×10 mL), and the combined organic phases washed with brine (20 mL), dried ($MgSO_4$) and concentrated under reduced pressure. Purification by flash chromatography (0-80%, EtOAc in iso-hexanes) afforded a white solid (154 mg, 87%). LCMS (method A) 245.2 $[M-OEt]^+$ at 1.25 min. $^1H$ NMR (500 MHz, $CDCl_3$) δ 7.38-7.32 (m, 1H), 7.32-7.25 (m, 1H), 7.18-7.12 (m, 1H), 7.12-7.05 (m, 1H), 4.36-4.33 (m, 2H), 4.33-4.27 (m, 4H), 2.37-2.25 (m, 2H), 1.25 (t, J=7.1 Hz, 3H).

27B Ethyl 3-(2,6-difluoropyridin-3-yl)-6,7-dihydro-5H-pyrazolo[5,1-b][1,3]oxazine-2-carboxylate

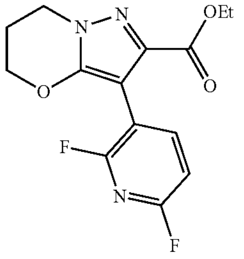 [SMILES: CCOC(=O)c1nn2c(c1-c1ccc(F)nc1F)OCCC2]

Prepared by an analogous procedure to that described for intermediate 27A. LCMS (method A) 264.3 $[M-OEt]^+$ at 1.19 min. $^1H$ NMR (500 MHz, $CDCl_3$) δ 7.93-7.84 (m, 1H), 6.84 (dd, J=8.1, 2.9 Hz, 1H), 4.38-4.35 (m, 2H), 4.34-4.30 (m, 4H), 2.39-2.24 (m, 2H), 1.29 (t, J=7.1 Hz, 3H).

28A Ethyl 7-(2-fluorophenyl)-2,3-dihydropyrazolo [5,1-b][1,3]oxazole-6-carboxylate

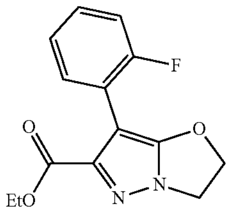 [SMILES: CCOC(=O)c1nn2c(c1-c1ccccc1F)OCC2]

Prepared by an analogous procedure to that described for intermediate 27A. LCMS (method A) 250.2 [M-OEt]$^+$ at 1.16 min. $^1$H NMR (500 MHz, $CDCl_3$) δ 7.42-7.35 (m, 1H), 7.32-7.26 (m, 1H), 7.18-7.12 (m, 1H), 7.11-7.07 (m, 1H), 5.17-5.11 (m, 2H), 4.48-4.42 (m, 2H), 4.31 (q, J=7.1 Hz, 2H), 1.29 (t, J=7.1 Hz, 3H).

29A Ethyl 2-[6-(ethylamino)-2-fluoropyridin-3-yl]-6,7-dihydro-5H-pyrazolo[5,1-b][1,3]oxazine-3-carboxylate

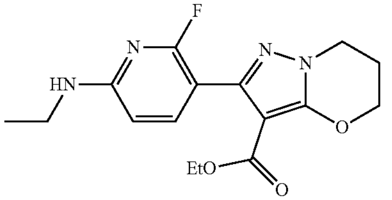 [SMILES: CCNc1ccc(-c2nn3c(c2C(=O)OCC)OCCC3)c(F)n1]

Ethylamine (1.46 mL, 2.91 mmol, 2 M in MeOH) and DIPEA (0.2 mL, 1.16 mmol) were added to a solution of intermediate 14C (180 mg, 0.58 mmol) in DMSO (3 mL) and heated at 130° C. for 0.5 h. The reaction was cooled to rt, diluted with water (10 mL) and brine (10 mL), extracted with EtOAc (3×10 mL), the combined organic fractions were dried ($Na_2SO_4$) and concentrated under reduced pressure. Purification by flash chromatography (50-100a EtOAc in heptane) afforded a white solid (79 mg, 41%). $^1$H NMR (400 MHz, DMSO-$d_6$) δ 7.45 (dd, J 10.0, 8.2 Hz, 1H), 7.02 (t, J=5.5 Hz, 1H), 6.32 (dd, J=8.3, 1.9 Hz, 1H), 4.42 (dd, J=6.0, 4.4 Hz, 2H), 4.10 (t, J=6.1 Hz, 2H), 4.03 (q, J=7.1 Hz, 2H), 3.25-3.18 (m, 2H), 2.26-2.18 (m, 2H), 1.13 (t, J=7.2 Hz, 3H), 1.09 (t, J=7.1 Hz, 3H). LRMS (APCI+) m/z 334.9 [M+H]$^+$.

The following intermediate compounds were prepared in an analogous manner to intermediate 29A. The stoichiometry of the amine reactant may be varied from 5-10 eq. Preparatory examples 29C and 33A were heated at 50° C. overnight. Preparatory example 30A was heated at 130° C. overnight. Preparatory examples 30B and 30C were heated at 130° C. for ~48 h.

TABLE 8

Preparatory examples prepared via general $S_NAr$ procedure

| Preparatory Example | Name | Structure | $^1$H NMR δ | LCMS (ES+); LRMS (APCI+) m/z; TLC $R_f$; |
|---|---|---|---|---|
| 29B | Ethyl 2-[2-fluoro-6-(propan-2-ylamino) pyridin-3-yl]-6,7-dihydro-5H-pyrazolo [5,1-b][1,3] oxazine-3-carboxylate | 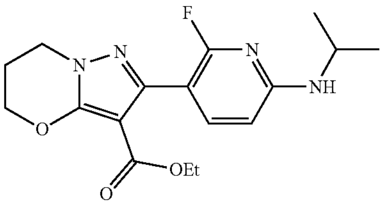 [SMILES: CCOC(=O)c1c(-c2ccc(NC(C)C)nc2F)nn2c1OCCC2] | (400 MHz, DMSO-$d_6$) δ 7.43 (dd, J = 10.0, 8.2 Hz, 1H), 6.91 (d, J = 7.6 Hz, 1H), 6.32 (dd, J = 8.3, 1.9 Hz, 1H), 4.48-4.39 (m, 2H), 4.10 (t, J = 6.1 Hz, 2H), 4.03 (q, J = 7.1 Hz, 2H), 3.95-3.82 (m, 1H), 2.30-2.14 (m, 2H), 1.14 (d, J = 6.4 Hz, 6H), 1.09 (t, J = 7.1 Hz, 3H) | 348.9 [M + H]$^+$ |
| 29C | Ethyl 2-[6-(cyclopropyl-amino)-2-fluoro-pyridin-3-yl]-6,7-dihydro-5H-pyrazolo[5,1-b][1,3] oxazine-3-carboxylate | 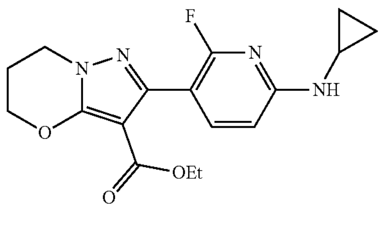 [SMILES: CCOC(=O)c1c(-c2ccc(NC3CC3)nc2F)nn2c1OCCC2] | (500 MHz, DMSO-$d_6$) δ 7.55 (dd, J = 9.8, 8.2 Hz, 1H), 7.29-7.23 (m, 1H), 6.47 (dd, J = 8.2, 1.8 Hz, 1H), 4.44-4.40 (m, 2H), 4.11 (t, J = 6.1 Hz, 2H), 4.03 (q, J = 7.1 Hz, 2H), 2.54-2.51 (m, 1H), 2.26-2.19 (m, 2H), 1.09 (t, J = 7.1 Hz, 3H), 0.76-0.66 (m, 2H), 0.49-0.39 (m, 2H) | LCMS (method A) 347.4 [M + H]$^+$ at 1.11 min. |

TABLE 8-continued

Preparatory examples prepared via general $S_NAr$ procedure

| Preparatory Example | Name | Structure | $^1$H NMR δ | LCMS (ES+); LRMS (APCI+) m/z; TLC $R_f$; |
|---|---|---|---|---|
| 30A | Ethyl 2-[6-(ethylamino)pyridin-3-yl]-6,7-dihydro-5H-pyrazolo[5,1-b][1,3]oxazine-3-carboxylate | 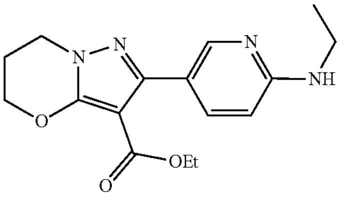 [SMILES: CCNc1ccc(-c2nn3c(c2C(=O)OCC)OCCC3)cn1] | (700 MHz, DMSO-$d_6$) δ 8.16 (dd, J = 2.4, 0.8 Hz, 1H), 7.55 (dd, J = 8.6, 2.4 Hz, 1H), 6.60 (t, J = 5.5 Hz, 1H), 6.41 (dd, J = 8.7, 0.8 Hz, 1H), 4.46-4.34 (m, 2H), 4.14-4.01 (m, 4H), 3.30-3.22 (m, 3H), 2.27-2.14 (m, 2H), 1.22-1.02 (m, 6H). | 316.8 $[M + H]^+$ |
| 30B | Ethyl 2-[6-(propan-2-ylamino)pyridin-3-yl]-6,7-dihydro-5H-pyrazolo[5,1-b][1,3]oxazine-3-carboxylate | 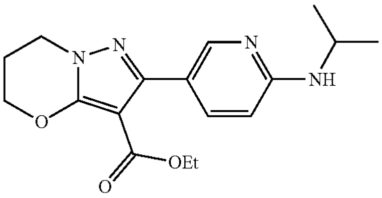 [SMILES: CCOC(=O)c1c(-c2ccc(NC(C)C)nc2)nn2c1OCCC2] | (400 MHz, DMSO-$d_6$) δ 8.15 (dd, J = 2.3, 0.7 Hz, 1H), 7.53 (dd, J = 8.7, 2.4 Hz, 1H), 6.47 (d, J = 7.6 Hz, 1H), 6.41 (dd, J = 8.7, 0.8 Hz, 1H), 4.47-4.35 (m, 2H), 4.14-4.06 (m, 4H), 4.06-3.93 (m, 1H), 2.27-2.16 (m, 2H), 1.22-1.09 (m, 9H). | 330.8 $[M + H]^+$ |
| 30C | Ethyl 2-[6-(cyclopropyl-amino)pyridin-3-yl]-6,7-dihydro-5H-pyrazolo[5,1-b][1,3]oxazine-3-carboxylate | 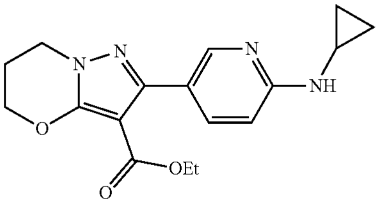 [SMILES: CCOC(=O)c1c(-c2ccc(NC3CC3)nc2)nn2c1OCCC2] | (400 MHz, DMSO-$d_6$) 8.19 (dd, J = 2.4, 0.8 Hz, 1H), 7.65 (dd, J = 8.6, 2.4 Hz, 1H), 6.90 (d, J = 2.5 Hz, 1H), 6.58 (dd, J = 8.7, 0.8 Hz, 1H), 4.46-4.38 (m, 2H), 4.13-3.98 (m, 4H), 2.27-2.17 (m, 2H), 1.16 (t, J = 7.1 Hz, 3H), 0.70 (td, J = 6.7, 4.5 Hz, 2H), 0.51-0.36 (m, 2H). | Rf = 0.13 (2:1 EtOAc: heptane) |
| 31A | Ethyl (5R)-2-[2-fluoro-6-(propan-2-ylamino)pyridin-3-yl]-5-methyl-6,7-dihydro-5H-pyrazolo[5,1-b][1,3]oxazine-3-carboxylate | 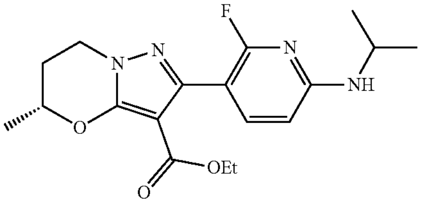 [SMILES: CCOC(=O)c1c(-c2ccc(NC(C)C)nc2F)nn2c1O[C@H](C)CC2] | (500 MHz, $CDCl_3$) δ 7.70-7.63 (m, 1H), 6.30-6.25 (m, 1H), 4.59-4.49 (m, 1H), 4.30-4.20 (m, 1H), 4.23-4.15 (m, 2H), 4.18-4.11 (m, 1H), 3.92-3.82 (m, 1H), 2.30-2.20 (m, 1H), 2.19-2.07 (m, 1H), 1.58 (d, J = 6.4 Hz, 3H), 1.26 (d, J = 6.4 Hz, 6H), 1.20 (t, J = 7.1 Hz, 3H). | LCMS (method A) 363.5 $[M + H]^+$ at 1.27 min |
| 32A | Ethyl (5S)-2-[2-fluoro-6-(propan-2-ylamino)pyridin-3-yl]-5-methyl-6,7-dihydro-5H-pyrazolo[5,1-b][1,3]oxazine-3-carboxylate | 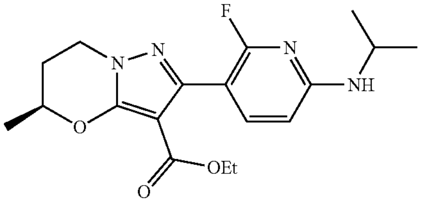 [SMILES: CCOC(=O)c1c(-c2ccc(NC(C)C)nc2F)nn2c1O[C@@H](C)CC2] | Not available | LCMS (method A) 363.4 $[M + H]^+$ at 1.27 min |
| 33A | Ethyl 3-[6-(cyclopropyl-amino)-2-fluoropyridin-3-yl]-6,7-dihydro-5H-pyrazolo[5,1-b][1,3]oxazine-2-carboxylate | 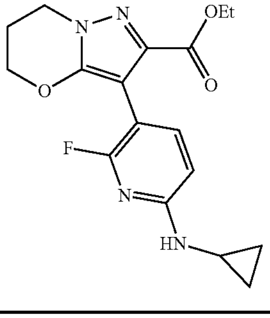 | Not available | LCMS (method A) 347.4 $[M + H]^+$ at 1.20 min. |

34A 2-(2-Fluorophenyl)-5,5-dimethyl-6,7-dihydro-pyrazolo[5,1-b][1,3]oxazine-3-carboxylic acid (Ester Hydrolysis Procedure A)

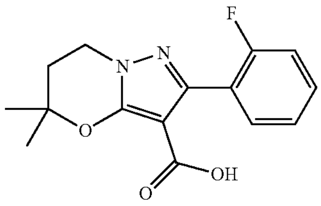 [SMILES: CC1(C)CCn2nc(-c3ccccc3F)c(C(=O)O)c2O1]

NaOH (2.5 M aq. soln, 0.88 mL, 2.18 mmol) was added to a solution of intermediate 22A (139 mg, 0.440 mmol) in EtOH (2 mL) and heated at 60° C. overnight. The volatiles were removed under reduced pressure, the residue suspended in water (15 mL) and acidified with 1 M HCl (aq; 2.62 mL) to pH≈2. The resultant precipitate was filtered, washing with water and dried under reduced pressure to afford a white solid (109 mg, 860) which was used without further purification. $^1$H NMR (700 MHz, DMSO-$d_6$) δ 11.65 (s, 1H), 7.44-7.36 (m, 2H), 7.25-7.17 (mi, 2H), 4.15 (t, J=6.4 Hz, 2H), 2.17 (t, J=6.4 Hz, 2H), 1.45 (s, 6H). LRMS (APCI+) m/z 291.2 $[M+H]^+$.

The following intermediate compounds were prepared by an analogous procedure to that described for intermediate 34A. The procedure may be performed at temperatures varying from 50-70° C. dependent upon the specific reaction substrate. The procedure may be modified by substituting 2.5 M aq. NaOH (5 eq.) with 5 M aq. NaOH (8 eq.).

TABLE 9

Preparatory examples prepared by ester hydrolysis procedure A

| Preparatory Example | Name | Structure | $^1$H NMR δ (DMSO-$d_6$) | LRMS (APCI+) m/z |
|---|---|---|---|---|
| 35A | 2-(2-Fluorophenyl)spiro[6,7-dihydropyrazolo[5,1-b][1,3]oxazine-5,1'-cyclopropane]-3-carboxylic acid | 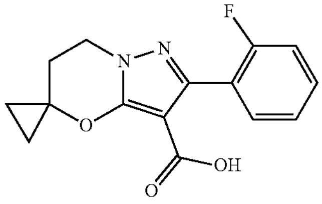 [SMILES: O=C(O)c1c(-c2ccccc2F)nn2c1OC1(CC2)CC1] | (700 MHz) 11.76 (s, 1H), 7.47-7.36 (m, 2H), 7.29-7.16 (m, 2H), 4.26 (t, J = 6.1 Hz, 2H), 2.28 (t, J = 6.1 Hz, 2H), 1.24-0.99 (m, 2H), 0.98-0.77 (m, 2H) | 289.2 $[M + H]^+$ |
| 36A | 2-(2-Fluorophenyl)-7-propan-2-yl-6,7-dihydro-5H-pyrazolo[5,1-b][1,3]oxazine-3-carboxylic acid | 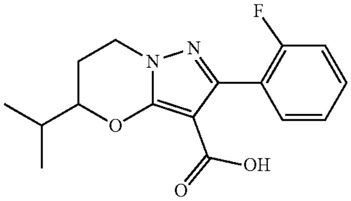 [SMILES: CC(C)C1CCn2nc(-c3ccccc3F)c(C(=O)O)c2O1] | (400 MHz) 11.68 (s, 1H), 7.55-7.29 (m, 2H), 7.29-6.98 (m, 2H), 4.30-4.06 (m, 3H), 2.30-2.18 (m, 1H), 2.16-1.85 (m, 2H), 1.14-0.86 (m, 6H) | 305.1 $[M + H]^+$ |
| 37A | (6S)-2-(2-Fluorophenyl)-6-methyl-6,7-dihydro-5H-pyrazolo[5,1-b][1,3]oxazine-3-carboxylic acid | 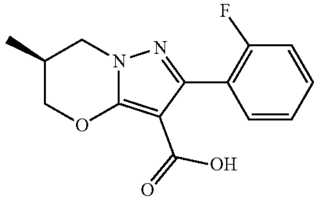 | (700 MHz) 11.76 (s, 1H), 7.44-7.35 (m, 2H), 7.24-7.17 (m, 2H), 4.44 (ddd, J = 10.7, 3.6, 1.3 Hz, 1H), 4.22 (ddd, J = 12.1, 5.4, 1.4 Hz, 1H), 4.07 (dd, J = 10.8, 9.5 Hz, 1H), 3.77 (dd, J = 12.1, 9.0 Hz, 1H), 2.49-2.41 (m, 1H), 1.05 (d, J = 6.8 Hz, 3H) | 277.2 $[M + H]^+$ |
| 38A | (6R)-2-(2-Fluorophenyl)-6-methyl-6,7-dihydro-5H-pyrazolo[5,1-b][1,3]oxazine-3-carboxylic acid | 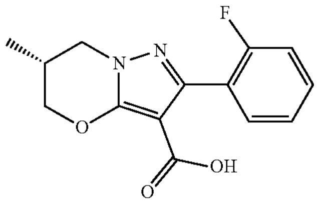 [SMILES: C[C@H]1COc2c(C(=O)O)c(-c3ccccc3F)nn2C1] | (400 MHz) 11.78 (s, 1H), 7.48-7.34 (m, 2H), 7.27-7.13 (m, 2H), 4.44 (ddd, J = 10.7, 3.6, 1.3 Hz, 1H), 4.22 (ddd, J = 12.2, 5.4, 1.3 Hz, 1H), 4.07 (dd, J = 10.8, 9.5 Hz, 1H), 3.77 (dd, J = 12.2, 9.1 Hz, 1H), 2.49-2.39 (m, 1H), 1.05 (d, J = 6.8 Hz, 3H) | 277.2 $[M + H]^+$ |

TABLE 9-continued

Preparatory examples prepared by ester hydrolysis procedure A

| Preparatory Example | Name | Structure | $^1H$ NMR δ ($DMSO-d_6$) | LRMS (APCI+) m/z |
|---|---|---|---|---|
| 39A | 6-Ethyl-2-(2-fluorophenyl)-6,7-dihydro-5H-pyrazolo[5,1-b][1,3]oxazine-3-carboxylic acid | 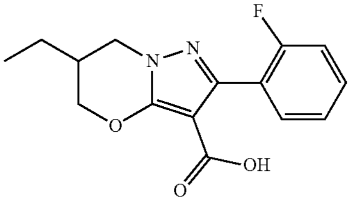 [SMILES: CCC1COc2c(C(=O)O)c(-c3ccccc3F)nn2C1] | (400 MHz) 11.78 (s, 1H), 7.48-7.27 (m, 2H), 7.27-7.07 (m, 2H), 4.59-4.40 (m, 1H), 4.31-4.19 (m, 1H), 4.12 (dd, J = 10.9, 9.3 Hz, 1H), 3.81 (dd, J = 12.2, 8.9 Hz, 1H), 2.34-2.19 (m, 1H), 1.54-1.26 (m, 2H), 0.98 (t, J = 7.5 Hz, 3H) | 291.0 $[M + H]^+$ |
| 40A | 2-(2-Fluorophenyl)-6-propan-2-yl-6,7-dihydro-5H-pyrazolo[5,1-b][1,3]oxazine-3-carboxylic acid | 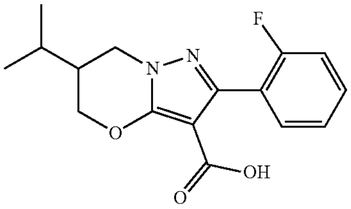 [SMILES: CC(C)C1COc2c(C(=O)O)c(-c3ccccc3F)nn2C1] | (400 MHz) 11.78 (s, 1H), 7.47-7.33 (m, 2H), 7.28-7.12 (m, 2H), 4.61-4.46 (m, 1H), 4.26-4.12 (m, 2H), 3.91 (dd, J = 12.2, 9.9 Hz, 1H), 2.21-2.03 (m, 1H), 1.77-1.55 (m, 1H), 1.05-0.83 (m, 6H) | 305.0 $[M + H]^+$ |
| 41A | 2-(2-Fluorophenyl)-6-propyl-6,7-dihydro-5H-pyrazolo[5,1-b][1,3]oxazine-3-carboxylic acid | 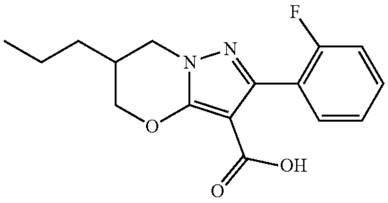 [SMILES: CCCC1COc2c(C(=O)O)c(-c3ccccc3F)nn2C1] | (400 MHz) 11.78 (s, 1H), 7.50-7.31 (m, 2H), 7.31-7.02 (m, 2H), 4.53-4.43 (m, 1H), 4.28-4.16 (m, 1H), 4.11 (dd, J = 10.8, 9.4 Hz, 1H), 3.81 (dd, J = 12.2, 9.0 Hz, 1H), 2.40-2.27 (m, 1H), 1.50-1.28 (m, 4H), 0.92 (t, J = 6.9 Hz, 3H). | 305.1 $[M + H]^+$ |
| 42A | 2-(2-Fluorophenyl)spiro[5,7-dihydropyrazolo[5,1-b][1,3]oxazine-6,1'-cyclopropane]-3-carboxylic acid | 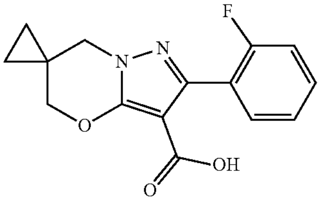 [SMILES: O=C(O)c1c(-c2ccccc2F)nn2c1OCC1(CC1)C2] | (400 MHz) 11.78 (s, 1H), 7.50-7.31 (m, 2H), 7.31-7.09 (m, 2H), 4.23 (s, 2H), 4.04 (s, 2H), 0.81 (s, 4H). | 289.0 $[M + H]^+$ |

43A (5R)-2-(2-Fluorophenyl)-5-methyl-6,7-dihydro-5H-pyrazolo[5,1-b][1,3]oxazine-3-carboxylic Acid

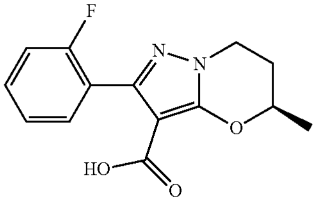 [SMILES: C[C@@H]1CCn2nc(-c3ccccc3F)c(C(=O)O)c2O1]

LiOH (1.5 M aq; 2.52 mL, 3.78 mmol) was added to a stirred solution of intermediate 16A (115 mg, 0.380 mmol) in THF:MeOH (1:1; 6 mL) and heated at 40° C. overnight. The cooled reaction mixture was washed with MTBE (3×10 mL), the aqueous phase acidified with 1 M aq. HCl to pH≈1, and extracted with $CHCl_3$:iPrOH (3:1; 3×10 mL). The combined organic extracts were dried ($Na_2SO_4$) and concentrated under reduced pressure to afford a white solid (92 mg, 780%). LCMS (Method A) 277.6 $[M+H]^+$ at 0.86 min. $^1H$ NMR (500 MHz, $DMSO-d_6$) δ 11.70 (s, 1H), 7.46-7.29 (m, 2H), 7.27-7.14 (m, 2H), 4.64-4.51 (m, 1H), 4.19-4.09 (m, 2H), 2.29-2.22 (m, 1H), 2.05 (d, J=7.0 Hz, 1H), 1.44 (d, J=6.3 Hz, 3H).

The following intermediate compounds were prepared by an analogous procedure to that described for intermediate 43A.

| Preparatory Example | Name | Structure | $^1$H NMR δ (500 MHz, DMSO-$d_6$) | LCMS (ES+) m/z |
|---|---|---|---|---|
| 44A | (5S)-2-(2-Fluorophenyl)-5-methyl-6,7-dihydro-5H-pyrazolo[5,1-b][1,3]oxazine-3-carboxylic acid | 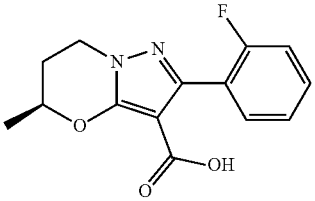 [SMILES: C[C@H]1CCn2nc(-c3ccccc3F)c(C(=O)O)c2O1] | 11.69 (s, 1H), 7.44-7.34 (m, 2H), 7.22-7.16 (m, 2H), 4.63-4.54 (m, 1H), 4.18-4.11 (m, 2H), 2.29-2.23 (m, 1H), 2.09-1.98 (m, 1H), 1.44 (d, J = 6.3 Hz, 3H). | (method A) 277.6 [M + H]$^+$ at 0.86 min |
| 45A | 2-Phenyl-6,7-dihydro-5H-pyrazolo[5,1-b][1,3]oxazine-3-carboxylic acid | 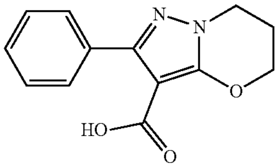 [SMILES: O=C(O)c1c(-c2ccccc2)nn2c1OCCC2] | 11.81 (s, 1H), 7.62-7.54 (m, 2H), 7.38-7.30 (m, 3H), 4.45-4.38 (m, 2H), 4.12 (t, J = 6.1 Hz, 2H), 2.27-2.18 (m, 2H). | (method A) 245.6 [M + H]$^+$ at 0.78 min. |
| 45B | 2-(2-Fluorophenyl)-6,7-dihydro-5H-pyrazolo[5,1-b][1,3]oxazine-3-carboxylic acid | 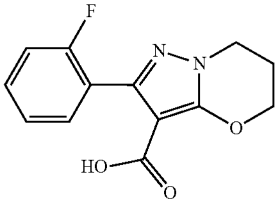 [SMILES: O=C(O)c1c(-c2ccccc2F)nn2c1OCCC2] | 11.73 (s, 1H), 7.44-7.34 (m, 2H), 7.23-7.16 (m, 2H), 4.45-4.40 (m, 2H), 4.13 (t, 2H), 2.27-2.20 (m, 2H). | (method A) 263.7 [M + H]$^+$ at 0.78 min |

46A 2-(2-Methylphenyl)-6,7-dihydro-5H-pyrazolo[5,1-b][1,3]oxazine-3-carboxylic Acid

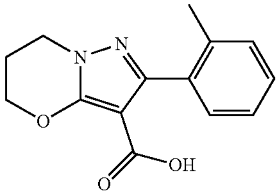 [SMILES: Cc1ccccc1-c1nn2c(c1C(=O)O)OCCC2]

A solution of intermediate 21B (115 mg, 0.4 mmol) and LiOH (1 M aq; 3.21 mL, 3.21 mmol) in MeOH:THF (1:1; 10 mL) was heated at 35° C. for 48 h. Additional LiOH (1 M aq.; 3.21 mL, 3.21 mmol) was added and the reaction heated at 60° C. overnight. The volatiles were removed under reduced pressure and the residue acidified to pH≈2 with 1 M aq. HCl and extracted with EtOAc (3×10 mL). The combined organic extracts were washed with water and brine (10 mL each), dried ($MgSO_4$), and the solvent removed under reduced pressure to afford an orange solid (78 mg, 75%). $R_f$=0.15 (2:1 EtOAc:heptane). LRMS (APCI+) m/z 258.8 [M+H]$^+$.

47A (5R)-2-[2-Fluoro-6-(propan-2-ylamino)pyridin-3-yl]-5-methyl-6,7-dihydro-5H-pyrazolo[5,1-b][1,3]oxazine-3-carboxylic Acid (Ester Hydrolysis Procedure B)

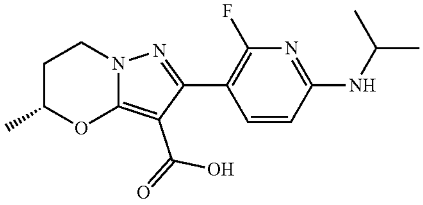 [SMILES: CC(C)Nc1ccc(-c2nn3c(c2C(=O)O)O[C@H](C)CC3)c(F)n1]

A solution of intermediate 31A (46 mg, 0.13 mmol) and LiOH (25 mg, 1.04 mmol) in 1:1:1 MeOH:THF:water (3 mL) was heated to 50° C. for 2 h. The reaction was cooled to rt, 1 M aq. HCl (5 mL) added and the mixture extracted with $CH_2Cl_2$ (3×10 mL). The combined organic fraction was passed through a phase separator containing brine and the solvent removed under reduced pressure to afford a white solid (38 mg, 89%). LCMS (Method A) 335.7 [M+H]$^+$ at 0.96 min. $^1$H NMR (500 MHz, DMSO-$d_6$) δ 11.63 (s, 1H), 7.41 (dd, J=9.9, 8.2 Hz, 1H), 6.86 (d, J=7.6 Hz, 1H), 6.30 (dd, J=8.2, 1.8 Hz, 1H), 4.59-4.50 (m, 1H), 4.12-4.03 (m, 2H), 3.94-3.84 (m, 1H), 2.28-2.21 (m, 1H), 2.06-1.95 (m, 1H), 1.42 (d, J=6.3 Hz, 3H), 1.14 (d, J=6.4 Hz, 6H).

The following intermediate compounds were prepared by the ester hydrolysis procedure described for intermediate 47A. The procedure may be modified by varying the stoichiometry of LiOH from 4 to 8 eq. dependent upon the reaction substrate.

TABLE 10

| Preparatory Example | Name | Structure | $^1H$ NMR δ (500 MHz, DMSO-$d_6$) | LCMS (ES+) m/z |
|---|---|---|---|---|
| | Preparatory examples prepared by ester hydrolysis procedure B | | | |
| 48A | (5S)-2-[2-Fluoro-6-(propan-2-ylamino)pyridin-3-yl]-5-methyl-6,7-dihydro-5H-pyrazolo[5,1-b][1,3]oxazine-3-carboxylic acid | 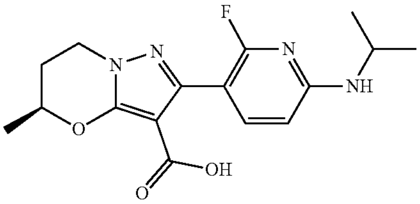 [SMILES: CC(C)Nc1ccc(-c2nn3c(c2C(=O)O)O[C@@H](C)CC3)c(F)n1] | 11.63 (s, 1H), 7.41 (dd, J = 9.9, 8.2 Hz, 1H), 6.86 (d, J = 7.6 Hz, 1H), 6.30 (dd, J = 8.2, 1.8 Hz, 1H), 4.58-4.50 (m, 1H), 4.12-4.03 (m, 2H), 3.94-3.84 (m, 1H), 2.27-2.20 (m, 1H), 2.06-1.95 (m, 1H), 1.42 (d, J = 6.3 Hz, 3H), 1.14 (d, J = 6.4 Hz, 6H). | (method A) 335.3 [M + H]+ at 0.96 min |
| 49A | 2-Phenylspiro[5,7-dihydropyrazolo[5,1-b][1,3]oxazine-6,3'-oxetane]-3-carboxylic acid | 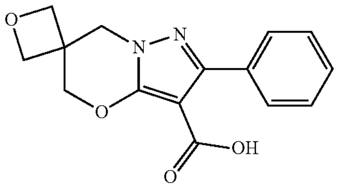 [SMILES: O=C(O)c1c(-c2ccccc2)nn2c1OCC1(COC1)C2] | 11.94 (s, 1H), 7.62-7.54 (m, 2H), 7.40-7.31 (m, 3H), 4.64 (s, 2H), 4.55 (d, J = 6.5 Hz, 2H), 4.51 (d, J = 6.5 Hz, 2H), 4.43 (s, 2H). | (method A) 287.4 [M + H]+ at 0.77 min |
| 49B | 2-(2-Fluorophenyl) spiro[5,7-dihydropyrazolo[5,1-b][1,3]oxazine-6,3'-oxetane]-3-carboxylic acid | 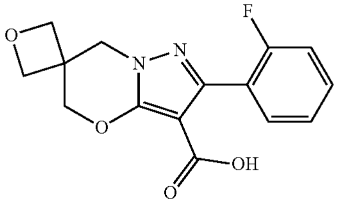 [SMILES: O=C(O)c1c(-c2ccccc2F)nn2c1OCC1(COC1)C2] | 11.86 (s, 1H), 7.46-7.35 (m, 2H), 7.24-7.16 (m, 2H), 4.66 (s, 2H), 4.56 (d, J = 6.5 Hz, 2H), 4.51 (d, J = 6.4 Hz, 2H), 4.45 (s, 2H). | (method A) 305.7 [M + H]+ at 0.77 min |
| 50A | 3-(2-Fluorophenyl)-6,7-dihydro-5H-pyrazolo[5,1-b][1,3]oxazine-2-carboxylic acid | 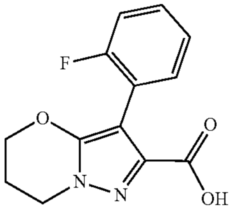 [SMILES: O=C(O)c1nn2c(c1-c1ccccc1F)OCCC2] | 12.47 (s, 1H), 7.35-7.27 (m, 2H), 7.20-7.12 (m, 2H), 4.36-4.27 (m, 2H), 4.23-4.17 (m, 2H), 2.28-2.16 (m, 2H). | (method A) 245.2 [M − OH]+ at 0.97 min |
| 50B | 3-[6-(Cyclopropylamino)-2-fluoropyridin-3-yl]-6,7-dihydro-5H-pyrazolo[5,1-b][1,3]oxazine-2-carboxylic acid | 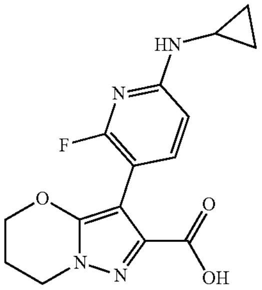 [SMILES: O=C(O)c1nn2c(c1-c1ccc(NC3CC3)nc1F)OCCC2] | Not available | (method A) 319.7 [M + H]+ at 0.98 min. |
| 51A | 7-(2-Fluorophenyl)-2,3-dihydropyrazolo[5,1-b][1,3]oxazole-6-carboxylic acid | 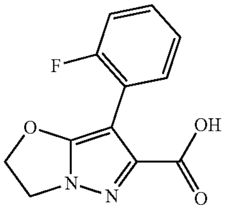 [SMILES: O=C(O)c1nn2c(c1-c1ccccc1F)OCC2] | Not available | (method A) 231.2 [M + H]+ at 0.92 min. |

52A 2-(2,4-Difluorophenyl)-6,7-dihydro-5H-pyrazolo[5,1-b][1,3]oxazine-3-carboxylic Acid

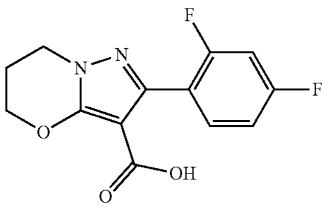 [SMILES: O=C(O)c1c(-c2ccc(F)cc2F)nn2c1OCCC2]

A solution of intermediate 21E (45 mg, 0.146 mmol) and LiOH (1 M aq; 1.17 mL, 1.17 mmol) in MeOH:THF (1:1; 4 mL) was heated at 50° C. for 16 h. The volatiles were removed under reduced pressure, the residue acidified to pH≈2 with 1 M aq. HCl and extracted with EtOAc (3×10 mL). The combined organic extracts were washed with water (10 mL) and brine (10 mL), dried ($Na_2SO_4$) and concentrated under reduced pressure to give a beige solid (36 mg, 880%). $^1H$ NMR (700 MHz, DMSO-$d_6$) δ 11.80 (s, 1H), 7.42 (td, J=8.4, 6.6 Hz, 1H), 7.25 (ddd, J=10.2, 9.4, 2.6 Hz, 1H), 7.17-7.01 (m, 1H), 4.48-4.37 (m, 2H), 4.13 (t, J=6.1 Hz, 2H), 2.23 (tt, J=6.0, 2.9 Hz, 2H). LRMS (APCI+) m/z 281.0 $[M+H]^+$.

The following compounds were prepared by in an analogous manner to intermediate 52A. The procedure may be performed at temperatures varying from 50° C. to 55° C.

53A 2-(2-Fluorophenyl)-6,7-dihydro-5H-pyrazolo[5,1-b][1,3]thiazine-3-carboxylic Acid

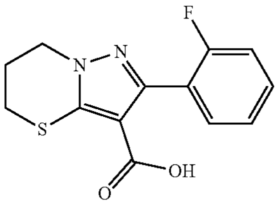

LiOH (98 mg, 4.08 mmol) was added to a solution of intermediate 20A (63 mg, 0.2 mmol) in THF:water:MeOH (1:1:1; 12 mL) and heated at 70° C. for 72 h. The reaction mixture was cooled to rt, acidified with 1 M aq. HCl (10 mL) and concentrated in vacuo to give a white solid (57 mg, 95%) which was used without further purification. LCMS (Method E): m/z 279.2 $[M+H]^+$ at 0.50 min.

The following compounds were prepared by in an analogous manner to intermediate 53A. The procedure may be performed at temperatures varying from 60° C. to 70° C. dependent upon the specific substrate. The stoichiometry of LiOH may be varied from 8 eq. to 20 eq.

| Preparatory Example | Name | Structure | LRMS (APCI+) m/z |
|---|---|---|---|
| 52B | 2-[6-(Ethylamino)-2-fluoropyridin-3-yl]-6,7-dihydro-5H-pyrazolo[5,1-b][1,3]oxazine-3-carboxylic acid | 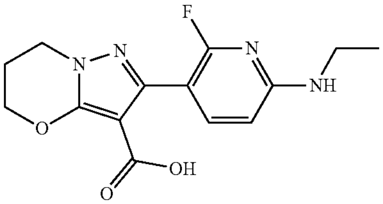 [SMILES: CCNc1ccc(-c2nn3c(c2C(=O)O)OCCC3)c(F)n1] | 307.0 $[M + H]^+$ |
| 52C | 2-[2-Fluoro-6-(propan-2-ylamino)pyridin-3-yl]-6,7-dihydro-5H-pyrazolo[5,1-b][1,3]oxazine-3-carboxylic acid | 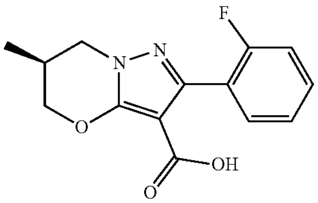 | 321.0 $[M + H]^+$ |

| Preparatory Example | Name | Structure | LCMS (ES+) m/z |
|---|---|---|---|
| 53B | 2-(2,4-Difluorophenyl)-6,7-dihydro-5H-pyrazolo[5,1-b][1,3]thiazine-3-carboxylic acid | 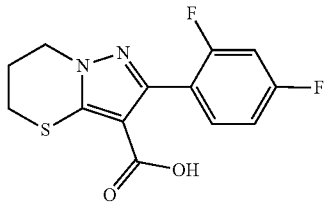 [SMILES: O=C(O)c1c(-c2ccc(F)cc2F)nn2c1SCCC2] | (method E) 297.5 $[M + H]^+$ at 0.52 min. |
| 54A | 2-(2,4-Difluorophenyl)-4,4-dioxo-6,7-dihydro-5H-pyrazolo[5,1-b][1,3]thiazine-3-carboxylic acid | 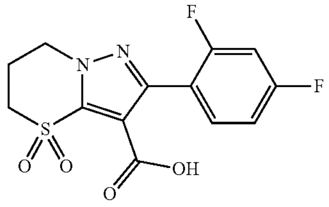 [SMILES: O=C(O)c1c(-c2ccc(F)cc2F)nn2c1S(=O)(=O)CCC2] | (method E) 329.7 $[M + H]^+$ at 0.49 min. |
| 54B | 2-(2-Fluorophenyl)-4,4-dioxo-6,7-dihydro-5H-pyrazolo[5,1-b][1,3]thiazine-3-carboxylic acid | 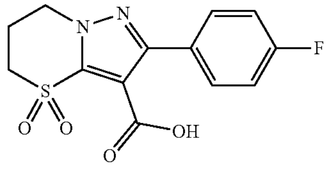 [SMILES: O=C(O)c1c(-c2ccc(F)cc2)nn2c1S(=O)(=O)CCC2] | (method E) 311.7 $[M + H]^+$ at 0.45 min. |
| 57A | (5R)-2-(5-Chloropyridin-3-yl)-5-methyl-6,7-dihydro-5H-pyrazolo[5,1-b][1,3]oxazine-3-carboxylic acid | 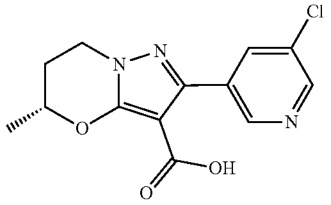 [SMILES: C[C@@H]1CCn2nc(-c3cncc(Cl)c3)c(C(=O)O)c2O1] | (method A) 294.3 $[M + H]^+$ at 0.87 min. |
| 58A | 2-(2-Fluorophenyl)-5-(hydroxymethyl)-6,7-dihydro-5H-pyrazolo[5,1-b][1,3]oxazine-3-carboxylic acid | 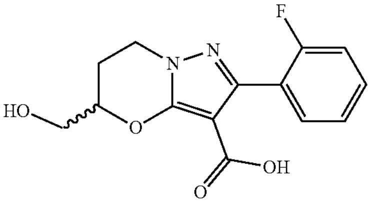 [SMILES: O=C(O)c1c(-c2ccccc2F)nn2c1OC(CO)CC2] | (method A) 292.6 $[M + H]^+$ at 0.75 min. |
| 58B | 2-(2-Fluorophenyl)-5-(methoxymethyl)-6,7-dihydro-5H-pyrazolo[5,1-b][1,3]oxazine-3-carboxylic acid | 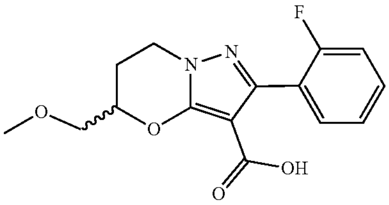 [SMILES: COCC1CCn2nc(-c3ccccc3F)c(C(=O)O)c2O1] | (method A) 307.7 $[M + H]^+$ at 0.87 min. |

55A 2-[6-(Cyclopropylamino)-2 fluoropyridin-3 yl]-6,7-dihydro-5H-pyrazolo[5,1-b][1,3]oxazine-3-carbocylic Acid

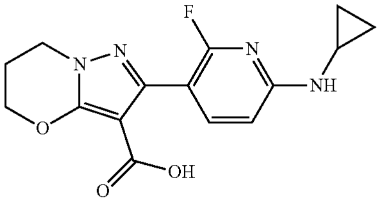 [SMILES: O=C(O)c1c(-c2ccc(NC3CC3)nc2F)nn2c1OCCC2]

LiOH (1.5 M aq; 1.92 mL, 28 mmol) was added to a stirred solution of intermediate 29C (100 mg, 0.288 mmol) in THF:MeOH (1:1; 4 mL) and heated at 40° C. over the weekend. The reaction mixture was cooled to rt, acidified with 1 M aq. HCl (1.9 mL) and concentrated in vacuo to give a white solid (57 mg, 950%) which was used without further purification. LCMS (Method E): m/z 319.6 $[M+H]^+$ at 0.83 min.

The following intermediate compounds were prepared by an analogous procedure to that described for intermediate 55A.

| Preparatory Example | Name | Structure | LCMS (ES+) m/z |
| --- | --- | --- | --- |
| 55B | 2-(2-Fluoro-5-methylpyridin-3-yl)-6,7-dihydro-5H-pyrazolo[5,1-b][1,3]oxazine-3-carboxylic acid | 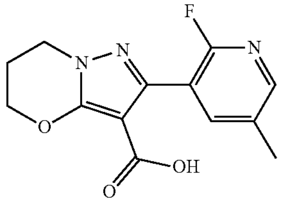 [SMILES: Cc1cnc(F)c(-c2nn3c(c2C(=O)O)OCCC3)c1] | (Method E) 278.8 $[M + H]^+$ at 0.73 min. |
| 56B | 2-Cyclopropyl-6,7-dihydro-5H-pyrazolo[5,1-b][1,3]oxazine-3-carboxylic acid | 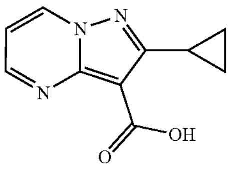 [SMILES: O=C(O)c1c(C2CC2)nn2cccnc12] | (Method E) 209.7 $[M + H]^+$ at 0.39 min. |

59A Ethyl 3,5-dibromo-1-(3,4-dihydroxybutyl)pyrazole-4-carboxylate

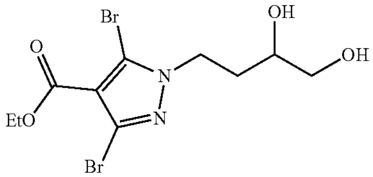 [SMILES: CCOC(=O)c1c(Br)nn(CCC(O)CO)c1Br]

A solution of intermediate 6J (2.91 g, 6.83 mmol) in AcOH (20 mL) and water (10 mL) was stirred at 110° C. for 2 h, after which time it was concentrated in vacuo. The resulting oil was taken up in $CH_2Cl_2$ (100 mL), washed with sat. aq. $NaHCO_3$ (100 mL) and brine (100 mL), then passed through a phase separation cartridge and the solvent removed under reduced pressure to give a colourless oil (2.80 g, 85%) which was used without further purification. LCMS (method A) 387.1 $[M+H]^+$ at 0.99 min. $^1H$ NMR (500 MHz, $CDCl_3$) δ 4.50-4.30 (m, 4H), 3.75-3.67 (m, 1H), 3.55-3.48 (m, 1H), 2.14-2.10 (m, 1H), 2.10-1.97 (m, 1H), 2.00-1.89 (m, 1H), 1.45-1.38 (m, 3H).

60A Ethyl 3,5-dibromo-1-[3-hydroxy-2-(hydroxymethyl)propyl]pyrazole-4-carboxylate

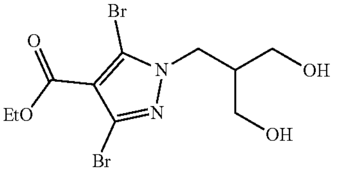 [SMILES: CCOC(=O)c1c(Br)nn(CC(CO)CO)c1Br]

HCl (1 M, aq.) (11 mL, 11 mmol) was added to a solution of intermediate 6K (12 g, 28.2 mmol) in acetone (120 mL) and the mixture was stirred at rt for 2 h. The mixture was concentrated to dryness and purified by flash chromatography using (30-70% EtOAc:heptane) affording a colourless oil (9.39 g, 86%). $^1H$ NMR (400 MHz, DMSO-$d_6$) δ 4.61 (t, J=5.0 Hz, 2H), 4.26 (q, J=7.1 Hz, 2H), 4.20 (d, J=7.2 Hz, 2H), 3.45-3.35 (m, 4H), 2.19-2.05 (m, 1H), 1.29 (t, J=7.1 Hz, 3H). LRMS m/z (APCI+) 385.6/387.6/389.6 $[M+H]^+$.

61A Ethyl 5-benzyl-3-bromo-1H-pyrazole-4-carboxylate

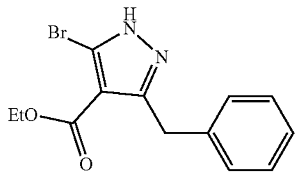 [SMILES: CCOC(=O)c1c(Cc2ccccc2)n[nH]c1Br]

A solution of sodium acetate (902 mg, 10.9 mmol) in water (10 mL) was added slowly to a solution of ethyl 5-benzyl-1H-pyrazole-4-carboxylate (500 mg, 2.17 mmol) in EtOH (7 mL), the mixture cooled to 0° C. with an ice bath, and $Br_2$ (0.22 mL, 4.34 mmol) added over 5 minutes. After 30 minutes the ice bath was removed. Additional EtOH (7 mL) was added and stirring was continued for 4 h. Sat. aq. $Na_2S_2O_3$ (20 mL) and EtOAc (15 mL) were added and the layers separated. The aqueous layer was extracted with EtOAc (2×15 mL), the combined organics washed with brine (20 mL), dried ($Na_2SO_4$) and concentrated under reduced pressure. Purification by flash column chromatography (10-50% EtOAc:heptane) afforded a white solid (385 mg, 57%). LRMS m/z (APCI+) 309.3/311.3 $[M+H]^+$. TLC $R_f$=0.63 (1:1 EtOAc:heptane).

62A Ethyl (5R)-2-benzyl-5-methyl-6,7-dihydro-5H-pyrazolo[5,1-b][1,3]oxazine-3-carboxylate

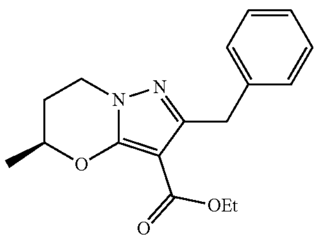 [SMILES: CCOC(=O)c1c(Cc2ccccc2)nn2c1O[C@@H](C)CC2]

A solution of intermediate 3B (317 mg, 1.30 mmol), intermediate 61A (365 mg, 1.18 mmol) and $K_2CO_3$ (490 mg, 3.54 mmol) in MeCN (10 mL) was heated at 60° C. for 17 h. The reaction was cooled to rt and filtered, washing with MeCN (3×10 mL) and the filtrate concentrated under reduced pressure. A mixture of ethyl 3-benzyl-5-bromo-1-[(2R)-4-hydroxybutan-2-yl]pyrazole-4-carboxylate and ethyl 5-benzyl-3-bromo-1-[(2S)-4-hydroxybutan-2-yl]pyrazole-4-carboxylate was obtained (480 mg), which was used without further purification. The crude residue (470 mg) was dissolved in THE (20 mL), cooled to 0° C. and NaH (60% dispersion in mineral oil, 99 mg, 2.46 mmol) added. The reaction was allowed to attain rt and stirred for 24 h. The reaction was quenched with water (10 mL) and extracted with EtOAc (3×10 mL). The organics were washed with water and brine (10 mL) each, dried $Na_2SO_4$, filtered and concentrated under reduced pressure. Purification by flash chromatography (1:1 EtOAc:heptane) afforded a white solid (138 mg, 39%). $^1$H NMR (400 MHz, DMSO-$d_6$) δ 7.29-7.05 (m, 5H), 4.56-4.47 (m, 1H), 4.11-3.99 (m, 5H), 2.21 (d, J=14.4 Hz, 1H), 2.02-1.89 (m, 1H), 1.39 (d, J=6.3 Hz, 3H), 1.15 (t, J=7.1 Hz, 3H). LRMS m/z (APCI+) 301.4 $[M+H]^+$.

63A 5-Bromo-2-ethylpyrimidine

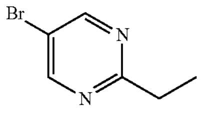

$Pd(PPh_3)_4$ (304 mg, 0.260 mmol) was added to a cooled (0° C.) solution of 5-bromo-2-iodopyrimidine (1.5 g, 5.27 mmol) in dry THF (15 mL) under $N_2$. Diethylzinc (1 M in hexane; 6.84 mL, 6.84 mmol) was added dropwise and the reaction stirred at 0° C. for 1 h and then at rt for 3 h. The reaction was quenched using saturated aqueous $NH_4Cl$ soln. (25 mL) and diluted with EtOAc (10 mL). The separated aqueous layer was extracted with EtOAc (3×20 mL), and the combined organics dried ($Na_2SO_4$) and the solvent removed under reduced pressure. Purification by flash chromatography (0-10% EtOAc in iso-hexanes) afforded a colourless oil (560 mg, 55%). LCMS (method E) 187.6/189.6 $[M+H]^+$ at 0.51 min. $^1$H NMR (500 MHz, $CDCl_3$) δ 8.69 (s, 2H), 2.94 (q, J=7.6 Hz, 2H), 1.34 (t, J=7.6 Hz, 3H).

64A 1-(5-Bromopyridin-2-yl)propan-2-ol

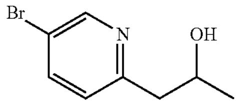

To a stirred solution of 5-bromo-2-methylpyridine (1.4 mL, 3.49 mmol) in THE (10 mL) at −78° C. was added lithium diisopropylamide (2 M in THF/heptane/ethylbenzene; 2.5 mL, 5.0 mmol) dropwise. The solution was stirred at −78° C. for 20 mins, then acetaldehyde (0.6 mL, 10.7 mmol) was added dropwise. The reaction was stirred at −78° C. for 1 h, then allowed to attain rt and stirred for 1 h. The reaction was quenched with sat. aq. $NH_4Cl$ (10 mL) and extracted with $CH_2Cl_2$ (3×20 mL), The organic extracts were combined, dried ($Na_2SO_4$) and concentrated under reduced pressure. Successive purification by flash chromatography (0-30% EtOAc in $CH_2Cl_2$), then (0-40% MeOH in $CH_2Cl_2$) afforded a yellow oil (285 mg, 36%). LCMS (method F) 216.1/218.1 $[M+H]^+$ at 0.66 min. $^1$H NMR (500 MHz, DMSO-$d_6$) δ 8.58 (d, J=2.5 Hz, 1H), 7.92 (dd, J=8.3, 2.5 Hz, 1H), 7.25 (d, J=8.3 Hz, 1H), 4.63 (d, J=4.9 Hz, 1H), 4.03-3.94 (m, 1H), 2.78 (dd, J=13.3, 7.3 Hz, 1H), 2.71 (dd, J=13.3, 5.6 Hz, 1H), 1.07 (d, J=6.2 Hz, 3H).

65A Ethyl (5R)-2-(2-methoxypyridin-4-yl)-5-methyl-6,7-dihydro-5H-pyrazolo[5,1-b][1,3]oxazine-3-carboxylate (Suzuki-Miyaura Procedure C)

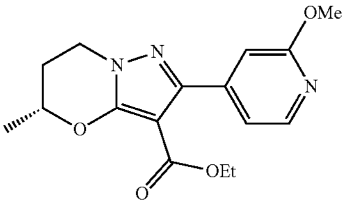 [SMILES: CCOC(=O)c1c(-c2ccnc(OC)c2)nn2c1O[C@H](C)CC2]

To a stirred solution of 2-methoxypyridine-4-boronic acid (115 mg, 0.75 mmol) in 1,4-dioxane:water (3:1; 4 mL), was added $K_3PO_4$ (400 mg, 1.88 mmol), XPhos Pd G2 (29 mg, 0.04 mmol) and intermediate 9B (180 mg, 0.62 mmol). The reaction vessel was sparged with $N_2$ and heated to 100° C. overnight. The reaction was partitioned between EtOAc (10 mL) and water (10 mL), and the separated aqueous extracted with EtOAc (3×10 mL). The combined organics were washed with brine (30 mL), dried ($Na_2SO_4$) and concentrated under reduced pressure. Purification by flash chromatography (30-100% EtOAc in iso-hexane) afforded a white solid (186 mg, 90%). LCMS (method A) 318.6 $[M+H]^+$ at 1.12 min. $^1$H NMR (500 MHz, DMSO-$d_6$) δ 8.16 (dd, J=5.3, 0.8 Hz, 1H), 7.18 (dd, J=5.3, 1.4 Hz, 1H), 7.02-7.02 (m, 1H), 4.63-4.56 (m, 1H), 4.20-4.07 (m, 4H), 3.87 (s, 3H), 2.32-2.23 (m, 1H), 2.08-1.98 (m, 1H), 1.44 (d, J=6.3 Hz, 3H), 1.16 (t, J=7.1 Hz, 3H).

The following intermediate compounds were prepared in an analogous manner to intermediate 65A. Intermediates 65C and 66A were prepared from the corresponding pinacol ester

TABLE 11

Preparatory examples prepared via Suzuki-Miyaura procedure C

| Preparatory Example | Name | Structure | $^1$H NMR δ (500 MHz) | LCMS (ES+) m/z |
|---|---|---|---|---|
| 65B | Ethyl (5R)-2-(5-fluoro-2-methylpyridin-4-yl)-5-methyl-6,7-dihydro-5H-pyrazolo[5,1-b][1,3]oxazine-3-carboxylate | 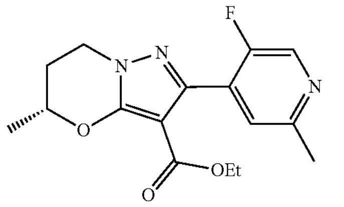 [SMILES: CCOC(=O)c1c(-c2cc(C)ncc2F)nn2c1O[C@H](C)CC2] | (DMSO-$d_6$) 9.32-9.27 (m, 1H), 8.84 (dd, J = 4.2, 1.8 Hz, 1H), 8.53-8.49 (m, 1H), 8.07 (dd, J = 8.6, 2.5 Hz, 1H), 7.32 (dd, J = 6.9, 4.2 Hz, 1H), 6.96-6.89 (m, 1H), 4.87 (t, J = 5.5 Hz, 1H), 4.38-4.32 (m, 2H), 4.26 (q, J = 7.1 Hz, 2H), 3.75 (q, J = 5.3 Hz, 2H), 1.24 (t, J = 7.1 Hz, 3H) | (method A) 320.3 $[M + H]^+$ at 1.00 min |
| 65C | Ethyl (5R)-2-(3-fluoropyridin-4-yl)-5-methyl-6,7-dihydro-5H-pyrazolo[5,1-b][1,3]oxazine-3-carboxylate | 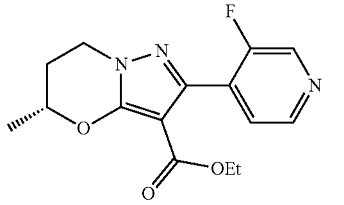 [SMILES: CCOC(=O)c1c(-c2ccncc2F)nn2c1O[C@H](C)CC2] | (DMSO-$d_6$) 8.61 (d, J = 1.8 Hz, 1H), 8.51-8.45 (m, 1H), 7.48 (dd, J = 6.2, 4.8 Hz, 1H), 4.68-4.59 (m, 1H), 4.24-4.12 (m, 2H), 4.08-3.99 (m, 2H), 2.34-2.27 (m, 1H), 2.13-2.01 (m, 1H), 1.45 (d, J = 6.3 Hz, 3H), 1.05 (t, J = 7.1 Hz, 3H). [2] | (method E) 306.4 $[M + H]^+$ at 0.52 min |
| 65D | Ethyl (5R)-2-(5-chloropyridin-3-yl)-5-methyl-6,7-dihydro-5H-pyrazolo[5,1-b][1,3]oxazine-3-carboxylate | 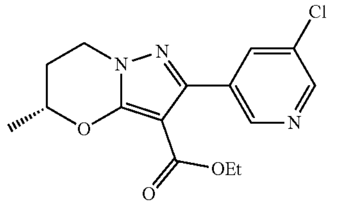 [SMILES: CCOC(=O)c1c(-c2cncc(Cl)c2)nn2c1O[C@H](C)CC2] | Not available | (method A) 322.3 $[M + H]^+$ at 1.23 min. |
| 65E | Ethyl (5R)-2-(5-chloro-2-fluoropyridin-3-yl)-5-methyl-6,7-dihydro-5H-pyrazolo[5,1-b][1,3]oxazine-3-carboxylate | 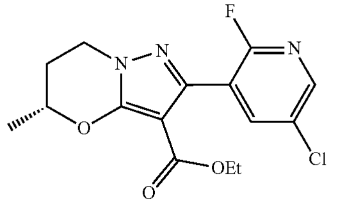 [SMILES: CCOC(=O)c1c(-c2cc(Cl)cnc2F)nn2c1O[C@H](C)CC2] | (DMSO-$d_6$) 8.38 (dd, J = 2.7, 1.2 Hz, 1H), 8.11 (dd, J = 7.8, 2.7 Hz, 1H), 4.67-4.60 (m, 1H), 4.22-4.12 (m, 2H), 4.06-3.99 (m, 2H), 2.34-2.26 (m, 1H), 2.10-2.00 (m, 1H), 1.45 (d, J = 6.3 Hz, 3H), 1.05 (t, J = 7.1 Hz, 3H). | (method B) 340.4 $[M + H]^+$ at 1.30 min |
| 65F | Ethyl (5R)-2-(2-fluoro-6-methylpyridin-3-yl)-5-methyl-6,7-dihydro-5H-pyrazolo[5,1-b][1,3]oxazine-3-carboxylate | 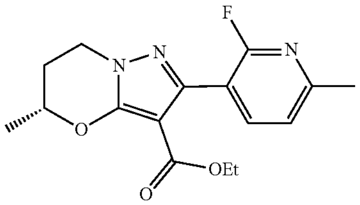 | (DMSO-$d_6$) 7.81 (dd, J = 9.7, 7.5 Hz, 1H), 7.24 (dd, J = 7.5, 1.8 Hz, 1H), 4.66-4.56 (m, 1H), 4.20-4.09 (m, 2H), 4.01 (q, J = 7.1 Hz, 2H), 2.46 (s, 3H), 2.32-2.24 (m, 1H), 2.10-1.98 (m, 1H), 1.44 (d, J = 6.3 Hz, 3H), 1.04 (t, J = 7.1 Hz, 3H). | (method B) 320.4 $[M + H]^+$ at 1.09 min |
| 65H | Ethyl-(5R)-5-methyl-2-phenyl-6,7-dihydro-5H-pyrazolo[5,1-b][1,3]oxazine-3-carboxylate | 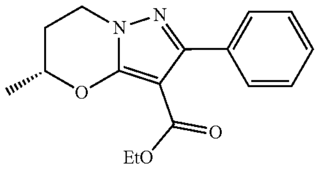 [SMILES: CCOC(=O)c1c(-c2ccccc2)nn2c1O[C@H](C)CC2] | ($CDCl_3$) δ 7.62 (dd, J = 7.7, 1.9 Hz, 2H), 7.41-7.31 (m, 3H), 4.61-4.47 (m, 1H), 4.25 (ddd, J = 12.6, 5.9, 3.1 Hz, 1H), 4.22-4.09 (m, 3H), 2.26 (ddt, J = 14.3, 5.6, 2.9 Hz, 1H), 2.19-2.08 (m, 1H), 1.58 (d, J = 6.3 Hz, 3H), 1.20 (t, J = 7.1 Hz, 3H). | (method A) 287.2 $[M + H]^+$ at 1.25 min |

TABLE 11-continued

Preparatory examples prepared via Suzuki-Miyaura procedure C

| Preparatory Example | Name | Structure | $^1$H NMR δ (500 MHz) | LCMS (ES+) m/z |
|---|---|---|---|---|
| 65I | Ethyl-(5R)-2-(2,4-difluorophenyl)-5-methyl-6,7-dihydro-5H-pyrazolo[5,1-b][1,3]oxazine-3-carboxylate | 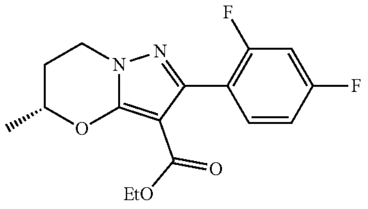 [SMILES: CCOC(=O)c1c(-c2ccc(F)cc2F)nn2c1O[C@H](C)CC2] | ($CDCl_3$) δ 7.41 (td, J = 8.3, 6.5 Hz, 1H), 6.91 (tdd, J = 8.3, 2.5, 1.0 Hz, 1H), 6.85 (ddd, J = 9.8, 9.1, 2.5 Hz, 1H), 4.55 (dtt, J = 12.7, 6.3, 3.1 Hz, 1H), 4.25 (ddd, J = 12.6, 5.9, 3.2 Hz, 1H), 4.21-J4.09 (m, 3H), 2.27 (ddt, J = 14.3, 5.5, 3.0 Hz, 1H), 2.15 (dtd, J = 14.3, 10.3, 5.9 Hz, 1H), 1.59 (d, J = 6.3 Hz, 3H), 1.13 (t, J = 7.1 Hz, 3H). | (method A) 323.3 [M + H]$^+$ at 1.31 min |
| 65I | Ethyl-(5R)-5-methyl-2-(1-methyl-1H-indazol-5-yl)-6,7-dihydro-5H-pyrazolo[5,1-b][1,3]oxazine-3-carboxylate | 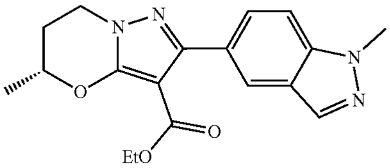 | (methanol-$d_4$) δ 8.04 (d, J = 1.0 Hz, 1H), 7.96 (dd, J = 1.6, 0.8 Hz, 1H), 7.64 (dd, J = 8.7, 1.5 Hz, 1H), 7.55 (dt, J = 8.7, 1.0 Hz, 1H), 4.63-4.55 (m, 1H), 4.24-4.16 (m, 2H), 4.16-4.10 (m, 2H), 4.09 (s, 3H), 2.38-2.32 (m, 1H), 2.17-2.09 (m, 1H), 1.55 (d, J = 6.3 Hz, 3H), 1.15 (t, J = 7.1 Hz, 3H). | (method A) 341.4 [M + H]$^+$ at 1.12 min |
| 65J | Ethyl (5R)-2-(1-ethylpyrazol-4-yl)-5-methyl-6,7-dihydro-5H-pyrazolo[5,1-b][1,3]oxazine-3-carboxylate | 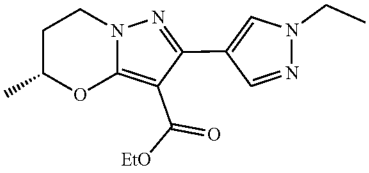 [SMILES: CCOC(=O)c1c(-c2cnn(CC)c2)nn2c1O[C@H](C)CC2] | (DMSO-$d_6$) 8.20 (d, J = 0.7 Hz, 1H), 7.81 (d, J = 0.7 Hz, 1H), 4.59-4.48 (m, 1H), 4.18-4.11 (m, 4H), 4.11-4.02 (m, 2H), 2.29-2.20 (m, 1H), 2.05-1.93 (m, 1H), 1.42 (d, J = 6.3 Hz, 3H), 1.38 (t, J = 7.3 Hz, 3H), 1.24 (t, J = 7.1 Hz, 3H). | (method A) 305.2 [M + H]$^+$ at 1.17 min |
| 66A | Ethyl 2-(3-fluoropyridin-4-yl)-6,7-dihydro-5H-pyrazolo[5,1-b][1,3]oxazine-3-carboxylate | 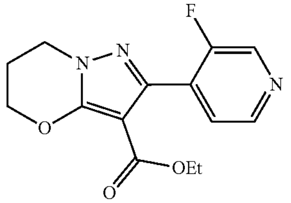 [SMILES: CCOC(=O)c1c(-c2ccncc2F)nn2c1OCCC2] | (DMSO-$d_6$) 8.61 (d, J = 1.8 Hz, 1H), 8.47 (dd, J = 4.8, 1.1 Hz, 1H), 7.47 (dd, J = 6.2, 4.8 Hz, 1H), 4.49-4.45 (m, 2H), 4.19-4.15 (m, 2H), 4.08-3.99 (m, 2H), 2.30-2.22 (m, 2H), 1.06 (t, J = 7.1 Hz, 3H). | (method A) 292.3 [M + H]$^+$ at 0.88 min |
| 67A | Ethyl (5S)-2-(6-fluoropyridin-3-yl)-5-methyl-6,7-dihydro-5H-pyrazolo[5,1-b][1,3]oxazine-3-carboxylate | 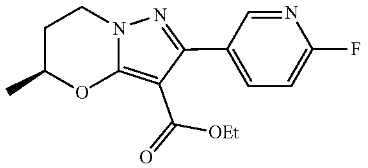 [SMILES: CCOC(=O)c1c(-c2ccc(F)nc2)nn2c1O[C@@H](C)CC2] | (DMSO-$d_6$) 8.42-8.36 (m, 1H), 8.15 (ddd, J = 8.3, 8.3, 2.5 Hz, 1H), 7.22 (dd, J = 8.5, 2.8 Hz, 1H), 4.66-4.56 (m, 1H), 4.22-4.11 (m, 2H), 4.08 (q, J = 7.1 Hz, 2H), 2.34-2.23 (m, 1H), 2.10-1.99 (m, 1H), 1.44 (d, J = 6.3 Hz, 3H), 1.14 (t, J = 7.1 Hz, 3H). | (method E) 306.2 [M + H]$^+$ at 1.68 min |
| 67B | Ethyl (5S)-2-(3-fluoropyridin-4-yl)-5-methyl-6,7-dihydro-5H-pyrazolo[5,1-b][1,3]oxazine-3-carboxylate | 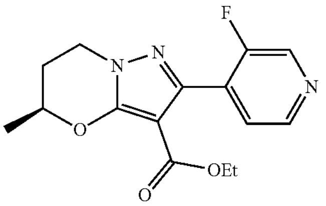 [SMILES: CCOC(=O)c1c(-c2ccncc2F)nn2c1O[C@@H](C)CC2] | (DMSO-$d_6$) 8.61 (d, J = 1.8 Hz, 1H), 8.48 (dd, J = 4.8, 1.1 Hz, 1H), 7.48 (dd, J = 6.2, 4.8 Hz, 1H), 4.68-4.60 (m, 1H), 4.23-4.14 (m, 2H), 4.03 (q, J = 7.1 Hz, 2H), 2.33-2.27 (m, 1H), 2.11-2.02 (m, 1H), 1.45 (d, J = 6.3 Hz, 3H), 1.05 (t, J = 7.1 Hz, 3H). | (method F) 306.2 [M + H]$^+$ at 1.53 min |

68A Ethyl (5R)-2-(6-ethyl-2-methylpyridin-3-yl)-5-methyl-6,7-dihydro-5H-pyrazolo[5,1-b][1,3]oxazine-3-carboxylate

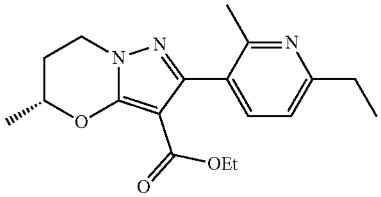 [SMILES: CCOC(=O)c1c(-c2ccc(CC)nc2C)nn2c1O[C@H](C)CC2]

KOAc (981 mg, 10 mmol) and bis(pinacolato)diboron (952 mg, 3.75 mmol) were added to a solution of 3-bromo-6-ethyl-2-methylpyridine (0.5 g, 2.50 mmol) in 1,4-dioxane (8 mL). The mixture was sparged with $N_2$ for 10 min, $Pd(dppf)Cl_2$ (91 mg, 0.12 mmol) added, and heated at 85° C. for 16 h. The reaction was cooled to rt, diluted with MTBE (10 mL) and filtered through Celite, washing with EtOAc (40 mL). The filtrate was concentrated under reduced pressure to afford a brown oil (600 mg) and the residue taken directly to the next reaction. A portion of the crude residue (246 mg, 0.99 mmol) was suspended in THF:water (3:2; 10 mL) with intermediate 9A (180 mg, 0.62 mmol), $K_3PO_4$ (529 mg, 2.49 mmol) and XPhos (59 mg, 0.125 mmol). The reaction was sparged with $N_2$, Pd-170 (42 mg, 0.06 mmol) added and the reaction heated for 1 h at 70° C. The reaction was diluted with EtOAc (10 mL), washed with brine (20 mL), the organic layer passed through a phase separation cartridge and the solvent removed under reduced pressure. Purification by flash chromatography (0-5% MeOH in $CH_2Cl_2$) afforded a brown oil (125 mg, 56%). LCMS (method E) m/z 330.3 $[M+H]^+$ at 0.27 min. $^1H$ NMR (500 MHz, DMSO-$d_6$) 7.43 (d, J=7.8 Hz, 1H), 7.08 (d, J=7.8 Hz, 1H), 4.72-4.53 (m, 1H), 4.24-4.08 (m, 2H), 3.96 (q, J=7.1 Hz, 2H), 2.73 (q, J=7.6 Hz, 2H), 2.30-2.26 (m, 1H) 2.28 (s, 3H), 2.14-1.99 (m, 1H), 1.45 (d, J=6.3 Hz, 3H), 1.23 (t, J=7.6 Hz, 3H), 0.99 (t, J=7.1 Hz, 3H).

The following intermediate compounds were prepared in an analogous manner to intermediate 68A.

| Preparatory Example | Name | Structure | $^1H$ NMR δ (500 MHz, DMSO-$d_6$) | LCMS (ES+) m/z |
|---|---|---|---|---|
| 68B | Ethyl (5R)-2-(2-ethylpyrimidin-5-yl)-5-methyl-6,7-dihydro-5H-pyrazolo[5,1-b][1,3]oxazine-3-carboxylate | 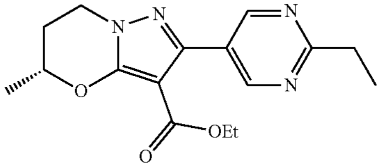 [SMILES: CCOC(=O)c1c(-c2cnc(CC)nc2)nn2c1O[C@H](C)CC2] | 8.86 (s, 2H), 4.67-4.57 (m, 1H), 4.25-4.12 (m, 2H), 4.09 (q, J = 7.1 Hz, 2H), 2.93 (q, J = 7.6 Hz, 2H), 2.37-2.22 (m, 1H), 2.14-1.97 (m, 1H), 1.44 (d, J = 6.3 Hz, 3H), 1.30 (t, J = 7.6 Hz, 3H), 1.14 (t, J = 7.1 Hz, 3H) | (method E) 317.4 $[M + H]^+$ at 0.53 min |
| 68C | Ethyl (5R)-2-(2,6-dimethylpyridin-3-yl)-5-methyl-6,7-dihydro-5H-pyrazolo[5,1-b][1,3]oxazine-3-carboxylate | 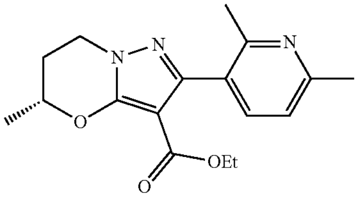 | 7.41 (d, J = 7.7 Hz, 1H), 7.07 (d, J = 7.8 Hz, 1H), 4.70-4.55 (m, 1H), 4.18-4.11 (m, 2H), 3.97 (q, J = 7.2 Hz, 2H), 2.46 (s, 3H), 2.35-2.28 (m, 1H), 2.27 (s, 3H), 2.12-2.00 (m, 1H), 1.45 (d, J = 6.4 Hz, 3H), 1.00 (d, J = 7.1 Hz, 3H). | (method E) 315.8 $[M + H]^+$ at 0.35 min |
| 68D | Ethyl (5R)-2-(1-ethylpyrazol-3-yl)-5-methyl-6,7-dihydro-5H-pyrazolo[5,1-b][1,3]oxazine-3-carboxylate | 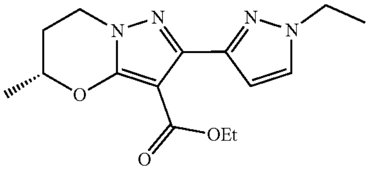 [SMILES: CCOC(=O)c1c(-c2ccn(CC)n2)nn2c1O[C@H](C)CC2] | 7.69 (d, J = 2.2 Hz, 1H), 6.50 (d, J = 2.2 Hz, 1H), 4.61-4.48 (m, 1H), 4.21-4.01 (m, 6H), 2.33-2.17 (m, 1H), 2.13-1.86 (m, 1H), 1.42 (d, J = 6.3 Hz, 3H), 1.38 (t, J = 7.3 Hz, 3H), 1.16 (t, J = 7.1 Hz, 3H) | (method E) 305.3 $[M + H]^+$ at 0.51 min |

69A Ethyl (5R)-2-[6-(2-hydroxypropyl)pyridin-3-yl]-5-methyl-6,7-dihydro-5H-pyrazolo[5,1-b][1,3]oxazine-3-carboxylate

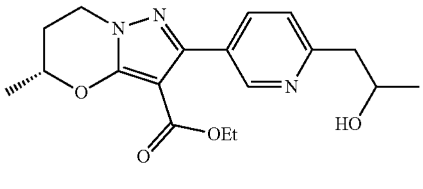 [SMILES: CCOC(=O)c1c(-c2ccc(CC(C)O)nc2)nn2c1O[C@H](C)CC2]

KOAc (367 mg, 3.74 mmol) and bis(pinacolato)diboron (349 mg, 1.37 mmol) were added to a solution of intermediate 64A (270 mg, 1.25 mmol) in 1,4-dioxane (5 mL). The mixture was sparged with $N_2$, $Pd(dppf)Cl_2$ (69 mg, 0.09 mmol) added, and heated at 100° C. overnight. The reaction was cooled to rt and filtered through Celite, washing with MeOH. The filtrate was concentrated under reduced pressure to afford a brown oil. The crude residue was suspended in 1,4-dioxane:water (4:1; 5 mL), and $K_3PO_4$ (463 mg, 2.18 mmol), intermediate 9A (210 mg, 0.73 mmol) and XPhos Pd G2 (57 mg, 0.07 mmol) added. The reaction was sparged with $N_2$ and the reaction heated for 16 h at 100° C. The reaction was partitioned between EtOAc (10 mL) and water (10 mL) and the separated aqueous phase was extracted with EtOAc (3×10 mL). The organic layers were combined, washed with brine (30 mL), dried ($Na_2SO_4$) and concentrated under reduced pressure. Purification by flash chromatography (0-6% MeOH in $CH_2Cl_2$) afforded a brown solid (221 mg, 84%). LCMS (method E) m/z 346.3 $[M+H]^+$ (ES+) at 0.70 min. $^1H$ NMR (500 MHz, DMSO-$d_6$) 8.62 (dd, J=2.3, 0.8 Hz, 1H), 7.84 (dd, J=8.0, 2.3 Hz, 1H), 7.26 (d, J=8.0, 0.9 Hz, 1H), 4.69 (d, J=4.8 Hz, 1H), 4.64-4.55 (m, 1H), 4.19-4.11 (m, 2H), 4.10-3.99 (m, 3H), 2.86 (dd, J=13.3, 7.0 Hz, 1H), 2.75 (dd, J=13.3, 5.9 Hz, 1H), 2.31-2.23 (m, 1H), 2.07-1.97 (m, 1H), 1.44 (d, J=6.3 Hz, 3H), 1.13 (t, J=7.1 Hz, 3H), 1.10-1.05 (in, 3H).

The following intermediate compounds were prepared in an analogous manner to intermediate 69A. Intermediates 69E, 69F and 69G were prepared using 30 mol % XPhos Pd G2 and 3 eq. $K_3PO_4$.

| Preparatory Example | Name | Structure | $^1H$ NMR δ (DMSO-$d_6$) | LCMS/LRMS m/z |
|---|---|---|---|---|
| 69B | Ethyl (5R)-2-(4-ethyl-2-fluorophenyl)-5-methyl-6,7-dihydro-5H-pyrazolo[5,1-b][1,3]oxazine-3-carboxylate | 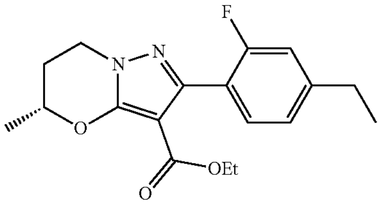 [SMILES: CCOC(=O)c1c(-c2ccc(CC)cc2F)nn2c1O[C@H](C)CC2] | (500 MHz) 7.31-7.25 (m, 1H), 7.07-7.02 (m, 2H), 4.63-4.55 (m, 1H), 4.18-4.08 (m, 2H), 4.05-3.95 (m, 2H), 2.65 (q, J = 7.6 Hz, 2H), 2.30-2.23 (m, 1H), 2.09-2.00 (m, 1H), 1.44 (d, J = 6.3 Hz, 3H), 1.20 (t, J = 7.6 Hz, 3H), 1.03 (t, J = 7.1 Hz, 3H). | LCMS ESI (method E) 333.4 $[M + H]^+$ at 0.66 min |
| 69C | Ethyl (5R)-2-(6-ethylpyridin-3-yl)-5-methyl-6,7-dihydro-5H-pyrazolo[5,1-b][1,3]oxazine-3-carboxylate | 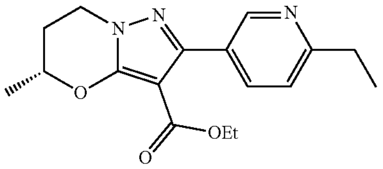 [SMILES: CCOC(=O)c1c(-c2ccc(CC)nc2)nn2c1O[C@H](C)CC2] | Not available | LCMS ESI (method A) 316.3 $[M + H]^+$ at 0.68 min |
| 69D | Ethyl (5R)-2-[6-(2-hydroxy-2-methylpropyl)pyridin-3-yl]-5-methyl-6,7-dihydro-5H-pyrazolo[5,1-b][1,3]oxazine-3-carboxylate | 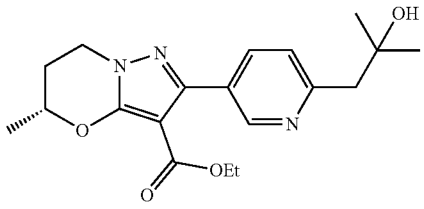 [SMILES: CCOC(=O)c1c(-c2ccc(CC(C)(C)O)nc2)nn2c1O[C@H](C)CC2] | (500 MHz) 8.61 (dd, J = 2.3, 0.8 Hz, 1H), 7.85 (dd, J = 8.0, 2.3 Hz, 1H), 7.31 (dd, J = 8.1, 0.9 Hz, 1H), 4.73 (s, 1H), 4.64-4.53 (m, 1H), 4.20-4.10 (m, 2H), 4.10-4.04 (m, 2H), 2.86 (s, 2H), 2.31-2.22 (m, 1H), 2.07-1.97 (m, 1H), 1.44 (d, J = 6.3 Hz, 3H), 1.14-1.10 (m, 9H) | LCMS ESI (method A) 360.4 $[M + H]^+$ at 0.74 min |
| 69E | Ethyl (5R)-5-methyl-2-[4-methyl-6-(propan-2-ylamino)pyridin-3-yl]-6,7-dihydro-5H-pyrazolo[5,1-b][1,3]oxazine-3-carboxylate | 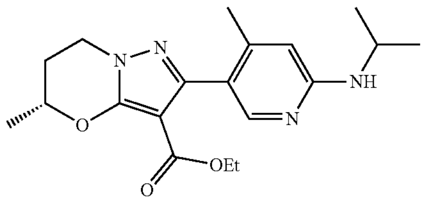 [SMILES: CCOC(=O)c1c(-c2cnc(NC(C)C)cc2C)nn2c1O[C@H](C)CC2] | (500 MHz) 7.69 (s, 1H), 6.27 (s, 1H), 4.62-4.54 (m, 1H), 4.15-4.08 (m, 2H), 3.99 (q, J = 7.0 Hz, 3H), 2.30-2.23 (m, 1H), 2.08-2.00 (m, 1H), 1.98 (s, 3H), 1.89 (s, 1H), 1.44 (d, J = 6.3 Hz, 3H), 1.18-1.11 (m, 7H), 1.06 (t, J = 7.1 Hz, 2H). | LCMS ESI (method A) 359.4 $[M + H]^+$ at 0.75 min |
| 69F | Ethyl (5R)-5-methyl-2-(6-propan-2-ylpyridin-3-yl)-6,7-dihydro-5H-pyrazolo[5,1-b][1,3]oxazine-3-carboxylate | 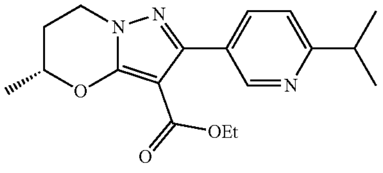 [SMILES: CCOC(=O)c1c(-c2ccc(C(C)C)nc2)nn2c1O[C@H](C)CC2] | (500 MHz) 8.64-8.60 (m, 1H), 7.85 (dd, J = 8.1, 2.3 Hz, 1H), 7.31-7.25 (m, 1H), 4.64-4.55 (m, 1H), 4.18-4.11 (m, 2H), 4.07 (q, J = 7.1 Hz, 2H), 3.04 (hept, J = 6.9 Hz, 1H), 2.32-2.24 (m, 1H), 2.10-1.97 (m, 1H), 1.44 (d, J = 6.3 Hz, 3H), 1.25 (d, J = 6.9 Hz, 6H), 1.13 (t, J = 7.1 Hz, 3H). | (method A) 330.4 $[M + H]^+$ at 0.84 min |

-continued

| Preparatory Example | Name | Structure | $^1$H NMR δ (DMSO-$d_6$) | LCMS/LRMS m/z |
|---|---|---|---|---|
| 69G | Ethyl (5R)-5-methyl-2-[2-methyl-6-(propan-2-ylamino)pyridin-3-yl]-6,7-dihydro-5H-pyrazolo[5,1-b][1,3]oxazine-3-carboxylate | 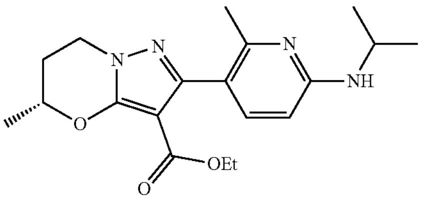 [SMILES: CCOC(=O)c1c(-c2ccc(NC(C)C)nc2C)nn2c1O[C@H](C)CC2] | (500 MHz) 7.11 (d, J = 8.4 Hz, 1H), 6.25-6.19 (m, 2H), 4.62-4.52 (m, 1H), 4.13-4.04 (m, 2H), 4.03-3.91 (m, 3H), 2.28-2.22 (m, 1H), 2.11 (s, 3H), 2.08-1.97 (m, 1H), 1.43 (d, J = 6.3 Hz, 3H), 1.18-1.11 (m, 6H), 1.05 (t, J = 7.1 Hz, 3H). | (method A) 359.6 $[M + H]^+$ at 0.73 min |
| 70A | Ethyl (5S)-2-(6-ethylpyridin-3-yl)-5-methyl-6,7-dihydro-5H-pyrazolo[5,1-b][1,3]oxazine-3-carboxylate | 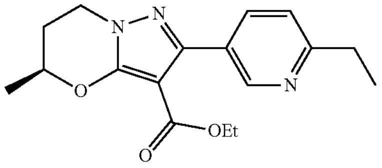 [SMILES: CCOC(=O)c1c(-c2ccc(CC)nc2)nn2c1O[C@@H](C)CC2] | (400 MHz) δ 8.61 (dd, J = 2.3, 0.8 Hz, 1H), 7.85 (dd, J = 8.0, 2.3 Hz, 1H), 7.37-7.20 (m, 1H), 4.73-4.54 (m, 1H), 4.22-4.03 (m, 4H), 2.77 (q, J = 7.6 Hz, 2H), 2.36-2.22 (m, 1H), 2.13-1.93 (m, 1H), 1.44 (d, J = 6.3 Hz, 3H), 1.24 (t, J = 7.6 Hz, 3H), 1.13 (t, J = 7.1 Hz, 3H). | 316.5 $[M + H]^+$ |
| 71A | Ethyl 2-(6-ethylpyridin-3-yl)-6,7-dihydro-5H-pyrazolo[5,1-b][1,3]oxazine-3-carboxylate | 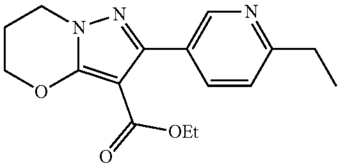 [SMILES: CCOC(=O)c1c(-c2ccc(CC)nc2)nn2c1OCCC2] | (500 MHz) δ 8.64-8.55 (m, 1H), 7.85 (dd, J = 8.0, 2.3 Hz, 1H), 7.27 (d, J = 8.0 Hz, 1H), 4.51-4.41 (m, 2H), 4.14 (t, J = 6.1 Hz, 2H), 4.09 (q, J = 7.1 Hz, 2H), 2.77 (q, J = 7.6 Hz, 2H), 2.31-2.19 (m, 2H), 1.24 (t, J = 7.6 Hz, 3H), 1.14 (t, J = 7.1 Hz, 3H). | 302.0 $[M + H]^+$ |

72A Ethyl (5R)-2-anilino-5-methyl-6,7-dihydro-5H-pyrazolo[5,1-b][1,3]oxazine-3-carboxylate

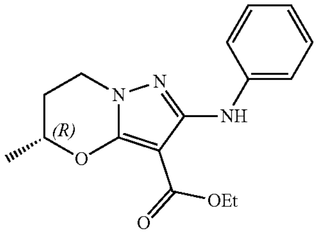

XPhos (50 mg, 0.10 mmol) and tris(dibenzylideneacetone)dipalladium(0) (48 mg, 0.05 mmol) were added to a suspension of aniline (95 μL, 1.04 mmol), $Cs_2CO_3$ (341 mg, 1.04 mmol) and intermediate 9B (150 mg, 0.52 mmol) in 1,4-dioxane (2 mL). The reaction mixture was sparged with $N_2$ and stirred at 100° C. overnight. The reaction was partitioned between EtOAc (10 mL) and water (10 mL), and the separated aqueous phase extracted with EtOAc (3×10 mL). The organic layers were combined, washed with brine (30 mL), dried ($Na_2SO_4$) and concentrated under reduced pressure. Purification by column chromatography (0-50% EtOAc in iso-hexane) afforded a cream solid (164 mg, 96%). LCMS (method F) m/z 302.2 $[M+H]^+$ at 2.30 min. $^1$H NMR (500 MHz, DMSO-$d_6$) δ 8.30 (s, 1H), 7.56-7.53 (m, 2H), 7.27-7.22 (m, 2H), 6.87-6.83 (m, 1H), 4.60-4.51 (m, 1H), 4.21 (q, J=7.1 Hz, 2H), 4.01-3.96 (m, 2H), 2.28-2.21 (m, 1H), 2.05-1.96 (m, 1H), 1.42 (d, J=6.3 Hz, 3H), 1.26 (t, J=7.1 Hz, 3H).

72B Ethyl (5R)-2-(4-fluoroanilino)-5-methyl-6,7-dihydro-5H-pyrazolo[5,1-b][1,3]oxazine-3-carboxylate

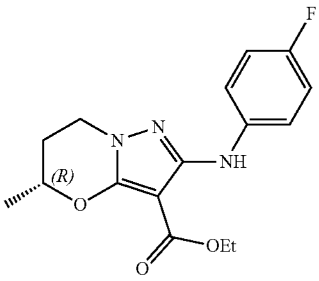

Prepared in an analogous manner to intermediate 72A, with additional purification by ion exchange chromatography (2 g SCX cartridge, eluting with 0.7 M $NH_3$ in MeOH). LCMS (method A) 320.0 $[M+H]^+$ at 1.55 min. $^1$H NMR (500 MHz, DMSO-$d_6$) δ 8.28 (s, 1H), 7.62-7.55 (m, 2H), 7.13-7.04 (m, 2H), 4.60-4.51 (m, 1H), 4.20 (q, J=7.1 Hz, 2H), 4.01-3.95 (m, 2H), 2.29-2.20 (m, 1H), 2.06-1.94 (m, 1H), 1.42 (d, J=6.3 Hz, 3H), 1.26 (t, J=7.1 Hz, 3H).

73A Ethyl (5R)-2-(5-cyclopropyl-2-fluoropyridin-3-yl)-5-methyl-6,7-dihydro-5H-pyrazolo[5,1-b][1,3]oxazine-3-carboxylate

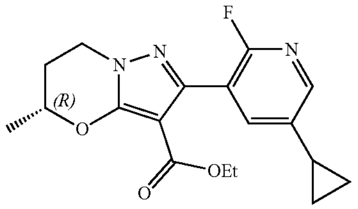

Potassium cyclopropyltrifluoroborate (75.8 mg, 0.51 mmol), Pd-170 (17.3 mg, 0.03 mmol) and $K_2CO_3$ (177 mg, 1.28 mmol) were added to a reaction vessel that was purged with nitrogen. A solution of intermediate 65E (145 mg, 0.43 mmol) in THF:water (1:1; 4 mL) was added, the reaction vessel sparged with nitrogen, and heated to 70° C. for 16 h. The reaction was cooled to rt, partitioned between water (30 mL) and EtOAc (30 mL), and the aqueous phase extracted with EtOAc (3×10 mL). The combined organic layers were washed with brine (40 mL), dried ($Na_2SO_4$) and concentrated under reduced pressure. Purification by column chromatography (0-80% EtOAc in iso-hexane) afforded a white solid (37 mg, 25%). LCMS (Method A) m/z 346.0 $[M+H]^+$ at 1.29 min. $^1$H NMR (500 MHz, DMSO-$d_6$) δ 8.07 (dd, J=2.5, 1.1 Hz, 1H), 7.56 (dd, J=8.9, 2.5 Hz, 1H), 4.67-4.59 (m, 1H), 4.23-4.12 (m, 2H), 4.02 (q, J=7.1 Hz, 2H), 2.33-2.27 (m, 1H), 2.10-1.99 (m, 2H), 1.46 (d, J=6.3 Hz, 3H), 1.08-0.98 (m, 5H), 0.78-0.74 (m, 2H).

74A Ethyl 2-(2,6-difluorophenyl)-5-(hydroxymethyl)-6,7-dihydro-5H-pyrazolo[5,1-b][1,3]oxazine-3-carboxylate

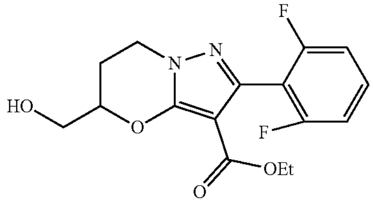 [SMILES: CCOC(=O)c1c(-c2c(F)cccc2F)nn2c1OC(CO)CC2]

Intermediate 9S (400 mg, 1.31 mmol), CsF (797 mg, 5.24 mmol), 2,6-difluorophenylboronic acid (1035 mg, 6.55 mmol) and XPhos Pd G2 (206 mg, 0.26 mmol) were combined in a vial, which was capped, evacuated and sparged with $N_2$ (3×). 1,4-Dioxane (4.5 mL) and water (2.25 mL), which had both been degassed with $N_2$, were added and the reaction heated at 100° C. for 17 h. The reaction was cooled to rt, then the 1,4-dioxane removed under reduced pressure. Water (15 ml) was added, and the mixture extracted with EtOAc (3×15 mL). The organic extracts were washed with water and brine (15 mL each), dried ($Na_2SO_4$), and concentrated under reduced pressure. The residue was purified by flash chromatography (70-100% EtOAc:heptane) to afford a colourless oil (180 mg, 41%). $^1$H NMR (400 MHz, DMSO-$d_6$) δ 7.58-7.42 (m, 1H), 7.22-7.04 (m, 2H), 5.16 (t, J=5.6 Hz, 1H), 4.56-4.45 (m, 1H), 4.28-4.14 (m, 2H), 3.99-3.92 (m, 2H), 3.76-3.63 (m, 2H), 2.37-2.25 (m, 1H), 2.25-2.09 (m, 1H), 0.97 (t, J=7.1 Hz, 3H). LRMS m/z (APCI+) 339.1 $[M+H]^+$.

The following intermediate compounds were prepared by an analogous procedure to that described for intermediate 74A. A catalyst loading of 10 mol % XPhos PdG2 was employed for both.

TABLE 12

| Preparatory Examples | | | | |
|---|---|---|---|---|
| Preparatory Example | Name | Structure | LRMS m/z (APCI+) | TLC $R_f$ |
| 75A | Ethyl 2-(2-fluoro-6-methoxyphenyl)-6,7-dihydro-5H-pyrazolo[5,1-b][1,3]oxazine-3-carboxylate | 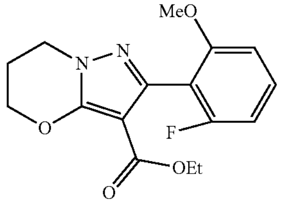 [SMILES: CCOC(=O)c1c(-c2c(F)cccc2OC)nn2c1OCCC2] | 321.2 [M + H]+ | Rf = 0.19 2:1 (EtOAc: Heptane) |
| 75B | Ethyl 2-(2-fluoro-6-methylphenyl)-6,7-dihydro-5H-pyrazolo[5,1-b][1,3]oxazine-3-carboxylate | 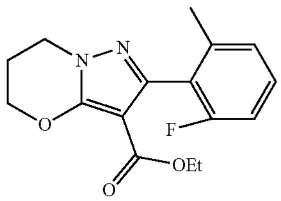 [SMILES: CCOC(=O)c1c(-c2c(C)cccc2F)nn2c1OCCC2] | 305.2 [M + H]+ | Rf = 0.36 2:1 (EtOAc: Heptane) |

76A Ethyl 2-(2,6-difluorophenyl)-6-(hydroxymethyl)-6,7-dihydro-5H-pyrazolo[5,1-b][1,3]oxazine-3-carboxylate

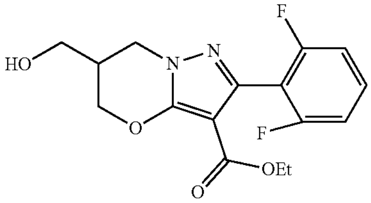 [SMILES: CCOC(=O)c1c(-c2c(F)cccc2F)nn2c1OCC(CO)C2]

Intermediate 9R (142 mg, 0.47 mmol), CsF (283 mg, 1.86 mmol), 2,6-difluorophenylboronic acid (735 mg, 4.65 mmol) and XPhos Pd G2 (36 mg, 0.05 mmol) were combined in a microwave vial, which was capped, evacuated and sparged with $N_2$ (3×). Water (0.9 mL) and 1,4-dioxane (1.8 mL), which had both been degassed with $N_2$, were added and the vial heated at 100° C. for 16 h. The reaction was cooled to rt, additional XPhos Pd G2 (37 mg, 0.05 mmol) added, sealed, then heated for a further 18 h. Analogous workup and purification to that described for intermediate 74A afforded a yellow oil (59 mg, 38%). TLC $R_f$=0.61 (EtOAc) LRMS m/z (APCI+) 339.4 $[M+H]^+$.

77A 1-Bromo-4-ethylsulfonyl-2-fluorobenzene

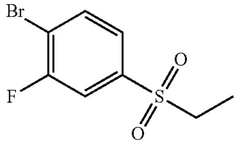

Hydrazine monohydrate (12.4 mL, 255 mmol) was added dropwise to a cooled (0° C.) solution of 4-bromo-3-fluorobenzene sulphonyl chloride (20.0 g, 73.1 mmol) in THE (200 mL). The reaction mixture was allowed to attain rt and stirred for 1 h. Heptane (1000 mL) was added and the resultant precipitate collected via filtration. The white precipitate was dissolved in anhydrous EtOH (400 mL), then NaOAc (36.0 g, 439 mmol) and EtI (29.4 mL, 366 mmol) were added and the reaction heated to reflux overnight. The reaction mixture was cooled to rt and concentrated under reduced pressure. Water (600 mL) was added and the mixture extracted with EtOAc (3×600 mL). The combined organic layers were washed with brine (600 mL), dried ($Na_2SO_4$) and the volatiles removed under reduced pressure. Purification by column chromatography (15-40% EtOAc in heptane) gave a white solid (12.1 g, 62%). $^1H$ NMR (400 MHz, $CDCl_3$) δ 7.78 (dd, J=8.3, 6.4 Hz, 1H), 7.64 (dd, J=7.5, 2.0 Hz, 1H), 7.57 (ddd, J=8.3, 2.0, 0.8 Hz, 1H), 3.12 (q, J=7.4 Hz, 2H), 1.28 (t, J=7.4 Hz, 3H). TLC $R_f$=0.57 (EtOAc).

78A 2-Bromo-1-fluoro-4-methylsulfonylbenzene

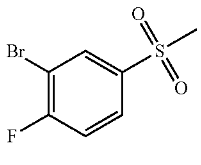

N-bromosuccinimide (8.22 g, 46.2 mmol) was added to a solution of 4-fluorophenyl methyl sulphone (8.05 g, 46.2 mmol) in concentrated $H_2SO_4$ (80 mL) and the reaction heated at 50° C. for 3.5 h. The reaction was cooled to rt and the mixture poured into ice water (270 mL). The resulting mixture was stirred until cool (≈10° C.) and the precipitate collected by filtration. The solid was washed with water and dried on the filter paper, then dried further under reduced pressure overnight to give a white solid (10.3 g, 88%). $^1H$ NMR (400 MHz, DMSO-$d_6$) δ 8.26 (dd, J=6.4, 2.3 Hz, 1H), 7.99 (ddd, J=8.7, 4.6, 2.3 Hz, 1H), 7.65 (t, J=8.6 Hz, 1H), 3.30 (s, 3H). TLC $R_f$=0.57 (EtOAc).

79A 4-Bromo-3-fluoro-N,N-dimethylbenzenesulfonamide

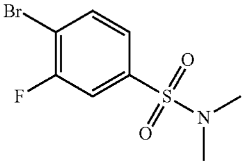

A solution of 4-bromo-3-fluorobenzene sulphonyl chloride (10.0 g, 36.6 mmol) in $CH_2Cl_2$ (120 mL) was cooled to ~ 10° C. in an ice bath. A solution of dimethylamine (33% in ethanol; 13.7 mL, 76.8 mmol) was added dropwise. The reaction was allowed to warm to rt and was stirred for 10 min. The reaction mixture was washed with 1 M aq. HCl (350 mL) and brine (215 mL). The organic phase was separated, dried ($MgSO_4$), filtered and the volatiles removed under reduced pressure to afford a white solid (10.7 g, quant) which was used without further purification. $^1H$ NMR (400 MHz, $CDCl_3$) δ 7.75 (dd, J=8.3, 6.5 Hz, 1H), 7.51 (dd, J=7.7, 2.0 Hz, 1H), 7.44 (ddd, J=8.3, 2.1, 0.8 Hz, 1H), 2.73 (s, 6H). TLC $R_f$=0.59 (EtOAc).

80A 2-(4-Ethylsulfonyl-2-fluorophenyl)-4,4,5,5-tetramethyl-1,3,2-dioxaborolane

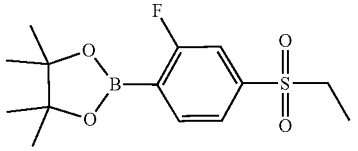 [SMILES: CCS(=O)(=O)c1ccc(B2OC(C)(C)C(C)(C)O2)c(F)c1]

A solution of intermediate 77A (11.6 g, 43.4 mmol), bis(pinacolato)diboron (13.2 g, 52.0 mmol) and KOAc (8.50 g, 86.7 mmol) in 1,4-dioxane (120 mL) was sparged with $N_2$ for ≈20 min. Pd(dppf)$Cl_2$—$CH_2Cl_2$ (0.952 g, 1.30 mmol, 3 mol %) was added and the reaction heated to 85-90° C. overnight. The reaction was cooled to rt, diluted with EtOAc (200 mL) and filtered through Celite, washing with EtOAc. The filtrate was washed with $H_2O$ (100 mL) and brine (100 mL), dried ($Na_2SO_4$), and the volatiles removed under reduced pressure. The residue was purified by column chromatography (0-100% EtOAc/heptane), then dissolved in $CH_2Cl_2$ and heptane (100 mL) was added. The $CH_2Cl_2$ was removed under reduced pressure and the suspension in heptane stirred at rt for 1 h. The solid was collected by filtration under reduced pressure, washed with heptane and dried under reduced pressure to give a white solid (11.0 g, 80%). $^1H$ NMR (400 MHz, $CDCl_3$) δ 7.94 (dd, J=7.7, 5.5 Hz, 1H), 7.66 (dd, J=7.7, 1.6 Hz, 1H), 7.57 (dd, J=8.1, 1.5 Hz, 1H), 3.11 (q, J=7.4 Hz, 2H), 1.37 (s, 12H), 1.27 (t, J=7.4 Hz, 3H). TLC $R_f$=0.43 (EtOAc).

The following intermediate compounds were prepared in an analogous manner to intermediate 80A.

TABLE 13

| Preparatory Examples | | | | |
|---|---|---|---|---|
| Preparatory Example | Name | Structure | $^1$H NMR δ (400 MHz) | TLC $R_f$ |
| 80B | 2-(2-Fluoro-5-methylsulfonylphenyl)-4,4,5,5-tetramethyl-1,3,2-dioxaborolane | 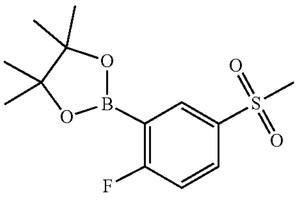 | ($CDCl_3$) 8.35 (dd, J = 5.3, 2.6 Hz, 1H), 8.02 (ddd, J = 8.7, 4.9, 2.6 Hz, 1H), 7.20 (t, J = 8.6 Hz, 1H), 3.06 (s, 3H), 1.36 (s, 12H). | 0.43 (EtOAc) |
| 80C | 3-Fluoro-4-(4,4,5,5-tetramethyl-1,3,2-dioxaborolan-2-yl)benzenesulfonamide | 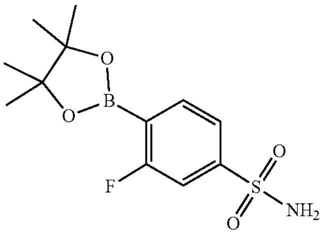 [SMILES: CC1(C)OB(c2ccc(S(N)(=O)=O)cc2F)OC1(C)C] | (DMSO-$d_6$) δ 7.85 (dd, J = 7.7, 5.8 Hz, 1H), 7.68 (dd, J = 7.8, 1.6 Hz, 1H), 7.56 (d, J = 8.6 Hz, 3H), 1.32 (s, 12H). | 0.43 (EtOAc) |
| 80D | 3-Fluoro-N,N-dimethyl-4-(4,4,5,5-tetramethyl-1,3,2-dioxaborolan-2-yl)benzenesulfonamide | 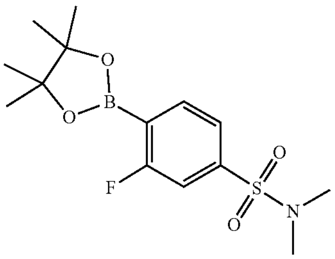 | ($CDCl_3$) δ 7.89 (dd, J = 8.0, 5.6 Hz, 1H), 7.51 (dd, J = 8.0, 1.6 Hz, 1H), 7.41 (dd, J = 8.4, 1.6 Hz, 1H), 2.69 (s, 6H), 1.35 (s, 12H). | 0.43 (EtOAc) |

The following intermediate Compounds were prepared in an analogous manner to intermediate 21A. The reaction time varied between 30 min to 3 h, with heating by MWI or by conventional heating. Intermediates 88T-88W were heated at 85° C. by conventional heating overnight. The catalyst loading varied from 5-10 mol % XPhos PdG2. Intermediates 81J-81W, 84B and 85A were prepared from the corresponding pinacol ester. $^1$H NMR were performed on a 400 MHz spectrometer in DMSO-$d_6$ unless specified.

TABLE 14

| Preparatory examples prepared via Suzuki-Miyaura procedure B. | | | | |
|---|---|---|---|---|
| Preparatory Example | Name | Structure | $^1$H NMR δ (400 MHz, DMSO-$d_6$) | LRMS m/z; TLC $R_f$ |
| 81A | Ethyl (5R)-2-(6-fluoropyridin-3-yl)-5-methyl-6,7-dihydro-5H-pyrazolo[5,1-b][1,3]oxazine-3-carboxylate | 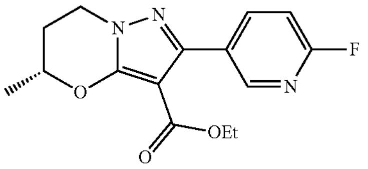 [SMILES: CCOC(=O)c1c(-c2ccc(F)nc2)nn2c1O[C@H](C)CC2] | δ 8.39 (d, J = 2.6 Hz, 1H), 8.15 (ddd, J = 8.2, 8.2, 2.5 Hz, 1H), 7.22 (dd, J = 8.5, 2.5 Hz, 1H), 4.66-4.56 (m, 1H), 4.22-4.10 (m, 2H), 4.08 (q, J = 7.3 Hz, 2H), 2.33-2.25 (m, 1H), 2.04 (dddd, J = 14.2, 10.1, 10.1, 6.4 Hz, 1H), 1.44 (d, J = 6.3 Hz, 3H), 1.14 (t, J = 7.1 Hz, 3H). | (APCI+) 306.3 $[M + H]^+$ |
| 81B | Ethyl (5R)-2-[1-(2-hydroxyethyl)pyrazol-4-yl]-5-methyl-6,7-dihydro-5H-pyrazolo[5,1-b][1,3]oxazine-3-carboxylate | 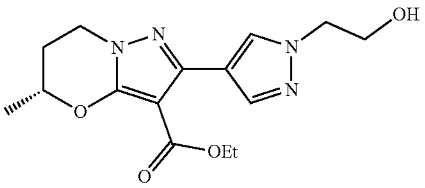 [SMILES: CCOC(=O)c1c(-c2cnn(CCO)c2)nn2c1O[C@H](C)CC2] | δ 8.22 (d, J = 0.7 Hz, 1H), 7.83 (d, J = 0.7 Hz, 1H), 4.91 (t, J = 5.3 Hz, 1H), 4.61-4.49 (m, 1H), 4.23-4.02 (m, 6H), 3.73 (q, J = 5.5 Hz, 2H), 2.29-2.17 (m, 1H), 2.06-1.88 (m, 1H), 1.42 (d, J = 6.3 Hz, 3H), 1.24 (t, J = 7.1 Hz, 3H). | (APCI+) 321.4 $[M + H]^+$ |

TABLE 14-continued

Preparatory examples prepared via Suzuki-Miyaura procedure B.

| Preparatory Example | Name | Structure | $^1H$ NMR δ (400 MHz, DMSO-$d_6$) | LRMS m/z; TLC $R_f$ |
|---|---|---|---|---|
| 81C | Ethyl (5R)-2-[1-(difluoromethyl) pyrazol-4-yl]-5-methyl-6,7-dihydro-5H-pyrazolo[5,1-b] [1,3]oxazine-3-carboxylate | 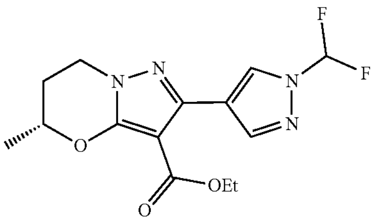 [SMILES: CCOC(=O)c1c(-c2cnn(C(F)F)c2)nn2c1O[C@H](C)CC2] | δ 8.71 (d, J = 0.6 Hz, 1H), 8.12 (d, J = 0.5 Hz, 1H), 7.87 (t, J = 58.9 Hz, 1H), 4.63-4.51 (m, 1H), 4.21-4.06 (m, 4H), 2.30-2.22 (m, 1H), 2.07-1.94 (m, 1H), 1.43 (d, J = 6.3 Hz, 3H), 1.23 (t, J = 7.1 Hz, 3H). | (APCI+) 327.4 $[M + H]^+$ |
| 81D | Ethyl (5R)-2-[1-(2-methoxyethyl) pyrazol-4-yl]-5-methyl-6,7-dihydro-5H-pyrazolo[5,1-b][1,3]oxazine-3-carboxylate | 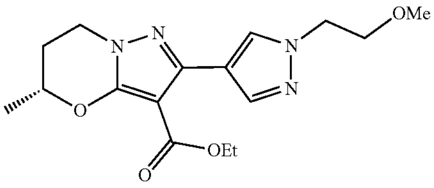 [SMILES: CCOC(=O)c1c(-c2cnn(CCOC)c2)nn2c1O[C@H](C)CC2] | δ 8.19 (d, J = 0.7 Hz, 1H), 7.83 (d, J = 0.7 Hz, 1H), 4.61-4.49 (m, 1H), 4.27 (t, J = 5.3 Hz, 2H), 4.19-4.03 (m, 4H), 3.68 (dd, J = 5.6, 4.9 Hz, 2H), 3.23 (s, 3H), 2.30-2.20 (m, 1H), 2.07-1.94 (m, 1H), 1.42 (d, J = 6.3 Hz, 3H), 1.24 (t, J = 7.1 Hz, 3H). | (APCI+) 335.4 $[M + H]^+$ |
| 81E | Ethyl (5R)-2-(2-fluoro-4-methylsulfonylphenyl)-5-methyl-6,7-dihydro-5H-pyrazolo[5,1-b] [1,3]oxazine-3-carboxylate | 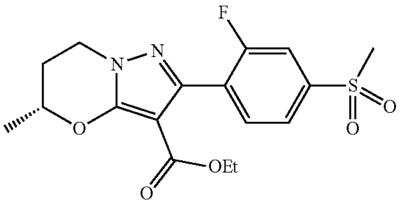 [SMILES: CCOC(=O)c1c(-c2ccc(S(C)(=O)=O)cc2F)nn2c1O[C@H](C)CC2] | Not available | (APCI+) 383.1 $[M + H]^+$ $R_f$ = 0.45 EtOAc |
| 81F | Ethyl (5R)-5-methyl-2-(1-methylsulfonylpyrazol-4-yl)-6,7-dihydro-5H-pyrazolo[5,1-b][1,3] oxazine-3-carboxylate | 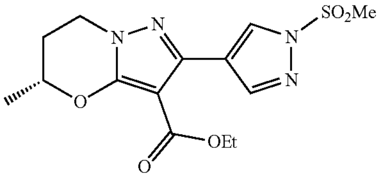 [SMILES: CCOC(=O)c1c(-c2cnn(S(C)(=O)=O)c2)nn2c1O[C@H](C)CC2] | Not available | (APCI+) 355.1 $[M + H]^+$; $R_f$ = 0.35 EtOAc |
| 81G | Ethyl (5R)-2-(1-cyclopropylpyrazol-4-yl)-5-methyl-6,7-dihydro-5H-pyrazolo[5,1-b][1,3]oxazine-3-carboxylate | 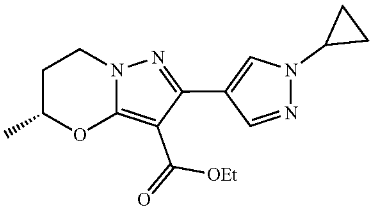 [SMILES: CCOC(=O)c1c(-c2cnn(C3CC3)c2)nn2c1O[C@H](C)CC2] | δ 8.24 (s, 1H), 7.78 (d, J = 0.7 Hz, 1H), 4.62-4.48 (m, 1H), 4.15 (q, J = 7.1 Hz, 2H), 4.14-4.00 (m, 3H), 3.80-3.70 (m, 1H), 2.28-2.19 (m, 1H), 2.07-1.92 (m, 1H), 1.42 (d, J = 6.3 Hz, 3H), 1.23 (t, J = 7.1 Hz, 3H), 1.05-0.92 (m, 4H). | (APCI+) 317.2 $[M + H]^+$ |
| 81H | Ethyl (5R)-2-[6-(hydroxymethyl) pyridin-3-yl]-5-methyl-6,7-dihydro-5H-pyrazolo[5,1-b][1,3]oxazine-3-carboxylate | 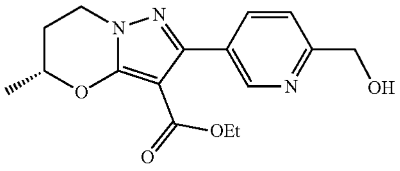 [SMILES: CCOC(=O)c1c(-c2ccc(CO)nc2)nn2c1O[C@H](C)CC2] | δ 8.62 (dd, J = 2.2, 0.8 Hz, 1H), 7.95 (dd, J = 8.1, 2.2 Hz, 1H), 7.48 (dd, J = 8.1, 0.9 Hz, 1H), 5.46 (t, J = 5.9 Hz, 1H), 4.59 (d, J = 5.9 Hz, 3H), 4.21-4.02 (m, 4H), 2.33-2.23 (m, 1H), 2.13-1.96 (m, 1H), 1.44 (d, J = 6.2 Hz, 3H), 1.14 (t, J = 7.1 Hz, 3H). | (APCI+) 318.2 $[M + H]^+$ |
| 81I | Ethyl (5R)-2-(2-fluoro-4-formylphenyl)-5-methyl-6,7-dihydro-5H-pyrazolo[5,1-b] [1,3]oxazine-3-carboxylate | 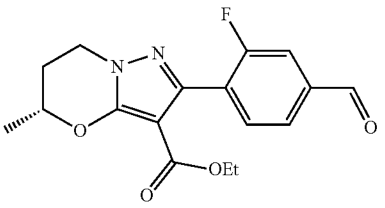 [SMILES: CCOC(=O)c1c(-c2ccc(C=O)cc2F)nn2c1O[C@H](C)CC2] | δ 10.04 (d, J = 1.6 Hz, 1H), 7.80 (dd, J = 7.8, 1.5 Hz, 1H), 7.73 (dd, J = 9.9, 1.5 Hz, 1H), 7.65 (dd, J = 7.7, 6.9 Hz, 1H), 4.71-4.53 (m, 1H), 4.24-4.08 (m, 2H), 4.08-3.91 (m, 2H), 2.35-2.23 (m, 1H), 2.15-2.00 (m, 1H), 1.45 (d, J = 6.3 Hz, 3H), 1.03 (t, J = 7.1 Hz, 3H). | (APCI+) 333.2 $[M + H]^+$ |

TABLE 14-continued

Preparatory examples prepared via Suzuki-Miyaura procedure B.

| Preparatory Example | Name | Structure | $^1$H NMR δ (400 MHz, DMSO-$d_6$) | LRMS m/z; TLC $R_f$ |
|---|---|---|---|---|
| 81J | Ethyl (5R)-2-(1,3-dimethylpyrazol-4-yl)-5-methyl-6,7-dihydro-5H-pyrazolo[5,1-b][1,3]oxazine-3-carboxylate | 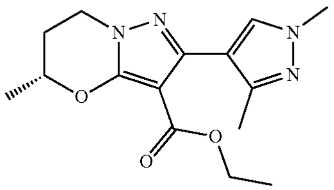 | δ 7.95 (s, 1H), 4.60-4.46 (m, 1H), 4.15-4.03 (m, 4H), 3.76 (s, 3H), 2.28-2.22 (m, 1H), 2.21 (s, 3H), 2.07-1.90 (m, 1H), 1.42 (d, J = 6.3 Hz, 3H), 1.19 (t, J = 7.1 Hz, 3H). | (APCI+) 305.5 $[M + H]^+$ |
| 81K | Ethyl (5R)-5-methyl-2-[1-(oxan-4-yl)pyrazol-4-yl]-6,7-dihydro-5H-pyrazolo[5,1-b][1,3]oxazine-3-carboxylate | 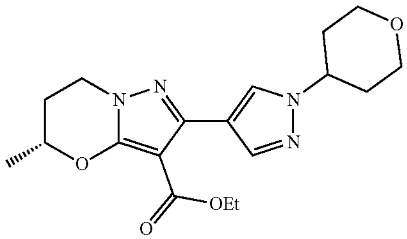 [SMILES: CCOC(=O)c1c(-c2cnn(C3CCOCC3)c2)nn2c1O[C@H](C)CC2] | — | (APCI+) 361.8 $[M + H]^+$; Rf = 0.13 (2:1 EtOAc: Heptane) |
| 81L | Ethyl (5R)-5-methyl-2-(1-propan-2-ylpyrazol-4-yl)-6,7-dihydro-5H-pyrazolo[5,1-b][1,3]oxazine-3-carboxylate | 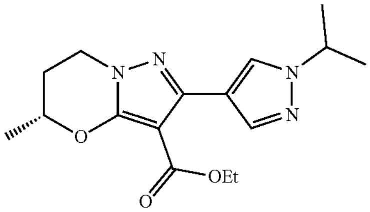 [SMILES: CCOC(=O)c1c(-c2cnn(C(C)C)c2)nn2c1O[C@H](C)CC2] | — | (APCI+) 319.7 $[M + H]^+$; Rf = 0.27 (2:1 EtOAc:Heptane) |
| 81M | Ethyl (5R)-5-methyl-2-(1-methylpyrazol-4-yl)-6,7-dihydro-5H-pyrazolo[5,1-b][1,3]oxazine-3-carboxylate | 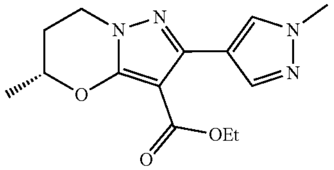 | δ 8.22-8.11 (m, 1H), 7.79 (d, J = 0.7 Hz, 1H), 4.58-4.49 (m, 1H), 4.15 (q, J = 7.1 Hz, 2H), 4.11-4.05 (m, 2H), 3.85 (s, 3H), 2.29-2.20 (m, 1H), 2.05-1.93 (m, 1H), 1.42 (d, J = 6.3 Hz, 3H), 1.23 (t, J = 7.1 Hz, 3H). | (APCI+) 291.6 $[M + H]^+$ |
| 81N | Ethyl (5R)-5-methyl-2-[1-(2,2,2-trifluoroethyl) pyrazol-4-yl]-6,7-dihydro-5H-pyrazolo[5,1-b][1,3] oxazine-3-carboxylate | 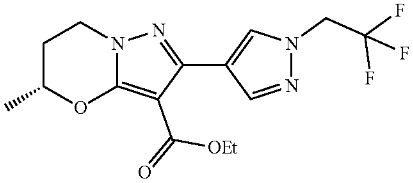 [SMILES: CCOC(=O)c1c(-c2cnn(CC(F)(F)F)c2)nn2c1O[C@H](C)CC2] | δ 8.39 (d, J = 0.6 Hz, 1H), 7.94 (d, J = 0.6 Hz, 1H), 5.19 (q, J = 9.2 Hz, 2H), 4.65-4.46 (m, 1H), 4.16 (q, J = 7.1 Hz, 2H), 4.13-4.04 (m, 2H), 2.30-2.18 (m, 1H), 2.10-1.89 (m, 1H), 1.42 (d, J = 6.3 Hz, 3H), 1.23 (t, J = 7.1 Hz, 3H). | (APCI+) 359.4 $[M + H]^+$ |
| 81O | Ethyl (5R)-5-methyl-2-[1-(oxetan-3-yl)pyrazol-4-yl]-6,7-dihydro-5H-pyrazolo[5,1-b][1,3] oxazine-3-carboxylate | 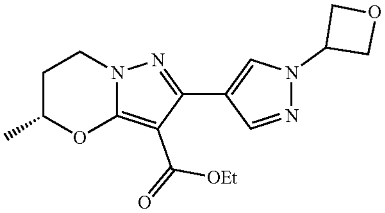 [SMILES: CCOC(=O)c1c(-c2cnn(C3COC3)c2)nn2c1O[C@H](C)CC2] | δ 8.35 (d, J = 0.7 Hz, 1H), 7.96 (s, 1H), 5.70-5.60 (m, 1H), 4.99-4.85 (m, 4H), 4.61-4.45 (m, 1H), 4.16 (q, J = 7.1 Hz, 2H), 4.12-4.03 (m, 2H), 2.29-2.21 (m, 1H), 2.10-1.93 (m, 1H), 1.42 (d, J = 6.3 Hz, 3H), 1.23 (t, J = 7.1 Hz, 3H). | (APCI+) 333.4 $[M + H]^+$ |
| 81P | Ethyl (5R)-2-(1,5-dimethylpyrazol-4-yl)-5-methyl-6,7-dihydro-5H-pyrazolo[5,1-b][1,3]oxazine-3-carboxylate | 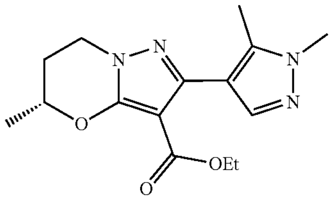 | δ 7.35 (s, 1H), 4.60-4.50 (m, 1H), 4.18-3.99 (m, 4H), 3.74 (s, 3H), 2.33-2.21 (m, 4H), 2.10-1.95 (m, 1H), 1.42 (d, J = 6.3 Hz, 3H), 1.16 (t, J = 7.1 Hz, 3H). | (APCI+) 305.4 $[M + H]^+$ |

TABLE 14-continued

Preparatory examples prepared via Suzuki-Miyaura procedure B.

| Preparatory Example | Name | Structure | $^1$H NMR δ (400 MHz, DMSO-$d_6$) | LRMS m/z; TLC $R_f$ |
|---|---|---|---|---|
| 81Q | Ethyl (5R)-2-[1-(2-hydroxy-2-methylpropyl) pyrazol-4-yl]-5-methyl-6,7-dihydro-5H-pyrazolo[5,1-b][1,3] oxazine-3-carboxylate | 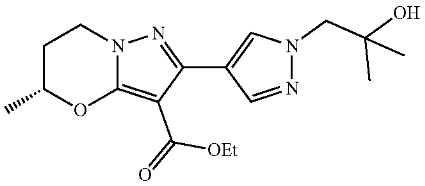 [SMILES: CCOC(=O)c1c(-c2cnn(CC(C)(C)O)c2)nn2c1O[C@H](C)CC2] | δ 8.22 (d, J = 0.7 Hz, 1H), 7.81 (d, J = 0.7 Hz, 1H), 4.70 (s, 1H), 4.59-4.49 (m, 1H), 4.15 (q, J = 7.1 Hz, 2H), 4.12-4.04 (m, 2H), 4.02 (s, 2H), 2.30-2.20 (m, 1H), 2.06-1.90 (m, 1H), 1.42 (d, J = 6.3 Hz, 3H), 1.23 (t, J = 7.1 Hz, 3H), 1.06 (s, 6H). | (APCI+) 349.5 $[M + H]^+$ |
| 81R | Ethyl (5R)-2-(cyclohexen-1-yl)-5-methyl-6,7-dihydro-5H-pyrazolo[5,1-b][1,3] oxazine-3-carboxylate | 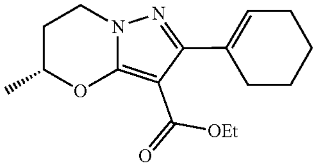 [SMILES: CCOC(=O)c1c(C2=CCCCC2)nn2c1O[C@H](C)CC2] | δ 5.97-5.86 (m, 1H), 4.56-4.43 (m, 1H), 4.13-3.98 (m, 4H), 2.31-2.15 (m, 3H), 2.14-2.03 (m, 2H), 2.05-1.88 (m, 1H), 1.70-1.50 (m, 4H), 1.39 (d, J = 6.2 Hz, 3H), 1.20 (t, J = 7.1 Hz, 4H). | (APCI+) 291.3 $[M + H]^+$ |
| 81S | Ethyl (5R)-5-methyl-2-(1,2,3,6-tetrahydropyridin-4-yl)-6,7-dihydro-5H-pyrazolo[5,1-b] [1,3]oxazine-3-carboxylate | 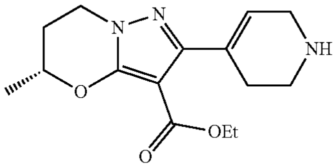 [SMILES: CCOC(=O)c1c(C2=CCNCC2)nn2c1O[C@H](C)CC2] | δ 6.11-6.03 (m, 1H), 4.57-4.42 (m, 1H), 4.15-3.97 (m, 4H), 2.83 (t, J = 5.6 Hz, 2H), 2.37-2.08 (m, 3H), 2.04-1.89 (m, 1H), 1.39 (d, J = 6.4 Hz, 3H), 1.20 (t, J = 7.1 Hz, 3H). | (APCI+) 292.3 $[M + H]^+$ |
| 81T | Ethyl (5R)-2-(4-ethylsulfonyl-2-fluorophenyl)-5-methyl-6,7-dihydro-5H-pyrazolo[5,1-b][1,3]oxazine-3-carboxylate | 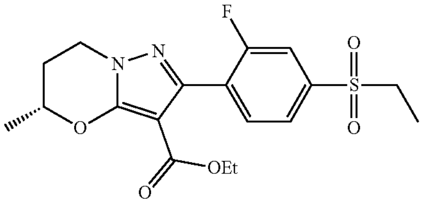 [SMILES: CCOC(=O)c1c(-c2ccc(S(=O)(=O)CC)cc2F)nn2c1O[C@H](C)CC2] | ($CDCl_3$, 400 MHz) δ 7.74-7.71 (m, 1H), 7.69-7.63 (m, 2H), 4.61-4.53 (m, 1H), 4.30-4.24 (m, 2H), 4.22-4.18 (m, 1H), 4.14 (q, J = 7.2 Hz, 2H), 3.14 (q, J = 7.6 Hz, 2H), 2.32-2.26 (m, 1H), 2.21-2.11 (m, 1H), 1.60 (d, J = 4.8 Hz, 3H), 1.29 (t, J = 7.6 Hz, 3H), 1.13 (t, J = 7.2 Hz, 3H). | (ESI+) 396.9 $[M + H]^+$ |
| 81U | Ethyl (5R)-2-(2-fluoro-5-methylsulfonylphenyl)-5-methyl-6,7-dihydro-5H-pyrazolo[5,1-b] [1,3]oxazine-3-carboxylate | 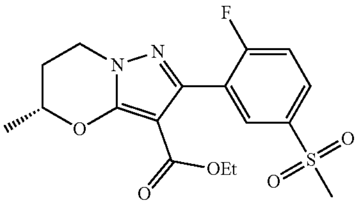 [SMILES: CCOC(=O)c1c(-c2cc(S(C)(=O)=O)ccc2F)nn2c1O[C@H](C)CC2] | ($CDCl_3$, 400 MHz) δ 8.07 (dd, J = 6.4, 2.4 Hz, 1H), 7.95 (ddd, J = 8.4, 4.4, 2.4 Hz, 1H), 7.26 (t, J = 9.0 Hz, 1H), 4.59-4.51 (m, 1H), 4.28-4.22 (m, 2H), 4.20-4.16 (m, 1H), 4.12 (q, J = 7.2 Hz, 2H), 3.06 (s, 3H), 2.31-2.25 (m, 1H), 2.19-2.09 (m, 1H), 1.58 (d, J = 6.0 Hz, 3H), 1.11 (t, J = 7.2 Hz, 3H). | Not available |
| 81V | Ethyl (5R)-2-(2-fluoro-4-sulfamoylphenyl)-5-methyl-6,7-dihydro-5H-pyrazolo[5,1-b] [1,3]oxazine-3-carboxylate | 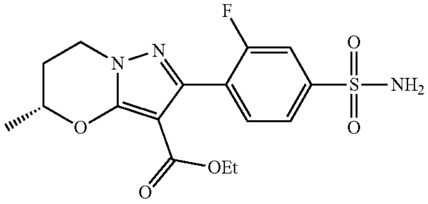 [SMILES: CCOC(=O)c1c(-c2ccc(S(N)(=O)=O)cc2F)nn2c1O[C@H](C)CC2] | ($CDCl_3$, 400 MHz) δ 7.61 (dd, J = 8.0, 1.6 Hz, 1H), 7.56 (dd, J = 8.8, 1.6 Hz, 1H), 7.47 (dd, J = 8.0, 6.8 Hz, 1H), 5.64 (s, 2H), 4.61-4.53 (m, 1H), 4.36-4.31 (m, 1H), 4.25-4.18 (m, 1H) 4.12 (q, J = 6.8 Hz, 2H), 2.33-2.26 (m, 1H), 2.21-2.11 (m, 1H), 1.59 (d, J = 6.4 Hz, 3H), 1.12 (t, J = 6.8 Hz, 3H). | (ESI+) 383.9 $[M + H]^+$ |
| 81W | Ethyl (5R)-2-[4-(dimethylsulfamoyl)-2-fluorophenyl]-5-methyl-6,7-dihydro-5H-pyrazolo[5,1-b][1,3]oxazine-3-carboxylate | 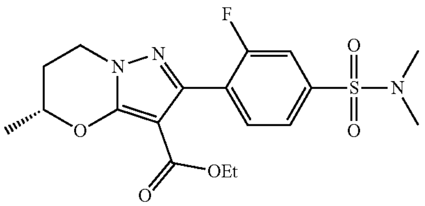 | ($CDCl_3$, 400 MHz) δ 7.64 (dd, J = 8.0, 6.4 Hz, 1H), 7.58 (dd, J = 8.0, 2.0 Hz, 1H), 7.50 (dd, J = 8.8, 1.6 Hz), 4.60-4.52 (m, 1H), 4.29-4.23 (m, 1H), 4.21-4.17 (m, 1H), 4.13 (q, J = 6.8 Hz, 2H), 2.72 (s, 6H), 1.59 (d, J = 6.4 Hz, 3H), 1.11 (t, J = 7.2 Hz, 3H). | (ESI+) 411.9 $[M + H]^+$ |

TABLE 14-continued

Preparatory examples prepared via Suzuki-Miyaura procedure B.

| Preparatory Example | Name | Structure | $^1$H NMR δ (400 MHz, DMSO-$d_6$) | LRMS m/z; TLC $R_f$ |
|---|---|---|---|---|
| 82A | Ethyl (5S)-5-methyl-2-[1-(oxan-4-yl)pyrazol-4-yl]-6,7-dihydro-5H-pyrazolo[5,1-b][1,3]oxazine-3-carboxylate | 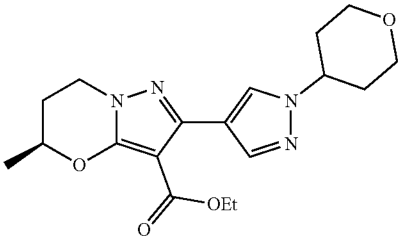 [SMILES: CCOC(=O)c1c(-c2cnn(C3CCOCC3)c2)nn2c1O[C@@H](C)CC2] | δ 8.25 (s, 1H), 7.85 (s, 1H), 4.54 (dtd, J = 12.5, 6.2, 2.2 Hz, 1H), 4.43 (tt, J = 10.1, 5.0 Hz, 1H), 4.16 (q, J = 7.1 Hz, 2H), 4.12-4.05 (m, 2H), 4.01-3.93 (m, 2H), 3.47 (td, J = 11.4, 3.1 Hz, 3H), 2.25 (ddt, J = 14.1, 5.6, 3.0 Hz, 1H), 2.08-1.84 (m, 5H), 1.43 (d, J = 6.3 Hz, 3H), 1.24 (t, J = 7.1 Hz, 3H). | (APCI+) 361.5 [M + H]$^+$ |
| 82B | Ethyl (5S)-5-methyl-2-[1-(2,2,2-trifluoroethyl) pyrazol-4-yl]-6,7-dihydro-5H-pyrazolo[5,1-b] [1,3]oxazine-3-carboxylate | 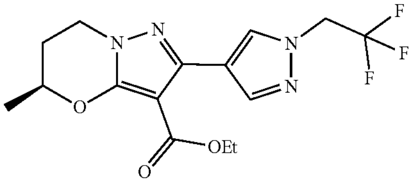 [SMILES: CCOC(=O)c1c(-c2cnn(CC(F)(F)F)c2)nn2c1O[C@@H](C)CC2] | δ 8.40 (s, 1H), 7.95 (s, 1H), 5.20 (q, J = 9.2 Hz, 2H), 4.56 (dtd, J = 12.5, 6.2, 2.2 Hz, 1H), 4.17 (q, J = 7.1 Hz, 2H), 4.13-4.03 (m, 2H), 2.26 (ddt, J = 14.2, 5.5, 2.8 Hz, 1H), 2.01 (dtd, J = 14.1, 10.0, 6.6 Hz, 1H), 1.43 (d, J = 6.3 Hz, 3H), 1.24 (t, J = 7.1 Hz, 4H). | (APCI+) 359.5 [M + H]$^+$ |
| 82C | Ethyl (5S)-2-(1-ethylpyrazol-4-yl)-5-methyl-6,7-dihydro-5H-pyrazolo[5,1-b] [1,3]oxazine-3-carboxylate | 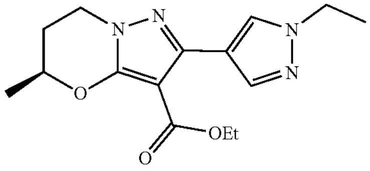 [SMILES: CCOC(=O)c1c(-c2cnn(CC)c2)nn2c1O[C@@H](C)CC2] | δ 8.21 (s, 1H), 7.81 (s, 1H), 4.61-4.48 (m, 1H), 4.15 (qd, J = 7.2, 3.5 Hz, 4H), 4.11-4.02 (m, 2H), 2.24 (ddt, J = 14.1, 5.7, 2.9 Hz, 1H), 1.99 (dtd, J = 14.1, 9.9, 6.8 Hz, 1H), 1.42 (d, J = 6.3 Hz, 3H), 1.37 (t, J = 7.3 Hz, 3H), 1.23 (t, J = 7.1 Hz, 3H). | (APCI+) 305.4 [M + H]$^+$ |
| 83A | Ethyl (2R)-6-(2-fluorophenyl)-2-methyl-2,3-dihydropyrazolo[5,1-b][1,3]oxazole-7-carboxylate | 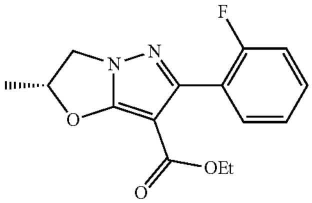 [SMILES: CCOC(=O)c1c(-c2ccccc2F)nn2c1O[C@H](C)C2] | δ 7.54-7.35 (m, 2H), 7.29-7.14 (m, 2H), 5.73-5.60 (m, 1H), 4.52 (dd, J = 9.5, 8.3 Hz, 1H), 4.11-3.94 (m, 3H), 1.61 (d, J = 6.3 Hz, 3H), 1.07 (t, J = 7.1 Hz, 3H). | (APCI+) 291.2 [M + H]$^+$ |
| 84A | Ethyl 2-(6-fluoropyridin-3-yl)spiro[5,7-dihydropyrazolo[5,1-b][1,3]oxazine-6,1'-cyclopropane]-3-carboxylate | 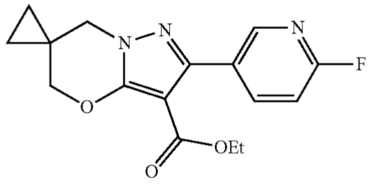 [SMILES: CCOC(=O)c1c(-c2ccc(F)nc2)nn2c1OCC1(CC1)C2] | (500 MHz, DMSO-$d_6$) δ 8.39 (d, J = 2.3 Hz, 1H), 8.16 (td, J = 8.3, 2.5 Hz, 1H), 7.22 (dd, J = 8.5, 2.8 Hz, 1H), 4.27 (s, 2H), 4.11 (q, J = 7.1 Hz, 2H), 4.06 (s, 2H), 1.14 (t, J = 7.1 Hz, 3H), 0.86-0.66 (m, 4H). | (APCI+) 317.9 [M + H]$^+$ |
| 84B | Ethyl 2-(6-ethylpyridin-3-yl)spiro[5,7-b][1,3]oxazine-6,1'-cyclopropane]-3-carboxylate | 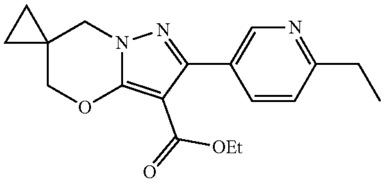 [SMILES: CCOC(=O)c1c(-c2ccc(CC)nc2)nn2c1OCC1(CC1)C2] | (500 MHz, DMSO-$d_6$) δ 8.62 (dd, J = 2.3, 0.8 Hz, 1H), 7.86 (dd, J = 8.0, 2.3 Hz, 1H), 7.28 (dd, J = 0.8, 0.8 Hz, 1H), 4.26 (s, 2H), 4.10 (q, J = 7.1 Hz, 2H), 4.05 (s, 2H), 2.78 (q, J = 7.6 Hz, 2H), 1.25 (t, J = 7.6 Hz, 3H), 1.14 (t, J = 7.1 Hz, 3H), 0.81 (d, J = 2.0 Hz, 4H). | (APCI+) 328.3 [M + H]$^+$ |
| 85A | Ethyl 2-(6-ethylpyridin-3-yl)spiro[5,7-dihydropyrazolo[5,1-b][1,3]oxazine-6,1'-cyclobutane]-3-carboxylate | 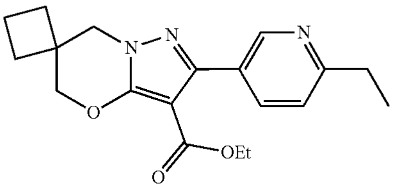 [SMILES: CCOC(=O)c1c(-c2ccc(CC)nc2)nn2c1OCC1(CCC1)C2] | (500 MHz, DMSO-$d_6$) δ 8.69-8.55 (m, 1H), 7.85 (dd, J = 8.0, 2.3 Hz, 1H), 7.27 (d, J = 8.0 Hz, 1H), 4.39 (s, 2H), 4.15 (s, 1H), 4.10 (q, J = 7.1 Hz, 2H), 3.92 (s, 1H), 2.77 (q, J = 7.6 Hz, 2H), 2.15-1.88 (m, 6H), 1.24 (t, J = 7.6 Hz, 3H), 1.18-1.10 (m, 3H), 1.07 (s, | (APCI+) 342.1 [M + H]$^+$ |

TABLE 14-continued

Preparatory examples prepared via Suzuki-Miyaura procedure B.

| Preparatory Example | Name | Structure | $^1$H NMR δ (400 MHz, DMSO-$d_6$) | LRMS m/z; TLC $R_f$ |
|---|---|---|---|---|
| | | | 4H). | |
| 86A | Ethyl 2-(2-fluorophenyl)-6-phenylmethoxy-6,7-dihydro-5H-pyrazolo[5,1-b][1,3]oxazine-3-carboxylate | 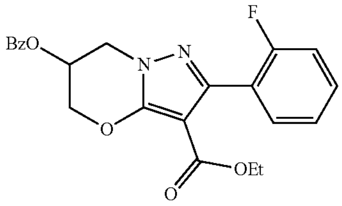 | (500 MHz, DMSO-$d_6$) δ 7.47-7.27 (m, 7H), 7.24-7.19 (m, 2H), 4.68 (dd, J = 11.9, 2.8 Hz, 3H), 4.46-4.40 (m, 1H), 4.37-4.25 (m, 3H), 4.01 (qd, J = 7.1, 1.3 Hz, 2H), 1.04 (t, J = 7.1 Hz, 3H). | (APCI+) 397.2 $[M + H]^+$ |
| 87A | Ethyl 2-(2-fluorophenyl)-5-(hydroxymethyl)-6,7-dihydro-5H-pyrazolo[5,1-b][1,3]oxazine-3-carboxylate | 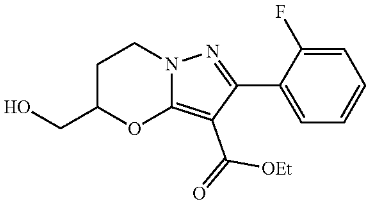 [SMILES: CCOC(=O)c1c(-c2ccccc2F)nn2c1OC(CO)CC2] | δ 7.49-7.35 (m, 2H), 7.26-7.15 (m, 2H), 5.14 (t, J = 5.6 Hz, 1H), 4.56-4.36 (m, 1H), 4.25-4.09 (m, 2H), 4.07-3.89 (m, 2H), 3.81-3.65 (m, 2H), 2.36-2.25 (m, 1H), 2.25-2.07 (m, 2H), 1.01 (t, J = 7.1 Hz, 3H). | (APCI+) 331.9 $[M + H]^+$ |
| 88A | Ethyl 2-(2-fluorophenyl)-6-(hydroxymethyl)-6,7-dihydro-5H-pyrazolo[5,1-b][1,3]oxazine-3-carboxylate | 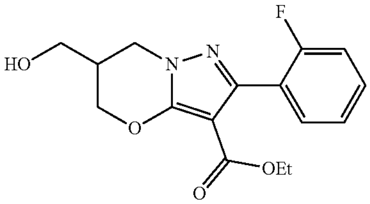 [SMILES: CCOC(=O)c1c(-c2ccccc2F)nn2c1OCC(CO)C2] | δ 7.50-7.34 (m, 2H), 7.28-7.12 (m, 2H), 5.03 (t, J = 5.3 Hz, 1H), 4.52 (dd, J = 10.9, 3.3 Hz, 1H), 4.29 (dd, J = 10.9, 7.9 Hz, 1H), 4.21 (dd, J = 12.3, 5.6 Hz, 1H), 4.04-3.90 (m, 3H), 3.52 (dd, J = 6.6, 5.3 Hz, 2H), 1.03 (t, J = 7.1 Hz, 3H). | (APCI+) 321.6 $[M + H]^+$ |
| 88B | Ethyl 2-(2,4-difluorophenyl)-6-(hydroxymethyl)-6,7-dihydro-5H-pyrazolo[5,1-b][1,3]oxazine-3-carboxylate | 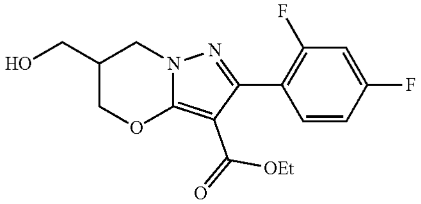 [SMILES: CCOC(=O)c1c(-c2ccc(F)cc2F)nn2c1OCC(CO)C2] | δ 7.44 (td, J = 8.5, 6.7 Hz, 1H), 7.28 (td, J = 9.9, 2.5 Hz, 1H), 7.21-7.04 (m, 1H), 5.03 (t, J = 5.1 Hz, 1H), 4.52 (dd, J = 10.9, 3.3 Hz, 1H), 4.29 (dd, J = 10.9, 8.0 Hz, 1H), 4.21 (dd, J = 12.3, 5.6 Hz, 1H), 4.07-3.92 (m, 3H), 3.51 (t, J = 5.7 Hz, 2H), 1.05 (t, J = 7.1 Hz, 3H). | (APCI+) 339.4 $[M + H]^+$ |
| 88C | Ethyl 2-(6-ethylpyridin-3-yl)-6-(hydroxymethyl)-6,7-dihydro-5H-pyrazolo[5,1-b][1,3]oxazine-3-carboxylate | 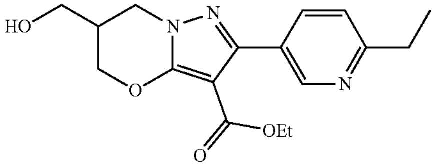 | δ 8.61 (dd, J = 2.3, 0.8 Hz, 1H), 7.85 (dd, J = 8.0, 2.3 Hz, 1H), 7.28 (dd, J = 8.1, 0.8 Hz, 1H), 5.03 (t, J = 5.3 Hz, 1H), 4.52 (dd, J = 10.9, 3.3 Hz, 1H), 4.29 (dd, J = 10.9, 7.8 Hz, 1H), 4.21 (dd, J = 12.3, 5.6 Hz, 1H), 4.17-4.01 (m, 2H), 4.01-3.89 (m, 1H), 3.51 (dd, J = 6.6, 5.3 Hz, 2H), 2.77 (q, J = 7.6 Hz, 2H), 1.24 (t, J = 7.6 Hz, 3H), 1.14 (t, J = 7.1 Hz, 3H). | (APCI+) 320.9 $[M + H]^+$ |
| 88D | Ethyl 2-(1-ethylpyrazol-4-yl)-6-(hydroxymethyl)-6,7-dihydro-5H-pyrazolo[5,1-b][1,3]oxazine-3-carboxylate | 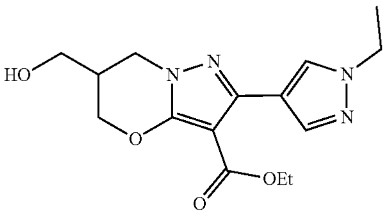 [SMILES: CCOC(=O)c1c(-c2cnn(CC)c2)nn2c1OCC(CO)C2] | δ 8.21 (s, 1H), 7.82 (s, 1H), 5.01 (s, 1H), 4.47 (dd, J = 10.9, 3.3 Hz, 1H), 4.31-4.07 (m, 6H), 3.89 (dd, J = 12.3, 7.3 Hz, 1H), 3.49 (s, 2H), 1.37 (t, J = 7.2 Hz, 3H), 1.23 (t, J = 7.1 Hz, 3H). | (APCI+) 321.4 $[M + H]^+$ |

TABLE 14-continued

Preparatory examples prepared via Suzuki-Miyaura procedure B.

| Preparatory Example | Name | Structure | $^1$H NMR δ (400 MHz, DMSO-$d_6$) | LRMS m/z; TLC $R_f$ |
|---|---|---|---|---|
| 89A | Ethyl 2-(2-fluorophenyl)-6-[(2-methylpropan-2-yl)oxycarbonylamino]-6,7-dihydro-5H-pyrazolo[5,1-b][1,3]oxazine-3-carboxylate | 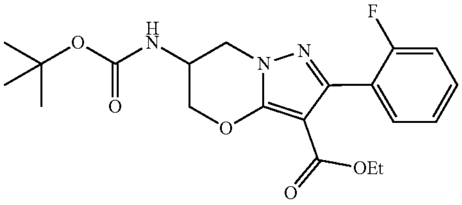 [SMILES: CCOC(=O)c1c(-c2ccccc2F)nn2c1OCC(NC(=O)OC(C)(C)C)C2] | δ 7.59 (d, J = 6.2 Hz, 1H), 7.48-7.36 (m, 2H), 7.26-7.18 (m, 2H), 4.44-4.28 (m, 3H), 4.19 (s, 1H), 4.08-3.95 (m, 3H), 1.41 (s, 9H), 1.04 (t, J = 7.1 Hz, 3H). | (APCI+) 406.8 $[M + H]^+$ |

90A Ethyl (5R)-2-[6-(3-methoxyazetidin-1-yl)pyridin-3-yl]-5-methyl-6,7-dihydro-5H-pyrazolo[5,1-b][1,3]oxazine-3-carboxylate

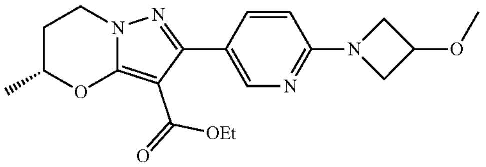

A solution of intermediate 81A (200 mg, 0.66 mmol), 3-methoxyazetidine hydrochloride (324 mg, 2.62 mmol) and DIPEA (913 μL, 5.24 mmol) in anhydrous DMSO (3 mL) was heated at 130° C. overnight. The reaction was cooled to rt, partitioned between brine and EtOAc (10 mL each) and the aqueous layer extracted with EtOAc (4×15 mL). The combined organic extracts were washed with brine (3×15 mL), dried ($Na_2SO_4$) and the solvent removed under reduced pressure. Purification by flash chromatography [10-36% ($EtOH:CH_2Cl_2:NH_4OH$; 50:8:1) in $CH_2Cl_2$] afforded a pale brown solid (191 mg, 78%). $^1$H NM/R (400 MHz, DMSO-$d_6$) δ 8.25 (dd, J=2.3, 0.8 Hz, 1H), 7.70 (dd, J=8.6, 2.3 Hz, 1H), 6.39 (dd, J=8.7, 0.8 Hz, 1H), 4.61-4.50 (m, 1H), 4.37-4.29 (m, 1H), 4.19-4.03 (m, 6H), 3.80-3.73 (m, 2H), 3.25 (s, 3H), 2.31-2.20 (m, 1H), 2.07-1.93 (m, 1H), 1.43 (d, J=6.3 Hz, 3H), 1.15 (t, J=7.1 Hz, 3H). LRMS m/z (APCI+) 373.6 $[M+H]^+$.

The following preparatory intermediates were prepared by an analogous procedure to intermediate 90A.

| Preparatory Example | Name | Structure | $^1$H NMR δ (400 MHz, DMSO-$d_6$) | LRMS APCI+ m/z |
|---|---|---|---|---|
| 90B | Ethyl (5R)-2-[6-[(3R)-3-methoxypyrrolidin-1-yl]pyridin-3-yl]-5-methyl-6,7-dihydro-5H-pyrazolo[5,1-b][1,3]oxazine-3-carboxylate | 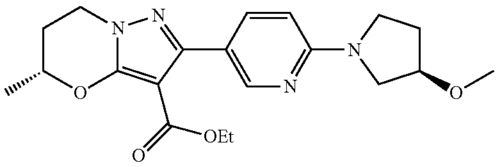 | 8.26 (dd, J = 2.3, 0.7 Hz, 1H), 7.68 (dd, J = 8.7, 2.4 Hz, 1H), 6.44 (dd, J = 8.8, 0.8 Hz, 1H), 4.61-4.49 (m, 1H), 4.16-4.01 (m, 5H), 3.49 (dd, J = 11.5, 4.1 Hz, 3H), 3.43-3.33 (m, 2H), 3.27 (s, 3H), 2.30-2.21 (m, 1H), 2.11-1.93 (m, 3H), 1.43 (d, J = 6.4 Hz, 3H), 1.16 (t, J = 7.1 Hz, 3H) | 387.6 $[M + H]^+$ |
| 90C | Ethyl (5R)-2-[6-[(3S)-3-methoxypyrrolidin-1-yl]pyridin-3-yl]-5-methyl-6,7-dihydro-5H-pyrazolo[5,1-b][1,3]oxazine-3-carboxylate | 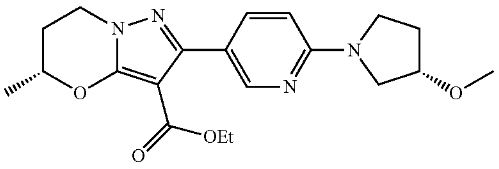 | 8.26 (dd, J = 2.4, 0.7 Hz, 1H), 7.68 (dd, J = 8.7, 2.4 Hz, 1H), 6.44 (dd, J = 8.8, 0.8 Hz, 1H), 4.60-4.51 (m, 1H), 4.15-4.04 (m, 5H), 3.55-3.44 (m, 3H), 3.43-3.33 (m, 2H), 3.27 (s, 3H), 2.30-2.22 (m, 1H), 2.09-1.95 (m, 3H), 1.43 (d, J = 6.3 Hz, 3H), 1.16 (t, J = 7.1 Hz, 3H) | 387.6 $[M + H]^+$ |

90D Ethyl-(5R)-5-methyl-2-[6-(trideuteriomethyl-amino)pyridin-3-yl]-6,7-dihydro-5H-pyrazolo[5,1-b][1,3]oxazine-3-carboxylate

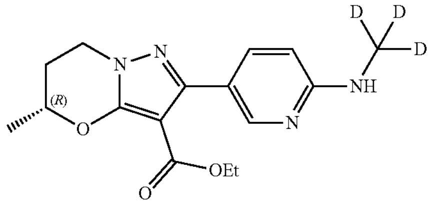

DIPEA (571 μL, 3.28 mmol) and methyl-$d_3$-amine hydrochloride (144 mg, 2.05 mmol) and were added to a solution of intermediate 81A (125 mg, 0.409 mmol) in DMSO (3 mL) and heated by MWI at 140° C. for 6 h. The reaction was diluted with water (10 mL) and extracted with $CH_2Cl_2$ (3×10 mL). The combined organic layers were washed with brine (3×20 mL), dried $Na_2SO_4$ and the solvent removed under reduced pressure. Purification by ion exchange chromatography (2 g SCX-2 cartridge, eluting with 2 N $NH_3$ in MeOH) afforded an orange solid (61 mg, 47%). LCMS (method B) m/z 385.4 $[M+H]^+$ at 0.67 min. LCMS (method A) m/z 320.3 $[M+H]^+$ at 0.62 min. $^1$H NMR (500 MHz, DMSO-$d_6$) δ 8.18 (d, J=2.4 Hz, 1H), 7.57 (dd, J=8.6, 2.4 Hz, 1H), 6.56 (s, 1H), 6.41 (d, J=8.7 Hz, 1H), 4.60-4.51 (m, 1H), 4.16-4.04 (m, 4H), 2.30-2.21 (m, 1H), 2.06-1.95 (m, 1H), 1.42 (d, J=6.3 Hz, 3H), 1.16 (t, J=7.1 Hz, 3H).

90E Ethyl (5R)-5-methyl-2-[6-(propan-2-ylamino)pyridin-3-yl]-6,7-dihydro-5H-pyrazolo[5,1-b][1,3]oxazine-3-carboxylate

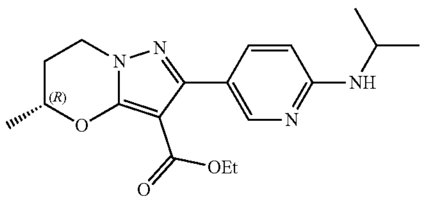

Isopropylamine (156 μL, 1.82 mmol) and DIPEA (79 μL, 0.45 mmol) were added to a solution of intermediate 81A (138 mg, 0.45 mmol) in DMSO (3 mL) and heated at 60° C. overnight. Further isopropylamine (312 μL, 3.64 mmol) was added and the reaction heated to 100° C. overnight, then heated by MWI at 100° C. for 16 h. The reaction was partitioned between $CH_2Cl_2$ (10 mL) and sat. aq. $NH_4Cl$ (10 mL), and the separated aqueous layer was extracted with $CH_2Cl_2$ (3×10 mL). The organic layers were combined, washed with brine (3×20 mL), dried ($Na_2SO_4$) and concentrated under reduced pressure. Purification by flash chromatography (50-100% EtOAc in iso-hexane) afforded a pink solid (56 mg, 35%). LCMS (method B) m/z 345.4 $[M+H]^+$ at 1.16 min. $^1$H NMR (500 MHz, DMSO-$d_6$) δ 8.16 (d, J=2.4 Hz, 1H), 7.53 (dd, J=8.7, 2.4 Hz, 1H), 6.45 (d, J=7.6 Hz, 1H), 6.41 (d, J=8.7 Hz, 1H), 4.60-4.51 (m, 1H), 4.13-4.05 (m, 4H), 4.04-3.96 (m, 1H), 2.29-2.20 (m, 1H), 2.06-1.94 (m, 1H), 1.42 (d, J=6.3 Hz, 3H), 1.19-1.13 (m, 9H).

90F Ethyl (5R)-5-methyl-2-(6-morpholin-4-ylpyridin-3-yl)-6,7-dihydro-5H-pyrazolo[5,1-b][1,3]oxazine-3-carboxylate

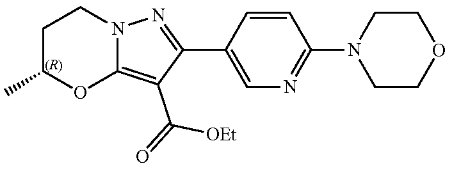

Morpholine (158 μL, 1.81 mmol) and DIPEA (79 μL, 0.45 mmol) were added to a solution of intermediate 81A (138 mg, 0.45 mmol) in DMSO (3 mL) and heated at 60° C. overnight. Further morpholine (158 μL, 1.81 mmol) was added and the reaction heated to 100° C. overnight. Analogous workup and purification to intermediate 90E afforded a pink solid (130 mg, 77%). LCMS (method B) m/z 373.5 $[M+H]^+$ at 1.09 min. $^1$H NMR (500 MHz, DMSO-$d_6$) δ 8.33 (d, J=2.4 Hz, 1H), 7.76 (dd, J=8.8, 2.4 Hz, 1H), 6.83 (d, J=8.9 Hz, 1H), 4.61-4.54 (m, 1H), 4.17-4.06 (m, 4H), 3.73-3.69 (m, 4H), 3.50-3.46 (m, 4H), 2.30-2.23 (m, 1H), 2.07-1.97 (m, 1H), 1.44 (d, J=6.3 Hz, 3H), 1.17 (t, J=7.1 Hz, 3H).

90G Ethyl (5R)-5-methyl-2-[6-[(1R,4R)-2-oxa-5-azabicyclo[2.2.1]heptan-5-yl]pyridin-3-yl]-6,7-dihydro-5H-pyrazolo[5,1-b][1,3]oxazine-3-carboxylate

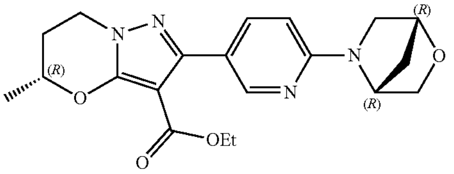

(1R,4R)-2-oxa-5-azabicyclo[2.2.1]heptane hydrochloride (115 mg, 0.85 mmol) and DIPEA (296 μL, 1.70 mmol) were added to a solution of intermediate 81A (130 mg, 0.426 mmol) in DMSO (3 mL) and heated by MWI at 130° C. for 4 h. Further (1R,4R)-2-oxa-5-azabicyclo[2.2.1]heptane hydrochloride (115 mg, 0.85 mmol) was added and the reaction heated by MWI at 130° C. for 8 h. Analogous workup and purification to intermediate 29A afforded a pink solid (58 mg, 35%). LCMS (method B) m/z 385.4 $[M+H]^+$ at 0.67 min. $^1$H NMR (500 MHz, DMSO-$d_6$) δ 8.26 (dd, J=2.4, 0.8 Hz, 1H), 7.69 (dd, J=8.7, 2.3 Hz, 1H), 6.52 (d, J=8.7 Hz, 1H), 4.89-4.85 (m, 1H), 4.68-4.64 (m, 1H), 4.61-4.52 (m, 1H), 4.17-4.04 (m, 4H), 3.78 (dd, J=7.3, 1.5 Hz, 1H), 3.65 (d, J=7.3 Hz, 1H), 3.47 (dd, J=10.1, 1.5 Hz, 1H), 3.33-3.22 (m, 1H), 2.30-2.22 (m, 1H), 2.10-1.95 (m, 1H), 1.92 (dd, J=9.8, 2.3 Hz, 1H), 1.89-1.82 (m, 1H), 1.43 (d, J=6.3 Hz, 3H), 1.16 (t, J=7.1 Hz, 3H).

90H Ethyl (5R)-5-methyl-2-[6-[(1S,4S)-2-oxa-5-azabicyclo[2.2.1]heptan-5-yl]pyridin-3-yl]-6,7-dihydro-5H-pyrazolo[5,1-b][1,3]oxazine-3-carboxylate

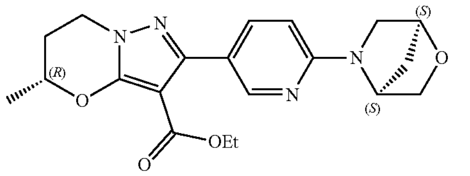

Prepared by an analogous procedure to that described for intermediate 90G. LCMS (method B) m/z 385.4 [M+H]+ at 0.67 min. $^1$H NMR (500 MHz, DMSO-$d_6$) δ 8.26 (d, J=2.3 Hz, 1H), 7.69 (dd, J=8.7, 2.4 Hz, 1H), 6.52 (d, J=8.7 Hz, 1H), 4.87 (s, 1H), 4.66 (d, J=2.5 Hz, 1H), 4.61-4.53 (m, 1H), 4.16-4.03 (m, 4H), 3.78 (dd, J=7.3, 1.5 Hz, 1H), 3.65 (d, J=7.3 Hz, 1H), 3.47 (dd, J=10.1, 1.5 Hz, 1H), 3.25 (d, J=10.0 Hz, 1H), 2.30-2.23 (m, 1H), 2.10-1.95 (m, 1H), 1.92 (dd, J=9.9, 2.3 Hz, 1H), 1.85 (d, J=9.5 Hz, 1H), 1.43 (d, J=6.3 Hz, 3H), 1.16 (t, J=7.1 Hz, 3H).

90I Ethyl (5R)-2-[6-(ethylamino)pyridin-3-yl]-5-methyl-6,7-dihydro-5H-pyrazolo[5,1-b][1,3]oxazine-3-carboxylate

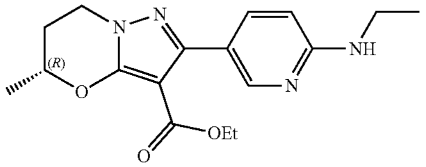

Prepared by an analogous procedure to intermediate 29A with heating by MWI at 100° C. for 30 min, then at 130° C. for 7.5 h. LCMS (method B) m/z 331.4 [M+H]+ at 1.05 min. $^1$H NMR (500 MHz, DMSO-$d_6$) δ 8.16 (d, J=2.3 Hz, 1H), 7.55 (dd, J=8.6, 2.4 Hz, 1H), 6.59 (t, J=5.5 Hz, 1H), 6.41 (dd, J=8.7, 0.8 Hz, 1H), 4.60-4.51 (m, 1H), 4.15-4.01 (m, 4H), 3.31-3.22 (m, 2H), 2.29-2.21 (m, 1H), 2.06-1.94 (m, 1H), 1.42 (d, J=6.3 Hz, 3H), 1.16 (t, J=7.1 Hz, 3H), 1.13 (t, J=7.1 Hz, 3H).

91A Ethyl (5S)-5-methyl-2-[6-(propan-2-ylamino)pyridin-3-yl]-6,7-dihydro-5H-pyrazolo[5,1-b][1,3]oxazine-3-carboxylate

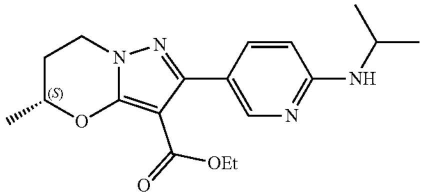

Prepared by an analogous procedure to intermediate 29A with heating by MWI at 130° C. for 6 h. LCMS (method A) 345.4 $[M+H]^+$ at 0.70 min. $^1$H NMR (500 MHz, DMSO-$d_6$) δ 8.18-8.13 (m, 1H), 7.53 (dd, J=8.6, 2.4 Hz, 1H), 6.46 (d, J=7.6 Hz, 1H), 6.43-6.38 (m, 1H), 4.60-4.50 (m, 1H), 4.15-4.05 (m, 4H), 4.04-3.95 (m, 1H), 2.29-2.22 (m, 1H), 2.06-1.94 (m, 1H), 1.42 (d, J=6.3 Hz, 3H), 1.19-1.12 (m, 9H).

91B Ethyl (5S)-5-methyl-2-[6-[-(1R,4R)-2-oxa-5-azabicyclo[2.2.1]heptan-5-yl]pyridin-3-yl]-6,7-dihydro-5H-pyrazolo[5,1-b][1,3]oxazine-3-carboxylate

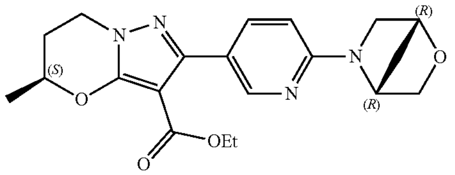

Prepared by an analogous procedure to that described for intermediate 90G. LCMS (method A) m/z 385.5 $[M+H]^+$ at 0.66 min. $^1$H NMR (500 MHz, DMSO-$d_6$) δ (DMSO-d6) 8.29-8.25 (m, 1H), 7.70 (dd, J=8.7, 2.4 Hz, 1H), 6.53 (d, J=8.7 Hz, 1H), 4.88 (s, 1H), 4.69-4.65 (m, 1H), 4.61-4.52 (m, 1H), 4.17-4.05 (m, 4H), 3.82-3.76 (m, 1H), 3.65 (d, J=7.2 Hz, 1H), 3.51-3.45 (m, 1H), 3.32-3.23 (m, 1H), 2.30-2.23 (m, 1H), 2.08-1.96 (m, 1H), 1.95-1.89 (m, 1H), 1.89-1.83 (m, 1H), 1.43 (d, J=6.3 Hz, 3H), 1.17 (t, J=7.1 Hz, 3H).

92A Ethyl 2-[6-(propan-2-ylamino)pyridin-3-yl]spiro[5,7-dihydropyrazolo[5,1-b][1,3]oxazine-6,1'-cyclopropane]-3-carboxylate

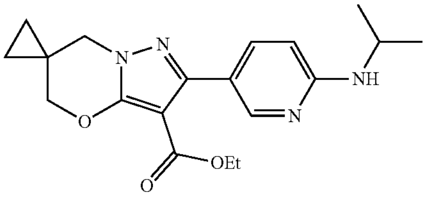 [SMILES: CCOC(=O)c1c(-c2ccc(NC(C)C)nc2)nn2c1OCC1(CC1)C2]

Isopropylamine (839 μL, 9.77 mmol) and DIPEA (340 μL, 1.95 mmol) were added to a solution of intermediate 84A (310 mg, 0.98 mmol) in DMSO (6 mL) and heated at 140° C. for 48 h. Analogous workup and purification to intermediate 29A afforded an orange solid (225 mg, 65%). $^1$H NMR (500 MHz, DMSO-$d_6$) δ 8.15 (d, J=2.3 Hz, 1H), 7.53 (dd, J=8.7, 2.4 Hz, 1H), 6.47 (d, J=7.6 Hz, 1H), 6.41 (d, J=8.7 Hz, 1H), 4.21 (s, 2H), 4.10 (q, J=7.1 Hz, 2H), 4.05-3.95 (m, 3H), 1.19-1.08 (m, 8H), 0.83-0.75 (m, 4H). LRMS (APCI+) m/z 357.4 $[M+H]^+$ 93A Ethyl 2-(2-fluorophenyl)-5-(methoxymethyl)-6,7-dihydro-5H-pyrazolo[5,1-b][1,3]oxazine-3-carboxylate

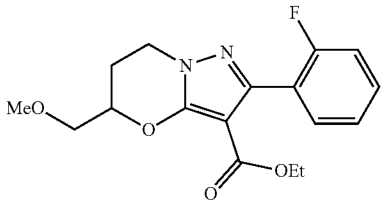 [SMILES: CCOC(=O)c1c(-c2ccccc2F)nn2c1OC(COC)CC2]

NaH (60% dispersion in mineral oil, 17 mg, 0.43 mmol) was added to a solution of intermediate 87A (55 mg, 0.17 mmol) in THE (6 mL) and stirred at rt for 15 min. Mel (53 μL, 0.86 mmol) was added and the reaction was stirred rt for 1.5 h, then quenched with sat. aq. $NH_4Cl$ (10 mL) and extracted with EtOAc (15 mL). The organic layer was washed with brine (20 mL), passed through a phase separation cartridge, and concentrated in vacuo. Purification by flash chromatography (0-100% MTBE in iso-hexane, then 10% MeOH in MTBE) afforded a colourless oil (34 mg, 59%). LCMS (method A) m/z 335.2 $[M+H]^+$ at 1.21 min.

93B Ethyl 2-(2-fluorophenyl)-6-(methoxymethyl)-6,7-dihydro-5H-pyrazolo[5,1-b][1,3]oxazine-3-carboxylate

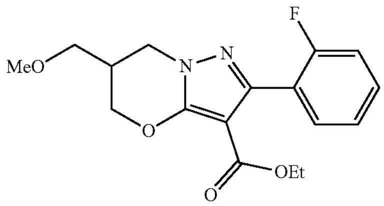 [SMILES: CCOC(=O)c1c(-c2ccccc2F)nn2c1OCC(COC)C2]

Prepared by an analogous procedure to that described for intermediate 93A. LRMS (APCI+) m/z 335.7 $[M+H]^+$. TLC $R_f$=0.84 (2:1 EtOAc:heptane).

94A Ethyl 2-(2-fluorophenyl)-6-methoxy-6,7-dihydro-5H-pyrazolo[5,1-b][1,3]oxazine-3-carboxylate

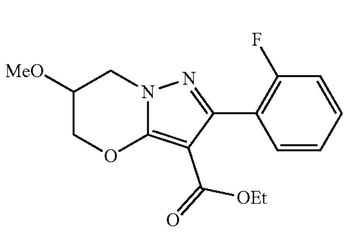 [SMILES: CCOC(=O)c1c(-c2ccccc2F)nn2c1OCC(OC)C2]

Prepare by an analogous procedure to t at described for intermediate 93A. LRMS (APCI+) m/z 321.2 $[M+H]^+$. TLC $R_f$=0.31 (EtOAc).

95A Ethyl 2-(2-fluorophenyl)-6-[methyl-[(2-methylpropan-2-yl)oxycarbonyl]amino]-6,7-dihydro-5H-pyrazolo[5,1-b][1,3]oxazine-3-carboxylate

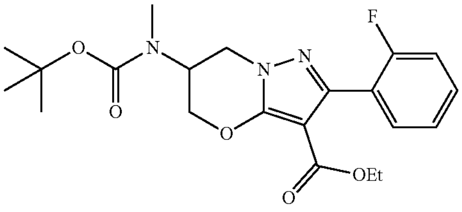 [SMILES: CCOC(=O)c1c(-c2ccccc2F)nn2c1OCC(N(C)C(=O)OC(C)(C)C)C2]

NaH (60% dispersion in mineral oil, 24.7 mg, 0.62 mmol) was added to a solution of intermediate 89A (100 mg, 0.25 mmol) in DMF (1 mL) and the mixture was stirred for 0.5 h at rt. Mel (0.04 mL, 0.62 mmol) was added and the mixture stirred at rt for 1.5 h. Analogous workup and purification to that described for intermediate 93A afforded a colourless oil (94 mg, 91%). LRMS m/z (APCI+) 420.4 $[M+H]^+$. TLC $R_f$=0.52 (1:1 EtOAc:heptane).

96A Ethyl 2-(2-fluorophenyl)-6-[(4-methylphenyl)sulfonyloxymethyl]-6,7-dihydro-5H-pyrazolo[5,1-b][1,3]oxazine-3-carboxylate

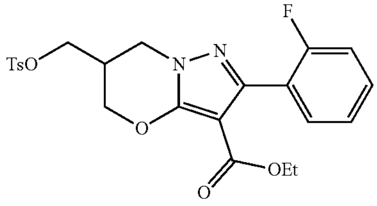 [SMILES: CCOC(=O)c1c(-c2ccccc2F)nn2c1OCC(COS(=O)(=O)c1ccc(C)cc1)C2]

A solution of TsCl (1.34 g, 7.02 mmol) in $CH_2Cl_2$ (5 mL) was added dropwise over 5 minutes to a cooled (0° C.) solution of 88A (900 mg, 2.81 mmol) and $NEt_3$ (0.98 mL, 7.02 mmol) in $CH_2Cl_2$ (5 mL). The reaction was stirred for 30 min at 0° C., then at rt for 19 h. Water (20 mL) was added, the organic layers separated, washed with water and brine (10 mL each), dried ($Na_2SO_4$), and concentrated under reduced pressure. Purification by flash chromatography (30-60% EtOAc:heptane) afforded a colourless oil (1.25 g, 94%). $^1H$ NMR (400 MHz, DMSO-$d_6$) δ 7.88-7.77 (m, 2H), 7.52-7.32 (m, 4H), 7.28-7.15 (m, 2H), 4.48 (dd, J=10.9, 3.2 Hz, 1H), 4.32-4.18 (m, 3H), 4.22-4.12 (m, 2H), 4.05-3.96 (m, 2H), 3.91 (dd, J=12.5, 7.0 Hz, 1H), 2.81 (s, 1H), 2.40 (s, 3H), 1.02 (t, J=7.1 Hz, 3H). LRMS (APCI+) m/z 334.9 $[M+H]^+$.

96B Ethyl 2-(2-fluorophenyl)-5-[(4-methylphenyl) sulfonyloxymethyl]-6,7-dihydro-5H-pyrazolo[5,1-b] [1,3]oxazine-3-carboxylate

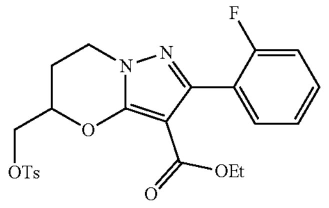 [SMILES: CCOC(=O)c1c(-c2ccccc2F)nn2c1OC(COS(=O)(=O)c1ccc(C)cc1)CC2]

Prepared by an analogous procedure to that described for intermediate 96A. $^{1}H$ NMR (400 MHz, DMSO-$d_6$) δ 7.92-7.82 (m, 2H), 7.52-7.47 (m, 2H), 7.47-7.35 (m, 2H), 7.25-7.18 (m, 2H), 4.86-4.73 (m, 1H), 4.43 (dd, J=11.2, 2.6 Hz, 1H), 4.31 (dd, J=11.2, 6.3 Hz, 1H), 4.23-4.08 (m, 2H), 4.08-3.91 (m, 2H), 2.42 (s, 3H), 2.34-2.19 (m, 1H), 2.19-2.06 (m, 1H), 1.03 (t, J=7.1 Hz, 3H). LRMS (APCI+) m/z 475.6 $[M+H]^+$.

97A Ethyl 6-[(dimethylamino)methyl]-2-(2-fluorophenyl)-6,7-dihydro-5H-pyrazolo[5,1-b][1,3]oxazine-3-carboxylate

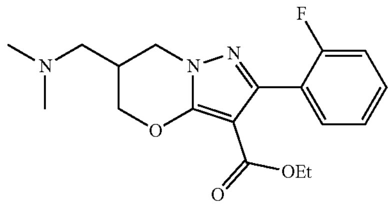 [SMILES: CCOC(=O)c1c(-c2ccccc2F)nn2c1OCC(CN(C)C)C2]

A solution of intermediate 96A (104 mg, 0.22 mmol) and dimethylamine (2 M in THF; 0.76 mL, 1.52 mmol) in 1,4-dioxane (1.5 mL) was heated at 120° C. for 24 h. The reaction was cooled to rt, the volatiles removed under reduced pressure and the residue purified by column chromatography [0-30% (50:8:1 $CH_2Cl_2$:EtOH:$NH_4OH$) in $CH_2Cl_2$] to afford an orange oil (103 mg, 78%). $^{1}H$ NMR (400 MHz, DMSO-$d_6$) δ 7.51-7.35 (m, 1H), 7.29-7.12 (m, 1H), 4.50 (dd, J=10.8, 3.3 Hz, 1H), 4.31-4.13 (m, 1H), 4.08-3.96 (m, 1H), 3.88 (dd, J=12.3, 7.9 Hz, 1H), 2.71-2.60 (m, 1H), 2.32-2.23 (m, 1H), 2.18 (s, 3H), 1.03 (t, J=7.1 Hz, 1H). LRMS (APCI+) m/z 348.4 $[M+H]^+$.

The following intermediate compounds were prepared in an analogous manner to that described for intermediate 97A. The procedure was performed at temperatures ranging from 110° C. to 140° C.

TABLE 15

Preparatory examples

| Preparatory Example | Name | Structure | $^{1}H$ NMR (400 MHz) δ | LRMS m/z (APCI+); TLC $R_f$ |
|---|---|---|---|---|
| 97B | Ethyl 2-(2-fluorophenyl)-6-(pyrrolidin-1-ylmethyl)-6,7-dihydro-5H-pyrazolo[5,1-b][1,3]oxazine-3-carboxylate | 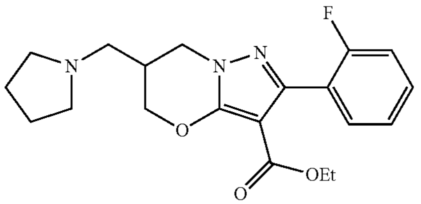 [SMILES: CCOC(=O)c1c(-c2ccccc2F)nn2c1OCC(CN1CCCC1)C2] | (DMSO-$d_6$) δ 7.51-7.34 (m, 2H), 7.27-7.14 (m, 2H), 4.58-4.46 (m, 1H), 4.30-4.19 (m, 2H), 4.06-3.95 (m, 2H), 3.91 (dd, J = 12.3, 7.6 Hz, 1H), 1.75-1.65 (m, 4H), 1.03 (t, J = 7.1 Hz, 3H). | 374.5 $[M + H]^+$ |
| 97C | Ethyl 2-(2-fluorophenyl)-6-[(4-methylpiperazin-1-yl)methyl]-6,7-dihydro-5H-pyrazolo[5,1-b][1,3]oxazine-3-carboxylate | 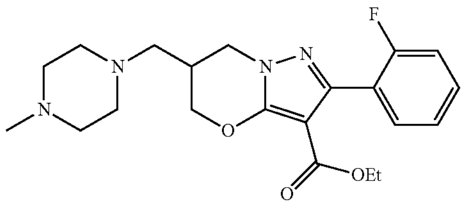 [SMILES: CCOC(=O)c1c(-c2ccccc2F)nn2c1OCC(CN1CCN(C)CC1)C2] | (DMSO-$d_6$) δ 7.48-7.36 (m, 2H), 7.27-7.14 (m, 2H), 4.50 (dd, J = 10.8, 3.3 Hz, 1H), 4.28-4.13 (m, 2H), 4.00 (qd, J = 7.1, 1.4 Hz, 2H), 3.88 (dd, J = 12.3, 7.9 Hz, 1H), 2.78-2.63 (m, 1H), 2.48-2.29 (m, 7H), 2.22 (s, 3H), 1.03 (t, J = 7.1 Hz, 3H). | 403.7 $[M + H]^+$ |
| 97D | Ethyl 2-(2-fluorophenyl)-6-(morpholin-4-ylmethyl)-6,7-dihydro-5H-pyrazolo[5,1-b][1,3]oxazine-3-carboxylate | 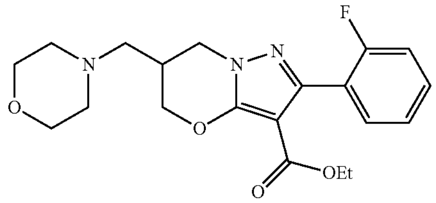 [SMILES: CCOC(=O)c1c(-c2ccccc2F)nn2c1OCC(CN1CCOCC1)C2] | Not available | 390.7 $[M + H]^+$ TLC $R_f$ = 0.21 (2:1 EtOAc:heptane) |

TABLE 15-continued

| Preparatory examples | | | | |
|---|---|---|---|---|
| Preparatory Example | Name | Structure | $^1$H NMR (400 MHz) δ | LRMS m/z (APCI+); TLC $R_f$ |
| 97E | Ethyl 6-(ethylaminomethyl)-2-(2-fluorophenyl)-6,7-dihydro-5H-pyrazolo[5,1-b][1,3]oxazine-3-carboxylate | 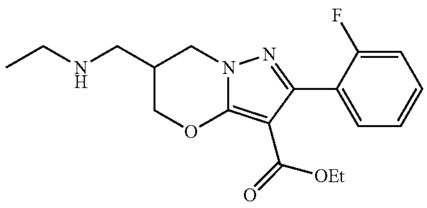 [SMILES: CCNCC1COc2c(C(=O)OCC)c(-c3ccccc3F)nn2C1] | (DMSO-$d_6$) δ 7.48-7.35 (m, 2H), 7.26-7.15 (m, 2H), 4.53 (dd, J = 10.8, 3.2 Hz, 1H), 4.30-4.17 (m, 2H), 4.06-3.89 (m, 3H), 2.65-2.52 (m, 4H), 1.07-0.95 (m, 6H). | 348.2 $[M + H]^+$ |
| 97F | Ethyl 6-(diethylaminomethyl)-2-(2-fluorophenyl)-6,7-dihydro-5H-pyrazolo[5,1-97Fb][1,3]oxazine-3-97Gcarboxylate | 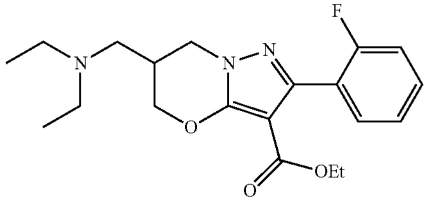 [SMILES: CCOC(=O)c1c(-c2ccccc2F)nn2c1OCC(CN(CC)CC)C2] | ($CDCl_3$) δ 7.48-7.39 (m, 1H), 7.41-7.31 (m, 1H), 7.17 (t, J = 7.5 Hz, 1H), 7.09 (t, J = 9.1 Hz, 1H), 4.58 (dd, J = 11.3, 2.9 Hz, 1H), 4.37-4.21 (m, 2H), 4.14 (q, J = 7.1 Hz, 2H), 3.99 (s, 1H), 2.80-2.39 (m, 6H), 1.19-0.98 (m, 8H). | 376.7 $[M + H]^+$ |
| 97G | Ethyl 6-[(3,3-difluoropyrrolidin-1-yl)methyl]-2-(2-fluorophenyl)-6,7-dihydro-5H-pyrazolo[5,1-b][1,3]oxazine-3-carboxylate | 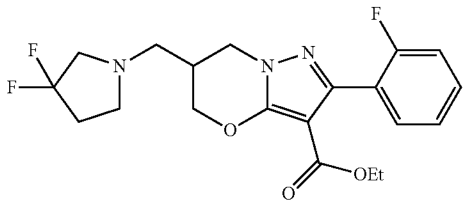 [SMILES: CCOC(=O)c1c(-c2ccccc2F)nn2c1OCC(CN1CCC(F)(F)C1)C2] | (DMSO-$d_6$ ) δ 7.53-7.37 (m, 2H), 7.31-7.16 (m, 2H), 4.51 (dd, J = 10.8, 3.2 Hz, 1H), 4.29-4.18 (m, 2H), 4.06-3.95 (m, 2H), 3.91 (dd, J = 12.3, 7.4 Hz, 1H), 3.03-2.87 (m, 2H), 2.74 (t, J = 7.0 Hz, 2H), 2.69-2.58 (m, 1H), 2.34-2.19 (m, 2H), 1.03 (t, J = 7.1 Hz, 3H). | 409.8 $[M + H]^+$ |
| 97H | Ethyl 6-[[benzyl(ethyl)amino]methyl]-2-(2-fluorophenyl)-6,7-dihydro-5H-pyrazolo[5,1-b][1,3]oxazine-3-carboxylate | 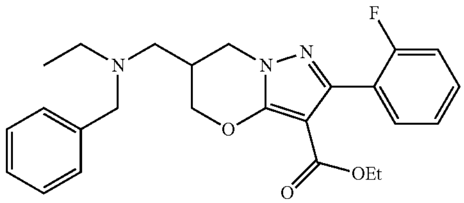 [SMILES: CCOC(=O)c1c(-c2ccccc2F)nn2c1OCC(CN(CC)Cc1ccccc1)C2] | (DMSO-$d_6$) δ 7.48-7.35 (m, 2H), 7.34-7.25 (m, 4H), 7.25-7.18 (m, 3H), 4.52 (dd, J = 10.9, 3.3 Hz, 1H), 4.24-4.14 (m, 2H), 4.00 (q, J = 7.1 Hz, 2H), 3.90 (dd, J = 12.2, 7.6 Hz, 1H), 3.72-3.48 (m, 3H), 1.03 (t, J = 7.1 Hz, 3H), 0.97 (t, J = 7.0 Hz, 3H). | 438.0 $[M + H]^+$ |
| 97I | Ethyl 2-(2-fluorophenyl)-6-[[methyl(oxan-4-yl)amino]methyl]-6,7-dihydro-5H-pyrazolo[5,1-b][1,3]oxazine-3-carboxylate | 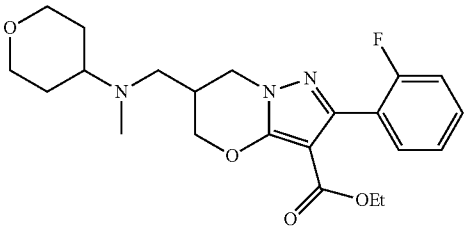 [SMILES: CCOC(=O)c1c(-c2ccccc2F)nn2c1OCC(CN(C)C1CCOCC1)C2] | (DMSO-$d_6$) δ 7.48-7.41 (m, 1H), 7.38 (td, J = 7.6, 1.9 Hz, 1H), 7.25-7.17 (m, 2H), 4.50 (dd, J = 10.8, 3.2 Hz, 1H), 4.29-4.13 (m, 2H), 4.00 (q, J = 7.1 Hz, 2H), 3.94-3.81 (m, 3H), 3.30-3.21 (m, 3H), 2.65-2.54 (m, 2H), 2.54 (d, J = 7.6 Hz, 1H), 2.24 (s, 3H), 1.85-1.69 (m, 1H), 1.64-1.49 (m, 2H), 1.49-1.29 (m, 2H), 1.03 (t, J = 7.1 Hz, 3H). | 418.3 $[M + H]^+$ |
| 98J | Ethyl 2-(2-fluorophenyl)-6-[[methyl(oxetan-3-yl)amino]methyl]-6,7-dihydro-5H-pyrazolo[5,1-b][1,3]oxazine-3-carboxylate | 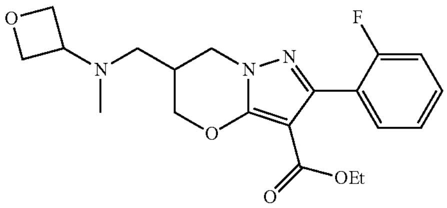 [SMILES: CCOC(=O)c1c(-c2ccccc2F)nn2c1OCC(CN(C)C1COC1)C2] | (DMSO-$d_6$ ) δ 7.48-7.41 (m, 1H), 7.38 (td, J = 7.6, 1.9 Hz, 1H), 7.25-7.17 (m, 2H), 4.56-4.45 (m, 3H), 4.39-4.17 (m, 4H), 4.04-3.91 (m, 3H), 3.58-3.47 (m, 1H), 2.21 (dd, J = 7.8, 3.2 Hz, 2H), 2.12 (s, 3H), 1.03 (t, J = 7.1 Hz, 3H). | 389.7 $[M + H]^+$ |

TABLE 15-continued

Preparatory examples

| Preparatory Example | Name | Structure | $^1H$ NMR (400 MHz) δ | LRMS m/z (APCI+); TLC $R_f$ |
|---|---|---|---|---|
| 98A | Ethyl 2-(2-fluorophenyl)-5-(pyrrolidin-1-ylmethyl)-6,7-dihydro-5H-pyrazolo[5,1-b][1,3]oxazine-3-carboxylate | 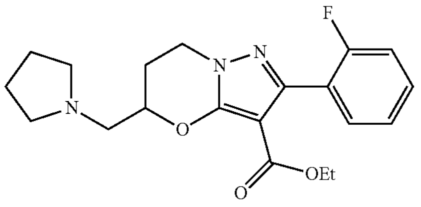 [SMILES: CCOC(=O)c1c(-c2ccccc2F)nn2c1OC(CN1CCCC1)CC2] | (DMSO-$d_6$) δ 7.49-7.32 (m, 2H), 7.26-7.15 (m, 2H), 4.61 (d, J = 10.1 Hz, 1H), 4.16 (dd, J = 8.2, 4.0 Hz, 2H), 3.99 (q, J = 7.1 Hz, 2H), 2.91 (dd, J = 13.1, 4.8 Hz, 1H), 2.74-2.60 (m, 3H), 2.34-2.24 (m, 1H), 2.17-2.05 (m, 1H), 1.78-1.58 (m, 4H), 1.05 (t, J = 7.1 Hz, 3H). | 374.1 $[M + H]^+$ |
| 98B | Ethyl 5-[(dimethylamino)methyl]-2-(2-fluorophenyl)-6,7-dihydro-5H-pyrazolo[5,1-b][1,3]oxazine-3-carboxyalate | 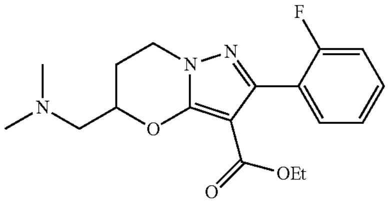 [SMILES: CCOC(=O)c1c(-c2ccccc2F)nn2c1OC(CN(C)C)CC2] | Not available | 347.9 $[M + H]^+$ |
| 98C | Ethyl 2-(2-fluorophenyl)-5-(morpholin-4-ylmethyl)-6,7-dihydro-5H-pyrazolo[5,1-b][1,3]oxazine-3-carboxylate | 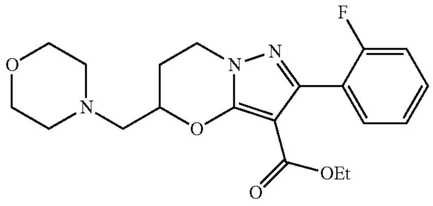 [SMILES: CCOC(=O)c1c(-c2ccccc2F)nn2c1OC(CN1CCOCC1)CC2] | (DMSO-$d_6$) δ 7.48-7.35 (m, 2H), 7.25-7.17 (m, 2H), 4.74-4.63 (m, 1H), 4.21-4.12 (m, 2H), 4.04-3.96 (m, 2H), 3.59 (t, J = 4.6 Hz, 4H), 2.76-2.60 (m, 4H), 2.32-2.22 (m, 2H), 2.19-2.04 (m, 2H), 1.05 (t, J = 7.1 Hz, 3H). | 389.3 $[M + H]^+$ |

99A Ethyl 2-(2 fluorophenyl)-6-(methylsulfanylmethyl)-6,7-dihydro-5H-pyrazolo[5,1-b][1,3]oxazine-3-carboxylate

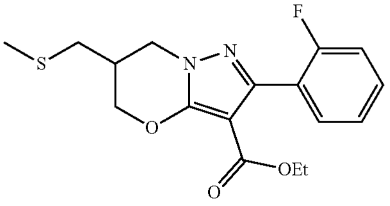 [SMILES: CCOC(=O)c1c(-c2ccccc2F)nn2c1OCC(CSC)C2]

Sodium methanethiolate (49.6 mg, 0.71 mmol) was added to a cooled (0° C.) solution of intermediate 96A (280 mg, 0.59 mmol) in EtOH (4 mL). The ice bath was removed after 1 h and the mixture stirred at rt for 16 h. The reaction was filtered, the filtrate concentrated and the residue purified by flash chromatography (0-50% EtOAc:heptane) affording a colourless oil (129 mg, 620%). $^1H$ NM/R (400 MHz, DMSO-$d_6$) δ 7.54-7.37 (m, 2H), 7.28-7.10 (m, 2H), 4.56 (dd, J=10.7, 2.6 Hz, 1H), 4.38-4.22 (m, 2H), 4.08-3.90 (m, 3H), 2.71-2.56 (m, 3H), 2.12 (s, 2H), 1.03 (t, J=7.1 Hz, 3H). LRMS (APCI+) m/z 351.1 $[M+H]^+$.

100A Ethyl 2-(2-fluorophenyl)-6-(methylsulfonylmethyl)-6,7-dihydro-5H-pyrazolo[5,1-b][1,3]oxazine-3-carboxylate

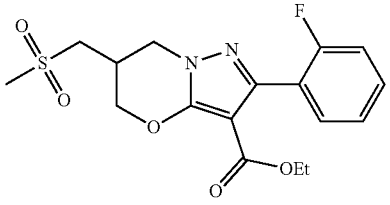 [SMILES: CCOC(=O)c1c(-c2ccccc2F)nn2c1OCC(CS(C)(=O)=O)C2]

A solution of mCPBA (240 mg, 1.07 mmol) in $CH_2Cl_2$ (5 mL) was added to a cooled (0° C.) solution of intermediate 99A (125 mg, 0.36 mmol) in $CH_2Cl_2$ (5 mL). The ice bath was removed after 1 h and the mixture was stirred at rt for 3 h. The mixture was washed with sat. aq. $NaHCO_3$ (2×10 mL) and brine (10 mL), dried ($Na_2SO_4$) and concentrated under reduced pressure. Purification by flash chromatography (20-100% EtOAc:heptane) afforded a colourless oil (101 mg, 74%). $^1H$ NMR (400 MHz, DMSO-$d_6$) δ 7.49-7.36 (m, 2H), 7.29-7.13 (m, 2H), 4.58 (dd, J=10.7, 3.2 Hz, 1H), 4.47-4.27 (m, 2H), 4.11 (dd, J=12.4, 7.3 Hz, 1H), 4.08-3.94 (m, 2H), 3.49-3.34 (m, 3H), 3.12 (s, 3H), 1.05 (t, J=7.0 Hz, 3H). LRMS (APCI+) m/z 383.1 $[M+H]^+$.

101A Ethyl (5R)-2-cyclohexyl-5-methyl-6,7-dihydro-5H-pyrazolo[5,1-b][1,3]oxazine-3-carboxylate

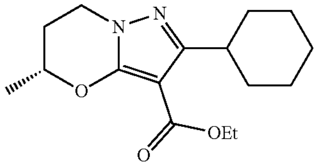 [SMILES: CCOC(=O)c1c(C2CCCCC2)nn2c1O[C@H](C)CC2]

Palladium on carbon (10% wt. loading; 25 mg, 0.24 mmol) was added to a solution of intermediate 81R (230 mg, 0.79 mmol) in EtOH (6 mL) in a pressure tube and the vessel purged successively with $N_2$ (5×) and hydrogen (5×), then stirred under a hydrogen atmosphere at 40 psi for 96 h at rt. The mixture was filtered through a glass microfiber pad, washing with EtOH (3×10 mL), and solvent was removed under reduced pressure to afford a beige solid (198 mg, 86%). LRMS (APCI+) m/z 293.5 $[M+H]^+$. TLC $R_f$=0.5 (2:1 EtOAc:heptane)

101B Ethyl (5R)-5-methyl-2-piperidin-4-yl-6,7-dihydro-5H-pyrazolo[5,1-b][1,3]oxazine-3-carboxylate

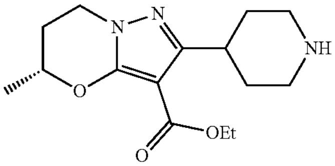 [SMILES: CCOC(=O)c1c(C2CCNCC2)nn2c1O[C@H](C)CC2]

Prepared by an analogous procedure to that described for intermediate 101A with additional purification by flash chromatography (50:8:1 $CH_2Cl_2$:EtOH:$NH_4OH$). $^1H$ NMR (700 MHz, DMSO-$d_6$) δ 4.53-4.45 (m, 1H), 4.11 (q, J=7.1 Hz, 2H), 4.07-3.95 (m, 2H), 3.12-3.02 (m, 1H), 2.96 (d, J=11.9 Hz, 2H), 2.23-2.15 (m, 1H), 1.99-1.89 (m, 1H), 1.73-1.65 (m, 2H), 1.53-1.42 (m, 2H), 1.39 (d, J=6.4 Hz, 3H), 1.22 (t, J=7.1 Hz, 3H). LRMS (APCI+) m/z 294.4 $[M+H]^+$.

102A Ethyl (5R)-5-methyl-2-(1-methylsulfonylpiperidin-4-yl)-6,7-dihydro-5H-pyrazolo[5,1-b][1,3]oxazine-3-carboxylate

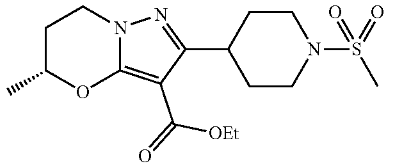

MsCl (70 μL, 0.89 mmol) was added to a cooled (0° C.) solution of intermediate 101B (175 mg, 0.60 mmol) and $NEt_3$ (0.25 mL, 1.79 mmol) in $CH_2Cl_2$ (10 mL) and the reaction stirred at rt for 21 h. The volatiles were removed under reduced pressure and the residue purified by flash chromatography [10-30% (50:8:1 $CH_2Cl_2$:EtOH:$NH_4OH$) in $CH_2Cl_2$] to afford a white solid (203 mg, 92%). $^1H$ NMR (400 MHz, DMSO-$d_6$) δ 4.58-4.43 (m, 1H), 4.13 (q, J=7.1 Hz, 2H), 4.09-3.97 (m, 2H), 3.62 (d, J=11.7 Hz, 2H), 3.17-3.06 (m, 1H), 2.87 (s, 3H), 2.77 (td, J=12.1, 2.6 Hz, 2H), 2.26-2.16 (m, 1H), 2.03-1.87 (m, 3H), 1.71-1.55 (m, 2H), 1.39 (d, J=6.3 Hz, 3H), 1.23 (t, J=7.1 Hz, 3H). LRMS (APCI+) m/z 372.4.

102B Ethyl (5R)-2-(1-ethylsulfonylpiperidin-4-yl)-5-methyl-6,7-dihydro-5H-pyrazolo[5,1-b][1,3]oxazine-3-carboxylate

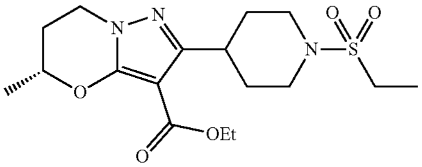 [SMILES: CCOC(=O)c1c(C2CCN(S(=O)(=O)CC)CC2)nn2c1O[C@H](C)CC2]

Prepared by an analogous procedure to that described for intermediate 102A with ethanesulfonyl chloride. LRMS APCI(+) 386.3 [M+H]H. TLC $R_f$=0.53 (200:8:1 $CH_2Cl_2$:EtOH:$NH_3$)

The following intermediate compounds were prepared by an analogous procedure to that described for intermediate 43A.

TABLE 16

Preparatory examples prepared by ester hydrolysis.

| Preparatory Example | Name | Structure | $^1H$ NMR δ (400 MHz) | LRMS (ESI+) m/z |
|---|---|---|---|---|
| 103A | (5R)-2-(4-Ethylsulfonyl-2-fluorophenyl)-5-methyl-6,7-dihydro-5H-pyrazolo[5,1-b][1,3]oxazine-3-carboxylic acid | 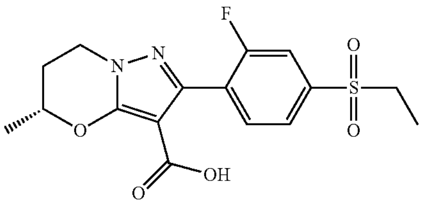 [SMILES: CCS(=O)(=O)c1ccc(-c2nn3c(c2C(=O)O)O[C@H](C)CC3)c(F)c1] | ($CDCl_3$,) δ 7.71 (dd, J = 8.0, 1.7 Hz, 1H), 7.67-7.59 (m, 2H), 4.66-4.52 (m, 1H), 4.32-4.12 (m, 2H), 3.15 (q, J = 7.4 Hz, 2H), 2.35-2.26 (m, 1H), 2.22-2.11 (m, 1H), 1.59 (d, J = 6.3 Hz, 3H), 1.31 (t, J = 7.4 Hz, 3H). | 369.0 $[M + H]^+$ |

TABLE 16-continued

| Preparatory Example | Name | Structure | $^1$H NMR δ (400 MHz) | LRMS (ESI+) m/z |
|---|---|---|---|---|
| | Preparatory examples prepared by ester hydrolysis. | | | |
| 103B | (5R)-2-(2-Fluoro-5-methylsulfonylphenyl)-5-methyl-6,7-dihydro-5H-pyrazolo[5,1-b][1,3]oxazine-3-carboxylic acid | 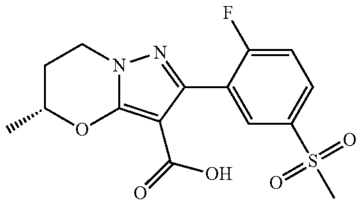 [SMILES: C[C@@H]1CCn2nc(-c3cc(S(C)(=O)=O)ccc3F)c(C(=O)O)c2O1] | ($CDCl_3$) δ 8.06 (dd, J = 6.4, 2.4 Hz, 1H), 7.98-7.94 (m, 1H), 7.28-7.24 (m, 1H), 4.64-4.55 (m, 1H), 4.29-4.15 (m, 2H), 3.06 (s, 3H), 2.34-2.25 (m, 1H), 2.21-2.11 (m, 1H), 1.59 (d, J = 6.4, 3H). | TLC $R_f$ 0.43 (EtOAc) |
| 103D | (5R)-2-(2-Fluoro-4-sulfamoylphenyl)5-methyl-6,7-dihydro-5H-pyrazolo[5,1-b][1,3]oxazine-3-carboxylic acid | 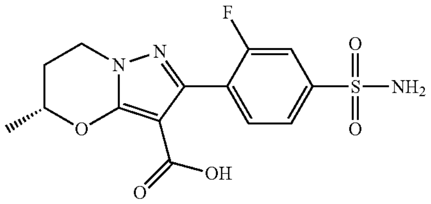 [SMILES: C[C@@H]1CCn2nc(-c3ccc(S(N)(=O)=O)cc3F)c(C(=O)O)c2O1] | (DMSO-d6) δ 7.66 (dd, J = 8.0, 1.6 Hz, 1H), 7.61-7.58 (m, 2H), 7.54 (br s, 2H), 4.64-4.56 (m, 1H), 4.19-4.14 (m, 2H), 2.30-2.24 (m, 1H), 2.10-1.99 (m, 1H), 1.44 (d, J = 6.4, 3H). | 355.9 $[M + H]^+$ |
| 103D | (5R)-2-[4-(Dimethylsulfamoyl)-2-fluorophenyl]-5-methyl-6,7-dihydro-5H-pyrazolo[5,1-b][1,3]oxazine-3-carboxylic acid | 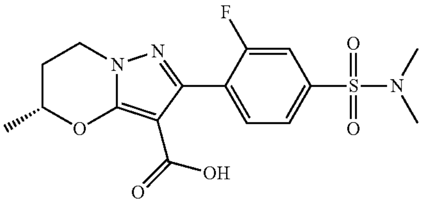 | ($CDCl_3$) δ 7.61 (dd, J = 8.0, 6.4 Hz, 1H), 7.57 (dd, J = 8.0, 1.6 Hz, 1H), 7.49 (dd, J = 8.8, 1.6 Hz, 1H), 4.64-4.56 (m, 1H), 4.29-4.15 (m, 2H), 2.74 (s, 6H), 2.34-2.27 (m, 1H), 2.21-2.11 (m, 1H), 1.59 (d, J = 6.4 Hz, 3H). | 383.9 $[M + H]^+$ |

The following intermediate compounds were prepared by an analogous procedure to that described for intermediate 34A with 5 M aq. NaOH (8 eq.) The procedure may be performed at temperatures of 50-70° C. Intermediate 113B was prepared with 5 M aq. NaOH (16 eq.). $^1$H NMR were performed on a 400 MHz spectrometer in DMSO-$d_6$ unless specified.

TABLE 17

| Preparatory Example | Name | Structure | $^1$H NMR δ (400 MHz, DMSO-$d_6$) | LRMS m/z (APCI+); TLC $R_f$ |
|---|---|---|---|---|
| | Preparatory examples prepared by ester hydrolysis procedure A. | | | |
| 104A | 2-Bromo-6,7-dihydro-5H-pyrazolo[5,1-b][1,3]oxazine-3-carboxylic acid | 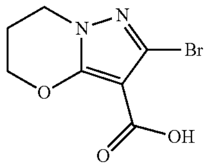 [SMILES: O=C(O)c1c(Br)nn2c1OCCC2] | δ 12.22 (s, 1H), 4.49-4.25 (m, 2H), 4.05 (t, J = 6.1 Hz, 2H), 2.18 (qd, J = 6.1, 4.4 Hz, 2H). | 247.0/ 249.0 $[M + H]^+$ |
| 104B | 2-(1-Ethylpyrazol-4-yl)-6,7-dihydro-5H-pyrazolo[5,1-b][1,3]oxazine-3-carboxylic acid | 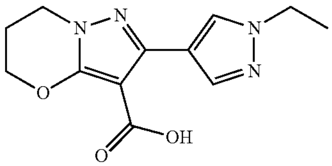 [SMILES: CCn1cc(-c2nn3c(c2C(=O)O)OCCC3)cn1] | δ 11.85 (s, 1H), 8.22 (s, 1H), 7.84 (s, 1H), 4.41-4.34 (m, 2H), 4.13 (q, J = 7.2 Hz, 2H), 4.07 (t, J = 6.1 Hz, 2H), 2.25-2.13 (m, 2H), 1.37 (t, J = 7.3 Hz, 3H). | 263.4 $[M + H]^+$ |

TABLE 17-continued

Preparatory examples prepared by ester hydrolysis procedure A.

| Preparatory Example | Name | Structure | $^1$H NMR δ (400 MHz, DMSO-$d_6$) | LRMS m/z (APCI+); TLC $R_f$ |
|---|---|---|---|---|
| 104C | 2-(6-Ethylpyridin-3-yl)-6,7-dihydro-5H-pyrazolo[5,1-b][1,3]oxazine-3-carboxylic acid | 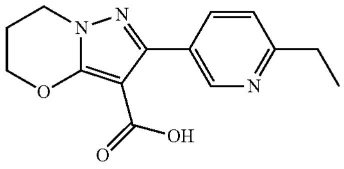 [SMILES: CCc1ccc(-c2nn3c(c2C(=O)O)OCCC3)cn1] | δ 11.97 (s, 1H), 8.64 (dd, J = 2.2, 0.8 Hz, 1H), 7.87 (dd, J = 8.0, 2.3 Hz, 1H), 7.27 (dd, J = 8.1, 0.8 Hz, 1H), 4.42 (dd, J = 6.0, 4.3 Hz, 2H), 4.14 (t, J = 6.1 Hz, 2H), 2.77 (q, J = 7.6 Hz, 2H), 2.30-2.17 (m, 2H), 1.25 (t, J = 7.6 Hz, 3H). | 274.4 [M + H]$^+$ |
| 104D | 2-[2-Fluoro-4-(hydroxy-methyl)phe-nyl]-6,7-dihydro-5H-pyrazolo[5,1-b][1,3]oxazine-3-carboxylic acid | 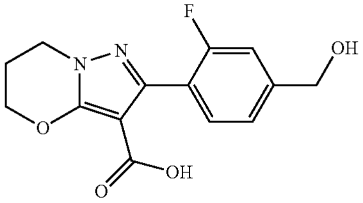 [SMILES: O=C(O)c1c(-c2ccc(CO)cc2F)nn2c1OCCC2] | δ 11.73 (s, 1H), 7.31 (t, J = 7.5 Hz, 1H), 7.15-7.07 (m, 2H), 5.34 (t, J = 5.8 Hz, 1H), 4.53 (d, J = 5.8 Hz, 2H), 4.46-4.39 (m, 2H), 4.13 (t, J = 6.0 Hz, H), 2.28-2.18 (m, 2H). | 292.6 [M + H]$^+$ |
| 104E | 2-(2-Fluoro-4-methyl-sulfonylphe-nyl)-6,7-dihydro-5H-pyrazolo[5,1-b][1,3]oxazine-3-carboxylic acid | 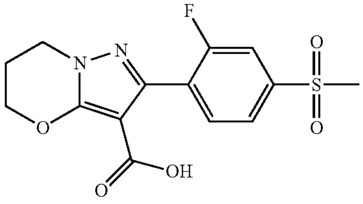 [SMILES: CS(=O)(=O)c1ccc(-c2nn3c(c2C(=O)O)OCCC3)c(F)c1] | δ 11.97 (s, 1H), 7.84-7.76 (m, 2H), 7.71-7.65 (m, 1H), 4.49-4.41 (m, 2H), 4.16 (t, J = 6.1 Hz, 2H), 3.33 (s, 3H), 2.29-2.21 (m, 2H). | 340.5 [M + H]$^+$ |
| 104F | 2-(2-Fluoropyridin-3-yl)-6,7-dihydro-5H-pyrazolo[5,1-b][1,3]oxazine-3-carboxylic acid | 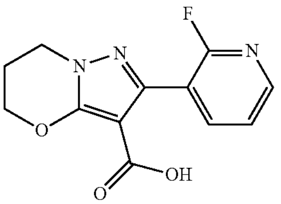 [SMILES: O=C(O)c1c(-c2cccnc2F)nn2c1OCCC2] | δ 11.89 (s, 1H), 8.25 (ddd, J = 4.9, 2.1, 1.0 Hz, 1H), 7.93 (ddd, J = 9.4, 7.3, 2.0 Hz, 1H), 7.39 (ddd, J = 7.1, 4.9, 1.9 Hz, 1H), 4.47-4.37 (m, 2H), 4.19-4.06 (m, 2H), 2.30-2.16 (m, 2H). | 263.7 [M + H]$^+$ |
| 104G | 2-(2-Fluoro-6-methoxyphenyl)-6,7-dihydro-5H-pyrazolo[5,1-b][1,3]oxazine-3-carboxylic acid | 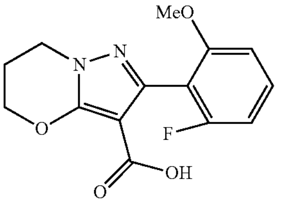 [SMILES: COc1cccc(F)c1-c1nn2c(c1C(=O)O)OCCC2] | δ 11.55 (s, 1H), 7.35 (td, J = 8.4, 6.8 Hz, 1H), 6.90-6.83 (m, 1H), 6.84-6.74 (m, 1H), 4.46-4.38 (m, 2H), 4.12 (t, J = 6.1 Hz, 2H), 3.68 (s, 3H), 2.28-2.17 (m, 2H). | 293.0 [M + H]$^+$ |
| 104H | 2-(2-Fluoro-6-methylphenyl)-6,7-dihydro-5H-pyrazolo[5,1-b][1,3]oxazine-3-carboxylic acid | 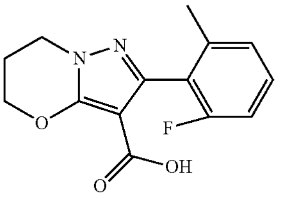 [SMILES: Cc1cccc(F)c1-c1nn2c(c1C(=O)O)OCCC2] | δ 11.66 (s, 1H), 7.28 (td, J = 8.0, 5.9 Hz, 1H), 7.07 (dt, J = 7.6, 1.0 Hz, 1H), 7.00 (t, J = 8.9 Hz, 1H), 4.84-4.39 (m, 2H), 4.13 (t, J = 6.1 Hz, 2H), 2.30-2.17 (m, 2H), 2.11 (s, 3H). | 277.0 [M + H]$^+$ |

TABLE 17-continued

| Preparatory examples prepared by ester hydrolysis procedure A. | | | | |
|---|---|---|---|---|
| Preparatory Example | Name | Structure | $^1H$ NMR δ (400 MHz, DMSO-$d_6$) | LRMS m/z (APCI+); TLC $R_f$ |
| 104I | 2-(1-Propan-2-ylpyrazol-4-yl)-6,7-dihydro-5H-pyrazolo[5,1-b][1,3]oxazine-3-carboxylic acid | 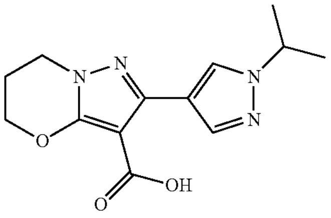 [SMILES: CC(C)n1cc(-c2nn3c(c2C(=O)O)OCCC3)cn1] | δ 11.89 (s, 1H), 8.22 (s, 1H), 7.85 (s, 1H), 4.56-4.43 (m, 1H), 4.38 (dd, J = 6.0, 4.3 Hz, 2H), 4.07 (t, J = 6.1 Hz, 2H), 2.25-2.15 (m, 2H), 1.41 (d, J = 6.7 Hz, 6H). | 277.4 $[M + H]^+$ |
| 104J | 2-(1-Methylindazol-4-yl)-6,7-dihydro-5H-pyrazolo[5,1-b][1,3]oxazine-3-carboxylic acid | 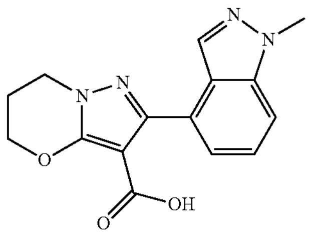 [SMILES: Cn1ncc2c(-c3nn4c(c3C(=O)O)OCCC4)cccc21] | δ 11.79 (s, 1H), 7.93 (d, J = 0.9 Hz, 1H), 7.61 (d, J = 8.3 Hz, 1H), 7.44-7.35 (m, 1H), 7.33 (d, J = 7.0 Hz, 1H), 4.45 (dd, J = 6.0, 4.3 Hz, 1H), 4.18 (t, J = 6.1 Hz, 2H), 4.05 (s, 3H), 2.26 (dt, J = 10.6, 5.2 Hz, 2H). | 299.4 $[M + H]^+$ |
| 104K | 2-[1-(2,2,2-Trifluoro-ethyl)pyra-zol-4-yl]-6,7-dihydro-5H-pyrazolo[5,1-b][1,3]oxazine-3-carboxylic acid | 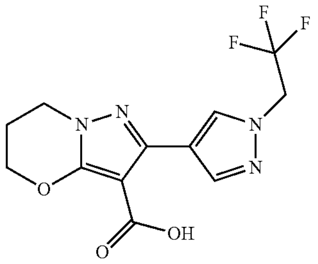 [SMILES: O=C(O)c1c(-c2cnn(CC(F)(F)F)c2)nn2c1OCCC2] | δ 11.96 (s, 1H), 8.41 (s, 1H), 7.96 (s, 1H), 5.18 (q, J = 9.1 Hz, 2H), 4.39 (dd, J = 6.0, 4.3 Hz, 2H), 4.09 (t, J = 6.1 Hz, 2H), 2.20 (dt, J = 10.8, 5.2 Hz, 2H). | 316.5 $[M + H]^+$ |
| 104L | 2-[1-(Oxan-4-yl)pyrazol-4-yl]-6,7-dihydro-5H-pyrazolo[5,1-b][1,3]oxazine-3-carboxylic acid | 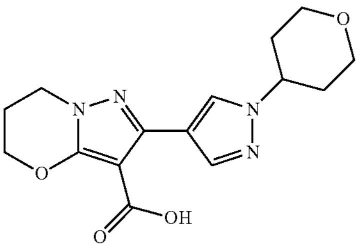 [SMILES: O=C(O)c1c(-c2cnn(C3CCOCC3)c2)nn2c1OCCC2] | δ 11.87 (s, 1H), 8.26 (s, 1H), 7.87 (s, 1H), 4.47-4.32 (m, 3H), 4.07 (t, J = 6.1 Hz, 2H), 4.00-3.89 (m, 2H), 3.46 (td, J = 11.4, 3.2 Hz, 2H), 2.19 (dt, J = 10.6, 5.2 Hz, 2H), 2.03-1.85 (m, 4H). | $R_f$ = 0.11 (200:8:1 $CH_2Cl_2$:EtOH:formic acid) |
| 104M | 2-[1-[(3-Methyloxetan-3-yl)methyl]pyrazol-4-yl]-6,7-dihydro-5H-pyrazolo[5,1-b][1,3]oxazine-3-carboxylic acid | 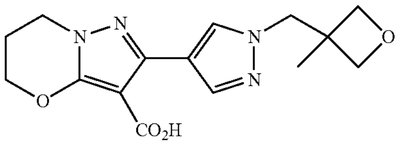 [SMILES: CC1(Cn2cc(-c3nn4c(c3C(=O)O)OCCC4)cn2)COC1] | (600 MHz) δ 11.89 (s, 2H), 8.24 (s, 1H), 7.87 (s, 1H), 4.59 (d, J = 5.9 Hz, 2H), 4.40-4.35 (m, 2H), 4.34 (s, 2H), 4.22 (d, J = 5.9 Hz, 2H), 4.07 (t, J = 6.2 Hz, 2H), 2.23-2.16 (m, 2H), 1.13 (s, 3H). | $R_f$ = 0.10 (200:8:1 $CH_2Cl_2$:EtOH:formic acid) |
| 104N | 2-[2-Fluoro-4-(methylsulfonimi-doyl) phenyl]-6,7-dihydro-5H-pyrazolo[5,1-b][1,3]oxazine-3-carboxylic acid | 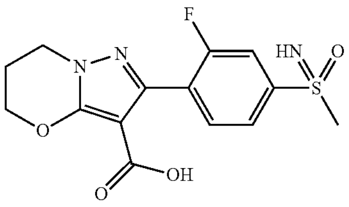 [SMILES: CS(=N)(=O)c1ccc(-c2nn3c(c2C(=O)O)OCCC3)c(F)c1] | δ 11.91 (s, 1H), 7.82-7.67 (m, 2H), 7.62 (dd, J = 8.0, 6.9 Hz, 1H), 4.52-4.41 (m, 3H), 4.16 (t, J = 6.1 Hz, 2H), 3.15 (d, J = 1.1 Hz, 3H), 2.30-2.16 (m, 2H). | 340.2 $[M + H]^+$ |

TABLE 17-continued

Preparatory examples prepared by ester hydrolysis procedure A.

| Preparatory Example | Name | Structure | $^1$H NMR δ (400 MHz, DMSO-$d_6$) | LRMS m/z (APCI+); TLC $R_f$ |
|---|---|---|---|---|
| 105A | (2R)-6-(2-Fluorophenyl)-2-methyl-2,3-dihydropyrazolo[5,1-b][1,3]oxazole-7-carboxylic acid | 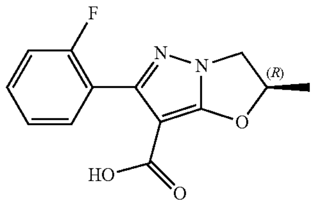 | δ 11.95 (s, 1H), 7.49-7.31 (m, 2H), 7.29-7.11 (m, 2H), 5.73-5.51 (m, 1H), 4.50 (dd, J = 9.5, 8.3 Hz, 1H), 4.00 (dd, J = 9.5, 8.1 Hz, 1H), 1.60 (d, J = 6.3 Hz, 3H). | 263.1 $[M + H]^+$ |
| 106A | 2-(2,6-Difluorophenyl)-5-(hydroxymethyl)-6,7-dihydro-5H-pyrazolo[5,1-b][1,3]oxazine-3-carboxylic acid | 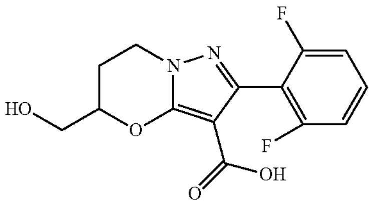 [SMILES: O=C(O)c1c(-c2c(F)cccc2F)nn2c1OC(CO)CC2] | δ 11.83 (s, 1H), 7.54-7.38 (m, 1H), 7.21-6.98 (m, 2H), 5.17 (s, 1H), 4.54-4.33 (m, 1H), 4.29-4.10 (m, 2H), 3.70 (d, J = 4.6 Hz, 2H), 2.31-2.21 (m, 1H), 2.23-2.06 (m, 1H). | 311.2 $[M + H]^+$ |
| 107A | 2-(2-Fluorophenyl)-6-(pyrazol-1-ylmethyl)-6,7-dihydro-5H-pyrazolo[5,1-b][1,3]oxazine-3-carboxylic acid | 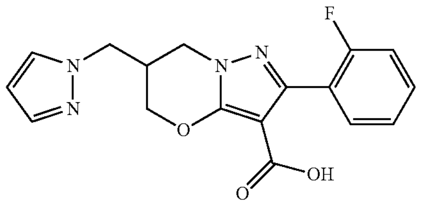 [SMILES: O=C(O)c1c(-c2ccccc2F)nn2c1OCC(Cn1cccn1)C2] | δ 11.84 (s, 1H), 7.80 (d, J = 2.2 Hz, 1H), 7.52 (d, J = 1.8 Hz, 1H), 7.40 (ddt, J = 14.9, 9.2, 3.8 Hz, 2H), 7.27-7.14 (m, 2H), 6.30 (t, J = 2.1 Hz, 1H), 4.45 (dd, J = 11.0, 3.1 Hz, 1H), 4.39-4.25 (m, 2H), 4.25-4.10 (m, 2H), 3.91 (dd, J = 12.4, 7.0 Hz, 1H), 3.02-2.87 (m, 1H). | 343.4 $[M + H]^+$ |
| 108A | 2-(2-Fluorophenyl)-6-(hydroxymethyl)-6,7-dihydro-5H-pyrazolo[5,1-b][1,3]oxazine-3-carboxylic acid | 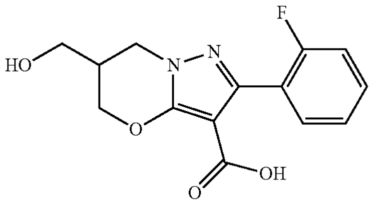 [SMILES: O=C(O)c1c(-c2ccccc2F)nn2c1OCC(CO)C2] | (600 MHz) δ 11.77 (s, 1H), 7.45-7.32 (m, 2H), 7.26-7.14 (m, 2H), 5.00 (t, J = 5.3 Hz, 1H), 4.50 (dd, J = 10.9, 3.3 Hz, 1H), 4.26 (dd, J = 10.9, 8.1 Hz, 1H), 4.20 (dd, J = 12.3, 5.6 Hz, 1H), 3.95 (dd, J = 12.3, 7.6 Hz, 1H), 3.52 (td, J = 5.2, 2.6 Hz, 2H). | 273.5 $[M + H]^+$ |
| 108B | 2-(2,4-Difluorophenyl)-6-(hydroxymethyl)-6,7-dihydro-5H-pyrazolo[5,1-b][1,3]oxazine-3-carboxylic acid | 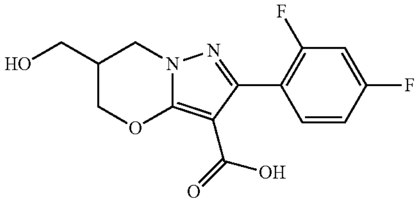 [SMILES: O=C(O)c1c(-c2ccc(F)cc2F)nn2c1OCC(CO)C2] | δ 11.85 (s, 1H), 7.43 (td, J = 8.5, 6.7 Hz, 1H), 7.26 (td, J = 9.9, 2.6 Hz, 1H), 7.10 (td, J = 8.5, 2.6 Hz, 1H), 5.02 (t, J = 5.2 Hz, 1H), 4.50 (dd, J = 10.9, 3.3 Hz, 1H), 4.30-4.16 (m, 2H), 3.94 (dd, J = 12.3, 7.6 Hz, 1H), 3.51 (t, J = 5.8 Hz, 2H). | 311.3 $[M + H]^+$ |
| 108C | 2-(2,6-Difluorophenyl)-6-(hydroxymethyl)-6,7-dihydro-5H-pyrazolo8 5,1-b][1,3]oxazine-3-carboxylic acid | 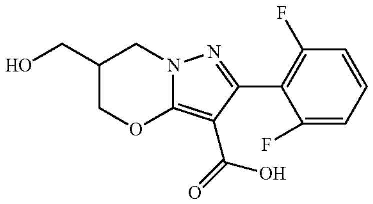 [SMILES: O=C(O)c1c(-c2c(F)cccc2F)nn2c1OCC(CO)C2] | δ 11.89 (s, 1H), 7.59-7.40 (m, 1H), 7.28-7.04 (m, 2H), 5.03 (t, J = 5.2 Hz, 1H), 4.52 (dd, J = 10.9, 3.4 Hz, 1H), 4.32-4.18 (m, 2H), 3.96 (dd, J = 12.4, 7.8 Hz, 1H), 3.51 (t, J = 5.9 Hz, 1H). | 311.4 $[M + H]^+$ |

TABLE 17-continued

Preparatory examples prepared by ester hydrolysis procedure A.

| Preparatory Example | Name | Structure | $^1$H NMR δ (400 MHz, DMSO-$d_6$) | LRMS m/z (APCI+); TLC $R_f$ |
|---|---|---|---|---|
| 108D | 2-(1-Ethylpyrazol-4-yl)-6-(hydroxymethyl)-6,7-dihydro-5H-pyrazolo[5,1-b][1,3]oxazine-3-carboxylic acid | 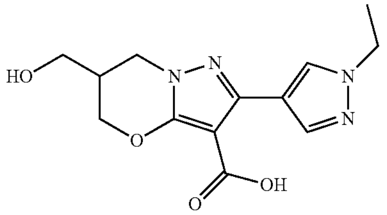 [SMILES: CCn1cc(-c2nn3c(c2C(=O)O)OCC(CO)C3)cn1] | δ 11.90 (s, 1H), 8.22 (s, 1H), 7.84 (s, 1H), 8.00 (t, J = 5.3 Hz, 1H), 4.45 (dd, J = 10.9, 3.3 Hz, 1H), 4.23 (dd, J = 10.9, 7.7 Hz, 1H), 4.19-4.08 (m, 3H), 3.88 (dd, J = 12.3, 7.3 Hz, 1H), 3.49 (t, J = 5.9 Hz, 2H), 2.42 (dd, J = 6.3, 3.0 Hz, 1H), 1.37 (t, J = 7.2 Hz, 3H). | 292.7 $[M + H]^+$ |
| 108E | 2-(6-Ethylpyridin-3-yl)-6-(hydroxymethyl)-6,7-dihydro-5H-pyrazolo[5,1-b][1,3]oxazine-3-carboxylic acid | 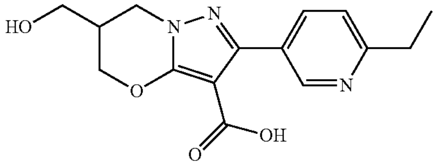 [SMILES: CCc1ccc(-c2nn3c(c2C(=O)O)OCC(CO)C3)cn1] | δ 12.03 (s, 1H), 8.65 (dd, J = 2.3, 0.8 Hz, 1H), 7.89 (dd, J = 8.0, 2.3 Hz, 1H), 7.28 (d, J = 8.0 Hz, 1H), 5.03 (s, 1H), 4.50 (dd, J = 10.8, 3.3 Hz, 1H), 4.31-4.16 (m, 2H), 3.95 (dd, J = 12.3, 7.4 Hz, 1H), 3.54-3.48 (m, 2H), 2.77 (q, J = 7.6 Hz, 2H), 1.25 (t, J = 7.6 Hz, 3H). | 303.9 $[M + H]^+$ |
| 109A | 2-(2-Fluorophenyl)-6-(methoxymethyl)-6,7-dihydro-5H-pyrazolo[5,1-b][1,3]oxazine-3-carboxylic acid | 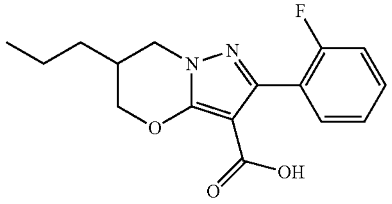 [SMILES: CCCC1COc2c(C(=O)O)c(-c3ccccc3F)nn2C1] | δ 11.81 (s, 1H), 7.47-7.31 (m, 2H), 7.31-7.06 (m, 2H), 4.49 (dd, J = 10.9, 3.3 Hz, 1H), 4.24 (ddd, J = 16.3, 11.6, 6.8 Hz, 2H), 3.93 (dd, J = 12.3, 7.6 Hz, 1H), 3.44 (d, J = 6.7 Hz, 2H), 3.30 (s, 3H), 2.76-2.63 (m, 1H). | 307.6 $[M + H]^+$ |
| 110A | 2-(2-Fluorophenyl)-6-[methyl-[(2-methylpropan-2-yl)oxy-carbonyl]amino]-6,7-dihydro-5H-pyrazolo[5,1-b[[1,3]oxazine-3-carboxylic acid | 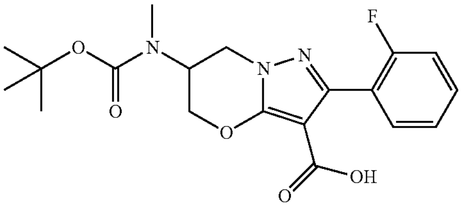 [SMILES: CN(C(=O)OC(C)(C)C)C1COc2c(C(=O)O)c(-c3ccccc3F)nn2C1] | δ 11.75 (s, 1H), 7.53-7.30 (m, 2H), 7.30-7.03 (m, 2H), 4.67-4.55 (m, 1H), 4.55-4.45 (m, 2H), 4.45-4.25 (m, 2H), 2.77 (s, 3H), 1.44 (s, 9H). | 392.7 $[M + H]^+$ |
| 111A | 2-(2-Fluorophenyl)-7-methyl-6,7-dihydro-5H-pyrazolo[5,1-b][1,3]oxazine-3-carboxylic acid | 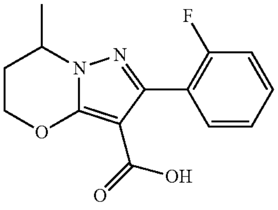 [SMILES: CC1CCOc2c(C(=O)O)c(-c3ccccc3F)nn21] | (500 MHz) δ 11.72 (s, 1H), 7.48-7.35 (m, 2H), 7.27-7.14 (m, 2H), 4.49 (m, 1H), 4.44-4.32 (m, 2H), 2.43-2.30 (m, 1H), 2.08-1.91 (m, 1H), 1.49 (d, J = 6.5 Hz, 3H). | 277.1 $[M + H]^+$ |
| 112A | (5S)-2-(1-Ethylpyrazol-4-yl)-5-methyl-6,7-dihydro-5H-pyrazolo[5,1-b][1,3]oxazine-3-carboxylic acid | 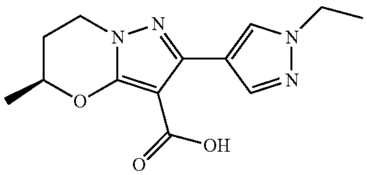 [SMILES: CCn1cc(-c2nn3c(c2C(=O)O)O[C@@H](C)CC3)cn1] | δ 11.82 (s, 1H), 8.22 (s, 1H), 7.84 (s, 1H), 4.59-4.46 (m, 1H), 4.13 (q, J = 7.3 Hz, 2H), 4.11-4.02 (m, 2H), 2.29-2.17 (m, 1H), 2.06-1.91 (m, 1H), 1.41 (d, J = 6.3 Hz, 3H), 1.37 (t, J = 7.3 Hz, 3H). | 277.1 $[M + H]^+$ |

TABLE 17-continued

Preparatory examples prepared by ester hydrolysis procedure A.

| Preparatory Example | Name | Structure | $^1$H NMR δ (400 MHz, DMSO-$d_6$) | LRMS m/z (APCI+); TLC $R_f$ |
|---|---|---|---|---|
| 112B | (5S)-5-Methyl-2-[1-(2,2,2-trifluoroethyl)pyrazol-4-yl]-6,7-dihydro-5H-pyrazolo[5,1-b][1,3]oxazine-3-carboxylic acid | 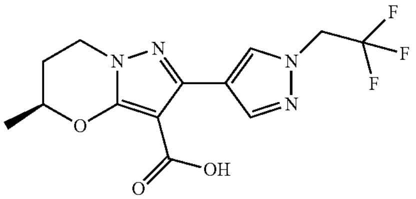 [SMILES: C[C@H]1CCn2nc(-c3cnn(CC(F)(F)F)c3)c(C(=O)O)c2O1] | δ 11.93 (s, 1H), 8.40 (s, 1H),7.96 (s, 1H), 5.18 (q, J = 9.2 Hz, 2H), 4.61-4.46 (m, 1H), 4.18-4.01 (m, 2H), 2.24 (dq, J = 14.2, 2.9 Hz, 1H), 1.99 (dtd, J = 14.2, 9.8, 6.9 Hz, 1H), 1.42 (d, J = 6.3 Hz, 3H). | 331.4 $[M + H]^+$ |
| 112C | (5S)-5-Methyl-2-[1-(oxan-4-yl)pyrazol-4-yl]-6,7-dihydro-5H-pyrazolo[5,1-b][1,3]oxazine-3-carboxylic acid | 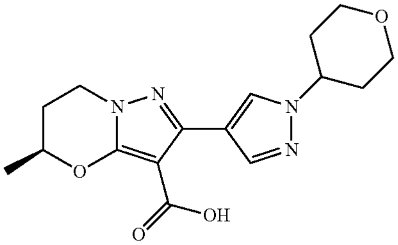 [SMILES: C[C@H]1CCn2nc(-c3cnn(C4CCOCC4)c3)c(C(=O)O)c2O1] | δ 11.83 (s, 1H), 8.26 (s, 1H), 7.87 (s, 1H), 4.59-4.46 (m, 1H), 4.41 (tt, J = 10.3, 5.2 Hz, 1H), 4.14-4.01 (m, 2H), 3.95 (dt, J = 11.8, 2.7 Hz, 2H), 3.46 (td, J = 11.3, 3.3 Hz, 2H), 2.23 (dq, J = 14.0, 2.8 Hz, 1H), 1.96 (qq, J = 11.2, 5.9, 4.7 Hz, 5H), 1.41 (d, J = 6.3 Hz, 3H). | 333.2 $[M + H]^+$ |
| 112D | (5S)-2-(6-Ethylpyridin-3-yl)-5-methyl-6,7-dihydro-5H-pyrazolo[5,1-b][1,3]oxazine-3-carboxlic acid | 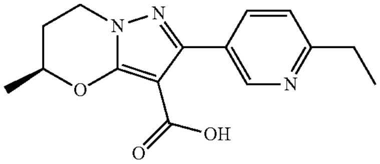 [SMILES: CCc1ccc(-c2nn3c(c2C(=O)O)O[C@@H](C)CC3)cn1] | δ 11.92 (s, 1H), 8.64 (d, J = 2.2 Hz, 1H), 7.88 (dd, J = 8.1, 2.3 Hz, 1H), 7.28 (d, J = 8.0 Hz, 1H), 4.65-4.51 (m, 1H), 4.22-4.04 (m, 2H), 2.77 (q, J = 7.6 Hz, 2H), 2.31-2.21 (m, 1H), 2.14-1.95 (m, 1H), 1.43 (d, J = 6.3 Hz, 3H), 1.25 (t, J = 7.6 Hz, 3H). | 288.3 $[M + H]^+$ |
| 113A | (5R)-2-Benzyl-5-methyl-6,7-dihydro-5H-pyrazolo[5,1-b][1,3]oxazine-3-carboxlic acid | 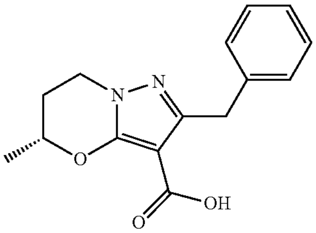 [SMILES: C[C@@H]1CCn2nc(Cc3ccccc3)c(C(=O)O)c2O1] | δ 11.79 (s, 1H), 7.33-6.99 (m, 5H), 4.57-4.36 (m, 1H), 4.01 (d, J = 8.7 Hz, 4H), 2.24-2.13 (m, 1H), 2.01-1.86 (m, 1H), 1.39 (d, J = 6.3 Hz, 3H). | 273.5 $[M + H]^+$ |
| 113B | (5R)-5-Methyl-2-(1-methylpyrazol-4-yl)-6,7-dihydro-5H-pyrazolo[5,1-b][1,3]oxazine-3-carboxylic acid | 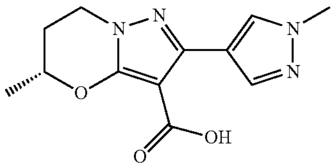 | δ 11.86 (s, 1H), 8.19 (d, J = 0.6 Hz, 1H), 7.81 (d, J = 0.7 Hz, 1H), 4.58-4.46 (m, 1H), 4.12-3.98 (m, 2H), 3.84 (s, 3H), 2.30-2.15 (m, 1H), 2.04-1.90 (m, 1H), 1.41 (d, J = 6.2 Hz, 3H). | 263.4 $[M + H]^+$ |
| 113C | (R)-5-Methyl-2-[1-(oxan-4-yl)pyrazol-4-yl]-6,7-dihydro-5H-pyrazolo[5,1-b][1,3]oxazine-3-carboxylic acid | 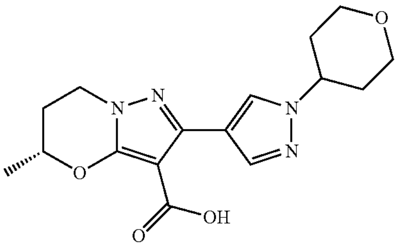 [SMILES: C[C@@H]1CCn2nc(-c3cnn(C4CCOCC4)c3)c(C(=O)O)c2O1] | δ 11.83 (s, 1H), 8.25 (s, 1H), 7.87 (s, 1H), 4.63-4.44 (m, 1H), 4.48-4.31 (m, 1H), 4.11-4.03 (m, 2H), 4.00-3.88 (m, 2H), 3.52-3.39 (m, 2H), 2.23 (d, J = 14.5 Hz, 1H), 2.07-1.82 (m, 5H), 1.42 (d, J = 6.3 Hz, 3H). | 333.7 $[M + H]^+$ |

TABLE 17-continued

| Preparatory examples prepared by ester hydrolysis procedure A. | | | | |
|---|---|---|---|---|
| Preparatory Example | Name | Structure | $^1$H NMR δ (400 MHz, DMSO-$d_6$) | LRMS m/z (APCI+); TLC $R_f$ |
| 113D | (5R)-5-Methyl-2-(1-propan-2-ylpyrazol-4-yl)-6,7-dihydro-5H-pyrazolo[5,1-b][1,3]oxazine-3-carboxylic acid | 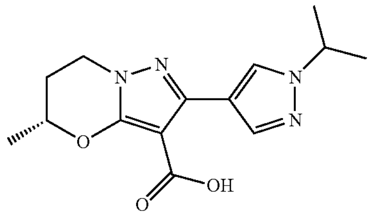 [SMILES: CC(C)n1cc(-c2nn3c(c2C(=O)O)O[C@H](C)CC3)cn1] | δ 11.82 (s, 1H), 8.22 (s, 1H), 7.85 (s, 1H), 4.62-4.43 (m, 2H), 4.18-3.94 (m, 2H), 2.30-2.15 (m, 1H), 2.07-1.86 (m, 1H), 1.41 (d, J = 6.6 Hz, 9H). | 291.6 $[M + H]^+$ |
| 113E | (5R)-2-Cyclohexyl-5-methyl-6,7-dihydro-5H-pyrazolo[5,1-b][1,3]oxazine-3-carboxylic acid | 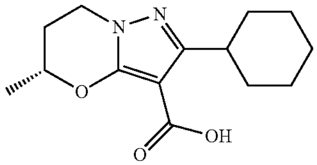 [SMILES: C[C@@H]1CCn2nc(C3CCCCC3)c(C(=O)O)c2O1] | δ 11.66 (s, 1H), 4.66-4.36 (m, 1H), 4.19-3.83 (m, 2H), 3.21-2.92 (m, 1H), 2.25-2.10 (m, 1H), 1.98-1.86 (m, 1H), 1.86-1.61 (m, 4H), 1.42-1.02 (m, 8H). | 265.4 $[M + H]^+$ |
| 113F | (5R)-2-(1,3-Dimethylpyrazol-4-yl)-5-methyl-6,7-dihydro-5H-pyrazolo[5,1-b][1,3]oxazine-3-carboxylic acid | 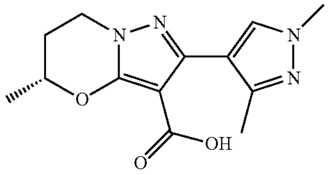 | δ 11.73 (s, 1H), 7.93 (s, 1H), 4.57-4.46 (m, 1H), 4.14-4.01 (m, 2H), 3.75 (s, 3H), 2.30-2.12 (m, 4H), 2.07-1.93 (m, 1H), 1.41 (d, J = 6.3 Hz, 3H). | 277.3 $[M + H]^+$ |
| 113G | (5R)-5-Methyl-2-[1-(oxetan-3-yl)pyrazol-4-yl]-6,7-dihydro-5H-pyrazolo[5,1-b][1,3]oxazine-3-carboxylic acid | 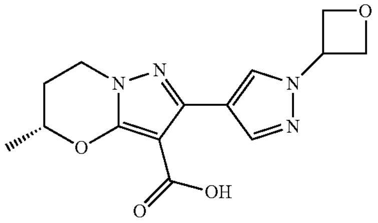 [SMILES: C[C@@H]1CCn2nc(-c3cnn(C4COC4)c3)c(C(=O)O)c2O1] | δ 11.90 (s, 1H), 8.35 (s, 1H), 7.98 (s, 1H), 5.68-5.56 (m, 1H), 4.97-4.85 (m, 4H), 4.59-4.46 (m, 1H), 4.14-3.99 (m, 2H), 2.29-2.18 (m, 1H), 2.06-1.92 (m, 1H), 1.41 (d, J = 6.3 Hz, 3H). | 305.3 $[M + H]^+$ |
| 113H | (5R)-2-[1-(2-Hydroxyethyl)pyrazol-4-yl]-5-methyl-6,7-dihydro-5H-pyrazolo[5,1-b][1,3]oxazine-3-carboxylic acid | 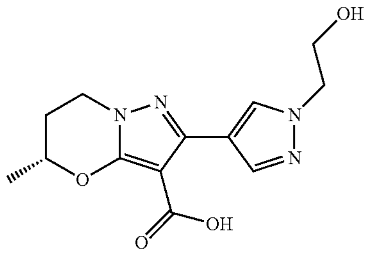 [SMILES: C[C@@H]1CCn2nc(-c3cnn(CCO)c3)c(C(=O)O)c2O1] | δ 11.82 (s, 1H), 8.22 (d, J = 0.7 Hz, 1H), 7.85 (d, J = 0.7 Hz, 1H), 4.90 (t, J = 5.3 Hz, 1H), 4.59-4.47 (m, 1H), 4.17-4.00 (m, 4H), 3.72 (q, J = 5.5 Hz, 2H), 2.29-2.18 (m, 1H), 2.07-1.92 (m, 1H), 1.41 (d, J = 6.3 Hz, 3H). | 293.4 $[M + H]^+$ |
| 113I | (5R)-5-Methyl-2-[1-(2,2,2-trifluoroethyl)pyrazol-4-yl]-6,7-dihydro-5H-pyrazolo[5,1-b][1,3]oxazine-3-carboxylic acid | 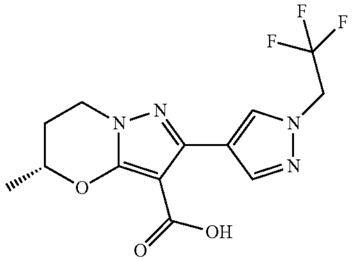 [SMILES: C[C@@H]1CCn2nc(-c3cnn(CC(F)(F)F)c3)c(C(=O)O)c2O1] | δ 11.93 (s, 1H), 8.40 (d, J = 1.6 Hz, 1H), 7.95 (d, J = 7.3 Hz, 1H), 5.25-5.10 (m, 2H), 4.62-4.48 (m, 1H), 4.16-4.00 (m, 3H), 2.31-2.20 (m, 1H), 2.09-1.93 (m, 1H), 1.42 (dd, J = 6.3, 2.2 Hz, 3H). | 331.4 $[M + H]^+$ |

TABLE 17-continued

Preparatory examples prepared by ester hydrolysis procedure A.

| Preparatory Example | Name | Structure | $^1$H NMR δ (400 MHz, DMSO-$d_6$) | LRMS m/z (APCI+); TLC $R_f$ |
|---|---|---|---|---|
| 113J | (5R)-2-[1-(Difluoro-methyl)pyra-zol-4-yl]-5-methyl-6,7-dihydro-5H-pyrazolo[5,1-b][1,3]oxazine-3-carboxylic acid | 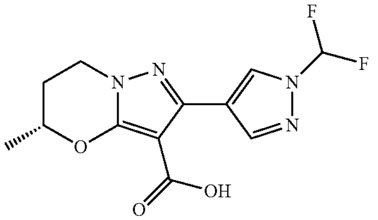 [SMILES: C[C@@H]1CCn2nc(-c3cnn(C(F)F)c3)c(C(=O)O)c2O1] | δ 12.03 (s, 1H), 8.72 (s, 1H), 8.13 (s, 1H), 7.87 (t, J = 59.0 Hz, 1H), 4.62-4.43 (m, 1H), 4.21-4.00 (m, 2H), 2.30-2.20 (m, 1H), 2.06-1.93 (m, 1H), 1.42 (d, J = 6.3 Hz, 3H). | 299.3 $[M + H]^+$ |
| 113K | (5R)-2-[1-(2-Methoxyethyl) pyrazol-4-yl]-5-methyl-6,7-dihydro-5H-pyrazolo[5,1-b][1,3]oxazine-3-carboxylic acid | 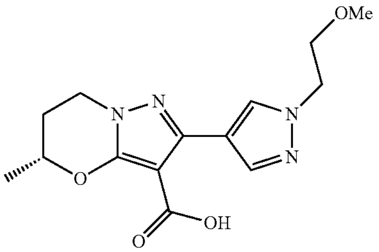 [SMILES: COCCn1cc(-c2nn3c(c2C(=O)O)O[C@H](C)CC3)cn1] | δ 11.80 (s, 1H), 8.21 (d, J = 0.7 Hz, 1H), 7.85 (d, J = 0.7 Hz, 1H), 4.59-4.46 (m, 1H), 4.26 (t, J = 5.3 Hz, 2H), 4.14-4.01 (m, 2H), 3.72-3.63 (m, 2H), 3.23 (s, 3H), 2.28-2.16 (m, 1H), 2.06-1.91 (m, 1H), 1.41 (d, J = 6.3 Hz, 3H). | 307.4 $[M + H]^+$ |
| 113L | (5R)-2-(1,5-Dimethylpyrazol-4-yl)-5-methyl-6,7-dihydro-5H-pyrazolo[5,1-b][1,3]oxazine-3-carboxylic acid | 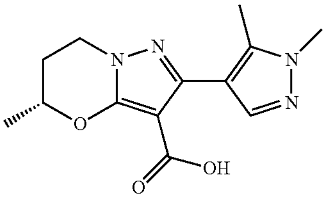 | δ 11.68 (s, 1H), 754 (s, 1H), 4.58-4.41 (m, 1H), 4.16-3.97 (m, 2H), 3.73 (s, 3H), 2.27 (s, 3H), 2.25-2.17 (m, 1H), 2.12-1.83 (m, 1H), 1.42 (d, J = 6.3 Hz, 3H). | 277.3 $[M + H]^+$ |
| 113M | (5R)-2-[1-(2-Hydroxy-2-methyl-propyl)pyra-zol-4-yl]-5-methyl-6,7-dihydro-5H-pyrazolo[5,1-b][1,3]oxazine-3-carboxylic acid | 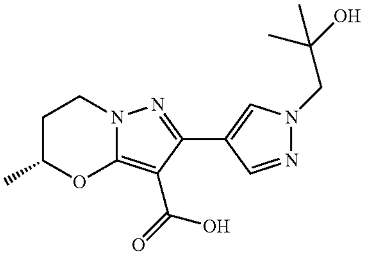 [SMILES: C[C@@H]1CCn2nc(-c3cnn(CC(C)(C)O)c3)c(C(=O)O)c2O1] | δ 11.81 (s, 1H), 8.22 (d, J = 0.7 Hz, 1H), 7.84 (d, J = 0.6 Hz, 1H), 4.69 (s, 1H), 4.60-4.46 (m, 1H), 4.11-4.05 (m, 2H), 4.01 (s, 2H), 2.29-2.15 (m, 1H), 2.08-1.90 (m, 1H), 1.42 (d, J = 6.3 Hz, 3H), 1.06 (s, 6H). | 321.5 $[M + H]^+$ |
| 113N | (5R)-2-(1-Cyclo-propylpyrazol-4-yl)-5-methyl-6,7-dihydro-5H-pyrazolo[5,1-b][1,3]oxazine-3-carboxylic acid | 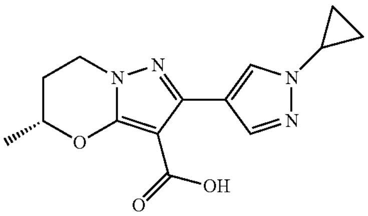 [SMILES: C[C@@H]1CCn2nc(-c3cnn(C4CC4)c3)c(C(=O)O)c2O1] | δ 11.85 (s, 1H), 8.25 (s, 1H), 7.80 (s, 1H), 4.60-4.45 (m, 1H), 4.15-4.00 (m, 2H), 3.82-3.69 (m, 1H), 2.29-2.18 (m, 1H), 2.05-1.90 (m, 1H), 1.41 (d, J = 6.3 Hz, 3H), 1.10-0.89 (m, 4H). | 289.3 $[M + H]^+$ |
| 113O | (5R)-2-(2-Fluoro-4-methyl-sulfonylphe-nyl)-5-methyl-6,7-dihydro-5H-pyrazolo[5,1-b][1,3]oxazine-3-carboxylic acid | 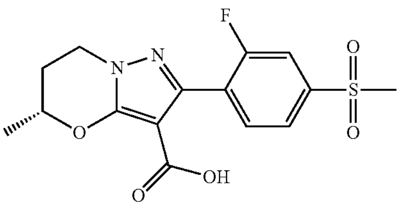 | δ 11.94 (s, 1H), 7.85-7.75 (m, 2H), 7.73-7.63 (m, 1H), 4.68-4.54 (m, 1H), 4.23-4.09 (m, 2H), 2.32-2.22 (m, 1H), 2.14-2.01 (m, 1H), 1.44 (dd, J = 6.3, 1.3 Hz, 3H). | 355.2 $[M + H]^+$ |

TABLE 17-continued

Preparatory examples prepared by ester hydrolysis procedure A.

| Preparatory Example | Name | Structure | $^1$H NMR δ (400 MHz, DMSO-$d_6$) | LRMS m/z (APCI+); TLC $R_f$ |
|---|---|---|---|---|
| 113P | (5R)-2-[6-(3-Methoxyazetidin-1-yl)pyridin-3-yl]-5-methyl-6,7-dihydro-5H-pyrazolo[5,1-b][1,3]oxazine-3-carboxylic acid | 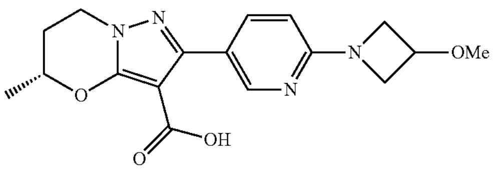 [SMILES: COC1CN(c2ccc(-c3nn4c(c3C(=O)O)O[C@H](C)CC4)cn2)C1] | δ 8.29 (d, J = 2.2 Hz, 1H), 7.74 (dd, J = 8.6, 2.3 Hz, 1H), 6.38 (dd, J = 8.7, 0.9 Hz, 1H), 4.52 (d, J = 6.5 Hz, 1H), 4.38-4.28 (m, 1H), 4.20-4.02 (m, 4H), 3.76 (ddd, J = 8.9, 4.1, 1.1 Hz, 2H), 3.25 (s, 3H), 2.28-2.19 (m, 1H), 2.05-1.92 (m, 1H), 1.42 (d, J = 6.3 Hz, 3H). | 344.5 $[M + H]^+$ |
| 113Q | (5R)-2-[6-[(3R)-3-Methoxy-pyrrolidin-1-yl]pyridin-3-yl]-5-methyl-6,7-dihydro-5H-pyrazolo[5,1-b][1,3]oxazine-3-carboxylic acid | 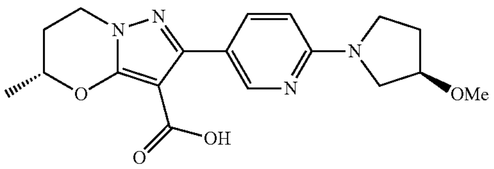 [SMILES: CO[C@@H]1CCN(c2ccc(-c3nn4c(c3C(=O)O)O[C@H](C)CC4)cn2)C1] | δ 11.74 (s, 1H), 8.28 (dd, J = 2.3, 0.8 Hz, 1H), 7.69 (dd, J = 8.7, 2.4 Hz, 1H), 6.43 (dd, J = 8.8, 0.8 Hz, 1H), 4.60-4.48 (m, 1H), 4.15-4.03 (m, 3H), 3.49 (t, J = 4.3 Hz, 3H), 3.41-3.35 (m, 1H), 3.27 (s, 3H), 2.29-2.18 (m, 1H), 2.10-1.94 (m, 3H), 1.42 (d, J = 6.3 Hz, 3H). | 359.6 $[M + H]^+$ |
| 113R | (5R)-2-[6-[(S)-3-Methoxy-pyrrolidin-1-yl]pyridin-3-yl]-5-methyl-6,7-dihydro-5H-pyrazolo[5,1-b][1,3]oxazine-3-carboxylic acid | 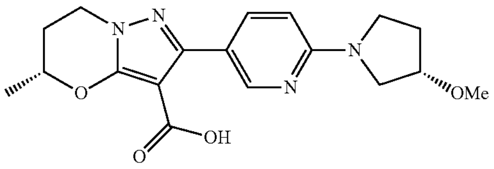 [SMILES: CO[C@H]1CCN(c2ccc(-c3nn4c(c3C(=O)O)O[C@H](C)CC4)cn2)C1] | δ 8.31 (s, 1H), 7.72 (d, J = 8.6 Hz, 1H), 6.42 (d, J = 8.8 Hz, 1H), 4.58-4.46 (m, 1H), 4.14-4.02 (m, 3H), 3.54-3.45 (m, 3H), 3.41-3.37 (m, 1H), 3.27 (s, 3H), 2.28-2.18 (m, 1H), 2.10-1.92 (m, 3H), 1.42 (d, J = 6.3 Hz, 3H). | 359.6 $[M + H]^+$ |
| 113S | (5R)-2-[2-Fluoro-4-(hydroxy-methyl)phe-nyl]-5-methyl-6,7-dihydro-5H-pyrazolo[5,1-b][1,3]oxazine-3-carboxylic acid | 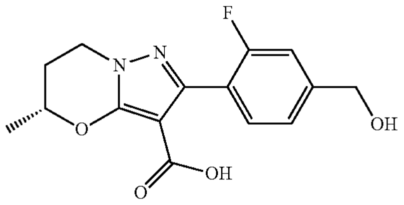 [SMILES: C[C@@H]1CCn2nc(-c3ccc(CO)cc3F)c(C(=O)O)c2O1] | δ 11.74 (s, 1H), 7.31 (t, J = 7.6 Hz, 1H), 7.15-7.07 (m, 2H), 5.35 (t, J = 5.8 Hz, 1H), 4.62-4.48 (m, 3H), 4.17-4.09 (m, 2H), 2.30-2.20 (m, 1H), 2.10-1.95 (m, 1H), 1.43 (d, J = 6.3 Hz, 3H). | 307.1 $[M + H]^+$ |
| 113T | (5R)-2-[6-(Hydroxy-methyl)pyri-din-3-yl]-5-methyl-6,7-dihydro-5H-pyrazolo[5,1-b[1,3]oxazine-3-carboxylic acid | 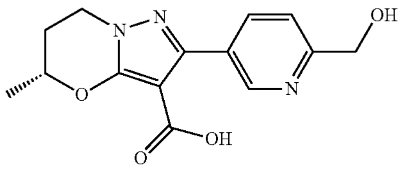 [SMILES: C[C@@H]1CCn2nc(-c3ccc(CO)nc3)c(C(=O)O)c2O1] | δ 11.93 (s, 1H), 8.63 (dd, J = 2.2, 0.8 Hz, 1H), 7.95 (dd, J = 8.1, 2.2 Hz, 1H), 7.47 (dd, J = 8.1, 0.9 Hz, 1H), 5.44 (t, J = 5.9 Hz, 2H), 4.23-4.07 (m, 2H), 2.32-2.23 (m, 1H), 2.10-1.96 (m, 1H), 1.44 (d, J = 6.3 Hz, 3H). | 290.1 $[M + H]^+$ |

113U (5R)-5-Methyl-2-(1H-pyrazol-4-yl)-6,7-dihydro-5H-pyrazolo[5,1-b][1,3]oxazine-3-carboxylic Acid

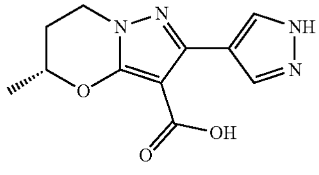 [SMILES: C[C@@H]1CCn2nc(-c3cn[nH]c3)c(C(=O)O)c2O1]

NaOH (5 M aq. 0.3 mL, 1.49 mmol) was added to a mixture of intermediate 81F (66 mg, 0.19 mmol) in EtOH (5 mL). The mixture was heated at 60° C. for 19 h. The volatiles were removed under reduced pressure and the mixture was acidified (pH≈4) with 1 M aq. HCl. The mixture was extracted with $CHCl_3$:iPrOH (3:1, 3×10 mL), the organics were washed with water and brine (10 mL each), dried ($Na_2SO_4$) and concentrated under reduced pressure to afford a white solid (43 mg, 93%). $^1$H NMR (400 MHz, DMSO-$d_6$) δ 12.30 (s, 2H), 8.05 (dd, J=8.9, 5.0 Hz, 2H), 4.52 (ddd, J=8.7, 6.5, 2.3 Hz, 1H), 4.15-4.03 (m, 2H), 3.16 (d, J=4.9 Hz, 2H), 2.23 (d, J=14.4 Hz, 1H), 1.98 (ddd, J=16.7, 13.1, 8.4 Hz, 1H), 1.42 (d, J=6.3 Hz, 3H). LRMS (APCI+) m/z 249.2 $[M+H]^+$.

113V (5R)-5-Methyl-2-(1-methylsulfonylpiperidin-4-yl)-6,7-dihydro-5H-pyrazolo[5,1-b][1,3]oxazine-3-carboxylic Acid

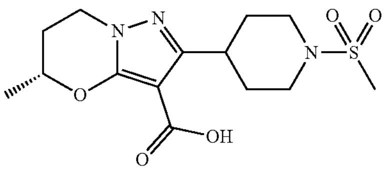

NaOH (5 M aq. 0.8 mL, 3.98 mmol) was added to a suspension of intermediate 102A in EtOH (20 mL). The mixture was heated at 60° C. for 3 h. NaOH (5 M aq. 0.8 mL, 3.98 mmol) was added and the mixture was heated at 70° C. for 2 h. NaOH (5 M aq. 1.59 mL, 7.97 mmol) was added and the mixture was heated at 80° C. for 18 h. The EtOH was removed under reduced pressure and the mixture was acidified to pH≈2 with 1 M aq. HCl and extracted with $CHCl_3$: iPrOH (3:1; 3×20 mL). The organics were washed with water and brine (20 mL each), dried ($MgSO_4$), and concentrated under reduced pressure to afford a white solid (151 mg, 88%). $^1$H NMR (400 MHz, DMSO-$d_6$) δ 11.79 (s, 1H), 4.55-4.43 (m, 1H), 4.10-3.95 (m, 2H), 3.60 (d, J=11.7 Hz, 2H), 3.21-3.08 (m, 1H), 2.87 (s, 3H), 2.77 (td, J=12.1, 2.6 Hz, 2H), 2.25-2.12 (m, 1H), 2.04-1.83 (m, 3H), 1.70-1.52 (m, 2H), 1.39 (d, J=6.3 Hz, 3H). LRMS (APCI+) m/z 344.5 $[M+H]^+$.

113W (5R)-2-(1-ethylsulfonylpiperidin-4-yl)-5-methyl-6,7-dihydro-5H-pyrazolo[5,1-b][1,3]oxazine-3-carboxylic Acid

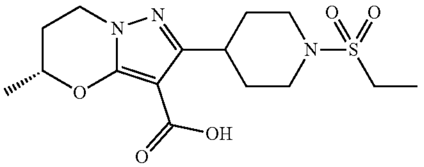 [SMILES: CCS(=O)(=O)N1CCC(c2nn3c(c2C(=O)O)O[C@H](C)CC3)CC1]

Prepared by an analogous procedure to that described for intermediate 113V. $^1$H NMR (700 MHz, DMSO-$d_6$) δ 11.76 (s, 1H), 4.54-4.43 (m, 1H), 4.08-3.96 (m, 2H), 3.70-3.58 (m, 2H), 3.23-3.13 (m, 1H), 3.04 (q, J=7.4 Hz, 2H), 2.86 (td, J=12.3, 2.6 Hz, 2H), 2.26-2.15 (m, 1H), 1.97-1.91 (m, 1H), 1.92-1.86 (m, 2H), 1.66-1.54 (m, 2H), 1.39 (d, J=6.3 Hz, 3H), 1.21 (t, J=7.4 Hz, 3H). LRMS (APCI+) 358.1 m/z $[M+H]^+$.

114A 6-[Ethyl-[(2-methylpropan-2-yl)oxycarbonyl]amino]-2-(2-fluorophenyl)-6,7-dihydro-5H-pyrazolo[5,1-b][1,3]oxazine-3-carboxylic Acid

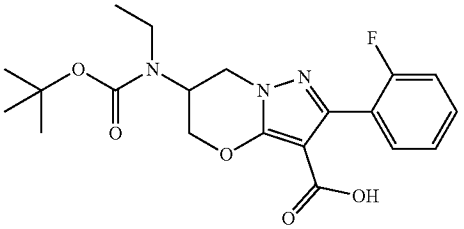 [SMILES: CCN(C(=O)OC(C)(C)C)C1COc2c(C(=O)O)c(-c3ccccc3F)nn2C1]

NaH (60% dispersion in mineral oil, 18.5 mg, 0.46 mmol) was added to a solution of intermediate 89A (75 mg, 0.19 mmol) in DMF (1 mL) and the mixture stirred for 0.5 h at rt. EtI (40 µL, 0.46 mmol) was added and the mixture stirred at rt for 1.5 h. The reaction was quenched with water (20 mL) and extracted with EtOAc (3×10 mL). The organics were washed with water (2×10 mL) and brine (10 mL), dried ($Na_2SO_4$), and concentrated under reduced pressure. Purification by flash chromatography (10-35% EtOAc:heptane) afforded a colourless oil (140 mg) which was taken directly to the next step. NaOH (5 M aq. 0.3 mL) was added to a portion of the crude residue (80 mg, 0.19 mmol) in EtOH (4 mL). The mixture was heated at 60° C. for 2 h, then stirred at rt for 16 h. The volatiles were removed under reduced pressure, and the residue acidified (pH 4) with 1 M aq. HCl. The mixture was extracted with EtOAc (3×10 mL), the organics washed with water and brine (10 mL each), dried ($MgSO_4$), and concentrated under reduced pressure. The residue was triturated with heptane (3×5 mL) and dried under reduced pressure to afford an off-white solid (59 mg, 79%). $^1$H NMR (400 MHz, DMSO-$d_6$) δ 11.88 (s, 1H), 7.52-7.28 (m, 2H), 7.28-7.14 (m, 2H), 4.62-4.39 (m, 3H), 4.39-4.19 (m, 2H), 3.21 (q, J=7.0 Hz, 2H), 1.43 (s, 8H), 1.04 (t, J=6.9 Hz, 3H). LRMS (APCI+) m/z 406.5 $[M+H]^+$.

115A Benzyl 2-bromo-6,7-dihydro-5H-pyrazolo[5,1-b][1,3]oxazine-3-carboxylate

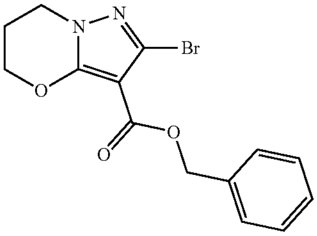 [SMILES: O=C(OCc1ccccc1)c1c(Br)nn2c1OCCC2]

1,8-Diazabicyclo[5.4.0]undec-7-ene (270 µL, 1.79 mmol) was added to a solution of intermediate 104A (340 mg, 1.38 mmol) in DMSO (7 mL). After 5 m benzyl bromide (0.16 mL, 1.38 mmol) in DMSO (7 mL) was added and the reaction stirred at t for 16 h. Water (30 mL) and brine (30 mL) were added and the mixture was extracted with EtOAc (3×25 mL). The organics were washed with brine (2×25 ml), dried ($Na_2SO_4$) and concentrated under reduced pressure. Purification by flash chromatography (10-80 EtOAc:heptane) afforded a colourless oil (356 mg, 77%). $^1$H NMR (400 MHz, DMSO-$d_6$) δ 7.45-7.25 (m, 5H), 5.23 (s, 2H), 4.49-4.37 (m, 2H), 4.06 (t, J=6.1 Hz, 2H), 2.27-2.15 (n, 2H). LRMS m/z (APCI+) 337.1/339.1 $[M+H]^+$.

The following intermediate compounds were prepared in an analogous manner to intermediate 21A. The reaction time varied between 45 min to 1 h 20 min, with heating by MWI or by conventional heating. Intermediate 116D was prepared from the corresponding pinacol ester.

TABLE 18

Preparatory examples prepared via Suzuki-Miyaura procedure B.

| Preparatory Example | Name | Structure | $^1H$ NMR δ (400 MHz, DMSO-$d_6$) | LRMS APCI+ m/z |
|---|---|---|---|---|
| 116A | Benzyl 2-(4-carbamoyl-2-fluorophenyl)-6,7-dihydro-5H-pyrazolo[5,1-b][1,3]oxazine-3-carboxylate | 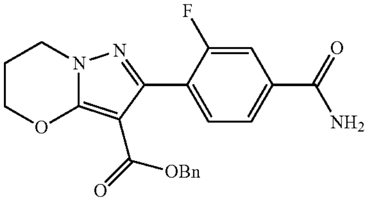 [SMILES: NC(=O)c1ccc(-c2nn3c(c2C(=O)OCc2ccccc2)OCCC3)c(F)c1] | δ 8.09 (s, 1H), 7.72 (dd, J = 7.9, 1.6 Hz, 1H), 7.62 (dd, J = 10.9, 1.6 Hz, 1H), 7.55 (s, 1H), 7.47 (t, J = 7.6 Hz, 1H), 7.31-7.20 (m, 3H), 7.17-7.08 (m, 2H), 5.08 (s, 2H), 4.52-4.45 (m, 2H), 4.16 (t, J = 6.0 Hz, 2H), 2.32-2.21 (m, 2H). | 396.1 $[M + H]^+$ |
| 116B | Benzyl 2-(2-Fluoro-2-formylphenyl)-6,7-dihydro-5H-pyrazolo[5,1-b][1,3]oxazine-3-carboxylate | 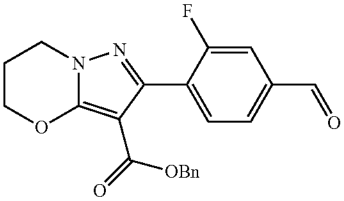 [SMILES: O=Cc1ccc(-c2nn3c(c2C(=O)OCc2ccccc2)OCCC3)c(F)c1] | δ 10.00 (d, J = 1.6 Hz, 1H), 7.76 (dd, J = 7.7, 1.5 Hz, 1H), 7.72-7.52 (m, 2H), 7.32-7.21 (m, 3H), 7.21-7.07 (m, 2H), 5.07 (s, 2H), 4.49 (dd, J = 5.9, 4.6 Hz, 2H), 4.18 (t, J = 6.1 Hz, 2H), 2.34-2.21 (m, 2H). | 381.1 $[M + H]^+$ |
| 116C | Benzyl 2-(2-fluoro-4-methylsulfanylphenyl)-6,7-dihydro-5H-pyrazolo[5,1-b][1,3]oxazine-3-carboxylate | 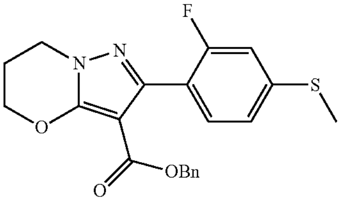 [SMILES: CSc1ccc(-c2nn3c(c2C(=O)OCc2ccccc2)OCCC3)c(F)c1] | δ 7.37-7.25 (m, 4H), 7.21-7.13 (m, 2H), 7.12-7.01 (m, 2H), 5.08 (s, 2H), 4.50-4.41 (m, 2H), 4.14 (t, J = 6.1 Hz, 2H), 3.34 (s, 4H), 2.29-2.19 (m, 2H) | 399.0 $[M + H]^+$ |
| 116D | Benzyl 2-(4-cyano-2-fluorophenyl)-6,7-dihydro-5H-pyrazolo[5,1-b][1,3]oxazine-3-carboxylate | 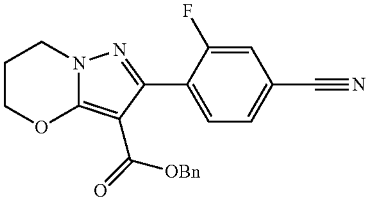 [SMILES: N#Cc1ccc(-c2nn3c(c2C(=O)OCc2ccccc2)OCCC3)c(F)c1] | δ 7.75 (dd, J = 9.7, 1.5 Hz, 1H), 7.68 (dd, J = 7.9, 1.6 Hz, 1H), 7.57 (dd, J = 7.8, 7.1 Hz, 1H), 7.39-7.23 (m, 4H), 7.23-7.10 (m, 2H), 5.06 (s, 2H), 4.54-4.44 (m, 2H), 4.17 (t, J = 6.1 Hz, 2H), 2.32-2.19 (m, 2H). | 378.2 $[M + H]^+$ |

117A Benzyl 2-[2-fluoro-4-(morpholin-4-ylmethyl) phenyl]-6,7-dihydro-5H-pyrazolo[5,1-b][1,3] oxazine-3-carboxylate

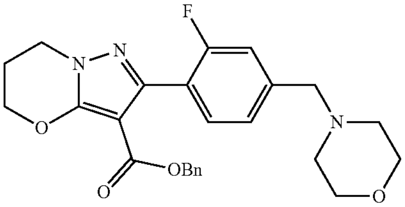 [SMILES: O=C(OCc1ccccc1)c1c(-c2ccc(CN3CCOCC3)cc2F)nn2c1OCCC2]

AcOH (0.03 mL, 0.53 mmol) was added to a solution of intermediate 116B (200 mg, 0.53 mmol) and morpholine (0.06 mL, 0.63 mmol) in $CH_2Cl_2$ (5 mL). The reaction was stirred for 1 h at rt, then sodium triacetoxyborohydride (178 mg, 0.84 mmol) added and stirred for 69 h at rt. The mixture was diluted with $CH_2Cl_2$ (10 mL), washed with sat. aq. $Na_2CO_3$ (2×10 mL), dried ($Na_2SO_4$), filtered and concentrated under reduced pressure. The residue was purified by flash chromatography [EtOAc, then 0-40% (50:8:1 $CH_2Cl_2$:EtOH:$NH_4OH$) in $CH_2Cl_2$] to afford a yellow oil (171 mg, 72%). $^1H$ NMR (400 MHz, DMSO-$d_6$) δ 7.39-7.22 (m, 4H), 7.18-7.11 (m, 3H), 7.06 (dd, J=11.0, 1.5 Hz, 1H), 5.07 (s, 2H), 4.49-4.42 (m, 2H), 4.14 (t, J=6.1 Hz, 2H), 3.61-3.54 (m, 4H), 3.48 (s, 2H), 2.38-2.30 (m, 4H), 2.31-2.20 (m, 2H). LRMS m/z (APCI+) 452.4 $[M+H]^+$.

The following intermediate compounds were prepared by an analogous procedure to that described for intermediate 117A.

TABLE 19

| Preparatory examples prepared by reductive amination procedure. | | | | |
|---|---|---|---|---|
| Preparatory Example | Name | Structure | $^1$H NMR δ (400 MHz, DMSO-$d_6$) | LRMS m/z (APCI+); TLC $R_f$ |
| 117B | Benzyl 2-[4-[(dimethylamino) methyl]-2-fluorophenyl]-6,7-dihydro-5H-pyrazolo[5,1-b][1,3]oxazine-3-carboxylate | 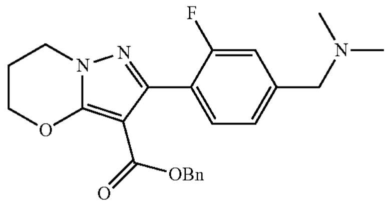 [SMILES: CN(C)Cc1ccc(-c2nn3c(c2C(=O)OCc2ccccc2)OCCC3)c(F)c1] | Not available | 410.1 $[M + H]^+$; $R_f$ = 0.13 (200:8:1 $CH_2Cl_2$:EtOH:$NH_4OH$) |
| 117C | Benzyl 2-[4-(diethylaminomethyl)-2-fluorophenyl]-6,7-dihydro-5H-pyrazolo[5,1-b][1,3]oxazine-3-carboxylate | 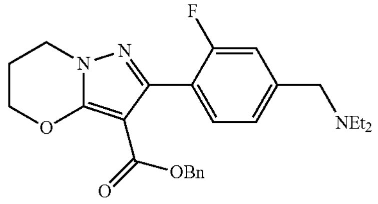 | δ 7.33-7.23 (m, 4H), 7.18-7.11 (m, 3H), 7.09-7.01 (m, 1H), 5.07 (s, 2H), 4.50-4.41 (m, 2H), 4.14 (t, J = 6.1 Hz, 2H), 3.54 (s, 2H), 2.49-2.40 (m, 4H), 2.31-2.21 (m, 2H), 0.98 (t, J = 7.1 Hz, 6H). | 438.4 $[M + H]^+$ |
| 117D | Benzyl 2-[2-fluoro-4-[(4-methylpiperazin-1-yl)methyl]phenyl]-6,7-dihydro-5H-pyrazolo[5,1-b][1,3]oxazine-3-carboxylate | 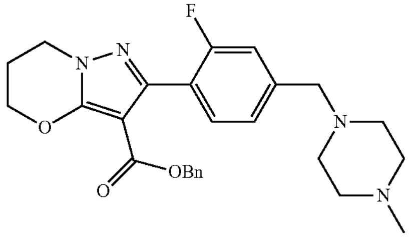 [SMILES: CN1CCN(Cc2ccc(-c3nn4c(c3C(=O)OCc3ccccc3)OCCC4)c(F)c2)CC1] | δ 7.35-7.22 (m, 4H), 7.18-7.09 (m, 3H), 7.07-6.99 (m, 1H), 5.06 (s, 2H), 4.50-4.42 (m, 2H), 4.14 (t, J = 6.1 Hz, 2H), 3.47 (s, 2H), 2.43-2.22 (m, 8H), 2.15 (s, 3H). | 465.5 $[M + H]^+$ |
| 118A | Ethyl (5R)-2-[4-[(dimethylamino) methyl]-2-fluorophenyl]-5-methyl-6,7-dihydro-5H-pyrazolo[5,1-b][1,3]oxazine-3-carboxylate | 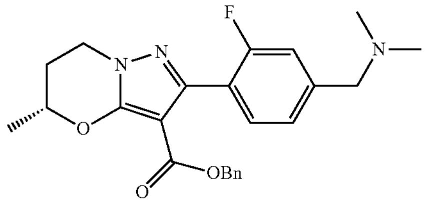 | δ 7.33 (t, J = 7.8 Hz, 1H), 7.17-7.01 (m, 2H), 4.66-4.53 (m, 1H), 4.22-4.08 (m, 2H), 3.98 (qd, J = 7.1, 0.7 Hz, 2H), 3.43 (s, 2H), 2.31-2.23 (m, 1H), 2.16 (s, 5H), 2.12-1.97 (m, 1H), 1.44 (d, J = 6.3 Hz, 3H), 1.01 (t,d J = 7.1 Hz, 3H). | 362.2 $[M + H]^+$ |
| 118B | Ethyl (5R)-2-[2-fluoro-4-[(propan-2-ylamino)methyl]phenyl]-5-methyl-6,7-dihydro-5H-pyrazolo[5,1-b][1,3]oxazine-3-carboxylate | 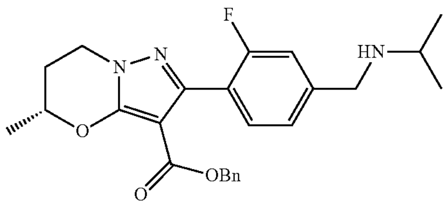 | δ 7.35-7.24 (m, 1H), 7.24-7.09 (m, 2H), 4.64-4.56 (m, 1H), 4.21-4.11 (m, 2H), 3.98 (q, J = 7.1 Hz, 2H), 3.73 (s, 2H), 2.32-2.19 (m, 2H), 2.10-2.01 (m, 2H), 1.44 (d, J = 6.3 Hz, 3H), 1.05-0.93 (m, 9H). | 376.2 $[M + H]^+$. |

119A Benzyl 2-(2 fluoro-4-methylsulfinylphenyl)-6,7-dihydro-5H-pyrazolo[5,1-b][1,3]oxazine-3-carboxylate

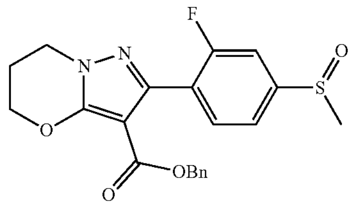 [SMILES: CS(=O)c1ccc(-c2nn3c(c2C(=O)OCc2ccccc2)OCCC3)c(F)c1]

A solution of mCPBA (124 mg, 0.55 mmol) in $CH_2Cl_2$ (10 mL) was added dropwise to a cooled (0° C.) solution of intermediate 116C (200 mg, 0.5 mmol) in $CH_2Cl_2$ (10 mL). After 1 h the ice bath was removed, and the mixture was stirred at rt for 0.5 h. The mixture was washed with sat. aq. $NaHCO_3$ (2×5 mL), dried ($Na_2SO_4$) and concentrated under reduced pressure. Purified by flash chromatography [10-30% (50:8:1 $CH_2Cl_2$:EtOH:$NH_4OH$) in $CH_2Cl_2$] to afford a colourless oil (159 mg, 76%). $^1H$ NMR (400 MHz, DMSO-$d_6$) δ 7.59 (dd, J=7.9, 6.8 Hz, 1H), 7.52 (dd, J=7.9, 1.6 Hz, 1H), 7.47 (dd, J=9.4, 1.6 Hz, 1H), 7.32-7.25 (m, 3H), 7.18-7.13 (m, 2H), 5.08 (s, 2H), 4.48 (dd, J=5.8, 4.5 Hz, 2H), 4.17 (t, J=6.1 Hz, 2H), 2.78 (s, 3H), 2.30-2.21 (m, 2H). LRMS (APCI+) m/z 415.1 $[M+H]^+$.

120A Benzyl 2-[2-fluoro-4-(methylsulfonimidoyl)phenyl]-6,7-dihydro-5H-pyrazolo[5,1-b][1,3]oxazine-3-carboxylate

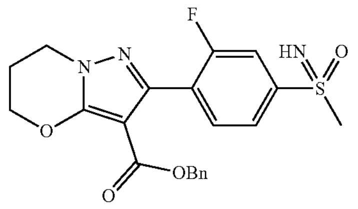 [SMILES: CS(=N)(=O)c1ccc(-c2nn3c(c2C(=O)OCc2ccccc2)OCCC3)c(F)c1]

(Diacetoxyiodo)benzene (404 mg, 1.25 mmol) and ammonium carbamate (78 mg, 1.0 mmol) were added to a solution of intermediate 116C (200 mg, 0.5 mmol) in MeOH (8 mL) and the reaction stirred at rt for 1.5 h. The volatiles were removed under reduced pressure and the residue purified by flash chromatography [0-30% (50:8:1 $CH_2Cl_2$:EtOH:$NH_4OH$) in $CH_2Cl_2$] to afford a colourless oil (185 mg, 86%). $^1H$ NMR (400 MHz, DMSO-$d_6$) δ 7.76 (dd, J=8.0, 1.7 Hz, 1H), 7.71-7.55 (m, 2H), 7.37-7.25 (m, 3H), 7.25-7.16 (m, 2H), 5.10 (s, 2H), 4.49 (dd, J=5.9, 4.4 Hz, 2H), 4.40 (d, J=1.4 Hz, 1H), 4.17 (t, J=6.1 Hz, 2H), 3.11 (d, J=1.1 Hz, 3H), 2.31-2.22 (m, 2H). LRMS (APCI+) m/z 430.1 $[M+H]^+$.

121A Ethyl 2-(2-fluorophenyl)-6-hydroxy-6,7-dihydro-5H-pyrazolo[5,1-b][1,3]oxazine-3-carboxylate

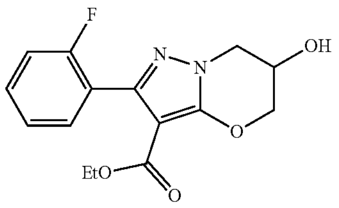 [SMILES: CCOC(=O)c1c(-c2ccccc2F)nn2c1OCC(O)C2]

Palladium hydroxide on carbon (20 wt. % loading, 50% water; 35 mg, 0.22 mmol) was added to a solution of intermediate 86A (650 mg, 1.64 mmol) in EtOH (15 mL) in a pressure tube, the vessel purged successively with $N_2$ (5×) and hydrogen (5×), then stirred under a hydrogen atmosphere at 40 psi and a temperature of 60° C. for 21 h. The reaction was filtered through a glass microfiber pad, washing with EtOH (3×10 mL) and $CH_2Cl_2$ (3×10 mL) and the solvent removed under reduced pressure to afford a white solid (390 mg, 78%). $^1H$ NMR (500 MHz, DMSO-$d_6$) δ 7.50-7.31 (m, 2H), 7.31-7.07 (m, 2H), 5.69 (d, J=2.8 Hz, 1H), 4.43-4.23 (m, 4H), 4.10-3.81 (m, 3H), 1.04 (t, J=7.0 Hz, 3H). LRMS (APCI+) m/z 307.4 $[M+H]^+$.

122A 2-(4-Cyano-2-fluorophenyl)-6,7-dihydro-5H-pyrazolo[5,1-b][1,3]oxazine-3-carboxylic Acid

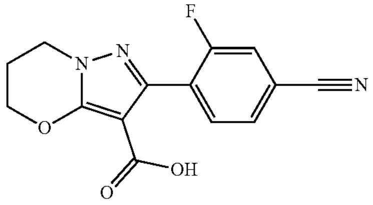 [SMILES: N#Cc1ccc(-c2nn3c(c2C(=O)O)OCCC3)c(F)c1]

Palladium hydroxide on carbon (20 wt. % loading, 50% water; 15 mg, 0.09 mmol) was added to a solution of intermediate 116D (117 mg, 0.31 mmol) in EtOH (6 mL) in a pressure tube, the vessel purged successively with $N_2$ (5×) and hydrogen (5×), then stirred under a hydrogen atmosphere at 40 psi at rt for 3 h. The reaction was filtered through a glass microfiber pad, washing with EtOH (3×5 mL) and $CH_2Cl_2$ (3×5 mL) and the solvent removed under reduced pressure to afford an off-white solid (80 mg, 90%). $^1H$ NMR (400 MHz, DMSO-$d_6$) δ 11.61 (s, 1H), 7.89 (dd, J=9.8, 1.5 Hz, 1H), 7.72 (dd, J=7.9, 1.6 Hz, 1H), 7.66-7.53 (m, 1H), 4.44 (dd, J=6.0, 4.3 Hz, 2H), 4.15 (t, J=6.1 Hz, 2H), 2.28-2.18 (m, 2H). LRMS (APCI+) m/z 288.2 $[M+H]^+$.

The following intermediate compounds were prepared in an analogous manner to intermediate 122A.

| Preparatory Example | Name | Structure | $^1H$ NMR δ (DMSO-$d_6$) | LRMS APCI+ m/z |
|---|---|---|---|---|
| 122B | 2-(4-Carbamoyl-2-fluorophenyl)-6,7-dihydro-5H-pyrazolo[5,1-b][1,3]oxazine-3-carboxylic acid | 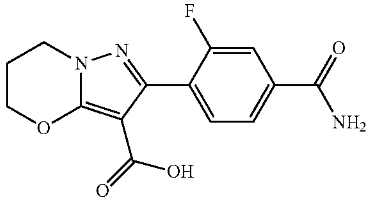 [SMILES: NC(=O)c1ccc(-c2nn3c(c2C(=O)O)OCCC3)c(F)c1] | (400 MHz) δ 11.85 (s, 1H), 8.09 (s, 1H), 7.80-7.61 (m, 2H), 7.54 (s, 1H), 7.46 (t, J = 7.6 Hz, 1H), 4.49-4.39 (m, 2H), 4.15 (t, J = 6.1 Hz, 2H), 2.31-2.18 (m, 2H). | 306.3 $[M + H]^+$ |
| 122C | 2-[4-[(Dimethylamino)methyl]-2-fluorophenyl]-6,7-dihydro-5H-pyrazolo[5,1-b][1,3]oxazine-3-carboxylic acid | 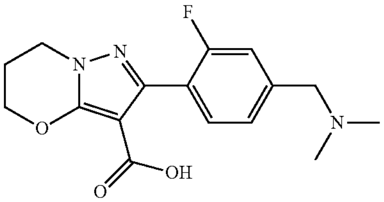 [SMILES: CN(C)Cc1ccc(-c2nn3c(c2C(=O)O)OCCC3)c(F)c1] | (400 MHz) δ 11.70 (s, 1H), 7.32 (t, J = 7.6 Hz, 1H), 7.18-7.03 (m, 2H), 4.42 (dd, J = 6.0, 4.3 Hz, 2H), 4.13 (t, J = 6.1 Hz, 2H), 3.50-3.38 (m, 3H), 2.29-2.18 (m, 2H), 2.17 (s, 6H). | 320.2 $[M + H]^+$ |
| 122D | 2-[2-Fluoro-4-(morpholin-4-ylmethyl)phenyl]-6,7-dihydro-5H-pyrazolo[5,1-b][1,3]oxazine-3-carboxylic acid | 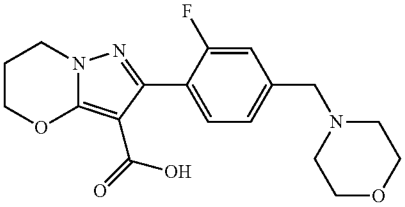 [SMILES: O=C(O)c1c(-c2ccc(CN3CCOCC3)cc2F)nn2c1OCCC2] | (400 MHz) δ 11.59 (s, 1H), 7.32 (t, J = 7.6 Hz, 1H), 7.23-7.07 (m, 2H), 4.42 (dd, J = 6.1, 4.3 Hz, 2H), 4.12 (t, J = 6.1 Hz, 2H), 3.59 (t, J = 4.6 Hz, 4H), 3.50 (s, 2H), 2.38 (t, J = 4.6 Hz, 4H), 2.27-2.18 (m, 2H). | 362.4 $[M + H]^+$ |
| 122E | 2-[4-(Diethylaminomethyl)-2-fluorophenyl]-6,7-dihydro-5H-pyrazolo[5,1-b][1,3]oxazine-3-carboxylic acid | 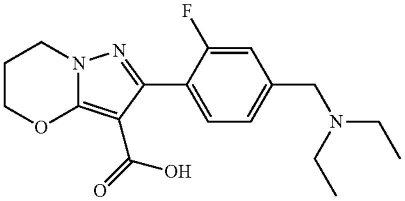 [SMILES: CCN(CC)Cc1ccc(-c2nn3c(c2C(=O)O)OCCC3)c(F)c1] | (400 MHz) δ 11.71 (s, 1H), 7.30 (t, J = 7.6 Hz, 1H), 7.17-7.07 (m, 2H), 4.42 (dd, J = 6.1, 4.3 Hz, 2H), 4.12 (t, J = 6.1 Hz, 2H), 3.56 (s, 2H), 2.29-2.18 (m, 2H), 0.99 (t, J = 7.1 Hz, 6H). | 348.4 $[M + H]^+$ |

123A Ethyl (5R)-2-[2-fluoro-6-[(1R,4R)-2-oxa-5-azabicyclo[2.2.1]heptan-5-yl]pyridin-3-yl]-5-methyl-6,7-dihydro-5H-pyrazolo[5,1-b][1,3]oxazine-3-carboxylate 123B Ethyl (5R)-2-[6-fluoro-2-[(1R,4R)-2-oxa-5-azabicyclo[2.2.1]heptan-5-yl]pyridin-3-yl]-5-methyl-5H,6H,7H-pyrazolo[3,2-b][1,3]oxazine-3-carboxylate

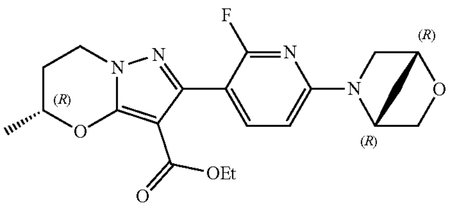

+

-continued

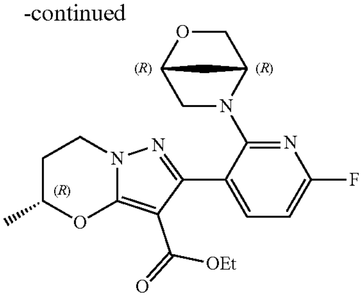

DIPEA (132 μL, 0.76 mmol) and (1R,4R)-2-oxa-5-azabicyclo[2.2.1]heptane hydrochloride (92 mg, 0.68 mmol) were added to a solution of intermediate 16B (200 mg, 0.62 mmol) in DMSO (3 mL) and heated by MWI at 130° C. for 7 h. Analogous workup to intermediate 90E followed by purification by flash chromatography [0-70% EtOAc (10% MeOH) in iso-hexane] afforded ~6:4 mixture of 123A:123B regioisomers by $^1H$ NMR which were inseparable by silica column chromatography and used without further purification (212 mg). LCMS (method A) m/z 403.3 $[M+H]^+$ at 1.12 (major) and 1.17 min (minor).

124A Ethyl (5R)-2-[2-fluoro-6-[(1S,4S)-2-oxa-5-azabicyclo[2.2.1]heptan-5-yl]pyridin-3-yl]-5-methyl-6,7-dihydro-5H-pyrazolo[5,1-b][1,3]oxazine-3-carboxylate 124B Ethyl (5R)-2-[6-fluoro-2-[(1S,4S)-2-oxa-5-azabicyclo[2.2.1]heptan-5-yl]pyridin-3-yl]-5-methyl-5H,6H,7H-pyrazolo[3,2-b][1,3]oxazine-3-carboxylate

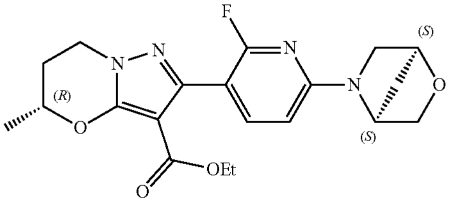

+

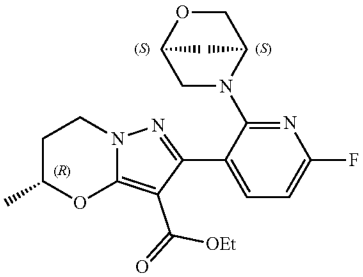

Prepared by an analogous procedure to that described for intermediate 123A to afford ~64:36 mixture of 124A:124B regioisomers by $^1$H NMR which were inseparable by silica column chromatography and used without further purification (200 mg). LCMS (method A) m/z 403.7 $[M+H]^+$ at 1.11 min (major) and 1.16 min (minor).

125A Ethyl (5R)-2-[2-fluoro-6-(2-oxa-6-azaspiro[3.3]heptan-6-yl)pyridin-3-yl]-5-methyl-6,7-dihydro-5H-pyrazolo[5,1-b][1,3]oxazine-3-carboxylate 125B Ethyl (5R)-2-[6-fluoro-2-(2-oxa-6-azaspiro[3.3]heptan-6-yl)pyridin-3-yl]-5-methyl-6,7-dihydro-5H-pyrazolo[5,1-b][1,3]oxazine-3-carboxylate

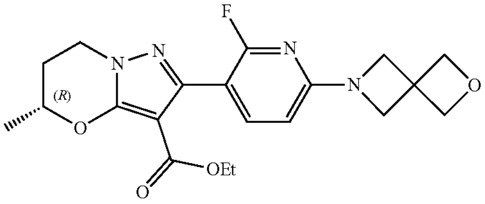

+

-continued

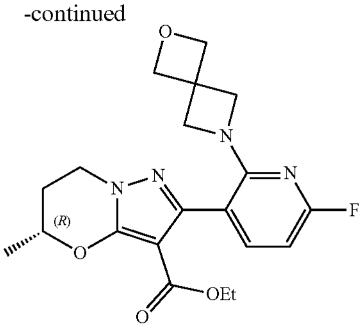

Prepared by an analogous procedure to that described for intermediate 123A. Purification by column chromatography (0-6% MeOH in DCM) afforded a ~62:38 mixture of 125A:125B regioisomers by $^1$H NMR which were inseparable by silica column chromatography and used without further purification (118 mg). LCMS (method A) m/z 403.8 $[M+H]^+$ at 1.07 min (major) and 1.10 min (minor).

EXAMPLES

1. 2-(2,4-Difluorophenyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide

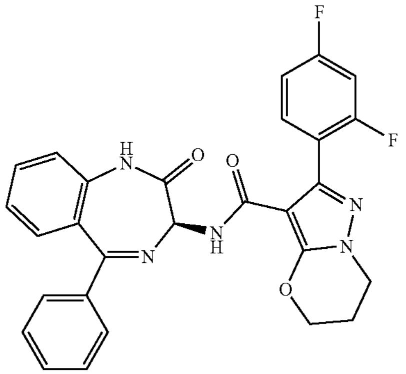 [SMILES: O=C(N[C@H]1N=C(c2ccccc2)c2ccccc2NC1=O)c1c(-c2ccc(F)cc2F)nn2c1OCCC2]

HATU (26.7 mg, 0.070 mmol), $NEt_3$ (0.02 mL, 0.128 mmol), and (3S)-3-amino-5-phenyl-1,3-dihydro-1,4-benzodiazepin-2-one (16.1 mg, 0.064 mmol) were added to a solution of intermediate 52A (18 mg, 0.064 mmol) in DMF (1 mL) and stirred at rt for 16 h. Water and brine (1:1; 20 mL) were added and the mixture was extracted with EtOAc (3×10 mL). The combined organic extracts were washed with water (10 mL) and brine (10 mL), dried ($Na_2SO_4$) and concentrated under reduced pressure. Purification by flash chromatography (100% EtOAc) afforded a white solid (27 mg, 82%). $^1$H NMR (400 MHz, DMSO-$d_6$) δ 10.99 (s, 1H), 7.87 (d, J=7.8 Hz, 1H), 7.63 (ddd, J=8.6, 6.9, 1.8 Hz, 1H), 7.55-7.47 (m, 1H), 7.47-7.33 (m, 5H), 7.33-7.10 (m, 4H), 7.10-6.98 (m, 1H), 5.29 (d, J=7.8 Hz, 1H), 4.66 (t, J=5.2 Hz, 2H), 4.21 (t, J=6.0 Hz, 2H), 2.38-2.31 (m, 2H). LRMS (APCI+) m/z 513.9 $[M+H]^+$.

The following compounds of the invention were prepared by the amide coupling procedure described for the compound of Example 1 with (3S)-3-amino-5-phenyl-1,3-dihydro-1,4-benzodiazepin-2-one or (3S)-3-amino-9-fluoro-5-phenyl-1,3-dihydro-1,4-benzodiazepin-2-one.

TABLE 20

Example compounds prepared by amide coupling procedure A

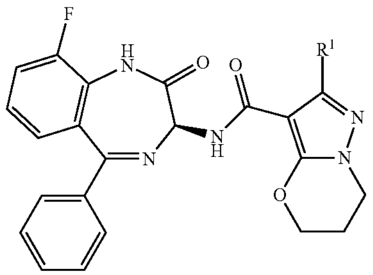

| Example | Name | $R^1$ | $^1H$ NMR δ (400 MHz, DMSO-$d_6$) | LRMS (APCI+) m/z |
|---|---|---|---|---|
| 2. | 2-(2,4-Difluorophenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carobxamide | 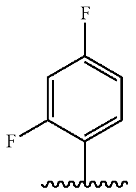 [SMILES: *c1ccc(F)cc1F] | 10.95 (s, 1H), 7.89 (d, J = 7.7 Hz, 1H), 7.64-7.35 (m, 7H), 7.30 (td, J = 8.1, 5.0 Hz, 1H), 7.26-7.02 (m, 3H), 5.37 (d, J = 7.7 Hz, 1H), 4.66 (t, J = 5.3 Hz, 2H), 4.21 (t, J = 6.0 Hz, 2H), 2.41-2.20 (m, 2H). | 531.9 $[M + H]^+$ |
| 3. | 2-[6-(Ethylamino)-2-fluoropyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | 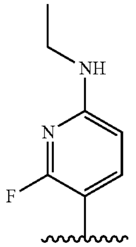 [SMILES: *c1ccc(NCC)nc1F] | 10.95 (s, 1H), 7.87 (d, J = 7.8 Hz, 1H), 7.62-7.37 (m, 7H), 7.30 (td, J = 8.1, 5.0 Hz, 1H), 7.13 (d, J = 8.1 Hz, 1H), 6.96 (t, J = 5.4 Hz, 1H), 6.27 (dd, J = 8.3, 1.9 Hz, 1H), 5.37 (d, J = 7.7 Hz, 1H), 4.68-4.52 (m, 2H), 4.17 (t, J = 6.1 Hz, 2H), 3.24-3.06 (m, 2H), 2.33 (dd, J = 3.9, 2.1 Hz, 2H), 1.10 (t, J = 7.2 Hz, 3H). | 557.9 $[M + H]^+$ |
| 4. | N-[(3S)-9-Fluoro-2-oxo-5-phenyl-1,3-dihydro-1,4-benzodiazepin-3-yl]-2-[2-fluoro-6-(propan-2-ylamino)pyridin-3-yl]-6,7-dihydro-5H-pyrazolo[5,1-b][1,3]oxazine-3-carboxamide | 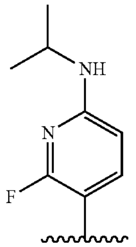 [SMILES: *c1ccc(NC(C)C)nc1F] | 10.95 (s, 1H), 7.87 (d, J = 7.8 Hz, 1H), 7.65-7.25 (m, 8H), 7.13 (d, J = 7.9 Hz, 1H), 6.84 (d, J = 7.6 Hz, 1H), 6.26 (dd, J = 8.2, 1.9 Hz, 1H), 5.38 (d, J = 7.7 Hz, 1H), 4.63 (t, J = 5.3 Hz, 2H), 4.17 (t, J = 6.1 Hz, 2H), 3.88 (dt, J = 13.6, 6.5 Hz, 1H), 2.35-2.30 (m, 2H), 1.11 (dd, J = 6.4, 0.9 Hz, 6H). | 571.8 $[M + H]^+$ |

5. N-[(3S)-9-fluoro-2-oxo-5-phenyl-2,3-dihydro-1H-1,4-benzodiazepin-3-yl]-2-(2-fluorophenyl)-5,5-dimethyl-5H,6H,7H-pyrazolo[3,2-b][1,3]oxazine-3 carboxamide

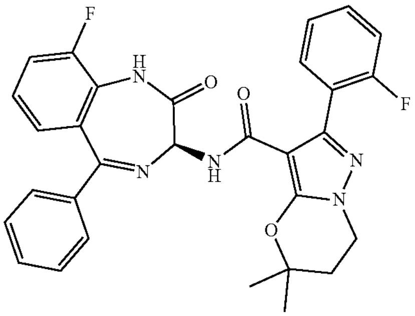 [SMILES: CC1(C)CCn2nc(-c3ccccc3F)c(C(=O)N[C@H]3N=C(c4ccccc4)c4cccc(F)c4NC3=O)c2O1]

DIPEA (63 μL, 0.362 mmol) was added to a solution of (3S)-3-amino-9-fluoro-5-phenyl-1,3-dihydro-1,4-benzodiazepin-2-one (51 mg, 0.190 mmol) and intermediate 34A (53 mg, 0.181 mmol) in DMF (1.2 mL), stirred for 3 min, then HATU (76 mg, 0.199 mmol) added and the reaction stirred at rt for 16 h. The reaction was quenched with water (10 mL) and the resultant precipitate collected by filtration, washing with water (3×5 mL). The precipitate was dissolved in EtOAc (20 mL), the solvent removed under reduced pressure and purified by flash chromatography (60-100% EtOAc in heptane) to afford a white solid (70 mg, 71%). $^1H$ NMR (700 MHz, DMSO-$d_6$) δ 10.93 (s, 1H), 8.19 (d, J=7.3 Hz, 1H), 7.58 (ddd, J=10.0, 8.3, 1.3 Hz, 1H), 7.55-7.50 (m, 1H), 7.49-7.43 (m, 4H), 7.42-7.34 (m, 2H), 7.30 (td, J=8.0, 4.9 Hz, 1H), 7.22-7.08 (m, 3H), 5.33 (d, J=7.3 Hz, 1H), 4.24 (dq, J=10.1, 6.6 Hz, 2H), 2.35-2.23 (m, 2H), 1.58 (d, J=11.6 Hz, 6H). LRMS (APCI+) m/z 542.4 $[M+H]^+$.

The following compounds of the invention were prepared by the amide coupling procedure described for the compound of Example 5. Example 14 was subject to additional purification by preparative HPLC (method 1) with a step gradient of 30-100% $CH_3CN$ in water (0.2% v/v $NH_3$).

TABLE 21

Example compounds prepared by amide coupling procedure B

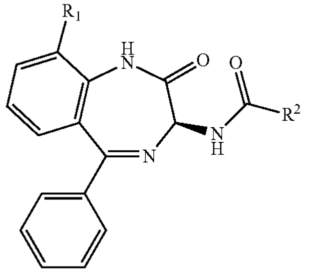

| Example | Name | $R^1$ | $R^2$ | $^1H$ NMR δ (DMSO-$d_6$) | LRMS (APCI+) m/z |
|---|---|---|---|---|---|
| 6. | N-[(3S)-9-Fluoro-2-oxo-5-phenyl-1,3-dihydro-1,4-benzodiazepin-3-yl]-2-(2-methylphenyl)-6,7-dihydro-5H-pyrazolo[5,1-b][1,3]oxazine-3-carboxamide | F | 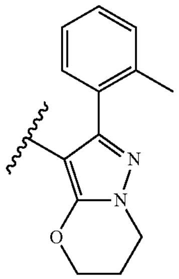 [SMILES: *c1c(-c2ccccc2C)nn2c1OCCC2] | (400 MHz) 10.93 (s, 1H), 8.73-8.52 (m, 1H), 7.84 (d, J = 7.7 Hz, 1H), 7.62-7.51 (m, 2H), 7.51-7.39 (m, 3H), 7.38-7.25 (m, 2H), 7.25-7.04 (m, 4H), 5.34 (d, J = 7.7 Hz, 1H), 4.65 (t, J = 5.2 Hz, 2H), 4.19 (t, J = 6.1 Hz, 2H), 3.88 (s, 1H), 2.13 (s, 2H). | 509.8 $[M + H]^+$ |
| 7. | N-[(3S)-9-fluoro-2-oxo-5-phenyl-1,3-dihydro-1,4-benzodiazepin-3-yl]-2-(2-fluorophenyl)spiro[6,7-dihydropyrazolo[5,1-b][1,3]oxazine-5,1'-cyclopropane]-3-carboxamide | F | 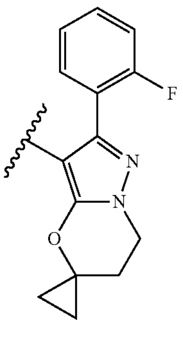 [SMILES: *c1c(-c2ccccc2F)nn2c1OC1(CC2)CC1] | (700 MHz) 10.94 (s, 1H), 7.92 (d, J = 7.3 Hz, 1H), 7.57 (ddd, J = 9.8, 8.2, 1.3 Hz, 1H), 7.52 (tt, J = 6.4, 2.1 Hz, 1H), 7.48-7.42 (m, 4H), 7.42-7.35 (m, 2H), 7.30 (td, J = 8.1, 5.0 Hz, 1H), 7.23-7.07 (m, 3H), 5.30 (d, J = 7.2 Hz, 1H), 4.39-4.27 (m, 2H), 2.50-2.35 (m, 2H), 1.34-1.12 (m, 2H), 1.11-0.94 (m, 2H). | 540.4 $[M + H]^+$ |

TABLE 21-continued

Example compounds prepared by amide coupling procedure B

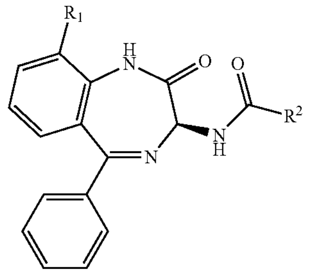

| Example | Name | $R^1$ | $R^2$ | $^1H$ NMR δ (DMSO-$d_6$) | LRMS (APCI+) m/z |
|---|---|---|---|---|---|
| 8. | N-[(3S)-9-fluoro-2-oxo-5-phenyl-2,3-dihydro-1H-1,4-benzodiazepin-3-yl]-2-(2-fluorophenyl)-5-(propan-2-yl)-5H,6H,7H-pyrazolo[3,2-b][1,3]oxazine-3-carboxamide | F | 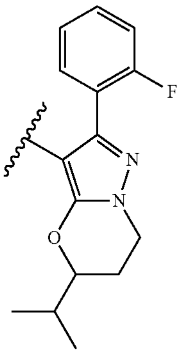 [SMILES: *c1c(-c2ccccc2F)nn2c1OC(C(C)C)CC2] | (600 MHz) 10.93 (s, 1H), 8.07 (d, J = 7.5 Hz, 0.5H), 8.03 (d, J = 7.5 Hz, 0.5H), 7.60-7.49 (m, 2H), 7.49-7.40 (m, 3H), 7.40-7.33 (m, 2H), 7.33-7.25 (m, 1H), 7.22-7.01 (m, 3H), 5.36 (d, J = 4.7 Hz, 0.5H), 5.35 (d, J = 4.7 Hz, 0.5H), 4.51-4.40 (m, 1H), 4.32-4.12 (m, 2H), 2.36-2.28 (m, 1H), 2.28-2.15 (m, 1H), 2.16-2.04 (m, 1H), 1.20-1.09 (m, 6H). | 556.2 $[M + H]^+$ |
| 9. | (6S)-N-[(3S)-9-fluoro-2-oxo-5-phenyl-1,3-dihydro-1,4-benzodiazepin-3-yl]-2-(2-fluorophenyl)-6-methyl-6,7-dihydro-5H-pyrazolo[5,1-b][1,3]oxazine-3-carboxamide | F | 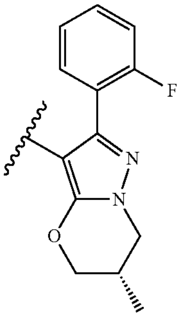 [SMILES: *c1c(-c2ccccc2F)nn2c1OC[C@@H](C)C2] | (700 MHz) 10.95 (s, 1H), 7.91 (d, J = 7.7 Hz, 1H), 7.58 (t, J = 9.2 Hz, 1H), 7.55-7.51 (m, 1H), 7.50-7.43 (m, 4H), 7.42-7.34 (m, 2H), 7.30 (td, J = 8.0, 4.9 Hz, 1H), 7.17 (td, J = 7.5, 1.1 Hz, 1H), 7.14 (t, J = 8.2 Hz, 2H), 5.38 (d, J = 7.7 Hz, 1H), 4.72-4.62 (m, 1H), 4.36-4.26 (m, 2H), 3.85 (dd, J = 12.1, 9.0 Hz, 1H), 2.60 (tt, J = 6.3, 2.6 Hz, 1H), 1.12 (d, J = 6.8 Hz, 3H). | 528.5 $[M + H]^+$ |
| 10. | (6R)-N-[(3S)-9-fluoro-2-oxo-5-phenyl-1,3-dihydro-1,4-benzodiazepin-3-yl]-2-(2-fluorophenyl)-6-methyl-6,7-dihydro-5H-pyrazolo[5,1-b][1,3]oxazine-3-carboxamide | F | 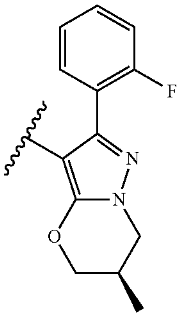 [SMILES: *c1c(-c2ccccc2F)nn2c1OC[C@H](C)C2] | (400 MHz) 10.95 (s, 1H), 7.90 (d, J = 7.7 Hz, 1H), 7.68-7.25 (m, 9H), 7.23-6.98 (m, 3H), 5.38 (d, J = 7.7 Hz, 1H), 4.67 (dd, J = 10.5, 3.5 Hz, 1H), 4.41-4.20 (m, 2H), 3.85 (dd, J = 12.2, 9.1 Hz, 1H), 1.11 (d, J = 6.8 Hz, 3H). | 528.5 $[M + H]^+$ |

TABLE 21-continued

Example compounds prepared by amide coupling procedure B

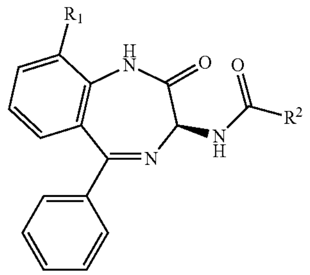

| Example | Name | $R^1$ | $R^2$ | $^1H$ NMR δ (DMSO-$d_6$) | LRMS (APCI+) m/z |
|---|---|---|---|---|---|
| 11. | 6-Ethyl-N-[(3S)-9-fluoro-2-oxo-5-phenyl-2,3-dihydro-1H-1,4-benzodiazepin-3-yl]-2-(2-fluorophenyl)-5H,6H,7H-pyrazolo[3,2-b][1,3]oxazine-3-carboxamide | F | 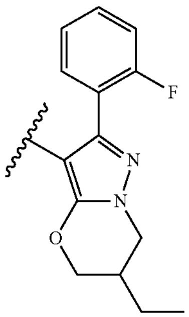 [SMILES: *c1c(-c2ccccc2F)nn2c1OCC(CC)C2] | (400 MHz) 10.96 (d, J = 5.0 Hz, 1H), 7.89 (dd, J = 7.7, 2.7 Hz, 1H), 7.64-7.23 (m, 9H), 7.23-7.04 (m, 3H), 5.37 (dd, J = 7.7, 2.7 Hz, 1H), 4.72 (d, J = 10.7 Hz, 1H), 4.44-4.17 (m, 2H), 3.89 (dd, J = 12.2, 9.1 Hz, 1H), 2.45-2.34 (m, 1H), 1.55-1.33 (m, 2H), 1.08-0.95 (m, 3H). | 542.0 $[M + H]^+$ |
| 12. | N-[(3S)-9-Fluoro-2-oxo-5-phenyl-2,3-dihydro-1H-1,4-benzodiazepin-3-yl]-2-(2-flurophenyl)-6-(propan-2-yl)-5H,6H,7H-pyrazolo[3,2-b][1,3]oxazine-3-carboxamide | F | 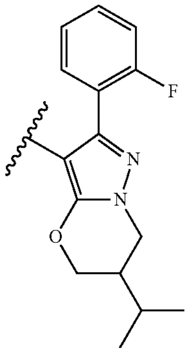 [SMILES: *c1c(-c2ccccc2F)nn2c1OCC(C(C)C)C2] | (400 MHz) 10.95 (d, J = 7.1 Hz, 1H), 7.88 (d, J = 7.8 Hz, 1H), 7.65-7.25 (m, 10H), 7.23-7.06 (m, 3H), 5.37 (dd, J = 7.7, 1.9 Hz, 1H), 4.84-4.73 (m, 1H), 4.46-4.36 (m, 1H), 4.28 (dd, J = 12.1, 5.3 Hz, 1H), 4.03-3.92 (m, 1H), 2.31-2.17 (m, 1H), 1.80-1.66 (m, 1H), 1.07-0.95 (m, 6H). | 556.0 $[M + H]^+$ |
| 13. | 6-Cyclopropyl-N-[(3S)-9-fluoro-2-oxo-5-phenyl-2,3-dihydro-1H-1,4-benzodiazepin-3-yl]-2-(2-fluorophenyl)-5H,6H,7H-pyrazolo[3,2-b][1,3]oxazine-3-carboxamide | F | 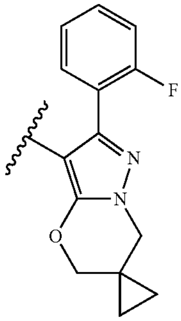 [SMILES: *c1c(-c2ccccc2F)nn2c1OCC1(CC1)C2] | (400 MHz) 10.95 (s, 1H), 7.92 (d, J = 7.8 Hz, 1H), 7.65-7.24 (m, 9H), 7.24-7.06 (m, 3H), 5.38 (d, J = 7.7 Hz, 1H), 4.61-4.39 (m, 2H), 4.17-4.02 (m, 2H), 1.32-1.21 (m, 1H), 0.99-0.76 (m, 4H). | 540.2 $[M + H]^+$ |

TABLE 21-continued

Example compounds prepared by amide coupling procedure B

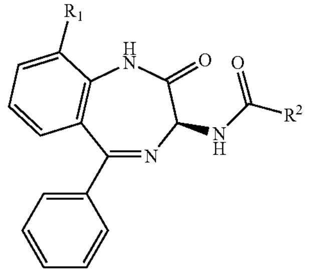

| Example | Name | $R^1$ | $R^2$ | $^1H$ NMR δ (DMSO-$d_6$) | LRMS (APCI+) m/z |
|---|---|---|---|---|---|
| 14. | N-[(3S)-9-fluoro-2-oxo-5-phenyl-2,3-dihydro-1H-1,4-benzodiazepin-3-yl]-2-(2-fluorophenyl)-6-propyl-5H,6H,7H-pyrazolo[3,2-b][1,3]oxazine-3-carboxamide | F | 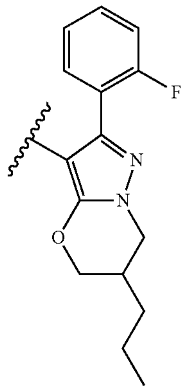 [SMILES: *c1c(-c2ccccc2F)nn2c1OCC(CCC)C2] | (600 MHz) δ 10.93 (s, 1H), 7.88 (dd, J = 7.8, 4.2 Hz, 1H), 7.60-7.49 (m, 2H), 7.49-7.42 (m, 4H), 7.42-7.33 (m, 2H), 7.33-7.26 (m, 1H), 7.19-7.04 (m, 3H), 5.37 (dd, J = 7.7, 3.4 Hz, 1H), 4.73-4.66 (m, 1H), 4.38-4.22 (m, 2H), 3.89 (ddd, J = 12.1, 9.1, 1.5 Hz, 1H), 1.52-1.39 (m, 3H), 0.99-0.88 (m, 3H). | 556.2 $[M + H]^+$ |

15. 2-[6-(Cyclopropylamino)pyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide

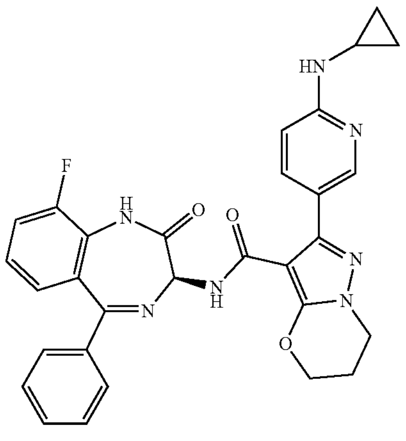 [SMILES: O=C(N[C@H]1N=C(c2ccccc2)c2cccc(F)c2NC1=O)c1c(-c2ccc(NC3CC3)nc2)nn2c1OCCC2]

A solution of intermediate 30C (47 mg, 0.14 mmol) and LiOH (1.0 M aq; 2.29 mL, 2.29 mmol) in THF:MeOH (1:1; 6 mL) was heated at 50° C. for 24 h. The reaction was cooled to rt, acidified to pH≈2 with 1 M aq. HCl and the solvent removed under reduced pressure. The residue was suspended in DMF (1 mL), $NEt_3$ (0.04 mL, 0.25 mmol) and HATU (48.1 mg, 0.13 mmol) were added and the reaction mixture stirred for 10 min at rt. (3S)-3-Amino-9-fluoro-5-phenyl-1,3-dihydro-1,4-benzodiazepin-2-one (34.1 mg, 0.13 mmol) was added and the reaction stirred at rt for 16 h. The reaction was diluted with water and brine (10 mL each) and extracted with EtOAc (3×10 ml). The combined organic extracts were washed with water (10 mL) and brine (3×10 mL), dried ($Na_2SO_4$), and the solvent removed under reduced pressure. Purification by flash chromatography [0-100% ($EtOH:CH_2Cl_2:NH_4OH$; 50:8:1) in $CH_2Cl_2$] afforded a white solid (27 mg, 34%). $^1H$ NMR (700 MHz, DMSO-$d_6$) δ 10.94 (s, 1H), 8.29 (s, 1H), 8.07 (d, J=7.5 Hz, 1H), 7.76 (s, 1H), 7.59 (ddd, J=10.3, 8.2, 1.3 Hz, 1H), 7.57-7.41 (m, 5H), 7.31 (td, J=8.1, 5.0 Hz, 1H), 7.15 (dd, J=8.0, 1.1 Hz, 1H), 6.88 (s, 1H), 6.56 (d, J=8.6 Hz, 1H), 5.42 (d, J=7.5 Hz, 1H), 4.66-4.59 (m, 2H), 4.17 (t, J=6.2 Hz, 2H), 2.37-2.24 (m, 2H), 1.32-1.18 (m, 1H), 0.78-0.57 (m, 2H), 0.42 (d, J=4.2 Hz, 2H). LRMS (APCI+) m/z 551.6 $[M+H]^+$ The following compounds were prepared by the amide coupling procedure described for the compound of Example 15. The procedure may be modified by substituting $NEt_3$ for DIPEA.

TABLE 22

Compounds prepared by amide coupling procedure C.

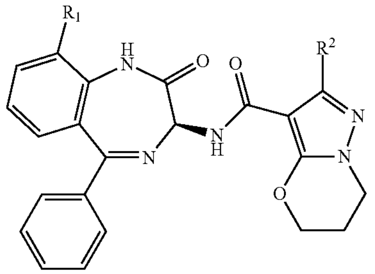

| Example | Name | $R^1$ | $R^2$ | $^1H$ NMR & (400 MHz, DMSO-$d_6$) | LRMS (APCI+) m/z |
|---|---|---|---|---|---|
| 16. | N-[(3S)-2-Oxo-5-phenyl-1,3-dihydro-1,4-benzodiazepin-3-yl]-2-pyridin-3-yl-6,7-dihydro-H-pyrazolo[5,1-b][1,3]oxazine-3-carboxamide | H | 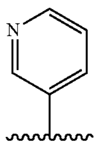 [SMILES: *c1cccnc1] | 11.01 (s, 1H), 8.78 (dd, J = 2.2, 0.9 Hz, 1H), 8.50 (dd, J = 4.8, 1.7 Hz, 1H), 8.11 (d, J = 7.6 Hz, 1H), 8.06-7.99 (m, 1H), 7.64 (ddd, J = 8.1, 7.1, 1.7 Hz, 1H), 7.55-7.41 (m, 5H), 7.41-7.18 (m, 4H), 5.34 (d, J = 7.6 Hz, 1H), 4.71-4.62 (m, 2H), 4.23 (t, J = 6.0 Hz, 2H), 2.42-2.23 (m, 2H). | 478.7 [M + H]$^+$ |
| 17. | N-[(3S)-9-Fluoro-2-oxo-5-phenyl-1,3-dihydro-1,4-benzodiazepin-3-yl]-2-pyridin-3-yl-6,7-dihydro-5H-pyrazolo[5,1-b][1,3]oxazine-3-carboxamide | F | 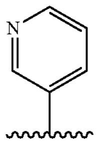 | 10.97 (s, 1H), 8.78 (dd, J = 2.2, 0.9 Hz, 1H), 8.50 (dd, J = 4.8, 1.7 Hz, 1H), 8.12 (d, J = 7.5 Hz, 1H), 8.02 (dt, J = 7.9, 2.0 Hz, 1H), 7.63-7.23 (m, 8H), 7.23-7.07 (m, 1H), 5.43 (d, J = 7.5 Hz, 1H), 4.71-4.59 (m, 2H), 4.22 (d, J = 6.1 Hz, 2H), 2.45-2.27 (m, 3H). | 496.9 [M + H]$^+$ |
| 18. | 2-(6-Cyclopropylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 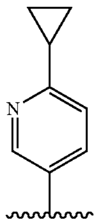 [SMILES: *c1ccc(C2CC2)nc1] | 10.96 (s, 1H), 8.59 (dd, J = 2.2, 0.8 Hz, 1H), 8.10 (d, J = 7.5 Hz, 1H), 7.85 (dd, J = 8.1, 2.3 Hz, 1H), 7.70-7.44 (m, 6H), 7.36-7.26 (m, 1H), 7.23 (dd, J = 8.2, 0.9 Hz, 1H), 7.19-7.11 (m, 1H), 5.41 (d, J = 7.5 Hz, 1H), 4.64 (t, J = 5.2 Hz, 2H), 4.20 (t, J = 6.0 Hz, 2H), 2.40-2.27 (m, 2H), 2.15-2.03 (m, 1H), 1.00-0.84 (m, 4H). | 536.7 [M + H]$^+$ |
| 19. | N-[(3S)-9-fluoro-2-oxo-5-phenyl-1,3-dihydro-1,4-benzodiazepin-3-yl]-2-[6-(propan-2-ylamino)pyridin-3-yl]-6,7-dihydro-5H-pyrazolo[5,1-b][1,3]oxazine-3-carboxamide | F | 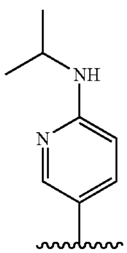 [SMILES: *c1ccc(NC(C)C)nc1] | 10.97 (s, 1H), 8.40 (s, 1H), 8.12 (d, J = 7.5 Hz, 1H), 7.95-7.76 (m, 1H), 7.65-7.41 (m, 6H), 7.37-7.24 (m, 1H), 7.24-7.08 (m, 1H), 6.74-6.48 (m, 1H), 5.42 (d, J = 7.4 Hz, 1H), 4.64 (dd, J = 6.0, 4.3 Hz, 2H), 4.18 (t, J = 6.0 Hz, 2H), 3.93 (d, J = 6.8 Hz, 1H), 2.40-2.25 (m, 2H), 1.17 (d, J = 6.3 Hz, 6H) | 554.1 [M + H]$^+$ |
| 20. | 2-[6-(Ethylamino)pyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 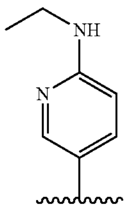 [SMILES: *c1ccc(NCC)nc1] | 10.97 (s, 1H), 8.41 (s, 1H), 8.13 (d, J = 7.4 Hz, 1H), 8.03-7.82 (m, 1H), 7.68-7.39 (m, 6H), 7.39-7.24 (m, 1H), 7.17 (d, J = 7.9 Hz, 1H), 6.81-6.56 (m, 1H), 5.42 (d, J = 7.4 Hz, 1H), 4.64 (t, J = 5.2 Hz, 2H), 4.19 (t, J = 6.1 Hz, 2H), 3.32-3.18 (m, 5H), 2.40-2.27 (m, 2H), 1.16 (t, J = 7.2 Hz, 3H) | 540.3 [M + H]$^+$ |

21. N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide

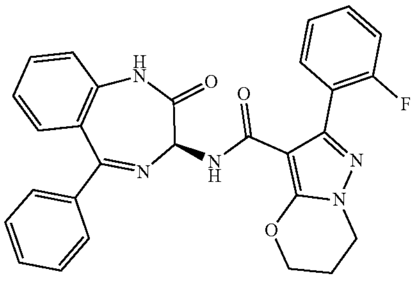 [SMILES: O=C(N[C@H]1N=C(c2ccccc2)c2ccccc2NC1=O)c1c(-c2ccccc2F)nn2c1OCCC2]

$NEt_3$ (59 μL, 0.42 mmol), HATU (78 mg, 0.21 mmol) and then (3S)-3-amino-9-fluoro-5-phenyl-1,3-dihydro-1,4-benzodiazepin-2-one (55 mg, 0.21 mmol) were added to a solution of intermediate 45B (54 mg, 0.21 mmol) in DMF (1.5 mL) and stirred at 40° C. for 1 h. The reaction was quenched with water, and the resultant precipitate filtered and washed with water (100 mL). The precipitate was dissolved with $CH_2Cl_2$, dried under vacuum, and purified by flash chromatography (0-5% MeOH in $CH_2Cl_2$) to afford a white solid (81 mg, 76%). LCMS (Method C) m/z 514.4 $[M+H]^+$ at 3.76 min. $^1$H NMR (500 MHz, DMSO-$d_6$) δ 10.93 (s, 1H), 7.89 (d, J=7.7 Hz, 1H), 7.60-7.50 (m, 2H), 7.49-7.42 (m, 4H), 7.42-7.32 (m, 2H), 7.32-7.26 (m, 1H), 7.17 (td, J=7.5, 1.1 Hz, 1H), 7.15-7.10 (m, 2H), 5.37 (d, J=7.7 Hz, 1H), 4.68-4.63 (m, 2H), 4.23-4.19 (m, 2H), 2.39-2.31 (m, 2H).

The following compounds were prepared by the amide coupling procedure described for the compound of Example 21. The procedure may be performed at 40° C. for >1 h, or at rt overnight.

TABLE 23

Compounds prepared by amide coupling procedure D

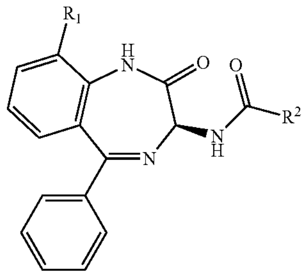

| Example | Name | $R^1$ | $R^2$ | $^1$H NMR δ (500 MHz, DMSO-$d_6$) | LCMS (method C) (ES+) m/z |
|---|---|---|---|---|---|
| 22. | N-[(3S)-2-oxo-5-phenyl-1,3-dihydro-1,4-benzodiazepin-3-yl]-2-phenyl-6,7-dihydro-5H-pyrazolo[5,1-b][1,3]oxazine-3-carboxamide | H | 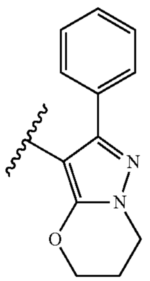 [SMILES: *c1c(-c2ccccc2)nn2c1OCCC2] | 10.98 (s, 1H), 8.09 (d, J = 7.6 Hz, 1H), 7.69-7.62 (m, 3H), 7.54-7.49 (m, 1H), 7.48-7.42 (m, 4H), 7.34-7.29 (m, 5H), 7.29-7.23 (m, 1H), 5.35 (d, J = 7.6 Hz, 1H), 4.64 (t, J = 5.2 Hz, 2H), 4.21 (t, J = 6.1 Hz, 2H), 2.39-2.29 (m, 2H). | 478.4 $[M + H]^+$ at 3.78 min |
| 23. | N-[(3S)-9-fluoro-2-oxo-5-phenyl-1,3-dihydro-1,4-benzodiazepin-3-yl]-2-phenyl-6,7-dihydro-5H-pyrazolo[5,1-b][1,3]oxazine-3-carboxamide | F | 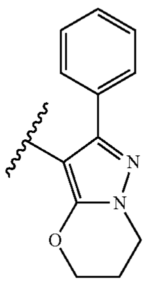 [SMILES: *c1c(-c2ccccc2)nn2c1OCCC2] | 10.94 (s, 1H), 8.11 (d, J = 7.5 Hz, 1H), 7.69-7.64 (m, 2H), 7.62-7.56 (m, 1H), 7.56-7.43 (m, 5H), 7.36-7.28 (m, 4H), 7.16 (d, J = 7.9 Hz, 1H), 5.43 (d, J = 7.5 Hz, 1H), 4.66-4.61 (m, 2H), 4.21 (t, J = 6.1 Hz, 2H), 2.38-2.30 (m, 2H). | 496.4 $[M + H]^+$ at 3.28 min |

TABLE 23-continued

Compounds prepared by amide coupling procedure D

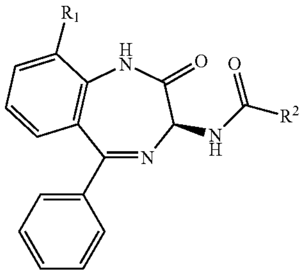

| Example | Name | $R^1$ | $R^2$ | $^1$H NMR δ (500 MHz, DMSO-$d_6$) | LCMS (method C) (ES+) m/z |
|---|---|---|---|---|---|
| 25. | (5R)-N-[(3S)-9-fluoro-2-oxo-5-phenyl-1,3-dihydro-1,4-benzodiazepin-3-yl]-2-(2-fluorophenyl)-5-methyl-6,7-dihydro-5H-pyrazolo[5,1-b][1,3]oxazine-3-carboxamide | F | 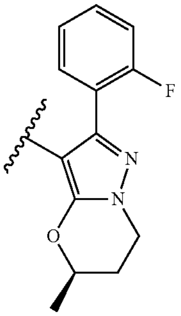 [SMILES: *c1c(-c2ccccc2F)nn2c1O[C@H](C)CC2] | 10.92 (s, 1H), 8.08 (d, J = 7.5 Hz, 1H), 7.60-7.54 (m, 1H), 7.54-7.49 (m, 1H), 7.49-7.42 (m, 4H), 7.41-7.33 (m, 2H), 7.30 (td, J = 8.1, 5.0 Hz, 1H), 7.20-7.10 (m, 3H), 5.34 (d, J = 7.5 Hz, 1H), 4.88-4.76 (m, 1H), 4.26-4.15 (m, 2H), 2.41-2.33 (m, 1H), 2.23-2.11 (m, 1H), 1.56 (d, J = 6.3 Hz, 3H). | 528.4 $[M + H]^+$ at 3,98 min |
| 28. | N-[(3S)-2-oxo-5-phenyl-1,3-dihydro-1,4-benzodiazepin-3-yl]-2-phenylspiro[5,7-dihydropyrazolo[5,1-b][1,3]oxazine-6,3'-oxetane]-3-carboxamide | H | 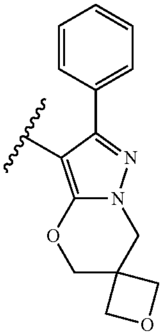 [SMILES: *c1c(-c2ccccc2)nn2c1OCC1(COC1)C2] | 10.96 (s, 1H), 8.12 (d, J = 7.5 Hz, 1H), 7.69-7.60 (m, 3H), 7.55-7.48 (m, 1H), 7.50-7.41 (m, 4H), 7.36-7.29 (m, 5H), 7.29-7.22 (m, 1H), 5.33 (d, J = 7.5 Hz, 1H), 4.87-4.81 (m, 2H), 4.63-4.55 (m, 4H), 4.55-4.46 (m, 2H). | 520.4 $[M + H]^+$ at 3.65 min |
| 29. | 2-(2-Fluorophenyl)-N-[(3S)-2-oxo-5-phenyl-1,3-dihydro-1,4-benzodiazepin-3-yl]spiro[5,7-dihydropyrazolo[5,1-b][1,3]oxazine-6,3'-oxetane]-2-carboxamide | H | 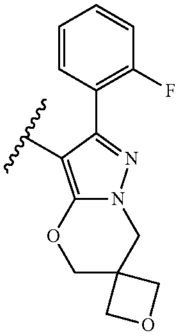 [SMILES: *c1c(-c2ccccc2F)nn2c1OCC1(COC1)C2] | 10.97 (s, 1H), 7.87 (d, J = 7.7 Hz, 1H), 7.66-7.59 (m, 1H), 7.55-7.47 (m, 1H), 7.46-7.42 (m, 4H), 7.42-7.33 (m, 2H), 7.33-7.26 (m, 2H), 7.27-7.21 (m, 1H), 7.20-7.09 (m, 2H), 5.28 (d, J = 7.7 Hz, 1H), 4.88 (q, J = 10.8 Hz, 2H), 4.64-4.57 (m, 4H), 4.57-4.48 (m, 2H). | 538.4 $[M + H]^+$ at 3.64 min |

TABLE 23-continued

Compounds prepared by amide coupling procedure D

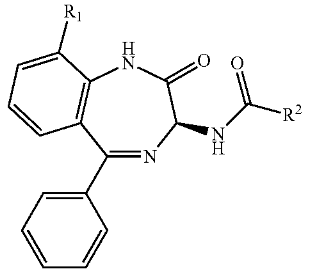

| Example | Name | $R^1$ | $R^2$ | $^1H$ NMR δ (500 MHz, DMSO-$d_6$) | LCMS (method C) (ES+) m/z |
|---|---|---|---|---|---|
| 30. | (5R)-N-[(3S)-9-fluoro-2-oxo-5-phenyl-1,3-dihydro-1,4-benzodiazepin-3-yl]-2-[2-fluoro-6-(propan-2-ylamino)pyridin-3-yl]-5-methyl-6,7-dihydro-5H-pyrazolo[5,1-b][1,3]oxazine-3-carboxamide | F | 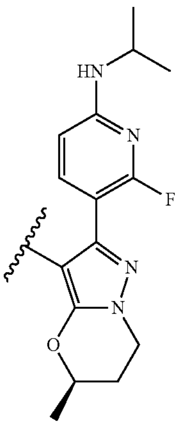 [SMILES: *c1c(-c2ccc(NC(C)C)nc2F)nn2c1O[C@H](C)CC2] | 10.91 (s, 1H), 8.07 (d, J = 7.5 Hz, 1H), 7.61-7.55 (m, 1H), 7.55-7.49 (m, 1H), 7.52-7.44 (m, 3H), 7.46-7.41 (m, 1H), 7.43-7.36 (m, 1H), 7.34-7.27 (m, 1H), 7.13 (d, J = 7.9 Hz, 1H), 6.82 (d, J = 7.6 Hz, 1H), 6.29-6.24 (m, 1H), 5.37-5.32 (m, 1H), 4.80-4.76 (m, 1H), 4.21-4.11 (m, 2H), 3.92-3.82 (m, 1H), 2.38-2.31 (m, 1H), 2.19-2.09 (m, 1H), 1.54 (d, J = 6.2 Hz, 3H), 1.12 (d, J = 6.4 Hz, 6H). | 586.4 $[M + H]^+$ at 4.23 min |
| 31. | (5S)-N-[(3S)-9-fluoro-2-oxo-5-phenyl-1,3-dihydro-1,4-benzodiazepin-3-yl]-2-[2-fluoro-6-(propan-2-ylamino)pyridin-3-yl]-5-methyl-6,7-dihydro-5H-pyrazolo[5,1-b][1,3]oxazine-3-carboxamide | F | 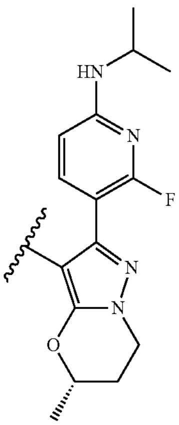 [SMILES: *c1c(-c2ccc(NC(C)C)nc2F)nn2c1O[C@@H](C)CC2] | 10.93 (s, 1H), 8.10 (d, J = 7.5 Hz, 1H), 7.61-7.54 (m, 1H), 7.56-7.49 (m, 1H), 7.49-7.36 (m, 5H), 7.34-7.26 (m, 1H), 7.13 (d, J = 7.9 Hz, 1H), 6.82 (d, J = 7.6 Hz, 1H), 6.29-6.24 (m, 1H), 5.34 (d, J = 7.4 Hz, 1H), 4.81-4.74 (m, 1H), 4.23-4.11 (m, 2H), 3.92-3.82 (m, 1H), 2.38-2.31 (m, 1H), 2.19-2.07 (m, 1H), 1.55 (d, J = 6.2 Hz, 3H), 1.12 (d, J = 6.4 Hz, 6H). | 586.3 $[M + H]^+$ at 4.31 min |
| 32. | 2-(2,4-Difluorophenyl)-N-[(3S)-9-fluoro-2-oxo-5-phenyl-2,3-dihydro-1H-1,4-benzodiazepin-3-yl]-4,4-dioxo-5H,6H,7H-4λ$^6$-pyrazolo[3,2-b][1,3]thiazine-3-carboxamide | F | 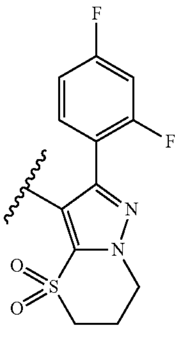 [SMILES: *c1c(-c2ccc(F)cc2F)nn2c1S(=O)(=O)CCC2] | 10.90 (s, 1H), 8.81 (d, J = 7.5 Hz, 1H), 7.65-7.57 (m, 2H), 7.57-7.52 (m, 1H), 7.52-7.44 (m, 4H), 7.37-7.28 (m, 2H), 7.18 (td, J = 8.4, 2.1 Hz, 2H), 5.37 (d, J = 7.5 Hz, 1H), 4.49 (t, J = 5.9 Hz, 2H), 3.97-3.85 (m, 2H), 2.63 (s, 2H). | 580.3 $[M + H]^+$ at 3.98 min |

TABLE 23-continued

Compounds prepared by amide coupling procedure D

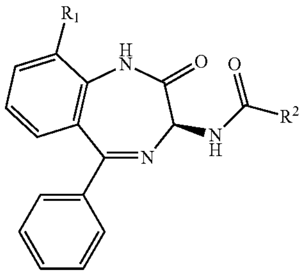

| Example | Name | $R^1$ | $R^2$ | $^1H$ NMR δ (500 MHz, DMSO-$d_6$) | LCMS (method C) (ES+) m/z |
|---|---|---|---|---|---|
| 33. | 2-(2-Fluorophenyl)-N-[(3S)-9-fluoro-2-oxo-5-phenyl-2,3-dihydro-1H-1,4-benzodiazepin-3-yl]-4,4-dioxo-5H,6H,7H-4λ$^6$-pyrazolo[3,2-b][1,3]thiazine-3-carboxamide | F | 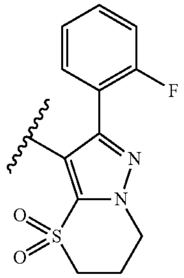 [SMILES: *c1c(-c2ccccc2F)nn2c1S(=O)(=O)CCC2] | 10.90 (s, 1H), 8.73 (d, J = 7.5 Hz, 1H), 7.62-7.46 (m, 8H), 7.29 (dtd, J = 10.6, 8.3, 7.1 Hz, 3H), 7.17 (d, J = 7.9 Hz, 1H), 5.36 (d, J = 7.4 Hz, 1H), 4.49 (t, J = 5.9 Hz, 2H), 3.92 (d, J = 10.9 Hz, 2H), 2.64 (s, 2H). | 562.3 $[M + H]^+$ at 3.75 min |
| 34. | 2-(2,4-Difluorophenyl)-N-[(3S)-9-fluoro-2-oxo-5-phenyl-2,3-dihydro-1H-1,4-benzodiazepin-3-yl]-5H,6H,7H-pyrazolo[3,2-b][1,3]thiazine-3-carboxamide | F | 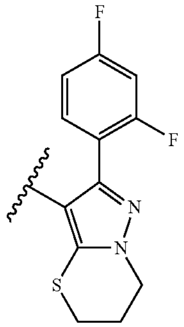 [SMILES: *c1c(-c2ccc(F)cc2F)nn2c1SCCC2] | 10.90 (s, 1H), 7.66-7.50 (m, 3H), 7.45 (d, J = 4.3 Hz, 4H), 7.40 (td, J = 0.9.8, 2.6 Hz, 1H), 7.35-7.27 (m, 2H), 7.24 (td, J = 8.5, 2.5 Hz, 1H), 7.15 (d, J = 7.9 Hz, 1H), 5.27 (d, J = 7.2 Hz, 1H), 4.27 (t, J = 5.9 Hz, 2H), 3.16 (dt, J = 7.7, 5.2 Hz, 2H), 2.37-2.31 (m, 2H). | 548.3 $[M + H]^+$ at 4.22 min |
| 35. | N-[(3S)-9-Fluoro-2-oxo-5-phenyl-2,3-dihydro-1H-1,4-benzodiazepin-3-yl]-2-(2-fluorophenyl)-5H,6H,7H-pyrazolo[3,2-b][1,3]thiazine-3-carboxamide | F | 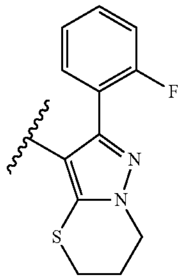 [SMILES: *c1c(-c2ccccc2F)nn2c1SCCC2] | 10.85 (s, 1H), 7.57 (td, J = 8.1, 7.6, 4.1 Hz, 3H), 7.53 (td, J = 5.9, 2.6 Hz, 1H), 7.50-7.42 (m, 4H), 7.39-7.31 (m, 2H), 7.31 (td, J = 8.0, 5.0 Hz, 1H), 7.23 (d, J = 7.3 Hz, 1H), 7.15 (d, J = 7.9 Hz, 1H), 5.28 (d, J = 7.3 Hz, 1H), 4.27 (t, J = 5.9 Hz, 2H), 3.16 (dt, J = 11.1, 5.5 Hz, 2H), 2.38-2.30 (m, 2H). | 530.3 $[M + H]^+$ at 4.02 min |
| 36. | 3-(2-Fluorophenyl)-N-[(3S)-2-oxo-5-phenyl-1,3-dihydro-1,4-benzodiazepin-3-yl]-6,7-dihydro-5H-pyrazolo[5,1-b][1,3]oxazine-2-carboxamide | H | 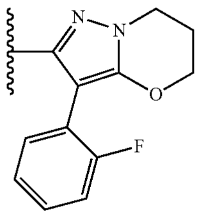 [SMILES: *c1nn2c(c1-c1ccccc1F)OCCC2] | 11.03 (s, 1H), 8.39 (d, J = 8.0 Hz, 1H), 7.67-7.60 (m, 1H), 7.54-7.48 (m, 1H), 7.48-7.41 (m, 4H), 7.35-7.24 (m, 5H), 7.16-7.08 (m, 2H), 5.27 (d, J = 8.0 Hz, 1H), 4.40-4.32 (m, 2H), 4.34-4.26 (m, 2H), 2.33-2.25 (m, 2H). | 496.4 $[M + H]^+$ at 4.27 min. |

TABLE 23-continued

Compounds prepared by amide coupling procedure D

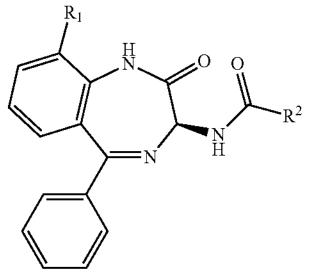

| Example | Name | $R^1$ | $R^2$ | $^1$H NMR δ (500 MHz, DMSO-$d_6$) | LCMS (method C) (ES+) m/z |
|---|---|---|---|---|---|
| 37. | 7-(2-Fluorophenyl)-N-[(3S)-2-oxo-5-phenyl-1,3-dihydro-1,4-benzodiazepin-3-yl]-2,3-dihydropyrazolo[5,1-b][1,3]oxazole-6-carboxamide | H | 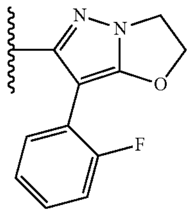 [SMILES: *c1nn2c(c1-c1ccccc1F)OCC2] | 11.04 (s, 1H), 8.47 (d, J = 7.9 Hz, 1H), 7.68-7.61 (m, 1H), 7.55-7.49 (m, 1H), 7.49-7.41 (m, 4H), 7.41-7.34 (m, 1H), 7.34-7.28 (m, 3H), 7.28-7.24 (m, 1H), 7.18-7.10 (m, 2H), 5.27 (d, J = 7.8 Hz, 1H), 5.25-5.15 (m, 2H), 4.50 (t, J = 8.1 Hz, 2H). | 482.4 [M + H]+ at 4.17 min |
| 38. | 3-[6-(Cyclopropylamino)-2-fluoropyridin-3-yl]-N-[(3S)-2-oxo-5-phenyl-1,3-dihydro-1,4-benzodiazepin-3-yl]-6,7-dihydro-5H-pyrazolo[5,1-b][1,3]oxazine-2-carboxamide | H | 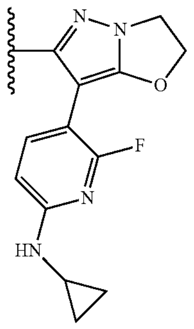 [SMILES: *c1nn2c(c1-c1ccc(NC3CC3)nc1F)OCC2] | 11.04 (s, 1H), 8.37 (d, J = 8.0 Hz, 1H), 7.68-7.61 (m, 1H), 7.55-7.48 (m, 1H), 7.48-7.40 (m, 5H), 7.34-7.29 (m, 2H), 7.26 (m, J = 7.4, 1.2 Hz, 1H), 7.09-7.05 (m, 1H), 6.44-6.38 (m, 1H), 5.27 (d, J = 8.0 Hz, 1H), 4.39-4.31 (m, 2H), 4.29-4.23 (m, 2H), 2.49-2.41 (m, 1H), 2.31-2.23 (m, 2H), 0.72-0.63 (m, 2H), 0.43-0.37 (m, 2H). | 552.4 $[M + H]^+$ at 4.20 min. |
| 39. | 2-[6-(Cyclopropylamino)-2-fluoropyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 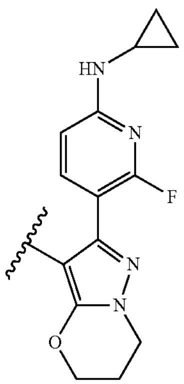 [SMILES: *c1c(-c2ccc(NC3CC3)nc2F)nn2c1OCCC2] | 10.93 (s, 1H), 7.88 (d, J = 7.7 Hz, 1H), 7.61-7.54 (m, 1H), 7.56-7.41 (m, 6H), 7.34-7.26 (m, 1H), 7.18 (d, J = 2.6 Hz, 1H), 7.13 (d, J = 7.9 Hz, 1H), 6.42 (dd, J = 8.3, 1.8 Hz, 1H), 5.37 (d, J = 7.7 Hz, 1H), 4.66-4.60 (m, 2H), 4.23-4.11 (m, 2H), 2.38-2.28 (m, 2H), 0.75-0.64 (m, 2H), 0.47-0.37 (m, 2H). | 570.4 $[M + H]^+$ at 3.77 min |

TABLE 23-continued

Compounds prepared by amide coupling procedure D

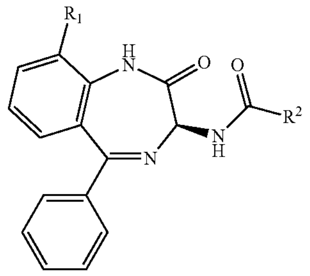

| Example | Name | $R^1$ | $R^2$ | $^1$H NMR δ (500 MHz, DMSO-$d_6$) | LCMS (method C) (ES+) m/z |
|---|---|---|---|---|---|
| 40. | 2-(2-Fluorophenyl)-6,6-dimethyl-N-[(3S)-2-oxo-5-phenyl-1,3-dihydro-1,4-benzodiazepin-3-yl]-5,7-dihydropyrazolo[5,1-b][1,3]oxazine-3-carboxamide | H | 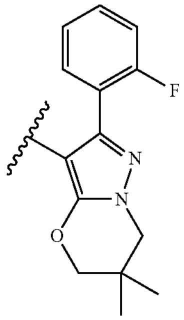 [SMILES: *c1c(-c2ccccc2F)nn2c1OCC(C)(C)C2] | 10.98 (s, 1H), 7.91 (d, J = 7.7 Hz, 1H), 7.63 (ddd, J = 8.5, 7.0, 1.7 Hz, 1H), 7.55-7.47 (m, 1H), 7.44 (d, J = 4.4 Hz, 4H), 7.38 (ddt, J = 10.5, 5.1, 3.5 Hz, 2H), 7.33-7.26 (m, 2H), 7.28-7.21 (m, 1H), 7.21-7.10 (m, 2H), 5.29 (d, J = 7.7 Hz, 1H), 4.35 (s, 2H), 3.98 (s, 2H), 1.16 (d, J = 2.7 Hz, 6H) | 524.4 $[M + H]^+$ at 4.16 min |
| 41. | N-[(3S)-9-fluoro-2-oxo-5-phenyl-1,3-dihydro-1,4-benzodiazepin-3-yl]-2-(2-fluorophenyl)-6,6-dimethyl-5,7-dihydropyrazolo[5,1-b][1,3]oxazine-3-carboxamide | F | 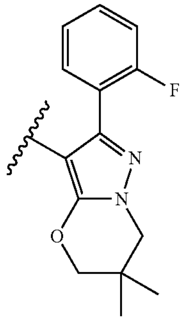 [SMILES: *c1c(-c2ccccc2F)nn2c1OCC(C)(C)C2] | 10.94 (s, 1H), 7.93 (d, J = 7.6 Hz, 1H), 7.61-7.53 (m, 1H), 7.56-7.48 (m, 1H), 7.51-7.46 (m, 2H), 7.45 (dd, J = 8.3, 6.5 Hz, 2H), 7.43-7.34 (m, 2H), 7.32-7.26 (m, 1H), 7.21-7.10 (m, 3H), 5.37 (d, J = 7.6 Hz, 1H), 4.35 (s, 2H), 3.98 (s, 2H), 1.16 (d, J = 3.3 Hz, 6H). | 542.4 $[M + H]^+$ at 4.22 min |

TABLE 23-continued

Compounds prepared by amide coupling procedure D

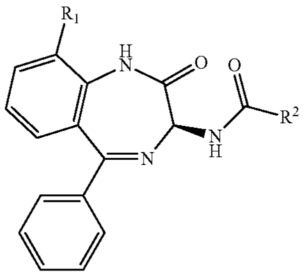

| Example | Name | $R^1$ | $R^2$ | $^1H$ NMR δ (500 MHz, DMSO-$d_6$) | LCMS (method C) (ES+) m/z |
| --- | --- | --- | --- | --- | --- |
| 46. | (5R)-2-(5-Chloropyridin-3-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 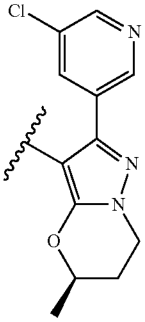 [SMILES: *c1c(-c2cncc(Cl)c2)nn2c1O[C@H](C)CC2] | 10.99 (s, 1H), 8.81 (d, J = 1.8 Hz, 1H), 8.59 (d, J = 2.4 Hz, 1H), 8.35 (d, J = 7.3 Hz, 1H), 8.23 (t, J = 2.1 Hz, 1H), 7.65 (ddd, J = 8.6, 7.1, 1.6 Hz, 1H), 7.52 (ddd, J = 10.0, 5.6, 2.4 Hz, 1H), 7.50-7.40 (m, 4H), 7.33 (dd, J = 7.8, 1.7 Hz, 2H), 7.27 (td, J = 7.5, 1.2 Hz, 1H), 5.33 (d, J = 7.3 Hz, 1H), 4.88-4.80 (m, 1H), 4.31-4.18 (m, 2H), 2.43-2.36 (m, 1H), 2.22-2.11 (m, 1H), 1.57 (d, J = 6.2 Hz, 3H). | 527.4 $[M + H]^+$ at 3.96 min |
| 47. | (5R)-2-(5-Chloropyridin-3-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 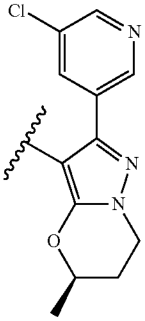 [SMILES: *c1c(-c2cncc(Cl)c2)nn2c1O[C@H](C)CC2] | 10.96 (s, 1H), 8.81 (d, J = 1.8 Hz, 1H), 8.59 (d, J = 2.4 Hz, 1H), 8.39 (d, J = 7.2 Hz, 1H), 8.23 (t, J = 2.1 Hz, 1H), 7.59 (t, J = 9.1 Hz, 1H), 7.56-7.42 (m, 5H), 7.36-7.28 (m, 1H), 7.17 (d, J = 7.9 Hz, 1H), 5.42 (d, J = 7.2 Hz, 1H), 4.89-4.80 (m, 1H), 4.32-4.18 (m, 2H), 2.43-2.36 (m, 1H), 2.22-2.11 (m, 1H), 1.58 (d, J = 6.3 Hz, 3H). | 545.4 $[M + H]^+$ at 4.03 min |

24. (5R)-2-(2-Fluorophenyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide

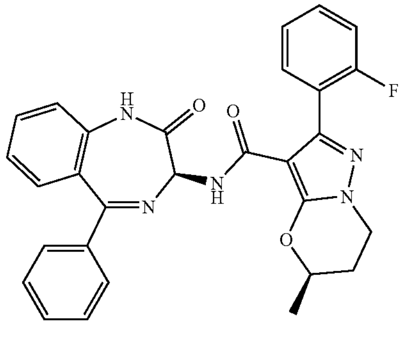 [SMILES: C[C@@H]1CCn2nc(-c3ccccc3F)c(C(=O)N[C@H]3N=C(c4ccccc4)c4ccccc4NC3=O)c2O1]

$NEt_3$ (47 μL, 0.34 mmol), HATU (63 mg, 0.17 mmol) and then (3S)-3-amino-5-phenyl-1,3-dihydro-1,4-benzodiazepin-2-one (40 mg, 0.16 mmol) were added to a solution of crude intermediate 43A (44 mg, 0.16 mmol) in DMF (1.5 mL) and stirred at 40° C. for 1 h. The reaction was diluted with EtOAc (20 mL) and washed with brine (5×20 mL), dried $Na_2SO_4$, concentrated under reduced pressure, and purified by flash chromatography (0-5% MeOH in $CH_2Cl_2$) to afford a white solid (61 mg, 74%). LCMS (Method C) m/z 510.4 $[M+H]^+$ at 3.91 min. $^1H$ NMR (500 MHz, DMSO-$d_6$) δ 10.94 (s, 1H), 8.05 (d, J=7.6 Hz, 1H), 7.65-7.60 (m, 1H), 7.53-7.47 (m, 1H), 7.45-7.42 (m, 4H), 7.41-7.33 (m, 2H), 7.32-7.27 (m, 2H), 7.27-7.22 (m, 1H), 7.19-7.10 (m, 2H), 5.26 (d, J=7.6 Hz, 1H), 4.86-4.77 (m, 1H), 4.26-4.16 (m, 2H), 2.41-2.32 (m, 1H), 2.21-2.10 (m, 1H), 1.56 (d, J=6.3 Hz, 3H).

The following compounds were prepared by the amide coupling procedure described for the compound of Example 24.

TABLE 24

Compounds prepared by amide coupling procedure E.

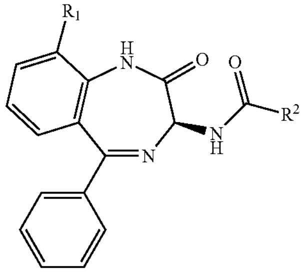

| Example | Name | $R^1$ | $R^2$ | $^1H$ NMR δ (500 MHz, DMSO-$d_6$) | LCMS (method C) (ES+) m/z |
|---|---|---|---|---|---|
| 26. | (5S)-2-(2-Fluorophenyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 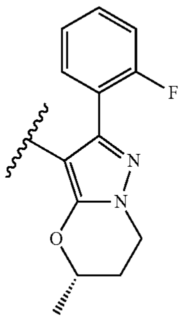 [SMILES: *c1c(-c2ccccc2F)nn2c1O[C@@H](C)CC2] | 10.96 (s, 1H), 8.09 (d, J = 7.6 Hz, 1H), 7.66-7.59 (m, 1H), 7.52-7.48 (m, 1H), 7.46-7.40 (m, 4H), 7.40-7.33 (m, 2H), 7.32-7.27 (m, 2H), 7.27-7.22 (m, 1H), 7.20-7.10 (m, 2H), 5.27 (d, J = 7.6 Hz, 1H), 4.88-4.75 (m, 1H), 4.28-4.16 (m, 2H), 2.42-2.34 (m, 1H), 2.23-2.12 (m, 1H), 1.57 (d, J = 6.3 Hz, 3H). | 510.3 $[M + H]^+$ at 4.05 min |
| 27. | (5S)-N-[(3S)-9-fluoro-2-oxo-5-phenyl-1,3-dihydro-1,4-benzodiazepin-3-yl]-2-(2-fluorophenyl)-5-methyl-6,7-dihydro-5H-pyrazolo[5,1-b][1,3]oxazine-3-carboxamide | F | 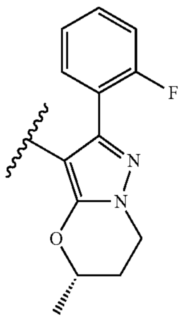 [SMILES: *c1c(-c2ccccc2F)nn2c1O[C@@H](C)CC2] | 10.93 (s, 1H), 8.11 (d, J = 7.5 Hz, 1H), 7.60-7.49 (m, 2H), 7.49-7.41 (m, 4H), 7.42-7.32 (m, 2H), 7.33-7.25 (m, 1H), 7.20-7.08 (m, 3H), 5.33 (d, J = 7.5 Hz, 1H), 4.85-4.77 (m, 1H), 4.27-4.16 (m, 2H), 2.41-2.32 (m, 1H), 2.23-2.10 (m, 1H), 1.56 (d, J = 6.3 Hz, 3H). | 528.4 $[M + H]^+$ at 4.05 min |

42. 2-(2-Fluoro-5-methylpyridin-3-yl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide

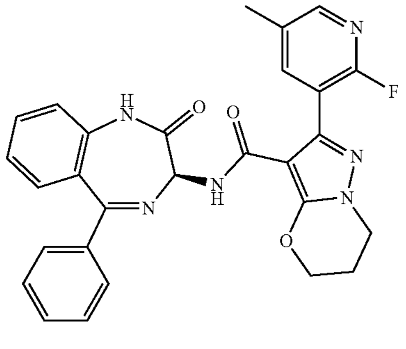 [SMILES: Cc1cnc(F)c(-c2nn3c(c2C(=O)N[C@H]2N=C(c4ccccc4)c4ccccc4NC2=O)OCCC3)c1]

$NEt_3$ (54 μL, 0.39 mmol), HATU (71 mg, 0.19 mmol) and then (3S)-3-amino-5-phenyl-1,3-dihydro-1,4-benzodiazepin-2-one (46 mg, 0.19 mmol) were added to a solution of crude intermediate 55B (51 mg, 0.19 mmol) in DMF (1.5 mL) and stirred at 40° C. for 1 h. Further HATU (71 mg, 0.19 mmol) was added and the reaction stirred at rt over the weekend. The reaction was quenched with water, and the resultant precipitate filtered, dissolved in EtOAc (30 mL), washed with brine (3×20 mL) concentrated under reduced pressure, and purified by flash chromatography (0-5% MeOH in $CH_2Cl_2$) to afford a white solid (14 mg, 13%). LCMS (Method C) m/z 511.4 $[M+H]^+$ at 3.47 min. $^1H$ NMR (500 MHz, DMSO-$d_6$) δ 10.99 (s, 1H), 8.01-7.99 (m, 1H), 7.89 (d, J=7.8 Hz, 1H), 7.71 (dd, J=8.9, 2.4 Hz, 1H), 7.65-7.59 (m, 1H), 7.54-7.47 (m, 1H), 7.45-7.42 (m, 4H), 7.32-7.22 (m, 3H), 5.29 (d, J=7.8 Hz, 1H), 4.67 (t, J=5.3 Hz, 2H), 4.22 (t, J=6.1 Hz, 2H), 2.42-2.32 (m, 2H), 2.28 (s, 3H).

43. 2-(2-Fluoro-5-methylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide

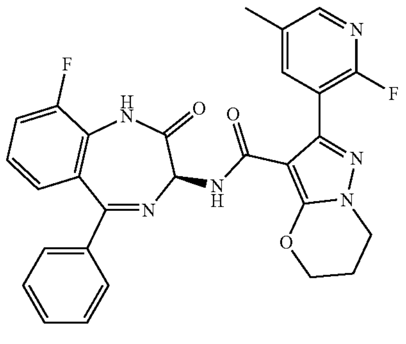 [SMILES: Cc1cnc(F)c(-c2nn3c(c2C(=O)N[C@H]2N=C(c4ccccc4)c4cccc(F)c4NC2=O)OCCC3)c1]

Prepared by an analogous procedure to that described for Example 42. LCMS (Method C) m/z 529.4 $[M+H]^+$ at 3.51 min. $^1H$ NMR (500 MHz, DMSO-$d_6$) δ 10.95 (s, 1H), 8.02-7.99 (m, 1H), 7.91 (d, J=7.7 Hz, 1H), 7.71 (dd, J=9.0, 2.5 Hz, 1H), 7.60-7.54 (m, 1H), 7.54-7.50 (m, 1H), 7.49-7.42 (m, 4H), 7.33-7.27 (m, 1H), 7.14-7.09 (m, 1H), 5.37 (d, J=7.7 Hz, 1H), 4.67 (t, J=5.3 Hz, 2H), 4.22 (t, J=6.1 Hz, 2H), 2.39-2.32 (m, 2H), 2.28 (s, 3H).

44. 2-[6-(Cyclopropylamino)-2-fluoropyridin-3-yl]-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide

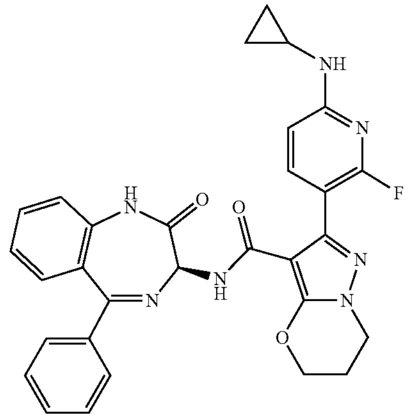 [SMILES: O=C(N[C@H]1N=C(c2ccccc2)c2ccccc2NC1=O)c1c(-c2ccc(NC3CC3)nc2F)nn2c1OCCC2]

$NEt_3$ (84 μL, 0.60 mmol), HATU (110 mg, 0.29 mmol) and then (3S)-3-amino-5-phenyl-1,3-dihydro-1,4-benzodiazepin-2-one (72 mg, 0.29 mmol) were added to a solution of crude intermediate 55B (92 mg, 0.29 mmol) in DMF (2.65 mL) and stirred at 40° C. for 1 h. Further $NEt_3$ (84 μL, 0.60 mmol) was added and the reaction stirred at 40° C. for 1 h. Further HATU (110 mg, 0.29 mmol) was added and the reaction stirred at rt over the weekend. Analogous workup and purification to that described for the compound of Example 21 afforded an off-white solid (89 mg, 54%). LCMS (Method C) m/z 552.4 $[M+H]^+$ at 3.72 min. $^1H$ NMR (500 MHz, DMSO-$d_6$) δ 10.97 (s, 1H), 7.86 (d, J=7.8 Hz, 1H), 7.66-7.59 (m, 1H), 7.53-7.47 (m, 2H), 7.46-7.41 (m, 4H), 7.32-7.28 (m, 2H), 7.27-7.22 (m, 1H), 7.19-7.16 (m, 1H), 6.44-6.39 (m, 1H), 5.30 (d, J=7.8 Hz, 1H), 4.65-4.61 (m, 2H), 4.20-4.15 (m, 2H), 2.36-2.29 (m, 2H), 0.72-0.65 (m, 2H), 0.46-0.38 (m, 2H).

45. 2-Cyclopropyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide

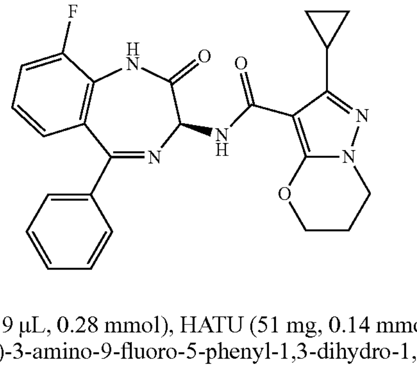

$NEt_3$ (39 μL, 0.28 mmol), HATU (51 mg, 0.14 mmol) and then (3S)-3-amino-9-fluoro-5-phenyl-1,3-dihydro-1,4-benzodiazepin-2-one (36 mg, 0.14 mmol) were added to a solution of crude intermediate 56A (28 mg, 0.14 mmol) in DMF (1.5 mL) and stirred at 40° C. for 1 h. Further HATU (26 mg, 0.07 mmol) and $NEt_3$ (39 μL, 0.28 mmol) were added and the reaction stirred at rt overnight. Analogous workup and purification to that described for the compound of Example 1 afforded a white solid (37 mg, 57%). LCMS (Method C) m/z 460.4 $[M+H]^+$ at 3.35 min. $^1H$ NMR (500 MHz, DMSO-$d_6$) δ 10.95 (s, 1H), 7.86 (d, J=7.7 Hz, 1H), 7.64-7.56 (m, 1H), 7.57-7.48 (m, 3H), 7.49-7.42 (m, 2H), 7.36-7.28 (m, 1H), 7.17 (d, J=7.9 Hz, 1H), 5.49-5.43 (m, 1H), 4.58-4.53 (m, 2H), 4.04-3.98 (m, 2H), 2.63-2.54 (m, 1H), 2.29-2.19 (m, 2H), 0.82-0.70 (m, 4H).

48. (5R)-2-(2-Methoxypyridin-4-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide

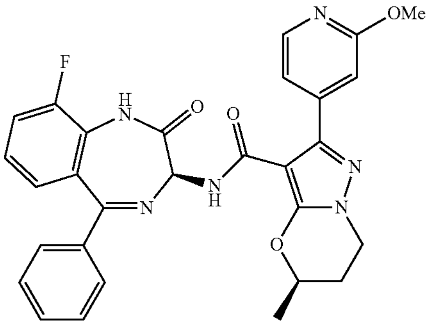 [SMILES: COc1cc(-c2nn3c(c2C(=O)N[C@H]2N=C(c4ccccc4)c4cccc(F)c4NC2=O)O[C@H](C)CC3)ccn1]

A solution of intermediate 65A (178 mg, 0.56 mmol) and 1.5 M aq. LiOH (1.87 mL, 2.8 mmol) in MeOH:THF (1:1; 4 mL) was heated at 50° C. overnight. The reaction was cooled to rt, acidified with 1 M aq. HCl to pH≈7 and the solvent removed under reduced pressure to afford an orange oil (162 mg, quantitative). A portion of the crude residue (81 mg, 0.28 mmol) was dissolved in DMF (3 mL), $NEt_3$ (89 μL, 0.64 mmol) and HATU (114 mg, 0.3 mmol) added, followed by (3S)-3-amino-9-fluoro-5-phenyl-1,3-dihydro-1,4-benzodiazepin-2-one (75 mg, 0.28 mmol), and the reaction stirred at 40° C. for 1 h. The reaction was quenched with water (15 mL), and the resultant precipitate isolated by filtration, washing with water (100 mL). Purification by column chromatography (0 to 6% MeOH in $CH_2Cl_2$) to afford a white solid (115 mg, 73%). LCMS (method C) m/z 541.4 $[M+H]^+$ at 3.69 min. $^1H$ NMR (500 MHz, DMSO-$d_6$) δ 10.94 (s, 1H), 8.40 (d, J=7.2H, 1H), 8.14-8.09 (m, 1H), 7.62-7.55 (m, 1H), 7.56-7.42 (m, 5H), 7.35-7.27 (n, 2H), 7.23 (s, 1H), 7.16 (d, J=7.9 Hz, 1H), 5.39 (d, J=7.2 Hz, 1H), 4.84-4.76 (m, 1H), 4.29-4.15 (m, 2H), 3.84 (s, 3H), 2.40-2.33 (m, 1H), 2.21-2.07 (m, 1H), 1.56 (d, J=6.3 Hz, 3H).

The following compounds were prepared by the amide coupling procedure described for the compound of Example 48. The procedure may be performed at 40° C. for 1 h, or at rt.

TABLE 25

Example compounds prepared by amide coupling procedure F

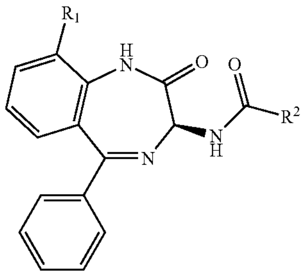

| Example | Name | $R^1$ | $R^2$ | $^1H$ NMR & (500 MHz, DMSO-$d_6$) | LCMS (ESI+) m/z |
|---|---|---|---|---|---|
| 49, | (5R)-2-(2-Methoxypyridin-4-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 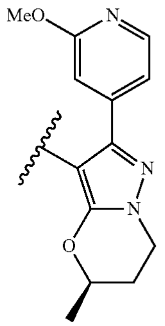 [SMILES: *c1c(-c2ccnc(OC)c2)nn2c1O[C@H](C)CC2] | 10.97 (s, 1H), 8.37 (d, J = 7.3 Hz, 1H), 8.11 (d, J = 5.3 Hz, 1H), 7.68-7.61 (m, 1H), 7.55-7.48 (m, 1H), 7.49-7.40 (m, 4H), 7.35-7.29 (m, 3H), 7.30-7.23 (m, 1H), 7.23 (s, 1H), 5.31 (d, J = 7.3 Hz, 1H), 4.85-4.75 (m, 1H), 4.28-4.12 (m, 2H), 3.84 (s, 3H), 2.41-2.32 (m, 1H), 2.20-2.08 (m, 1H), 1.55 (d, J = 6.3 Hz, 3H) | (method C) 523.4 $[M + H]^+$ at 3.52 min |

TABLE 25-continued

Example compounds prepared by amide coupling procedure F

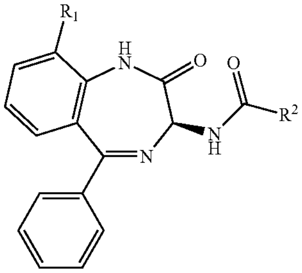

| Example | Name | $R^1$ | $R^2$ | $^1H$ NMR δ (500 MHz, DMSO-$d_6$) | LCMS (ESI+) m/z |
|---|---|---|---|---|---|
| 50. | (5R)-2-[6-(2-Hydroxypropyl)pyridin-3-yl]-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 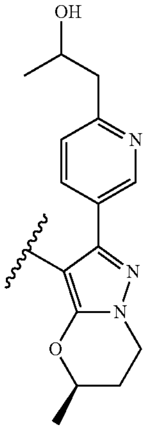 [SMILES: *c1c(-c2ccc(CC(C)O)nc2)nn2c1O[C@H](C)CC2] | 10.96 (s, 1H), 8.73-8.70 (m, 1H), 8.29 (d, J = 7.3 Hz, 1H), 7.96 (d, J = 7.8 Hz, 1H), 7.66-7.61 (m, 1H), 7.53-7.48 (m, 1H), 7.47-7.40 (m, 4H), 7.31 (dd, J = 8.0, 1.8 Hz, 2H), 7.28-7.24 (m, 1H), 7.22 (d, J = 8.1 Hz, 1H), 5.31 (d, J = 7.3 Hz, 1H), 4.85-4.77 (m, 1H), 4.73-4.64 (m, 1H), 4.28-4.16 (m, 2H), 4.05-3.97 (m, 1H), 2.83 (dd, J = 13.3, 7.1 Hz, 1H), 2.73 (dd, J = 13.4, 5.8 Hz, 1H), 2.41-2.34 (m, 1H), 2.21-2.08 (m, 1H), 1.56 (d, J = 6.2 Hz, 3H), 1.07 (d, J = 6.1 Hz, 3H). | (method C) 551.4 $[M + H]^+$ at 2.16 min |
| 51. | (5R)-2-(3-Fluoropyridin-4-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 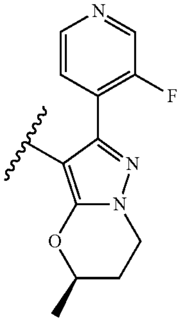 [SMILES: *c1c(-c2ccncc2F)nn2c1O[C@H](C)CC2] | 10.94 (s, 1H), 8.53 (d, J = 1.6 Hz, 1H), 8.43 (d, J = 4.7 Hz, 1H), 8.14 (d, J = 7.5 Hz, 1H), 76.2-7.54 (m, 1H), 7.57-7.49 (m, 1H), 7.54-7.51 (m, 1H), 7.48-7.43 (m, 4H), 7.31 (td, J = 8.1, 5.0 Hz, 1H), 7.14 (d, J = 7.9 Hz, 1H), 5.35 (d, J = 7.4 Hz, 1H), 4.99-4.73 (m, 1H), 4.53-3.97 (m, 2H), 2.45-2.33 (m, 1H), 2.32-2.08 (m, 1H), 1.57 (d, J = 6.3 Hz, 3H). | (method C) 554.5 $[M + H]^+$ at 3.22 min |
| 52. | (5R)-2-[6-(Ethylamino)-3-pyridyl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 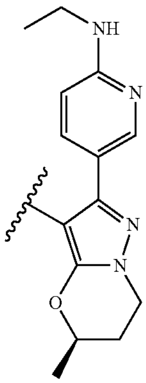 [SMILES: *c1c(-c2ccc(NCC)nc2)nn2c1O[C@H](C)CC2] | 10.92 (s, 1H), 8.31-8.23 (m, 2H), 7.67 (dd, J = 8.7, 2.4 Hz, 1H), 7.61-7.56 (m, 1H), 7.54-7.42 (m, 5H), 7.32 (ddd, J = 8.1, 5.0 Hz, 1H), 7.16 (d, J = 7.9 Hz, 1H), 6.58-6.51 (m, 1H), 6.37 (d, J = 8.7 Hz, 1H), 5.38 (d, J = 7.2 Hz, 1H), 4.82-4.71 (m, 1H), 4.22-4.11 (m, 2H), 3.28-3.20 (m, 2H), 2.38-2.30 (m, 1H), 2.18-2.04 (m, 1H), 1.55 (d, J = 6.2 Hz, 3H), 1.12 (t, J = 7.1 Hz, 3H) | (method C) 554.5 $[M + H]^+$ at 2.21 min |

TABLE 25-continued

Example compounds prepared by amide coupling procedure F

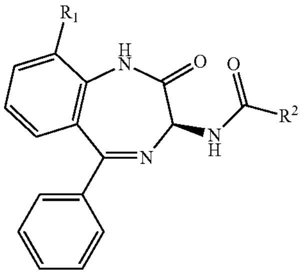

| Example | Name | $R^1$ | $R^2$ | $^1H$ NMR & (500 MHz, DMSO-$d_6$) | LCMS (ESI+) m/z |
|---|---|---|---|---|---|
| 53. | (5R)-2-(5-Cyclopropyl-2-fluoro-3-pyridyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 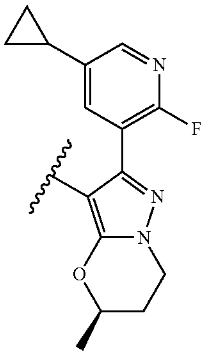 [SMILES: *c1c(-c2cc(C3CC3)cnc2F)nn2c1O[C@H](C)CC2] | 10.93 (s, 1H), 8.11 (d, J = 7.5 Hz, 1H), 8.00 (d, J = 2.5 Hz, 1H), 7.60-7.41 (m, 6H), 7.28 (s, 1H), 7.12 (d, J = 8.0 Hz, 1H), 5.35-5.30 (m, 1H), 4.86-4.78 (m, 1H), 4.28-4.14 (m, 2H), 2.42-2.34 (m, 1H), 2.22-2.10 (m, 1H), 2.02-1.93 (m, 1H), 1.56 (d, J = 6.3 Hz, 3H), 1.26-1.21 (m, 1H), 1.00-0.93 (m, 2H), 0.73-0.68 (m, 2H). | (method C) 569.6 $[M + H]^+$ at 4.12 min |
| 54. | (5R)-2-(4-Ethyl-2-fluoro-phenyl)-3-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 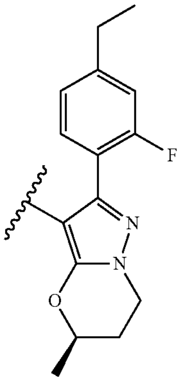 [SMILES: *c1c(-c2ccc(CC)cc2F)nn2c1O[C@H](C)CC2] | 10.95 (s, 1H), 8.04 (d, J = 7.6 Hz, 1H), 7.66-7.59 (m, 1H), 7.50 (h, J = 4.3 Hz, 1H) ,7.45-7.41 (m, 4H), 7.32-7.21 (m, 4H), 7.03-6.95 (m, 2H), 5.25 (d, J = 7.6 Hz, 1H), 4.84-4.76 (m, 1H), 4.26-4.14 (m, 2H), 2.61 (q, J = 7.6 Hz, 2H), 2.39-2.32 (m, 1H), 2.21-2.07 (m, 1H), 1.55 (d, J = 6.2 Hz, 3H), 0.17 (t, J = 7.6 Hz, 3H) | (method C) 538.5 $[M + H]^+$ at 4.60 min |
| 55. | (5R)-5-Methyl-2-(6-morpholino-3-pyridyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 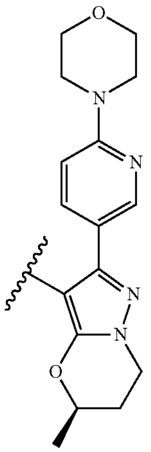 [SMILES: *c1c(-c2ccc(N3CCOCC3)nc2)nn2c1O[C@H](C)CC2] | 10.96 (s, 1H), 8.44 (d, J = 2.4 Hz, 1H), 8.27 (d, J = 7.3 Hz, 1H), 7.87 (dd, J = 8.9, 2.4 Hz, 1H), 7.65 (ddd, J = 8.5, 7.2, 1.7 Hz, 1H), 7.55-7.48 (m, 1H), 7.47-7.41 (m, 4H), 7.32 (dd, J = 7.7, 1.7 Hz, 2H), 7.30-7.24 (m, 1H), 6.78 (d, J = 8.9 Hz, 1H), 5.31 (d, J = 7.3 Hz, 1H), 4.84-4.74 (m, 1H), 4.25-4.14 (m, 2H), 3.72-3.66 (m, 4H), 3.48-3.44 (m, 4H), 2.40-2.32 (m, 1H), 2.19-2.08 (m, 1H), 1.56 (d, J = 6.3 Hz, 3H). | (method C) 578.4 $[M + H]^+$ at 2.44 min |

TABLE 25-continued

Example compounds prepared by amide coupling procedure F

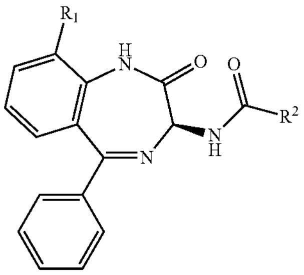

| Example | Name | $R^1$ | $R^2$ | $^1H$ NMR & (500 MHz, DMSO-$d_6$) | LCMS (ESI+) m/z |
|---|---|---|---|---|---|
| 56. | (5R)-N-[(3S)-9-fluoro-2-oxo-5-phenyl-1,3-dihydro-1,4-benzodiazepin-3-yl]-5-methyl-2-(6-morpholino-3-pyridyl)-6,7-dihydro-5H-pyrazolo[5,1-b][1,3]oxazine-3-carboxamide | F | 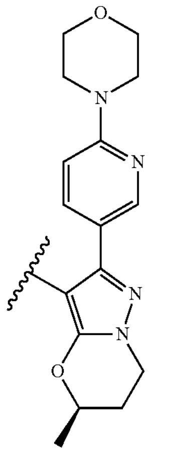 [SMILES: *c1c(-c2ccc(N3CCOCC3)nc2)nn2c1O[C@H](C)CC2] | 10.93 (s, 1H), 8.44 (d, J = 2.4 Hz, 1H), 8.29 (d, J = 7.3 Hz, 1H), 7.86 (dd, J = 8.9, 2.4 Hz, 1H), 7.61-7.55 (m, 1H), 7.55-7.42 (m, 5H), 7.34-7.28 (m, 1H), 7.15 (d, J = 7.9 Hz, 1H), 6.78 (d, J = 8.9 Hz, 1H), 5.38 (d, J = 7.2 Hz, 4.79 (ddd, J = 10.4, 6.3, 2.2 Hz, 1H), 4.18 (qd, J = 11.9, 5.6 Hz, 2H), 3.71-3.65 (m, 4H), 3.47-3.42 (m, 4H), 2.40-2.32 (m, 1H), 2.18-2.07 (m, 1H), 1.55 (d, J = 6.2 Hz, 3H). | (method C) 596.5 $[M + H]^+$ at 2.46 min |
| 57. | (5R)-2-(2,6-Dimethyl-3-pyridyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 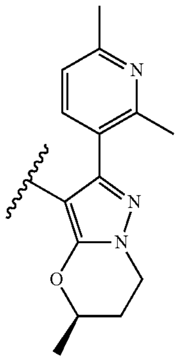 [SMILES: *c1c(-c2ccc(C)nc2C)nn2c1O[C@H](C)CC2] | 10.94 (s, 1H), 8.06 (d, J = 7.4 Hz, 1H), 7.66-7.59 (m, 1H), 7.54-7.47 (m, 1H), 7.47-7.37 (m, 5H), 7.32-7.20 (m, 3H), 7.02 (d, J = 7.8 Hz, 1H), 5.23 (d, J = 7.4 Hz, 1H), 4.93-4.74 (m, 1H), 4.38-4.15 (m, 2H), 2.41 (s, 3H), 2.37 (d, J = 14.2 Hz, 1H), 2.27 (s, 3H), 2.23-2.10 (m, 1H), 1.56 (d, J = 6.3 Hz, 3H). | (method C) 521.3 $[M + H]^+$ at 1.94 min |
| 58. | (5R)-2-(2,6-Dimethyl-3-pyridyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 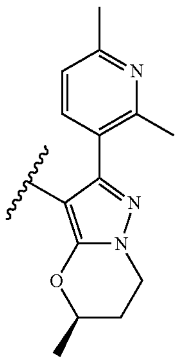 [SMILES: *c1c(-c2ccc(C)nc2C)nn2c1O[C@H](C)CC2] | 10.73 (s, 1H), 8.10 (d, J = 7.4 Hz, 1H), 7.61-7.49 (m, 2H), 74.7-7.42 (m, 4H), 7.40 (d, J = 7.8 Hz, 1H), 7.31-7.24 (m, 1H), 7.11 (d, J = 7.9 Hz, 1H), 7.02 (d, J = 7.8 Hz, 1H), 5.30 (d, J = 7.3 Hz, 1H), 4.86-4.74 (m, 1H), 4.26-4.15 (m, 2H), 2.41 (s, 3H), 2.39-2.33 (m, 1H), 2.28 (s, 3H), 2.22-2.11 (m, 1H), 1.56 (d, J = 6.2 Hz, 3H) | (method C) 539.4 $[M + H]^+$ at 1.95 min |

TABLE 25-continued

Example compounds prepared by amide coupling procedure F

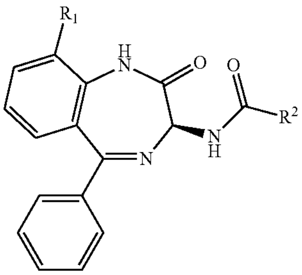

| Example | Name | $R^1$ | $R^2$ | $^1$H NMR & (500 MHz, DMSO-$d_6$) | LCMS (ESI+) m/z |
|---|---|---|---|---|---|
| 59. | (5R)-2-(2-Ethylpyrimidin-5-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 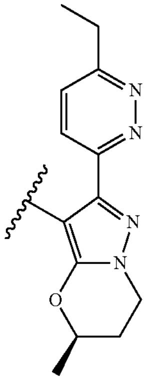 [SMILES: *c1c(-c2ccc(CC)nn2)nn2c1O[C@H](C)CC2] | 10.97 (s, 1H), 8.91 (s, 2H), 8.30 (d, J = 7.3 Hz, 1H), 7.68-7.61 (m, 1H), 7.54-7.48 (m, 1H), 7.47-7.40 (m, 4H), 7.34-7.29 (m, 2H), 7.29-7.23 (m, 1H), 5.31 (d, J = 7.3 Hz, 1H), 4.88-4.77 (m, 1H), 4.32-4.15 (m, 2H), 2.89 (q, J = 7.6 Hz, 2H), 2.43-2.33 (m, 1H), 2.24-2.08 (m, 1H), 1.57 (d, J = 6.3 Hz, 3H), 1.28 (t, J = 7.6 Hz, 3H). | (method C) 522.3 $[M + H]^+$ at 3.39 min |
| 60. | (5R)-2-(2-Ethylpyrimidin-5-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 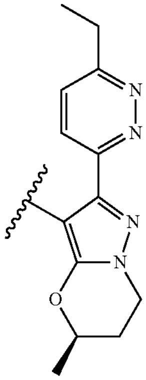 [SMILES: *c1c(-c2ccc(CC)nn2)nn2c1O[C@H](C)CC2] | 10.95 (s, 1H), 8.91 (s, 2H), 8.33 (d, J = 7.2 Hz, 1H), 7.63-7.55 (m, 1H), 7.56-7.49 (m, 1H), 7.51-7.41 (m, 4H), 7.35-7.28 (m, 1H), 7.15 (d, J = 7.9 Hz, 1H), 5.40 (d, J = 7.2 Hz, 1H), 4.89-4.76 (m, 1H), 4.32-4.17 (m, 2H), 2.90 (q, J = 7.6 Hz, 2H), 2.43-2.31 (m, 1H), 2.27-2.07 (m, 1H), 1.57 (d, J = 6.2 Hz, 3H), 1.28 (t, J = 7.6 Hz, 3H). | (method C) 540.3 $[M + H]^+$ at 3.43 min |
| 61. | (5R)-N-[(3S)-9-fluoro-2-oxo-5-phenyl-1,3-dihydro-1,4-benzodiazepin-3-yl]-2-(3-furyl)-5-methyl-6,7-dihydro-5H-pyrazolo[5,1-b][1,3]oxazine-3-carboxamide | F | 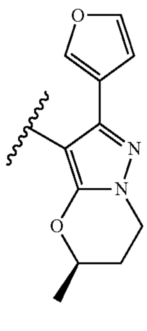 [SMILES: *c1c(-c2ccoc2)nn2c1O[C@H](C)CC2] | 10.91 (s, 1H), 8.10 (d, J = 7.3 Hz, 1H), 7.60-7.53 (m, 1H), 7.55-7.47 (m, 1H), 7.49-7.37 (m, 5H), 7.33-7.24 (m, 1H), 7.11 (d, J = 7.9 Hz, 1H), 7.03 (d, J = 7.8 Hz, 1H), 5.32 (d, J = 7.4 Hz, 1H), 4.98-4.72 (m, 1H), 4.33-4.14 (m, 2H), 2.69 (q, J = 7.6 Hz, 2H), 2.37 (d, J = 14.2 Hz, 1H), 2.29 (s, 3H), 2.22-2.09 (m, 1H), 1.56 (d, J = 6.3 Hz, 3H), 1.21 (t, J = 7.6 Hz, 3H). | (method C) 500.3 $[M + H]^+$ at 3.83 min |

TABLE 25-continued

Example compounds prepared by amide coupling procedure F

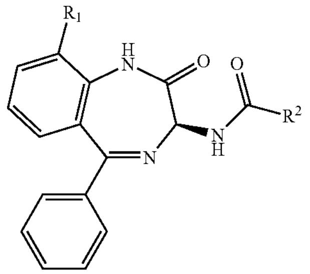

| Example | Name | $R^1$ | $R^2$ | $^1H$ NMR & (500 MHz, DMSO-$d_6$) | LCMS (ESI+) m/z |
|---|---|---|---|---|---|
| 62. | (5R)-2-(3-Furyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 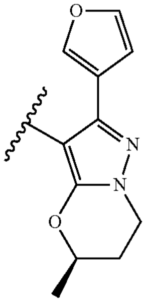 [SMILES: *c1c(-c2ccoc2)nn2c1O[C@H](C)CC2] | 10.98 (s, 1H), 8.51 (dd, J = 1.7, 0.7 Hz, 1H), 8.35 (d, J = 7.3 Hz, 1H), 7.68-7.63 (m, 1H), 7.62 (t, J = 1.7 Hz, 1H), 7.53-7.49 (m, 1H), 7.49-7.42 (m, 4H), 7.37-7.31 (m, 2H), 7.30-7.26 (m, 1H), 6.90-6.86 (m, 1H), 5.36 (d, J = 7.3 Hz, 1H), 4.84-4.72 (m, 1H), 4.33-4.08 (m, 2H), 2.42-2.30 (m, 1H), 2.20-2.04 (m, 1H), 1.55 (d, J = 6.3 Hz, 3H). | (method C) 482.4 $[M + H]^+$ at 3.83 min |
| 63. | (5R)-N-[(3S)-9-fluoro-2-oxo-5-phenyl-1,3-dihydro-1,4-benzodiazepin-3-yl]-5-methyl-2-(3-thienyl)-6,7-dihydro-5H-pyrazolo[5,1-b][1,3]oxazine-3-carboxamide | F | 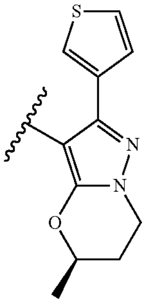 [SMILES: *c1c(-c2ccsc2)nn2c1O[C@H](C)CC2] | 10.95 (s, 1H), 8.43 (d, J = 7.1 Hz, 1H), 8.36 (dd, J = 3.0, 1.2 Hz, 1H), 7.64-7.60 (m, 1H), 7.58 (dd, J = 5.1, 1.2 Hz, 1H), 7.55-7.48 (m, 3H), 7.49-7.43 (m, 3H), 7.38-7.30 (m, 1H), 7.19 (dd, J = 8.1, 1.3 Hz, 1H), 5.44 (d, J = 7.1 Hz, 1H), 4.85-4.73 (m, 1H), 4.29-4.11 (m, 2H), 2.42-2.32 (m, 1H), 2.22-2.08 (m, 1H), 1.57 (d, J = 6.3 Hz, 3H). | (method C) 516.3 $[M + H]^+$ at 4.00 min |
| 64. | (5R)-5-Methyl-N-[(3S)-2-oxo-5-phenyl-1,3-dihydro-1,4-benzodiazepin-3-yl]-2-(3-thienyl)-6,7-dihydro-5H-pyrazolo[5,1-b][1,3]oxazine-3-carboxamide | H | 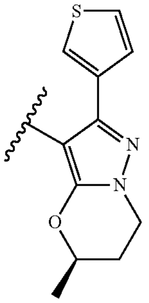 [SMILES: *c1c(-c2ccsc2)nn2c1O[C@H](C)CC2] | 10.98 (s, 1H), 8.40 (d, J = 7.2 Hz, 1H), 8.36 (dd, J = 3.0, 1.2 Hz, 1H), 7.69-7.62 (m, 1H), 7.58 (dd, J = 5.0, 1.2 Hz, 1H), 7.55-7.48 (m, 1H), 7.50-7.41 (m, 5H), 7.38-7.31 (m, 2H), 7.32-7.25 (m, 1H), 5.36 (d, J = 7.2 Hz, 1H), 4.85-4.74 (m, 1H), 4.28-4.12 (m, 2H), 2.41-2.33 (m, 1H), 2.21-2.08 (m, 1H), 1.56 (d, J = 6.3 Hz, 3H). | (method C) 498.3 $[M + H]^+$ at 3.98 min |

TABLE 25-continued

Example compounds prepared by amide coupling procedure F

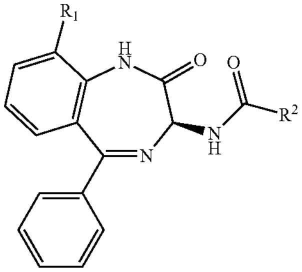

| Example | Name | $R^1$ | $R^2$ | $^1H$ NMR & (500 MHz, DMSO-$d_6$) | LCMS (ESI+) m/z |
|---|---|---|---|---|---|
| 65. | (5R)-2-(6-Ethyl-2-methyl-3-pyridyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 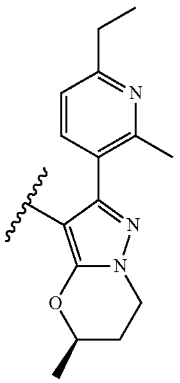 [SMILES: *c1c(-c2ccc(CC)nc2C)nn2c1O[C@H](C)CC2] | 10.94 (s, 1H), 8.07 (d, J = 7.4 Hz, 1H), 7.68-7.56 (m, 1H), 7.54-7.47 (m, 1H), 7.46-7.37 (m, 5H), 7.32-7.19 (m, 3H), 7.03 (d, J = 7.8 Hz, 1H), 5.23 (d, J = 7.4 Hz, 1H), 5.00-4.64 (m, 1H), 4.33-4.08 (m, 2H), 2.69 (q, J = 7.6 Hz, 2H), 2.42-2.32 (m, 1H), 2.29 (s, 3H), 2.23-2.06 (m, 1H), 1.56 (d, J = 6.2 Hz, 3H), 1.21 (t, J = 7.6 Hz, 3H). | (method C) 535.5 $[M + H]^+$ at 2.19 min |
| 66. | (5R)-2-(6-Ethyl-2-methyl-3-pyridyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 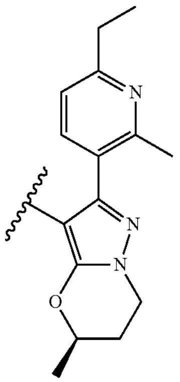 [SMILES: *c1c(-c2ccc(CC)nc2C)nn2c1O[C@H](C)CC2] | 10.91 (s, 1H), 8.10 (d, J = 7.3 Hz, 1H), 7.60-7.53 (m, 1H), 7.55-7.47 (m, 1H), 7.49-7.37 (m, 5H), 7.33-7.24 (m, 1H), 7.11 (d, J = 7.9 Hz, 1H), 7.03 (d, J = 7.8 Hz, 1H), 5.32 (d, J = 7.4 Hz, 1H), 4.98-4.72 (m, 1H), 4.33-4.14 (m, 2H), 2.69 (q, J = 7.6 Hz, 2H), 2.37 (d, J = 14.2 Hz, 1H), 2.29 (s, 3H), 2.22-2.09 (m, 1H), 1.56 (d, J = 6.3 Hz, 3H), 1.21 (t, J = 7.6 Hz, 3H). | (method C) 553.4 $[M + H]^+$ at 2.12 min |
| 67. | (5R)-N-[(3S)-9-fluoro-2-oxo-5-phenyl-1,3-dihydro-1,4-benzodiazepin-3-yl]-2-[6-(isopropylamino)-3-pyridyl]-5-methyl-6,7-dihydro-5H-pyrazolo[4,1-b][1,3]oxazine-3-carboxamide | F | 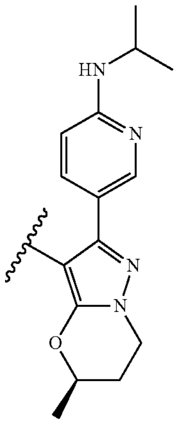 [SMILES: *c1c(-c2ccc(NC(C)C)nc2)nn2c1O[C@H](C)CC2] | 10.92 (s, 1H), 8.30-8.25 (m, 2H), 7.65 (dd, J = 8.7, 2.4 Hz, 1H), 7.59 (ddd, J = 9.7, 8.3, 1.3 Hz, 1H), 7.56-7.49 (m, 1H), 7.51-7.41 (m, 4H), 7.36-7.28 (m, 1H), 7.16 (d, J = 7.9 Hz, 1H), 6.40 (d, J = 7.5 Hz, 1H), 6.36 (d, J = 9.1 Hz, 1H), 5.38 (dd, J = 7.3, 1.4 Hz, 1H), 4.81-4.71 (m, 1H), 4.22-4.10 (m, 2H), 4.05-3.93 (m, 1H), 2.33 (s, 1H), 2.18-2.05 (m, 1H), 1.55 (d, J = 6.3 Hz, 3H), 1.12 (d, J = 6.5 Hz, 6H) | (method C) 568.4 $[M + H]^+$ at 2.37 min |

TABLE 25-continued

Example compounds prepared by amide coupling procedure F

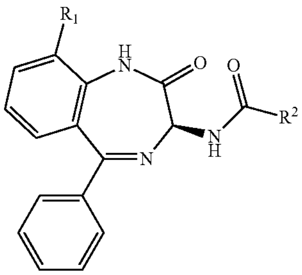

| Example | Name | $R^1$ | $R^2$ | $^1H$ NMR & (500 MHz, DMSO-$d_6$) | LCMS (ESI+) m/z |
|---|---|---|---|---|---|
| 68. | (5R)-2-(1-Ethylpyrazol-3-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 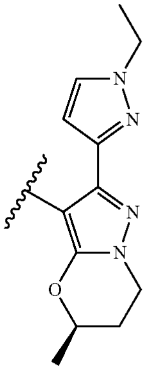 [SMILES: *c1c(-c2ccn(CC)n2)nn2c1O[C@H](C)CC2] | 11.34 (d, J = 7.0 Hz, 1H), 10.81 (s, 1H), 7.86 (d, J = 2.3 Hz, 1H), 7.64-7.57 (m, 1H), 7.55-7.49 (m, 3H), 7.48-7.40 (m, 2H), 7.37-7.27 (m, 1H), 7.16 (d, J = 7.9 Hz, 1H), 6.64 (d, J = 2.3 Hz, 1H), 5.45 (d, J = 7.0 Hz, 1H), 4.55-4.46 (m, 1H), 4.28 (q, J = 7.2 Hz, 2H), 4.19-4.08 (m, 2H), 2.30-2.20 (m, 1H), 2.09-1.93 (m, 1H), 1.45-1.35 (m, 6H). | (method C) 528.3 $[M + H]^+$ at 3.57 min |
| 69. | (5S)-5-methyl-2-[6-(propan-2-ylamino)pyridin-3-yl]-N-(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 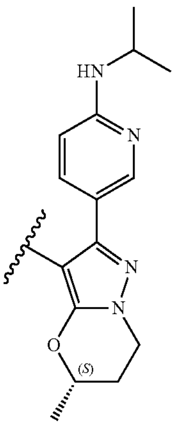 | 0.96-10.91 (m, 1H), 8.31 (d, J = 7.2 Hz, 1H), 8.29-8.27 (m, 1H), 7.66 (dd, J = 8.7, 2.4 Hz, 1H), 7.63-7.56 (m, 1H), 7.56-7.42 (m, 5H), 7.36-7.28 (m, 1H), 7.17 (d, J = 7.9 Hz, 1H), 6.41 (d, J = 7.7 Hz, 1H), 6.37 (d, J = 8.7 Hz, 1H), 5.39 (d, J = 7.3 Hz, 1H), 4.80-4.72 (m, 1H), 4.24-4.11 (m, 2H), 4.00 (dq, J = 13.3, 6.5 Hz, 1H), 2.39-2.32 (m, 1H), 2.20-2.10 (m, 1H), 1.59-1.53 (m, 3H), 1.13 (d, J = 6.4 Hz, 6H) | (method D) 568.5 $[M + H]^+$ at 3.83 min |

TABLE 25-continued

Example compounds prepared by amide coupling procedure F

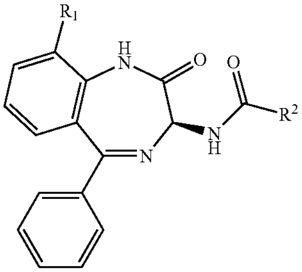

| Example | Name | $R^1$ | $R^2$ | $^1H$ NMR & (500 MHz, DMSO-$d_6$) | LCMS (ESI+) m/z |
|---|---|---|---|---|---|
| 70. | (5R)-5-Methyl-2-(6-propan-2-ylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 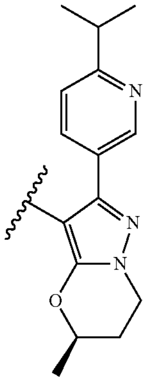 [SMILES: *c1c(-c2ccc(C(C)C)nc2)nn2c1O[C@H](C)CC2] | 10.94 (s, 1H), 8.73-8.69 (m, 1H), 8.32 (d, J = 7.3 Hz, 1H), 7.95 (dd, J = 8.1, 2.3 Hz, 1H), 7.62-7.56 (m, 1H), 7.55-7.51 (m, 1H), 7.51-7.43 (m, 4H), 7.36-7.28 (m, 1H), 7.27-7.21 (m, 1H), 7.19-7.13 (m, 1H), 5.39 (d, J = 7.2 Hz, 1H), 4.86-4.78 (m, 1H), 4.29-4.16 (m, 2H), 3.02 (p, J = 6.9 Hz, 1H), 2.42-2.34 (m, 1H), 2.22-2.10 (m, 1H), 1.57 (d, J = 6.3 Hz, 3H), 1.24 (d, J = 6.9 Hz, 6H). | (method C) 553.4 $[M + H]^+$ at 3.65 min |
| 71. | (5R)-5-Methyl-N-[(3S)-9-fluoro-2-oxo-5-phenyl-1,3-dihydro-1,4-benzodiazepin-3-yl]-2-[6-(trideuteriomethylamino)pyridin-3-yl]-6,7-dihydro-5H-pyrazolo[5,1-b][1,3]oxazine-3-carboxamide | | 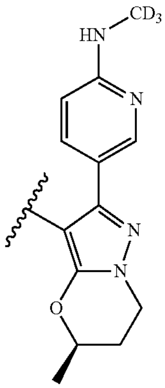 [SMILES: *c1c(-c2ccc(NC([2H])([2H])[2H])nc2)nn2c1O[C@H](C)CC2] | δ 10.92 (s, 1H), 8.32-8.25 (m, 2H), 7.68 (dd, J = 8.7, 2.4 Hz, 1H), 7.63-7.56 (m, 1H), 7.56-7.41 (m, 5H), 7.35-7.28 (m, 1H), 7.16 (d, J = 8.0 Hz, 1H), 6.50 (s, 1H), 6.37 (d, J = 8.7 Hz, 1H), 5.38 (d, J = 7.2 Hz, 1H), 4.79-4.75 (m, 1H), 4.21-4.11 (m, 2H), 2.35-2.32 (m, 1H), 2.18-2.06 (m, 1H), 1.55 (d, J = 6.3 Hz, 3H). | (method C) 543.4 $[M + H]^+$ at 2.14 min |

The following compounds were prepared by the amide coupling procedure described for the compound of Example 48 with additional purification by HPLC/SFC as indicated.

TABLE 26

Example compounds prepared by amide coupling procedure F

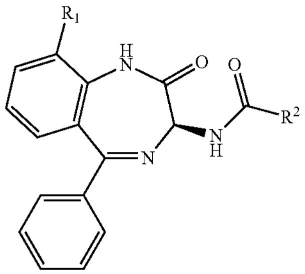

| Example | Name | $R^1$ | $R^2$ | $^1$H NMR δ (500 MHz, DMSO-$d_6$) | LCMS (ES+) m/z | HPLC/SFC method: (gradient) |
|---|---|---|---|---|---|---|
| 72 | (5R)-2-(2-Fluoro-6-methylpyridin-3-yl)-5-methyl-N-[(3S)-2-oxo-5-phenyl-1,3-dihydro-1,4-benzodiazepin-3-yl]-6,7-dihydro-5H-pyrazolo[5,1-b][3,1]oxazine-3-carboxamide | H | 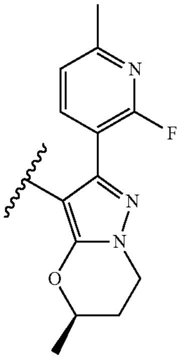 [SMILES: *c1c(-c2ccc(C)nc2F)nn2c1O[C@H](C)CC2] | 10.97 (s, 1H), 8.08 (d, J = 7.5 Hz, 1H), 7.77 (dd, J = 9.6, 7.5 Hz, 1H), 7.67-7.60 (m, 1H), 7.55-7.47 (m, 1H), 7.48-7.42 (m, 4H), 7.34-7.27 (m, 2H), 7.29-7.22 (m, 1H), 7.19 (d, J = 7.3 Hz, 1H), 5.26 (d, J = 7.5 Hz, 1H), 4.88-4.79 (m, 1H), 4.28-4.16 (m, 2H), 2.43 (s, 3H), 2.42-2.35 (m, 1H), 2.23-2.11 (m, 1H), 1.57 (d, J = 6.2 Hz, 3H). | method C 523.3 $[M + H]^+$ at 3.57 min | HPLC method 3: (20-100% MeCN in water with 0.1% $NH_3$) |
| 73 | (5R)-2-(2-Fluoro-6-methylpyridin-3-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 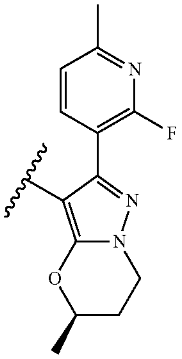 [SMILES: *c1c(-c2ccc(C)nc2F)nn2c1O[C@H](C)CC2] | 10.94 (s, 1H), 8.13 (d, J = 7.5 Hz, 1H), 7.78 (dd, J = 9.6, 7.5 Hz, 1H), 7.60-7.49 (m, 2H), 7.51-7.42 (m, 4H), 7.28 (s, 1H), 7.20 (d, J = 7.6 Hz, 1H), 7.12 (d, J = 7.9 Hz, 1H), 5.32 (d, J = 7.2 Hz, 1H), 4.87-4.78 (m, 1H), 4.28-4.16 (m, 2H), 2.43 (s, 3H), 2.42-2.34 (m, 1H), 2.23-2.11 (m, 1H), 1.57 (d, J = 6.3 Hz, 3H). | method C 543.3 $[M + H]^+$ at 3.64 min | HPLC method 3: (20-100% MeCN in water with 0.1% $NH_3$) |
| 74 | (5R)-2-(6-Ethylpyridin-3-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 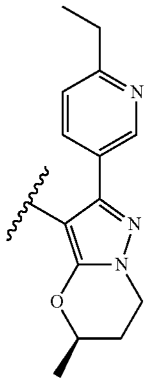 [SMILES: *c1c(-c2ccc(CC)nc2)nn2c1O[C@H](C)CC2] | 10.90 (s, 1H), 8.72-8.68 (m, 1H), 8.32 (d, J = 7.2 Hz, 1H), 7.95 (dd, J = 8.1, 2.2 Hz, 1H), 7.62-7.56 (m, 1H), 7.56-7.41 (m, 5H), 7.35-7.27 (m, 1H), 7.22 (d, J = 8.1 Hz, 1H), 7.18-7.12 (m, 1H), 5.38 (d, J = 7.2 Hz, 1H), 4.86-4.78 (m, 1H), 4.28-4.15 (m, 2H), 2.74 (q, J = 7.6 Hz, 2H), 2.41-2.33 (m, 1H), 2.21-2.09 (m, 1H), 1.56 (d, J = 6.3 Hz, 3H), 1.22 (t, J = 7.6 Hz, 3H). | method C 539.3 $[M + H]^+$ at 2.34 min | Chiral HPLC method 1 (90% MeCN in water with 0.1% $NH_3$). |

TABLE 26-continued

Example compounds prepared by amide coupling procedure F

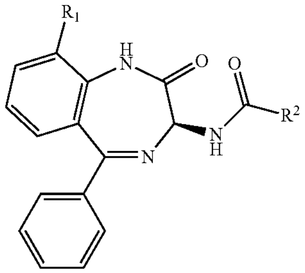

| Example | Name | $R^1$ | $R^2$ | $^1H$ NMR δ (500 MHz, DMSO-$d_6$) | LCMS (ES+) m/z | HPLC/SFC method: (gradient) |
|---|---|---|---|---|---|---|
| 75 | (5R)-2-(4-Ethyl-2-fluorophenyl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 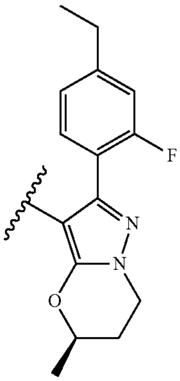 [SMILES: *c1c(-c2ccc(CC)cc2F)nn2c1O[C@H](C)CC2] | 10.93 (s, 1H), 8.08 (d, J = 7.5 Hz, 1H), 7.62-7.55 (m, 1H), 7.57-7.50 (m, 1H), 7.52-7.42 (m, 4H), 7.35-7.27 (m, 1H), 7.26 (dd, J = 7.7 Hz, 1H), 7.14 (d, J = 7.9 Hz, 1H), 7.05-6.97 (m, 2H), 5.34 (d, J = 7.4 Hz, 1H), 4.87-4.77 (m, 1H), 4.27-4.15 (m, 2H), 2.63 (q, J = 7.6 Hz, 2H), 2.41-2.34 (m, 1H), 2.23-2.11 (m, 1H), 1.57 (d, J = 6.2 Hz, 3H), 1.19 (t, J = 7.6 Hz, 3H). | method C 556.3 $[M + H]^+$ at 4.62 min | Chiral HPLC method 1: (70% MeCN in water with 0.3% $NH_3$) |
| 76 | (5S)-N-[(3S)-9-fluoro-2-oxo-5-phenyl-1,3-dihydro-1,4-benzodiazepin-3-yl]-2-(3-fluoropyridin-4-yl)-5-methyl-6,7-dihydro-5H-pyrazolo[5,1-b][1,3]oxazine-3-carboxamide | F | 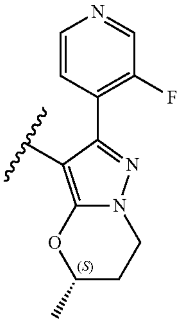 | 10.96 (s, 1H), 8.53 (d, J = 1.6 Hz, 1H), 8.42 (dd, J = 4.8, 1.1 Hz, 1H), 8.17 (d, J = 7.5 Hz, 1H), 7.59-7.49 (m, 2H), 7.49-7.41 (m, 5H), 7.28 (d, J = 6.5 Hz, 1H), 7.12 (d, J = 7.9 Hz, 1H), 5.33 (d, J = 7.4 Hz, 1H), 4.88-4.78 (m, 1H), 4.30-4.17 (m, 2H), 2.42-2.34 (m, 1H), 2.23-2.12 (m, 1H), 1.57 (d, J = 6.3 Hz, 3H). | method C 529.4 $[M + H]^+$ at 3.31 min | Chiral SFC method 1. [55% EtOH (0.1% $NH_3$)]. |

77. (5R)-5-Methyl-2-(6-methylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide

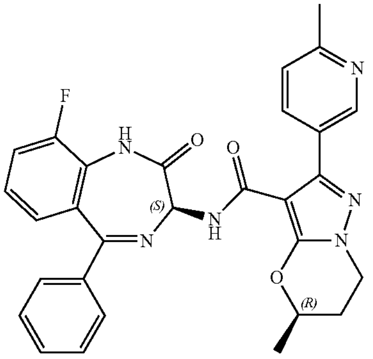

A solution of intermediate 16C (171 mg, 0.56 mmol) and 1.5 M aq. LiOH (2 mL, 3 mmol) in MeOH:THF (1:1; 4 mL) was heated at 40° C. overnight. The reaction was cooled to rt, acidified with 1 M aq. HCl (3.2 mL, 3.2 mmol) to pH≈7 and the solvent removed under reduced pressure. The crude residue was dissolved in DMF (3 mL), HATU (213 mg, 0.56 mmol) and $NEt_3$ (234 μL, 1.68 mmol) added, followed by (3S)-3-amino-9-fluoro-5-phenyl-1,3-dihydro-1,4-benzodiazepin-2-one (151 mg, 0.56 mmol), and the reaction stirred at 40° C. for 2 h. The reaction was quenched with water (20 mL) and extracted with EtOAc (2×20 mL). The combined organics were washed with brine (3×50 mL), dried ($MgSO_4$) and the solvent removed under reduced pressure.

Purification by column chromatography (0 to 5% MeOH in $CH_2Cl_2$) afforded a white solid (140 mg, 45%). LCMS (method C) m/z 525.4 $[M+H]^+$ at 2.10 min. $^1H$ NMR (500 MHz, DMSO-$d_6$) δ 10.94 (s, 1H), 8.68 (dd, J=2.3, 0.9 Hz, 1H), 8.31 (d, J=7.2 Hz, 1H), 7.95 (dd, J=8.0, 2.3 Hz, 1H), 7.62-7.56 (m, 1H), 7.56-7.50 (m, 1H), 7.50-7.42 (m, 4H), 7.35-7.27 (m, 1H), 7.21 (d, J=8.1 Hz, 1H), 7.15 (d, J=7.9 Hz, 1H), 5.39 (d, J=7.1 Hz, 1H), 4.86-4.76 (m, 1H), 4.27-4.16 (m, 2H), 2.46 (s, 3H), 2.41-2.33 (m, 1H), 2.21-2.09 (m, 1H), 1.56 (d, J=6.3 Hz, 3H).

The following compounds were prepared by an analogous procedure to that described for the compound of Example 77. Example 80 was further purified by reverse phase chromatography [15-50% MeCN (0.1% formic acid) in water (0.1% formic acid)]. For the preparation of Examples 81, 82 and 83, 6 eq. of $NEt_3$ was employed in the amide coupling step and further purification was conducted by reverse phase chromatography [15-50% MeCN (0.1% formic acid) in water (0.1% formic acid)].

TABLE 27

Example compounds by amide coupling procedure G

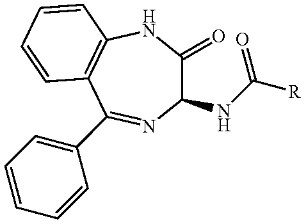

| Example | Name | R | $^1H$ NMR δ (500 MHz, DMSO-$d_6$) | LCMS (ES+) m/z |
|---|---|---|---|---|
| 78. | (5R)-2-[6-(2-Hydroxypropyl)pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | 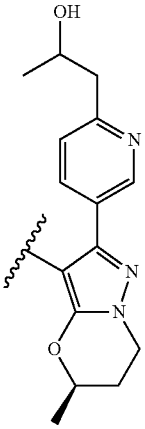 [SMILES: *c1c(-c2ccc(CC(C)O)nc2)nn2c1O[C@H](C)CC2] | 10.94 (s, 1H), 8.71 (d, J = 2.2 Hz, 1H), 8.33 (d, J = 7.3 Hz, 1H), 7.97-7.93 (m, 1H), 7.61-7.56 (m, 1H), 7.55-7.50 (m, 1H), 7.50-7.42 (m, 4H), 7.31 (ddd, J = 8.1, 5.0 Hz, 1H), 7.21 (d, J = 8.0 Hz, 1H), 7.15 (d, J = 7.9 Hz, 1H), 5.39 (d, J = 7.2 Hz, 1H), 4.86-4.76 (m, 1H), 4.68 (dd, J = 4.8, 1.1 Hz, 1H), 4.28-4.16 (m, 2H), 4.05-3.97 (m, 1H), 2.83 (dd, J = 13.3, 7.0 Hz, 1H), 2.72 (dd, J = 13.3, 5.8 Hz, 1H), 2.40-2.33 (m, 1H), 2.19-2.10 (m, 1H), 1.56 (d, J = 6.3 Hz, 3H), 1.07 (d, J = 6.2 Hz, 3H). | (method C) 569.3 $[M + H]^+$ at 2.17 min |

TABLE 27-continued

Example compounds by amide coupling procedure G

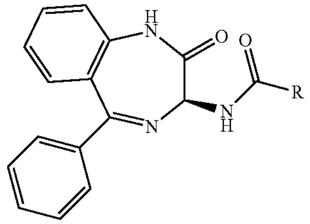

| Example | Name | R | $^1$H NMR δ (500 MHz, DMSO-$d_6$) | LCMS (ES+) m/z |
|---|---|---|---|---|
| 79. | (5R)-2-(5-Fluoro-2-methylpyridin-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | 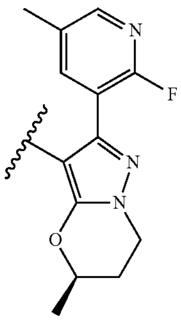 [SMILES: *c1c(-c2cc(C)cnc2F)nn2c1O[C@H](C)CC2] | 10.94 (s, 1H), 8.15 (d, J = 1.5 Hz, 1H), 8.12 (d, J = 7.5 Hz, 1H), 76.1-7.41 (m, 6H), 7.34-7.25 (m, 2H), 7.13 (dd, J = 8.0, 1.4 Hz, 1H), 5.35 (d, J = 7.4 Hz, 1H), 4.89-4.79 (m, 1H), 4.28-4.17 (m, 2H), 2.47-2.43 (m, 3H), 2.39-2.35 (m, 1H), 2.23-2.11 (m, 1H), 1.56 (d, J = 6.3 Hz, 3H). | (method C) 543.4 [M + H]$^+$ at 3.11 min |
| 80. | N-[(3S)-9-fluoro-2-oxo-5-phenyl-1,3-dihydro-1,4-benzodiazepin-3-yl]-2-(3-fluoropyridin-4-yl)-6,7-dihydro-5H-pyrazolo[5,1-b][1,3]oxazine-3-carboxamide | 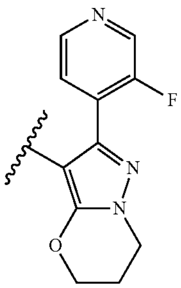 [SMILES: *c1c(-c2ccncc2F)nn2c1OCCC2] | 10.96 (s, 1H), 8.52 (d, J = 1.7 Hz, 1H), 8.42 (d, J = 4.9 Hz, 1H), 7.95 (d, J = 7.6 Hz, 1H), 7.60-7.50 (m, 2H), 7.49-7.41 (m, 5H), 7.33-7.25 (m, 1H), 7.13 (d, J = 8.0 Hz, 1H), 5.37 (d, J = 7.6 Hz, 1H), 4.68 (t, J = 5.3 Hz, 2H), 4.24 (t, J = 6.1 Hz, 2H), 2.42-2.28 (m, 2H). | (method C) 515.4 [M + H]$^+$ at 2.98 min |
| 81. | (5R)-5-Methyl-2-phenyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | 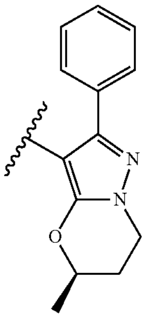 [SMILES: *c1c(-c2ccccc2)nn2c1O[C@H](C)CC2] | 10.92 (s, 1H), 8.31 (d, J = 7.2 Hz, 1H), 7.71-7.66 (m, 2H), 7.61-7.55 (m, 1H), 7.54-7.42 (m, 5H), 7.35-7.27 (m, 4H), 7.15 (d, J = 7.9 Hz, 1H), 5.38 (d, J = 7.2 Hz, 1H), 4.84-4.74 (m, 1H), 4.26-4.14 (m, 2H), 2.40-2.32 (m, 1H), 2.21-2.09 (m, 1H), 1.56 (d, J = 6.3 Hz, 3H). | (method C) 510.5 [M + H]$^+$ at 4.00 min. |

TABLE 27-continued

Example compounds by amide coupling procedure G

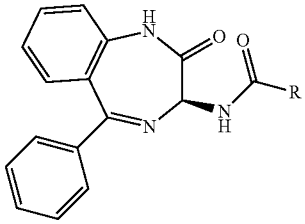

| Example | Name | R | $^1$H NMR δ (500 MHz, DMSO-$d_6$) | LCMS (ES+) m/z |
|---|---|---|---|---|
| 82. | (5R)-2-(2,4-Difluorophenyl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | 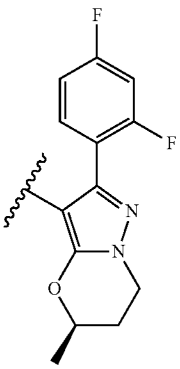 [SMILES: *c1c(-c2ccc(F)cc2F)nn2c1O[C@H](C)CC2] | 10.92 (s, 1H), 8.09 (d, J = 7.5 Hz, 1H), 7.61-7.53 (m, 1H), 7.56-7.49 (m, 1H), 7.50-7.36 (m, 5H), 7.33-7.25 (m, 1H), 7.22-7.14 (m, 1H), 7.13 (d, J = 7.9 Hz, 1H), 7.10-7.02 (m, 1H), 5.33 (d, J = 7.4 Hz, 1H), 4.87-4.77 (m, 1H), 4.27-4.13 (m, 2H), 2.41-2.32 (m, 1H), 2.22-2.09 (m, 1H), 1.56 (d, J = 6.2 Hz, 3H). | (method C) 546.3 $[M + H]^+$ at 4.13 min |
| 83. | (5R)-5-Methyl-2-(1-methylindazol-5-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | 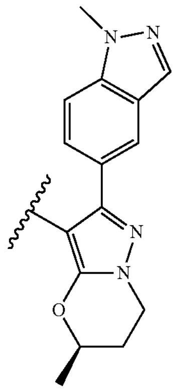 [SMILES: *c1c(-c2ccc3c(cnn3C)c2)nn2c1O[C@H](C)CC2] | 10.93 (s, 1H), 8.32 (d, J = 7.3 Hz, 1H), 8.19-8.15 (m, 1H), 8.05-8.01 (m, 1H), 7.74 (dd, J = 8.8, 1.6 Hz, 1H), 7.62-7.50 (m, 3H), 7.50-7.42 (m, 4H), 7.15 (d, J = 7.9 Hz, 1H), 5.41 (d, J = 7.2 Hz, 1H), 4.82-4.79 (m, 1H), 4.25-4.16 (m, 2H), 4.03 (s, 3H), 2.41-2.34 (m, 1H), 2.21-2.10 (m, 1H), 1.57 (d, J = 6.2 Hz, 3H). | (method C) 564.5 $[M + H]^+$ at 3.67 min |

84. (5R)-2-(1-Ethylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide

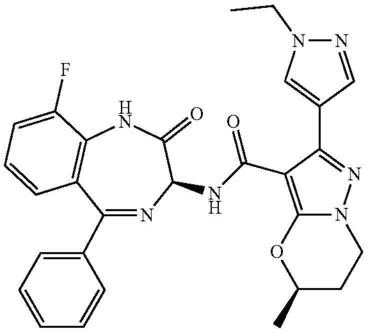 [SMILES: CCn1cc(-c2nn3c(c2C(=O)N[C@H]2N=C(c4ccccc4)c4cccc(F)c4NC2=O)O[C@H](C)CC3)cn1]

A solution of intermediate 65J (88 mg, 0.197 mmol) and 1.5 M aq. LiOH (0.657 mL, 0.985 mmol) in MeOH:THF (1:1; 2 mL) was heated at 50° C. overnight. Further 1.5 M aq. LiOH (0.131 mL, 0.197 mmol) was added, and the reaction heated at 50° C. overnight, then an additional portion of 1.5 M aq. LiOH (0.131 mL, 0.197 mmol) added and the reaction heated at 50° C. overnight. The reaction mixture was neutralised with 1 M aq. citric acid to pH≈7 and concentrated under reduced pressure. The crude residue (54 mg, 0.197 mmol) was dissolved in DMF (2 mL), $NEt_3$ (62 μL, 0.44 mmol) and HATU (80 mg, 0.21 mmol) added, followed by (3S)-3-amino-9-fluoro-5-phenyl-1,3-dihydro-1,4-benzodiazepin-2-one (53 mg, 0.197 mmol), and the reaction stirred at 40° C. for 1 h, then at rt overnight. Further $NEt_3$ (62 μL, 0.44 mmol) and HATU (80 mg, 0.21 mmol) was added and the reaction stirred at 40° C. for 1 h. Analogous workup and purification to Example 48, followed by additional purification by chiral SFC method 1 [55% EtOH (0.1% $NH_3$)] afforded a white solid (59 mg, 56%). LCMS (method C) m/z (method C) 528.4 $[M+H]^+$ at 3.48 min. $^1$H NMR (500 MHz, DMSO-$d_6$) δ 10.95 (s, 1H), 8.40 (s, 1H), 8.35 (d, J=7.3 Hz, 1H), 7.88 (s, 1H), 7.62-7.57 (m, 1H), 7.55-7.48 (m, 3H), 7.47-7.43 (m, 2H), 7.36-7.29 (m, 1H), 7.22-7.17 (m, 1H), 5.44 (d, J=7.2 Hz, 1H), 4.82-4.72 (m, 1H), 4.21-4.06 (m, 4H), 2.38-2.30 (m, 1H), 2.17-2.05 (m, 1H), 1.55 (d, J=6.2 Hz, 3H), 1.34 (t, J=7.2 Hz, 3H).

85. (5R)-2-[6-(2-Hydroxy-2-methylpropyl)pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide

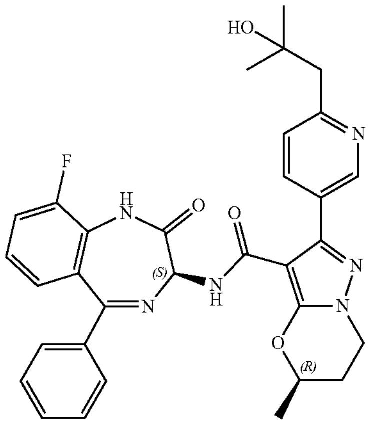

A solution of intermediate 69D (103 mg, 0.29 mmol) and 1.5 M aq. LiOH (0.96 mL, 1.44 mmol) in MeOH:THF (1:1; 4 mL) was heated at 50° C. overnight. The reaction was cooled to rt, acidified with 1 M aq. HCl to pH≈7 and the solvent removed under reduced pressure. The crude residue was dissolved in DMF (3 mL), HATU (116 mg, 0.31 mmol) and $NEt_3$ (91 μL, 0.65 mmol) added, followed by (3S)-3-amino-9-fluoro-5-phenyl-1,3-dihydro-1,4-benzodiazepin-2-one (77 mg, 0.29 mmol), and the reaction stirred at rt overnight. The reaction was quenched with water (15 mL), and the resultant precipitate isolated by filtration, washing with water (100 mL). The isolated solid was purified by column chromatography (0-7% MeOH in $CH_2Cl_2$), followed by reverse phase column chromatography [10-40% MeCN (0.1% formic acid) in water (0.1% formic acid)]. The crude product was dissolved in $CH_2Cl_2$ (10 mL), washed with sat. aq. $NaHCO_3$ (5 mL), passed through a phase separator and the solvent removed under reduced pressure. The residue was taken up in MeCN (2 mL) and concentrated under reduced pressure (3×) to afford an orange solid (15 mg, 9%). LCMS (method C) m/z 583.5 $[M+H]^+$ at 2.28 min. $^1$H NMR (500 MHz, DMSO-$d_6$) δ 10.94 (s, 1H), 8.72 (d, J=2.3 Hz, 1H), 8.33 (d, J=7.2 Hz, 1H), 7.97 (dd, J=8.1, 2.3 Hz, 1H), 7.61-7.56 (m, 1H), 7.54-7.42 (m, 5H), 7.34-7.28 (m, 1H), 7.26 (d, J=8.1 Hz, 1H), 7.17-7.14 (m, 1H), 5.39 (d, J=7.2 Hz, 1H), 4.87-4.77 (m, 1H), 4.73 (s, 1H), 4.28-4.14 (m, 2H), 2.83 (s, 2H), 2.41-2.33 (m, 1H), 2.21-2.10 (m, 1H), 1.57 (d, J=6.3 Hz, 3H), 1.09 (s, 6H).

86. (5R)-5-Methyl-N-[(3S)-9-fluoro-2-oxo-5-phenyl-1,3-dihydro-1,4-benzodiazepin-3-yl]-2-[6-[(1R, 4R)-2-oxa-5-azabicyclo[2.2.1]heptan-5-yl]pyridin-3-yl]-6,7-dihydro-5H-pyrazolo[5,1-b][1,3]oxazine-3-carboxamide

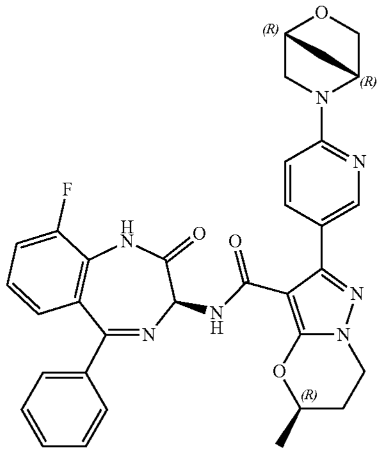

A solution of intermediate 90G (58 mg, 0.151 mmol) and 1.5 M aq. LiOH (1.5 mL, 2.25 mmol) in MeOH:THF (1:1; 3 mL) was heated at 50° C. overnight. The reaction was cooled to rt, acidified to pH≈7 with 1 M aq. HCl and the solvent removed under reduced pressure. The crude residue was dissolved in DMF (3 mL), HATU (57 mg, 0.151 mmol) and $NEt_3$ (63 μL, 0.453 mmol) added, followed by (3S)-3-amino-9-fluoro-5-phenyl-1,3-dihydro-1,4-benzodiazepin-2-one (41 mg, 0.151 mmol), and the reaction stirred at 40° C. for overnight. The reaction was diluted with MeOH and purified by ion exchange chromatography (SCX-2, eluting with MeOH, followed by product elution with ~2 N $NH_3$ in MeOH), followed by column chromatography [0-5% MeOH (0.7 N $NH_3$) in $CH_2Cl_2$]. Further purification by reverse phase column chromatography [15-70% MeCN (0.1% formic acid) in water (0.1% formic acid)] afforded a white solid (7 mg, 8% yield). LCMS (method C) m/z 608.4 $[M+H]^+$ at 2.23 min. $^1$H NMR (500 MHz, DMSO-$d_6$) δ 8.37 (d, J=2.5 Hz, 1H), 7.80 (dd, J=8.8, 2.4 Hz, 1H), 7.53-7.40 (m, 6H), 7.18 (s, 1H), 7.10 (d, J=7.8 Hz, 1H), 6.46 (d, J=8.8 Hz, 1H), 5.29-5.20 (m, 1H), 4.84 (s, 1H), 4.79-4.75 (m, 1H), 4.64 (d, J=2.4 Hz, 1H), 4.21-4.13 (m, 2H), 3.76 (dd, J=7.3, 1.5 Hz, 1H), 3.63 (d, J=7.3 Hz, 1H), 3.45 (dd, J=10.2, 1.6 Hz, 1H), 3.22 (d, J=10.0 Hz, 1H), 2.35-2.32 (m, 1H), 2.18-2.07 (m, 1H), 1.93-1.87 (m, 1H), 1.86-1.81 (m, 1H), 1.66 (s, 2H), 1.55 (d, J=6.2 Hz, 3H).

87. (5S)-5-Methyl-N-[(3R)-9-fluoro-2-oxo-5-phenyl-1,3-dihydro-1,4-benzodiazepin-3-yl]-2-[6-[(1S,4S)-2-oxa-5-azabicyclo[2.2.1]heptan-5-yl]pyridin-3-yl]-6,7-dihydro-5H-pyrazolo[5,1-b][1,3]oxazine-3-carboxamide

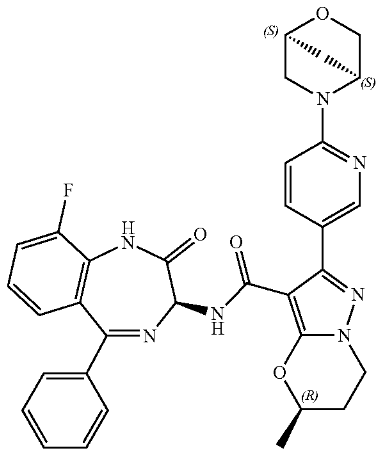

Prepared by an analogous procedure to the compound of Example 86, with purification by HPLC in place of reverse phase column chromatography using HPLC method 2 (15-100% MeCN in water containing 0.1% formic acid). LCMS (method A) m/z 608.6 $[M+H]^+$ at 1.00 min. $^1H$ NMR (500 MHz, DMSO-$d_6$) δ 8.37 (d, J=2.5 Hz, 1H), 7.80 (dd, J=8.8, 2.4 Hz, 1H), 7.53-7.40 (m, 6H), 7.18 (s, 1H), 7.10 (d, J=7.8 Hz, 1H), 6.46 (d, J=8.8 Hz, 1H), 5.29-5.20 (m, 1H), 4.84 (s, 1H), 4.79-4.75 (m, 1H), 4.64 (d, J=2.4 Hz, 1H), 4.21-4.13 (m, 2H), 3.76 (dd, J=7.3, 1.5 Hz, 1H), 3.63 (d, J=7.3 Hz, 1H), 3.45 (dd, J=10.2, 1.6 Hz, 1H), 3.22 (d, J=10.0 Hz, 1H), 2.35-2.32 (m, 1H), 2.18-2.07 (m, 1H), 1.93-1.87 (m, 1H), 1.86-1.81 (m, 1H), 1.66 (s, 2H), 1.55 (d, J=6.2 Hz, 3H).

88. (5R)-2-[2-Fluoro-6-[(1S,4S)-2-oxa-5-azabicyclo[2.2.1]heptan-5-yl]-3-pyridyl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide 89. (5R)-2-[6-Fluoro-2-[(1S,4S)-2-oxa-5-azabicyclo[2.2.1]heptan-5-yl]pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide

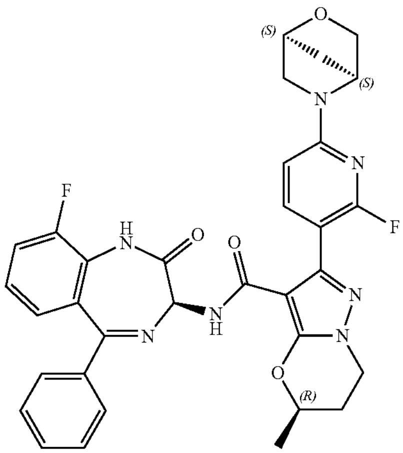

-continued

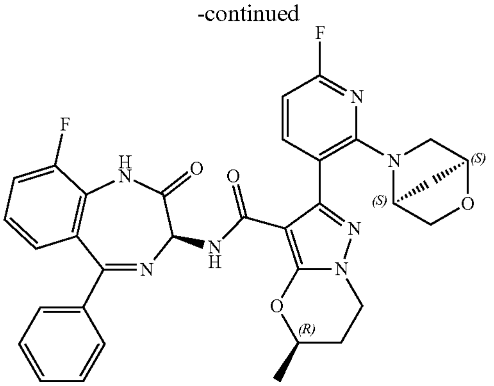

A solution of intermediates 124A/124B (199 mg, 0.50 mmol) and 1.5 M aq. LiOH (1.7 mL, 2.6 mmol) in MeOH:THF (1:1; 4 mL) was heated at 50° C. for 72 h. The reaction was cooled to rt, acidified to pH≈7 with 1 M aq. HCl and the solvent removed under reduced pressure. The crude residue was dissolved in DMF (3 mL), $NEt_3$ (136 μL, 0.98 mmol) and HATU (186 mg, 0.49 mmol) were added followed by (3S)-3-amino-9-fluoro-5-phenyl-1,3-dihydro-1,4-benzodiazepin-2-one (131 mg, 0.49 mmol) and the reaction heated at 40° C. for 1 h. The reaction was quenched with water, and the resultant precipitate isolated by filtration, washing with water (100 mL). Purification by column chromatography (0 to 6% MeOH in $CH_2Cl_2$) followed by purification by HPLC method 2 (33-100% MeCN in water containing 0.1% $NH_3$, 16 min run time) afforded Example 88 (first eluting regioisomer) and Example 89 (second eluting regioisomer). Example 88: white solid (67 mg, 20%). LCMS (method C) m/z 626.5 $[M+H]^+$ at 3.6 min. $^1H$ NMR (500 MHz, DMSO-$d_6$) 10.92 (s, 1H), 8.09 (d, J=7.5 Hz, 1H), 7.60-7.54 (m, 2H), 7.54-7.50 (m, 1H), 7.50-7.42 (m, 4H), 7.30 (ddd, J=8.1, 5.0 Hz, 1H), 7.13 (d, J=7.9 Hz, 1H), 6.37 (d, J=8.3 Hz, 1H), 5.35 (d, J=7.5 Hz, 1H), 4.84-4.73 (m, 2H), 4.69-4.62 (m, 1H), 4.24-4.10 (m, 2H), 3.78-3.71 (m, 1H), 3.63 (d, J=7.3 Hz, 1H), 3.44-3.40 (m, 1H), 3.21 (d, J=10.1 Hz, 1H), 2.40-2.30 (m, 1H), 2.20-2.07 (m, 1H), 1.91-1.80 (m, 2H), 1.55 (d, J=6.3 Hz, 3H).

Example 89: white solid (37 mg, 11%). LCMS (method C) m/z 626.5 $[M+H]^+$ at 3.78 min. $^1H$ NMR (500 MHz, DMSO-$d_6$) 10.92 (s, 1H), 8.04 (d, J=7.4 Hz, 1H), 7.61-7.52 (m, 1H), 7.55-7.47 (m, 1H), 7.50-7.37 (m, 5H), 7.33-7.25 (m, 1H), 7.12 (d, J=7.9 Hz, 1H), 6.24 (dd, J=7.9, 3.1 Hz, 1H), 5.32 (d, J=7.3 Hz, 1H), 4.84-4.74 (m, 1H), 4.55 (s, 1H), 4.46 (s, 1H), 4.24-4.09 (m, 2H), 3.73-3.64 (m, 2H), 3.04 (d, J=10.3 Hz, 1H), 2.81 (d, J=10.2 Hz, 1H), 2.39-2.30 (m, 1H), 2.19-2.07 (m, 1H), 1.75-1.67 (m, 2H), 1.55 (d, J=6.3 Hz, 3H).

90. (5R)-2-[2-Fluoro-6-[(1R,4R)-2-oxa-5-azabicyclo[2.2.1]heptan-5-yl]pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide

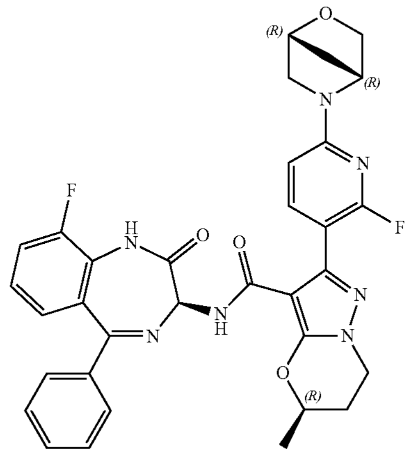

Prepared by an analogous procedure to that described for the compound of Example 88 from intermediate 123A/123B (212 mg, 0.53 mmol). Purification by HPLC method 3 (25-100% MeCN in water containing 0.1% $NH_3$) afforded Example 90 (first eluting regioisomer) as a white solid (71 mg, 22%). LCMS (method C) m/z 626.5 $[M+H]^+$ at 3.63 min. $^1H$ NMR (500 MHz, DMSO-$d_6$) δ 10.91 (s, 1H), 8.11 (d, J=7.5 Hz, 1H), 7.60-7.48 (m, 3H), 7.50-7.40 (m, 4H), 7.27 (s, 1H), 7.12 (d, J=7.9 Hz, 1H), 6.37 (d, J=8.3 Hz, 1H), 5.31 (d, J=7.1 Hz, 1H), 4.79 (d, J=12.3 Hz, 2H), 4.66 (d, J=2.4 Hz, 1H), 4.24-4.10 (m, 2H), 3.76 (d, J=7.4 Hz, 1H), 3.64 (d, J=7.4 Hz, 1H), 3.42 (d, J=10.1 Hz, 1H), 3.21 (d, J=10.1 Hz, 1H), 2.35 (d, J=14.4 Hz, 1H), 2.20-2.06 (m, 1H), 1.91-1.81 (m, 2H), 1.55 (d, J=6.3 Hz, 3H).

91. (5R)-2-[2-Fluoro-6-(2-oxa-6-azaspiro[3.3]heptan-6-yl)pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide

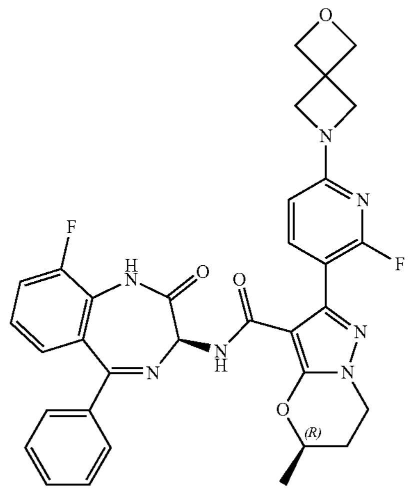

Prepared by an analogous procedure to that described for the compound of Example 88 from intermediates 125A/125B (118 mg, 0.29 mmol). Purification by HPLC method 2 (30-100% MeCN in water with 0.1% formic acid) afforded Example 91 (first eluting regioisomer) as a white solid (18 mg, 10%). LCMS (method C) m/z 626.5 $[M+H]^+$ at 3.53 min. $^1H$ NMR (500 MHz, DMSO-$d_6$) 10.92 (s, 1H), 8.07 (d, J=7.5 Hz, 1H), 7.60-7.55 (m, 2H), 7.54-7.49 (m, 1H), 7.48-7.42 (m, 4H), 7.30 (ddd, J=8.1, 8.1, 5.0 Hz, 1H), 7.13 (d, J=7.9 Hz, 1H), 6.21 (dd, J=8.1, 1.7 Hz, 1H), 5.33 (d, J=7.4 Hz, 1H), 4.82-4.74 (m, 1H), 4.70 (s, 4H), 4.22-4.14 (m, 2H), 4.11 (s, 4H), 2.38-2.31 (m, 1H), 2.19-2.06 (m, 1H), 1.54 (d, J=6.3 Hz, 3H).

92. (5R)-5-Methyl-2-[4-methyl-6-(propan-2-ylamino)pyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide

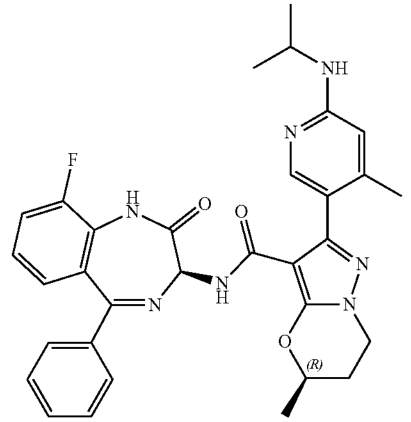

A solution of intermediate 69E (68 mg, 0.15 mmol) and 1.5 M aq. LiOH (0.51 mL, 0.77 mmol) in MeOH:THF (1:1; 2 mL) was heated at 50° C. for 90 h. Further 1.5 M aq. LiOH (0.51 mL, 0.77 mmol) was added and the reaction heated at 50° C. for 24 h. The reaction was cooled to rt, acidified to pH≈2 with 1 M aq. HCl and the solvent removed under reduced pressure. The crude residue was dissolved in DMF (1.5 mL), $NEt_3$ (50 μL, 0.36 mmol) and (3S)-3-amino-9-fluoro-5-phenyl-1,3-dihydro-1,4-benzodiazepin-2-one (32 mg, 0.12 mmol) were added followed by HATU (48 mg, 0.13 mmol) and the reaction stirred at rt for 1.5 h. The reaction was quenched with water (2 mL), acidified to pH≈4 with AcOH, and purified by ion exchange chromatography (2 g SCX-2 cartridge, washing with water, methanol, then eluting with 7 N $NH_3$ in MeOH). The fractions containing product were concentrated in vacuo and purified by column chromatography (0 to 5% MeOH in $CH_2Cl_2$) to afford a white solid (19 mg, 22%). LCMS (method C) m/z 582.6 $[M+H]^+$ at 2.38 min. $^1H$ NMR (500 MHz, DMSO-$d_6$) δ 10.90 (s, 1H), 8.06 (d, J=7.4 Hz, 1H), 7.70 (s, 1H), 7.62-7.54 (m, 1H), 7.56-7.50 (m, 1H), 7.50-7.41 (m, 4H), 7.35-7.26 (m, 1H), 7.16-7.10 (m, 1H), 6.24-6.21 (m, 1H), 6.20 (d, J=7.8 Hz, 1H), 5.33 (d, J=7.3 Hz, 1H), 4.83-4.75 (m, 1H), 4.23-4.13 (m, 2H), 4.03-3.92 (m, 1H), 2.34 (s, 1H), 2.21-2.10 (m, 1H), 1.99 (s, 3H), 1.55 (d, J=6.3 Hz, 3H), 1.12 (dd, J=6.5, 1.3 Hz, 6H).

93. (5R)-5-Methyl-2-[2-methyl-6-(propan-2-ylamino)pyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide

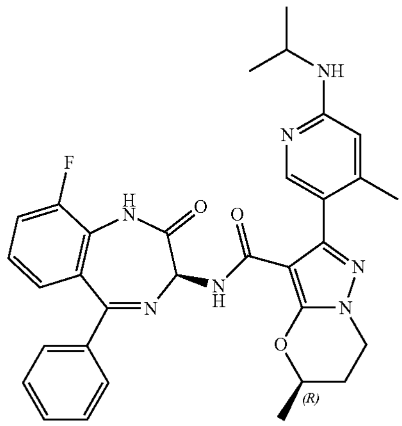

Prepared by an analogous procedure to that described for the compound of Example 92. LCMS (method C) m/z 582.5 $[M+H]^+$ at 2.38 min. $^1H$ NMR (500 MHz, DMSO-$d_6$) δ 10.91 (s, 1H), 8.10-8.03 (m, 1H), 7.62-7.55 (m, 1H), 7.55-7.49 (m, 1H), 7.49-7.41 (m, 4H), 7.35-7.26 (m, 1H), 7.16-7.11 (m, 2H), 6.22-6.17 (m, 2H), 5.33 (d, J=7.3, 1.2 Hz, 1H), 4.81-4.75 (m, 1H), 4.20-4.12 (m, 2H), 4.01-3.90 (m, 1H), 2.38-2.31 (m, 1H), 2.14 (s, 4H), 1.58-1.52 (m, 3H), 1.13 (dd, J=6.4, 1.4 Hz, 6H).

94. (5S)-5-Methyl-N-[(3S)-9-fluoro-2-oxo-5-phenyl-1,3-dihydro-1,4-benzodiazepin-3-yl]-2-[6-[(1R,4R)-2-oxa-5-azabicyclo[2.2.1]heptan-5-yl]pyridin-3-yl]-6,7-dihydro-5H-pyrazolo[5,1-b][1,3]oxazine-3-carboxamide

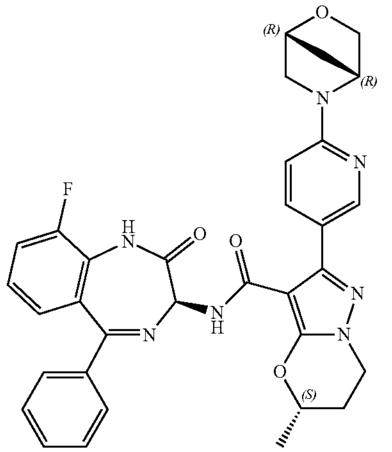

A solution of intermediate 91B (116 mg, 0.30 mmol) and 1.5 M aq. LiOH (2.1 mL, 3.0 mmol) in MeOH:THF (1:1, 3 mL) was heated at 50° C. for 64 h. The reaction was cooled to rt, acidified to pH≈2 with 1 M aq. HCl and the solvent removed under reduced pressure. The crude residue was dissolved in DMF (2 mL), $Et_3N$ (85 μL, 0.61 mmol) and (3S)-3-amino-9-fluoro-5-phenyl-1,3-dihydro-1,4-benzodiazepin-2-one (71 mg, 0.2 mmol) were added followed by HATU (81 mg, 0.2 mmol) and the reaction stirred at rt for 30 min. The reaction was quenched with water (15 mL), and the resultant precipitate isolated by filtration, washing with water (2×10 mL), then purified by column chromatography (0 to 6% MeOH in $CH_2Cl_2$). The aqueous filtrate was acidified to pH≈4 with AcOH, then purified by ion exchange chromatography (2 g SCX-2 cartridge, washing with water, methanol then eluting with 7 N $NH_3$ in MeOH). The fractions containing product were concentrated in vacuo and purified by column chromatography (0 to 5% MeOH in $CH_2Cl_2$) to afford an off-white solid (47 mg, 39%). LCMS (method C) m/z 608.5 $[M+H]^+$ at 2.31 min. $^1H$ NMR (500 MHz, DMSO-$d_6$) δ 10.94 (s, 1H), 8.40-8.36 (m, 1H), 8.32 (d, J=7.2 Hz, 1H), 7.81 (dd, J=8.8, 2.3 Hz, 1H), 7.59 (t, J=9.2 Hz, 1H), 7.55-7.43 (m, 5H), 7.36-7.28 (m, 1H), 7.16 (d, J=7.9 Hz, 1H), 6.48 (d, J=8.8 Hz, 1H), 5.39 (d, J=7.2 Hz, 1H), 4.85 (s, 1H), 4.77 (t, J=7.6 Hz, 1H), 4.65 (s, 1H), 4.25-4.14 (m, 2H), 3.80-3.74 (m, 1H), 3.63 (d, J=7.2 Hz, 1H), 3.49-3.42 (m, 1H), 3.23 (d, J=10.0 Hz, 1H), 2.40-2.32 (m, 1H), 2.18-2.10 (m, 1H), 1.93-1.87 (m, 1H), 1.87-1.81 (m, 1H), 1.57 (d, J=6.3 Hz, 3H).

95. (5R)-2-Anilino-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide

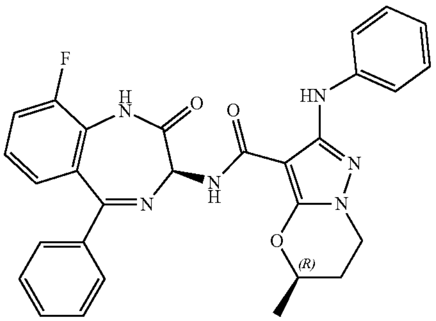

A solution of intermediate 72A (150 mg, 0.50 mmol) and 1.5 M aq. LiOH (0.33 mL, 0.50 mmol) in MeOH:THF (1:1; 2 mL) was heated at 50° C. for ~3 days. Further LiOH (1.5 M aq., 0.33 mL, 0.50 mmol) was added and the reaction heated for a further 24 h. The reaction was cooled to rt, neutralised with 1 M aq. citric acid to pH≈7 and the solvent removed under reduced pressure to afford a brown solid (136 mg, quantitative). A portion of the crude residue (82 mg, 0.30 mmol) was dissolved in DMF (2.5 mL), HATU (122 mg, 0.32 mmol) and $NEt_3$ (95 μL, 0.68 mmol) added, followed by (3S)-3-amino-9-fluoro-5-phenyl-1,3-dihydro-1,4-benzodiazepin-2-one (81 mg, 0.32 mmol), and the reaction stirred at 40° C. for 1 h. Analogous workup and purification to Example 48 afforded a white solid (31 mg, 19%). LCMS (method C) m/z 525.3 $[M+H]^+$ at 4.96 min. $^1H$ NMR (500 MHz, DMSO-$d_6$) δ 10.98 (s, 1H), 8.80 (s, 1H), 7.89 (d, J=7.4 Hz, 1H), 7.63-7.57 (m, 1H), 7.55-7.48 (m, 5H), 7.48-7.43 (m, 2H), 7.36-7.29 (m, 1H), 7.25-7.17 (m, 3H), 6.84-6.79 (m, 1H), 5.45 (d, J=7.3 Hz, 1H), 4.81-4.73 (m, 1H), 4.10-4.02 (m, 2H), 2.38-2.30 (m, 1H), 2.17-2.07 (m, 1H), 1.54 (d, J=6.2 Hz, 3H).

The following compounds were prepared by an analogous procedure to that described for the compound of Example 95. Examples 96 and 97 were subject to addition purification by reverse phase chromatography [35-65% MeCN (0.1% formic acid) in water (0.1% formic acid)].

TABLE 28

Example compounds.

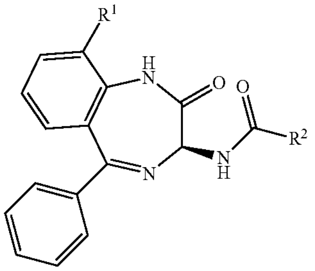

| Example | Name | $R^1$ | $R^2$ | $^1$H NMR δ (500 MHz, DMSO-$d_6$) | LCMS (ES+) m/z |
|---|---|---|---|---|---|
| 96. | (5R)-2-Anilino-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 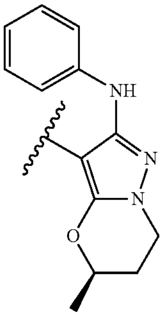 [SMILES: *c1c(Nc2ccccc2)nn2c1O[C@H](C)CC2] | 11.01 (s, 1H), 8.81 (s, 1H), 7.86 (d, J = 7.5 Hz, 1H), 7.69-7.63 (m, 1H), 7.54-7.42 (m, 7H), 7.38-7.32 (m, 2H), 7.31-7.27 (m, 1H), 7.26-7.20 (m, 2H), 6.84-6.79 (m, 1H), 5.38 (d, J = 7.5 Hz, 1H), 4.80-4.72 (m, 1H), 4.10-4.02 (m, 2H), 2.34 (d, J = 15.0 Hz, 1H), 2.17-2.06 (m, 1H), 1.53 (d, J = 6.3 Hz, 3H). | (method C) 507.4 $[M + H]^+$ at 4.94 min |
| 97. | (5R)-2-(4-Fluoroanilino)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 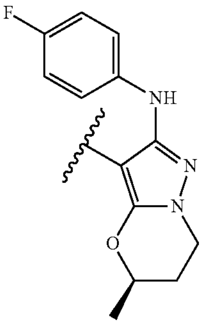 [SMILES: *c1c(Nc2ccc(F)cc2)nn2c1O[C@H](C)CC2] | 10.98 (s, 1H), 8.78 (s, 1H), 7.89 (d, J = 7.4 Hz, 1H), 7.63-7.57 (m, 1H), 7.57-7.48 (m, 5H), 7.45 (dd, J = 8.1, 6.8 Hz, 2H), 7.36-7.29 (m, 1H), 7.19 (d, J = 7.9 Hz, 1H), 7.10-7.04 (m, 2H), 5.44 (d, J = 7.3 Hz, 1H), 4.80-4.71 (m, 1H), 4.08-4.00 (m, 2H), 2.37-2.30 (m, 1H), 2.17-2.06 (m, 1H), 1.53 (d, J = 6.2 Hz, 3H). | (method C) 543.5 $[M + H]^+$ at 5.10 min |

The following compounds were prepared by an analogous procedure to that described for the compound of Example 1. DIPEA was used instead of $NEt_3$.

TABLE 29

Compounds prepared by amide coupling procedure A

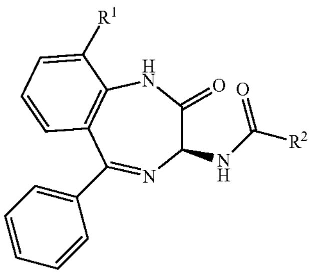

| Example | Name | $R^1$ | $R^2$ | $^1H$ NMR δ (400 MHz, DMSO-$d_6$) | LRMS APCI+ m/z |
|---|---|---|---|---|---|
| 98 | (5R)-N-[(3S)-9-fluoro-2-oxo-5-phenyl-1,3-dihydro-1,4-benzodiazepin-3-yl]-5-methyl-2-(1-methylpyrazol-4-yl)-6,7-dihydro-5H-pyrazolo[5,1-b][1,3]oxazine-3-carboxamide | F | 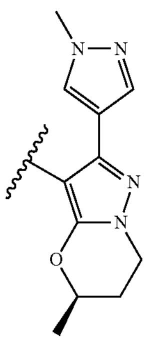 [SMILES: *c1c(-c2cnn(C)c2)nn2c1O[C@H](C)CC2] | 10.96 (s, 1H), 8.39 (s, 1H), 8.35 (d, J = 7.2 Hz, 1H), 7.85 (d, J = 0.7 Hz, 1H), 7.66-7.56 (m, 1H), 7.56-7.42 (m, 5H), 7.33 (td, J = 8.1, 5.0 Hz, 1H), 7.20 (dd, J = 8.0, 1.1 Hz, 1H), 5.44 (d, J = 7.2 Hz, 1H), 4.82-4.71 (m, 1H), 4.23-4.08 (m, 2H), 3.81 (s, 3H), 2.39-2.30 (m, 1H), 2.19-2.00 (m, 1H), 1.55 (d, J = 6.2 Hz, 3H). | 514.7 $[M + H]^+$ |
| 99 | 2-(1-Ethylpyrazol-4-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 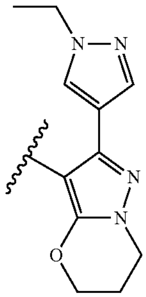 [SMILES: *c1c(-c2cnn(CC)c2)nn2c1OCCC2] | 10.98 (s, 1H), 8.38 (s, 1H), 8.11 (d, J = 7.6 Hz, 1H), 7.86 (s, 1H), 7.66-7.56 (m, 1H), 7.57-7.40 (m, 5H), 7.33 (td, J = 8.1, 5.0 Hz, 1H), 7.19 (d, J = 7.8 Hz, 1H), 5.49 (d, J = 7.6 Hz, 1H), 4.71-4.56 (m, 2H), 4.26-4.02 (m, 4H), 2.37-2.23 (m, 2H), 1.33 (t, J = 7.2 Hz, 3H). | 513.7 $[M + H]^+$ |
| 100 | 2-[4-[(Dimethylamino)methyl[-2-fluorophenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 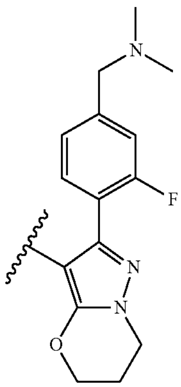 [SMILES: *c1c(-c2ccc(CN(C)C)cc2F)nn2c1OCCC2] | 10.96 (s, 1H), 7.89 (d, J = 7.8 Hz, 1H), 7.63-7.40 (m, 6H), 7.38-7.24 (m, 2H), 7.22-6.99 (m, 3H), 5.37 (d, J = 7.7 Hz, 1H), 4.72-4.62 (m, 2H), 4.20 (t, J = 6.1 Hz, 2H), 3.63-3.42 (m, 2H), 2.41-2.29 (m, 3H), 2.23 (s, 6H). | 570.9 $[M + H]^+$ |

TABLE 29-continued

Compounds prepared by amide coupling procedure A

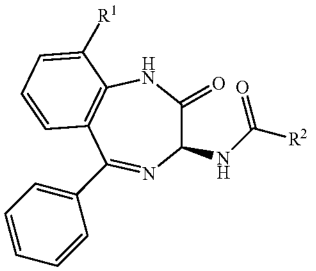

| Example | Name | $R^1$ | $R^2$ | $^1H$ NMR δ (400 MHz, DMSO-$d_6$) | LRMS APCI+ m/z |
|---|---|---|---|---|---|
| 101 | 2-[2-Fluoro-4-(morpholin-4-ylmethyl)phenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 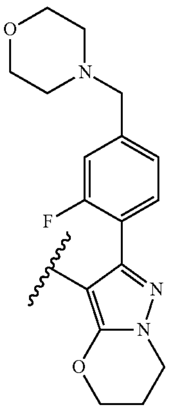 [SMILES: *c1c(-c2ccc(CN3CCOCC3)cc2F)nn2c1OCCC2] | 10.95 (s, 1H), 7.88 (d, J = 7.8 Hz, 1H), 7.72-7.38 (m, 6H), 7.38-7.19 (m, 2H), 7.19-6.92 (m, 3H), 5.37 (d, J = 7.8 Hz, 1H), 4.73-4.58 (m, 2H), 4.20 (t, J = 6.0 Hz, 2H), 3.56 (t, J = 4.6 Hz, 4H), 3.46 (s, 2H), 2.42-2.21 (m, 6H). | 613.6 $[M + H]^+$ |
| 102 | 2-[4-(Diethylaminomethyl)-2-fluorophenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 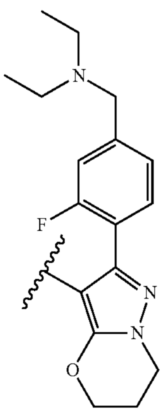 [SMILES: *c1c(-c2ccc(CN(CC)CC)cc2F)nn2c1OCCC2] | 10.96 (s, 1H), 7.89 (d, J = 7.8 Hz, 1H), 7.64-7.40 (m, 6H), 7.39-7.23 (m, 2H), 7.12 (td, J = 8.0, 1.3 Hz, 2H), 7.05 (d, J = 11.0 Hz, 1H), 5.38 (d, J = 7.8 Hz, 1H), 4.66 (dd, J = 6.0, 4.3 Hz, 2H), 4.21 (t, J = 6.1 Hz, 2H), 3.54 (s, 2H), 2.50-2.41 (m, 4H), 2.39-2.31 (m, 2H), 0.97 (t, J = 7.1 Hz, 6H). | 599.6 $[M + H]^+$ |

TABLE 29-continued

Compounds prepared by amide coupling procedure A

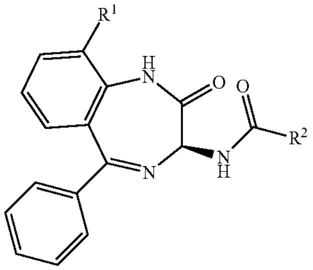

| Example | Name | $R^1$ | $R^2$ | $^1H$ NMR δ (400 MHz, DMSO-$d_6$) | LRMS APCI+ m/z |
|---|---|---|---|---|---|
| 103 | N-[(3S)-2-oxo-5-phenyl-1,3-dihydro-1,4-benzodiazepin-3-yl]-2-(1-propan-2-ylpyrazol-4-yl)-6,7-dihydro-5H-pyrazolo[5,1-b][1,3]oxazine-3-carboxamide | H | 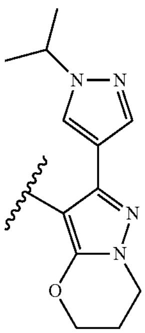 [SMILES: *c1c(-c2cnn(C(C)C)c2)nn2c1OCCC2] | 11.01 (s, 1H), 8.36 (s, 1H), 8.09 (d, J = 7.7 Hz, 1H), 7.87 (s, 1H), 7.66 (ddd, J = 8.6, 7.2, 1.7 Hz, 1H), 7.55-7.40 (m, 5H), 7.38-7.24 (m, 3H), 5.42 (d, J = 7.7 Hz, 1H), 4.67-4.56 (m, 2H), 4.54-4.41 (m, 1H), 4.15 (t, J = 6.0 Hz, 2H), 2.32 (dd, J = 7.7, 3.6 Hz, 2H), 1.37 (d, J = 6.6 Hz, 6H). | 510.6 $[M + H]^+$ |
| 104 | N-[(3S)-9-fluoro-2-oxo-5-phenyl-1,3-dihydro-1,4-benzodiazepin-3-yl]-2-[1-[(3-methyloxetan-3-yl)methyl]pyrazol-4-yl]-6,7-dihydro-5H-pyrazolo[5,1-b][1,3]oxazine-3-carboxamide | F | 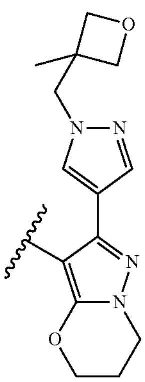 [SMILES: *c1c(-c2cnn(CC3(C)COC3)c2)nn2c1OCCC2] | 10.99 (s, 1H), 8.42 (d, 1H), 8.12 (d, J = 7.6 Hz, 1H), 7.90 (d, J = 0.6 Hz, 1H), 7.61 (ddd, J = 10.4, 8.1, 1.4 Hz, 1H), 7.56-7.42 (m, 5H), 7.33 (td, J = 8.1, 5.0 Hz, 1H), 7.19 (d, J = 7.8 Hz, 1H), 5.49 (d, J = 7.5 Hz, 1H), 4.65-4.59 (m, 2H), 4.56 (dd, J = 5.9, 2.2 Hz, 2H), 4.30 (s, 2H), 4.20-4.12 (m, 4H), 2.35-2.27 (m, 2H), 1.09 (s, 3H). | 568.1 $[M - H]^-$ |

The following compounds were prepared by an analogous procedure to that described for the compound of Example 5. Example 107 was subject to additional purification by SFC Method 1 (25:75% MeOH/$CO_2$). $^1H$ NMR were performed on a 400 MHz spectrometer in DMSO-$d_6$ unless otherwise specified. LRMS was performed with APCI ion source unless otherwise specified.

TABLE 30

Compounds prepared by amide coupling procedure B.

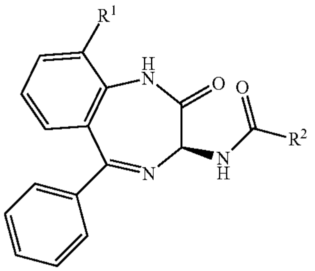

| Example | Name | $R^1$ | $R^2$ | $^1H$ NMR δ (400 MHz, DMSO-$d_6$) | LRMS m/z |
|---|---|---|---|---|---|
| 105 | N-[(3S)-9-fluoro-2-oxo-5-phenyl-1,3-dihydro-1,4-benzodiazepin-3-yl]-2-(2-fluorophenyl)-7-methyl-6,7-dihydro-5H-pyrazolo[5,1-b][1,3]oxazine-3-carboxamide | F | 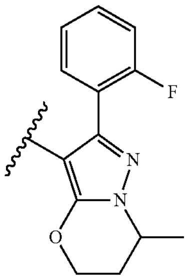 [SMILES: *c1c(-c2ccccc2F)nn2c1OCCC2C] | (500 MHz) δ 10.93 (d, J = 3.9 Hz, 1H), 7.89 (dd, J = 7.8, 4.2 Hz, 1H), 7.62-7.54 (m, 1H), 7.54-7.42 (m, 5H), 7.41-7.25 (m, 3H), 7.17 (td, J = 7.5, 1.1 Hz, 1H), 7.15-7.09 (m, 2H), 5.37 (dd, J = 7.8, 1.8 Hz, 1H), 4.79-4.68 (m, 1H), 4.67-4.59 (m, 1H), 4.50-4.39 (m, 1H), 2.47-2.41 (m, 1H), 2.18-2.05 (m, 1H), 1.54 (dd, J = 6.5, 2.1 Hz, 3H). | 526.1 $[M + H]^+$ |
| 106 | 2-(6-Ethylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 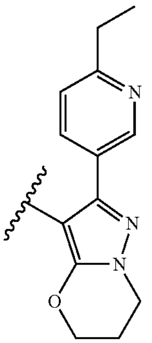 [SMILES: *c1c(-c2ccc(CC)nc2)nn2c1OCCC2] | (500 MHz) δ 10.95 (s, 1H), 8.67 (dd, J = 2.3, 0.8 Hz, 1H), 8.10 (d, J = 7.5 Hz, 1H), 7.92 (dd, J = 8.0, 2.3 Hz, 1H), 7.63-7.55 (m, 1H), 7.57-7.42 (m, 5H), 7.31 (td, J = 8.1, 5.0 Hz, 1H), 7.21 (dd, J = 8.1, 0.8 Hz, 1H), 7.15 (dd, J = 7.9, 1.3 Hz, 1H), 5.42 (d, J = 7.5 Hz, 1H), 4.69-4.60 (m, 2H), 4.21 (t, J = 6.1 Hz, 2H), 2.74 (q, J = 7.6 Hz, 2H), 2.40-2.24 (m, 2H), 1.22 (t, J = 7.6 Hz, 3H). | 525.4 $[M + H]^+$ |
| 107 | tert-butyl N-[3-[[(3S)-9-fluoro-2-oxo-5-phenyl-1,3-dihydro-1,4-benzodiazepin-3-yl]carbamoyl]-2-(2-fluorophenyl)-6,7-dihydro-5H-pyrazolo[5,1-b][1,3]oxazin-6-yl]-N-methylcarbamate | F | 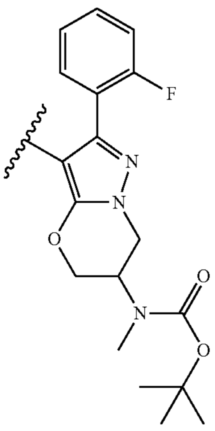 [SMILES: *c1c(-c2ccccc2F)nn2c1OCC(N(C)C(=O)OC(C)(C)C)C2] | δ 10.95 (s, 1H), 7.90 (d, J = 7.7 Hz, 1H), 7.61-7.32 (m, 8H), 7.29 (d, J = 5.0 Hz, 1H), 7.23-7.04 (m, 3H), 5.36 (dd, J = 7.6, 1.9 Hz, 1H), 4.77-4.66 (m, 3H), 4.54-4.31 (m, 2H), 2.83 (d, J = 4.5 Hz, 3H), 1.45 (s, 9H). | 644.3 $[M + H]^+$ |

TABLE 30-continued

Compounds prepared by amide coupling procedure B.

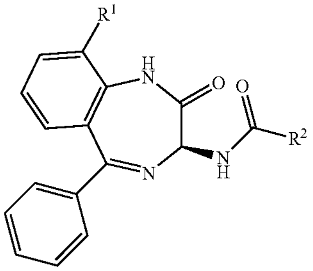

| Example | Name | $R^1$ | $R^2$ | $^1H$ NMR δ (400 MHz, DMSO-$d_6$) | LRMS m/z |
|---|---|---|---|---|---|
| 108 | tert-butyl N-ethyl-N-[3-[[(3S)-9-fluoro-2-oxo-5-phenyl-1,3-dihydro-1,4-benzodiazepin-3-yl]carbamoyl]-2-(2-fluorophenyl)-6,7-dihydro-5H-pyrazolo[5,1-b][1,3]oxazin-6-yl]carbamate | F | 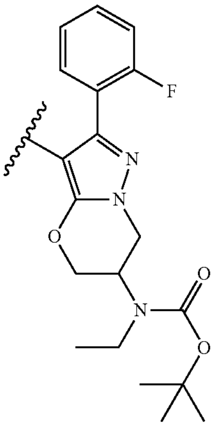 [SMILES: *c1c(-c2ccccc2F)nn2c1OCC(N(CC)C(=O)OC(C)(C)C)C2] | δ 10.93 (s, 1H), 7.93-7.81 (m, 1H), 7.61-7.33 (m, 7H), 7.35-7.24 (m, 1H), 7.24-7.07 (m, 3H), 5.41-5.30 (m, 1H), 4.81-4.59 (m, 3H), 4.46-4.30 (m, 2H), 3.30-3.20 (m, 2H), 1.45 (s, 8H), 1.15-1.0 (m, 3H). | 657.9 $[M + H]^+$ |
| 109 | (5S)-2-Benzyl-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 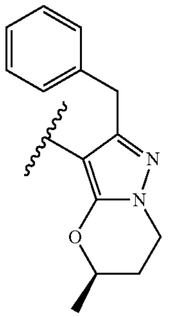 [SMILES: *c1c(Cc2ccccc2)nn2c1O[C@H](C)CC2] | δ 10.94 (s, 1H), 8.08 (d, J = 7.5 Hz, 1H), 7.64-7.54 (m, 1H), 7.56-7.43 (m, 5H), 7.32 (td, J = 8.1, 5.0 Hz, 1H), 7.26-7.15 (m, 5H), 7.15-7.09 (m, 1H), 5.41 (d, J = 7.4 Hz, 1H), 4.78-4.65 (m, 1H), 4.17-4.00 (m, 4H), 2.35-2.24 (m, 1H), 2.17-1.99 (m, 1H), 1.51 (d, J = 6.3 Hz, 3H). | 524.7 $[M + H]^+$ |
| 110 | N-[(3S)-9-fluoro-2-oxo-5-phenyl-1,3-dihydro-1,4-benzodiazepin-3-yl]-2-(2-fluorophenyl)-6-(hydroxymethyl)-6,7-dihydro-5H-pyrazolo[5,1-b][1,3]oxazine-3-carboxamide | F | 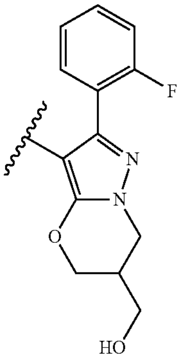 [SMILES: *c1c(-c2ccccc2F)nn2c1OCC(CO)C2] | δ 10.96 (s, 1H), 7.98-7.82 (m, 1H), 7.63-7.25 (m, 9H), 7.23-7.07 (m, 3H), 5.42-5.33 (m, 1H), 5.13-5.03 (m, 1H), 4.78-4.67 (m, 1H), 4.56-4.44 (m, 1H), 4.33-4.22 (m, 1H), 4.10-3.95 (m, 1H), 3.59 (t, J = 6.1 Hz, 2H), 2.66-2.55 (m, 1H). | 544.9 $[M + H]^+$ |

TABLE 30-continued

Compounds prepared by amide coupling procedure B.

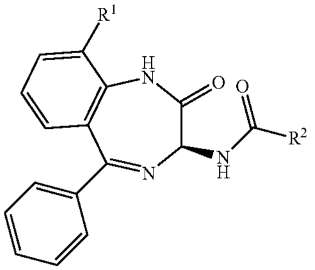

| Example | Name | $R^1$ | $R^2$ | $^1H$ NMR δ (400 MHz, DMSO-$d_6$) | LRMS m/z |
|---|---|---|---|---|---|
| 111 | (5R)-N-[(3S)-9-fluoro-2-oxo-5-phenyl-1,3-dihydro-1,4-benzodiazepin-3-yl]-5-methyl-2-[1-(oxan-4-yl)pyrazol-4-yl]-6,7-dihydro-5H-pyrazolo[5,1-b][1,3]oxazine-3-carboxamide | F | 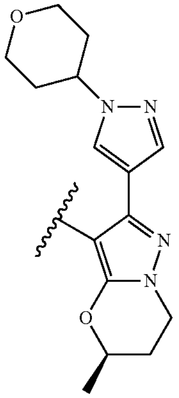 [SMILES: *c1c(-c2cnn(C3CCOCC3)c2)nn2c1O[C@H](C)CC2] | δ 10.97 (s, 1H), 8.45 (s, 1H), 8.35 (d, J = 7.3 Hz, 1H), 7.91 (s, 1H), 7.66-7.56 (m, 1H), 7.56-7.40 (m, 5H), 7.34 (td, J = 8.0, 5.0 Hz, 1H), 7.20 (d, J = 7.9 Hz, 1H), 5.45 (d, J = 7.2 Hz, 1H), 4.87-4.69 (m, 1H), 4.48-4.30 (m, 1H), 4.22-4.08 (m, 2H), 3.92 (d, J = 11.4 Hz, 2H), 3.50-3.36 (m, 2H), 2.35-2.29 (m, 1H), 2.23-2.05 (m, 1H), 2.05-1.83 (m, 4H), 1.55 (d, J = 6.3 Hz, 3H). | 585.1 [M + H]+ |
| 112 | (5R)-N-[(3S)-9-fluoro-2-oxo-5-phenyl-1,3-dihydro-1,4-benzodiazepin-3-yl]-5-methyl-2-(1-propan-2-ylpyrazol-4-yl)-6,7-dihydro-5H-pyrazolo[5,1-b][1,3]oxazine-3-carobxamide | F | 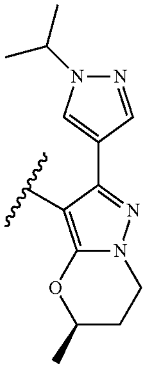 [SMILES: *c1c(-c2cnn(C(C)C)c2)nn2c1O[C@H](C)CC2] | δ 10.97 (s, 1H), 8.39 (s, 1H), 8.35 (d, J = 7.3 Hz, 1H), 7.89 (s, 1H), 7.66-7.56 (m, 1H), 7.57-7.41 (m, 5H), 7.33 (td, J = 8.1, 5.0 Hz, 1H), 7.20 (d, J = 7.9 Hz, 1H), 5.45 (d, J = 7.3 Hz, 1H), 4.85-4.71 (m, 1H), 4.54-4.40 (m, 1H), 4.21-4.08 (m, 2H), 2.36-2.28 (m, 1H), 2.23-2.03 (m, 1H), 1.55 (d, J = 6.2 Hz, 3H), 1.38 (dd, J = 6.6, 1.4 Hz, 6H). | 543.0 [M + H]+ |
| 113 | N-[(3S)-9-fluoro-2-oxo-5-phenyl-1,3-dihydro-1,4-benzodiazepin-3-yl]-2-(2-fluorophenyl)-6-(methoxymethyl)-6,7-dihydro-5H-pyrazolo[5,1-b][1,3]oxazine-3-carboxmaide | F | 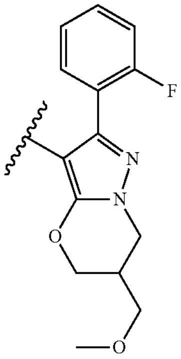 [SMILES: *c1c(-c2ccccc2F)nn2c1OCC(COC)C2] | δ 10.95 (s, 1H), 7.89 (t, J = 7.4 Hz, 1H), 7.63-7.24 (m, 9H), 7.23-7.05 (m, 3H), 5.36 (dd, J = 7.7, 2.2 Hz, 1H), 4.78-4.65 (m, 1H), 4.57-4.43 (m, 1H), 4.29 (dd, J = 12.3, 5.5 Hz, 1H), 4.02 (dd, J = 12.3, 7.5 Hz, 1H), 3.51 (dd, J = 7.4, 2.6 Hz, 2H), 3.33 (s, 3H), 2.81 (s, 1H). | 559.1 [M + H]+ |

TABLE 30-continued

Compounds prepared by amide coupling procedure B.

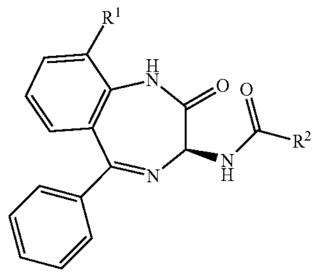

| Example | Name | $R^1$ | $R^2$ | $^1H$ NMR δ (400 MHz, DMSO-$d_6$) | LRMS m/z |
|---|---|---|---|---|---|
| 114 | (5R)-2-Cyclohexyl-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 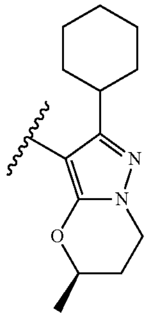 [SMILES: *c1c(C2CCCCC2)nn2c1O[C@H](C)CC2] | δ 10.93 (s, 1H), 8.08 (d, J = 7.4 Hz, 1H), 7.64-7.56 (m, 1H), 75.6-7.41 (m, 5H), 7.33 (td, J = 8.1, 5.0 Hz, 1H), 7.18 (d, J = 8.1 Hz, 1H), 5.41 (d, J = 7.4 Hz, 1H), 4.81-4.61 (m, 1H), 4.17-3.98 (m, 2H), 3.20-3.06 (m, 1H), 2.38-2.22 (m, 1H), 2.15-2.00 (m, 1H), 1.89-1.59 (m, 5H), 1.51 (d, J = 6.2 Hz, 3H), 1.49-1.06 (m, 6H). | 516.7 [M + H]+ |
| 115 | (5R)-2-(1,3-Dimethylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 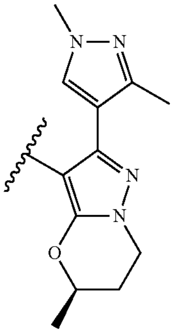 [SMILES: *c1c(-c2cn(C)nc2C)nn2c1O[C@H](C)CC2] | δ 10.95 (s, 1H), 8.29 (d, J = 7.2 Hz, 1H), 8.19 (s, 1H), 7.64-7.56 (m, 1H), 7.56-7.40 (m, 5H), 7.32 (td, J = 8.1, 5.1 Hz, 1H), 7.22-7.15 (m, 1H), 5.40 (d, J = 7.2 Hz, 1H), 4.82-4.71 (m, 1H), 4.22-4.09 (m, 2H), 3.72 (s, 3H), 2.38-2.31 (m, 1H), 2.27 (s, 3H), 2.19-2.03 (m, 1H), 1.54 (d, J = 6.3 Hz, 3H). | 528.5 [M + H]+ |
| 116 | (5R)-N-[(3S)-9-fluoro-2-oxo-5-phenyl-1,3-dihydro-1,4-benzodiazepin-3-yl]-5-methyl-2-[1-(oxetan-3-yl)pyrazol-4-yl]-6,7-dihydro-5H-pyrazolo[5,1-b][1,3]oxazine-3-carboxamide | F | 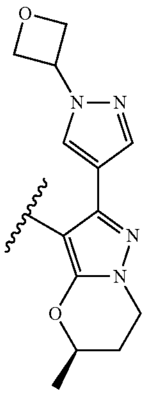 [SMILES: *c1c(-c2cnn(C3COC3)c2)nn2c1O[C@H](C)CC2] | δ 10.97 (s, 1H), 8.53 (d, J = 0.7 Hz, 1H), 8.36 (d, J = 7.2 Hz, 1H), 8.02 (s, 1H), 7.67-7.59 (m, 1H), 7.59-7.42 (m, 5H), 7.33 (td, J = 8.1, 5.0 Hz, 1H), 7.20 (dd, J = 7.9, 1.3 Hz, 1H), 5.67-5.57 (m, 1H), 5.44 (d, J = 7.2 Hz, 1H), 4.91-4.84 (m, 4H), 4.84-4.73 (m, 1H), 4.23-4.09 (m, 2H), 2.39-2.32 (m, 1H), 2.19-2.05 (m, 1H), 1.55 (d, J = 6.2 Hz, 3H). | 556.4 [M + H]+ |

TABLE 30-continued

Compounds prepared by amide coupling procedure B.

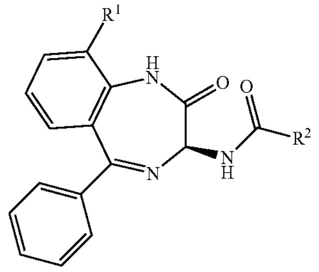

| Example | Name | $R^1$ | $R^2$ | $^1H$ NMR δ (400 MHz, DMSO-$d_6$) | LRMS m/z |
|---|---|---|---|---|---|
| 117 | (5R)-N-[(3S)-9-fluoro-2-oxo-5-phenyl-1,3-dihydro-1,4-benzodiazepin-3-yl]-2-[1-(2-hydroxyethyl)pyrazol-4-yl]-5-methyl-6,7-dihydro-5H-pyrazolo[5,1-b][1,3]oxazine-3-carboxamide | F | 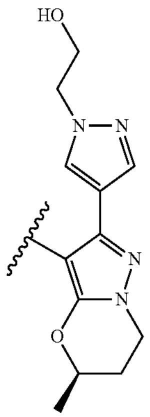 [SMILES: *c1c(-c2cnn(CCO)c2)nn2c1O[C@H](C)CC2] | δ 10.96 (s, 1H), 8.41 (d, J = 0.7 Hz, 1H), 8.36 (d, J = 7.2 Hz, 1H), 7.89 (d, J = 0.7 Hz, 1H), 7.65-7.57 (m, 1H), 7.57-7.38 (m, 5H), 7.33 (td, J = 8.1, 5.0 Hz, 1H), 7.20 (d, J = 7.9 Hz, 1H), 5.44 (d, J = 7.2 Hz, 1H), 4.84 (t, J = 5.3 Hz, 1H), 4.82-4.72 (m, 1H), 4.24-4.06 (m, 4H), 3.69 (q, J = 5.6 Hz, 2H), 2.37-2.32 (m, 1H), 2.18-2.06 (m, 1H), 1.55 (d, J = 6.3 Hz, 3H). | 544.6 $[M + H]^+$ |
| 118 | (5R)-N-[(3S)-9-fluoro-2-oxo-5-phenyl-1,3-dihydro-1,4-benzodiazepin-3-yl]-5-methyl-2-[1-(2,2,2-trifluoroethyl)pyrazol-4-yl]-6,7-dihydro-5H-pyrazolo[5,1-b][1,3]oxazine-3-carboxamide | F | 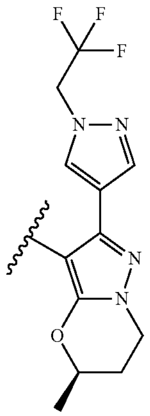 [SMILES: *c1c(-c2cnn(CC(F)(F)F)c2)nn2c1O[C@H](C)CC2] | δ 10.97 (s, 1H), 8.65 (s, 1H), 8.38 (d, J = 7.2 Hz, 1H), 8.00 (d, J = 0.6 Hz, 1H), 7.66-7.57 (m, 1H), 7.57-7.38 (m, 5H), 7.33 (td, J = 8.1, 5.1 Hz, 1H), 7.20 (dd, J = 8.0, 1.3 Hz, 1H), 5.45 (d, J = 7.2 Hz, 1H), 5.22-5.09 (m, 2H), 4.85-4.73 (m, 1H), 4.22-4.08 (m, 2H), 2.40-2.33 (m, 1H), 2.20-2.05 (m, 1H), 1.56 (d, J = 6.3 Hz, 3H). | 582.6 $[M + H]^+$ |

TABLE 30-continued

Compounds prepared by amide coupling procedure B.

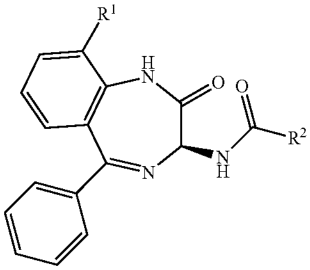

| Example | Name | $R^1$ | $R^2$ | $^1$H NMR δ (400 MHz, DMSO-$d_6$) | LRMS m/z |
|---|---|---|---|---|---|
| 119 | (5R)-N-[(3S)-9-fluoro-2-oxo-5-phenyl-1,3-dihydro-1,4-benzodiazepin-3-yl]-2-[1-(2-methoxyethyl)pyrazol-4-yl]-5-methyl-6,7-dihydro-5H-pyrazolo[5,1-b][1,3]oxazine-3-carboxamide | F | 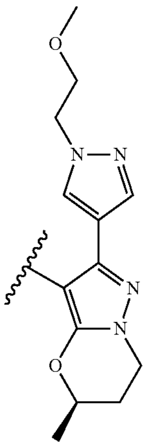 [SMILES: *c1c(-c2cnn(CCOC)c2)nn2c1O[C@H](C)CC2] | δ 10.96 (s, 1H), 8.39 (d, J = 0.6 Hz, 1H), 8.36 (d, J = 7.2 Hz, 1H), 7.90 (d, J = 0.7 Hz, 1H), 7.66-7.56 (m, 1H), 7.57-7.41 (m, 5H), 7.33 (td, J = 8.1, 5.0 Hz, 1H), 7.20 (dd, J = 7.9, 1.3 Hz, 1H), 5.44 (d, J = 7.2 Hz, 1H), 4.83-4.72 (m, 1H), 4.23 (t, J = 5.3 Hz, 2H), 4.22-4.10 (m, 2H), 3.65 (t, J = 5.4 Hz, 2H), 3.19 (s, 3H), 2.36-2.29 (m, 1H), 2.19-2.06 (m, 1H), 1.55 (d, J = 6.2 Hz, 3H). | 558.7 $[M + H]^+$ |
| 120 | (5R)-2-[1-(Difluoromethyl)pyrazol-4-yl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 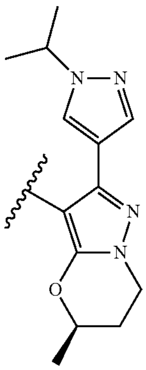 [SMILES: *c1c(-c2cnn(C(C)C)c2)nn2c1O[C@H](C)CC2] | δ 10.98 (s, 1H), 8.95 (d, J = 0.6 Hz, 1H), 8.41 (d, J = 7.1 Hz, 1H), 8.18 (s, 1H), 7.84 (t, J = 58.9 Hz, 1H), 7.67-7.55 (m, 1H), 7.56-7.41 (m, 5H), 7.33 (td, J = 8.1, 5.0 Hz, 1H), 7.20 (dd, J = 7.9, 1.3 Hz, 1H), 5.45 (d, J = 7.1 Hz, 1H), 4.87-4.76 (m, 1H), 4.27-4.09 (m, 2H), 2.41-2.29 (m, 1H), 2.21-2.06 (m, 1H), 1.56 (d, J = 6.2 Hz, 3H). | 550.7 $[M + H]^+$ |
| 121 | (5R)-2-(1,5-Dimethylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 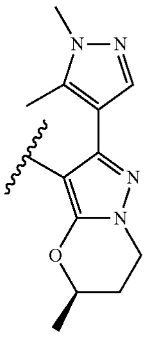 [SMILES: *c1c(-c2cnn(C)c2C)nn2c1O[C@H](C)CC2] | δ 10.93 (s, 1H), 8.19 (d, J = 7.3 Hz, 1H), 7.69-7.40 (m, 7H), 7.32 (td, J = 8.1, 5.0 Hz, 1H), 7.27-7.09 (m, 1H), 5.37 (d, J = 7.3 Hz, 1H), 4.84-4.67 (m, 1H), 4.23-4.09 (m, 2H), 3.71 (s, 3H), 2.38-2.31 (m, 1H), 2.29 (s, 3H), 2.19-2.04 (m, 1H), 1.54 (d, J = 6.2 Hz, 3H). | 528.5 $[M + H]^+$ |

TABLE 30-continued

Compounds prepared by amide coupling procedure B.

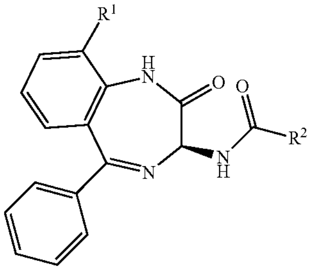

| Example | Name | $R^1$ | $R^2$ | $^1H$ NMR δ (400 MHz, DMSO-$d_6$) | LRMS m/z |
|---|---|---|---|---|---|
| 122 | (5R)-N-[(3S)-9-fluoro-2-oxo-5-phenyl-1,3-dihydro-1,4-benzodiazepin-3-yl]-2-[1-(2-hydroxy-2-methylpropyl)pyrazol-4-yl]-5-methyl-6,7-dihydro-5H-pyrazolo[5,1-b][1,3]oxazine-3-carboxamide | F | 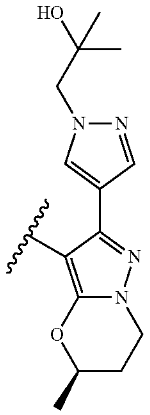 [SMILES: *c1c(-c2cnn(CC(C)(C)O)c2)nn2c1O[C@H](C)CC2] | δ 10.96 (s, 1H), 8.43 (d, J = 0.7 Hz, 1H), 8.36 (d, J = 7.2 Hz, 1H), 7.89 (d, J = 0.6 Hz, 1H), 7.65-7.55 (m, 1H), 7.56-7.42 (m, 5H), 7.33 (td, J = 8.1, 5.1 Hz, 1H), 7.20 (dd, J = 7.9, 1.3 Hz, 1H), 5.44 (d, J = 7.2 Hz, 1H), 4.86-4.72 (m, 1H), 4.64 (s, 1H), 4.25-4.07 (m, 2H), 3.98 (s, 2H), 2.36-2.27 (m, 1H), 2.22-2.06 (m, 1H), 1.55 (d, J = 6.3 Hz, 3H), 1.03 (d, J = 4.3 Hz, 6H). | 572.6 [M + H]+ |
| 123 | N-[(3S)-9-Fluoro-2-oxo-5-phenyl-1,3-dihydro-1,4-benzodiazepin-3-yl]-2-(2-fluorophenyl)-5-(hydroxymethyl)-6,7-dihydro-5H-pyrazolo[5,1-b][1,3]oxazine-3-carboxamide | F | 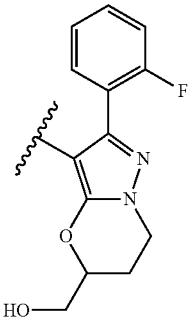 [SMILES: *c1c(-c2ccccc2F)nn2c1OC(CO)CC2] | δ 10.94 (s, 1H), 8.11 (d, J = 7.6 Hz, 0.5H), 8.07 (d, J = 7.5 Hz, 0.5H), 7.65-7.21 (m, 8H), 7.21-7.03 (m, 3H), 5.35 (d, J = 7.5 Hz, 0.5H), 5.33 (d, J = 7.4 Hz, 0.5H), 5.27-5.12 (m, 1H), 4.78-4.59 (m, 1H), 4.31-4.13 (m, 2H), 3.94-3.73 (m, 2H), 2.41-2.15 (m, 2H). | 545.5 [M + H]+ |
| 124 | N-[(3S)-9-fluoro-2-oxo-5-phenyl-1,3-dihydro-1,4-benzodiazepin-3-yl]-2-(2-fluorophenyl)-6-(pyrazol-1-ylmethyl)-6,7-dihydro-5H-pyrazolo[5,1-b][1,3]oxazine-3-carboxamide | F | 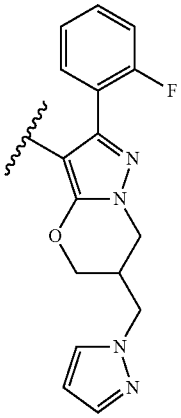 [SMILES: *c1c(-c2ccccc2F)nn2c1OCC(Cn1cccn1)C2] | δ 10.95 (s, 1H), 7.97-7.87 (m, 1H), 7.87-7.79 (m, 1H), 7.65-7.25 (m, 10H), 7.25-7.06 (m, 3H), 6.35-6.28 (m, 1H), 5.44-5.28 (m, 1H), 4.74-4.56 (m, 1H), 4.56-4.29 (m, 3H), 4.29-4.15 (m, 1H), 4.10-3.73 (m, 2H), 3.12-2.94 (m, 1H). | 594.5 [M + H]+ |

TABLE 30-continued

Compounds prepared by amide coupling procedure B.

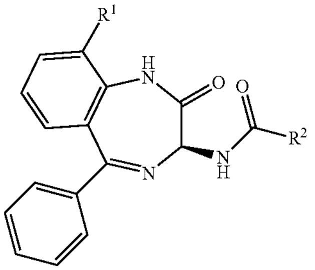

| Example | Name | $R^1$ | $R^2$ | $^1H$ NMR δ (400 MHz, DMSO-$d_6$) | LRMS m/z |
|---|---|---|---|---|---|
| 125 | (5R)-2-(1-Cyclopropylpyrazol-4-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 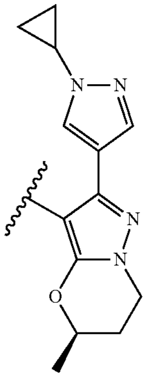 [SMILES: *c1c(-c2cnn(C3CC3)c2)nn2c1O[C@H](C)CC2] | δ 10.99 (s, 1H), 8.44 (s, 1H), 8.32 (d, J = 7.3 Hz, 1H), 7.84 (s, 1H), 7.71-7.61 (m, 1H), 7.56-7.40 (m, 5H), 7.40-7.22 (m, 3H), 5.37 (d, J = 7.3 Hz, 1H), 4.84-4.68 (m, 1H), 4.25-4.07 (m, 2H), 3.78-3.65 (m, 1H), 2.38-2.28 (m, 1H), 2.18-2.02 (m, 1H), 1.54 (d, J = 6.2 Hz, 3H), 1.04-0.95 (m, 2H), 0.98-0.86 (m, 2H). | 522.7 $[M + H]^+$ |
| 126 | (5R)-2-(1-Cyclopropylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 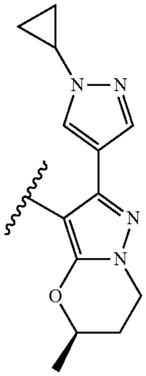 [SMILES: *c1c(-c2cnn(C3CC3)c2)nn2c1O[C@H](C)CC2] | δ 10.97 (s, 1H), 8.44 (s, 1H), 8.36 (d, J = 7.2 Hz, 1H), 7.84 (s, 1H), 7.66-7.56 (m, 1H), 7.57-7.40 (m, 5H), 7.34 (td, J = 8.1, 5.0 Hz, 1H), 7.20 (d, J = 7.9 Hz, 1H), 5.45 (d, J = 7.2 Hz, 1H), 4.83-4.71 (m, 1H), 4.20-4.08 (m, 2H), 3.77-3.65 (m, 1H), 2.36-2.28 (m, 1H), 2.19-2.04 (m, 1H), 1.55 (d, J = 6.2 Hz, 3H), 1.02-0.88 (m, 4H). | 540.8 $[M + H]^+$ |
| 127 | (5S)-2-(6-Ethylpyridin-3-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 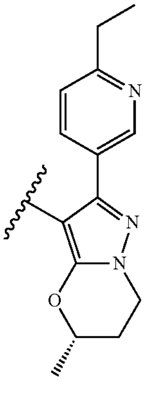 [SMILES: *c1c(-c2ccc(CC)nc2)nn2c1O[C@@H](C)CC2] | δ 10.97 (s, 1H), 8.70 (d, J = 2.2 Hz, 1H), 8.35 (d, J = 7.2 Hz, 1H), 7.96 (dd, J = 8.0, 2.3 Hz, 1H), 7.63-7.39 (m, 6H), 7.31 (td, J = 8.1, 5.0 Hz, 1H), 7.23 (d, J = 8.1 Hz, 1H), 7.15 (d, J = 7.9 Hz, 1H), 5.39 (d, J = 7.2 Hz, 1H), 4.86-4.74 (m, 1H), 4.28-4.15 (m, 2H), 2.74 (q, J = 7.6 Hz, 2H), 2.42-2.28 (m, 1H), 2.28-2.08 (m, 1H), 1.57 (d, J = 6.3 Hz, 3H), 1.22 (t, J = 7.6 Hz, 3H). | 539.6 $[M + H]^+$ |

TABLE 30-continued

Compounds prepared by amide coupling procedure B.

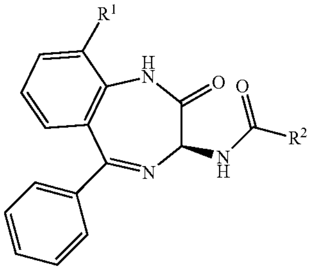

| Example | Name | $R^1$ | $R^2$ | $^1H$ NMR δ (400 MHz, DMSO-$d_6$) | LRMS m/z |
|---|---|---|---|---|---|
| 128 | 2-(2,4-Difluorophenyl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide | F | 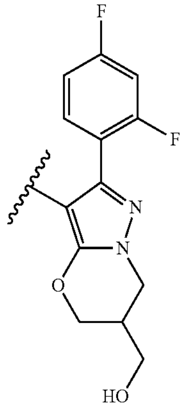 [SMILES: *c1c(-c2ccc(F)cc2F)nn2c1OCC(CO)C2] | δ 10.96 (d, J = 4.9 Hz, 1H), 7.90 (t, J = 7.7 Hz, 1H), 7.66-7.36 (m, 7H), 7.30 (td, J = 8.1, 5.0 Hz, 1H), 7.26-6.99 (m, 3H), 5.36 (dd, J = 7.6, 2.7 Hz, 1H), 5.08 (td, J = 5.3, 1.5 Hz, 1H), 4.72 (dd, J = 10.8, 3.3 Hz, 1H), 4.62-4.39 (m, 1H), 4.27 (dd, J = 12.3, 5.5 Hz, 1H), 4.03 (dd, J = 12.3, 7.5 Hz, 2H), 3.83-3.48 (m, 2H), 2.64-2.54 (m, 1H). | 562.7 [M + H]$^+$ |
| 129 | 2-(2,6-Difluorophenyl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide | F | 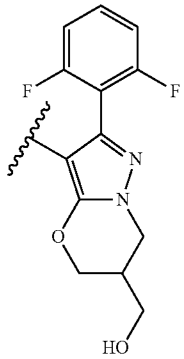 [SMILES: *c1c(-c2c(F)cccc2F)nn2c1OCC(CO)C2] | δ 10.96 (s, 1H), 7.95-7.79 (m, 1H), 7.64-7.38 (m, 6H), 7.37-7.24 (m, 1H), 7.18-6.97 (m, 3H), 5.42-5.24 (m, 1H), 5.19-5.01 (m, 1H), 4.85-4.69 (m, 1H), 4.60-4.46 (m, 1H), 4.39-4.20 (m, 1H), 4.15-3.96 (m, 1H), 3.65-3.49 (m, 2H), 2.67-2.56 (m, 1H). | 562.8 [M + H]$^+$ |
| 130 | 2-(1-Ethylpyrazol-4-yl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide | F | 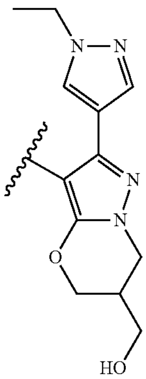 [SMILES: *c1c(-c2cnn(CC)c2)nn2c1OCC(CO)C2] | δ 10.98 (s, 1H), 8.37 (s, 1H), 8.16-8.09 (m, 1H), 7.86 (s, 1H), 7.66-7.56 (m, 1H), 7.57-7.42 (m, 5H), 7.33 (td, J = 8.1, 5.0 Hz, 1H), 7.19 (d, J = 7.9 Hz, 1H), 5.48 (dd, J = 7.5, 4.1 Hz, 1H), 5.12-5.02 (m, 1H), 4.74-4.66 (m, 1H), 4.47 (dt, J = 10.8, 7.2 Hz, 1H), 4.22 (dd, J = 12.5, 5.5 Hz, 1H), 4.10 (q, J = 7.2 Hz, 2H), 3.97 (dd, J = 12.3, 7.2 Hz, 1H), 3.56 (t, J = 6.2 Hz, 2H), 1.33 (td, J = 7.3, 0.9 Hz, 3H). | 544.8 [M + H]$^+$ |

TABLE 30-continued

Compounds prepared by amide coupling procedure B.

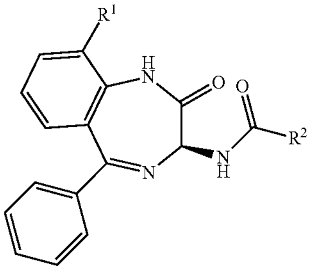

| Example | Name | $R^1$ | $R^2$ | $^1H$ NMR δ (400 MHz, DMSO-$d_6$) | LRMS m/z |
|---|---|---|---|---|---|
| 131 | 2-(2,4-Difluorophenyl)-6-(hydroxymethyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 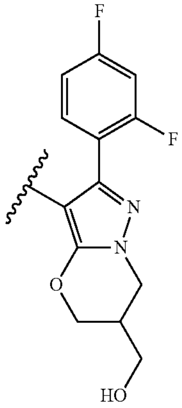 [SMILES: *c1c(-c2ccc(F)cc2F)nn2c1OCC(CO)C2] | δ 11.00 (s, 0.5H), 10.99 (s, 0.5H), 7.93-7.84 (m, 1H), 7.68-7.58 (m, 1H), 7.55-7.46 (m, 1H), 7.47-7.36 (m, 5H), 7.32-7.14 (m, 4H), 7.11-7.01 (m, 1H), 5.33-5.24 (m, 1H), 5.13-5.05 (m, 1H), 4.77-4.67 (m, 1H), 4.55-4.44 (m, 1H), 4.32-4.20 (m, 1H), 4.09-3.98 (m, 1H), 3.62-3.49 (m, 2H), 2.66-2.55 (m, 1H). | 544.5 [M + H]+ |
| 132 | (5S)-2-(6-Ethylpyridin-3-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 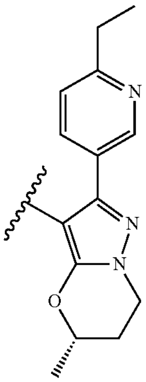 [SMILES: *c1c(-c2ccc(CC)nc2)nn2c1O[C@@H](C)CC2] | δ 11.00 (s, 1H), 8.74-8.67 (m, 1H), 8.33 (d, J = 7.3 Hz, 1H), 7.96 (dd, J = 8.1, 2.3 Hz, 1H), 7.70-7.61 (m, 1H), 7.56-7.47 (m, 1H), 7.47-7.41 (m, 4H), 7.35-7.17 (m, 5H), 5.31 (d, J = 7.3 Hz, 1H), 4.88-4.76 (m, 1H), 4.31-4.12 (m, 2H), 2.74 (q, J = 7.6 Hz, 2H), 2.35 (d, J = 10.1 Hz, 1H), 2.24-2.06 (m, 1H), 1.57 (d, J = 6.3 Hz, 3H), 1.22 (t, J = 7.6 Hz, 3H). | 521.4 [M + H]+ |
| 133 | 2-(6-Ethylpyridin-3-yl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide | F | 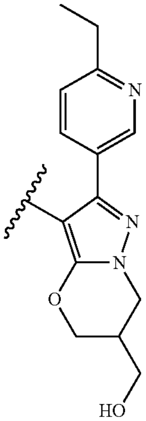 [SMILES: *c1c(-c2ccc(CC)nc2)nn2c1OCC(CO)C2] | 10.98 (s, 0.5H), 10.97 (s, 0.5H), 8.71-8.64 (m, 1H), 8.17-8.06 (m, 1H), 7.99-7.89 (m, 1H), 7.65-7.42 (m, 6H), 7.36-7.26 (m, 1H), 7.26-7.11 (m, 2H), 5.47-5.37 (m, 1H), 5.15-5.05 (m, 1H), 4.79-4.61 (m, 1H), 4.55-4.43 (m, 1H), 4.34-4.18 (m, 1H), 4.18-3.96 (m, 1H), 3.71-3.54 (m, 2H), 2.83-2.70 (m, 2H), 1.31-1.15 (m, 3H). | 554.6 [M + H]+ |

TABLE 30-continued

Compounds prepared by amide coupling procedure B.

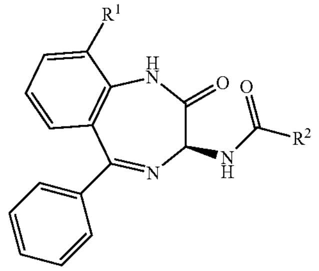

| Example | Name | $R^1$ | $R^2$ | $^1H$ NMR δ (400 MHz, DMSO-$d_6$) | LRMS m/z |
|---|---|---|---|---|---|
| 134 | 2-[2-Fluoro-4-(hydroxymethyl)phenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 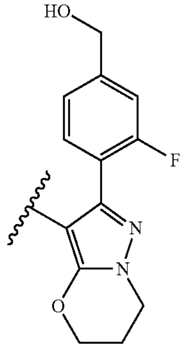 [SMILES: *c1c(-c2ccc(CO)cc2F)nn2c1OCCC2] | δ 10.95 (s, 1H), 7.88 (d, J = 7.7 Hz, 1H), 7.64-7.40 (m, 6H), 7.34-7.25 (m, 2H), 7.17-7.00 (m, 3H), 5.36 (d, J = 7.7 Hz, 1H), 5.32 (t, J = 5.8 Hz, 1H), 4.69-4.59 (m, 2H), 4.50 (d, J = 5.8 Hz, 2H), 4.20 (t, J = 6.0 Hz, 2H), 2.38-2.31 (m, 2H). | 543.3 [M + H]+ |
| 135 | 2-(2-Fluoro-4-methylsulfonylphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 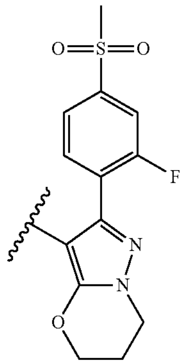 [SMILES: *c1c(-c2ccc(S(C)(=O)=O)cc2F)nn2c1OCCC2] | δ 10.97 (s, 1H), 7.93 (d, J = 7.7 Hz, 1H), 7.77-7.70 (m, 2H), 7.70-7.61 (m, 1H), 7.61-7.40 (m, 6H), 7.30 (td, J = 8.1, 5.0 Hz, 1H), 7.16-7.09 (m, 1H), 5.37 (d, J = 7.7 Hz, 1H), 4.68 (t, J = 5.2 Hz, 2H), 4.24 (t, J = 6.0 Hz, 2H), 3.28 (s, 3H), 2.37 (t, J = 5.8 Hz, 2H). | 591.3 [M + H]+ |
| 136 | 2-(2-Fluoropyridin-3-yl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 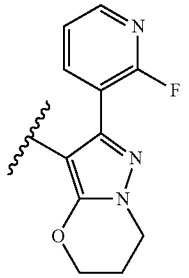 [SMILES: *c1c(-c2cccnc2F)nn2c1OCCC2] | δ 11.00 (s, 1H), 8.24-8.17 (m, 1H), 7.94-7.86 (m, 2H), 7.67-7.58 (m, 1H), 7.56-7.46 (m, 1H), 7.47-7.38 (m, 3H), 7.39-7.30 (m, 1H), 7.31-7.20 (m, 3H), 5.29 (d, J = 7.8 Hz, 1H), 4.74-4.63 (m, 2H), 4.23 (t, J = 6.1 Hz, 2H), 2.43-2.28 (m, 2H). | 496.7 [M + H]+ |

TABLE 30-continued

Compounds prepared by amide coupling procedure B.

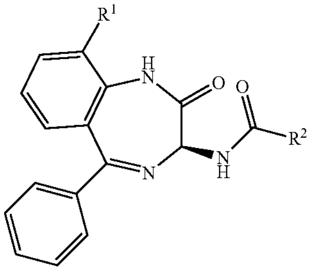

| Example | Name | $R^1$ | $R^2$ | $^1H$ NMR δ (400 MHz, DMSO-$d_6$) | LRMS m/z |
|---|---|---|---|---|---|
| 137 | (5R)-2-(2-Fluoro-4-methylsulfonylphenyl)-N-[(3S)-9-fluoro-2-oxo-5-penyl-1,3-dihydro-1,4-benzodiazepin-3-yl]-5-methyl-6,7-dihydro-5H-pyrazolo[5,1-b][1,3]oxazine-3-carboxamide | F | 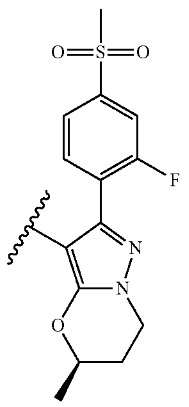 [SMILES: *c1c(-c2ccc(S(C)(=O)=O)cc2F)nn2c1O[C@H](C)CC2] | δ 10.96 (s, 1H), 8.13 (d, J = 7.4 Hz, 1H), 7.79-7.70 (m, 2H), 7.66 (dd, J = 8.2, 6.7 Hz, 1H), 7.62-7.37 (m, 6H), 7.30 (td, J = 8.1, 5.1 Hz, 1H), 7.16-7.10 (m, 1H), 5.34 (d, J = 7.4 Hz, 1H), 4.93-4.77 (m, 1H), 4.30-4.13 (m, 2H), 3.29 (s, 3H), 2.43-2.31 (m, 1H), 2.24-2.11 (m, 1H), 1.56 (d, J = 6.2 Hz, 3H). | 606.1 [M + H]+ |
| 138 | 2-(4-Cyano-2-fluorophenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 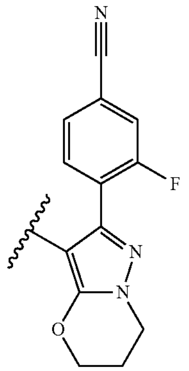 [SMILES: *c1c(-c2ccc(C#N)cc2F)nn2c1OCCC2] | δ 10.98 (s, 1H), 7.93 (d, J = 7.7 Hz, 1H), 7.82 (dd, J = 9.6, 1.5 Hz, 1H), 7.69 (dd, J = 7.9, 1.5 Hz, 1H), 7.62-7.40 (m, 7H), 7.35-7.24 (m, 1H), 7.19-7.08 (m, 1H), 5.36 (d, J = 7.7 Hz, 1H), 4.67 (t, J = 5.2 Hz, 2H), 4.23 (t, J = 6.1 Hz, 2H), 2.43-2.25 (m, 2H). | 539.1 [M + H]+ |
| 139 | 2-(2-Fluoro-6-methoxyphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 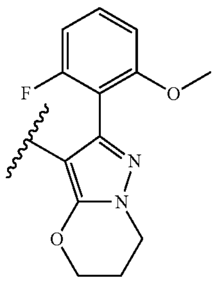 [SMILES: *c1c(-c2c(F)cccc2OC)nn2c1OCCC2] | δ 10.94 (s, 1H), 7.80 (d, J = 7.9 Hz, 1H), 7.61-7.39 (m, 6H), 7.39-7.22 (m, 2H), 7.16-7.08 (m, 1H), 6.83 (d, J = 8.4 Hz, 1H), 6.75 (t, J = 8.6 Hz, 1H), 5.34 (d, J = 7.9 Hz, 1H), 4.65 (t, J = 5.2 Hz, 2H), 4.20 (t, J = 6.0 Hz, 2H), 3.67 (s, 3H), 2.39-2.27 (m, 2H). | 544.4 [M + H]+ |

TABLE 30-continued

Compounds prepared by amide coupling procedure B.

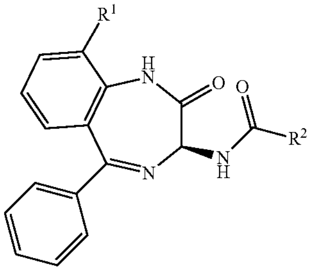

| Example | Name | $R^1$ | $R^2$ | $^1H$ NMR δ (400 MHz, DMSO-$d_6$) | LRMS m/z |
|---|---|---|---|---|---|
| 140 | 2-(2-Fluoro-6-methylphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 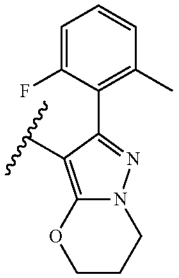 [SMILES: *c1c(-c2c(C)cccc2F)nn2c1OCCC2] | δ 10.95 (s, 1H), 7.84 (d, J = 7.8 Hz, 1H), 7.61-7.37 (m, 6H), 7.34-7.19 (m, 2H), 7.15-7.06 (m, 1H), 7.02 (d, J = 7.6 Hz, 1H), 6.95 (t, J = 8.9 Hz, 1H), 5.35 (d, J = 7.8 Hz, 1H), 4.76-4.58 (m, 2H), 4.21 (t, J = 6.0 Hz, 2H), 2.39-2.30 (m, 2H), 2.09 (s, 3H). | 528.4 $[M + H]^+$ |
| 141 | (5R)-2-(2-Fluoro-4-methylsulfonylphenyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 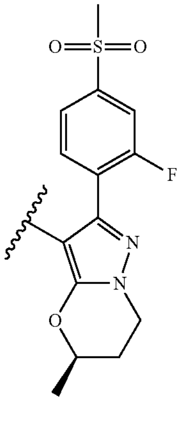 [SMILES: *c1c(-c2ccc(S(C)(=O)=O)cc2F)nn2c1O[C@H](C)CC2] | δ 10.98 (s, 1H), 8.09 (d, J = 7.5 Hz, 1H), 7.79-7.70 (m, 2H), 7.70-7.56 (m, 2H), 7.56-7.46 (m, 1H), 7.46-7.39 (m, 4H), 7.33-7.18 (m, 3H), 5.25 (d, J = 7.5 Hz, 1H), 4.90-4.78 (m, 1H), 4.30-4.17 (m, 2H), 3.28 (s, 3H), 2.45-2.35 (m, 1H), 2.24-2.11 (m, 1H), 1.56 (d, J = 6.2 Hz, 3H). | 588.2 $[M + H]^+$ |
| 142 | 2-(4-Carbamoyl-2-fluorophenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 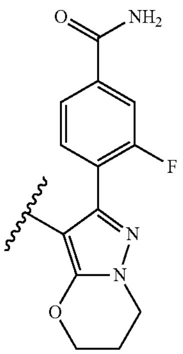 [SMILES: *c1c(-c2ccc(C(N)=O)cc2F)nn2c1OCCC2] | δ 10.96 (s, 1H), 8.06 (s, 1H), 7.90 (d, J = 7.7 Hz, 1H), 7.68 (dd, J = 8.0, 1.6 Hz, 1H), 7.63-7.38 (m, 8H), 7.30 (td, J = 8.1, 5.1 Hz, 1H), 7.22-7.05 (m, 1H), 5.37 (d, J = 7.7 Hz, 1H), 4.73-4.58 (m, 2H), 4.22 (t, J = 6.0 Hz, 2H), 2.43-2.28 (m, 2H). | 557.3 $[M + H]^+$ |

TABLE 30-continued

Compounds prepared by amide coupling procedure B.

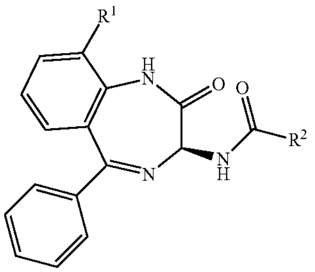

| Example | Name | $R^1$ | $R^2$ | $^1H$ NMR δ (400 MHz, DMSO-$d_6$) | LRMS m/z |
|---|---|---|---|---|---|
| 143 | 2-[2-Fluoro-4-(methylsulfonimidoyl) phenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 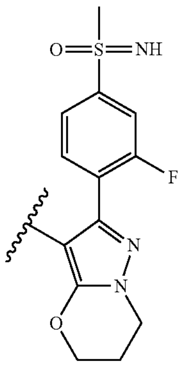 [SMILES: *c1c(-c2ccc(S(C)(=N)=O)cc2F)nn2c1OCCC2] | δ 10.97 (s, 1H), 8.01-7.88 (m, 1H), 7.73 (dd, J = 8.0, 1.8 Hz, 1H), 7.70-7.41 (m, 7H), 7.35-7.23 (m, 1H), 7.18-7.08 (m, 1H), 5.42-5.34 (m, 1H), 4.68 (t, J = 5.3 Hz, 2H), 4.38 (t, J = 1.5 Hz, 1H), 4.23 (t, J = 6.1 Hz, 2H), 3.10 (d, J = 1.2 Hz, 3H), 2.42-2.29 (m, 2H). | 591.5 $[M + H]^+$ |
| 144 | (5R)-N-[(3S)-9-fluoro-2-oxo-5-phenyl-1,3-dihydro-1,4-benzodiazepin-3-yl]-2-[6-(3-methoxyazetidin-1-yl)pyridin-3-yl]-5-methyl-6,7-dihydro-5H-pyrazolo[5,1-b][1,3]oxazine-3-carboxamide | F | 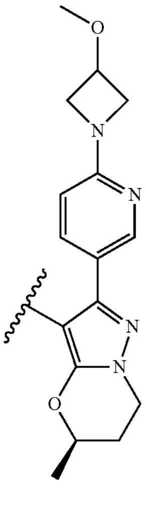 [SMILES: *c1c(-c2ccc(N3CC(OC)C3)nc2)nn2c1O[C@H](C)CC2] | δ 10.94 (s, 1H), 8.35 (dd, J = 2.2, 0.8 Hz, 1H), 8.29 (d, J = 7.3 Hz, 1H), 7.81 (dd, J = 8.6, 2.3 Hz, 1H), 7.59 (ddd, J = 10.3, 8.4, 1.3 Hz, 1H), 7.55-7.42 (m, 5H), 7.31 (td, J = 8.1, 5.0 Hz, 1H), 7.15 (dd, J = 7.9, 1.2 Hz, 1H), 6.34 (dd, J = 8.7, 0.8 Hz, 1H), 5.38 (d, J = 7.2 Hz, 1H), 4.82-4.74 (m, 1H), 4.36-4.26 (m, 1H), 4.24-4.10 (m, 4H), 3.74 (dd, J = 9.1, 4.0 Hz, 2H), 3.23 (s, 3H), 2.39-2.31 (m, 1H), 2.18-2.07 (m, 1H), 1.55 (d, J = 6.3 Hz, 3H). | 596.6 $[M + H]^+$ |

TABLE 30-continued

Compounds prepared by amide coupling procedure B.

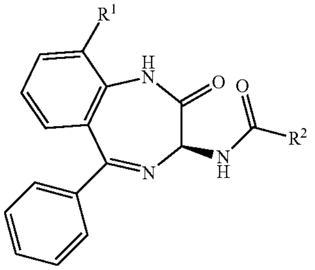

| Example | Name | $R^1$ | $R^2$ | $^1H$ NMR δ (400 MHz, DMSO-$d_6$) | LRMS m/z |
|---|---|---|---|---|---|
| 145 | (5R)-N-[(3S)-9-fluoro-2-oxo-5-phenyl-1,3-dihydro-1,4-benzodiazepin-3-yl]-2-[6-[(3R)-3-methoxypyrrolidin-1-yl]pyridin-3-yl]-5-methyl-6,7-dihydro-5H-pyrazolo[5,1-b][1,3]oxazine-3-carboxamide | F | 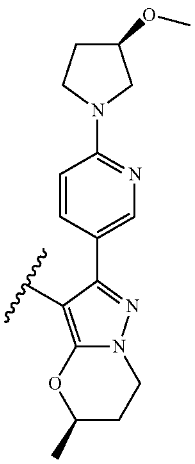 [SMILES: *c1c(-c2ccc(N3CC[C@@H](OC)C3)nc2)nn2c1O[C@H](C)CC2] | δ 10.94 (s, 1H), 8.37 (dd, J = 2.3, 0.8 Hz, 1H), 8.28 (d, J = 7.2 Hz, 1H), 7.79 (dd, J = 8.8, 2.3 Hz, 1H), 7.59 (ddd, J = 10.1, 8.2, 1.4 Hz, 1H), 7.55-7.42 (m, 5H), 7.32 (td, J = 8.1, 5.1 Hz, 1H), 7.15 (d, J = 7.9 Hz, 1H), 6.39 (dd, J = 8.9, 0.8 Hz, 1H), 5.38 (d, J = 7.2 Hz, 1H), 4.82-4.73 (m, 1H), 4.23-4.12 (m, 2H), 4.06 (t, J = 3.7 Hz, 1H), 3.51-3.43 (m, 3H), 3.39-3.35 (m, 1H), 3.25 (s, 3H), 2.38-2.31 (m, 1H), 2.18-1.99 (m, 3H), 1.55 (d, J = 6.2 Hz, 3H). | ESI+ 610.6 $[M + H]^+$ |
| 146 | (5R)-N-[(3S)-9-fluoro-2-oxo-5-phenyl-1,3-dihydro-1,4-benzodiazepin-3-yl]-2-[6-[(3S)-3-methoxypyrrolidin-1-yl]pyridin-3-yl]-5-methyl-6,7-dihydro-5H-pyrazolo[5,1-b][1,3]oxazine-3-carboxamide | F | 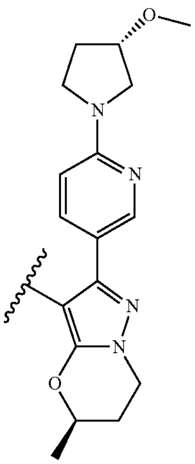 [SMILES: *c1c(-c2ccc(N3CC[C@H](OC)C3)nc2)nn2c1O[C@H](C)CC2] | δ 10.94 (s, 1H), 8.38 (d, J = 2.2 Hz, 1H), 8.29 (d, J = 7.2 Hz, 1H), 7.81 (d, J = 8.9 Hz, 1H), 7.63-7.55 (m, 1H), 7.55-7.41 (m, 5H), 7.32 (td, J = 8.1, 5.1 Hz, 1H), 7.16 (d, J = 7.9 Hz, 1H), 6.41 (d, J = 8.9 Hz, 1H), 5.38 (d, J = 7.2 Hz, 1H), 4.83-4.72 (m, 1H), 4.25-4.11 (m, 2H), 4.09-4.02 (m, 1H), 3.52-3.44 (m, 3H), 3.42-3.34 (m, 3H), 3.25 (s, 3H), 2.39-2.30 (m, 1H), 2.18-2.01 (m, 3H), 1.55 (d, J = 6.3 Hz, 3H). | ESI+ 610.6 $[M + H]^+$ |

TABLE 30-continued

Compounds prepared by amide coupling procedure B.

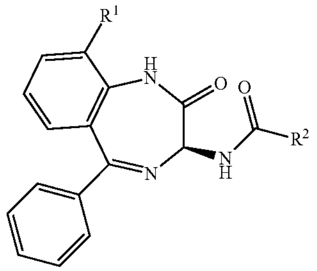

| Example | Name | $R^1$ | $R^2$ | $^1H$ NMR δ (400 MHz, DMSO-$d_6$) | LRMS m/z |
|---|---|---|---|---|---|
| 147 | N-[(3S)-9-fluoro-2-oxo-5-phenyl-1,3-dihydro-1,4-benzodiazepin-3-yl]-2-(1-methylindazol-4-yl)-6,7-dihydro-5H-pyrazolo[5,1-b][1,3]oxazine-3-carboxamide | F | 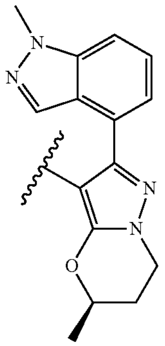 [SMILES: *c1c(-c2cccc3c2cnn3C)nn2c1O[C@H](C)CC2] | δ 10.95 (s, 1H), 8.12 (d, J = 7.5 Hz, 1H), 8.00 (d, J = 0.9 Hz, 1H), 7.61-7.41 (m, 8H), 7.38-7.25 (m, 2H), 7.12 (d, J = 7.9 Hz, 1H), 5.36 (d, J = 7.4 Hz, 1H), 4.65 (t, J = 5.2 Hz, 2H), 4.26 (t, J = 6.1 Hz, 2H), 4.04 (s, 3H), 2.41-2.31 (m, 2H). | 550.6 $[M + H]^+$ |
| 148 | N-[(3S)-9-fluoro-2-oxo-5-phenyl-1,3-dihydro-1,4-benzodiazepin-3-yl]-2-(1-propan-2-ylpyrazol-4-yl)-6,7-dihydro-5H-pyrazolo[5,1-b][1,3]oxazine-3-carboxamide | H | 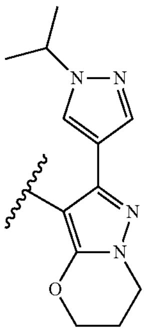 [SMILES: *c1c(-c2cnn(C(C)C)c2)nn2c1OCCC2] | δ 10.98 (s, 1H), 8.36 (s, 1H), 8.11 (d, J = 7.6 Hz, 1H), 7.88 (s, 1H), 7.66-7.56 (m, 1H), 7.56-7.42 (m, 5H), 7.33 (td, J = 8.1, 5.0 Hz, 1H), 7.19 (d, J = 7.9 Hz, 1H), 5.49 (d, J = 7.6 Hz, 1H), 4.66-4.57 (m, 2H), 4.53-4.42 (m, 1H), 4.15 (t, J = 6.1 Hz, 2H), 2.36-2.26 (m, 2H), 1.38 (d, J = 6.9 Hz, 6H). | 528.5 $[M + H]^+$ |
| 149 | 2-(1-Methylindazol-4-yl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 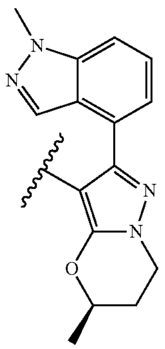 [SMILES: *c1c(-c2cccc3c2cnn3C)nn2c1O[C@H](C)CC2] | δ 10.99 (s, 1H), 8.11 (d, J = 7.6 Hz, 1H), 8.00 (d, J = 0.9 Hz, 1H), 7.67-7.56 (m, 2H), 7.56-7.47 (m, 1H), 7.48-7.41 (m, 5H), 7.40-7.31 (m, 1H), 7.34-7.19 (m, 3H), 5.28 (d, J = 7.5 Hz, 1H), 4.69-4.61 (m, 2H), 4.26 (t, J = 6.1 Hz, 2H), 4.04 (s, 3H), 2.36 (td, J = 10.7, 4.6 Hz, 2H). | 532.6 $[M + H]^+$ |

TABLE 30-continued

Compounds prepared by amide coupling procedure B.

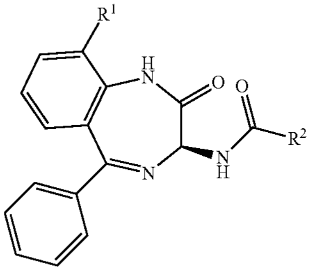

| Example | Name | $R^1$ | $R^2$ | $^1H$ NMR δ (400 MHz, DMSO-$d_6$) | LRMS m/z |
|---|---|---|---|---|---|
| 150 | N-[(3S)-9-fluoro-2-oxo-5-phenyl-1,3-dihydro-1,4-benzodiazepin-3-yl]-2-[1-(2,2,2-trifluoroethyl)pyrazol-4-yl]-6,7-dihydro-5H-pyrazolo[5,1-b][1,3]oxazine-3-carboxamide | F | 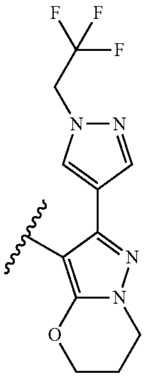 [SMILES: *c1c(-c2cnn(CC(F)(F)F)c2)nn2c1OCCC2] | δ 10.99 (s, 1H), 8.62 (s, 1H), 8.14 (d, J = 7.5 Hz, 1H), 7.99 (s, 1H), 7.66-7.56 (m, 1H), 7.56-7.42 (m, 5H), 7.33 (td, J = 8.1, 5.0 Hz, 1H), 7.20 (d, J = 8.1 Hz, 1H), 5.49 (d, J = 7.5 Hz, 1H), 5.14 (q, J = 9.2 Hz, 2H), 4.64 (t, J = 5.1 Hz, 2H), 4.17 (t, J = 6.0 Hz, 2H), 2.37-2.28 (m, 2H). | 568.6 $[M + H]^+$ |
| 151 | N-[(3S)-2-oxo-5-phenyl-1,3-dihydro-1,4-benzodiazepin-3-yl]-2-[1-(2,2,2-trifluoroethyl)pyrazol-4-yl]-6,7-dihydro-5H-pyrazolo[5,1-b][1,3]oxazine-3-carboxamide | H | 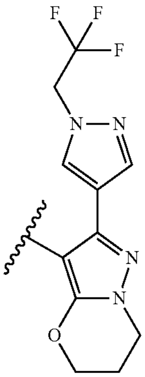 [SMILES: *c1c(-c2cnn(CC(F)(F)F)c2)nn2c1OCCC2] | δ 11.02 (s, 1H), 8.62 (s, 1H), 8.12 (d, J = 7.6 Hz, 1H), 7.99 (s, 1H), 7.70-7.61 (m, 1H), 7.54-7.39 (m, 5H), 7.38-7.24 (m, 3H), 5.42 (d, J = 7.6 Hz, 1H), 5.14 (q, J = 9.0 Hz, 2H), 4.64 (t, J = 5.3 Hz, 2H), 4.17 (t, J = 6.0 Hz, 2H), 2.37-2.27 (m, 2H). | 550.7 $[M + H]^+$ |
| 152 | N-[(3S)-9-Fluoro-2-oxo-5-phenyl-1,3-dihydro-1,4-benzodiazepin-3-yl]-2-[1-(oxan-4-yl)pyrazol-4-yl]-6,7-dihydro-5H-pyrazolo[5,1-b][1,3]oxazine-3-carboxamide | F | 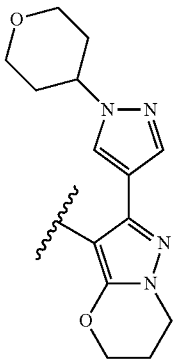 [SMILES: *c1c(-c2cnn(C3CCOCC3)c2)nn2c1OCCC2] | δ 10.98 (s, 1H), 8.42 (s, 1H), 8.11 (d, J = 7.6 Hz, 1H), 7.89 (s, 1H), 7.66-7.56 (m, 1H), 7.56-7.43 (m, 5H), 7.33 (td, J = 8.0, 5.0 Hz, 1H), 7.20 (d, J = 7.9 Hz, 1H), 5.49 (d, J = 7.6 Hz, 1H), 4.62 (t, J = 5.2 Hz, 2H), 4.45-4.32 (m, 1H), 4.15 (t, J = 6.1 Hz, 2H), 3.96-3.87 (m, 2H), 3.47-3.35 (m, 3H), 2.36-2.26 (m, 2H), 1.96-1.83 (m, 4H). | 570.9 $[M + H]^+$ |

TABLE 30-continued

Compounds prepared by amide coupling procedure B.

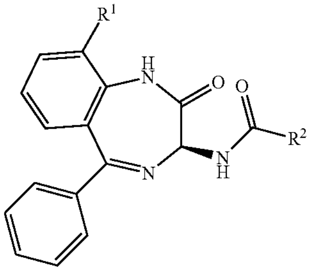

| Example | Name | $R^1$ | $R^2$ | $^1H$ NMR δ (400 MHz, DMSO-$d_6$) | LRMS m/z |
|---|---|---|---|---|---|
| 153 | (5R)-2-[2-Fluoro-4-(hydroxymethyl)phenyl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 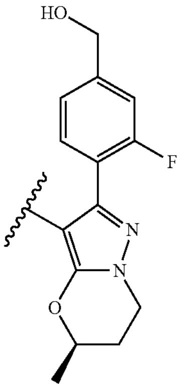 [SMILES: *c1c(-c2ccc(CO)cc2F)nn2c1O[C@H](C)CC2] | δ 10.94 (s, 1H), 8.08 (d, J = 7.5 Hz, 1H), 7.61-7.49 (m, 2H), 7.48-7.41 (m, 4H), 7.33-7.26 (m, 2H), 7.14-7.02 (m, 3H), 5.35-5.30 (m, 2H), 4.86-4.76 (m, 1H), 4.50 (d, J = 5.7 Hz, 2H), 4.26-4.14 (m, 2H), 2.41-2.31 (m, 2H), 2.22-2.10 (m, 1H), 1.55 (d, J = 6.2 Hz, 3H). | 557.5 [M + H]+ |
| 154 | (5R)-2-[2-Fluoro-4-(hydroxymethyl)phenyl]-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 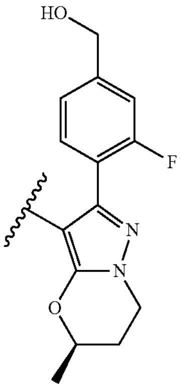 [SMILES: *c1c(-c2ccc(CO)cc2F)nn2c1O[C@H](C)CC2] | δ 10.96 (s, 1H), 8.04 (d, J = 7.6 Hz, 1H), 7.67-7.58 (m, 1H), 7.54-7.39 (m, 5H), 7.33-7.17 (m, 4H), 7.13-6.97 (m, 2H), 5.32 (t, J = 5.8 Hz, 1H), 5.25 (d, J = 7.6 Hz, 1H), 4.86-4.75 (m, 1H), 4.50 (d, J = 5.8 Hz, 2H), 4.28-4.13 (m, 2H), 2.39-2.29 (m, 1H), 2.21-2.09 (m, 1H), 1.55 (d, J = 6.2 Hz, 3H). | 540.3 [M + H]+ |
| 155 | (5R)-N-[(3S)-9-fluoro-2-oxo-5-phenyl-1,3-dihydro-1,4-benzodiazepin-3-yl]-2-[6-(hydroxymethyl)pyridin-3-yl]-5-methyl-6,7-dihydro-5H-pyrazolo[5,1-b][1,3]oxazine-3-carboxamide | F | 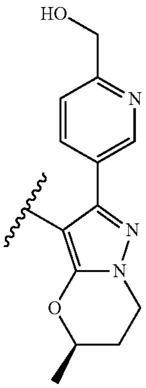 [SMILES: *c1c(-c2ccc(CO)nc2)nn2c1O[C@H](C)CC2] | δ 10.96 (s, 1H), 8.71 (dd, J = 2.2, 0.8 Hz, 1H), 8.33 (d, J = 7.2 Hz, 1H), 8.06 (dd, J = 8.2, 2.2 Hz, 1H), 7.67-7.39 (m, 7H), 7.31 (td, J = 8.1, 5.1 Hz, 1H), 7.25-7.07 (m, 1H), 5.48-5.34 (m, 2H), 4.90-4.75 (m, 1H), 4.56 (d, J = 4.9 Hz, 2H), 4.33-4.12 (m, 2H), 2.45-2.34 (m, 2H), 2.26-2.04 (m, 1H), 1.56 (d, J = 6.3 Hz, 3H). | 541.2 [M + H]+ |

TABLE 30-continued

Compounds prepared by amide coupling procedure B.

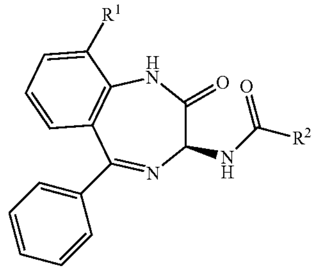

| Example | Name | $R^1$ | $R^2$ | $^1H$ NMR δ (400 MHz, DMSO-$d_6$) | LRMS m/z |
|---|---|---|---|---|---|
| 156 | (5S)-N-[(3S)-9-fluoro-2-oxo-5-phenyl-1,3-dihydro-1,4-benzodiazepin-3-yl]-5-methyl-2-[1-(oxan-4-yl)pyrazol-4-yl]-6,7-dihydro-5H-pyrazolo[5,1-b][1,3]oxazine-3-carboxamide | F | 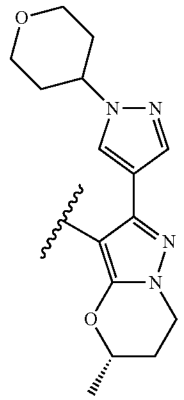 [SMILES: *c1c(-c2cnn(C3CCOCC3)c2)nn2c1O[C@@H](C)CC2] | δ 10.98 (s, 1H), 8.45 (d, J = 1.8 Hz, 1H), 8.38 (d, J = 7.2 Hz, 1H), 7.91 (s, 1H), 7.66-7.56 (m, 2H), 7.56-7.41 (m, 5H), 7.34 (td, J = 8.1, 5.0 Hz, 1H), 7.20 (d, J = 7.8 Hz, 1H), 5.50-5.38 (m, 1H), 4.83-4.68 (m, 1H), 4.47-4.31 (m, 2H), 4.25-4.08 (m, 2H), 3.98-3.83 (m, 4H), 3.47-3.35 (m, 3H), 2.42-2.29 (m, 1H), 2.21-2.05 (m, 1H), 1.97-1.81 (m, 6H), 1.55 (d, J = 6.3 Hz, 3H). | 584.3 [M + H]$^+$ |
| 157 | (5S)-N-[(3S)-9-fluoro-2-oxo-5-phenyl-1,3-dihydro-1,4-benzodiazepin-3-yl]-5-methyl-2-[1-(2,2,2-trifluoroethyl)pyrazol-4-yl]-6,7-dihydro-5H-pyrazolo[5,1-b][1,3]oxazine-3-carboxamide | F | 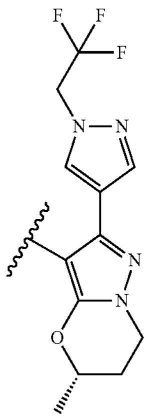 [SMILES: *c1c(-c2cnn(CC(F)(F)F)c2)nn2c1O[C@@H](C)CC2] | δ 10.99 (s, 1H), 8.66 (s, 1H), 8.41 (d, J = 7.1 Hz, 1H), 8.00 (s, 1H), 7.60 (ddd, J = 9.9, 8.2, 1.4 Hz, 1H), 7.57-7.40 (m, 6H), 7.33 (td, J = 8.1, 5.0 Hz, 1H), 7.20 (d, J = 7.9 Hz, 1H), 5.46 (d, J = 7.1 Hz, 1H), 5.20-5.10 (m, 2H), 4.84-4.69 (m, 1H), 4.26-4.09 (m, 2H), 2.42-2.28 (m, 1H), 2.21-2.05 (m, 1H), 1.56 (d, J = 6.3 Hz, 3H). | 582.2 [M + H]$^+$ |
| 158 | (5S)-2-(1-Ethylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 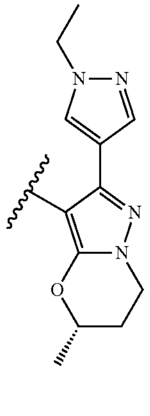 [SMILES: *c1c(-c2cnn(CC)c2)nn2c1O[C@@H](C)CC2] | δ 10.98 (d, J = 5.7 Hz, 1H), 8.41 (s, 1H), 8.38 (d, J = 7.2 Hz, 1H), 7.88 (s, 1H), 7.61 (ddd, J = 10.1, 8.2, 1.3 Hz, 1H), 7.57-7.40 (m, 5H), 7.34 (td, J = 8.1, 5.0 Hz, 1H), 7.20 (d, J = 7.9 Hz, 1H), 5.45 (dd, J = 7.3, 1.9 Hz, 1H), 4.75 (ddd, J = 10.4, 6.1, 2.0 Hz, 1H), 4.23-4.03 (m, 4H), 2.34 (d, J = 13.8 Hz, 1H), 2.13 (ddt, J = 14.2, 10.2, 5.1 Hz, 1H), 1.55 (d, J = 6.3 Hz, 3H), 1.33 (t, J = 7.2 Hz, 3H). | 528.3 [M + H]$^+$ |

TABLE 30-continued

Compounds prepared by amide coupling procedure B.

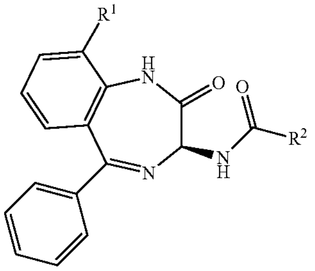

| Example | Name | $R^1$ | $R^2$ | $^1$H NMR δ (400 MHz, DMSO-$d_6$) | LRMS m/z |
|---|---|---|---|---|---|
| 159 | (5R)-N-[(3S)-9-fluoro-2-oxo-5-phenyl-1,3-dihydro-1,4-benzodiazepin-3-yl]-5-methyl-2-(1H-pyrazol-4-yl)-6,7-dihydro-5H-pyrazolo[5,1-b][1,3]oxazine-3-carboxamide | F | 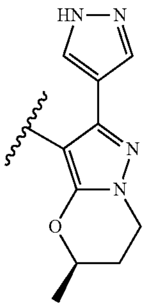 [SMILES: *c1c(-c2cn[nH]c2)nn2c1O[C@H](C)CC2] | δ 12.79 (s, 1H), 10.96 (s, 1H), 84.0-8.33 (m, 2H), 7.95-7.89 (m, 1H), 7.65-7.27 (m, 8H), 7.19 (dd, J = 7.9, 1.3 Hz, 1H), 5.44 (d, J = 7.2 Hz, 1H), 4.83-4.72 (m, 1H), 4.24-4.10 (m, 2H), 2.42-2.29 (m, 1H), 2.21-2.05 (m, 1H), 1.55 (d, J = 6.2 Hz, 3H). | 500.3 [M + H]$^+$ |
| 160 | 2-(2-Fluorophenyl)-6-hydroxy-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 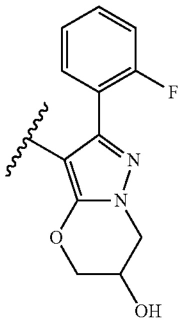 [SMILES: *c1c(-c2ccccc2F)nn2c1OCC(O)C2] | (500 MHz) δ 10.95 (s, 0.5H), 10.94 (s, 0.5H), 8.02-7.76 (m, 1H), 7.64-7.24 (m, 9H), 7.24-7.06 (m, 3H), 5.92-5.77 (m, 1H), 5.47-5.29 (m, 1H), 4.69-4.52 (m, 2H), 4.46-4.25 (m, 2H), 4.14-4.02 (m, 1H). | 530.3 [M + H]$^+$ |
| 161 | (5R)-N-[(3S)-9-fluoro-2-oxo-5-phenyl-1,3-dihydro-1,4-benzodiazepin-3-yl]-5-methyl-2-(1-methylsulfonylpiperidin-4-yl)-6,7-dihydro-5H-pyrazolo[5,1-b][1,3]oxazine-3-carboxamide | F | 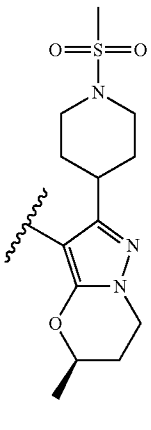 [SMILES: *c1c(C2CCN(S(C)(=O)=O)CC2)nn2c1O[C@H](C)CC2] | δ 10.94 (s, 1H), 8.10 (d, J = 7.4 Hz, 1H), 7.64-7.41 (m, 6H), 7.33 (td, J = 8.1, 5.1 Hz, 1H), 7.24-7.10 (m, 1H), 5.41 (d, J = 7.3 Hz, 1H), 4.80-4.67 (m, 1H), 4.20-4.04 (m, 2H), 3.67-3.53 (m, 2H), 3.27-3.17 (m, 1H), 2.84 (s, 3H), 2.80-2.63 (m, 2H), 2.40-2.22 (m, 1H), 2.22-2.02 (m, 1H), 2.02-1.84 (m, 2H), 1.76-1.54 (m, 2H), 1.52 (d, J = 6.3 Hz, 3H). | 595.7 [M + H]$^+$ |

TABLE 30-continued

Compounds prepared by amide coupling procedure B.

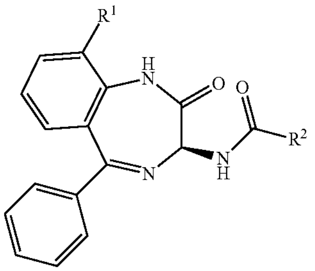

| Example | Name | $R^1$ | $R^2$ | $^1H$ NMR δ (400 MHz, DMSO-$d_6$) | LRMS m/z |
|---|---|---|---|---|---|
| 162 | (5R)-5-Methyl-2-(1-methylsulfonylpiperidin-4-yl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 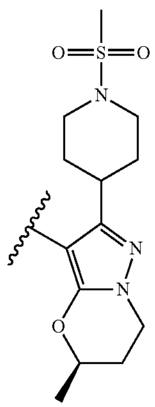 [SMILES: *c1c(C2CCN(S(C)(=O)=O)CC2)nn2c1O[C@H](C)CC2] | δ 10.96 (s, 1H), 8.07 (d, J = 7.5 Hz, 1H), 7.70-7.59 (m, 1H), 7.59-7.39 (m, 5H), 7.39-7.19 (m, 3H), 5.33 (d, J = 7.5 Hz, 1H), 4.81-4.65 (m, 1H), 4.18-4.04 (m, 2H), 3.66-3.52 (m, 2H), 3.29-3.16 (m, 1H), 2.84 (s, 3H), 2.80-2.64 (m, 2H), 2.38-2.26 (m, 1H), 2.16-2.02 (m, 1H), 2.02-1.89 (m, 2H), 1.76-1.54 (m, 2H), 1.51 (d, J = 6.3 Hz, 3H). | 577.7 [M + H]$^+$ |
| 163 | (2S)-N-[(3S)-9-fluoro-2-oxo-5-phenyl-1,3-dihydro-1,4-benzodiazepin-3-yl]-6-(2-fluorophenyl)-2-methyl-2,3-dihydropyrazolo[5,1-b][1,3]oxazole-7-carboxamide | F | 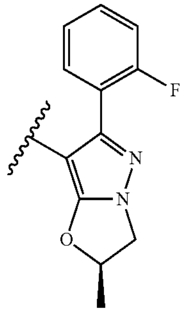 [SMILES: *c1c(-c2ccccc2F)nn2c1O[C@H](C)C2] | δ 10.95 (s, 1H), 7.62-7.36 (m, 9H), 7.30 (td, J = 8.1, 5.1 Hz, 1H), 7.24-7.10 (m, 3H), 5.86-5.77 (m, 1H), 5.33 (d, J = 7.6 Hz, 1H), 4.59 (dd, J = 9.5, 8.2 Hz, 1H), 4.10 (dd, J = 9.5, 8.1 Hz, 1H), 1.70 (d, J = 6.3 Hz, 3H). | 514.6 [M + H]$^+$ |

164. 6-(Diethylaminomethyl)-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide

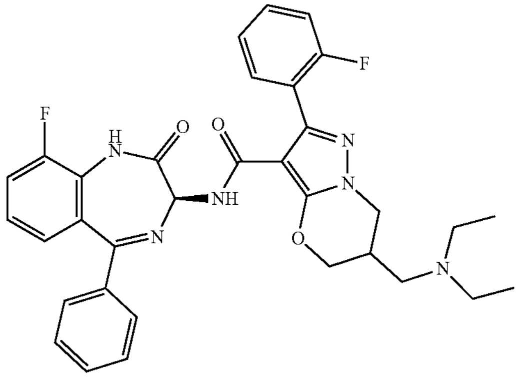 [SMILES: CCN(CC)CC1COc2c(C(=O)N[C@H]3N=C(c4ccccc4)c4cccc(F)c4NC3=O)c(-c3ccccc3F)nn2C1]

NaOH (5 M aq. soln., 180 μL, 0.89 mmol) was added to a solution of intermediate 97F (42 mg, 0.11 mmol) in EtOH (4 mL) and heated at 60° C. overnight. The reaction was cooled to rt, acidified to pH≈4 with 1 M aq. HCl, the solvent removed under reduced pressure and the crude residue used directly in the next reaction. The residue was suspended in DMF (2 mL), DIPEA (39 μL, 0.22 mmol) and HATU (47 mg, 0.12 mmol) added, and the reaction stirred for 10 min at rt. (3S)-3-Amino-9-fluoro-5-phenyl-1,3-dihydro-1,4-benzodiazepin-2-one (39 mg, 0.11 mmol) was added and the reaction stirred at rt for 16 h. Analogous workup and purification to that described for the compound of Example 15 afforded a white solid (49 mg, 73%). $^1H$ NMR (400 MHz, DMSO-$d_6$) δ 10.96 (s, 0.5H), 10.95 (s, 0.5H), 7.99-7.82 (m, 1H), 7.68-7.21 (m, 9H), 7.21-7.04 (m, 3H), 5.51-5.30 (m, 1H), 4.79-4.57 (m, 1H), 4.57-4.42 (m, 1H), 4.34-4.17 (m, 1H), 4.06-3.88 (m, 1H), 1.07-0.86 (m, 6H). LRMS (APCI+) m/z 599.8 $[M+H]^+$.

The following compounds were prepared by an analogous procedure to that described for the compound of Example 164. Example 172 was subject to additional purification by preparative SFC method 2 [10-90% $CO_2$/MeOH (0.2% v/v $NH_3$)]. Example 173 was subject to additional purification by preparative HPLC method 1 (10-100% $CH_3CN$ in water with 0.2% v/v formic acid).

TABLE 31

Example compounds

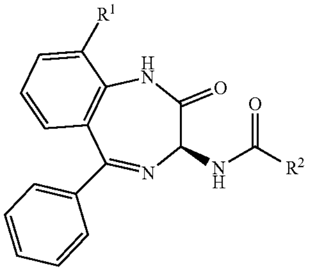

| Example | Name | $R^1$ | $R^2$ | $^1H$ NMR δ (DMSO-$d_6$) | LRMS APCI+ m/z |
|---|---|---|---|---|---|
| 165 | (5R)-2-[1-[2-(Dimethylamino)ethyl]pyrazol-4-yl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 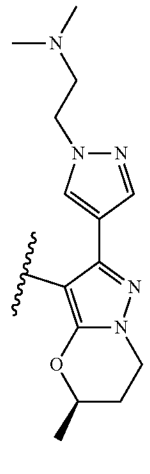 [SMILES: *c1c(-c2cnn(CCN(C)C)c2)nn2c1O[C@H](C)CC2] | (400 MHz) δ 10.98 (s, 1H), 8.40 (s, 1H), 8.36 (d, J = 7.2 Hz, 1H), 7.89 (s, 1H), 7.67 − 7.55 (m, 1H), 7.55 − 7.38 (m, 5H), 7.33 (td, J = 8.1, 5.0 Hz, 1H), 7.20 (d, J = 7.9 Hz, 1H), 5.44 (d, J = 7.2 Hz, 1H), 4.87 − 4.72 (m, 1H), 4.28 − 4.07 (m, 4H), 2.63 (t, J = 6.6 Hz, 2H), 2.14 (s, 7H), 1.55 (d, J = 6.2 Hz, 3H). | 570.6 $[M + H]^+$ |

TABLE 31-continued

Example compounds

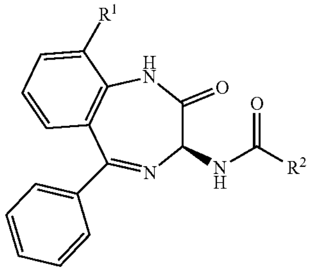

| Example | Name | $R^1$ | $R^2$ | $^1H$ NMR δ (DMSO-$d_6$) | LRMS APCI+ m/z |
|---|---|---|---|---|---|
| 166 | 5-[(Dimethylamino)methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide | F | 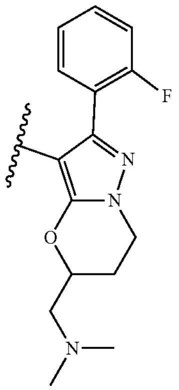 [SMILES: *c1c(-c2ccccc2F)nn2c1OC(CN(C)C)CC2] | (600 MHz) δ 10.91 (s, 0.5H), 10.90 (s, 0.5H), 8.04 - 7.96 (m, 1H), 7.60 - 7.54 (m, 1H), 7.55 - 7.51 (m, 1H), 7.50 - 7.42 (m, 4H), 7.42 - 7.32 (m, 2H), 7.33 - 7.26 (m, 1H), 7.20 - 7.14 (m, 1H), 7.15 - 7.10 (m, 2H), 5.38 - 5.32 (m, 1H), 4.90 - 4.79 (m, 1H), 4.27 - 4.19 (m, 2H), 2.89 - 2.73 (m, 2H), 2.41 - 2.31 (m, 6H), 2.31 - 2.19 (m, 2H). | 570.9 [M + H]+ |
| 167 | N-[(3S)-9-fluoro-2-oxo-5-phenyl-1,3-dihydro-1,4-benzodiazepin-3-yl]-2-(2-fluorophenyl)-5-(morpholin-4-ylmethyl)-6,7-dihydro-5H-pyrazolo[5,1-b][1,3]oxazine-3-carboxamide | F | 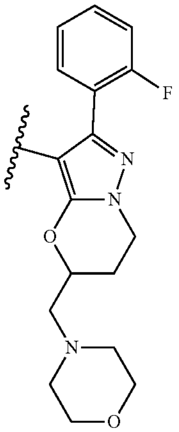 [SMILES: *c1c(-c2ccccc2F)nn2c1OC(CN1CCOCC1)CC2] | (400 MHz) δ 10.95 (s, 0.5H), 10.93 (s, 0.5H), 8.00 (d, J = 8.0 Hz, 0.5H), 7.95 (d, J = 7.8 Hz, 0.5H), 7.63 - 7.42 (m, 6H), 7.42 - 7.24 (m, 3H), 7.21 - 7.07 (m, 3H), 5.42 - 5.33 (m, 1H), 4.93 - 4.84 (m, 1H), 4.30 - 4.16 (m, 2H), 3.58 - 3.46 (m, 4H), 2.89 - 2.70 (m, 2H), 2.61 - 2.53 (m, 4H), 2.42 - 2.17 (m, 3H). | 612.6 [M + H]+ |
| 168 | N-[(3S)-9-fluoro-2-oxo-5-phenyl-1,3-dihydro-1,4-benzodiazepin-3-yl]-2-(2-fluorophenyl)-6-[[methyl(oxan-4-yl)amino]methyl]-6,7-dihydro-5H-pyrazolo[5,1-b][1,3]oxazine-3-carboxamide | F | 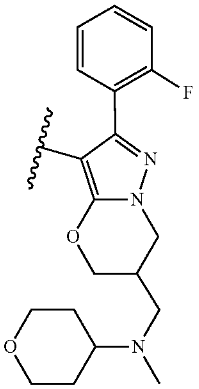 [SMILES: *c1c(-c2ccccc2F)nn2c1OCC(CN(C)C1CCOCC1)C2] | (400 MHz) δ 10.96 (s, 0.5H), 10.95 (s, 0.5H), 7.96 - 7.86 (m, 1H), 7.63 - 7.24 (m, 9H), 7.21 - 7.04 (m, 3H), 5.40 - 5.33 (m, 1H), 4.76 - 4.65 (m, 1H), 4.51 - 4.41 (m, 1H), 4.31 - 4.21 (m, 1H), 4.01 - 3.94 (m, 1H), 3.94 - 3.81 (m, 2H), 3.32 - 3.22 (m, 2H), 2.76 - 2.68 (m, 1H), 2.64 - 2.55 (m, 1H), 2.28 (s, 1.5H), 2.28 (s, 1.5H), 1.70 - 1.57 (m, 2H), 1.50 - 1.34 (m, 2H). | 640.4 [M + H]+ |

TABLE 31-continued

Example compounds

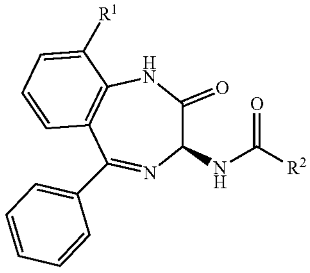

| Example | Name | $R^1$ | $R^2$ | $^1H$ NMR δ (DMSO-$d_6$) | LRMS APCI+ m/z |
|---|---|---|---|---|---|
| 169 | N-[(3S)-9-fluoro-2-oxo-5-phenyl-1,3-dihydro-1,4-benzodiazepin-3-yl]-2-(2-fluorophenyl)-6-[[methyl(oxetan-3-yl)amino]methyl]-6,7-dihydro-5H-pyrazolo[5,1-b][1,3]oxazine-3-carboxamide | F | 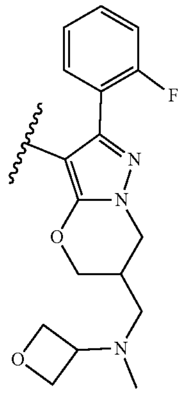 [SMILES: *c1c(-c2ccccc2F)nn2c1OCC(CN(C)C1COC1)C2] | (400 MHz) δ 10.96 (s, 0.5H), 10.96 (s, 0.5H), 7.95 - 7.81 (m, 1H), 7.60 - 7.27 (m, 9H), 7.19 - 7.10 (m, 3H), 5.40 - 5.32 (m, 1H), 4.77 - 4.67 (m, 1H), 4.59 - 4.25 (m, 6H), 4.07 - 3.97 (m, 1H), 3.62 - 3.51 (m, 1H), 2.82 - 2.73 (m, 1H), 2.35 - 2.21 (m, 2H), 2.21 - 2.04 (m, 3H). | 612.8 $[M + H]^+$ |
| 170 | (5R)-2-[4-[(Dimethylamino)methyl]-2-fluorophenyl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 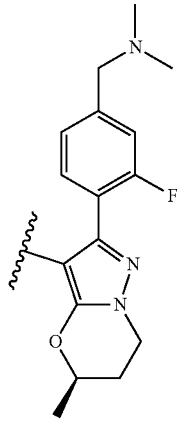 [SMILES: *c1c(-c2ccc(CN(C)C)cc2F)nn2c1O[C@H](C)CC2] | (400 MHz) δ 10.93 (s, 1H), 8.08 (d, J = 7.5 Hz, 1H), 7.63 - 7.40 (m, 6H), 7.39 - 7.20 (m, 2H), 7.14 - 7.00 (m, 3H), 5.34 (d, J = 7.5 Hz, 1H), 4.86 - 4.75 (m, 1H), 4.25 - 4.16 (m, 2H), 3.43 (s, 2H), 2.39 - 2.32 (m, 1H), 2.17 (s, 6H), 1.55 (d, J = 6.2 Hz, 3H). | 585.4 $[M + H]^+$ |

TABLE 31-continued

Example compounds

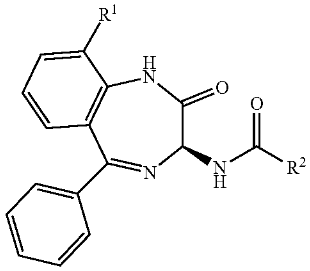

| Example | Name | $R^1$ | $R^2$ | $^1H$ NMR δ (DMSO-$d_6$) | LRMS APCI+ m/z |
|---|---|---|---|---|---|
| 171 | 6-[(Dimethylamino)methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide | F | 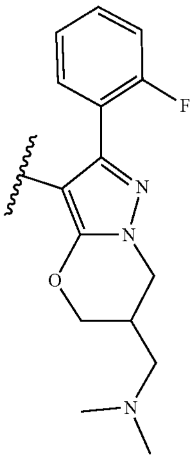 [SMILES: *c1c(-c2ccccc2F)nn2c1OCC(CN(C)C)C2] | (400 MHz) δ 10.97 (s, 0.5H), 10.95 (s, 0.5H), 7.97 - 7.84 (m, 1H), 7.65 - 7.24 (m, 9H), 7.25 - 7.03 (m, 3H), 5.45 - 5.32 (m, 1H), 4.74 - 4.64 (m, 1H), 4.48 - 4.34 (m, 1H), 4.32 - 4.19 (m, 1H), 4.05 - 3.87 (m, 1H), 2.86 - 2.70 (m, 1H), 2.40 - 2.29 (m, 2H), 2.21 (s, 6H). | 571.8 [M + H]$^+$ |
| 172 | N-[(3S)-9-fluoro-2-oxo-5-phenyl-1,3-dihydro-1,4-benzodiazepin-3-yl]-2-(2-fluorophenyl)-6-[(4-methylpiperazin-1-yl)methyl]-6,7-dihydro-5H-pyrazolo[5,1-b][1,3]oxazine-3-carboxamide | F | 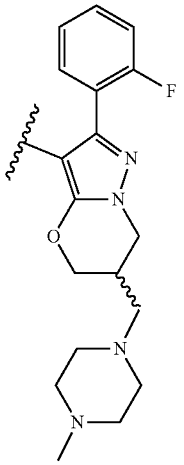 [SMILES: *c1c(-c2ccccc2F)nn2c1OCC(CN1CCN(C)CC1)C2] | (400 MHz) δ 10.95 (s, 1H), 7.94 - 7.86 (m, 1H), 7.61 - 7.42 (m, 6H), 7.42 - 7.24 (m, 3H), 7.20 - 7.08 (m, 3H), 5.36 (d, J = 7.6 Hz, 1H), 4.77 - 4.64 (m, 1H), 4.48 - 4.38 (m, 1H), 4.32 - 4.18 (m, 1H), 4.01 - 3.88 (m, 1H), 2.87 - 2.75 (m, 1H), 2.47 - 2.23 (m, 8H), 2.16 (s, 3H). | 626.9 [M + H]$^+$ |

TABLE 31-continued

Example compounds

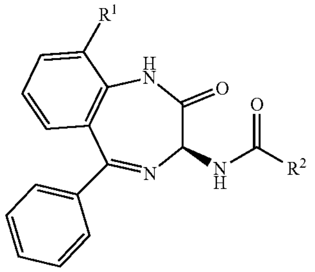

| Example | Name | $R^1$ | $R^2$ | $^1H$ NMR δ (DMSO-$d_6$) | LRMS APCI+ m/z |
|---|---|---|---|---|---|
| 173 | N-[(3S)-9-fluoro-2-oxo-5-phenyl-1,3-dihydro-1,4-benzodiazepin-3-yl]-2-(2-fluorophenyl)-6-(morpholin-4-ylmethyl)-6,7-dihydro-5H-pyrazolo[5,1-b][1,3]oxazine-3-carboxamide | F | 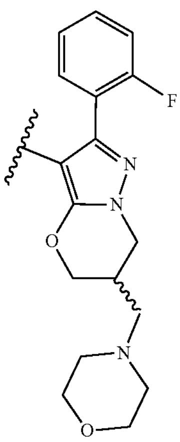 [SMILES: *c1c(-c2ccccc2F)nn2c1OCC(CN1CCOCC1)C2] | (400 MHz) δ 10.95 (s, 1H), 7.94 - 7.86 (m, 1H), 7.61 - 7.42 (m, 6H), 7.42 - 7.25 (m, 3H), 7.20 - 7.09 (m, 3H), 5.40 - 5.33 (m, 1H), 4.77 - 4.68 (m, 1H), 4.50 - 4.38 (m, 1H), 4.33 - 4.23 (m, 1H), 4.02 - 3.92 (m, 1H), 3.66 - 3.53 (m, 4H), 2.89 - 2.78 (m, 1H), 2.46 - 2.38 (m, 5H). | 614.0 $[M+H]^+$ |

174. 6-[[Benzyl(ethyl)amino]methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide

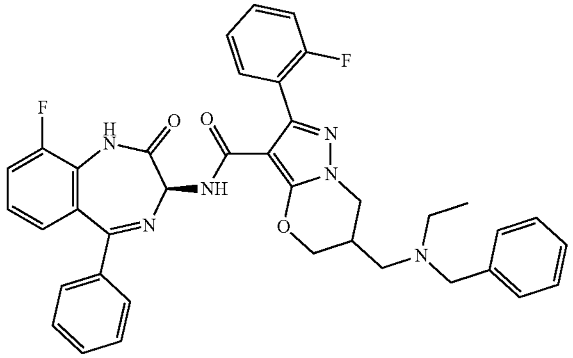 [SMILES: CCN(Cc1ccccc1)CC1COc2c(C(=O)N[C@H]3N=C(c4ccccc4)c4cccc(F)c4NC3=O)c(-c3ccccc3F)nn2C1]

NaOH (5 M aq. Soln., 370 μL, 1.83 mmol) was added to a solution of intermediate 97H (100 mg, 0.23 mmol) in EtOH (5 mL) and heated at 60° C. overnight. The reaction was cooled to rt, acidified to pH≈4 with 1 M aq. HCl, the solvent removed under reduced pressure and the crude residue used directly in the next reaction. The residue was suspended in DMF (3 mL), DIPEA (80 μL, 0.46 mmol) and HATU (96 mg, 0.25 mmol) were added and the reaction mixture stirred for 10 min at rt. (3S)-3-Amino-9-fluoro-5-phenyl-1,3-dihydro-1,4-benzodiazepin-2-one (62 mg, 0.23 mmol) was added and the reaction stirred at rt overnight. The reaction was quenched with water (10 mL) and the resultant precipitate collected by filtration, washing with water (2×5 mL). The precipitate was dissolved in $CH_2Cl_2$ (20 mL), the solvent removed under reduced pressure and the residue purified by flash chromatography [20-60% (EtOH:$CH_2Cl_2$:$NH_4OH$; 50:8:1) in $CH_2Cl_2$] to afford a white solid (58 mg, 38%). $^1H$ NMR (600 MHz, DMSO-$d_6$) δ 10.93 (d, J=5.0 Hz, 1H), 7.87 (dd, J=7.7, 6.3 Hz, 1H), 7.62-7.55 (m, 1H), 7.49-7.41 (m, 3H), 7.41-7.27 (m, 6H), 7.27-7.22 (m, 1H), 7.19-7.11 (m, 2H), 5.36 (dd, J=7.7, 2.9 Hz, 1H), 4.72 (dt, J=10.1, 4.3 Hz, 1H), 4.42 (dd, J=10.7, 7.8 Hz, 1H), 4.28 (dd, J=12.2, 5.3 Hz, 1H), 3.99-3.90 (m, 1H), 3.70-3.57 (m, 2H), 2.78 (s, 1H), 1.00 (td, J=7.0, 5.5 Hz, 3H). LRMS (APCI+) m/z 660.7 $[M+H]^+$.

The following compounds were prepared by an analogous procedure to that described for the compound of Example 174. Examples 185 was subject to additional purification by preparative HPLC method 4 [50:50 MeCN:water (0.1% v/v formic acid)].

TABLE 32

Example compounds

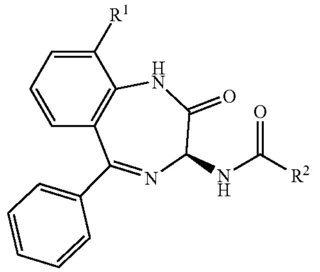

| Example | Name | $R^1$ | $R^2$ | $^1$H NMR δ (DMSO-$d_6$) | LRMS APCI+ m/z |
|---|---|---|---|---|---|
| 175 | 2-(2-Fluorophenyl)-6-methoxy-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide | F | 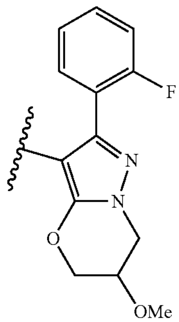 [SMILES: *c1c(-c2ccccc2F)nn2c1OCC(OC)C2] | (500 MHz) δ 10.94 (s, 1H), 7.86 (dd, J = 11.5, 7.7 Hz, 1H), 7.61 – 7.27 (m, 9H), 7.19 – 7.09 (m, 3H), 5.38 (dd, J = 7.7, 3.9 Hz, 1H), 4.87 – 4.78 (m, 1H), 4.61 (dd, J = 11.4, 4.2 Hz, 1H), 4.40 – 4.27 (m, 2H), 4.22 – 4.11 (m, 1H), 3.44 (d, J = 1.0 Hz, 3H). | 544.3 $[M + H]^+$ |
| 176 | 2-(6-Ethylpyridin-3-yl)-N-[(3S)-2-oxo-5-phenyl-1,3-dihydro-1,4-benzodiazepin-3-yl]spiro[5,7-dihydropyrazolo[5,1-b][1,3]oxazine-6,1'-cyclobutane]-3-carboxamide | H | 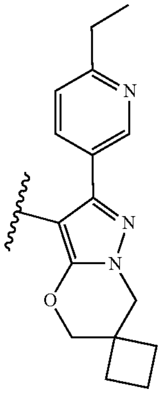 [SMILES: *c1c(-c2ccc(CC)nc2)nn2c1OCC1(CCC1)C2] | (500 MHz) δ 10.98 (s, 1H), 8.67 (dd, J = 2.3, 0.8 Hz, 1H), 8.12 (d, J = 7.5 Hz, 1H), 7.93 (dd, J = 8.1, 2.3 Hz, 1H), 7.64 (ddd, J = 8.4, 7.1, 1.7 Hz, 1H), 7.58 – 7.38 (m, 4H), 7.36 – 7.15 (m, 4H), 5.33 (d, J = 7.5 Hz, 1H), 4.74 – 4.53 (m, 2H), 4.23 (s, 2H), 2.74 (q, J = 7.6 Hz, 2H), 2.18 – 1.93 (m, 6H), 1.22 (t, J = 7.6 Hz, 3H). | 547.2 $[M + H]^+$ |
| 177 | 2-(6-Ethylpyridin-3-yl)-N-[(3S)-9-fluoro-2-oxo-5-phenyl-1,3-dihydro-1,4-benzodiazepin-3-yl]spiro[5,7-dihydropyrazolo[5,1-b][1,3]oxazine-6,1'-cyclobutane]-3-carboxamide | F | 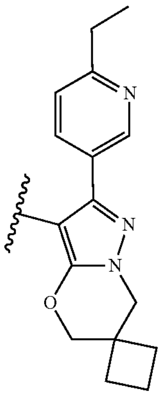 [SMILES: *c1c(-c2ccc(CC)nc2)nn2c1OCC1(CCC1)C2] | (500 MHz) δ 10.95 (s, 1H), 8.67 (dd, J = 2.3, 0.8 Hz, 1H), 8.13 (d, J = 7.4 Hz, 1H), 7.92 (dd, J = 8.1, 2.3 Hz, 1H), 7.59 (ddd, J = 10.1, 8.3, 1.3 Hz, 1H), 7.56 – 7.41 (m, 5H), 7.31 (td, J = 8.1, 5.0 Hz,1H), 7.21 (dd, J = 8.1, 0.8 Hz, 1H), 7.15 (d, J = 7.9 Hz, 1H), 5.41 (d, J = 7.4 Hz, 1H), 4.67 – 4.54 (m, 2H), 4.23 (s, 2H), 2.74 (q, J = 7.6 Hz, 2H), 2.17 – 1.93 (m, 6H), 1.22 (t, J = 7.6 Hz, 3H). | 565.2 $[M + H]^+$ |

TABLE 32-continued

Example compounds

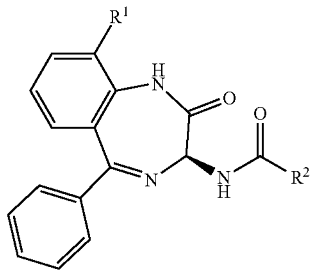

| Example | Name | $R^1$ | $R^2$ | $^1H$ NMR δ (DMSO-$d_6$) | LRMS APCI+ m/z |
| --- | --- | --- | --- | --- | --- |
| 178 | 2-[6-(Propan-2-ylamino)pyridin-3-yl]-N-[(3S)-2-oxo-5-phenyl-1,3-dihydro-1,4-benzodiazepin-3-yl]spiro[5,7-dihydropyrazolo[5,1-b][1,3]oxazine-6,1'-cyclopropane]-3-carboxamide | H | 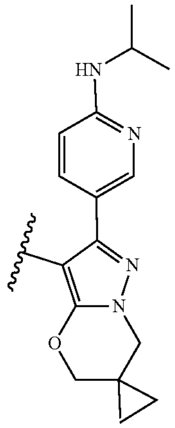 | (500 MHz) δ 10.97 (s, 1H), 8.29 (s, 1H), 8.09 (d, J = 7.6 Hz, 1H), 7.80 - 7.58 (m, 2H), 7.57 - 7.36 (m, 4H), 7.35 - 7.14 (m, 3H), 6.87 - 6.39 (m, 2H), 5.40 - 5.29 (m, 1H), 4.52 - 4.39 (m, 2H), 4.11 - 4.03 (m, 2H), 4.03 - 3.91 (m, 1H), 1.14 (d, J = 6.5 Hz, 6H), 1.01 - 0.69 (m, 4H). | 562.3 $[M + H]^+$ |
| 179 | 2-[6-(Propan-2-ylamino)pyridin-3-yl]-N-[(3S)-9-fluoro-2-oxo-5-phenyl-1,3-dihydro-1,4-benzodiazepin-3-yl]spiro[5,7-dihydropyrazolo[5,1-b][1,3]oxazine-6,1'-cyclopropane]-3-carboxamide | F | 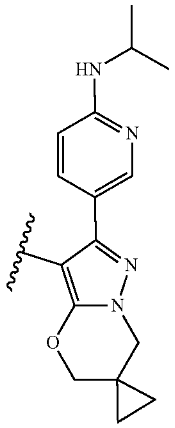 [SMILES: *c1c(-c2ccc(NC(C)C)nc2)nn2c1OCC1(CC1)C2] | (500 MHz) δ 10.93 (s, 1H), 8.25 (d, J = 2.3 Hz, 1H), 8.09 (d, J = 7.6 Hz, 1H), 7.72 - 7.40 (m, 7H), 7.32 (td, J = 8.1, 5.0 Hz, 1H), 7.16 (d, J = 7.9 Hz, 1H), 6.64 - 6.26 (m, 3H), 5.43 (d, J = 7.5 Hz, 1H), 4.53 - 4.34 (m, 2H), 4.13 - 4.02 (m, 2H), 4.02 - 3.94 (m, 1H), 1.13 (d, J = 6.4 Hz, 6H), 0.93 - 0.74 (m, 4H). | 580.4 $[M + H]^+$ |
| 180 | 2-(6-Ethylpyridin-3-yl)-N-[(3S)-2-oxo-5-phenyl-1,3-dihydro-1,4-benzodiazepin-3-yl]spiro[5,7-dihydropyrazolo[5,1-b][1,3]oxazine-6,1'-cyclopropane]-3-carboxamide | H | 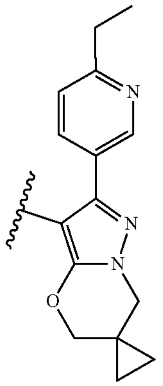 [SMILES: *c1c(-c2ccc(CC)nc2)nn2c1OCC1(CC1)C2] | (500 MHz) δ 10.98 (s, 1H), 8.67 (d, J = 2.2 Hz, 1H), 8.12 (d, J = 7.6 Hz, 1H), 7.92 (dd, J = 8.0, 2.3 Hz, 1H), 7.69 - 7.57 (m, 1H), 7.57 - 7.33 (m, 5H), 7.33 - 7.13 (m, 4H), 5.35 (d, J = 7.6 Hz, 1H), 4.55 - 4.38 (m, 2H), 4.21 - 4.03 (m, 2H), 2.74 (q, J = 7.6 Hz, 2H), 1.22 (t, J = 7.6 Hz, 3H), 0.96 - 0.75 (m, 4H). | 533.4 $[M + H]^+$ |

TABLE 32-continued

Example compounds

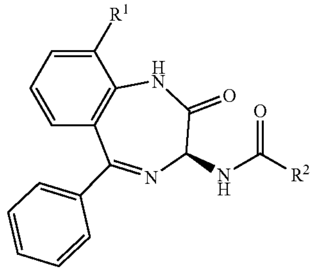

| Example | Name | $R^1$ | $R^2$ | $^1$H NMR δ (DMSO-$d_6$) | LRMS APCI+ m/z |
|---|---|---|---|---|---|
| 181 | 2-(6-Ethylpyridin-3-yl)-N-[(3S)-9-fluoro-2-oxo-5-phenyl-1,3-dihydro-1,4-benzodiazepin-3-yl]spiro[5,7-dihydropyrazolo[5,1-b][1,3]oxazine-6,1'-cyclopropane]-3-carboxamide | F | 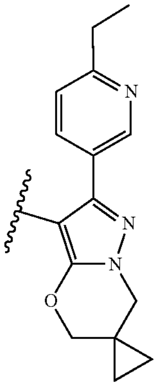 [SMILES: *c1c(-c2ccc(CC)nc2)nn2c1OCC1(CC1)C2] | (500 MHz) δ 10.94 (s, 1H), 8.67 (dd, J = 2.3, 0.8 Hz, 1H), 8.13 (d, J = 7.5 Hz, 1H), 7.92 (dd, J = 8.0, 2.3 Hz, 1H), 7.74 - 7.36 (m, 6H), 7.31 (dt, J = 8.1, 4.0 Hz, 1H), 7.22 (d, J = 8.1 Hz, 1H), 7.15 (d, J = 7.9 Hz, 1H), 5.43 (d, J = 7.5 Hz, 1H), 4.61 - 4.38 (m, 2H), 4.24 - 3.99 (m, 2H), 2.74 (q, J = 7.6 Hz, 2H), 1.22 (t, J = 7.6 Hz, 3H), 0.99 - 0.74 (m, 4H). | 551.3 [M + H]$^+$ |
| 182 | N-[(3S)-9-fluoro-2-oxo-5-phenyl-1,3-dihydro-1,4-benzodiazepin-3-yl]-2-(2-fluorophenyl)-6-(pyrrolidin-1-ylmethyl)-6,7-dihydro-5H-pyrazolo[5,1-b][1,3]oxazine-3-carboxamide | F | 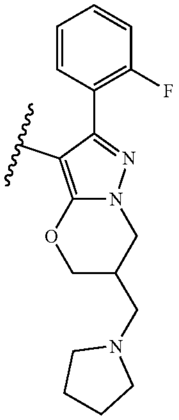 [SMILES: *c1c(-c2ccccc2F)nn2c1OCC(CN1CCCC1)C2] | (400 MHz) δ 10.95 (d, J = 6.6 Hz, 1H), 7.89 (t, J = 7.6 Hz, 1H), 7.61 - 7.25 (m, 9H), 7.20 - 7.08 (m, 3H), 5.37 (dd, J = 7.7, 2.3 Hz, 1H), 4.72 (d, J = 10.3 Hz, 1H), 4.51 - 4.41 (m, 1H), 4.29 (dd, J = 12.3, 5.3 Hz, 1H), 3.99 (dd, J = 12.3, 7.5 Hz, 1H), 2.73 (s, 1H), 1.80 - 1.62 (m, 4H). | 598.0 [M + H]$^+$ |
| 183 | (5R)-N-[(3S)-9-fluoro-2-oxo-5-phenyl-1,3-dihydro-1,4-benzodiazepin-3-yl]-2-[2-fluoro-4-[(propan-2-ylamino)methyl] phenyl]-5-methyl-6,7-dihydro-5H-pyrazolo[5,1-b][1,3]oxazine-3-carboxamide | F | 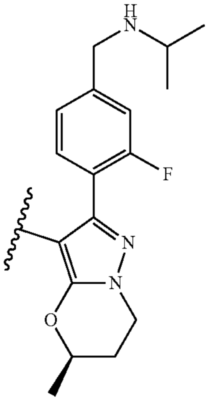 [SMILES: *c1c(-c2ccc(CNC(C)C)cc2F)nn2c1O[C@H](C)CC2] | (400 MHz) δ 10.88 (s, 1H), 8.08 (d, J = 7.5 Hz, 1H), 7.62 - 7.39 (m, 6H), 7.35 - 7.22 (m, 2H), 7.16 - 7.05 (m, 3H), 5.33 (d, J = 7.5 Hz, 1H), 4.81 (ddd, J = 10.4, 6.2, 2.1 Hz, 1H), 4.26 - 4.13 (m, 2H), 3.69 (s, 2H), 2.73 - 2.62 (m, 1H), 2.42 - 2.30 (m, 2H), 2.25 - 2.08 (m, 2H), 1.55 (d, J = 6.3 Hz, 3H), 0.98 (d, J = 6.2 Hz, 6H). | 599.3 [M + H]$^+$ |

TABLE 32-continued

Example compounds

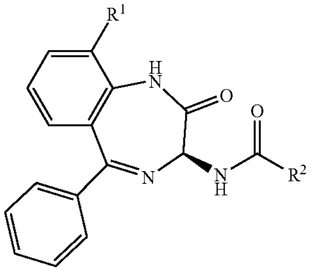

| Example | Name | $R^1$ | $R^2$ | $^1H$ NMR δ ($DMSO-d_6$) | LRMS APCI+ m/z |
|---|---|---|---|---|---|
| 184 | N-[(3S)-9-fluoro-2-oxo-5-phenyl-1,3-dihydro-1,4-benzodiazepin-3-yl]-2-(2-fluorophenyl)-6-(methylsulfonylmethyl)-6,7-dihydro-5H-pyrazolo[5,1-b][1,3]oxazine-3-carboxamide | F | 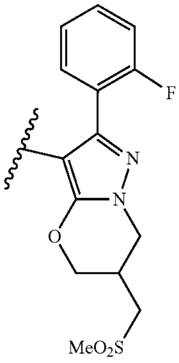 [SMILES: *c1c(-c2ccccc2F)nn2c1OCC(CS(C)(=O)=O)C2] | (400 MHz) δ 10.96 (d, J = 7.2 Hz, 1H), 7.91 (dd, J = 9.2, 7.6 Hz, 1H), 7.65 - 7.24 (m, 9H), 7.24 - 7.06 (m, 3H), 5.37 (dd, J = 7.6, 2.8 Hz, 1H), 4.86 - 4.73 (m, 1H), 4.62 - 4.41 (m, 2H), 4.26 - 4.11 (m, 1H), 3.58 - 3.39 (m, 2H), 3.23 - 3.09 (m, 4H). | 606.6 $[M + H]^+$ |
| 185 | 2-(2-Fluorophenyl)-N-[(3S)-9-fluoro-2-oxo-5-phenyl-1,3-dihydro-1,4-benzodiazepin-3-yl]spiro[5,7-dihydropyrazolo[5,1-b][1,3]oxazine-6,1'-cyclobutane]-3-carboxamide | F | 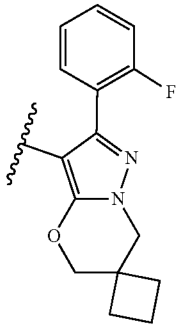 [SMILES: *c1c(-c2ccccc2F)nn2c1OCC1(CCC1)C2] | (500 MHz) δ 10.93 (s, 1H), 7.90 (d, J = 7.7 Hz, 1H), 7.61 - -7.50 (m, 2H), 7.50 - 7.42 (m, 3H), 7.42 - 7.33 (m, 2H), 7.33 - 7.21 (m, 2H), 7.21 - 7.05 (m, 3H), 5.36 (d, J = 7.7 Hz, 1H), 4.66 - 4.58 (m, 2H), 4.26 - 4.20 (m, 2H), 2.25 - 1.91 (m, 6H). | 554.2 $[M + H]^+$ |
| 186 | 6-[(3,3-Difluoropyrrolidin-1-yl)methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo [5,1-b][1,3]oxazine-3-carboxamide | F | 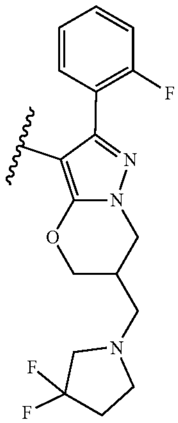 [SMILES: *c1c(-c2ccccc2F)nn2c1OCC(CN1CCC(F)(F)C1)C2] | (600 MHz) δ 10.94 (d, J = 8.8 Hz, 1H), 8.80 (dd, J = 4.4, 1.4 Hz, 0.5H), 8.68 (dd, J = 8.4, 1.3 Hz, 0.5H), 7.89 (dd, J = 9.7, 7.7 Hz, 1H), 7.61 (dd, J = 8.4, 4.5 Hz, 0.5H), 7.59 - 7.55 (m, 1H), 7.54 - 7.43 (m, 5H), 7.43 - 7.32 (m, 2H), 7.32 - 7.22 (m, 2H), 7.19 - 7.10 (m, 2.5H), 5.37 (dd, J = 7.7, 2.8 Hz, 1H), 4.74 - 4.68 (m, 1.5H), 4.48 - 4.43 (m, 1.5H), 4.35 (dd, J = 12.4, 5.4 Hz, 0.5H), 4.29 (dd, J = 12.4, 5.4 Hz, 1H), 4.04 (dd, J = 12.5, 7.5 Hz, 1H), 3.98 (dd, J = 12.3, 7.5 Hz, 1H), 3.06 - 2.93 (m, 3H), 2.79 (t, J = 7.5 Hz, 4H), 2.64 - 2.56 (m, 3H), 2.33 - 2.22 (m, 3H). | 632.6 $[M + H]^+$ |

TABLE 32-continued

Example compounds

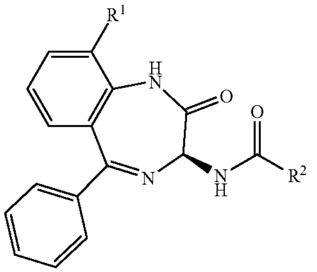

| Example | Name | $R^1$ | $R^2$ | $^1H$ NMR δ (DMSO-$d_6$) | LRMS APCI+ m/z |
|---|---|---|---|---|---|
| 187 | N-[(3S)-9-fluoro-2-oxo-5-phenyl-1,3-dihydro-1,4-benzodiazepin-3-yl]-2-(2-fluorophenyl)-5-(pyrrolidin-1-ylmethyl)-6,7-dihydro-5H-pyrazolo[5,1-b][1,3]oxazine-3-carboxamide | F | 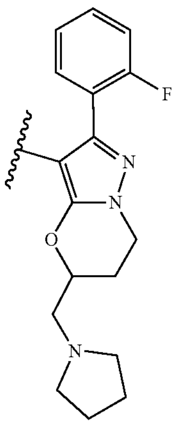 [SMILES: *c1c(-c2ccccc2F)nn2c1OC(CN1CCCC1)CC2] | (600 MHz) δ 10.87 (d, J = 13.1 Hz, 1H), 7.94 (dd, J = 13.3, 7.7 Hz, 1H), 7.54 (dd, J = 10.3, 8.2 Hz, 1H), 7.52 - 7.39 (m, 5H), 7.38 - 7.29 (m, 2H), 7.26 (td, J = 8.0, 5.0 Hz, 1H), 7.16 - 7.06 (m, 3H), 5.33 (dd, J = 10.7, 7.7 Hz, 1H), 4.79 (d, J = 9.5 Hz, 1H), 4.24 - 4.15 (m, 2H), 2.91 (q, J = 13.1, 11.3 Hz, 2H), 2.70 - 2.54 (m, 4H), 2.37 - 2.30 (m, 1H), 2.29 - 2.17 (m, 1H), 1.68 - 1.57 (m, 3H), 1.29 - 1.17 (m, 1H). | 596.9 $[M + H]^+$ |

The following compounds were prepared as single diasteromers by resolution by chiral PLC or SFC and isolated as single diastereomers of unknown absolute stereochemistry. Examples 188-1, 188-2, 189-1 and 189-2 were prepared by the amide coupling procedure described for the compound of Example 5, with resolution by the chiral HPLC/SFC method indicated. Examples 190-1, 190-2, 191-1 and 191-2 were prepared by the amide coupling procedure described for the compound of Example 21 at rt for 1 h with 5 eq. $NEt_3$, with resolution by the chiral HPLC method indicated. The stereochemical configuration of these compounds has been designated as R* or S*, with the arbitrarily defined stereocenter indicated by an asterisk. The retention time for each resolved diastereomer under the indicated analytical conditions is denoted by $t_R$.

TABLE 33

Resolution of Diastereomers

| Parent Example | Preparative Resolution Method (Mobile Phase) | Analytical Method (Mobile Phase) | Diastereomer 1 $t_R$ (min) | Diastereomer 2 $t_R$ (min) |
|---|---|---|---|---|
| 110 | Chiral HPLC Method 2 EtOH (0.2% v/v $NH_3$) | Chiral SFC Method 1A 50:50 EtOH:$CO_2$ (0.2% v/v $NH_3$) | 110-1 $t_R$ = 5.16 min | 110-2 $t_R$ = 4.12 min |
| 129 | Chiral SFC Method 2 25:75 MeOH:$CO_2$ (0.2% v/v NH3) | Chiral SFC Method 2A 25:75 MeOH:$CO_2$ (0.2% v/v $NH_3$) | 129-1 $t_R$ = 5.35 min | 129-2 $t_R$ = 6.03 min |
| 171 | Chiral SFC Method 3 50:50 MeOH:$CO_2$ (0.2% v/v $NH_3$) | Chiral SFC Method 3A 50:50 MeOH:$CO_2$ (0.2% v/v $NH_3$) | 171-1 $t_R$ = 3.41 min | 171-2 $t_R$ = 4.55 min |
| 188 | Chiral HPLC Method 2 MeOH (0.2% v/v $NH_3$) | Chiral SFC Method 1A 50:50 EtOH:$CO_2$ (0.2% v/v $NH_3$) | 188-1 $t_R$ = 2.30 min | 188-2 $t_R$ = 3.16 min |
| 189 | Chiral HPLC Method 2 MeOH (0.2% v/v $NH_3$) | Chiral SFC Method 1A 45:55 EtOH:$CO_2$ (0.2% v/v $NH_3$) | 189-1 $t_R$ = 2.11 min | 189-2 $t_R$ = 3.21 min |
| 190 | Chiral HPLC Method 1 70:30 MeCN:water (0.3% v/v $NH_3$) | Chiral HPLC Method 1A 50:50 MeCN: water (0.1% v/v diethylamine) | 190-1 $t_R$ = 4.58 min | 190-2 $t_R$ = 8.41 min |

TABLE 33-continued

| Resolution of Diastereomers | | | | |
|---|---|---|---|---|
| Parent Example | Preparative Resolution Method (Mobile Phase) | Analytical Method (Mobile Phase) | Diastereomer 1 $t_R$ (min) | Diastereomer 2 $t_R$ (min) |
| 191 | Chiral HPLC Method 1 70:30 MeCN:water (0.3% v/v $NH_3$) | Chiral HPLC Method 1A 60:40 MeCN:water (0.1% v/v diethylamine) | 191-1 $t_R$ = 2.90 min | 191-2 $t_R$ = 10.29 min |

TABLE 34

Examples prepared as single diastereomers

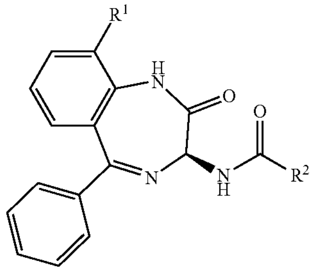

| Example | Name | $R^1$ | $R^2$ | $^1$H NMR δ (400 MHz, DMSO-$d_6$) | LRMS/ LCMS m/z |
|---|---|---|---|---|---|
| 110-1 | (6R*)-N-[(3S)-9-fluoro-2-oxo-5-phenyl-1,3-dihydro-1,4-benzodiazepin-3-yl]-2-(2-fluorophenyl)-6-(hydroxymethyl)-6,7-dihydro-5H-pyrazolo[5,1-b][1,3]oxazine-3-carboxamide | F | 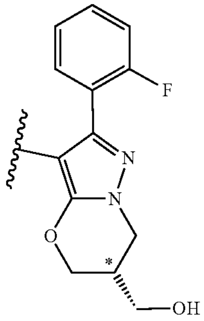 | δ 10.94 (s, 1H), 7.90 (d, J = 7.7 Hz, 1H), 7.63 - 7.25 (m, 9H), 7.21 - 7.05 (m, 3H), 5.36 (d, J = 7.6 Hz, 1H), 5.07 (t, J = 5.3 Hz, 1H), 4.72 (dd, J = 10.9, 3.2 Hz, 1H), 4.50 (dd, J = 10.8, 7.9 Hz, 1H), 4.28 (dd, J = 12.3, 5.5 Hz, 1H), 4.03 (dd, J = 12.3, 7.5 Hz, 1H), 3.59 (t, J = 5.9 Hz, 2H), 2.66 - 2.56 (m, 1H). | LRMS APCI+ 543.8 [M + H]$^+$ |
| 110-2 | (6S*)-N-[(3S)-9-fluoro-2-oxo-5-phenyl-1,3-dihydro-1,4-benzodiazepin-3-yl]-2-(2-fluorophenyl)-6-(hydroxymethyl)-6,7-dihydro-5H-pyrazolo[5,1-b][1,3]oxazine-3-carboxamide | F | 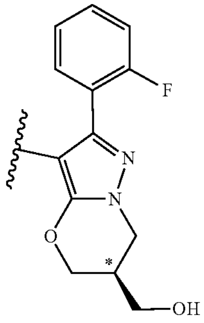 [SMILES: *c1c(-c2ccccc2F)nn2c1OC[C@H](CO)C2] | δ 10.93 (s, 1H), 7.88 (d, J = 7.7 Hz, 1H), 7.61 - 7.24 (m, 9H), 7.22 - 7.07 (m, 3H), 5.36 (d, J = 7.6 Hz, 1H), 5.06 (t, J = 5.3 Hz, 1H), 4.72 (dd, J = 10.8, 3.2 Hz, 1H), 4.49 (dd, J = 10.8, 7.9 Hz, 1H), 4.28 (dd, J = 12.4, 5.5 Hz, 1H), 4.03 (dd, J = 12.3, 7.5 Hz, 1H), 3.59 (t, J = 6.0 Hz, 2H), 2.65 - 2.55 (m, 1H). | LRMS APCI+ 543.8 [M + H]$^+$ |

TABLE 34-continued

Examples prepared as single diastereomers

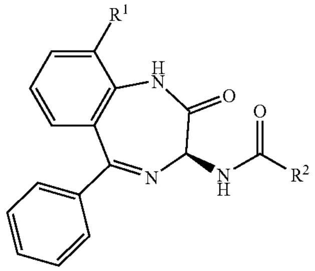

| Example | Name | $R^1$ | $R^2$ | $^1H$ NMR δ (400 MHz, DMSO-$d_6$) | LRMS/ LCMS m/z |
|---|---|---|---|---|---|
| 129-1 | (6R*)-2-(2,6-Difluorophenyl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide | F | 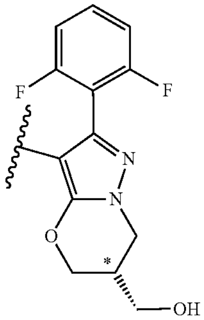 | δ 10.86 (s, 1H), 7.90 (d, J = 7.7 Hz, 1H), 7.66 - 7.36 (m, 7H), 7.34 - 7.21 (m, 1H), 7.21 - 6.94 (m, 3H), 5.35 (d, J = 7.7 Hz, 1H), 5.08 (t, J = 5.4 Hz, 1H), 4.75 (dd, J = 10.9, 3.2 Hz, 1H), 4.53 (dd, J = 10.8, 8.0 Hz, 1H), 4.30 (dd, J = 12.4, 5.5 Hz, 1H), 4.05 (dd, J = 12.4, 7.6 Hz, 1H), 3.59 (t, J = 5.7 Hz, 2H), 2.70 - 2.59 (m, 1H). | LRMS APCI+ 561.8 [M + H]+ |
| 129-2 | (6S*)-2-(2,6-Difluorophenyl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide | F | 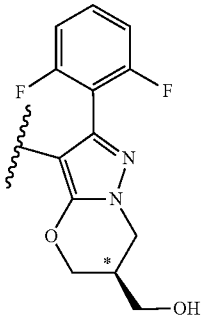 [SMILES: *c1c(-c2c(F)cccc2F)nn2c1OC[C@H](CO)C2] | δ 9.77 (s, 1H), 7.89 (d, J = 7.7 Hz, 1H), 7.64 - 7.37 (m, 7H), 7.25 (s, 1H), 7.16 - 6.95 (m, 3H), 5.32 (d, J = 7.6 Hz, 1H), 5.11 - 4.99 (m, 1H), 4.75 (dd, J = 10.8, 3.3 Hz, 1H), 4.52 (dd, J = 10.8, 8.0 Hz, 1H), 4.30 (dd, J = 12.3, 5.5 Hz, 1H), 4.05 (dd, J = 12.4, 7.6 Hz, 1H), 3.58 (t, J = 5.5 Hz, 2H), 2.66 - 2.57 (m, 1H). | LRMS APCI+ 561.9 [M + H]+ |
| 171-1 | (6R*)-6-[(Dimethylamino) methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide | F | 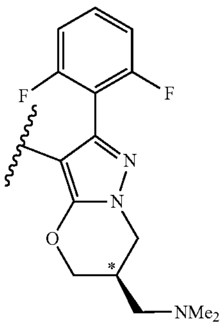 [SMILES: *c1c(-c2c(F)cccc2F)nn2c1OC[C@H](CN(C)C)C2] | δ 10.96 (s, 1H), 7.90 (d, J = 7.7 Hz, 1H), 7.61 - 7.33 (m, 7H), 7.29 (td, J = 8.1, 5.0 Hz, 1H), 7.21 - 7.07 (m, 3H), 5.36 (d, J = 7.7 Hz, 1H), 4.69 (dd, J = 10.8, 3.3 Hz, 1H), 4.43 (dd, J = 10.8, 8.2 Hz, 1H), 4.26 (dd, J = 12.2, 5.4 Hz, 1H), 3.95 (dd, J = 12.3, 7.8 Hz, 1H), 2.84 - 2.71 (m, 1H), 2.38 - 2.29 (m, 2H), 2.21 (s, 6H). | LRMS APCI+ 571.0 [M + H]+ |

TABLE 34-continued

Examples prepared as single diastereomers

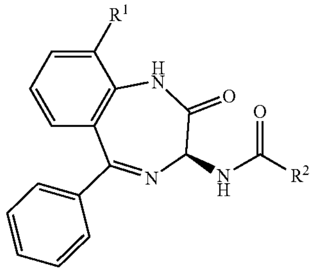

| Example | Name | $R^1$ | $R^2$ | $^1$H NMR δ (400 MHz, DMSO-$d_6$) | LRMS/ LCMS m/z |
|---|---|---|---|---|---|
| 171-2 | (6S*)-6-[(Dimethylamino) methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide | F | 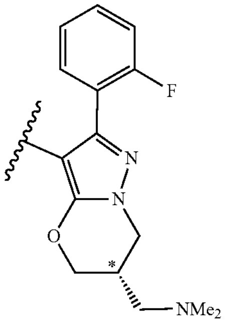 [SMILES: *c1c(-c2ccccc2F)nn2c1OC[C@@H](CN(C)C)C2] | δ 10.95 (s, 1H), 7.89 (d, J = 7.7 Hz, 1H), 7.65 - 7.34 (m, 8H), 7.30 (td, J = 8.1, 5.1 Hz, 1H), 7.21 - 7.10 (m, 3H), 5.37 (d, J = 7.7 Hz, 1H), 4.71 (dd, J = 10.7, 3.3 Hz, 1H), 4.44 (dd, J = 10.8, 8.2 Hz, 1H), 4.27 (dd, J = 12.3, 5.3 Hz, 1H), 3.96 (dd, J = 12.3, 7.8 Hz, 1H), 2.84 - 2.72 (m, 1H), 2.40 - 2.31 (m, 3H), 2.22 (s, 6H). | LRMS APCI+ 571.0 $[M + H]^+$ |
| 188-1 | (5R*)-2-(2,6-Difluorophenyl)-5-(hydroxymethyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 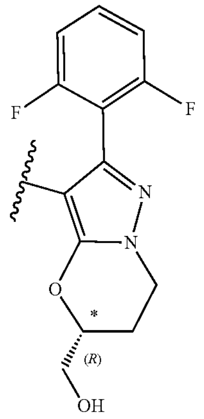 | (400 MHz) δ 10.94 (s, 1H), 8.08 (d, J = 7.7 Hz, 1H), 7.61 (t, J = 7.7 Hz, 1H), 7.54 - 7.38 (m, 6H), 7.31 - 7.19 (m, 3H), 7.06 (t, J = 7.8 Hz, 2H), 5.26 (d, J = 7.6 Hz, 1H), 5.24 - 5.17 (m, 1H), 4.75 - 4.67 (m, 1H), 4.34 - 4.18 (m, 2H), 3.83 (q, J = 4.6 Hz, 2H), 2.39 - 2.22 (m, 2H). | LRMS APCI+ 543.9 $[M + H]^+$ |
| 188-2 | (5S*)-2-(2,6-Difluorophenyl)-5-(hydroxymethyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide | H | 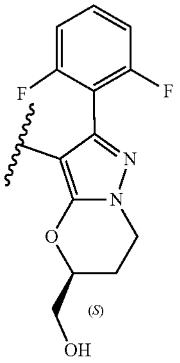 | (400 MHz) δ 10.87 (s, 1H), 8.05 (d, J = 7.6 Hz, 1H), 7.61 (t, J = 7.7 Hz, 1H), 7.55 - 7.38 (m, 6H), 7.31 - 7.25 (m, 2H), 7.26 - 7.17 (m, 1H), 7.07 (t, J = 8.1 Hz, 2H), 5.27 - 5.09 (m, 2H), 4.76 - 4.62 (m, 1H), 4.34 - 4.18 (m, 2H), 3.91 - 3.74 (m, 2H), 2.37 (d, J = 14.8 Hz, 1H), 2.33 - 2.18 (m, 1H). | LRMS APCI+ 543.9 $[M + H]^+$ |

TABLE 34-continued

Examples prepared as single diastereomers

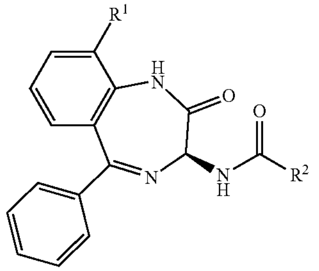

| Example | Name | $R^1$ | $R^2$ | $^1$H NMR δ (400 MHz, DMSO-$d_6$) | LRMS/ LCMS m/z |
|---|---|---|---|---|---|
| 189-1 | (5R*)-2-(2,6-Difluorophenyl)-N-[(3S)-9-fluoro-2-oxo-5-phenyl-1,3-dihydro-1,4-benzodiazepin-3-yl]-5-(hydroxymethyl)-6,7-dihydro-5H-pyrazolo[5,1-b][1,3]oxazine-3-carboxamide | F | 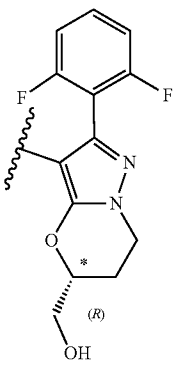 | (400 MHz) δ 10.87 (s, 1H), 8.05 (d, J = 7.6 Hz, 1H), 7.61 (t, J = 7.7 Hz, 1H), 7.55 - 7.38 (m, 6H), 7.31 - 7.25 (m, 2H), 7.26 - 7.17 (m, 1H), 7.07 (t, J = 8.1 Hz, 2H), 5.27 - 5.09 (m, 2H), 4.76 - 4.62 (m, 1H), 4.34 - 4.18 (m, 2H), 3.91 - 3.74 (m, 2H), 2.37 (d, J = 14.8 Hz, 1H), 2.33 - 2.18 (m, 1H). | LRMS APCI+ 561.8 [M + H]$^+$ |
| 189-2 | (5S*)-2-(2,6-Difluorophenyl)-N-[(3S)-9-fluoro-2-oxo-5-phenyl-1,3-dihydro-1,4-benzodiazepin-3-yl]-5-(hydroxymethyl)-6,7-dihydro-5H-pyrazolo[5,1-b][1,3]oxazine-3-carboxamide | F | 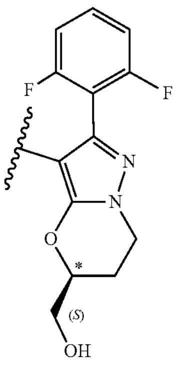 | (400 MHz) δ 10.91 (s, 1H), 8.05 (d, J = 7.4 Hz, 1H), 7.60 - 7.38 (m, 7H), 7.28 (td, J = 8.0, 5.0 Hz, 1H), 7.15 - 7.03 (m, 3H), 5.32 (d, J = 7.4 Hz, 1H), 5.18 (t, J = 5.7 Hz, 1H), 4.77 - 4.65 (m, 1H), 4.34 - 4.18 (m, 2H), 3.90 - 3.74 (m, 2H), 2.43 - 2.19 (m, 2H). | LRMS APCI+ 561.8 [M + H]$^+$ |
| 190-1 | (5R*)-N-[(3S)-9-Fluoro-2-oxo-5-phenyl-1,3-dihydro-1,4-benzodiazepin-3-yl]-2-(2-fluorophenyl)-5-(hydroxymethyl)-6,7-dihydro-5H-pyrazolo[5,1-b][1,3]oxazine-3-carboxamide | F | 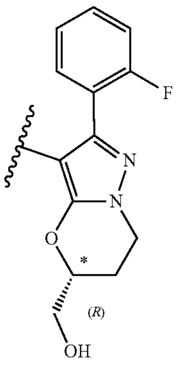 | 10.93 (s, 1H), 8.16 (s, 1H), 7.58 - 7.42 (m, 6H), 7.42 - 7.33 (m, 2H), 7.26 (s, 1H), 7.21 - 7.09 (m, 3H), 5.31 (s, 1H), 5.21 (t, J = 5.8 Hz, 1H), 4.70 - 4.66 (m, 1H), 4.31 - 4.18 (m, 2H), 3.89 - 3.78 (m, 2H), 2.39 - 2.32 (m, 1H), 2.32 - 2.21 (m, 1H). | LCMS ESI+ method C 544.4 [M + H]$^+$ at 3.36 min |

TABLE 34-continued

Examples prepared as single diastereomers

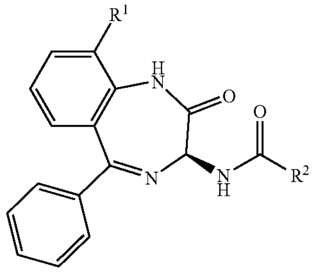

| Example | Name | $R^1$ | $R^2$ | $^1$H NMR δ (400 MHz, DMSO-$d_6$) | LRMS/ LCMS m/z |
|---|---|---|---|---|---|
| 190-2 | (5S*)-2-(2-Fluorophenyl)-5-(hydroxymethyl)-N-[(3S)-9-fluoro-2-oxo-5-phenyl-1,3-dihydro-1,4-benzodiazepin-3-yl]-6,7-dihydro-5H-pyrazolo [5,1-b][1,3]oxazine-3-carboxamide | F | 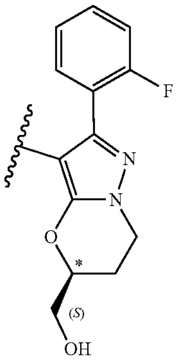 | 10.92 (s, 1H), 8.12 (s, 1H), 7.54 - 7.45 (m, 6H), 7.42-7.33 (m, 2H), 7.26 (s, 2H), 7.19 - 7.11 (m, 3H), 5.29 (s, 1H), 5.18 (t, J = 5.7 Hz, 1H), 4.69 (s, 1H), 4.34 - 4.16 (m, 1H), 3.89 - 3.76 (m, 2H), 2.36 (s, 1H), 2.30 - 2.21 (m, 1H). | LCMS ESI+ method C 544.4 [M + H]+ at 3.38 min |
| 191-1 | (5R*)-N-[(3S)-9-fluoro-2-oxo-5-phenyl-1,3-dihydro-1,4-benzodiazepin-3-yl]-2-(2-fluorophenyl)-5-(methoxymethyl)-6,7-dihydro-5H-pyrazolo[5,1-b][1,3]oxazine-3-carboxamide | F | 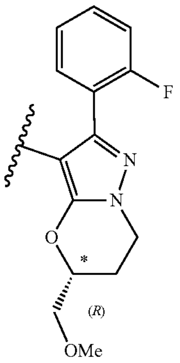 | 10.92 (s, 1H), 8.05 (d, J = 7.4 Hz, 1H), 7.59 - 7.49 (m, 2H), 7.51 - 7.45 (m, 2H), 7.48 - 7.42 (m, 2H), 7.42 - 7.33 (m, 2H), 7.28 (s, 1H), 7.21 - 7.10 (m, 3H), 5.32 (s, 1H), 4.90 - 4.84 (m, 1H), 4.29 - 4.18 (m, 2H), 3.80 (d, J = 4.4 Hz, 2H), 3.42 (s, 3H), 2.38 - 2.23 (m, 2H) | LCMS ESI+ method C 558.4 [M + H]+ at 3.87 min |
| 191-2 | (5S*)-N-[(3S)-9-fluoro-2-oxo-5-phenyl-1,3-dihydro-1,4-benzodiazepin-3-yl]-2-(2-fluorophenyl)-5-(methoxymethyl)-6,7-dihydro-5H-pyrazolo[5,1-b][1,3]oxazine-3-carboxamide | F | 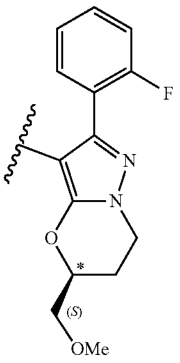 | 10.93 (s, 1H), 8.07 (s, 1H), 7.71 - 7.22 (m, 9H), 7.21 - 7.05 (m, 3H), 5.32 (s, 1H), 4.84 (d, J = 3.0 Hz, 1H), 4.31 - 4.19 (m, 2H), 3.83 - 3.75 (m, 2H), 3.44 (s, 3H), 2.36 - 2.25 (m, 2H). | LCMS ESI+ method C 558.3 [M + H]+ at 3.81 min |

192. 6-(Ethylaminomethyl)-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide

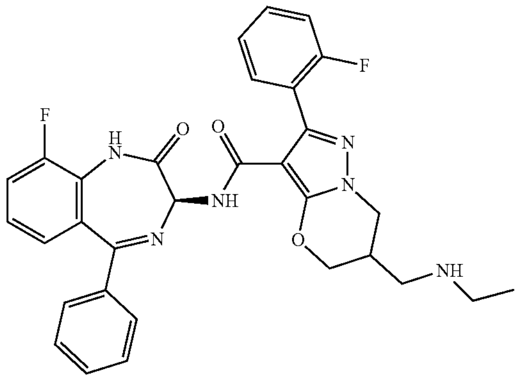 [SMILES: CCNCC1COc2c(C(=O)N[C@H]3N=C(c4ccccc4)c4cccc(F)c4NC3=O)c(-c3ccccc3F)nn2C1]

NaOH (5 M aq. 0.69 mL, 3.45 mmol) was added to a solution of intermediate 97E (150 mg, 0.43 mmol) in EtOH (8 mL). The mixture was heated at 60° C. for 18 h. On cooling, the mixture was acidified to pH≈4 with 1 M aq. HCl, then concentrated to dryness. The crude residue was dissolved in DMF (9 mL), (3S)-3-amino-9-fluoro-5-phenyl-1,3-dihydro-1,4-benzodiazepin-2-one (349 mg, 1.3 mmol) and DIPEA (150 μL, 0.86 mmol) added and the reaction stirred for 5 min at rt. HATU (181 mg, 0.48 mmol) was added and the reaction stirred at rt for 22 h. The mixture was filtered, washing with EtOAc (2×5 ml). Water (30 mL) was added to the filtrate, which was extracted with EtOAc (3×10 mL). The organic extracts were washed with water (2×10 ml) and brine (3×10 mL), dried ($Na_2SO_4$) and the solvent removed under reduced pressure. Purification by flash chromatography [35-80% (50:8:1 $CH_2Cl_2$:EtOH:$NH_4OH$) in $CH_2Cl_2$] afforded a white solid (112 mg, 46%). $^1H$ NMR (400 MHz, DMSO-$d_6$) δ 7.90 (t, J=7.7 Hz, 1H), 7.63-7.22 (m, 10H), 7.22-7.07 (m, 3H), 5.36 (dd, J=7.7, 3.1 Hz, 1H), 4.74 (dd, J=10.7, 2.8 Hz, 1H), 4.51-4.38 (m, 1H), 4.29 (dd, J=12.4, 4.8 Hz, 1H), 4.01 (dd, J=12.4, 6.9 Hz, 1H), 2.74-2.54 (m, 5H), 1.04 (t, J=7.1 Hz, 4H). LRMS (APCI+) m/z 571.2 $[M+H]^+$.

193. 2-(2-Fluoro-4-methylsulfanylphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide 194. 2-(2-Fluoro-4-methylsulfinylphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide

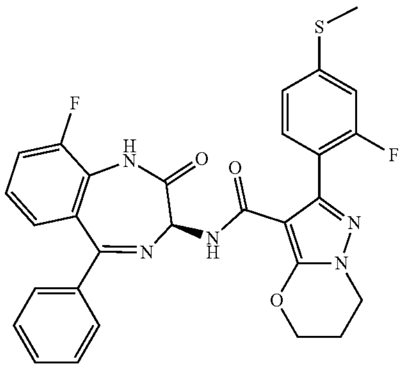

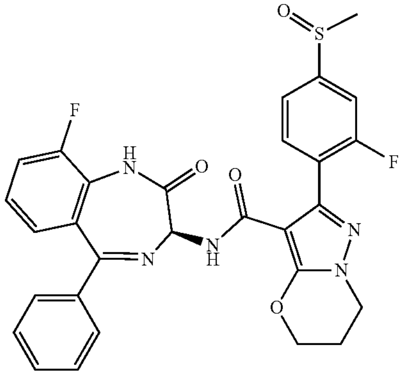

Palladium hydroxide on carbon (20 wt. %, 50% water, 14 mg, 0.09 mmol) was added to a solution of intermediate 119A (150 mg, 0.36 mmol) in EtOH (8 mL) in a pressure tube and the vessel purged successively with $N_2$ (5×) and hydrogen (5×), then stirred under a hydrogen atmosphere at 40 psi at rt for 3 h, and then under a hydrogen atmosphere at 40 psi at 50° C. for 24 h. The reaction was filtered through a glass microfiber pad, washing with EtOH (3×5 mL) and $CH_2Cl_2$ (3×5 mL) and the solvent removed under reduced pressure. EtOH (8 mL) and NaOH (5 M aq. 0.36 mL, 2.9 mmol) were added and the mixture was heated at 60° C. for 16 h. The EtOH was removed under reduced pressure, the mixture acidified to pH≈2 with 1 M aq. HCl and extracted with (3:1 $CHCl_3$:iPrOH; 3×10 mL). The combined organics were washed with water and brine (10 mL each), dried ($Na_2SO_4$) and concentrated under reduced pressure. A mixture of 2-(2-fluoro-4-methylsulfinylphenyl)-6,7-dihydro-5H-pyrazolo[5,1-b][1,3]oxazine-3-carboxylic acid and 2-(2-fluoro-4-methylsulfanylphenyl)-6,7-dihydro-5H-pyrazolo[5,1-b][1,3]oxazine-3-carboxylic acid was obtained (89 mg), which was used without further purification.

The crude mixture (89 mg) was dissolved in DMF (2 mL), and DIPEA (96 μL, 0.55 mmol) and HATU (115 mg, 0.302 mmol) added, and the reaction stirred for 10 min at rt. (3S)-3-Amino-9-fluoro-5-phenyl-1,3-dihydro-1,4-benzodiazepin-2-one (74 mg, 0.28 mmol) was added and the reaction stirred at rt for 16 h. Analogous workup and purification to that described for the compound of Example 5 followed by purification by flash chromatography [10-70% (50:8:1 $CH_2Cl_2$:EtOH:$NH_4OH$) in $CH_2Cl_2$] afforded first Example 193 (30 mg) followed by Example 194 (33 mg) as white solids.

Example 193. $^1$H NMR (400 MHz, DMSO-$d_6$) δ $^1$H NMR (400 MHz, DMSO-$d_6$) δ 10.96 (s, 1H), 7.94-7.81 (m, 1H), 7.61-7.23 (m, 8H), 7.18-7.00 (m, 3H), 5.37 (dd, J=7.7, 2.4 Hz, 1H), 4.74-4.59 (m, 2H), 4.26-4.09 (m, 2H), 2.48 (s, 3H), 2.39-2.28 (m, 2H). LRMS (APCI+) m/z 560.5 $[M+H]^+$.

Example 194. $^1$H NMR (400 MHz, DMSO-$d_6$) δ 10.97 (s, 1H), 7.92 (dd, J=7.7, 1.7 Hz, 1H), 7.65-7.38 (m, 9H), 7.30 (td, J=8.1, 5.1 Hz, 1H), 7.21-7.07 (m, 1H), 5.37 (d, J=7.7 Hz, 1H), 4.67 (t, J=5.2 Hz, 2H), 4.23 (t, J=6.1 Hz, 2H), 2.79 (s, 3H), 2.42-2.27 (m, 2H). LRMS (APCI+) m/z 576.5 $[M+H]^+$.

195. 2-Bromo-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide 196. 2-(2,6-Difluorophenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide

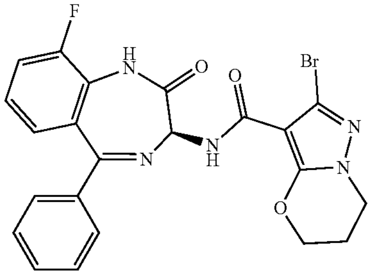

-continued

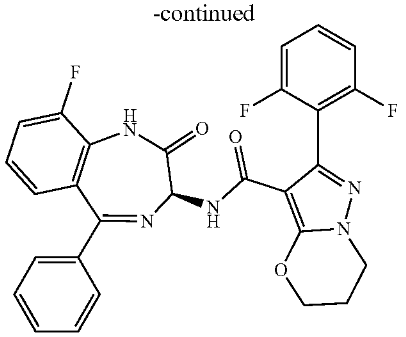

2,6-Difluorophenylboronic acid (1148 mg, 7.27 mmol), CsF (884 mg, 5.82 mmol), XPhos Pd G2 (229 mg, 0.290 mmol) and intermediate 9A (400 mg, 1.45 mmol) were combined in a vial, which was capped evacuated and sparged with $N_2$ (3×). 1,4-Dioxane (5 mL) and water (2 mL), which had both been degassed with $N_2$, were added and the reaction heated at 100° C. for 18 h. The reaction was cooled to rt, then the 1,4-dioxane removed under reduced pressure. Analogous workup and purification to intermediate 74A afforded a mixture of ethyl 2-(2,6-difluorophenyl)-6,7-dihydro-5H-pyrazolo[5,1-b][1,3]oxazine-3-carboxylate and ethyl 2-bromo-6,7-dihydro-5H-pyrazolo[5,1-b][1,3]oxazine-3-carboxylate (178 mg), which was inseparable by silica column chromatography and used without further purification. The mixture was dissolved in EtOH (5 mL), NaOH (5 M aq. soln, 0.59 mL, 2.95 mmol) added, then heated at 60° C. for 20 h. Analogous workup to intermediate 34A afforded a crude mixture of 2-(2,6-difluorophenyl)-6,7-dihydro-5H-pyrazolo[5,1-b][1,3]oxazine-3-carboxylic acid and 2-bromo-6,7-dihydro-5H-pyrazolo[5,1-b][1,3]oxazine-3-carboxylic acid (180 mg) which was used without further purification. A portion of the crude mixture (77 mg) was dissolved in DMF (1.5 mL), and DIPEA (96 μL, 0.55 mmol) and HATU (115 mg, 0.302 mmol) added, and the reaction stirred for 10 min at rt. (3S)-3-Amino-9-fluoro-5-phenyl-1,3-dihydro-1,4-benzodiazepin-2-one (74 mg, 0.28 mmol) was added and the reaction stirred at rt for ~72 h. Analogous workup and purification to that described for the compound of Example 5 followed by purification by flash chromatography (50-70% EtOAc in heptane) afforded first Example 195 (36 mg) followed by Example 196 (58 mg) as white solids.

Example 195. $^1$H NMR (400 MHz, DMSO-$d_6$) δ 10.99 (s, 1H), 7.93 (d, J=7.5 Hz, 1H), 7.65-7.55 (m, 1H), 7.56-7.40 (m, 5H), 7.33 (td, J=8.1, 5.0 Hz, 1H), 7.21-7.12 (m, 1H), 5.43 (d, J=7.5 Hz, 1H), 4.67-4.57 (m, 2H), 4.12 (t, J=6.0 Hz, 2H), 2.33-2.26 (m, 2H). LRMS (APCI+) m/z 487.2/499.2 $[M+H]^+$.

Example 196. $^1$H NMR (400 MHz, DMSO-$d_6$) δ 10.96 (s, 1H), 7.87 (d, J=7.8 Hz, 1H), 7.64-7.37 (m, 7H), 7.29 (td, J=8.1, 5.1 Hz, 1H), 7.14-6.95 (m, 3H), 5.37 (d, J=7.8 Hz, 1H), 4.73-4.63 (m, 2H), 4.23 (t, J=6.0 Hz, 2H), 2.40-2.33 (m, 2H). LRMS (APCI+) m/z 531.4 $[M+H]^+$.

200. (5R)-2-[4-(Dimethylsulfamoyl)-2-fluorophenyl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide

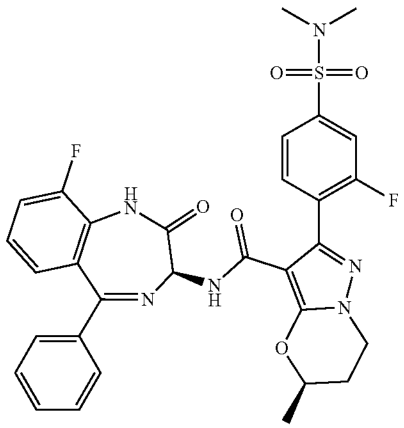 [SMILES: C[C@@H]1CCn2nc(-c3ccc(S(=O)(=O)N(C)C)cc3F)c(C(=O)N[C@H]3N=C(c4ccccc4)c4cccc(F)c4NC3=O)c2O1]

DIPEA (91 μL 0.522 mmol) was added to a solution of intermediate 103D (100 mg, 0.261 mmol), (3S)-3-amino-9-fluoro-5-phenyl-1,3-dihydro-1,4-benzodiazepin-2-one (74 mg, 0.274 mmol) in DMF (3 mL) and the reaction mixture was stirred at rt for 3 min. HATU (109 mg, 0.287 mmol) was added and the reaction mixture was stirred at rt overnight. The reaction mixture was quenched with $H_2O$ (15 mL), EtOAc (10 mL) added, and the aqueous phase extracted with EtOAc (2×10 mL). The combined organic extracts were washed with $H_2O$ (10 mL), dried ($Na_2SO_4$), and the volatiles removed under reduced pressure. The residue was purified by column chromatography (0-10% MeOH in $CH_2Cl_2$). The isolated material was dissolved in $CH_2Cl_2$, washed with 1 M aq. HCl (10 mL), dried ($Na_2SO_4$), and the volatiles removed under reduced pressure. The residue was dissolved in $CH_2Cl_2$, washed with sat. aq. $NaHCO_3$ (20 mL), dried ($Na_2SO_4$), and the volatiles removed under reduced pressure to afford a white solid (116 mg, 70%). $^1H$ NMR (400 MHz, $CDCl_3$) δ 8.23 (d, J=8.0 Hz, 1H), 8.01 (s, 1H), 7.65 (dd, J=8.0, 6.8 Hz, 1H), 7.56 (dd, J=8.0, 1.6 Hz, 1H), 7.53-7.49 (m, 2H), 7.46-7.42 (m, 1H), 7.38-7.34 (m, 2H), 7.32-7.27 (m, 1H), 7.16-7.09 (m, 2H), 7.75 (d, J=8.0 Hz, 1H), 4.73-4.66 (m, 1H), 4.36-4.31 (m, 1H), 4.28-4.21 (m, 1H), 2.71 (s, 6H), 2.39-2.32 (m, 1H), 2.31-2.22 (m, 1H), 1.70 (d, J=6.4 Hz, 3H). LRMS (ESI+) m/z 635.0 $[M+H]^+$.

The following compounds were prepared by an analogous procedure to that described for the compound of Example 200.

TABLE 35

Examples

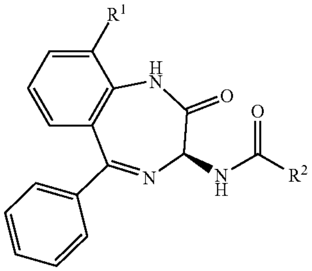

| Example | Name | $R^1$ | $R^2$ | $^1H$ NMR δ ($DMSO-d_6$) | LRMS (ES+) m/z |
|---|---|---|---|---|---|
| 197 | (5R)-2-(4-Ethylsulfonyl-2-fluorophenyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 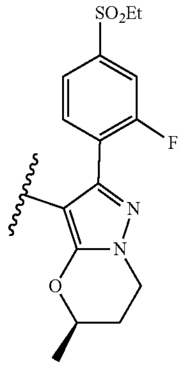 | δ 8.25 (d, J = 8.0 Hz, 1H), 8.03 (s, 1H), 7.69-7.68 (m, 2H), 7.64-7.61 (m, 1H), 7.52-7.50 (m, 2H), 7.46-7.42 (m, 1H), 7.37-7.33 (m, 2H), 7.32-7.27 (m, 1H), 7.16-7.08 (m, 2H), 5.74 (d, J = 8.0 Hz, 1H), 4.73-4.65 (m, 1H), 4.36-4.31 (m, 1H), 4.28-4.21 (m, 1H), 3.08 (q, J = 7.6, 2H), 2.39-2.33 (m, 1H), 2.32-2.22 (m, 1H), 1.70 (d, J = 6.4, 3H), 1.27 (t, J = 7.6, 3H). | 620.1 $[M + H]^+$ |

TABLE 35-continued

Examples

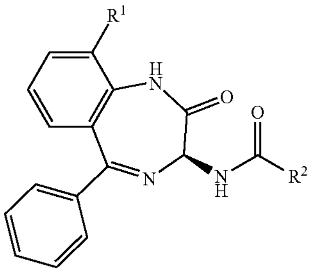

| Example | Name | $R^1$ | $R^2$ | $^1H$ NMR δ (DMSO-$d_6$) | LRMS (ES+) m/z |
|---|---|---|---|---|---|
| 198 | (5R)-2-(2-Fluoro-5-methylsulfonylphenyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 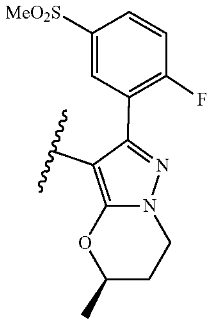 [SMILES: *c1c(-c2cc(S(C)(=O)=O)ccc2F)nn2c1O[C@H](C)CC2] | δ 8.24 (d, J = 8.0 Hz, 1H), 8.08 (dd, J = 6.0, 2.4 Hz, 1H), 8.00 (s, 1H), 7.91 (ddd, J = 8.8, 4.4, 2.4 Hz, 1H), 7.53-7.50 (m, 2H), 7.46-7.42 (m, 1H), 7.38-7.33 (m, 2H), 7.32-7.27 (m, 1H), 7.24 (t, J = 8.8 Hz, 1H), 7.16-7.08 (m, 2H), 5.73 (d, J = 7.6 Hz, 1H), 4.73-4.65 (m, 1H), 4.36-4.31 (m, 1H), 4.28-4.21 (m, 1H), 3.04 (s, 3H), 2.39-2.32 (m, 1H), 2.30-2.22 (m, 1H), 1.69 (d, J = 6.0 Hz, 3H) | 606.0 $[M + H]^+$ |
| 199 | (5R)-N-[(3S)-9-Fluoro-2-oxo-5-phenyl-1,3-dihydro-1,4-benzodiazepin-3-yl]-2-(2-fluoro-4-sulfamoylphenyl)-5-methyl-6,7-dihydro-5H-pyrazolo[5,1-b][1,3]oxazine-3-carboxamide | F | 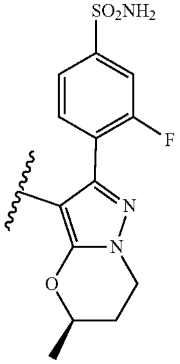 [SMILES: *c1c(-c2ccc(S(N)(=O)=O)cc2F)nn2c1O[C@H](C)CC2] | δ 8.23 (d, J = 8.0 Hz, 1H), 8.20 (s, 1H), 7.56 (dd, J = 8.4, 2.0 Hz, 1H), 7.52-7.48 (m, 4H), 7.46-7.41 (m, 1H), 7.36-7.33 (m, 2H), 7.30-7.25 (m, 1H), 7.14-7.07 (m, 2H), 5.71 (d, J = 7.6 Hz, 1H), 5.27 (s, 2H), 4.72-4.64 (m, 1H), 4.37-4.32 (m, 1H), 4.27-4.20 (m, 1H), 2.37-2.31 (m, 1H), 2.30-2.19 (m, 1H), 1.68 (d, J = 6.4 Hz, 3H). | 607.0 $[M + H]^+$ |

The following compounds were prepared by an analogous procedure to that described for the compound of Example 5.

| Example | Name | $R^1$ | $R^2$ | $^1H$ NMR δ (DMSO-$d_6$) | LRMS APCI+ m/z |
|---|---|---|---|---|---|
| 201 | (5R)-2-(1-Ethylsulfonylpiperidin-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide | F | 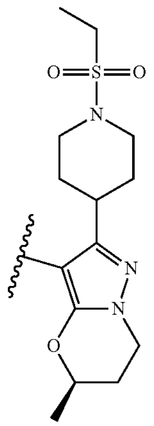 [SMILES: *c1c(C2CCN(S(=O)(=O)CC)CC2)nn2c1O[C@H](C)CC2] | (700 MHz) δ 10.93 (s, 1H), 8.10 (d, J = 7.2 Hz, 1H), 7.59 (s, 1H), 7.55 - 7.42 (m, 5H), 7.33 (s, 1H), 7.18 (d, J = 7.3 Hz, 1H), 5.44 - 5.38 (m, 1H), 4.78 - 4.67 (m, 1H), 4.15 - 4.04 (m, 2H), 3.71 - 3.55 (m, 2H), 3.31 - 3.18 (m, 2H), 3.08 - 2.96 (m, 2H), 2.86 - 2.73 (m, 2H), 2.35 - 2.27 (m, 1H), 2.07 (s, 1H), 1.97 - 1.86 (m, 2H), 1.71 - 1.62 (m, 1H), 1.60 - 1.49 (m, 4H), 1.31 - 1.13 (m, 4H). | 609.1 [M + H]+ |
| 202 | (2R)-6-(2-Fluorophenyl)-2-methyl-N-[(3S)-2-oxo-5-phenyl-1,3-dihydro-1,4-benzodiazepin-3-yl]-2,3-dihydropyrazolo[5,1-b][1,3]oxazole-7-carboxamide | H | 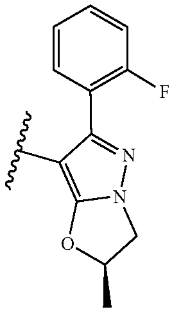 [SMILES: *c1c(-c2ccccc2F)nn2c1O[C@H](C)C2] | (700 MHz) δ 10.97 (s, 1H), 7.65 - 7.60 (m, 1H), 7.54 - 7.48 (m, 1H), 7.46 - 7.39 (m, 7H), 7.32 - 7.27 (m, 2H), 7.28 - 7.23 (m, 1H), 7.23 - 7.13 (m, 2H), 5.85 - 5.77 (m, 1H), 5.25 (d, J = 7.7 Hz, 1H), 4.59 (dd, J = 9.5, 8.2 Hz, 1H), 4.10 (dd, J = 9.5, 8.1 Hz, 1H), 1.70 (d, J = 6.3 Hz, 3H) | 496.3 [M + H]+ |

Example 203: Preparation of Salts

Preparation of Hydrochloride Salts: Procedure 1

A 4 M HCl solution in 1,4-dioxane (3 eq.) was added to a solution of compound in 1,4-dioxane (15-30 vol). The mixture was stirred for up to 1 h or until the formation of a precipitate. The mixture was filtered, the precipitate washed with cold (0° C.) diethyl ether and dried under reduced pressure.

Preparation of Hydrochloride Salts: Procedure 2

A 4 M HCl solution in 1,4-dioxane (1 eq.) was added to a solution of compound in THF (30 vol) at 50° C. and the mixture allowed to cool to rt and stirred until the formation of a precipitate. The mixture was filtered, the precipitate washed with cold (0° C.) diethyl ether and dried under reduced pressure.

Preparation of Other Salts: Procedure 3

Examples 106·BSA, 106·$H_2SO_4$, 106·MSA, 106·pTSA were prepared by the following method. A 1 M solution of acid in THF (1.1 eq.) was added to a solution of Example 106 in THE (30 vol) at 50° C. and the mixture was cooled to rt slowly. For Example 106·$H_2SO_4$, a solid precipitated and was filtered, washed with cold (0° C.) diethyl ether and dried under reduced pressure. For Example 106 BSA, the mixture was concentrated under reduced pressure, the residue triturated with EtOAc (3×5 mL) and dried under reduced pressure. For Example 106 MSA, addition of EtOAc to the acidic solution resulted in a precipitate which was filtered, washed with cold (0° C.) diethyl ether and dried under reduced pressure. For Example 106 pTSA, EtOAc (~20 mL) was added and the precipitate formed was collected, washed with EtOAc and discarded (~2 mg). The filtrate was concentrated to a volume of ~5 mL and was cooled to 0° C. in an ice bath. The mixture was triturated with EtOAc (3×5 mL) and dried under reduced pressure.

| Example/ Counterion | $^1H$ NMR δ (400 MHz, DMSO-$d_6$) | Procedure |
|---|---|---|
| 100•HCl | δ 10.97 (d, J = 6.5 Hz, 1H), 10.59-10.41 (m, 1H), 7.89 (dd, J = 14.4, 7.7 Hz, 1H), 7.70-7.26 (m, 9H), 7.26-7.08 (m, 3H), 5.38 (dd, J = 7.7, 2.2 Hz, 1H), 4.95-4.81 (m, 1H), 4.59-4.40 (m, 2H), 4.23-4.05 (m, 1H), 3.36-3.23 (m, 2H), 3.17-3.04 (m, 1H), 2.99-2.72 (m, 6H). | 1 |
| 171•HCl | δ 10.97 (s, 1H), 10.43-10.24 (m, 1H), 7.90 (d, J = 7.8 Hz, 1H), 7.68-7.24 (m, 10H), 7.13 (d, J = 7.9 Hz, 1H), 5.37 (d, J = 7.7 Hz, 1H), 4.67 (t, J = 5.2 Hz, 2H), 4.29 (d, J = 5.4 Hz, 2H), 4.21 (t, J = 6.0 Hz, 2H), 2.70 (d, J = 4.8 Hz, 6H), 2.40-2.30 (m, 2H). | 1 |

-continued

| Example/ Counterion | $^1H$ NMR δ (400 MHz, DMSO-$d_6$) | Procedure |
|---|---|---|
| 106•HCl | δ 11.00 (s, 1H), 9.01 (s, 1H), 8.56 (d, J = 5.6Hz, 1H), 8.19 (d, J = 7.4 Hz, 1H), 7.76 (d, J = 8.4 Hz, 1H), 7.69-7.22 (m, 8H), 7.17 (d, J = 7.9 Hz, 1H), 5.43 (d, J = 7.4 Hz, 1H), 4.69 (t, J = 5.2 Hz, 2H), 4.26 (t, J = 6.0 Hz, 2H), 2.96 (q, J = 7.6 Hz, 2H), 2.41-2.34 (m, 2H), 1.29 (t, J = 7.6 Hz, 3H). | 2 |
| 106•BSA | δ 11.02 (s, 1H), 9.03 (s, 1H), 8.62-8.49 (m, 1H), 8.19 (d, J = 7.4 Hz, 1H), 7.77 (d, J = 8.4 Hz, 1H), 7.71-7.21 (m, 13H), 7.17 (d, J = 7.9 Hz, 1H), 5.43 (d, J = 7.4 Hz, 1H), 4.69 (t, J = 5.2 Hz, 2H), 4.26 (t, J = 6.0 Hz, 2H), 2.94 (q, J = 7.6 Hz, 3H), 2.42-2.34 (m, 2H), 1.28 (t, J = 7.6 Hz, 3H). | 3 |
| 106•$H_2SO_4$ | δ 11.00 (s, 1H), 9.03 (d, J = 2.1 Hz, 1H), 8.60-8.50 (m, 1H), 8.19 (d, J = 7.4 Hz, 1H), 7.77 (d, J = 8.4 Hz, 1H), 7.65-7.41 (m, 7H), 7.32 (td, J = 8.1, 5.0 Hz, 1H), 7.16 (d, J = 7.9 Hz, 1H), 5.43 (d, J = 7.4 Hz, 1H), 4.69 (t, J = 5.2 Hz, 2H), 4.26 (t, J = 6.0 Hz, 2H), 2.95 (q, J = 7.6 Hz, 2H), 2.43-2.34 (m, 2H), 1.29 (t, J = 7.6 Hz, 3H). | 3 |
| 106•MSA | δ 11.01 (s, 1H), 9.09 (d, J = 2.1 Hz, 1H), 8.66 (d, J = 8.3 Hz, 1H), 8.20 (d, J = 7.4 Hz, 1H), 7.87 (d, J = 8.4 Hz, 1H), 7.65-7.41 (m, 6H), 7.32 (td, J = 8.1, 5.0 Hz, 1H), 7.17 (d, J = 7.9 Hz, 1H), 5.43 (d, J = 7.3 Hz, 1H), 4.75-4.66 (m, 2H), 4.27 (t, J = 6.1 Hz, 2H), 2.98 (q, J = 7.6 Hz, 2H), 2.38 (q, J = 5.6 Hz, 2H), 2.31 (s, 3H), 1.30 (t, J = 7.6 Hz, 3H). | 3 |
| 106• p-TSA | δ 11.01 (s, 1H), 9.06 (d, J = 2.1 Hz, 1H), 8.61 (d, J = 8.4 Hz, 1H), 8.20 (d, J = 7.4 Hz, 1H), 7.82 (d, J = 8.4 Hz, 1H), 7.72-7.25 (m, 9H), 7.17 (d, J = 7.9 Hz, 1H), 7.11 (d, J = 7.7 Hz, 2H), 5.44 (d, J = 7.4 Hz, 1H), 4.79-4.66 (m, 2H), 4.27 (t, J = 6.0 Hz, 2H), 2.97 (q, J = 7.6 Hz, 3H), 2.46-2.35 (m, 2H), 2.29 (s, 3H), 1.30 (t, J = 7.6 Hz, 3H). | 3 |

Example 204: Efficacy In Vitro

Compounds w ere subjected to RSV plaque reduction assays according to the following protocol.

Plaque Reduction Assay.

Hep-G2 cells (ECACC, 85011430) were passaged in flasks and seeded in 24-well plates in DMEM containing antibiotics and supplemented with 10% FBS. During inoculation and subsequent incubation, cells were cultured in DMEM containing 2% FBS. 100 plaque forming unit/well of RSV (RSV A2 ECACC, 0709161v) was mixed with eight serial dilutions of compound. Subsequently, 100 μL of the virus/compound mixtures was added to confluent Hep-G2 cell monolayers. The cells and virus/compound mixtures were incubated at 37° C. in a humidified 5% $CO_2$ incubator for 2 h prior to removal of the inoculum and addition of 1 mL of overlay (DMEM containing 2% FBS and 0.8% CMC) containing compound dilutions. The cells and were incubated at 37° C. in a humidified 5% $CO_2$ incubator for 2 days.

Cells were washed with PBS before adding 75/25% v/v EtOH MeOH, for 3 min. Fixative was removed and plates were washed with PBS. A pre-titrated amount of the primary antibody was added in 200 μL PBS/2% milk powder, and plates incubated for 90 min at 37° C. The plates were washed 3 times with PBS/0.05% Tween20 before addition of rabbit anti-goat horse radish peroxidase in 200 μL PBS/2% milk powder, and incubated for 1 h at 37° C. Following three wash steps with PBS/0.05% Tween20, 200 μL ready-to-use TrueBlue was added and plates were incubated at rt for 10-15 min before washing with water. After removal of water, plates were air-dried in the dark.

Plates were scanned and analysed using the Immunospot S6 Macro analyser, which is equipped with BioSpot analysis software for counting immunostained plaques (virospots). Plaque counts were used to calculate % infection relative to the mean of the plaque count in the virus control wells for RSV. The $EC_{50}$ value was calculated as 50% reduction in signal, respectively, by interpolation of inhibition curves fitted with a 4-parameter nonlinear regression with a variable slope in Dotmatics. Unless otherwise noted, plaque $EC_{50}$ and cell toxicity $CC_{50}$ values are a mean of at least two experiments and figures are rounded to whole units.

Results

| Example | RSV A2 Plaque $EC_{50}$ (nM) | Cell Cytotoxicity $CC_{50}$ (nM) |
|---|---|---|
| 1 | 33 | >25,000 |
| 2 | 22 | >25,000 |
| 3 | 20 | >25,000 |
| 4 | 29 | >25,000 |
| 5 | 54 | >25,000 |
| 6 | 165 | >25,000 |
| 7 | 32 | >25,000 |
| 8 | 37 | >25,000 |
| 9 | 30 | >18,760 |
| 10 | 23 | >25,000 |
| 11 | 33 | >25,000 |
| 12 | 39 | >25,000 |
| 13 | 28 | >23,965 |
| 14 | 36 | >25,000 |
| 15 | 30 | >25,000 |
| 16 | 454 | >25,000 |
| 17 | 180 | >25,000 |
| 18 | 96 | >25,000 |
| 19 | 31 | >25,000 |
| 20 | 42 | >25,000 |
| 21 | 64 | >25,000 |
| 22 | 140 | >25,000 |
| 23 | 60 | >25,000 |
| 24 | 77 | >25,000 |
| 25 | 24 | >25,000 |
| 26 | 43 | >25,000 |
| 27 | 20 | >25,000 |
| 28 | 76 | >25,000 |
| 29 | 78 | >25,000 |
| 30 | 16 | >25,000 |
| 31 | 11 | >25,000 |
| 32 | 411 | >25,000 |
| 33 | 474 | >25,000 |

-continued

| Example | RSV A2 Plaque $EC_{50}$ (nM) | Cell Cytotoxicity $CC_{50}$ (nM) |
|---|---|---|
| 34 | 143 | >25,000 |
| 35 | 117 | >25,000 |
| 36 | 444 | >25,000 |
| 37 | 333 | >25,000 |
| 38 | 189 | >25,000 |
| 39 | 40 | >25,000 |
| 40 | 57 | >25,000 |
| 41 | 29 | >25,000 |
| 42 | 124 | >25,000 |
| 43 | 101 | >25,000 |
| 44 | 55 | >25,000 |
| 45 | 301 | >25,000 |
| 46 | 119 | >25,000 |
| 47 | 84 | >25,000 |
| 48 | 246 | >25,000 |
| 49 | 243 | >25,000 |
| 50 | 429 | >25,000 |
| 51 | 80 | >25,000 |
| 52 | 28 | >25,000 |
| 53 | 92 | >25,000 |
| 54 | 15 | >25,000 |
| 55 | 246 | >25,000 |
| 56 | 123 | >25,000 |
| 57 | 353 | >25,000 |
| 58 | 188 | >25,000 |
| 59 | 309 | >25,000 |
| 60 | 167 | >25,000 |
| 61 | 161 | >25,000 |
| 62 | 192 | >25,000 |
| 63 | 94 | >25,000 |
| 64 | 133 | >25,000 |
| 65 | 84 | >25,000 |
| 66 | 60 | >25,000 |
| 67 | 19 | >25,000 |
| 68 | 307 | >25,000 |
| 69 | 34 | >25,000 |
| 70 | 50 | >25,000 |
| 71 | 91 | >25,000 |
| 72 | 100 | >25,000 |
| 73 | 91 | >25,000 |
| 74 | 39 | >25,000 |
| 75 | 158 | >25,000 |
| 76 | 93 | >25,000 |
| 77 | 159 | >25,000 |
| 78 | 217 | >25,000 |
| 79 | 115 | >25,000 |
| 80 | 64 | >25,000 |
| 81 | 84 | >25,000 |
| 82 | 31 | >25,000 |
| 83 | 115 | >25,000 |
| 84 | 70 | >25,000 |
| 85 | 121 | >25,000 |
| 86 | 44 | >25,000 |
| 87 | 179 | >25,000 |
| 88 | 146 | >25,000 |
| 89 | 122 | >25,000 |
| 90 | 20 | >25,000 |
| 91 | 239 | >25,000 |
| 92 | 131 | >25,000 |
| 93 | 50 | >25,000 |
| 94 | 44 | >25,000 |
| 95 | 357 | >25,000 |
| 96 | 464 | >25,000 |
| 97 | 439 | >25,000 |
| 98 | 80 | >25,000 |
| 99 | 71 | >25,000 |
| 100 | 75 | >25,000 |
| 100•HCl | 89 | >25,000 |
| 101 | 123 | >25,000 |
| 102 | 135 | >25,000 |
| 103 | 132 | >25,000 |
| 104 | 128 | >25,000 |
| 105 | 48 | >25,000 |
| 106 | 48 | >25,000 |
| 106•HCl | 51 | >25,000 |
| 106•BSA | 52 | >25,000 |

-continued

| Example | RSV A2 Plaque $EC_{50}$ (nM) | Cell Cytotoxicity $CC_{50}$ (nM) |
|---|---|---|
| 106•$H_2SO_4$ | 66 | >25,000 |
| 106•MSA | 48 | >25,000 |
| 106•pTsSA | 41 | >25,000 |
| 107 | 93 | >25,000 |
| 108 | 117 | >25,000 |
| 109 | 114 | >25,000 |
| 110 | 51 | >25,000 |
| 111 | 64 | >25,000 |
| 112 | 50 | >25,000 |
| 113 | 53 | >19385 |
| 114 | 117 | 17125 |
| 115 | 226 | >25,000 |
| 116 | 127 | >25,000 |
| 117 | 434 | >25,000 |
| 118 | 43 | >25,000 |
| 119 | 69 | >25,000 |
| 120 | 97 | >25,000 |
| 121 | 374 | >25,000 |
| 122 | 166 | >25,000 |
| 123 | 79 | >25,000 |
| 124 | 76 | >25,000 |
| 125 | 70 | >25,000 |
| 126 | 54 | >25,000 |
| 127 | 41 | >25,000 |
| 128 | 41 | >25,000 |
| 129 | 37 | >25,000 |
| 130 | 350 | >25,000 |
| 131 | 93 | >25,000 |
| 132 | 72 | >25,000 |
| 133 | 220 | >25,000 |
| 134 | 83 | >25,000 |
| 135 | 15 | >25,000 |
| 136 | 182 | >25,000 |
| 137 | 15 | >25,000 |
| 138 | 54 | >25,000 |
| 139 | 66 | >25,000 |
| 140 | 38 | >25,000 |
| 141 | 20 | >25,000 |
| 142 | 282 | >25,000 |
| 143 | 149 | >25,000 |
| 144 | 101 | >25,000 |
| 145 | 278 | >25,000 |
| 146 | 294 | >25,000 |
| 147 | 137 | >25,000 |
| 148 | 72 | >25,000 |
| 149 | 194 | >25,000 |
| 150 | 61 | >25,000 |
| 151 | 108 | >25,000 |
| 152 | 84 | >25,000 |
| 153 | 63 | >25,000 |
| 154 | 91 | >25,000 |
| 155 | 219 | >25,000 |
| 156 | 39 | >25,000 |
| 157 | 48 | >25,000 |
| 158 | 48 | >25,000 |
| 159 | 395 | >25,000 |
| 160 | 148 | >25,000 |
| 161 | 54 | >25,000 |
| 162 | 166 | >25,000 |
| 163 | 76 | >25,000 |
| 164 | 87 | >25,000 |
| 165 | 349 | >25,000 |
| 166 | 201 | >25,000 |
| 167 | 91 | >25,000 |
| 168 | 104 | >25,000 |
| 169 | 114 | >25,000 |
| 170 | 60 | >25,000 |
| 171 | 59 | >25,000 |
| 171•HCl | 62 | >25,000 |
| 172 | 235 | >19909 |
| 173 | 91 | >25,000 |
| 174 | 406 | >25,000 |
| 175 | 61 | >25,000 |
| 176 | 63 | >25,000 |
| 177 | 125 | >25,000 |
| 178 | 75 | >25,000 |

-continued

| Example | RSV A2 Plaque $EC_{50}$ (nM) | Cell Cytotoxicity $CC_{50}$ (nM) |
|---|---|---|
| 179 | 34 | >25,000 |
| 180 | 75 | >25,000 |
| 181 | 42 | >25,000 |
| 182 | 78 | 20062 |
| 183 | 294 | >25,000 |
| 184 | 300 | >25,000 |
| 185 | 32 | >25,000 |
| 186 | 59 | >25,000 |
| 187 | 249 | >8839 |
| 110-1 | 42 | >25,000 |
| 110-2 | 61 | >25,000 |
| 129-1 | 39 | >25,000 |
| 129-2 | 73 | >25,000 |
| 171-1 | 53 | >25,000 |
| 171-2 | 56 | >25,000 |
| 188-1 | 141 | >25,000 |
| 188-2 | 281 | >25,000 |
| 189-1 | 41 | >25,000 |
| 189-2 | 72 | >25,000 |
| 190-1 | 98 | >25,000 |
| 190-2 | 154 | >25,000 |
| 191-1 | 83 | >25,000 |
| 191-2 | 280 | >25,000 |
| 192 | 243 | >24361 |
| 193 | 19 (n = 1) | >25,000 |
| 194 | 43 | >25,000 |
| 195 | 355 | >25,000 |
| 196 | 25 | >25,000 |
| 197 | 97 | >25,000 |
| 198 | 35 | >25,000 |
| 199 | 64 | >25,000 |
| 200 | 1 (n = 1) | >25,000 |
| 201 | 49 (n = 1) | >25,000 |
| 202 | 127 | >25,000 |

Example 205: In Vitro Pharmacokinetics

Compounds were subjected to the following assays to investigate liver microsomal stability and hepatocyte stability.

Pooled liver microsomes were purchased from a reputable commercial supplier and stored at −80° C. prior to use. Microsomes (final protein concentration 0.5 mg/mL), 0.1 M phosphate buffer pH 7.4 and test compound (final substrate concentration 1 μM; final DMSO concentration 0.25%) were pre-incubated at 37° C. prior to the addition of NADPH (final concentration 1 mM) to initiate the reaction. The final incubation volume was 50 μL. A control incubation was included for each compound tested where 0.1 M phosphate buffer pH 7.4 was added instead of NADPH (minus NADPH). Two control compounds were included with each species. All incubations were performed singularly for each test compound. Each compound was incubated for 0, 5, 15, 30 and 45 min. The control (minus NADPH) was incubated for 45 min only. The reactions were stopped by transferring incubate into acetonitrile at the appropriate time points, in a 1:3 ratio. The termination plates are centrifuged at 3,000 rpm for 20 min at 4° C. to precipitate the protein. Following protein precipitation, the sample supernatants were combined in cassettes of up to 4 compounds, internal standard added, and samples analysed by LC-MS/MS. From a plot of ln peak area ratio (compound peak area/internal standard peak area) against time, the gradient of the line was determined. Subsequently, half-life ($t_{1/2}$) and intrinsic clearance ($CL_{int}$) were calculated. Compounds with low clearance (>80% remaining at 45 min) under the assay conditions are denoted as $t_{1/2}$>140 min.

Hepatocyte Incubation: Experimental Procedure

Cryopreserved pooled hepatocytes were purchased from a reputable commercial supplier and stored in liquid nitrogen prior to use. Williams E media supplemented with 2 mM L-glutamine and 25 mM HEPES and test compound (final substrate concentration 3 μM; final DMSO concentration 0.25%) are pre-incubated at 37° C. prior to the addition of a suspension of cryopreserved hepatocytes (final cell density $0.5\times10^6$ viable cells/mL in Williams E media supplemented with 2 mM L-glutamine and 25 mM HEPES) to initiate the reaction. The final incubation volume is 500 μL. Two control compounds were included with each species, alongside appropriate vehicle control. The reactions are stopped by transferring 50 μL of incubate to 100 μL acetonitrile containing internal standard at the appropriate time points. Samples were removed at 6 time points (0, 5, 15, 30, 45 and 60 min) over the course of a 60 min experiment. The termination plates are centrifuged at 2500 rpm at 4° C. for 30 min to precipitate the protein. Following protein precipitation, the sample supernatants were combined in cassettes of up to 4 compounds and analysed using generic LC-MS/MS conditions. From a plot of ln peak area ratio (compound peak area/internal standard peak area) against time, the gradient of the line is determined. Subsequently, half-life (t½) and intrinsic clearance ($CL_{int}$) were calculated. Compounds with low clearance (>80% remaining at 60 min) under the assay conditions are denoted as t½>186 min.

Results

| Example | Liver Microsomal Stability t½ (min); rat/dog/human | Liver Hepatocyte Stability t½ (min); rat/dog/human |
|---|---|---|
| 25 | >140/>140/1010 | 108/>186/284 |
| 27 | 83.9/463/135 | 485/>186/>186 |
| 51 | 65.7/>140/62.6 | 113/986/88.3 |
| 106 | 48.9/109/186 | 95.6/120/>186 |

Example 206: In Vivo Pharmacokinetics

The pharmacokinetics of compounds were studied in vivo in rats at doses of 1 mg/kg (IV) and 10 mg/kg (PO).

Rat Pharmacokinetics

Methods

Male rats [Sprague Dawley (SD)] surgically prepared with a jugular vein cannula were treated with experimental compounds via intravenous administration (IV; n=3; 1 mg/kg) or oral administration (PO; n=3; 10 mg/kg). Compounds were formulated as a solution in 40:60 dimethylacetamide:saline (IV administration) and a solution of 10% DMSO, 10% cremaphor in water (80%) (PO administration). Animals were observed for any overt clinical signs or symptoms. Serial blood samples were collected via the cannula at 0.02, 0.08, 0.25, 0.5, 1, 2, 4, 6, 8 and 24 h post IV dosing of compound, and at 0.08, 0.25, 0.5, 1, 2, 4, 6, 8 and 24 h post oral dosing of compound, and plasma was prepared by centrifugation and stored immediately at −80° C. Samples were subsequently thawed, prepared for analysis by protein precipitation with acetonitrile, and analysed by tandem LCMS using electrospray ionisation using a matrix-matched calibration curve. PK parameters were calculated from the resulting data.

Results

| Example | 25 | 27 | 51 | 106 |
|---|---|---|---|---|
| PO $AUC_{last}$ (hr*ng/mL) | 14883 | 3137 | 1582 | 5690 |
| Cl (mL/min/kg) | 4.7 | 24.9 | 46.4 | 14.6 |
| $V_d$ (L/kg) | 0.6 | 0.9 | 1.0 | 0.7 |
| $C_{max}$ (ng/mL) | 1882 | 960 | 730 | 1030 |
| C 8 h (ng/mL) | 812 | 75.9 | 7.6 | 271 |
| IV t½ (h) | 2.20 | 0.72 | 0.48 | 1.20 |
| PO t½ (h) | 3.4 | 2.8 | 1.1 | 3.6 |
| F (%) | 40.3% | 49.6% | 44.3% | 59.4% |

Example 207: Aqueous Formulation

The compound of Example 1 is formulated as a solution in 30% w/v captisol (i.e. sulfobutylether-beta-cyclodextrin) at pH4 according to the following procedure.

A carrier of 30% w/v captisol (i.e. sulfobutylether-beta-cyclodextrin) is prepared by weighing the required amount of captisol into a suitable vessel, adding approximately 80% of the final volume of water and magnetically stirring until a solution is formed. The carrier is then made up to volume with water.

An aqueous solution of a compound of Example 1 is prepared by weighing 175 mg of the compound into a suitable vessel and adding approximately 80% of the required volume of the carrier. Using an aqueous solution of hydrochloric acid, the pH is adjusted to pH2 and the resulting mixture is magnetically stirred until a solution is formed. The formulation is then made up to volume with carrier and the pH is adjusted to pH4 using an aqueous solution of sodium hydroxide.

Example 208: Tablet Composition

Tablets, each weighing 0.15 g and containing 25 mg of a compound of the invention are manufactured as follows:

Composition for 10,000 Tablets

Compound of the invention (250 g)

Lactose (800 g)

Corn starch (415 g)

Talc powder (30 g)

Magnesium stearate (5 g)

The compound of the invention, lactose and half of the corn starch are mixed. The mixture is then forced through a sieve 0.5 mm mesh size. Corn starch (10 g) is suspended in warm water (90 mL). The resulting paste is used to granulate the powder. The granulate is dried and broken up into small fragments on a sieve of 1.4 mm mesh size. The remaining quantity of starch, talc and magnesium is added, carefully mixed and processed into tablets.

Example 209: Injectable Formulation

| | |
|---|---|
| Compound of the invention | 200 mg |
| Hydrochloric Acid Solution 0.1M or Sodium Hydroxide Solution 0.1M q.s. to pH | 4.0 to 7.0 |
| Sterile water q.s. to | 10 mL |

The compound of the invention is dissolved in most of the water (35° C.-40° C.) and the pH adjusted to between 4.0 and 7.0 with the hydrochloric acid or the sodium hydroxide as appropriate. The batch is then made up to volume with water and filtered through a sterile micropore filter into a sterile 10 mL amber glass vial (type 1) and sealed with sterile closures and overseals.

Example 210: Intramuscular Injection

| | |
|---|---|
| Compound of the invention | 200 mg |
| Benzyl Alcohol | 0.10 g |
| Glycofurol 75 | 1.45 g |
| Water for injection q.s to | 3.00 mL |

The compound of the invention is dissolved in the glycofurol. The benzyl alcohol is then added and dissolved, and water added to 3 mL. The mixture is then filtered through a sterile micropore filter and sealed in sterile 3 mL glass vials (type 1).

Example 211: Syrup Formulation

| | |
|---|---|
| Compound of invention | 250 mg |
| Sorbitol Solution | 1.50 g |
| Glycerol | 2.00 g |
| Sodium benzoate | 0.005 g |
| Flavour | 0.0125 mL |
| Purified Water q.s. to | 5.00 mL |

The compound of the invention is dissolved in a mixture of the glycerol and most of the purified water. An aqueous solution of the sodium benzoate is then added to the solution, followed by addition of the sorbital solution and finally the flavour. The volume is made up with purified water and mixed well.

We claim:

1. A compound of formula (Ie'):

(Ie')

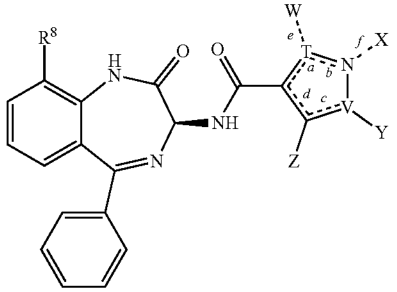

wherein:

$R^1$ is H or halo;

T is C, V is N, b, d and e are bonds, and a, c and f are absent;

X is ab sent;

W is selected from H, $C_3$-$C_6$ cycloalkyl, halo, —$NHR^9$, benzyl, phenyl, 4- to 10-membered heterocyclyl and 4- to 10-membered heteroaryl, wherein phenyl, heterocyclyl and heteroaryl are unsubstituted or substituted by one or two substituents selected from the list consisting of $C_1$-$C_6$ alkyl, $C_1$-$C_6$ hydroxyalkyl, $C_1$-$C_6$ haloalkyl, $C_3$-$C_6$ cycloalkyl, halo, —OR, —$(CH_2)_m$OR, —$NR_2$, —$(CH_2)_m NR_2$, —NHR", —$SO_m NR_2$, —$SO_m$R, —SR, nitro, —$CO_2$R, —CN, —$CONR_2$, —NHCOR, —$CH_2NR^{10}R^{11}$, —$NR^{10}R^{11}$, and 4- to 10-membered heterocyclyl which is unsubstituted or substituted by OR, in which each R is independently H or $C_1$-$C_6$ alkyl, R" is $C_3$-$C_6$ cycloalkyl and m is 1 or 2;

$R^9$ is selected from phenyl and 4- to 10-membered heteroaryl wherein phenyl and heteroaryl are unsubstituted or substituted by halo;

$R^{10}$ and $R^{11}$ are each independently H or $C_1$-$C_6$ alkyl; or $R^{10}$ and $R^{11}$ form, together with the N atom to which they are attached, either (a) a morpholine ring which is optionally bridged by a —$CH_2$— group linking two ring carbon atoms that are positioned para to each other, or (b) a spiro group of the following formula (b):

(b)

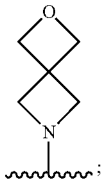

and

Y and Z form, with the N and C atoms to which they are attached, a ring of formula (I-1):

(I-1)

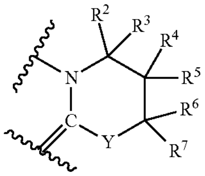

wherein Y is O, S and $SO_2$;

and each of $R^2$ to $R^7$ is independently H, $C_1$-$C_6$ alkyl, $C_1$-$C_6$ hydroxyalkyl, $C_3$-$C_6$ cycloalkyl, halo, —OR, —$CH_2$OR, —$NR_2$, —$CH_2NR^{12}R^{13}$, —NRCOOR, —$SO_mNR_2$, —$SO_m$R, —$CH_2SO_m$R, nitro, —$CO_2$R, —CN, —$CONR_2$ or —NHCOR, in which R and m are as defined above and $R^{12}$ and $R^{13}$ are each independently H, $C_1$-$C_6$ alkyl, benzyl, 4- to 10-membered heterocyclyl or $R^{12}$ and $R^{13}$ form, together with the N atom to which they are attached, a 4- to 10-membered heteroaryl which is unsubstituted or a 4- to 10-membered heterocyclyl which is unsubstituted or substituted with $C_1$-$C_6$ alkyl or halo, or any two of $R^2$ to $R^7$ that bond to the same carbon atom form a spiro ring selected from a $C_3$-$C_6$ cycloalkyl spiro ring and a spiro oxetane ring of the following structure:

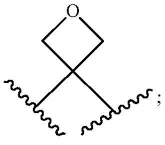 [SMILES: *C1(*)COC1]

or a pharmaceutically acceptable salt thereof.

2. A compound according to claim 1 wherein W is selected from H, halo, cyclopropyl, cyclohexyl and the following structures:

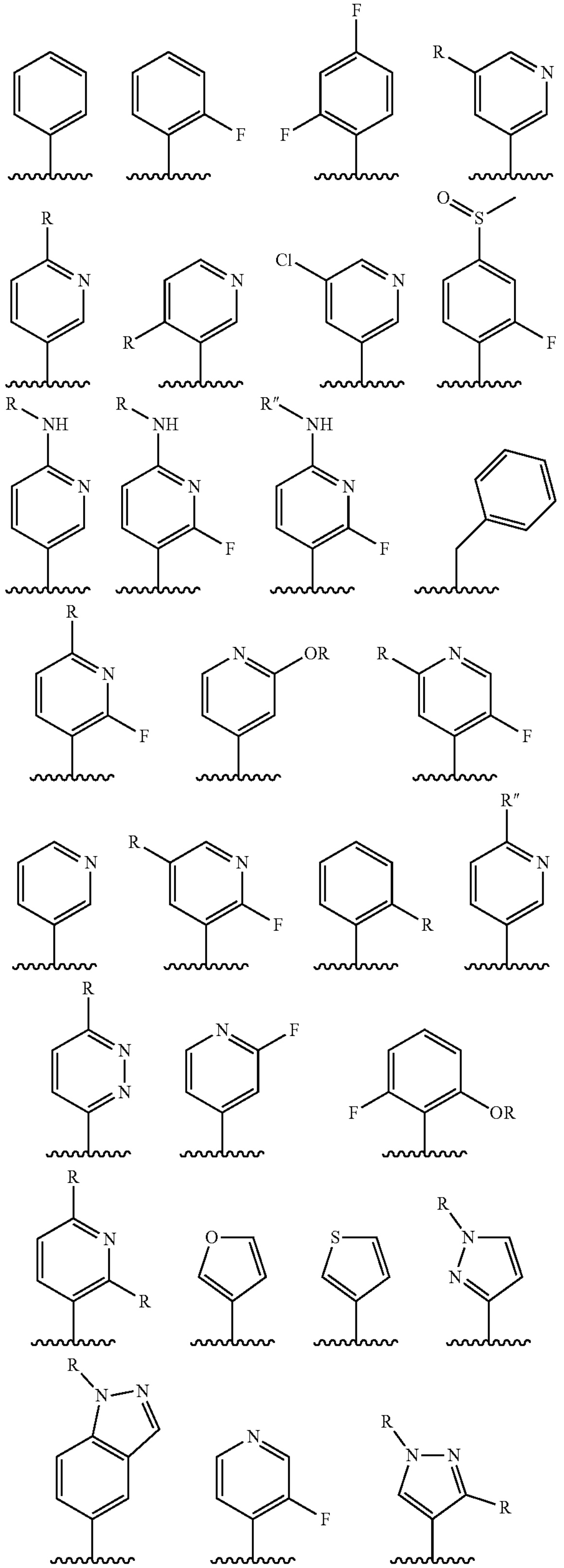

-continued

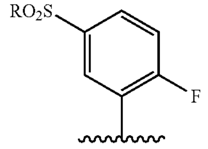
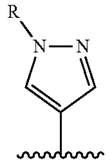
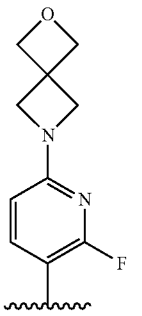
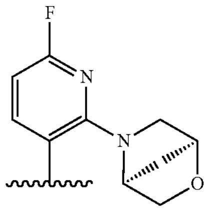
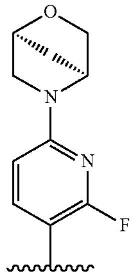
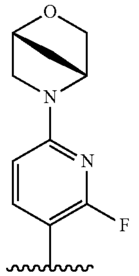
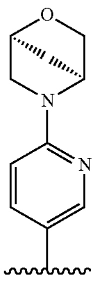
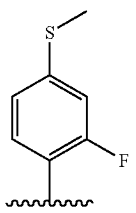
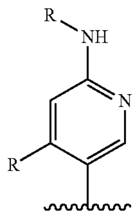
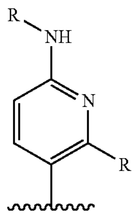
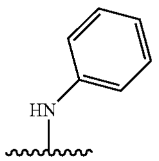
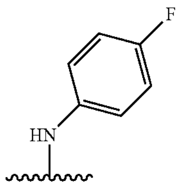
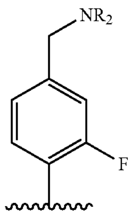
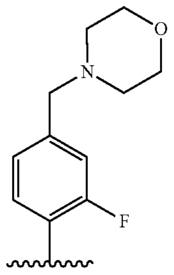
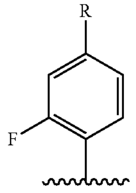
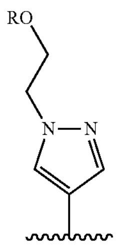
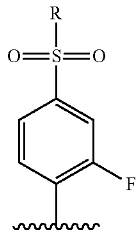
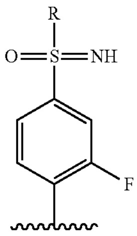
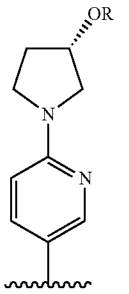

-continued

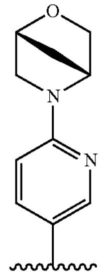
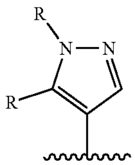
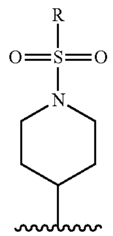
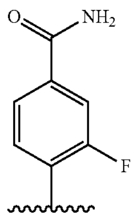
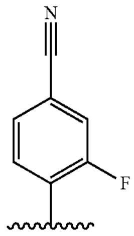
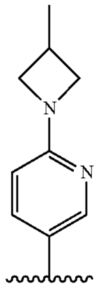
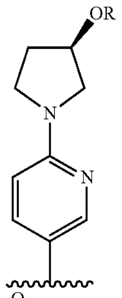
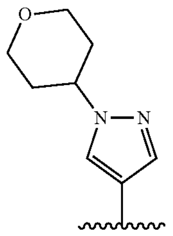
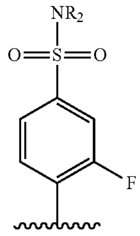
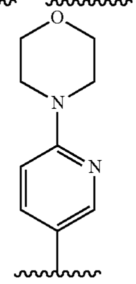
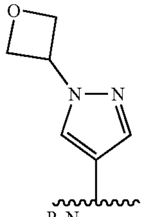
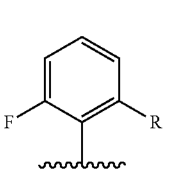
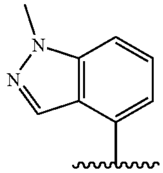
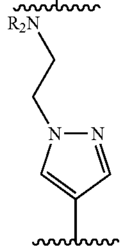

in which R and R" are as defined in claim 1.

3. A compound according to claim 1 wherein, each of $R^2$ to $R^7$ is independently H, $C_1$-$C_6$ alkyl, $C_1$-$C_6$ hydroxyalkyl, $C_3$-$C_6$ cycloalkyl, —$CH_2OR$, —$CH_2NR^{12}R^{13}$, —NR-COOR, —$CH_2SO_mR$, or halo, in which R and m are as defined in claim 1 and $R^{12}$ and $R^{13}$ are each independently H, $C_1$-$C_6$ alkyl, benzyl, 4-to 10-membered heterocyclyl or $R^{12}$ and $R^{13}$ form, together with the N atom to which they are attached, a 4-to 10-membered heteroaryl which is unsubstituted or a 4-to 10-membered heterocyclyl which is unsubstituted or substituted with $C_1$-$C_6$ alkyl or halo, or any two of $R^2$ to $R^7$ that bond to the same carbon atom form a spiro ring selected from a $C_3$-$C_6$ cycloalkyl spiro ring and a spiro oxetane ring of the following structure:

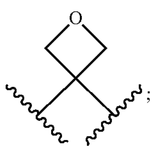 [SMILES: *C1(*)COC1]

and the rest of $R^2$ to $R^7$ are H.

4. A compound according to claim 1 wherein Y in the ring of formula (I-1) is O.

5. A compound according to claim 1 which is selected from:

2-(2,4-Difluorophenyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

2-(2,4-Difluorophenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-[6-(Ethylamino)-2-fluoropyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

N-[(3S)-9-Fluoro-2-oxo-5-phenyl-1,3-dihydro-1,4-benzodiazepin-3-yl]-2-[2-fluoro-6-(propan-2-ylamino)pyridin-3-yl]-6,7-dihydro-5H-pyrazolo[5,1-b][1,3]oxazine-3-carboxamide;

N-[(3S)-9-fluoro-2-oxo-5-phenyl-2,3-dihydro-1H-1,4-benzodiazepin-3-yl]-2-(2-fluorophenyl)-5,5-dimethyl-5H,6H, 7H-pyrazolo[3,2-b][1,3]oxazine-3-carboxamide;

N-[(3S)-9-Fluoro-2-oxo-5-phenyl-1,3-dihydro-1,4-benzodiazepin-3-yl]-2-(2-methylphenyl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)spiro[6,7-dihydropyrazolo[5,1-b][1,3]oxazine-5,1'-cyclopropane]-3-carboxamide;

N-[(3S)-9-fluoro-2-oxo-5-phenyl-2,3-dihydro-1H-1,4-benzodiazepin-3-yl]-2-(2-fluorophenyl)-5-(propan-2-yl)-5H,6H,7H-pyrazolo[3,2-b][1,3]oxazine-3-carboxamide;

(6S)—N-[(3S)-9-fluoro-2-oxo-5-phenyl-1,3-dihydro-1,4-benzodiazepin-3-yl]-2-(2-fluorophenyl)-6-methyl-6,7-dihydro-5H-pyrazolo[5,1-b][1,3]oxazine-3-carboxamide;

(6R)—N-[(3S)-9-fluoro-2-oxo-5-phenyl-1,3-dihydro-1,4-benzodiazepin-3-yl]-2-(2-fluorophenyl)-6-methyl-6,7-dihydro-5H-pyrazolo[5,1-b][1,3]oxazine-3-carboxamide;

6-Ethyl-N-[(3S)-9-fluoro-2-oxo-5-phenyl-2,3-dihydro-1H-1,4-benzodiazepin-3-yl]-2-(2-fluorophenyl)-5H,6H,7H-pyrazolo[3,2-b][1,3]oxazine-3-carboxamide;

N-[(3S)-9-Fluoro-2-oxo-5-phenyl-2,3-dihydro-1H-1,4-benzodiazepin-3-yl]-2-(2-fluorophenyl)-6-(propan-2-yl)-5H,6H, 7H-pyrazolo[3,2-b][1,3]oxazine-3-carboxamide;

6-Cyclopropyl-N-[(3S)-9-fluoro-2-oxo-5-phenyl-2,3-dihydro-1H-1,4-benzodiazepin-3-yl]-2-(2-fluorophenyl)-5H,6H, 7H-pyrazolo[3,2-b][1,3]oxazine-3-carboxamide;

N-[(3S)-9-fluoro-2-oxo-5-phenyl-2,3-dihydro-1H-1,4-benzodiazepin-3-yl]-2-(2-fluorophenyl)-6-propyl-5H,6H,7H-pyrazolo[3,2-b][1,3]oxazine-3-carboxamide;

2-[6-(Cyclopropylamino)pyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

N-[(3S)-2-Oxo-5-phenyl-1,3-dihydro-1,4-benzodiazepin-3-yl]-2-pyridin-3-yl-6,7-dihydro-5H-pyrazolo[5,1-b][1,3]oxazine-3-carboxamide;

N-[(3S)-9-Fluoro-2-oxo-5-phenyl-1,3-dihydro-1,4-benzodiazepin-3-yl]-2-pyridin-3-yl-6,7-dihydro-5H-pyrazolo[5,1-b][1,3]oxazine-3-carboxamide;

2-(6-Cyclopropylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-[6-(propan-2-ylamino)pyridin-3-yl]-6,7-dihydro-5H-pyrazolo[5,1-b][1,3]oxazine-3-carboxamide;

2-[6-(Ethylamino)pyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

N-[(3S)-2-oxo-5-phenyl-1,3-dihydro-1,4-benzodiazepin-3-yl]-2-phenyl-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-phenyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-(2-fluorophenyl)-5-methyl-6,7-dihydro-5H-pyrazolo[5,1-b][1,3]oxazine-3-carboxamide;

N-[(3S)-2-oxo-5-phenyl-1,3-dihydro-1,4-benzodiazepin-3-yl]-2-phenylspiro[5,7-dihydropyrazolo[5,1-b][1,3]oxazine-6,3'-oxetane]-3-carboxamide;

2-(2-Fluorophenyl)-N-[(3S)-2-oxo-5-phenyl-1,3-dihydro-1,4-benzodiazepin-3-yl]spiro[5,7-dihydropyrazolo[5,1-b][1,3]oxazine-6,3'-oxetane]-3-carboxamide;

(5R)—N-[(3S)-9-fluoro-2-oxo-5-phenyl-1,3-dihydro-1,4-benzodiazepin-3-yl]-2-[2-fluoro-6-(propan-2-ylamino)pyridin-3-yl]-5-methyl-6,7-dihydro-5H-pyrazolo[5,1-b][1,3]oxazine-3-carboxamide;

(5S)—N-[(3S)-9-fluoro-2-oxo-5-phenyl-1,3-dihydro-1,4-benzodiazepin-3-yl]-2-[2-fluoro-6-(propan-2-ylamino)pyridin-3-yl]-5-methyl-6,7-dihydro-5H-pyrazolo[5,1-b][1,3]oxazine-3-carboxamide;

2-(2,4-Difluorophenyl)-N-[(3S)-9-fluoro-2-oxo-5-phenyl-2,3-dihydro-1H-1,4-benzodiazepin-3-yl]-4,4-dioxo-5H,6H,7H-4λ6-pyrazolo[3,2-b][1,3]thiazine-3-carboxamide;

2-(2-Fluorophenyl)-N-[(3S)-9-fluoro-2-oxo-5-phenyl-2,3-dihydro-1H-1,4-benzodiazepin-3-yl]-4,4-dioxo-5H,6H, 7H-4λ6-pyrazolo[3,2-b][1,3]thiazine-3-carboxamide;

2-(2,4-Difluorophenyl)-N-[(3S)-9-fluoro-2-oxo-5-phenyl-2,3-dihydro-1H-1,4-benzodiazepin-3-yl]-5H,6H,7H-pyrazolo[3,2-b][1,3]thiazine-3-carboxamide;

N-[(3S)-9-Fluoro-2-oxo-5-phenyl-2,3-dihydro-1H-1,4-benzodiazepin-3-yl]-2-(2-fluorophenyl)-5H,6H,7H-pyrazolo[3,2-b][1,3]thiazine-3-carboxamide;

3-(2-Fluorophenyl)-N-[(3S)-2-oxo-5-phenyl-1,3-dihydro-1,4-benzodiazepin-3-yl]-6,7-dihydro-5H-pyrazolo[5,1-b][1,3]oxazine-2-carboxamide;

7-(2-Fluorophenyl)-N-[(3S)-2-oxo-5-phenyl-1,3-dihydro-1,4-benzodiazepin-3-yl]-2,3-dihydropyrazolo[5,1-b][1,3]oxazole-6-carboxamide;

3-[6-(Cyclopropylamino)-2-fluoropyridin-3-yl]-N-[(3S)-2-oxo-5-phenyl-1,3-dihydro-1,4-benzodiazepin-3-yl]-6,7-dihydro-5H-pyrazolo[5,1-b][1,3]oxazine-2-carboxamide;

2-[6-(Cyclopropylamino)-2-fluoropyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(2-Fluorophenyl)-6,6-dimethyl-N-[(3S)-2-oxo-5-phenyl-1,3-dihydro-1,4-benzodiazepin-3-yl]-5,7-dihydropyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6,6-dimethyl-5,7-dihydropyrazolo[5,1-b][1,3]oxazine-3-carboxamide;

(5R)-2-(5-Chloropyridin-3-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(5-Chloropyridin-3-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2-Fluorophenyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5S)-2-(2-Fluorophenyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5S)—N-[(3S)-9-fluoro-2-oxo-5-phenyl-1,3-dihydro-1,4-benzodiazepin-3-yl]-2-(2-fluorophenyl)-5-methyl-6,7-dihydro-5H-pyrazolo[5,1-b][1,3]oxazine-3-carboxamide;

2-(2-Fluoro-5-methylpyridin-3-yl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

2-(2-Fluoro-5-methylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-[6-(Cyclopropylamino)-2-fluoropyridin-3-yl]-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

2-Cyclopropyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2-Methoxypyridin-4-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2-methoxypyridin-4-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-[6-(2-Hydroxypropyl)pyridin-3-yl]-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(3-fluoropyridin-4-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-[6-(ethylamino)-3-pyridyl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-(5-cyclopropyl-2-fluoro-3-pyridyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-(4-ethyl-2-fluoro-phenyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-5-methyl-2-(6-morpholino-3-pyridyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-(6-morpholino-3-pyridyl)-6,7-dihydro-5H-pyrazolo[5,1-b][1,3]oxazine-3-carboxamide;

(5R)-2-(2,6-dimethyl-3-pyridyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2,6-dimethyl-3-pyridyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-(2-ethylpyrimidin-5-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2-ethylpyrimidin-5-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-(3-furyl)-5-methyl-6,7-dihydro-5H-pyrazolo[5,1-b][1,3]oxazine-3-carboxamide;

(5R)-2-(3-furyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-(3-thienyl)-6,7-dihydro-5H-pyrazolo[5,1-b][1,3]oxazine-3-carboxamide;

(5R)-5-methyl-N-[(3S)-2-oxo-5-phenyl-1,3-dihydro-1,4-benzodiazepin-3-yl]-2-(3-thienyl)-6,7-dihydro-5H-pyrazolo[5,1-b][1,3]oxazine-3-carboxamide;

(5R)-2-(6-ethyl-2-methyl-3-pyridyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(6-ethyl-2-methyl-3-pyridyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[6-(isopropylamino)-3-pyridyl]-5-methyl-6,7-dihydro-5H-pyrazolo[5,1-b][1,3]oxazine-3-carboxamide;

(5R)-2-(1-Ethylpyrazol-3-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5S)-5-methyl-2-[6-(propan-2-ylamino)pyridin-3-yl]-N-(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-5-Methyl-2-(6-propan-2-ylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-5-Methyl-N-[(3S)-9-fluoro-2-oxo-5-phenyl-1,3-dihydro-1,4-benzodiazepin-3-yl]-2-[6-(trideuteriomethylamino)pyridin-3-yl]-6,7-dihydro-5H-pyrazolo[5,1-b][1,3]oxazine-3-carboxamide;

(5R)-2-(2-Fluoro-6-methylpyridin-3-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2-Fluoro-6-methylpyridin-3-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(6-Ethylpyridin-3-yl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(4-Ethyl-2-fluorophenyl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5S)—N-[(3S)-9-fluoro-2-oxo-5-phenyl-1,3-dihydro-1,4-benzodiazepin-3-yl]-2-(3-fluoropyridin-4-yl)-5-methyl-6,7-dihydro-5H-pyrazolo[5,1-b][1,3]oxazine-3-carboxamide;

(5R)-5-Methyl-2-(6-methylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-[6-(2-Hydroxypropyl)pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(5-Fluoro-2-methylpyridin-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(3-fluoropyridin-4-yl)-6,7-dihydro-5H-pyrazolo[5,1-b][1,3]oxazine-3-carboxamide;

(5R)-5-methyl-2-phenyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2,4-difluorophenyl)-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-5-methyl-2-(1-methylindazol-5-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(1-Ethylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-[6-(2-Hydroxy-2-methylpropyl)pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-5-Methyl-N-[(3S)-9-fluoro-2-oxo-5-phenyl-1,3-dihydro-1,4-benzodiazepin-3-yl]-2-[6-[(1R,4R)-2-oxa-5-azabicyclo[2.2.1]heptan-5-yl]pyridin-3-yl]-6,7-dihydro-5H-pyrazolo[5,1-b][1,3]oxazine-3-carboxamide;

(5S)-5-methyl-N-[(3R)-9-fluoro-2-oxo-5-phenyl-1,3-dihydro-1,4-benzodiazepin-3-yl]-2-[6-[(1S,4S)-2-oxa-5-azabicyclo[2.2.1]heptan-5-yl]pyridin-3-yl]-6,7-dihydro-5H-pyrazolo[5,1-b][1,3]oxazine-3-carboxamide;

(5R)-2-[2-Fluoro-6-[(1S,4S)-2-oxa-5-azabicyclo[2.2.1]heptan-5-yl]-3-pyridyl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-[6-Fluoro-2-[(1S,4S)-2-oxa-5-azabicyclo[2.2.1]heptan-5-yl]pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-[2-Fluoro-6-[(1R,4R)-2-oxa-5-azabicyclo[2.2.1]heptan-5-yl]pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-[2-Fluoro-6-(2-oxa-6-azaspiro[3.3]heptan-6-yl)pyridin-3-yl]-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-5-Methyl-2-[4-methyl-6-(propan-2-ylamino)pyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-5-Methyl-2-[2-methyl-6-(propan-2-ylamino)pyridin-3-yl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5S)-5-Methyl-N-[(3S)-9-fluoro-2-oxo-5-phenyl-1,3-dihydro-1,4-benzodiazepin-3-yl]-2-[6-[(1R,4R)-2-oxa-5-azabicyclo[2.2.1]heptan-5-yl]pyridin-3-yl]-6,7-dihydro-5H-pyrazolo[5,1-b][1,3]oxazine-3-carboxamide;

(5R)-2-Anilino-5-methyl-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-Anilino-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(4-Fluoroanilino)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-(1-methylpyrazol-4-yl)-6,7-dihydro-5H-pyrazolo[5,1-b][1,3]oxazine-3-carboxamide;

2-(1-Ethylpyrazol-4-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-[4-[(Dimethylamino)methyl]-2-fluorophenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-[2-Fluoro-4-(morpholin-4-ylmethyl)phenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-[4-(Diethylaminomethyl)-2-fluorophenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

N-[(3S)-2-oxo-5-phenyl-1,3-dihydro-1,4-benzodiazepin-3-yl]-2-(1-propan-2-ylpyrazol-4-yl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-[1-[(3-methyloxetan-3-yl)methyl]pyrazol-4-yl]-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-7-methyl-6,7-dihydro-5H-pyrazolo[5,1-b][1,3]oxazine-3-carboxamide;

2-(6-Ethylpyridin-3-yl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide-carboxamide;

tert-butyl N-[3-[(3S)-9-fluoro-2-oxo-5-phenyl-1,3-dihydro-1,4-benzodiazepin-3-yl]carbamoyl]-2-(2-fluorophenyl)-6,7-dihydro-5H-pyrazolo[5,1-b][1,3]oxazin-6-yl]-N-methylcarbamate;

tert-butyl N-ethyl-N-[3-[[(3S)-9-fluoro-2-oxo-5-phenyl-1,3-dihydro-1,4-benzodiazepin-3-yl]carbamoyl]-2-(2-fluorophenyl)-6,7-dihydro-5H-pyrazolo[5,1-b][1,3]oxazin-6-yl]carbamate;

(5S)-2-benzyl-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6-(hydroxymethyl)-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-[1-(oxan-4-yl) pyrazol-4-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-(1-propan-2-ylpyrazol-4-yl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6-(methoxymethyl)-6,7-dihydro-5H-pyrazolo[5,1-b][1,3]oxazine-3-carboxamide;

(5R)-2-cyclohexyl-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-(1,3-dimethylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-[1-(oxetan-3-yl) pyrazol-4-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[1-(2-hydroxyethyl) pyrazol-4-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-[1-(2,2,2-trifluoroethyl) pyrazol-4-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[1-(2-methoxyethyl) pyrazol-4-yl]-5-methyl-6,7-dihydro-5H-pyrazolo[5,1-b][1,3]oxazine-3-carboxamide;

(5R)-2-[1-(Difluoromethyl) pyrazol-4-yl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-(1,5-Dimethylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[1-(2-hydroxy-2-methylpropyl) pyrazol-4-yl]-5-methyl-6,7-dihydro-5H-pyrazolo[5,1-b][1,3]oxazine-3-carboxamide;

N-[(3S)-9-Fluoro-2-oxo-5-phenyl-1,3-dihydro-1,4-benzodiazepin-3-yl]-2-(2-fluorophenyl)-5-(hydroxymethyl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6-(pyrazol-1-ylmethyl)-6,7-dihydro-5H-pyrazolo[5,1-b][1,3]oxazine-3-carboxamide;

(5R)-2-(1-cyclopropylpyrazol-4-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(1-cyclopropylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5S)-2-(6-ethylpyridin-3-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

2-(2,4-Difluorophenyl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide;

2-(2,6-Difluorophenyl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide;

2-(1-Ethylpyrazol-4-yl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide;

2-(2,4-Difluorophenyl)-6-(hydroxymethyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5S)-2-(6-ethylpyridin-3-yl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

2-(6-Ethylpyridin-3-yl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide;

2-[2-Fluoro-4-(hydroxymethyl)phenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(2-Fluoro-4-methylsulfonylphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(2-Fluoropyridin-3-yl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2-Fluoro-4-methylsulfonylphenyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

2-(4-Cyano-2-fluorophenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(2-Fluoro-6-methoxyphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(2-Fluoro-6-methylphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(2-Fluoro-4-methylsulfonylphenyl)-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

2-(4-Carbamoyl-2-fluorophenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-[2-Fluoro-4-(methylsulfonimidoyl)phenyl]-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[6-(3-methoxyazetidin-1-yl)pyridin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[6-[(3R)-3-methoxypyrrolidin-1-yl]pyridin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[6-[(3S)-3-methoxypyrrolidin-1-yl]pyridin-3-yl]-5-methyl-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(1-methylindazol-4-yl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(1-propan-2-ylpyrazol-4-yl)-6,7-dihydro-5H-pyrazolo[5,1-b][1,3]oxazine-3-carboxamide;

2-(1-Methylindazol-4-yl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-[1-(2,2,2-trifluoroethyl) pyrazol-4-yl]-6,7-dihydro-5H-pyrazolo[5,1-b][1,3]oxazine-3-carboxamide;

N-[(3S)-2-oxo-5-phenyl-1,3-dihydro-1,4-benzodiazepin-3-yl]-2-[1-(2,2,2-trifluoroethyl) pyrazol-4-yl]-6,7-dihydro-5H-pyrazolo[5,1-b][1,3]oxazine-3-carboxamide;

N-[(3S)-9-Fluoro-2-oxo-5-phenyl-1,3-dihydro-1,4-benzodiazepin-3-yl]-2-[1-(oxan-4-yl) pyrazol-4-yl]-6,7-dihydro-5H-pyrazolo[5,1-b][1,3]oxazine-3-carboxamide;

(5R)-2-[2-Fluoro-4-(hydroxymethyl)phenyl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-[2-Fluoro-4-(hydroxymethyl)phenyl]-5-methyl-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[6-(hydroxymethyl)pyridin-3-yl]-5-methyl-6,7-dihydro-5H-pyrazolo[5,1-b][1,3]oxazine-3-carboxamide;

(5S)—N-[(3S)-9-fluoro-2-oxo-5-phenyl-1,3-dihydro-1,4-benzodiazepin-3-yl]-5-methyl-2-[1-(oxan-4-yl) pyrazol-4-yl]-6,7-dihydro-5H-pyrazolo[5,1-b][1,3]oxazine-3-carboxamide;

(5S)—N-[(3S)-9-fluoro-2-oxo-5-phenyl-1,3-dihydro-1,4-benzodiazepin-3-yl]-5-methyl-2-[1-(2,2,2-trifluoroethyl) pyrazol-4-yl]-6,7-dihydro-5H-pyrazolo[5,1-b][1,3]oxazine-3-carboxamide;

(5S)-2-(1-Ethylpyrazol-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-(1H-pyrazol-4-yl)-6,7-dihydro-5H-pyrazolo[5,1-b][1,3]oxazine-3-carboxamide;

2-(2-Fluorophenyl)-6-hydroxy-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-5-methyl-2-(1-methylsulfonylpiperidin-4-yl)-6,7-dihydro-5H-pyrazolo[5,1-b][1,3]oxazine-3-carboxamide;

(5R)-5-Methyl-2-(1-methylsulfonylpiperidin-4-yl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(2S)—N-[(3S)-9-fluoro-2-oxo-5-phenyl-1,3-dihydro-1,4-benzodiazepin-3-yl]-6-(2-fluorophenyl)-2-methyl-2,3-dihydropyrazolo[5,1-b][1,3]oxazole-7-carboxamide;

6-(Diethylaminomethyl)-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

(5R)-2-[1-[2-(dimethylamino)ethyl]pyrazol-4-yl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

5-[(Dimethylamino)methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-5-(morpholin-4-ylmethyl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6-[[methyl (oxan-4-yl)amino]methyl]-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6-[[methyl (oxetan-3-yl)amino]methyl]-6,7-dihydro-5H-pyrazolo[5,1-b][1,3]oxazine-3-carboxamide;

(5R)-2-[4-[(dimethylamino)methyl]-2-fluorophenyl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

6-[(Dimethylamino)methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6-[(4-methylpiperazin-1-yl)methyl]-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6-(morpholin-4-ylmethyl)-6,7-dihydro-5H-pyrazolo[5,1-b][1,3]oxazine-3-carboxamide;

6-[[Benzyl (ethyl)amino]methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

2-(2-Fluorophenyl)-6-methoxy-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(6-Ethylpyridin-3-yl)-N-[(3S)-2-oxo-5-phenyl-1,3-dihydro-1,4-benzodiazepin-3-yl]spiro[5,7-dihydropyrazolo[5,1-b][1,3]oxazine-6,1'-cyclobutane]-3-carboxamide;

2-(6-Ethylpyridin-3-yl)-N-[(3S)-9-fluoro-2-oxo-5-phenyl-1,3-dihydro-1,4-benzodiazepin-3-yl]spiro[5,7-dihydropyrazolo[5,1-b][1,3]oxazine-6,1'-cyclobutane]-3-carboxamide;

2-[6-(Propan-2-ylamino)pyridin-3-yl]-N-[(3S)-2-oxo-5-phenyl-1,3-dihydro-1,4-benzodiazepin-3-yl]spiro[5,7-dihydropyrazolo[5,1-b][1,3]oxazine-6,1'-cyclopropane]-3-carboxamide;

2-[6-(Propan-2-ylamino)pyridin-3-yl]-N-[(3S)-9-fluoro-2-oxo-5-phenyl-1,3-dihydro-1,4-benzodiazepin-3-yl]spiro[5,7-dihydropyrazolo[5,1-b][1,3]oxazine-6,1'-cyclopropane]-3-carboxamide;

2-(6-Ethylpyridin-3-yl)-N-[(3S)-2-oxo-5-phenyl-1,3-dihydro-1,4-benzodiazepin-3-yl]spiro[5,7-dihydropyrazolo[5,1-b][1,3]oxazine-6,1'-cyclopropane]-3-carboxamide;

2-(6-Ethylpyridin-3-yl)-N-[(3S)-9-fluoro-2-oxo-5-phenyl-1,3-dihydro-1,4-benzodiazepin-3-yl]spiro[5,7-dihydropyrazolo[5,1-b][1,3]oxazine-6,1'-cyclopropane]-3-carboxamide;

N-[(3S)-9-fluoro-2-oxo-5-phenyl-1,3-dihydro-1,4-benzodiazepin-3-yl]-2-(2-fluorophenyl)-6-(pyrrolidin-1-ylmethyl)-6,7-dihydro-5H-pyrazolo[5,1-b][1,3]oxazine-3-carboxamide;

(5R)—N-[(3S)-9-fluoro-2-oxo-5-phenyl-1,3-dihydro-1,4-benzodiazepin-3-yl]-2-[2-fluoro-4-[(propan-2-ylamino)methyl]phenyl]-5-methyl-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-6-(methylsulfonylmethyl)-6,7-dihydro-5H-pyrazolo[5,1-b][1,3]oxazine-3-carboxamide;

2-(2-Fluorophenyl)-N-[(3S)-9-fluoro-2-oxo-5-phenyl-1,3-dihydro-1,4-benzodiazepin-3-yl]spiro[5,7-dihydropyrazolo[5,1-b][1,3]oxazine-6,1'-cyclobutane]-3-carboxamide;

6-[(3,3-Difluoropyrrolidin-1-yl)methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

N-[(3S)-9-fluoro-2-oxo-5-phenyl-1,3-dihydro-1,4-benzodiazepin-3-yl]-2-(2-fluorophenyl)-5-(pyrrolidin-1-ylmethyl)-6,7-dihydro-5H-pyrazolo[5,1-b][1,3]oxazine-3-carboxamide;

(6R*)—N-[(3S)-9-fluoro-2-oxo-5-phenyl-1,3-dihydro-1,4-benzodiazepin-3-yl]-2-(2-fluorophenyl)-6-(hydroxymethyl)-6,7-dihydro-5H-pyrazolo[5,1-b][1,3]oxazine-3-carboxamide;

(6S*)—N-[(3S)-9-fluoro-2-oxo-5-phenyl-1,3-dihydro-1,4-benzodiazepin-3-yl]-2-(2-fluorophenyl)-6-(hydroxymethyl)-6,7-dihydro-5H-pyrazolo[5,1-b][1,3]oxazine-3-carboxamide;

(6R*)-2-(2,6-Difluorophenyl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide;

(6S*)-2-(2,6-Difluorophenyl)-N-[(3S)-9-fluoro-2-oxo-5-phenyl-1,3-dihydro-1,4-benzodiazepin-3-yl]-6-(hydroxymethyl)-6,7-dihydro-5H-pyrazolo[5,1-b][1,3]oxazine-3-carboxamide;

(6R*)-6-[(Dimethylamino)methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

(6S*)-6-[(Dimethylamino)methyl]-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

(5R*)-2-(2,6-Difluorophenyl)-5-(hydroxymethyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5S*)-2-(2,6-Difluorophenyl)-5-(hydroxymethyl)-N-[(3S)-2-oxo-5-phenyl-1,3-dihydro-1,4-benzodiazepin-3-yl]-6,7-dihydro-5H-pyrazolo[5,1-b][1,3]oxazine-3-carboxamide;

(5R*)-2-(2,6-Difluorophenyl)-N-[(3S)-9-fluoro-2-oxo-5-phenyl-1,3-dihydro-1,4-benzodiazepin-3-yl]-5-(hydroxymethyl)-6,7-dihydro-5H-pyrazolo[5,1-b][1,3]oxazine-3-carboxamide;

(5S*)-2-(2,6-Difluorophenyl)-N-[(3S)-9-fluoro-2-oxo-5-phenyl-1,3-dihydro-1,4-benzodiazepin-3-yl]-5-(hydroxymethyl)-6,7-dihydro-5H-pyrazolo[5,1-b][1,3]oxazine-3-carboxamide;

(5R*)—N-[(3S)-9-Fluoro-2-oxo-5-phenyl-1,3-dihydro-1,4-benzodiazepin-3-yl]-2-(2-fluorophenyl)-5-(hydroxymethyl)-6,7-dihydro-5H-pyrazolo[5,1-b][1,3]oxazine-3-carboxamide;

(5S*)-2-(2-Fluorophenyl)-5-(hydroxymethyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R*)—N-[(3S)-9-fluoro-2-oxo-5-phenyl-1,3-dihydro-1,4-benzodiazepin-3-yl]-2-(2-fluorophenyl)-5-(methoxymethyl)-6,7-dihydro-5H-pyrazolo[5,1-b][1,3]oxazine-3-carboxamide;

(5S*)—N-[(3S)-9-fluoro-2-oxo-5-phenyl-1,3-dihydro-1,4-benzodiazepin-3-yl]-2-(2-fluorophenyl)-5-(methoxymethyl)-6,7-dihydro-5H-pyrazolo[5,1-b][1,3]oxazine-3-carboxamide;

6-(Ethylaminomethyl)-N-[(3S)-9-fluoro-2-oxo-5-phenyl-1,3-dihydro-1,4-benzodiazepin-3-yl]-2-(2-fluorophenyl)-6,7-dihydro-5H-pyrazolo[5,1-b][1,3]oxazine-3-carboxamide;

2-(2-Fluoro-4-methylsulfanylphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(2-Fluoro-4-methylsulfinylphenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-Bromo-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

2-(2,6-Difluorophenyl)-N-[(3S)-9-fluoro-2-oxo-5-phenyl-1,3-dihydro-1,4-benzodiazepin-3-yl]-6,7-dihydro-5H-pyrazolo[5,1-b][1,3]oxazine-3-carboxamide;

(5R)-2-(4-Ethylsulfonyl-2-fluorophenyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-(2-Fluoro-5-methylsulfonylphenyl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)—N-[(3S)-9-Fluoro-2-oxo-5-phenyl-1,3-dihydro-1,4-benzodiazepin-3-yl]-2-(2-fluoro-4-sulfamoylphenyl)-5-methyl-6,7-dihydro-5H-pyrazolo[5,1-b][1,3]oxazine-3-carboxamide;

(5R)-2-[4-(Dimethylsulfamoyl)-2-fluorophenyl]-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

(5R)-2-(1-Ethylsulfonylpiperidin-4-yl)-N-[(3S)-9-fluoro-2-oxo-5-phenyl-1,3-dihydro-1,4-benzodiazepin-3-yl]-5-methyl-6,7-dihydro-5H-pyrazolo[5,1-b][1,3]oxazine-3-carboxamide;

and the pharmaceutically acceptable salts thereof.

6. A pharmaceutical composition which comprises a compound according to claim 1 and a pharmaceutically acceptable carrier or diluent.

7. A pharmaceutical composition which comprises a compound according to claim 5 and a pharmaceutically acceptable carrier or diluent.

8. A method of treating a subject suffering from an RSV infection wherein the method comprises administering to the subject an effective amount of a compound of claim 1.

9. A method according to claim 8, wherein the method further comprises administering to the subject a therapeutic agent selected from the group consisting of:

(i) a RSV nucleocapsid (N)-protein inhibitor;

(ii) a protein inhibitor, (iii) an anti-RSV monoclonal antibody;

(iv) an immunomodulating toll-like receptor compound;

(v) a respiratory virus anti-viral; and/or (vi) an anti-inflammatory compound.

* * * * *